US012409195B2

(12) United States Patent
Falb et al.

(10) Patent No.: US 12,409,195 B2

(45) **Date of Patent: *Sep. 9, 2025**

(54) BACTERIA ENGINEERED TO REDUCE HYPERPHENYLALANINEMIA

(71) Applicant: Synlogic Operating Company, Inc., Cambridge, MA (US)

(72) Inventors: Dean Falb, Sherborn, MA (US); Vincent M. Isabella, Cambridge, MA (US); Jonathan W. Kotula, Somerville, MA (US); Paul F. Miller, Salem, CT (US); Yves Millet, Newton, MA (US); Sarah Rowe, Somerville, MA (US)

(73) Assignee: Synlogic Operating Company, Inc., Cambridge, MA (US)

( * ) Notice: Subject to any disclaimer, the term of this patent is extended or adjusted under 35 U.S.C. 154(b) by 1086 days.

This patent is subject to a terminal disclaimer.

(21) Appl. No.: 16/788,458

(22) Filed: Feb. 12, 2020

(65) Prior Publication Data

US 2020/0246394 A1 Aug. 6, 2020

Related U.S. Application Data

(62) Division of application No. 15/154,934, filed on May 13, 2016, now Pat. No. 10,610,546.

(60) Provisional application No. 62/256,052, filed on Nov. 16, 2015, provisional application No. 62/161,137, filed on May 13, 2015.

(51) Int. Cl.

| | |
|---|---|
| ***A61K 35/74*** | (2015.01) |
| ***A61K 35/741*** | (2015.01) |
| ***A61K 39/02*** | (2006.01) |
| ***C07K 14/195*** | (2006.01) |
| ***C07K 14/245*** | (2006.01) |
| ***C07K 14/425*** | (2006.01) |
| ***C12N 9/06*** | (2006.01) |
| ***C12N 9/88*** | (2006.01) |
| ***C12N 15/70*** | (2006.01) |
| *A61K 35/00* | (2006.01) |
| *A61K 38/00* | (2006.01) |

(52) U.S. Cl.

CPC ............ *A61K 35/74* (2013.01); *A61K 35/741* (2013.01); *A61K 39/02* (2013.01); *C07K 14/195* (2013.01); *C07K 14/245* (2013.01); *C12N 9/0014* (2013.01); *C12N 9/0022* (2013.01); *C12N 9/88* (2013.01); *C12N 15/70* (2013.01); *C12Y 104/03002* (2013.01); *C12Y 403/01024* (2013.01); *A61K 2035/11* (2013.01); *A61K 38/00* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 5,589,168 | A | 12/1996 | Allen et al. |
| 5,989,463 | A | 11/1999 | Tracy et al. |
| 6,203,797 | B1 | 3/2001 | Perry |
| 6,835,376 | B1 | 12/2004 | Neeser et al. |
| 7,314,974 | B2 | 1/2008 | Cao et al. |
| 7,731,976 | B2 | 6/2010 | Cobb et al. |
| 8,541,208 | B1 | 9/2013 | Plesch et al. |
| 8,735,107 | B2 | 5/2014 | Weiner et al. |
| 9,150,845 | B2 | 10/2015 | Weiner et al. |
| 9,688,967 | B2 | 6/2017 | Falb et al. |
| 9,889,164 | B2 | 2/2018 | Falb et al. |
| 9,943,555 | B2 | 4/2018 | Falb et al. |
| 10,195,234 | B2 | 2/2019 | Falb et al. |
| 10,294,499 | B2 | 5/2019 | Simon Vecilla et al. |
| 10,610,546 | B2 | 4/2020 | Falb et al. |
| 10,883,115 | B2 | 1/2021 | Ayal et al. |
| 11,060,073 | B2 | 7/2021 | Falb et al. |
| 11,618,894 | B2 | 4/2023 | Falb et al. |
| 11,766,463 | B2 | 9/2023 | Adolfsen et al. |
| 11,879,123 | B2 | 1/2024 | Falb et al. |
| 12,171,790 | B2 | 12/2024 | Adolfsen et al. |
| 2013/0230893 | A1 * | 9/2013 | Ruebling-Jass ........ C07K 14/24 435/252.33 |
| 2014/0079701 | A1 | 3/2014 | Miller et al. |
| 2014/0314843 | A1 | 10/2014 | Huisman et al. |
| 2015/0238545 | A1 | 8/2015 | Borody |
| 2015/0246085 | A1 * | 9/2015 | Al-Hafid ............. A61K 35/747 424/490 |
| 2015/0359894 | A1 | 12/2015 | Weinrich et al. |
| 2016/0068832 | A1 | 3/2016 | Weiner et al. |
| 2016/0177274 | A1 | 6/2016 | Falb et al. |
| 2017/0136073 | A1 | 5/2017 | Falb et al. |

(Continued)

FOREIGN PATENT DOCUMENTS

| | | | |
|---|---|---|---|
| CN | 1154845 | A | 7/1997 |
| CN | 1341715 | A | 3/2002 |

(Continued)

OTHER PUBLICATIONS

Zhang et al Multifaceted Regulations of Gateway Enzyme Phenylalanine Ammonia-Lyase in the Biosynthesis of Phenylpropanoids Molecular Plant 8, Jan. 17-27, 2015.*

Ashida et al., Bacteria and host interactions in the gut epithelial barrier Nature Chemical Biology vol. 8, pp. 36-45 (2012).*

Adams et al. (Jul. 15, 1990) "Nucleotide sequence and genetic characterization reveal six essential genes for the LIV-I and LS transport systems of *Escherichia coli*" *J Biol Chem*. 265(20):11436-43.

Al Hafid et al. (Jun. 2002) "Phenylketonuria: a Review of Current and Future Treatments" *Transl Pediatr*. 3:49-62.

(Continued)

*Primary Examiner* — Robert M Kelly

(74) *Attorney, Agent, or Firm* — McCarter & English LLP; Marcie B. Clarke

(57) ABSTRACT

Genetically engineered bacteria, pharmaceutical compositions thereof, and methods of modulating and treating diseases associated with hyperphenylalaninemia are disclosed.

9 Claims, 90 Drawing Sheets

Specification includes a Sequence Listing.

(56) References Cited

U.S. PATENT DOCUMENTS

| | | | |
|---|---|---|---|
| 2017/0216370 | A1 | 8/2017 | Falb et al. |
| 2017/0232043 | A1 | 8/2017 | Falb et al. |
| 2020/0172857 | A1 | 6/2020 | Falb et al. |
| 2024/0076645 | A1 | 3/2024 | Falb et al. |
| 2024/0316121 | A1 | 9/2024 | Adolfsen et al. |
| 2024/0368531 | A1 | 11/2024 | Falb et al. |

FOREIGN PATENT DOCUMENTS

| | | | | |
|---|---|---|---|---|
| CN | 101068919 | A | | 11/2007 |
| CN | 101586111 | A | | 11/2009 |
| EP | 1383897 | B1 | | 6/2006 |
| EP | 1666588 | A1 | | 6/2006 |
| EP | 2344626 | B1 | | 7/2011 |
| WO | 2006/034373 | A2 | | 3/2006 |
| WO | 2006/079790 | A2 | | 8/2006 |
| WO | WO 2008/073148 | A2 | | 6/2008 |
| WO | 2008/118176 | A2 | | 10/2008 |
| WO | WO 2009/004595 | A2 | | 1/2009 |
| WO | 2011/080505 | A2 | | 7/2011 |
| WO | 2011/106874 | A1 | | 9/2011 |
| WO | WO 2012/078311 | A1 | | 6/2012 |
| WO | WO 2013/134174 | A2 | | 9/2013 |
| WO | 2013/175358 | A1 | | 11/2013 |
| WO | WO 2013/134174 | | * | 12/2013 |
| WO | WO 2013/192543 | A2 | | 12/2013 |
| WO | WO 2014/018832 | A1 | | 1/2014 |
| WO | WO 2014/066945 | | * | 5/2014 |
| WO | WO 2014/066945 | A1 | | 5/2014 |
| WO | 2014/093852 | A1 | | 6/2014 |
| WO | WO 2014/138324 | A1 | | 9/2014 |
| WO | 2014/172541 | A2 | | 10/2014 |
| WO | WO 2016/183531 | A1 | | 11/2016 |
| WO | WO 2016/183532 | A1 | | 11/2016 |
| WO | WO 2016/210373 | A2 | | 12/2016 |
| WO | 2017/216704 | A1 | | 12/2017 |
| WO | 2018/237198 | A1 | | 12/2018 |
| WO | 2020/013951 | A1 | | 1/2020 |
| WO | 2021/188819 | A1 | | 9/2021 |
| WO | 2023/044479 | A1 | | 3/2023 |

OTHER PUBLICATIONS

Al Hafid et al. (Oct. 2015) "Phenylketonuria: a review of current and future treatments" *Transl Pediatr*. 4(4):304-317.

Albiniak et al. (2013) "High-level secretion of a recombinant protein to the culture medium with a Bacillus subtilis twin-arginine translocation system in *Escherichia coli*" *FEBS J*. 280:3810-3821.

Altenhoefer et al. (Apr. 9, 2004) "The probiotic *Escherichia coli* strain Nissle 1917 interferes with invasion of human intestinal epithelial cells by different enteroinvasive bacterial pathogens" *FEMS Immunol Med Microbiol*. 40(3):223-229.

Andersen et al. (Apr. 1995) "Uracil uptake in *Escherichia coli* K-12: isolation of uraA mutants and cloning of the gene" *J Bacteriol*. 177(8):2008-2013.

Anderson et al. (Apr. 1977) "*Escherichia coli* transport mutants lacking binding protein and other components of the branched-chain amino acid transport systems" *J Bacteriol*. 130(1):384-92.

Anderson et al. (Oct. 1978) "Genetic separation of high- and low-affinity transport systems for branched-chain amino acids in *Escherichia coli* K-12" *J Bacteriol*. 136(1):168-74.

Arai et al. (Aug. 2, 19958) "Expression of the nir and nor genes for denitrification of Pseudomonas aeruginosa requires a novel CRP/FNR-related transcriptional regulator, DNR, in addition to ANR" *FEBS Lett*. 371(1):73-76.

Argos (1989) "A possible homology between immunodeficiency virus p24 core protein and picornaviral VP2 coat protein: prediction of HIV p24 antigenic sites" *EMBO J*. 8(3):779-785.

Arrach et al. (Jun. 1, 20085) "*Salmonella* promoters preferentially activated inside tumors" *Cancer Res*. 68(12):4827-32.

Arthur et al. (Oct. 5, 2012) "Intestinal inflammation targets cancer-inducing activity of the microbiota" *Science* 338(6103):120-123. NIH Public Access Author Manuscript; available in PMC May 6, 2013 (11 pages).

Ashida et al. (2012) "Bacteria and host interactions in the gut epithelial barrier" *Nature Chem Biol*. 8: 36-45.

Baek et al. (Apr. 2011) "Expression and characterization of a second L-amino acid deaminase isolated from *Proteus mirabilis* in *Escherichia coli*" *J Basic Microbiol*. 51:129-135.

Barel et al. (Feb. 6, 2015) "The complex amino acid diet of Francisella in infected macrophages" *Front Cell Infect Microbiol*. 5:9. 5 pages.

Bearden et al. (Apr. 1999) "The Yfe system of Yersinia pestis transports iron and manganese and is required for full virulence of plague" *Mol Microbiol*. 32(2):403-14.

Becker et al. (Aug. 1996) "$0_2$ as the regulatory signal for FNR-dependent gene regulation in *Escherichia coli*" *J Bacteriol*. 178(15):4515-21.

Becker et al. (Oct. 1997) "Regulatory $0_2$ tensions for the synthesis of fermentation products in *Escherichia coli* and relation to aerobic respiration" Arch Microbiol. 168(4):290-6.

Bifulco et al. (2013) "A thermostable L-aspartate oxidase: a new tool for biotechnological applications" *App/Microbiol Biotechnol*. 97:7285-7295.

Blau et al. (2015) "Alternative therapies to address the unmet medical needs of patients with phenylketonuria" *Expert Opin Pharmacother*. 16(6):791-800.

Boysen et al. (Apr. 2010) "Translational Regulation of Gene Expression by an Anaerobically Induced Small Non-coding RNA in *Escherichia coli*" *J Biol Chem*. 285(14):10690-10702.

Braat et al (2006) "A Phase I Trial With Transgenic Bacteria Expressing Interleukin-10 in Crohn's Disease" *Clinical Gastroenterology and Hepatology* 4:754-759.

Bucarey et al. (Oct. 2005) "The *Salmonella enterica* serovar Typhi tsx gene, encoding a nucleoside-specific porin, is essential for prototrophic growth in the absence of nucleosides" *Infect Immun*. 73(10):6210-9.

Cabrita et al. (2002) "Molecular biology and regulation of nucleoside and nucleobase transporter proteins in eukaryotes and prokaryotes" *Biochem Cell Biol*. 80(5):623-38.

Caldara et al. (Oct. 1, 20079) "ArgR-dependent repression of arginine and histidine transport genes in *Escherichia coli*" K-12. *J Mol Biol*. 373(2):251-67.

Callura et al. (Sep. 7, 2010) "Tracking, tuning, and terminating microbial physiology using synthetic riboregulators" *Proc Natl Acad Sci USA*, 107(36):15898-15903.

Castiglione et al. (Sep. 2009) "The transcription factor DNR from *Pseudomonas aeruginosa* specifically requires nitric oxide and haem for the activation of a target promoter in *Escherichia coli*" *Microbiology*, 155(Pt 9):2838-2844.

Celis (Jun. 1977) "Properties of an *Escherichia coli* K-12 mutant defective in the transport of arginine and ornithine" *J Bacteriol*. 130(3):1234-43.

Cellier et al. (Jun. 1996) "Resistance to intracellular infections: comparative genomic analysis of Nramp" *Trends Genet*. 12(6):201-4.

Chang (2007) "Use of Enzyme Artificial Cells for Genetic Enzyme Defects" In *Artificial Cells: Biotechnology, Nanomedicine, Regenerative Medicine, Blood Substitutes, Bioencapsulation, and Cell/Stem Cell Therapy. Regenerative Medicine, Artificial Cells and Nanomedicine—vol. 1*. Singapore: World Scientific Publishing pp. 147-159.

Charbonneau et al. (Apr. 8, 2020) "Developing a new class of engineered live bacterial therapeutics to treat human diseases" *Nat Commun* 11, 1738 (2020). https://doi.org/10.1038/s41467-020-15508-1.

Chen et al. (Mar. 2006) "High-level Expression of Phenylalanine Ammonia-lyase in *Lactococcus lactis* via Synthesized Sequence Based on Bias Codons" *Chin J Biotech*. 22(2): 187-190.

Christodoulou et al. (Nov. 2012) "Enzyme substitution therapy for phenylketonuria delivered orally using a genetically modified probiotic:

(56) References Cited

OTHER PUBLICATIONS

Proof of principle" $62^{nd}$ Annual Meeting of the American Society of Human Genetics, Nov. 6-10, 2012, San Francisco, CA; Program No. 166, Nov. 8, 2012.
Chye et al. (Jan. 1987) Transcription control of the aroP gene in *Escherichia coli* K-12: analysis of operator mutants. *J Bacteriol.* 169(1):386-93.
Clarkson et al. (1971) "Diaminopimelic Acid and Lysine Auxotrophs of *Pseudomonas aeruginosa* 8602" *J Gen Microbiol.* 66:161-169.
Coban et al. (2014) "Screening of phenylpyruvic acid producers and optimization of culture conditions in bench scale bioreactors" Bioprocess Biosyst Eng. 37:2343-2352.
Collinson et al. (2015) "Channel crossing: how are proteins shipped across the bacterial plasma membrane?" *Philos Trans R Soc B* 370:20150025 [online]. Retrieve from: http://rstb.royalsocietypublishing.org/, on Jun. 16, 2016 (13 pages).
Costa et al. (May 2015) "Secretion systems in Gram-negative bacteria: structural and mechanistic insights" *Nat Rev Microbiol.* 13(6):343-359.
Cuevas-Ramos et al. (Jun. 2, 20102) "*Escherichia coli* induces DNA damage in vivo and triggers genomic instability in mammalian cells" *Proc Natl Acad Sci USA*, 107(25):11537-11542.
Danino et al. (May 2015) "Programmable probiotics for detection of cancer in urine" *Sci Transl Med.* 7(289):289ra84 [online]. Retrieved from: www.sciencetranslational medicine.org, on Jul. 30, 2015 (11 pages).
Den Hengst et al. (May 2006) "Identification and functional characterization of the Lactococcus lactis CodY-regulated branched-chain amino acid permease BcaP (CtrA)" *J Bacteriol.* 188(9):3280-9.
Deutscher (Apr. 2008) "The mechanisms of carbon catabolite repression in bacteria" *Curr Opin Microbiol.* 11(2):87-93.
Dinleyici et al. (Nov. 2014) "*Saccharomyces boulardii* CNCM I-745 in different clinical conditions" *Expert Opin Biol Ther.* 14(11):1593-1609.
Dobbelaere et al. (2003) "Evaluation of nutritional status and pathophysiology of growth retardation in patients with phenylketonuria" *J Inherit Metab Dis*, 26(1):1-11.
Drouault et al. (Jun. 2002)Oral Treatment with Lactococcus Lactis Expressing Syaphylococcus Hyicus Lipase Enhances lipid Digestion in Pigs with Induced Pancreatic Insufficienty *Applied and Envoronmental Microbiology*, pp. 3166-3168.
Duan et al. (2008) "Secretion of Insulinotropic Proteins by Commensal Bacteria: Rewiring the Gut to Treat Diabetes" *Appl. Environ. Microbial.* pp. 7437-7438.
Duarte et al. (Feb. 2010) "PerR vs OhrR: selective peroxide sensing in *Bacillus subtilis" Mol Biosyst.* 6(2):316-23.
Dubbs et al. (Oct. 2012) "Peroxide-sensing transcriptional regulators in bacteria" *J Bacteriol.* 194(20):5495-503.
Duerre et al. (Feb. 1975) "L-Amino Acid Oxidases of *Proteus rettgeri" J Bacteriol.* 121(2):656-663.
Dunn et al. (Jul. 1, 2010) "The alternative oxidase (AOX) gene in Vibrio fischeri is controlled by NsrR and upregulated in response to nitric oxide" *Mol Microbiol.* 77(1):44-55.
Durand et al. (Mar. 2010) "Reprogramming of Anaerobic Metabolism by the FnrS Small RNA" *Mol Microbiol.* 75(5):1215-1231. NIH Public Access Author Manuscript; available in PMC Sep. 17, 2010 (28 pages).
Durrer et al. (May 2017) "Genetically engineered probiotic for the treatment of phenylketonuria (PKU); assessment of a novel treatment in vitro and in the PAHenu2 mouse model of PKU" *Plos One*, 12(5): e0176286.
Eiglmeier et al. (Jul. 1989) "Molecular genetic analysis of FNR-dependent promoters" *Mol Microbiol.* 3(7):869-878.
Elkins et al. (Dec. 2001) "Genes encoding bile salt hydrolases and conjugated bile salt transporters in Lactobacillus johnsonii 100-100 and other Lactobacillus species" *Microbiology* 147(Pt 12):3403-12.
Estrem et al. (Aug. 1998) "Identification of an UP element consensus sequence for bacterial promoters" *Proc Natl Acad Sci USA*, 95(17):9761-9766.
Folling (1994) "The Discovery of Phenylketonuria" *Act Paediatr Suppl* 407:4-10.
Forbes (Nov. 2010) "Engineering the perfect (bacterial) cancer therapy" *Nat Rev Cancer*10(11 ): 785-94.
Galimand et al. (Mar. 1991) "Positive FNR-like control of anaerobic arginine degradation and nitrate respiration in *Pseudomonas aeruginosa*" J Bacteriol. 173(5):1598-1606.
Gardner et al. (2000) "Construction of a genetic toggle switch in *Escherichia coli*" *Nature*, 403:339-342.
GenBank Database Accession No. AAA86752 (Feb. 3, 1996) "amino acid deaminase [Proteus mirabilis HI4320" [online]. National Center for Biotechnology Information (NCBI), U.S. National Library of Medicine; http://www.ncbi.nlm.nih.gov/protein/AAA86752 (1 page).
GenBank Database Accession No. AAH26251.1 (Jul. 15, 2006) "Phenylalanine hydroxylase [*Homo sapiens*]" [online]. National Center for Biotechnology Information (NCBI), U.S. National Library of Medicine; http://www.ncbi.nlm.nih.gov/protein/AAH26251 (2 pages).
GenBank Database Accession No. ABA23593.1 (Jan. 28, 2014) "histidine ammonia-lyase [Anabaena variabilis ATCC 29413]" [online]. National Center for Biotechnology Information (NCBI), U.S. National Library of Medicine; http://www.ncbi.nlm.nih.gov/protein/ABA23593 (2 pages).
GenBank Database Accession No. ACD36582.1 (Aug. 15, 2011) "L-amino acid deaminase [Proteus mirabilis]" [online]. National Center for Biotechnology Information (NCBI), U.S. National Library of Medicine; http://www.ncbi.nlm.nih.gov/protein/ACD36582 (1 page).
GenBank Database Accession No. BAA90864.1 (Feb. 18, 2000) "L-amino acid deaminase [Proteus vulgaris]" [online]. National Center for Biotechnology Information (NCBI), U.S. National Library of Medicine; http://www.ncbi.nlm.nih.gov/protein/BAA90864 (1 page).
GenBank Database Accession No. CAE15566.1 (Feb. 27, 2015) "Histidine ammonia-lyase (histidase) [Photorhabdus luminescens subsp. laumondii TTO1]" [online]. National Center for Biotechnology Information (NCBI), U.S. National Library of Medicine; http://www.ncbi.nlm.nih.gov/protein/CAE15566 (2 pages).
GenBank Database Accession No. EDV65095.1 (Jun. 20, 2008) "arromatic amino acid transport protein AroP [*Escherichia coli* F11]" [online]. National Center for Biotechnology Information (NCBI), U.S. National Library of Medicine; http://www.ncbi.nlm.nih.gov/protein/EDV65095 (2 pages).
GenBank Database Accession No. EU669819.1 (Aug. 15, 2011) "Proteus mirabilis L-amino acid deaminase gene, complete cds" [online]. National Center for Biotechnology Information (NCBI), U.S. National Library of Medicine; http://www.ncbi.nlm.nih.gov/nuccore/EU669819 (2 pages).
GenBank Database Accession No. U35383.1 (Feb. 3, 1996) "Proteus mirabilis amino acid deaminase (aad) gene, complete cds" [online]. National Center for Biotechnology Information (NCBI), U.S. National Library of Medicine; http://www.ncbi.nlm.nih.gov/nuccore/U35383 (2 pages).
Gerdes et al. (Oct. 2006) "Essential genes on metabolic maps" *Curr Opin Biotechnol.* 17(5):448-456.
Gilbert et al. (Jan. 1985) "Molecular cloning of the phenylalanine ammonia lyase gene from *Rhodosporidium toruloides* in *Escherichia coli* K-12" *J Bacteriol.* 161(1):314-320.
Görke et al. (Aug. 2008) "Carbon catabolite repression in bacteria: many ways to make the most out of nutrients" *Nat Rev Microbiol*, 6(8):613-624.
Gouzy et al. (Feb. 20, 2014) "Mycobacterium tuberculosis exploits asparagine to assimilate nitrogen and resist acid stress during infection" *PLoS Pathog.* 10{2):e1003928. 14 pages.
Grothe et al. (Apr. 1986) "Proline transport and osmotic stress response in *Escherichia coli* K-12" *J Bacteriol.* 166(1):253-9.
Guardiola et al. (Feb. 1974) "Mutations affecting the different transport systems for isoleucine, leucine, and valine in *Escherichia coli* K-12" *J Bacteriol.* 117(2):393-405.
Guardiola et al., (Dec. 1971) "*Escherichia coli* K-12 mutants altered in the transport of branched-chain amino acids" *J Bacteriol.* 108{3):1034-44.

(56) References Cited

OTHER PUBLICATIONS

Guarner et al. (Feb. 8, 2003) "Gut flora in health and disease" *Lancet* 361 (9356):512-9.
Haney et al. (Jan. 1992) "Lrp, a leucine-responsive protein, regulates branched-chain amino acid transport genes in *Escherichia coli*" J Bacteriol. 174(1):108-15.
Hasegawa et al. (Sep. 1, 19985) "Activation of a consensus FNR-dependent promoter by DNR of *Pseudomonas aeruginosa* in response to nitrite" *FEMS Microbiol Lett.* 166(2):213-217.
He et al. (Apr. 1, 19993) "Noninvasive measurement of anatomic structure and intraluminal oxygenation in the gastrointestinal tract of living mice with spatial and spectral EPR imaging" *Proc Natl Acad Sci USA*, 96(8):4586-4591.
Heatwole et al. (Jun. 1991) The tryptophan-specific permease gene, mtr, is differentially regulated by the tryptophan and tyrosine repressors in *Escherichia coli* K-12 *J Bacteriol.* 173(11):3601-4.
Higgins (1992) "ABC transporters: from microorganisms to man" *Annu Rev Cell Biol.* 8:67-113.
Ho et al. (2014) "Phenylkentonuria: translating research into novel therapies" *Transl Pediatr.* 3:49-62.
Hoeks et al. (Jan. 2009) "Adult issues in phenylketonuria" *Neth J Med.* 67(1):2-7.
Hoeren et al. (Nov. 15, 1993) "Sequence and expression of the gene encoding the respiratory nitrous-oxide reductase from *Paracoccus denitrificans" Eur J Biochem.* 218(1):49-57.
Horsburgh et al. (Jun. 2002) "MntR modulates expression of the PerR regulon and superoxide resistance in *Staphylococcus aureus* through control of manganese uptake" *Mol Microbiol.* 44(5):1269-86.
Horsburgh et al. (May 2004) "PheP, a putative amino acid permease of *Staphylococcus aureus*, contributes to survival in vivo and during starvation" *Infect Immun.* 72(5):3073-6.
Hosseini et al. (May 2011) "Propionate as a health-promoting microbial metabolite in the human gut" *Nutr Rev.* 69(5):245-258.
Hou et al. (Oct. 2015) "Production of phenylpyruvic acid from L-phenylalanine using an L-amino acid deaminase from *Proteus mirabilis*: comparison of enzymatic and whole-cell biotransformation approaches" *Appl Microbiol Biotechnol.* 99(20):8391-8402.
Hu et al. (Nov. 1, 19985) "Membrane topology of the *Escherichia coli* gamma-aminobutyrate transporter: implications on the topography and mechanism of prokaryotic and eukaryotic transporters from the APC superfamily" *Biochem J.* 336 (Pt 1):69-76.
Huibregtse et al (2012) "Genetically Modified *Lactococcus lactis* for Delivery of Human Interleukin-10 to Dendritic Cells" *Gastroenterology Research and Practice*, vol. 2012, Article ID 639291 (7 pages).
International Patent Application No. PCT/US2016/032562, filed May 13, 2016, by Synlogic, Inc.: International Search Report and Written Opinion; mailed Aug. 22, 2016.
International Patent Application No. PCT/US2016/062369, filed Nov. 16, 2016, by Synlogic, Inc.: International Search Report and Written Opinion; mailed Mar. 10, 2017.
International Patent Application No. PCT/US2016/032565, filed May 13, 2016, by Synlogic, Inc.: International Search Report and Written Opinion; mailed Aug. 5, 2016.
Isabella et al. (Jan. 2009) "Functional analysis of NsrR, a nitric oxide-sensing Rrf2 repressor in Neisseria gonorrhoeae" *Mol Microbiol.* 71(1):227-39.
Isabella et al. (Jan. 20, 2011) "Deep sequencing-based analysis of the anaerobic stimulon in *Neisseria gonorrhoeae*" BMC Genomics, 12:51 (24 pages).
Isabella et al. (Oct. 2011) "Identification of a conserved protein involved in anaerobic unsaturated fatty acid synthesis in Neiserria gonorrhoeae: implications for facultative and obligate anaerobes that lack FabA" *Mol Microbiol.* 82(2):489-501.
Ivanovska et al. (2014) "Pediatric Drug Formulations: A Review of Challenges and Progress" *Pediatrics*, 134:361-372.
Jack et al. (Aug. 2000) "The amino acid/polyamine/organocation (APC) superfamily of transporters specific for amino acids, polyamines and organocations" *Microbiology* 146 (Pt 8):1797-814.
Jennings et al. (Jan. 1995) "Cloning and molecular analysis of the *Salmonella enterica* ansP gene, encoding an L-asparagine permease" *Microbiology* 141 (Pt 1):141-6.
Jensen et al. (2015) "Manganese Transport, Trafficking and Function in Invertebrates" Issues in Toxicology No. 22, Manganese in Health and Disease. Lucio G. Costa (Ed.). The Royal Society of Chemistry. Chapter 1, pp. 1-33(2015).
Jia, X. et al. (2000) "A new strategeutics of gene therapy for hyperphenylalaninemia rats" *National Medical Journal of China*, 2000 Issue 06, English Abstract. [online]. Retrieved from: http://en.cnki.com.cn/Article_en/CJFDTOTAL-ZHYX200006029.htm, on Jan. 30, 2017 (3 pages).
Jia, X. et al. (2000) "A new strategeutics of gene therapy for hyperphenylalaninemia rats" *National Medical Journal of China*, 2000 Issue 06. English translation, Phoenix Translations, Elgin, TX: Nov. 2015 (15 pages).
Jolkver et al. (Feb. 2009) "Identification and characterization of a bacterial transport system for the uptake of pyruvate, propionate, and acetate in Corynebacterium glutamicum" *J Bacteriol.* 191(3):940-8.
Kadaba et al. (Jul. 11, 2008) "The high-affinity *E. coli* methionine ABC transporter: structure and allosteric regulation" *Science.* 321(5886):250-3.
Kadner et al. (Aug. 1974) "Methionine transport in *Escherichia coli*: physiological and genetic evidence for two uptake systems" *J Bacteriol.* 119(2):401-9.
Kang et al. (2010) "Converting an injectable protein therapeutic into an oral form: Phenylalanine ammonia lyase for phenylketonuria" *Mol Genet Metabol.* 99:4-9.
Kehres et al. (Jun. 2002) "SilABCD Is the Alkaline Mn2+ Transporter of *Salmonella enterica* Serovar Typhimurium" *Journal of Bacteriology* 184(12):3159-3166.
Kobe et al. (Jun. 1997) "Regulation and crystallization of phosphorylated and dephosphorylated forms of truncated dimeric phenylalanine hydroxylase" *Protein Sci.* 6(6): 1352-1357.
Koo et al. (Jun. 2, 2003) "A reducing system of the superoxide sensor SoxR in *Escherichia coli*" *EMBO J* 22(11):2614-22.
Kwok et al. (Jan. 29, 1985) "Nucleotide sequence of a full-length complementary DNA clone and amino acid sequence of human phenylalanine hydroxylase" *Biochemistry*, 24(3):556-561.
Landick et al., (Jul. 15, 1985) "The complete nucleotide sequences of the *Escherichia coli* LIV-BP and LS-BP genes. Implications for the mechanism of high-affinity branched-chain amino acid transport" *J Biol Chem.* 260(14):8257-61.
Lee et al. (2011) "Cumulative Number of Cell Divisions as a Meaningful Timescale for Adaptive Laboratory Evolution of *Escherichia coli*" *PLoS ONE*, 6:e26172, http://dx.doi.org/10.1371/journal.pone.0026172 (8 pages).
Lee et al. (May 17, 2012) "Systems metabolic engineering of microorganisms for natural and non-natural chemicals" *Nat Chem Biol.* 8(6):536-46.
Leonard, "Disorders of the urea cycle and related enzymes" in *Inborn Metabolic Diseases*, 4th ed. Heidelberg: Springer Medizin Verlag, 2006; pp. 263-272.
Levanon et al. (2005) "Effect of oxygen on the *Escherichia coli* ArcA and FNR regulation systems and metabolic responses" *Biotech. Bioeng.* pp. 556-564.
Li et al. (Apr. 13, 2001) "Monomeric state and ligand binding of recombinant GABA transporter from *Escherichia coli*" *FEBS Lett.* 494(3):165-9.
LIU (Jul. 1997) Beijing Red Cross Chaoyang Hospital attached to Capital Medical College, pp. 1-4.
Liu et al. (2002) "Study on a Novel Strategy to Treatment of Phenylketonuria" *Art Cells, Blood Subs, and Immob Biotech.* 30(4):243-257.
Longo et al. (Jul. 5, 2014) "Phase 1 Trial of Subcutaneous rAvPAL-PEG in Subjects with Phenylketonuria" *Lancet*, 384(9937):37-44. HHS Public Access Author Manuscript; available in PMC Jul. 5, 2015 (18 pages).
Lopez et al. (Dec. 2015) "Synthetic Auxotrophs with Ligand-Dependent Essential Genes for a BL21(DE3) Biosafety Strain" *ACS Synthetic Biology*, 4(12):1279-1286.

(56) References Cited

OTHER PUBLICATIONS

Ma et al. (2014) Oral Administration of Recombinant Lastococcus Lactis Expressing HSP65 and Tandemly Repeated P277 Reduces the Incidence of Type 1 Diabetes in Non-Obese Diabetic Mice PLoS One 9:105701.
MacDonald et al. (2007) "A modern view of phenylalanine ammonia lyase" *Biochem Cell Biol.* 85(3):273-282.
MacLeod et al. (Jun. 2010) "Nutritional Management of Phenylketonuria" *Ann Nestle Eng.* 68(2):58-69.
Marbach et al. (2012) "lac operon Indcution in *Escherichia coli*: Systematic Comparison of IPTG and TMG induction and influence of Transacetylase LacA" *Journal of Biotechnology*, 157:82-88.
Matano et al. (Jun. 2014) "Engineering of Corynebacterium glutamicum for growth and L-lysine and lycopene production from N-acelyl-glucosamine" *Appl Microbiol Biotechnol.* 98(12):5633-43.
McAllister et al. (Aug. 2004) "Molecular analysis of the psa permease complex of *Streptococcus* pneumoniae" *Mol Microbiol.* 53(3):889-901.
McEwen et al. (Mar. 2013) "Engineering Synechococcus elongatus PCC 7942 for continuous growth under diurnal conditions" *Appl Environ Microbiol.* 79(5):1668-75.
Meadow et al. (1959) "Biosynthesis of diaminopimelic acid and lysine in *Escherichia coli*" *Biochem J.* 72(3):396-400.
Mengesha, A. et al. (2006) "Development of a flexible and potent hypoxia-inducible promoter for tumor-targeted gene expression in attenuated *Salmonella*" *Cancer Biology & Therapy*, 5:9, 1120-1128.
Menzel et al. (Sep. 25, 1981) "Purification of the putA gene product. A bifunctional membrane-bound protein from *Salmonella* typhimurium responsible for the two-step oxidation of proline to glutamate" *J Biol Chem.* 256(18):9755-61.
Merlin et al. (Oct. 2002) "The *Escherichia coli* metD locus encodes an ABC transporter which includes Abe (MetN), YaeE (Metl), and YaeC (MetQ)" *J Bacteriol.* 184(19):5513-7.
Mironov et al. (Jul. 15, 1999) "Computer analysis of transcription regulatory patterns in completely sequenced bacterial genomes" *Nucleic Acids Res.* 27(14):2981-9.
Moffitt et al. (Jan. 30, 2007) "Discovery of two cyanobacterial phenylalanine ammonia lyases: kinetic and structural characterization" *Biochemistry*, 46(4):1004-1012.
Moore et al. (Nov. 3, 2006) "Regulation of FNR dimerization by subunit charge repulsion" *J Biol Chem.* 281(44):33268-33275.
Nazos et al. (Sep. 1985) "Identification of livG, a membrane-associated component of the branched-chain amino acid transport in *Escherichia coli*" *J Bacteriol.* 163(3):1196-202.
Nazos et al. (May 1986) Cloning and characterization of livH, the structural gene encoding a component of the leucine transport system in *Escherichia coli. J Bacteriol.* 166(2):565-73.
Nji et al. (Oct. 2014) Cloning, expression, purification, crystallization and preliminary X-ray diffraction of a lysine-specific permease from Pseudomonas aeruginosa *Acta Crystallogr F Struct Biol Commun.* 70(Pt 10):1362-7.
Norholm et al. (Aug. 2001) "Specificity and topology of the *Escherichia coli* xanthosine permease, a representative of the NHS subfamily of the major facilitator superfamily" *J Bacteriol.* 183(16):4900-4.
Nougayrede et al. (Aug. 11, 2006) "*Escherichia coli* induces DNA double-strand breaks in eukaryotic cells" *Science*, 313(5788):848-851.
Ogawa et al. (Dec. 1997) "Isolation and characterization of an *Escherichia coli* mutant lacking the major serine transporter, and cloning of a serine transporter gene" *J Biochem.* 122(6):1241-5.
Ogawa et al. (Dec. 1998) "Cloning and expression of the gene for the Na+-coupled serine transporter from *Escherichia coli* and characteristics of the transporter" *J Bacteriol.* 180(24):6749-52.
Oh et al. (Oct. 2, 19941) "Structural basis for multiple ligand specificity of the periplasmic lysine-, arginine-, ornithine-binding protein" *J Biol Chem.* 269(42):26323-30.
Ohnishi et al. (Aug. 1988) "Cloning and nucleotide sequence of the brnQ gene, the structural gene for a membrane-associated component of the LIV-II transport system for branched-chain amino acids in *Salmonella* typhimurium" *Jpn J Genet.* 63(4 ):343-57.
Olier et al. (Nov.-Dec. 2012) "Genotoxicity of *Escherichia coli* Nissle 1917 strain cannot be dissociated from its probiotic activity" *Gut Microbes*, 3(6):501-509.
Ortuno-Olea et al. (Aug. 15, 2000) "The L-asparagine operon of Rhizobium elli contains a gene encoding an atypical asparaginase" *FEMS Microbiol Lett.* 189(2):177-82.
Ostrovsky De Spicer et al. (May 1, 1993) "PulA protein, a membrane-associated flavin dehydrogenase, acts as a redox—: lependent transcriptional regulator" *Proc Natl Acad Sci U S A.* 90(9):4295-8.
Oxender et al. (Mar. 1980) "Structural and functional analysis of cloned DNA containing genes responsible for branched-chain amino acid transport in *Escherichia coli*" *Proc Natl Acad Sci US A.* 77(3):1412-6.
Pelmont et al. (1972) "L-aminoacide oxydases des enveloppes de Proteus mirabilis: propriétés générales (L-amino acid oxidases of *Proteus mirabilis*: general properties)" *Biochimie* 54(10):1359-1374 (French; English summary on p. 1359).
Pi et al. (Jun. 1991) "Cloning and sequencing of the *pheP* gene, which encodes the phenylalanine-specific transport system of *Escherichia coli*" *J Bacteriol.* 173(12):3622-3629.
Pi et al. (May 1996) "Topology of the phenylalanine-specific permease of *Escherichia coli*" *J Bacteriol.* 178(9):2650-2655.
Pi et al. (Nov. 1998) "Functional consequences of changing proline residues in the phenylalanine-specific permease of *Escherichia coli*" *J Bacteriol.* 180(21):5515-5519.
Porcheron et al. (Dec. 5, 2013) "Iron, copper, zinc, and manganese transport and regulation in pathogenic Enterobacteria: correlations between strains, site of infection and the relative importance of the different metal transport systems for virulence" *Front Cell Infect Microbiol.* 3:90.
Pugsley (Mar. 1993) "The complete general secretory pathway in gram-negative bacteria" *Microbiol Rev.* 57(1):50-108.
Purcell et al. (2013) "Towards a whole-cell modeling approach for synthetic biology" *Chaos*, 23(2):025112 (8 pages).
Quay et al. (Mar. 1977) "Role of transport systems in amino acid metabolism: leucine toxicity and the branched-chain amino acid transport systems" *J Bacteriol.* 129(3):1257-65.
Que et al. (Mar. 2000)"Manganese homeostasis in Bacillus subtilis is regulated by MntR, a bifunctional regulator related to the diphtheria toxin repressor family of proteins" *Mol Microbiol.* 35(6):1454-68.
Rahmanian et al. (Dec. 1973) "Multiplicity of leucine transport systems in *Escherichia coli* K-12" *J Bacteriol.* 116(3):1258-66.
Ray et al. (Nov. 1, 19975) "The effects of mutation of the anr gene on the aerobic respiratory chain of *Pseudomonas aeruginosa*" *FEMS Microbiol Lett.* 156(2):227-232.
Rees et al. (Mar. 2009) "ABC transporters: The power to change" *Nat Rev Mol Cell Biol.* 10(3):218-227.
Reeves et al. (Apr. 2015) "Engineering *E. coli* into a protein delivery system for mammalian cells" *ACS Synth Biol.* Just Accepted Manuscript, DOI: 10.1021/acssynbio.5b00002 [online]. Retrieved from: http://pubs.acs.org, on Apr. 20, 2015 (26 pages). Final publication in vol. 5, pp. 644-654.
REFSEQ Database Accession No. NP_415108.1 (Dec. 16, 2014) "phenylalanine transporter [*Escherichia coli* str. K-12 substr. MG1655]" [online]. National Center for Biotechnology Information (NCBI), U.S. National Library of Medicine; http://www.ncbi.nlm.nih.gov/protein/NP_415108 (3 pages).
REFSEQ Database Accession No. WP_011146484.1 (May 24, 2013) "histidine ammonia-lyase [Photorhabdus luminescens]" [online]. National Center for Biotechnology Information (NCBI), U.S. National Library of Medicine; http://www.ncbi.nlm.nih.gov/protein/WP_011146484 (1 page).
Reister et al. (Oct. 10, 2014) "Complete genome sequence of the Gram-negative probiotic *Escherichia coli* strain Nissle 1917" *J Biotechnol.* 187:106-107.
Rembacken et al. (Aug. 2, 19991) "Non-pathogenic *Escherichia coli* versus mesalazine for the treatment of ulcerative colitis: a randomised trial" *Lancet*, 354(9179):635-639.
Rigel et al. (2008) "A new twist on an old pathway—accessory secretion systems" *Mol Microbiol.* 69(2):291-302.

(56) References Cited

OTHER PUBLICATIONS

Rodionov et al. (Dec. 1, 2003) "Regulation of lysine biosynthesis and transport genes in bacteria: yet another RNA riboswitch?" *Nucleic Acids Res.* 31(23):6748-57.
Rosen (Jun. 10, 1971) "Basic amino acid transport in *Escherichia coli*" *J Biol Chem.* 246(11 ):3653-62.
Ryan et al. (May 2007) "The uncoupled chloride conductance of a bacterial glutamate transporter homolog" *Nat Struct Mol Biol.* 14(5):365-71.
Ryan et al. (Mar. 2009) "Bacterial delivery of a novel cytolysin to hypoxic areas of solid tumors" *Gene Ther.* 16(3):329-39.
Saier Jr. (2006) "Protein Secretion and Membrane Insertion Systems in Gram-Negative Bacteria" *J Membrane Biol.* 214:75-90.
Saier Jr., M.H. (2006) "Protein Secretion Systems in Gram-Negative Bacteria. Gram-negative bacteria possess many protein secretion-membrane insertion systems that apparently evolved independently" *Microbe*, 1(9):414-419.
Salmon et al. (Aug. 8, 2003) "Global gene expression profiling in *Escherichia coli* K12. The effects of oxygen availability and FNR" *J Biol Chem.* 278(32):29837-29855.
Sarkissian et al. (Mar. 1999) "A different approach to treatment of phenylketonuria: Phenylalanine degradation with recombinant phenylalanine ammonia lyase" *Proc Natl Acad Sci USA*, 96(5):2339-2344.
Sarkissian et al. (Jun. 2007) "Quantitation of phenylalanine and its trans-cinnamic, benzoic and hippuric acid metabolites in biological fluids in a single GC-MS analysis" *J Mass Spectrom.* 42(6):811-817.
Sarkissian et al. (Nov. 2011) "Evaluation of orally administered PEGylated phenylalanine ammonia lyase in mice for the treatment of Phenylketonuria" *Mol Genet Metab.* 104(3): 249-254. NIH Public Access Author Manuscript; available in PMC Nov. 1, 2012 (15 pages).
Sat et al. (Mar. 2003) "The *Escherichia coli* mazEF suicide module mediates thymineless death" *J Bacteriol.* 185(6):1803-1807.
Sawers (Jun. 1991) "Identification and molecular characterization of a transcriptional regulator from Pseudomonas aeruginosa PAO1 exhibiting structural and functional similarity to the FNR protein of *Escherichia coli*" *Mol Microbiol*, 5(6):1469-1481.
Schultz (Jul. 2008) "Clinical use of *E. coli* Nissle 1917 in inflammatory bowel disease" *Inflamm Bowel Dis*, 14(7):1012-1018.
Seep-Feldhaus et al. (Dec. 1991) "Molecular analysis of the Corynebacterium glutamicum lysl gene involved in lysine uptake" Mol Microbiol. 5(12):2995-3005.
Shao et al. (Jun. 15, 1994) "Sequencing and characterization of the sdaC gene and identification of the sdaCB operon in *Escherichia coli* K12" *Eur J Biochem.* 222(3):901-7.
Sheehan et al.(Mar. 2006) "Heterologous expression of Bell, a belaine uptake system, enhances the stress tolerance of laclobacillus salivarius UCC118" *Appl Environ Microbiol.* 72(3):2170-7.
Silhavy et al. (2010) "The bacterial cell envelope" *Cold Spring Harb Perspect Biol.* 2, a000414 (17 pages).
Sleator et al. (2009) "Rational Design of Improved Pharmabiotics" *Journal of Biomedicine and Biotechnology*, vol. 9 (7pages).
Slotboom et al. (Jun. 1999) "Structural features of the glutamate transporter family" *Microbiol Mol Biol Rev.* 63(2):293-307.
Sonnenborn et al. (2009) "The non-pathogenic *Escherichia coli* strain Nissle 1917—features of a versatile probiotic" *Microbial Ecology in Health and Disease*, 21:122-158.
Stanley et al. (Oct. 2003) "Acute infection and macrophage subversion by Mycobacterium tuberculosis require a specialized secretion system" *PNAS*, 100(22):13001-13006.
Steele (Jun. 1986) "Blood-brain barrier transport of the alpha-keto acid analogs of amino acids" *Fed Proc.* 45(7):2060-2064.
Steffes et al. (May 1992) "The lysP gene encodes the lysine-specific permease" *J Bacteriol.* 174(10):3242-9.
Steidler et al (Jul. 1, 2003) "Biological containment of genetically modified Lactococcus lactis for intestinal delivery of human interleukin 10" *Nature Biotechnology*, 21(7)785-789.
Strauch et al (Feb. 1985) "Oxygen Regulation in *Salmonella* typhimurium" *J. Bacteriol.* 161(2):673-680.
Takahashi et al. (Sep. 2015) "Multiple Functions of Glutamate Uptake via Meningococcal GIIT-GltM L-Glutamate ABC Transporter in Neisseria meningitidis Internalization into Human Brain Microvascular Endothelial Cells" Infect Immun. 83(9):3555-67.
Tolner et al. (Oct. 1992) "Characterization and functional expression in *Escherichia coli* of the sodium/proton/glutamate symport proteins of Bacillus stearothermophilus and Bacillus caldotenax" *Mol Microbiol.* 6(19):2845-56.
Trip et al. (Jan. 2013;) "Cloning, expression, and functional characterization of secondary amino acid transporters of Lactococcus lactis" *J Bacteriol.* 195(2):340-50.
Trotschel et al. (Jun. 2005) "Characterization of methionine export in Corynebacterium glutamicum" *J Bacteriol.* 187 (11):3786-94.
Trunk et al. (Jun. 2010) "Anaerobic adaptation in *Pseudomonas aeruginosa*: definition of the Anr and Dnr regulons" *Environ Microbiol.* 12(6):1719-1733.
Ukena et al. (Dec. 12, 2007) "Probiotic *Escherichia coli* Nissle 1917 inhibits leaky gut by enhancing mucosal integrity" *PLoS One*, 2(12):e1308. [online] DOI: 10.1371/journal.pone.0001308 (11 pages).
Unden et al (2002) "Control of FNR Function of *Escherichia coli* by $O_2$ and Reducing Conditions" *J. Mol. Microbiol. Biotechnol.* 4(3):263-268.
Unden et al. (Jul. 4, 1997) "Alternative respiratory pathways of *Escherichia coli*: energetics and transcriptional regulation in response to electron acceptors" *Biochim Biophys Acta*, 1320(3):217-234.
UNIPROTKB/SWISS-PROT Database Accession No. Q3M5Z3.1 (Nov. 11, 2015) "RecName: Full=Phenylalanine ammonia-lyase" National Center for Biotechnology Information (NCBI), U.S. National Library of Medicine, http://www.ncbi.nlm.nih.gov/protein/Q3M5Z3 (7 pages).
Vaziri et al. (Mar. 2013) Use of molecular modelling to probe the mechanism of the nucleoside transporter NupG*Mol Membr Biol.* 30(2):114-28.
Vockley et al. (Feb. 2014) "Phenylalanine hydroxylase deficiency: diagnosis and management guideline" *Genet Med.* 16(2):188-200.
Wanner et al. (Jan. 1995) "The phenylalanine ammonia-lyase gene family in *Arabidopsis thaliana*" *Plant Mol Biol.* 27(2):327-338.
Weisser et al. (Jun. 1995) "Functional expression of the glucose transporter of Zymomonas mobilis leads to restoration of glucose and fructose uptake in *Escherichia coli* mutants and provides evidence for its facilitator action" *J Bacteriol.* 177(11):3351-4.
Widhalm et al. "Identification of a Plastidial Phenylalanine Exporter the Influences Flux Distribution Through the Phenylalanine Biosynthetic Network" *Nature Comomunications* pp. 1-11.
Williams et al. (Aug. 2005) "The gene stiA encodes a phenylalanine ammonia-lyase that is involved in the production of a stilbene antibiotic in *Photorhabdus luminescens* TT01" *Microbiology*, 151(Pt 8): 2543-2550.
Willis et al. (Sep. 1975) "L-asparagine uptake in *Escherichia coli*" *J Bacteriol.* 123(3):937-45.
Winteler et al. (Mar. 1996) "The homologous regulators ANR of *Pseudomonas aeruginosa* and FNR of *Escherichia coli* have overlapping but distinct specificities for anaerobically inducible promoters" *Microbiology*, 142(Pt 3):685-693.
Wissenbach et al. (Jun. 1993) "Physical map location of the new artPIQMJ genes of *Escherichia coli*, encoding a periplasmic arginine transport system" J Bacteriol. 175(11):3687-8.
Wissenbach et al. (Aug. 1995) "A third periplasmic transport system for L-arginine in *Escherichia coli*: molecular characterization of the artPIQMJ genes, arginine binding and transport" *Mol Microbiol.* 17(4):675-86.
Wolken et al. (Mar. 2006) "The mechanism of the tyrosine transporter TyrP supports a proton motive tyrosine decarboxylation pathway in Lactobacillus brevis" *J Bacteriol.* 188(6):2198-206.
Wood (Jun. 2, 19755) "Leucine transport in *Escherichia coli*. The resolution of multiple transport systems and their coupling to metabolic energy" *J Biol Chem.* 250(12):4477-85.
Wright et al. (Mar. 20, 2015) "GeneGuard: A modular plasmid system designed for biosafety" *ACS Synth Biol.* 4(3):307-316.
Wu et al. (Oct. 7, 2015) "Direct regulation of the natural competence regulator gene tfoX by cyclic AMP (cAMP) and cAMP receptor protein in *Vibrios*" Sci Rep. 5:14921 (15 pages).

(56) References Cited

OTHER PUBLICATIONS

Xiang et al. (Jun. 2005) "Biochemical characterization of a prokaryotic phenylalanine ammonia lyase" *J Bacteriol.* 187(12):4286-4289.
Xingyuan et al. (1999) "A New Strategeutics of Gene Therapy for Hyperphenylalaninemia Rats" Beijing Red-Cross Chaoyang Hospital, Capital University of Medical Sciences Beijing, 100020: China.
Yamato et al. (Apr. 1979) "Genetic and biochemical studies of transport systems for branched-chain amino acids in *Escherichia coli*" J Bacteriol. 138(1):24-32.
Yamato et al. (Oct. 1980) "Genetic and biochemical studies of transport systems for branched-chain amino acids in *Escherichia coli* K-12: isolation and properties of mutants defective in leucine-repressible transport activities" *J Bacteriol.* 144(1):36-44.
Yanofsky et al. (Oct. 1991) "Physiological studies of tryptophan transport and tryptophanase operon induction in *Escherichia coli*" *J Bacteriol.*. 173(19):6009-17.
Zaprasis et al. (Jan. 2015) "Uptake of amino acids and their metabolic conversion into the compatible solute proline confers osmoprotection to Bacillus subtilis" *Appl Environ Microbiol.* 81(1):250-9.
Zhang et al. (2009) "DEG 5.0, a database of essential genes in both prokaryotes and eukaryotes" *Nucl Acids Res.* 37(suppl. 1):D455-D458.
Zhou et al. (Apr. 1999) "*Salmonella* typhimurium encodes a putative iron transport system within the centisome 63 pathogenicity island" *Infect Immun.* 67(4):1974-81.
U.S. Appl. No. 15/154,934, filed May 13, 2016, U.S. Pat. No. 10,610,546, Issued.
U.S. Appl. No. 15/260,211, filed Sep. 8, 2016, U.S. Pat. No. 9,943,555, Issued.
U.S. Appl. No. 15/301,324, filed Sep. 30, 2016, U.S. Pat. No. 10,195,234, Issued.
U.S. Appl. No. 15/775,936, filed May 14, 2018, U.S. Pat. No. 11,618,894, Issued.
U.S. Appl. No. 18/068,004, filed Dec. 19, 2022, 2024-0076645, Published.
U.S. Appl. No. 16/621,792, filed Dec. 12, 2019, U.S. Pat. No. 11,879,123, Issued.
U.S. Appl. No. 18/512,389, filed Nov. 17, 2023, 2024-0368531, Published.
U.S. Appl. No. 17/832,487, filed Jun. 3, 2022, U.S. Pat. No. 11,766,463, Issued.
U.S. Appl. No. 18/446,970, filed Aug. 9, 2023, U.S. Pat. No. 12,171,790, Issued.
U.S. Appl. No. 18/941,023, filed Nov. 8, 2024, Pending.
U.S. Appl. No. 18/270,102, filed Jun. 28, 2023, 2024-0316121, Published.
Winteler et al., The homologous regulators ANR of Pseudomonas aeruginosa and FNR of *Escherichia coli* have overlapping but distinct specificities for anaerobically inducible promoters. Microbiology. Mar. 1996; 142 ( Pt 3):685-93.
Zhang et al., Construction of Prophage CP-933Y Deletion Mutant Strain of Enter-hemorrhagic *E.coli* O157:H7. Lett. Biotech. Nov. 2016;27(6):804-7.
Zhang et al., DEG 5.0, a database of essential genes in both prokaryotes and eukaryotes. Nucleic Acids Res. Jan. 2009;37(Database issue):D455-8.
Zimmerman et al., Engineering and Application of LOV2-Based Photoswitches. Methods Enzymol. 2016;580:169-90.
European Office Action for Application No. 16728448.8, dated Dec. 20, 2020, 9 pages.
European Office Action for Application No. 22167588.7, dated Oct. 14, 2022, 19 pages.
International Search Report and Written Opinion for Application No. PCT/US2016/032565, dated Aug. 5, 2016.
International Search Report and Written Opinion for Application No. PCT/US2018/038840, dated Nov. 21, 2018, 17 pages.
International Search Report and Written Opinion for Application No. PCT/US2021/063976, dated Apr. 21, 2022, 11 pages.
International Search Report and Written Opinion for Application No. PCT/US2023/077060, dated Feb. 28, 2024, 12 pages.
U.S. Appl. No. 62/183,935, filed Jun. 24, 2015, by Kotula et al.
U.S. Appl. No. 62/184,811, filed Jun. 25, 2015 by Falb et al.
U.S. Appl. No. 62/263,329, filed Dec. 4, 2015, by Kotula et al.
Albiniak et al., High-level secretion of a recombinant protein to the culture medium with a Bacillus subtilis twin-arginine translocation system in *Escherichia coli*. FEBS J. Aug. 2013;280(16):3810-21.
Andersen et al., Uracil uptake in *Escherichia coli* K-12: isolation of uraA mutants and cloning of the gene. J Bacteriol. Apr. 1995;177(8):2008-13.
Anderson et al., Environmentally controlled invasion of cancer cells by engineered bacteria. J Mol Biol. Jan. 27, 2006;355(4):619-27.
Arai et al., Expression of the nir and nor genes for denitrification of Pseudomonas aeruginosa requires a novel CRP/FNR-related transcriptional regulator, DNR, in addition to ANR. FEBS Lett. Aug. 28, 1995;371(1):73-6.
Archer et al., Engineered *E. coli* that detect and respond to gut inflammation through nitric oxide sensing. ACS Synth Biol. Oct. 19, 2012;1(10):451-7.
Argos et al., A possible homology between immunodeficiency virus p24 core protein and picornaviral VP2 coat protein: prediction of HIV p24 antigenic sites. EMBO J. Mar. 1989;8(3):779-85.
Arthur et al., Intestinal inflammation targets cancer-inducing activity of the microbiota. Science. Oct. 5, 2012;338(6103):120-3.
Bikandi et al., In silico analysis of complete bacterial genomes: PCR, AFLP-PCR and endonuclease restriction. Bioinformatics. Mar. 22, 2004;20(5):798-9.
Bobay et al., Pervasive domestication of defective prophages by bacteria. Proc Natl Acad Sci U S A. Aug. 19, 2014;111(33):12127-32.
Boysen et al., Translational regulation of gene expression by an anaerobically induced small non-coding RNA in *Escherichia coli*. J Biol Chem. Apr. 2, 2010;285(14):10690-702.
Brophy et al., Principles of genetic circuit design. Nat Methods. May 2014;11(5):508-20.
Clinicaltrials, NCT04984525, Safety and Tolerability of SYNB1934 in Healthy Adult Volunteers. 11 pages, May 18, 2022.
Cosgriff et al., A study of AroP-PheP chimeric proteins and identification of a residue involved in tryptophan transport. J Bacteriol. Apr. 2000;182(8):2207-17.
De Ruyter et al., Controlled gene expression systems for Lactococcus lactis with the food-grade inducer nisin. Appl Environ Microbiol. Oct. 1996;62(10):3662-7.
GenBank. *Escherichia coli* Nissle 1917, complete genome. GenBank No. CP007799.1. Jun. 25, 2015.
Hwang et al., Engineered probiotic *Escherichia coli* can eliminate and prevent Pseudomonas aeruginosa gut infection in animal models. Nat Commun. Apr. 11, 2017;8:15028.
Isabella et al., Development of a synthetic live bacterial therapeutic for the human metabolic disease phenylketonuria. Nat Biotechnol. Oct. 2018;36(9):857-864.
Jia et al., A new strategy of gene therapy for hyperphenylalaninemia rats. Zhonghua Yi Xue Za Zhi. Jun. 2000;80(6):464-7.
Kovacs et al., Expression and properties of the highly alkalophilic phenylalanine ammonia-lyase of thermophilic Rubrobacter xylanophilus. PLoS One. Jan. 27, 2014;9(1):e85943, 10 pages.
Kyndt et al., Characterization of a bacterial tyrosine ammonia lyase, a biosynthetic enzyme for the photoactive yellow protein. FEBS Lett. Feb. 13, 2002;512(1-3):240-4.
Lam et al., Retention of phenylalanine ammonia-lyase activity in wheat seedlings during storage and in vitro digestion. J Agric Food Chem. Dec. 10, 2008;56(23):11407-12.
Lamas et al., CARD9 impacts colitis by altering gut microbiota metabolism of tryptophan into aryl hydrocarbon receptor ligands. Nat Med. Jun. 2016;22(6):598-605.
Longo et al., Single-dose, subcutaneous recombinant phenylalanine ammonia lyase conjugated with polyethylene glycol in adult patients with phenylketonuria: an open-label, multicentre, phase 1 dose-escalation trial. Lancet. Jul. 5, 2014;384(9937):37-44.

(56) References Cited

OTHER PUBLICATIONS

McWhorter et al., Dietary management outcomes during SYnPheny-1, a Phase 2 clinical trial of a live biotherapeutic, SYNB1618, for the management of phenylketonuria. Molecular Genetics and Metabolism. May 2022;136S1:S23-S24.
Moore et al., Regulation of FNR dimerization by subunit charge repulsion. J Biol Chem. Nov. 3, 2006;281(44):33268-75.
Ou et al., Genetic engineering of probiotic *Escherichia coli* Nissle 1917 for clinical application. Appl Microbiol Biotechnol. Oct. 2016;100(20):8693-9.
Pi et al., Cloning and sequencing of the pheP gene, which encodes the phenylalanine-specific transport system of *Escherichia coli*. J Bacteriol. Jun. 1991;173(12):3622-9.
Pi et al., Functional consequences of changing proline residues in the phenylalanine-specific permease of *Escherichia coli*. J Bacteriol. Nov. 1998;180(21):5515-9.
Pi et al., Topology of the phenylalanine-specific permease of *Escherichia coli*. J Bacteriol. May 1996;178(9):2650-5.
Purcell et al., Rule-based design of synthetic transcription factors in eukaryotes. ACS Synth Biol. Oct. 17, 2014;3(10):737-44.
Purcell et al., Towards a whole-cell modeling approach for synthetic biology. Chaos. Jun. 2013;23(2):025112, 8 pages.
Puurunen et al., Safety and pharmacodynamics of an engineered *E. coli* Nissle for the treatment of phenylketonuria: a first-in-human phase 1/2a study. Nat Metab. Aug. 2021;3(8):1125-1132.
Rajagopal et al., Use of inducible feedback-resistant N-acetylglutamate synthetase (argA) genes for enhanced arginine biosynthesis by genetically engineered *Escherichia coli* K-12 strains. Appl Environ Microbiol. May 1998;64(5):1805-11.
Ray et al., The effects of mutation of the anr gene on the aerobic respiratory chain of Pseudomonas aeruginosa. FEMS Microbiol Lett. Nov. 15, 1997;156(2):227-32.
Reeves et al., Engineering *Escherichia coli* into a protein delivery system for mammalian cells. ACS Synth Biol. May 15, 2015;4(5):644-54.
Reichert, Antibodies to watch in 2016. MAbs. 2016;8(2):197-204.
Reister et al., Complete genome sequence of the gram-negative probiotic *Escherichia coli* strain Nissle 1917. J Biotechnol. Oct. 10, 2014;187:106-7.
Rembacken et al., Non-pathogenic *Escherichia coli* versus mesalazine for the treatment of ulcerative colitis: a randomised trial. Lancet. Aug. 21, 1999;354(9179):635-9.
Rigel et al., A new twist on an old pathway—accessory Sec [corrected] systems. Mol Microbiol. Jul. 2008;69 (2):291-302.
Roquet et al., Digital and analog gene circuits for biotechnology. Biotechnol J. May 2014;9(5):597-608.
Shah et al., Stabilization of phenylalanine ammonia lyase against organic solvent mediated deactivation. Int J Pharm. Feb. 22, 2007;331(1):107-15.
Siuti et al., Engineering genetic circuits that compute and remember. Nat Protoc. 2014;9(6):1292-300.
Song et al., Molecular cloning, expression and characterization of a phenylalanine ammonia-lyase gene (SmPAL1) from Salvia miltiorrhiza. Mol Biol Rep. May 2009;36(5):939-52.
Sonnenborn et al., The non-pathogenic *Escherichia coli* strain Nissle 1917—features of a versatile probiotic. Microbial Ecology in Health and Disease. 2009;21(3-4):122-158.
Stanley et al., Acute infection and macrophage subversion by Mycobacterium tuberculosis require a specialized secretion system. Proc Natl Acad Sci U S A. Oct. 28, 2003;100(22):13001-6.
Sun et al., Genomic peculiarity of coding sequences and metabolic potential of probiotic *Escherichia coli* strain Nissle 1917 inferred from raw genome data. J Biotechnol. May 4, 2005;117(2):147-61.
Trunk et al., Anaerobic adaptation in Pseudomonas aeruginosa: definition of the Anr and Dnr regulons. Environ Microbiol. Jun. 2010;12(6):1719-33.
Van Der Meer et al., Where microbiology meets microengineering: design and applications of reporter bacteria. Nat Rev Microbiol. Jul. 2010;8(7):511-22.
Vockley et al., Efficacy and safety of a synthetic biotic for treatment of phenylketonuria: a phase 2 clinical trial. Nat Metab. Oct. 2023;5(10):1685-1690.
Wang et al., Structural and biochemical characterization of the therapeutic Anabaena variabilis phenylalanine ammonia lyase. J Mol Biol. Jul. 18, 2008;380(4):623-35.

* cited by examiner

PAL = Phenylalanine Ammonia Lyase
PheP =High Affinity Phenylalanine Transporter

L-Phe
L-Tyr

L-Phe

*trans*-cinnamic acid

Phenylalanine

Phenylpyruvate

- PAL = phenylalanine ammonia lyase from an Enterobacteriaciae species
- PheP = high affinity phenylalanine transporter

- In vitro activity of cells: 8umol/hr/1e9 cells

P-values: ANOVA with Tukey pairwise comparison
* p<0.05,  p<0.01, * p<0.001, **** p<0.0001

P-values: ANOVA with Tukey pairwise comparison
* p<0.05,  p<0.01, * p<0.001, **** p<0.0001

Phenylalanine

Phenylpyruvic acid

Phenyllactic acid

Tyrosine

Phenylalanine

*trans*-Cinnamic acid

Hippuric acid

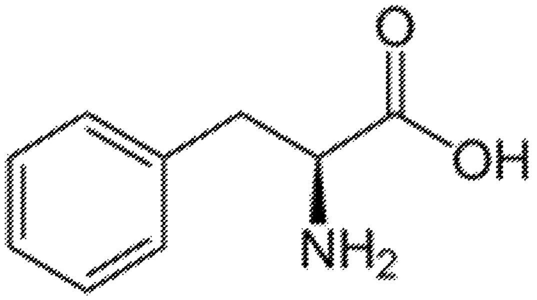
phenylalanine
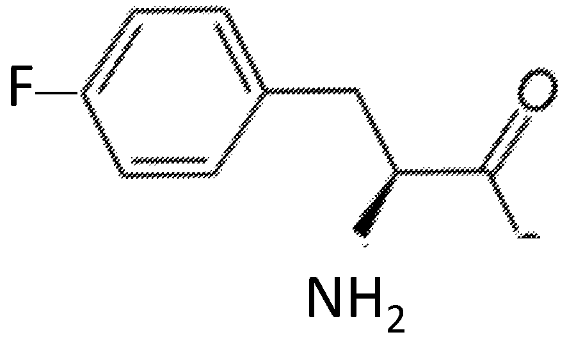
p-fluoro-DL-phenylalanine
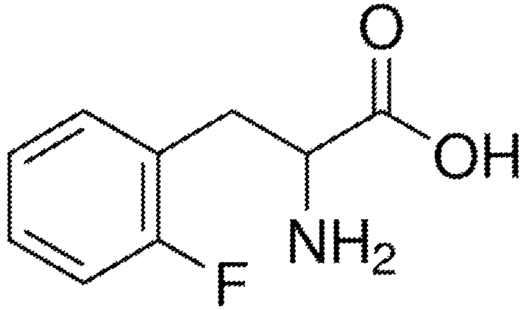
o-fluoro-DL-phenylalanine
Fig. 35

Brightness of constitutive RFP integrated in three locations:

1. AraB/C
2. MalE/K
3. MetY/ArgG
4. Nissle (non-fluorescent)

Synthetic Biotics: Single Product; Multiple MoAs

MALPT-kn-KIKO with fnrS-Int5 unflipped PAL3 rrnBUP (5351 ..9091)

3741 bp

MALPT-kn-KIKO with fnrS-Int5 flipped T7 polymerase rrnBUP (5351 ..9091)

4794 bp

| Wild-type clbA (SEQ ID NO: 64) |
|---|
| caaatatcacataatcttaacatatcaataaacacagtaaagtttcatgtgaaaaacatcaaaca<br>taaaatacaagctcggaatacgaatcacgctatacacattgctaacaggaatgagattatctaaa<br>tgaggattgatatattaattggacatactagtttttttcatcaaaccagtagagataacttcctt<br>cactatctcaatgaggaagaaataaaacgctatgatcagtttcattttgtgagtgataaagaact<br>ctatatttaagccgtatcctgctcaaaacagcactaaaaagatatcaacctgatgtctcattac<br>aatcatggcaatttagtacgtgcaaatatggcaaaccatttatagtttttcctcagttggcaaaa<br>aagattttttttaacctttcccatactatagatacagtagccgttgctattagttctcactgcga<br>gcttggtgtcgatattgaacaaataagagatttagacaactcttatctgaatatcagtcagcatt<br>tttttactccacaggaagctactaacatagtttcacttcctcgttatgaaggtcaattactttt<br>tggaaaatgtggacgctcaaagaagcttacatcaaatatcgaggtaaaggcctatctttaggact<br>ggattgtattgaatttcatttaacaaataaaaaactaacttcaaaatatagaggttcacctgttt<br>atttctctcaatggaaaatatgtaactcatttctcgcattagcctctccactcatcacccctaaa<br>ataactattgagctatttcctatgcagtcccaactttatcaccacgactatcagctaattcattc<br>gtcaaatgggcagaattgaatcgccacggataatctagacacttctgagccgtcgataatattga<br>ttttcatattccgtcggtggtgtaagtatcccgcataatcgtgccattcacatttag |
| **clbA knockout (SEQ ID NO: 65)** |
| ggatgggggaaacatggataagttcaaagaaaaaaacccgttatctctgcgtgaaagacaagta<br>ttgcgcatgctggcacaaggtgatgagtactctcaaatatcacataatcttaacatatcaataaa<br>cacagtaaagtttcatgtgaaaaacatcaaacataaaatacaagctcggaatacgaatcacgcta<br>tacacattgctaacaggaatgagattatctaaatgaggattgaTGTGTAGGCTGGAGCTGCTTCG<br>AAGTTCCTATACTTTCTAGAGAATAGGAACTTCGGAATAGGAACTTCGGAATAGGAACTAAGGAG<br>GATATTCATATGtcgtcaaatgggcagaattgaatcgccacggataatctagacacttctgagcc<br>gtcgataatattgattttcatattccgtcggtgg |

Fig. 49

SEQUENCE LISTING

<160> NUMBER OF SEQ ID NOS: 66

<210> SEQ ID NO 1
<211> LENGTH: 567
<212> TYPE: PRT
<213> ORGANISM: Anabaena variabilis

<400> SEQUENCE: 1

Met Lys Thr Leu Ser Gln Ala Gln Ser Lys Thr Ser Ser Gln Gln Phe
1 5 10 15

Ser Phe Thr Gly Asn Ser Ser Ala Asn Val Ile Ile Gly Asn Gln Lys
20 25 30

Leu Thr Ile Asn Asp Val Ala Arg Val Ala Arg Asn Gly Thr Leu Val
35 40 45

Ser Leu Thr Asn Asn Thr Asp Ile Leu Gln Gly Ile Gln Ala Ser Cys
50 55 60

Asp Tyr Ile Asn Asn Ala Val Glu Ser Gly Glu Pro Ile Tyr Gly Val
65 70 75 80

Thr Ser Gly Phe Gly Gly Met Ala Asn Val Ala Ile Ser Arg Glu Gln
85 90 95

Ala Ser Glu Leu Gln Thr Asn Leu Val Trp Phe Leu Lys Thr Gly Ala
100 105 110

Gly Asn Lys Leu Pro Leu Ala Asp Val Arg Ala Ala Met Leu Leu Arg
115 120 125

Ala Asn Ser His Met Arg Gly Ala Ser Gly Ile Arg Leu Glu Leu Ile
130 135 140

Lys Arg Met Glu Ile Phe Leu Asn Ala Gly Val Thr Pro Tyr Val Tyr
145 150 155 160

Glu Phe Gly Ser Ile Gly Ala Ser Gly Asp Leu Val Pro Leu Ser Tyr
165 170 175

Ile Thr Gly Ser Leu Ile Gly Leu Asp Pro Ser Phe Lys Val Asp Phe
180 185 190

Asn Gly Lys Glu Met Asp Ala Pro Thr Ala Leu Arg Gln Leu Asn Leu
195 200 205

Ser Pro Leu Thr Leu Leu Pro Lys Glu Gly Leu Ala Met Met Asn Gly
210 215 220

Thr Ser Val Met Thr Gly Ile Ala Ala Asn Cys Val Tyr Asp Thr Gln
225 230 235 240

Ile Leu Thr Ala Ile Ala Met Gly Val His Ala Leu Asp Ile Gln Ala
245 250 255

Leu Asn Gly Thr Asn Gln Ser Phe His Pro Phe Ile His Asn Ser Lys
260 265 270

Pro His Pro Gly Gln Leu Trp Ala Ala Asp Gln Met Ile Ser Leu Leu
275 280 285

Ala Asn Ser Gln Leu Val Arg Asp Glu Leu Asp Gly Lys His Asp Tyr
290 295 300

Arg Asp His Glu Leu Ile Gln Asp Arg Tyr Ser Leu Arg Cys Leu Pro
305 310 315 320

Gln Tyr Leu Gly Pro Ile Val Asp Gly Ile Ser Gln Ile Ala Lys Gln
325 330 335

Ile Glu Ile Glu Ile Asn Ser Val Thr Asp Asn Pro Leu Ile Asp Val
340 345 350

Asp Asn Gln Ala Ser Tyr His Gly Gly Asn Phe Leu Gly Gln Tyr Val
355 360 365

```
Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565


<210> SEQ ID NO 2
<211> LENGTH: 567
<212> TYPE: PRT
<213> ORGANISM: Anabaena variabilis

<400> SEQUENCE: 2

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175
```

-continued

```
Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565
```

<210> SEQ ID NO 3
<211> LENGTH: 532

<212> TYPE: PRT
<213> ORGANISM: Photorhabdus luminescens

<400> SEQUENCE: 3

Met Lys Ala Lys Asp Val Gln Pro Thr Ile Ile Ile Asn Lys Asn Gly
1 5 10 15

Leu Ile Ser Leu Glu Asp Ile Tyr Asp Ile Ala Ile Lys Gln Lys Lys
20 25 30

Val Glu Ile Ser Thr Glu Ile Thr Glu Leu Leu Thr His Gly Arg Glu
35 40 45

Lys Leu Glu Glu Lys Leu Asn Ser Gly Glu Val Ile Tyr Gly Ile Asn
50 55 60

Thr Gly Phe Gly Gly Asn Ala Asn Leu Val Val Pro Phe Glu Lys Ile
65 70 75 80

Ala Glu His Gln Gln Asn Leu Leu Thr Phe Leu Ser Ala Gly Thr Gly
85 90 95

Asp Tyr Met Ser Lys Pro Cys Ile Lys Ala Ser Gln Phe Thr Met Leu
100 105 110

Leu Ser Val Cys Lys Gly Trp Ser Ala Thr Arg Pro Ile Val Ala Gln
115 120 125

Ala Ile Val Asp His Ile Asn His Asp Ile Val Pro Leu Val Pro Arg
130 135 140

Tyr Gly Ser Val Gly Ala Ser Gly Asp Leu Ile Pro Leu Ser Tyr Ile
145 150 155 160

Ala Arg Ala Leu Cys Gly Ile Gly Lys Val Tyr Tyr Met Gly Ala Glu
165 170 175

Ile Asp Ala Ala Glu Ala Ile Lys Arg Ala Gly Leu Thr Pro Leu Ser
180 185 190

Leu Lys Ala Lys Glu Gly Leu Ala Leu Ile Asn Gly Thr Arg Val Met
195 200 205

Ser Gly Ile Ser Ala Ile Thr Val Ile Lys Leu Glu Lys Leu Phe Lys
210 215 220

Ala Ser Ile Ser Ala Ile Ala Leu Ala Val Glu Ala Leu Leu Ala Ser
225 230 235 240

His Glu His Tyr Asp Ala Arg Ile Gln Gln Val Lys Asn His Pro Gly
245 250 255

Gln Asn Ala Val Ala Ser Ala Leu Arg Asn Leu Leu Ala Gly Ser Thr
260 265 270

Gln Val Asn Leu Leu Ser Gly Val Lys Glu Gln Ala Asn Lys Ala Cys
275 280 285

Arg His Gln Glu Ile Thr Gln Leu Asn Asp Thr Leu Gln Glu Val Tyr
290 295 300

Ser Ile Arg Cys Ala Pro Gln Val Leu Gly Ile Val Pro Glu Ser Leu
305 310 315 320

Ala Thr Ala Arg Lys Ile Leu Glu Arg Glu Val Ile Ser Ala Asn Asp
325 330 335

Asn Pro Leu Ile Asp Pro Glu Asn Gly Asp Val Leu His Gly Gly Asn
340 345 350

Phe Met Gly Gln Tyr Val Ala Arg Thr Met Asp Ala Leu Lys Leu Asp
355 360 365

Ile Ala Leu Ile Ala Asn His Leu His Ala Ile Val Ala Leu Met Met
370 375 380

Asp Asn Arg Phe Ser Arg Gly Leu Pro Asn Ser Leu Ser Pro Thr Pro
385 390 395 400

Gly Met Tyr Gln Gly Phe Lys Gly Val Gln Leu Ser Gln Thr Ala Leu
405 410 415

Val Ala Ala Ile Arg His Asp Cys Ala Ala Ser Gly Ile His Thr Leu
420 425 430

Ala Thr Glu Gln Tyr Asn Gln Asp Ile Val Ser Leu Gly Leu His Ala
435 440 445

Ala Gln Asp Val Leu Glu Met Glu Gln Lys Leu Arg Asn Ile Val Ser
450 455 460

Met Thr Ile Leu Val Val Cys Gln Ala Ile His Leu Arg Gly Asn Ile
465 470 475 480

Ser Glu Ile Ala Pro Glu Thr Ala Lys Phe Tyr His Ala Val Arg Glu
485 490 495

Ile Ser Ser Pro Leu Ile Thr Asp Arg Ala Leu Asp Glu Asp Ile Ile
500 505 510

Arg Ile Ala Asp Ala Ile Ile Asn Asp Gln Leu Pro Leu Pro Glu Ile
515 520 525

Met Leu Glu Glu
530

<210> SEQ ID NO 4
<211> LENGTH: 514
<212> TYPE: PRT
<213> ORGANISM: Photorhabdus luminescens

<400> SEQUENCE: 4

Met Lys Gln Leu Thr Ile Tyr Pro Gly Lys Leu Thr Leu Asp Glu Leu
1 5 10 15

Arg Gln Val Tyr Leu Gln Pro Val Lys Ile Thr Leu Asp Ser Gln Ile
20 25 30

Phe Pro Ala Ile Glu Arg Ser Val Glu Cys Val Asn Ala Ile Leu Ala
35 40 45

Glu Asn Arg Thr Ala Tyr Gly Ile Asn Thr Gly Phe Gly Leu Leu Ala
50 55 60

Ser Thr Arg Ile Glu Glu Asp Asn Leu Glu Lys Leu Gln Arg Ser Leu
65 70 75 80

Val Val Ser His Ala Ala Gly Val Gly Lys Ala Leu Asp Asp Asn Met
85 90 95

Thr Arg Leu Ile Met Val Leu Lys Ile Asn Ser Leu Ser Arg Gly Tyr
100 105 110

Ser Gly Ile Arg Leu Ala Val Ile Gln Ala Leu Ile Ala Leu Val Asn
115 120 125

Ala Glu Ile Tyr Pro His Ile Pro Cys Lys Gly Ser Val Gly Ala Ser
130 135 140

Gly Asp Leu Ala Pro Leu Ala His Met Ser Leu Leu Leu Leu Gly Glu
145 150 155 160

Gly Gln Ala Arg Tyr Gln Gly Glu Trp Leu Pro Ala Lys Glu Ala Leu
165 170 175

Ala Lys Ala Asn Leu Gln Pro Ile Thr Leu Ala Ala Lys Glu Gly Leu
180 185 190

Ala Leu Leu Asn Gly Thr Gln Val Ser Thr Ala Phe Ala Leu Arg Gly
195 200 205

Leu Phe Glu Ala Glu Asp Leu Leu Ala Ala Ala Ile Val Cys Gly Ser
210 215 220

Leu Ser Val Glu Ala Ala Leu Gly Ser Arg Lys Pro Phe Asp Ala Arg

-continued

```
225                 230                 235                 240

Val His Val Val Arg Gly Gln Gln Gly Gln Ile Asp Val Ala Ala Leu
                245                 250                 255

Tyr Arg His Val Leu Glu Glu Ser Ser Glu Leu Ser Asp Ser His Ile
            260                 265                 270

Asn Cys Pro Lys Val Gln Asp Pro Tyr Ser Leu Arg Cys Gln Pro Gln
        275                 280                 285

Val Met Gly Ala Cys Leu Thr Gln Leu Arg His Ala Ala Asp Val Ile
    290                 295                 300

Leu Thr Glu Ala Asn Ala Val Ser Asp Asn Pro Leu Val Phe Ala Glu
305                 310                 315                 320

Gln Gly Glu Val Ile Ser Gly Gly Asn Phe His Ala Glu Pro Val Ala
                325                 330                 335

Met Ala Ser Asp Asn Leu Ala Leu Val Leu Ala Glu Ile Gly Ala Leu
            340                 345                 350

Ser Glu Arg Arg Ile Ala Leu Leu Met Asp Ser His Met Ser Gln Leu
        355                 360                 365

Pro Pro Phe Leu Val Glu Asn Gly Gly Val Asn Ser Gly Phe Met Ile
    370                 375                 380

Ala Gln Val Thr Ala Ala Ala Leu Ala Ser Glu Asn Lys Ala Leu Ala
385                 390                 395                 400

His Pro Ala Ser Val Asp Ser Leu Pro Thr Ser Ala Asn Gln Glu Asp
                405                 410                 415

His Val Ser Met Ala Pro Ala Ala Gly Arg Arg Leu Trp Glu Met Ala
            420                 425                 430

Glu Asn Thr Arg Gly Ile Leu Ala Ile Glu Trp Leu Ser Ala Cys Gln
        435                 440                 445

Gly Ile Asp Phe Arg Asn Gly Leu Lys Ser Ser Pro Ile Leu Glu Glu
    450                 455                 460

Ala Arg Val Ile Leu Arg Ala Lys Val Asp Tyr Tyr Asp Gln Asp Arg
465                 470                 475                 480

Phe Phe Ala Pro Asp Ile Asp Ala Ala Val Lys Leu Leu Ala Glu Gln
                485                 490                 495

His Leu Ser Ser Leu Leu Pro Ser Gly Gln Ile Leu Gln Arg Lys Asn
            500                 505                 510

Asn Arg


<210> SEQ ID NO 5
<211> LENGTH: 471
<212> TYPE: PRT
<213> ORGANISM: Proteus mirabilis

<400> SEQUENCE: 5

Met Ala Ile Ser Arg Arg Lys Phe Ile Leu Gly Gly Thr Val Val Ala
1               5                   10                  15

Val Ala Ala Gly Ala Gly Val Leu Thr Pro Met Leu Thr Arg Glu Gly
            20                  25                  30

Arg Phe Val Pro Gly Thr Pro Arg His Gly Phe Val Glu Gly Thr Gly
        35                  40                  45

Gly Pro Leu Pro Lys Gln Asp Asp Val Val Val Ile Gly Ala Gly Ile
    50                  55                  60

Leu Gly Ile Met Thr Ala Ile Asn Leu Ala Glu Arg Gly Leu Ser Val
65                  70                  75                  80

Thr Ile Val Glu Lys Gly Asn Ile Ala Gly Glu Gln Ser Ser Arg Phe
```

-continued

```
                85                  90                  95

Tyr Gly Gln Ala Ile Ser Tyr Lys Met Pro Asp Glu Thr Phe Leu Leu
            100                 105                 110

His His Leu Gly Lys His Arg Trp Arg Glu Met Asn Ala Lys Val Gly
        115                 120                 125

Ile Asp Thr Thr Tyr Arg Thr Gln Gly Arg Val Glu Val Pro Leu Asp
    130                 135                 140

Glu Glu Asp Leu Glu Asn Val Arg Lys Trp Ile Asp Ala Lys Ser Lys
145                 150                 155                 160

Asp Val Gly Ser Asp Ile Pro Phe Arg Thr Lys Met Ile Glu Gly Ala
                165                 170                 175

Glu Leu Lys Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
        195                 200                 205

Val Met Ala Glu Tyr Ala Lys Lys Met Gly Ile Lys Ile Phe Thr Asn
    210                 215                 220

Cys Ala Ala Arg Gly Leu Glu Thr Gln Ala Gly Val Ile Ser Asp Val
225                 230                 235                 240

Val Thr Glu Lys Gly Pro Ile Lys Thr Ser Arg Val Val Val Ala Gly
                245                 250                 255

Gly Val Gly Ser Arg Leu Phe Met Gln Asn Leu Asn Val Asp Val Pro
            260                 265                 270

Thr Leu Pro Ala Tyr Gln Ser Gln Gln Leu Ile Ser Ala Ala Pro Asn
        275                 280                 285

Ala Pro Gly Gly Asn Val Ala Leu Pro Gly Gly Ile Phe Phe Arg Asp
    290                 295                 300

Gln Ala Asp Gly Thr Tyr Ala Thr Ser Pro Arg Val Ile Val Ala Pro
305                 310                 315                 320

Val Val Lys Glu Ser Phe Thr Tyr Gly Tyr Lys Tyr Leu Pro Leu Leu
                325                 330                 335

Ala Leu Pro Asp Phe Pro Val His Ile Ser Leu Asn Glu Gln Leu Ile
            340                 345                 350

Asn Ser Phe Met Gln Ser Thr His Trp Asp Leu Asn Glu Glu Ser Pro
        355                 360                 365

Phe Glu Lys Tyr Arg Asp Met Thr Ala Leu Pro Asp Leu Pro Glu Leu
    370                 375                 380

Asn Ala Ser Leu Glu Lys Leu Lys Lys Glu Phe Pro Ala Phe Lys Glu
385                 390                 395                 400

Ser Thr Leu Ile Asp Gln Trp Ser Gly Ala Met Ala Ile Ala Pro Asp
                405                 410                 415

Glu Asn Pro Ile Ile Ser Asp Val Lys Glu Tyr Pro Gly Leu Val Ile
            420                 425                 430

Asn Thr Ala Thr Gly Trp Gly Met Thr Glu Ser Pro Val Ser Ala Glu
        435                 440                 445

Ile Thr Ala Asp Leu Leu Leu Gly Lys Lys Pro Val Leu Asp Ala Lys
    450                 455                 460

Pro Phe Ser Leu Tyr Arg Phe
465                 470
```

<210> SEQ ID NO 6
<211> LENGTH: 473
<212> TYPE: PRT
<213> ORGANISM: Proteus mirabilis

<400> SEQUENCE: 6

Met Asn Ile Ser Arg Arg Lys Leu Leu Leu Gly Val Gly Ala Ala Gly
1 5 10 15

Val Leu Ala Gly Gly Ala Ala Leu Val Pro Met Val Arg Arg Asp Gly
20 25 30

Lys Phe Val Glu Ala Lys Ser Arg Ala Ser Phe Val Glu Gly Thr Gln
35 40 45

Gly Ala Leu Pro Lys Glu Ala Asp Val Val Ile Ile Gly Ala Gly Ile
50 55 60

Gln Gly Ile Met Thr Ala Ile Asn Leu Ala Glu Arg Gly Met Ser Val
65 70 75 80

Thr Ile Leu Glu Lys Gly Gln Ile Ala Gly Glu Gln Ser Gly Arg Ala
85 90 95

Tyr Ser Gln Ile Ile Ser Tyr Gln Thr Ser Pro Glu Ile Phe Pro Leu
100 105 110

His His Tyr Gly Lys Ile Leu Trp Arg Gly Met Asn Glu Lys Ile Gly
115 120 125

Ala Asp Thr Ser Tyr Arg Thr Gln Gly Arg Val Glu Ala Leu Ala Asp
130 135 140

Glu Lys Ala Leu Asp Lys Ala Gln Ala Trp Ile Lys Thr Ala Lys Glu
145 150 155 160

Ala Ala Gly Phe Asp Thr Pro Leu Asn Thr Arg Ile Ile Lys Gly Glu
165 170 175

Glu Leu Ser Asn Arg Leu Val Gly Ala Gln Thr Pro Trp Thr Val Ala
180 185 190

Ala Phe Glu Glu Asp Ser Gly Ser Val Asp Pro Glu Thr Gly Thr Pro
195 200 205

Ala Leu Ala Arg Tyr Ala Lys Gln Ile Gly Val Lys Ile Tyr Thr Asn
210 215 220

Cys Ala Val Arg Gly Ile Glu Thr Ala Gly Gly Lys Ile Ser Asp Val
225 230 235 240

Val Ser Glu Lys Gly Ala Ile Lys Thr Ser Gln Val Val Leu Ala Gly
245 250 255

Gly Ile Trp Ser Arg Leu Phe Met Gly Asn Met Gly Ile Asp Ile Pro
260 265 270

Thr Leu Asn Val Tyr Leu Ser Gln Gln Arg Val Ser Gly Val Pro Gly
275 280 285

Ala Pro Arg Gly Asn Val His Leu Pro Asn Gly Ile His Phe Arg Glu
290 295 300

Gln Ala Asp Gly Thr Tyr Ala Val Ala Pro Arg Ile Phe Thr Ser Ser
305 310 315 320

Ile Val Lys Asp Ser Phe Leu Leu Gly Pro Lys Phe Met His Leu Leu
325 330 335

Gly Gly Gly Glu Leu Pro Leu Glu Phe Ser Ile Gly Glu Asp Leu Phe
340 345 350

Asn Ser Phe Lys Met Pro Thr Ser Trp Asn Leu Asp Glu Lys Thr Pro
355 360 365

Phe Glu Gln Phe Arg Val Ala Thr Ala Thr Gln Asn Thr Gln His Leu
370 375 380

Asp Ala Val Phe Gln Arg Met Lys Thr Glu Phe Pro Val Phe Glu Lys
385 390 395 400

Ser Glu Val Val Glu Arg Trp Gly Ala Val Val Ser Pro Thr Phe Asp

```
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470


<210> SEQ ID NO 7
<211> LENGTH: 471
<212> TYPE: PRT
<213> ORGANISM: Proteus vulgaris

<400> SEQUENCE: 7

Met Ala Ile Ser Arg Arg Lys Phe Ile Ile Gly Gly Thr Val Val Ala
1               5                   10                  15

Val Ala Ala Gly Ala Gly Ile Leu Thr Pro Met Leu Thr Arg Glu Gly
            20                  25                  30

Arg Phe Val Pro Gly Thr Pro Arg His Gly Phe Val Glu Gly Thr Glu
        35                  40                  45

Gly Ala Leu Pro Lys Gln Ala Asp Val Val Val Val Gly Ala Gly Ile
    50                  55                  60

Leu Gly Ile Met Thr Ala Ile Asn Leu Val Glu Arg Gly Leu Ser Val
65                  70                  75                  80

Val Ile Val Glu Lys Gly Asn Ile Ala Gly Glu Gln Ser Ser Arg Phe
                85                  90                  95

Tyr Gly Gln Ala Ile Ser Tyr Lys Met Pro Asp Glu Thr Phe Leu Leu
            100                 105                 110

His His Leu Gly Lys His Arg Trp Arg Glu Met Asn Ala Lys Val Gly
        115                 120                 125

Ile Asp Thr Thr Tyr Arg Thr Gln Gly Arg Val Glu Val Pro Leu Asp
    130                 135                 140

Glu Glu Asp Leu Val Asn Val Arg Lys Trp Ile Asp Glu Arg Ser Lys
145                 150                 155                 160

Asn Val Gly Ser Asp Ile Pro Phe Lys Thr Arg Ile Ile Glu Gly Ala
                165                 170                 175

Glu Leu Asn Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
        195                 200                 205

Val Met Ala Glu Tyr Ala Lys Lys Met Gly Val Arg Ile Tyr Thr Gln
    210                 215                 220

Cys Ala Ala Arg Gly Leu Glu Thr Gln Ala Gly Val Ile Ser Asp Val
225                 230                 235                 240

Val Thr Glu Lys Gly Ala Ile Lys Thr Ser Gln Val Val Val Ala Gly
                245                 250                 255

Gly Val Trp Ser Arg Leu Phe Met Gln Asn Leu Asn Val Asp Val Pro
            260                 265                 270

Thr Leu Pro Ala Tyr Gln Ser Gln Gln Leu Ile Ser Gly Ser Pro Thr
        275                 280                 285

Ala Pro Gly Gly Asn Val Ala Leu Pro Gly Gly Ile Phe Phe Arg Glu
    290                 295                 300
```

Gln Ala Asp Gly Thr Tyr Ala Thr Ser Pro Arg Val Ile Val Ala Pro
305 310 315 320

Val Val Lys Glu Ser Phe Thr Tyr Gly Tyr Lys Tyr Leu Pro Leu Leu
325 330 335

Ala Leu Pro Asp Phe Pro Val His Ile Ser Leu Asn Glu Gln Leu Ile
340 345 350

Asn Ser Phe Met Gln Ser Thr His Trp Asn Leu Asp Glu Val Ser Pro
355 360 365

Phe Glu Gln Phe Arg Asn Met Thr Ala Leu Pro Asp Leu Pro Glu Leu
370 375 380

Asn Ala Ser Leu Glu Lys Leu Lys Ala Glu Phe Pro Ala Phe Lys Glu
385 390 395 400

Ser Lys Leu Ile Asp Gln Trp Ser Gly Ala Met Ala Ile Ala Pro Asp
405 410 415

Glu Asn Pro Ile Ile Ser Glu Val Lys Glu Tyr Pro Gly Leu Val Ile
420 425 430

Asn Thr Ala Thr Gly Trp Gly Met Thr Glu Ser Pro Val Ser Ala Glu
435 440 445

Leu Thr Ala Asp Leu Leu Leu Gly Lys Lys Pro Val Leu Asp Pro Lys
450 455 460

Pro Phe Ser Leu Tyr Arg Phe
465 470

<210> SEQ ID NO 8
<211> LENGTH: 452
<212> TYPE: PRT
<213> ORGANISM: Homo sapiens

<400> SEQUENCE: 8

Met Ser Thr Ala Val Leu Glu Asn Pro Gly Leu Gly Arg Lys Leu Ser
1 5 10 15

Asp Phe Gly Gln Glu Thr Ser Tyr Ile Glu Asp Asn Cys Asn Gln Asn
20 25 30

Gly Ala Ile Ser Leu Ile Phe Ser Leu Lys Glu Glu Val Gly Ala Leu
35 40 45

Ala Lys Val Leu Arg Leu Phe Glu Glu Asn Asp Val Asn Leu Thr His
50 55 60

Ile Glu Ser Arg Pro Ser Arg Leu Lys Lys Asp Glu Tyr Glu Phe Phe
65 70 75 80

Thr His Leu Asp Lys Arg Ser Leu Pro Ala Leu Thr Asn Ile Ile Lys
85 90 95

Ile Leu Arg His Asp Ile Gly Ala Thr Val His Glu Leu Ser Arg Asp
100 105 110

Lys Lys Lys Asp Thr Val Pro Trp Phe Pro Arg Thr Ile Gln Glu Leu
115 120 125

Asp Arg Phe Ala Asn Gln Ile Leu Ser Tyr Gly Ala Glu Leu Asp Ala
130 135 140

Asp His Pro Gly Phe Lys Asp Pro Val Tyr Arg Ala Arg Arg Lys Gln
145 150 155 160

Phe Ala Asp Ile Ala Tyr Asn Tyr Arg His Gly Gln Pro Ile Pro Arg
165 170 175

Val Glu Tyr Met Glu Glu Gly Lys Lys Thr Trp Gly Thr Val Phe Lys
180 185 190

Thr Leu Lys Ser Leu Tyr Lys Thr His Ala Cys Tyr Glu Tyr Asn His
195 200 205

-continued

```
Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450
```

<210> SEQ ID NO 9
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atccccatca ctcttgatgg agatcaattc cccaagctgc tagagcgtta ccttgccctt      60

aaacattagc aatgtcgatt tatcagaggg ccgacaggct cccacaggag aaaaccg        117
```

<210> SEQ ID NO 10
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
ctcttgatcg ttatcaattc ccacgctgtt tcagagcgtt accttgccct taaacattag      60

caatgtcgat ttatcagagg gccgacaggc tcccacagga gaaaaccg                  108
```

<210> SEQ ID NO 11
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gtcagcataa caccctgacc tctcattaat tgttcatgcc gggcggcact atcgtcgtcc    60
ggccttttcc tctcttactc tgctacgtac atctatttct ataaatccgt tcaatttgtc   120
tgttttttgc acaaacatga aatatcagac aattccgtga cttaagaaaa tttatacaaa   180
tcagcaatat accccttaag gagtatataa aggtgaattt gatttacatc aataagcggg   240
gttgctgaat cgttaaggta ggcggtaata gaaaagaaat cgaggcaaaa                290

<210> SEQ ID NO 12
<211> LENGTH: 433
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
cggcccgatc gttgaacata gcggtccgca ggcggcactg cttacagcaa acggtctgta    60
cgctgtcgtc tttgtgatgt gcttcctgtt aggtttcgtc agccgtcacc gtcagcataa   120
caccctgacc tctcattaat tgctcatgcc ggacggcact atcgtcgtcc ggccttttcc   180
tctcttcccc cgctacgtgc atctatttct ataaacccgc tcattttgtc tattttttgc   240
acaaacatga aatatcagac aattccgtga cttaagaaaa tttatacaaa tcagcaatat   300
acccattaag gagtatataa aggtgaattt gatttacatc aataagcggg gttgctgaat   360
cgttaaggta ggcggtaata gaaaagaaat cgaggcaaaa atgtttgttt aactttaaga   420
aggagatata cat                                                       433

<210> SEQ ID NO 13
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtcagcataa caccctgacc tctcattaat tgctcatgcc ggacggcact atcgtcgtcc    60
ggccttttcc tctcttcccc cgctacgtgc atctatttct ataaacccgc tcattttgtc   120
tattttttgc acaaacatga aatatcagac aattccgtga cttaagaaaa tttatacaaa   180
tcagcaatat acccattaag gagtatataa aggtgaattt gatttacatc aataagcggg   240
gttgctgaat cgttaaggta ggcggtaata gaaaagaaat cgaggcaaaa                290

<210> SEQ ID NO 14
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atttcctctc atcccatccg gggtgagagt cttttccccc gacttatggc tcatgcatgc 60
atcaaaaaag atgtgagctt gatcaaaaac aaaaaatatt tcactcgaca ggagtattta 120
tattgcgccc gttacgtggg cttcgactgt aaatcagaaa ggagaaaaca cct 173

<210> SEQ ID NO 15
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtcagcataa caccctgacc tctcattaat tgttcatgcc gggcggcact atcgtcgtcc 60
ggccttttcc tctcttactc tgctacgtac atctatttct ataaatccgt tcaatttgtc 120 tgtttttgc acaaacatga aatatcagac aattccgtga cttaagaaaa tttatacaaa 180
tcagcaatat accccttaag gagtatataa aggtgaattt gatttacatc aataagcggg 240
gttgctgaat cgttaaggat ccctctagaa ataattttgt ttaactttaa gaaggagata 300
tacat 305

<210> SEQ ID NO 16
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
catttcctct catcccatcc ggggtgagag tcttttcccc cgacttatgg ctcatgcatg 60
catcaaaaaa gatgtgagct tgatcaaaaa caaaaaatat ttcactcgac aggagtattt 120
atattgcgcc cggatccctc tagaaataat tttgtttaac tttaagaagg agatatacat 180

<210> SEQ ID NO 17
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
agttgttctt attggtggtg ttgctttatg gttgcatcgt agtaaatggt tgtaacaaaa 60
gcaatttttc cggctgtctg tatacaaaaa cgccgtaaag tttgagcgaa gtcaataaac 120
tctctaccca ttcagggcaa tatctctctt ggatccctct agaaataatt ttgtttaact 180
ttaagaagga gatatacat 199

<210> SEQ ID NO 18
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
agttgttctt attggtggtg ttgctttatg gttgcatcgt agtaaatggt tgtaacaaaa 60

-continued gcaatttttc cggctgtctg tatacaaaaa cgccgcaaag tttgagcgaa gtcaataaac 120
tctctaccca ttcagggcaa tatctctctt ggatccaaag tgaactctag aaataatttt 180
gtttaacttt aagaaggaga tatacat 207

<210> SEQ ID NO 19
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
tcgtctttgt gatgtgcttc ctgttaggtt tcgtcagccg tcaccgtcag cataacaccc 60
tgacctctca ttaattgctc atgccggacg gcactatcgt cgtccggcct tttcctctct 120 tccccccgcta cgtgcatcta tttctataaa cccgctcatt ttgtctattt tttgcacaaa 180
catgaaatat cagacaattc cgtgacttaa gaaaatttat acaaatcagc aatataccca 240
ttaaggagta tataaaggtg aatttgattt acatcaataa gcggggttgc tgaatcgtta 300
aggtagaaat gtgatctagt tcacatttgc ggtaatagaa aagaaatcga ggcaaaaatg 360
tttgtttaac tttaagaagg agatatacat 390

<210> SEQ ID NO 20
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
agttgttctt attggtggtg ttgctttatg gttgcatcgt agtaaatggt tgtaacaaaa 60
gcaatttttc cggctgtctg tatacaaaaa cgccgcaaag tttgagcgaa gtcaataaac 120
tctctaccca ttcagggcaa tatctctcaa atgtgatcta gttcacattt tttgtttaac 180
tttaagaagg agatatacat 200

<210> SEQ ID NO 21
<211> LENGTH: 1485
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
ctcttgatcg ttatcaattc ccacgctgtt tcagagcgtt accttgccct taaacattag 60
caatgtcgat ttatcagagg gccgacaggc tcccacagga gaaaaccgat gaaaaacgcg 120
tcaaccgtat cggaagatac tgcgtcgaat caagagccga cgcttcatcg cggattacat 180
aaccgtcata ttcaactgat tgcgttgggt ggcgcaattg gtactggtct gtttcttggc 240
attggcccgg cgattcagat ggcgggtccg gctgtattgc tgggctacgg cgtcgccggg 300
atcatcgctt tcctgattat gcgccagctt ggcgaaatgg tggttgagga gccggtatcc 360
ggttcatttg cccactttgc ctataaatac tggggaccgt ttgcgggctt cctctctggc 420
tggaactact gggtaatgtt cgtgctggtg ggaatggcag agctgaccgc tgcgggcatc 480
tatatgcagt actggttccc ggatgttcca acgtggattt gggctgccgc cttctttatt 540
atcatcaacg ccgttaacct ggtgaacgtg cgcttatatg gcgaaaccga gttctggttt 600
gcgttgatta aagtgctggc aatcatcggt atgatcggct ttggcctgtg gctgctgttt 660
tctggtcacg gcggcgagaa agccagtatc gacaacctct ggcgctacgg tggtttcttc 720
gccaccggct ggaatgggct gattttgtcg ctggcggtaa ttatgttctc cttcggcggt 780
ctggagctga ttgggattac tgccgctgaa gcgcgcgatc cggaaaaaag cattccaaaa 840
gcggtaaatc aggtggtgta tcgcatcctg ctgttttaca tcggttcact ggtggtttta 900
ctggcgctct atccgtgggt ggaagtgaaa tccaacagta gcccgtttgt gatgattttc 960
cataatctcg acagcaacgt ggtagcttct gcgctgaact tcgtcattct ggtagcatcg 1020
ctgtcagtgt ataacagcgg ggtttactct aacagccgca tgctgtttgg cctttctgtg 1080
cagggtaatg cgccgaagtt tttgactcgc gtcagccgtc gcggtgtgcc gattaactcg 1140
ctgatgcttt ccggagcgat cacttcgctg gtggtgttaa tcaactatct gctgccgcaa 1200
aaagcgtttg gtctgctgat ggcgctggtg gtagcaacgc tgctgttgaa ctggattatg 1260
atctgtctgg cgcatctgcg ttttcgtgca gcgatgcgac gtcaggggcg tgaaacacag 1320
tttaaggcgc tgctctatcc gttcggcaac tatctctgca ttgccttcct cggcatgatt 1380
ttgctgctga tgtgcacgat ggatgatatg cgcttgtcag cgatcctgct gccggtgtgg 1440
attgtattcc tgtttatggc atttaaaacg ctgcgtcgga aataa 1485

<210> SEQ ID NO 22
<211> LENGTH: 4428
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22
ctcttgatcg ttatcaattc ccacgctgtt tcagagcgtt accttgccct taaacattag 60
caatgtcgat ttatcagagg gccgacaggc tcccacagga gaaaaccgat gaaaacacta 120
tcacaggccc aatctaaaac ttcttcacag caattcagct ttaccgggaa ctcgtctgcg 180
aatgtaatta tcggcaatca aaagctgacc attaatgatg tagctcgcgt tgcccggaat 240
ggcactttgg tgtcactgac gaacaatacc gacattctgc aaggtattca agctagctgc 300
gattatatca ataacgccgt tgaatctggc gagccaatct acggggtaac aagcggtttt 360
ggtgggatgg cgaacgttgc cattagccgt gaacaggcga gcgaacttca gaccaacctc 420
gtttggttcc taaagacagg agctggtaat aagttacctc tggctgacgt aagagccgcg 480
atgctgcttc gcgctaatag tcacatgcgc ggcgccagtg gtatccgtct tgagcttatc 540
aagaggatgg aaatcttcct caacgcgggt gtcacaccat atgtttatga gtttggtagt 600
atcggagcca gtggtgatct tgttcccctg agttatatta cgggttcatt gattggttta 660
gacccgtcct ttaaagtgga ttttaacggg aaagaaatgg acgccccgac cgctttacga 720
cagcttaatc tgagcccact tactttgctc cctaaagaag gtcttgccat gatgaatggc 780
acctctgtga tgactggaat tgccgcgaat tgtgtgtatg acacgcagat cctaacggcc 840
attgccatgg gtgttcacgc gttggacatt caagccctga atggtacaaa ccagtcgttt 900
catccgttta tccataattc aaaaccccat ccgggacagc tttgggctgc tgatcagatg 960
atctcactcc tggccaatag tcaactggtt cgggacgagc tcgacggcaa acatgattat 1020
cgcgatcatg agctcatcca ggaccggtat tcacttcgtt gtctcccaca atacctgggg 1080

-continued

```
cctatcgttg atggtatatc tcaaattgcg aagcaaattg aaattgagat caatagcgta   1140
accgacaacc cgcttatcga tgttgataat caggcctctt atcacggtgg caattttctg   1200
ggccagtatg ttggtatggg gatggatcac ctgcggtact atattgggct tctggctaaa   1260
catcttgatg tgcagattgc cttattagct tcaccagaat tttcaaatgg actgccgcca   1320
tcattgctcg gtaacagaga aaggaaagta aatatgggcc ttaagggcct tcagatatgt   1380
ggtaactcaa tcatgcccct cctgaccttt tatgggaact caattgctga tcgttttccg   1440
acacatgctg aacagtttaa ccaaaacatt aactcacagg gctatacatc cgcgacgtta   1500
gcgcgtcggt ccgtggatat cttccagaat tatgttgcta tcgctctgat gttcggcgta   1560
caggccgttg atttgcgcac ttataaaaaa accggtcact acgatgctcg ggcttgcctg   1620
tcgcctgcca ccgagcggct ttatagcgcc gtacgtcatg ttgtgggtca gaaaccgacg   1680
tcggaccgcc cctatatttg gaatgataat gaacaagggc tggatgaaca catcgcccgg   1740
atatctgccg atattgccgc cggaggtgtc atcgtccagg cggtacaaga catacttcct   1800
tgcctgcatt aagcttggcg taatcatggt catagctgtt tcctgtgtga aattgttatc   1860
cgctcacaat tccacacaac atacgagccg gaagcataaa gtgtaaagcc tggggtgcct   1920
aatgagtgag ctaactcaca ttaattgcgt tgcgctcact gcccgctttc cagtcgggaa   1980
acctgtcgtg ccagctgcat taatgaatcg gccaacgcgc ggggagaggc ggtttgcgta   2040
ttgggcgctc ttccgcttcc tcgctcactg actcgctgcg ctcggtcgtt cggctgcggc   2100
gagcggtatc agctcactca aaggcggtaa tacggttatc cacagaatca ggggataacg   2160
caggaaagaa catgtgagca aaaggccagc aaaaggccag gaaccgtaaa aaggccgcgt   2220
tgctggcgtt tttccatagg ctccgccccc ctgacgagca tcacaaaaat cgacgctcaa   2280
gtcagaggtg gcgaaacccg acaggactat aaagatacca ggcgtttccc cctggaagct   2340
ccctcgtgcg ctctcctgtt ccgaccctgc cgcttaccgg atacctgtcc gcctttctcc   2400
cttcgggaag cgtggcgctt tctcatagct cacgctgtag gtatctcagt tcggtgtagg   2460
tcgttcgctc caagctgggc tgtgtgcacg aaccccccgt tcagcccgac cgctgcgcct   2520
tatccggtaa ctatcgtctt gagtccaacc cggtaagaca cgacttatcg ccactggcag   2580
cagccactgg taacaggatt agcagagcga ggtatgtagg cggtgctaca gagttcttga   2640
agtggtggcc taactacggc tacactagaa gaacagtatt tggtatctgc gctctgctga   2700
agccagttac cttcggaaaa agagttggta gctcttgatc cggcaaacaa accaccgctg   2760
gtagcggtgg tttttttgtt tgcaagcagc agattacgcg cagaaaaaaa ggatctcaag   2820
aagatccttt gatcttttct acggggtctg acgctcagtg gaacgaaaac tcacgttaag   2880
ggattttggt catgagatta tcaaaaagga tcttcaccta gatcctttta aattaaaaat   2940
gaagttttaa atcaatctaa agtatatatg agtaaacttg gtctgacagt taccaatgct   3000
taatcagtga ggcacctatc tcagcgatct gtctatttcg ttcatccata gttgcctgac   3060
tccccgtcgt gtagataact acgatacggg agggcttacc atctggcccc agtgctgcaa   3120
tgataccgcg agacccacgc tcaccggctc cagatttatc agcaataaac cagccagccg   3180
gaagggccga gcgcagaagt ggtcctgcaa ctttatccgc ctccatccag tctattaatt   3240
gttgccggga agctagagta agtagttcgc cagttaatag tttgcgcaac gttgttgcca   3300
ttgctacagg catcgtggtg tcacgctcgt cgtttggtat ggcttcattc agctccggtt   3360
cccaacgatc aaggcgagtt acatgatccc ccatgttgtg caaaaaagcg gttagctcct   3420
tcggtcctcc gatcgttgtc agaagtaagt tggccgcagt gttatcactc atggttatgg   3480
```

cagcactgca taattctctt actgtcatgc catccgtaag atgcttttct gtgactggtg 3540
agtactcaac caagtcattc tgagaatagt gtatgcggcg accgagttgc tcttgcccgg 3600
cgtcaatacg ggataatacc gcgccacata gcagaacttt aaaagtgctc atcattggaa 3660
aacgttcttc ggggcgaaaa ctctcaagga tcttaccgct gttgagatcc agttcgatgt 3720
aacccactcg tgcacccaac tgatcttcag catcttttac tttcaccagc gtttctgggt 3780
gagcaaaaac aggaaggcaa aatgccgcaa aaaagggaat aagggcgaca cggaaatgtt 3840
gaatactcat actcttcctt tttcaatatt attgaagcat ttatcagggt tattgtctca 3900
tgagcggata catatttgaa tgtatttaga aaaataaaca aataggggtt ccgcgcacat 3960
ttccccgaaa agtgccacct gacgtctaag aaaccattat tatcatgaca ttaacctata 4020
aaaataggcg tatcacgagg ccctttcgtc tcgcgcgttt cggtgatgac ggtgaaaacc 4080
tctgacacat gcagctcccg gagacggtca cagcttgtct gtaagcggat gccgggagca 4140
gacaagcccg tcagggcgcg tcagcgggtg ttggcgggtg tcggggctgg cttaactatg 4200
cggcatcaga gcagattgta ctgagagtgc accatatgcg gtgtgaaata ccgcacagat 4260
gcgtaaggag aaaataccgc atcaggcgcc attcgccatt caggctgcgc aactgttggg 4320
aagggcgatc ggtgcgggcc tcttcgctat tacgccagct ggcgaaaggg ggatgtgctg 4380
caaggcgatt aagttgggta acgccagggt tttcccagtc acgacgtt 4428

<210> SEQ ID NO 23
<211> LENGTH: 4323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ctcttgatcg ttatcaattc ccacgctgtt tcagagcgtt accttgccct taaacattag 60
caatgtcgat ttatcagagg gccgacaggc tcccacagga gaaaaccgat gaaagctaaa 120
gatgttcagc caaccattat tattaataaa aatggcctta tctctttgga agatatctat 180
gacattgcga taaaacaaaa aaaagtagaa atatcaacgg agatcactga acttttgacg 240
catggtcgtg aaaaattaga ggaaaaatta aattcaggag aggttatata tggaatcaat 300
acaggatttg gagggaatgc caatttagtt gtgccatttg agaaaatcgc agagcatcag 360
caaaatctgt taacttttct ttctgctggt actggggact atatgtccaa accttgtatt 420
aaagcgtcac aatttactat gttactttct gtttgcaaag gttggtctgc aaccagacca 480
attgtcgctc aagcaattgt tgatcatatt aatcatgaca ttgttcctct ggttcctcgc 540
tatggctcag tgggtgcaag cggtgattta attcctttat cttatattgc acgagcatta 600
tgtggtatcg gcaaagttta ttatatgggc gcagaaattg acgctgctga agcaattaaa 660
cgtgcagggt tgacaccatt atcgttaaaa gccaaagaag gtcttgctct gattaacggc 720
acccgggtaa tgtcaggaat cagtgcaatc accgtcatta aactggaaaa actatttaaa 780
gcctcaattt ctgcgattgc ccttgctgtt gaagcattac ttgcatctca tgaacattat 840
gatgcccgga ttcaacaagt aaaaaatcat cctggtcaaa acgcggtggc aagtgcattg 900
cgtaatttat tggcaggttc aacgcaggtt aatctattat ctggggttaa agaacaagcc 960
aataaagctt gtcgtcatca agaaattacc caactaaatg ataccttaca ggaagtttat 1020
tcaattcgct gtgcaccaca agtattaggt atagtgccag aatctttagc taccgctcgg 1080

-continued

```
aaaatattgg aacgggaagt tatctcagct aatgataatc cattgataga tccagaaaat   1140
ggcgatgttc tacacggtgg aaattttatg gggcaatatg tcgcccgaac aatggatgca   1200
ttaaaactgg atattgcttt aattgccaat catcttcacg ccattgtggc tcttatgatg   1260
gataaccgtt tctctcgtgg attacctaat tcactgagtc cgacacccgg catgtatcaa   1320
ggttttaaag gcgtccaact ttctcaaacc gctttagttg ctgcaattcg ccatgattgt   1380
gctgcatcag gtattcatac cctcgccaca gaacaataca atcaagatat tgtcagttta   1440
ggtctgcatg ccgctcaaga tgttttagag atggagcaga aattacgcaa tattgtttca   1500
atgacaattc tggtagtttg tcaggccatt catcttcgcg gcaatattag tgaaattgcg   1560
cctgaaactg ctaaatttta ccatgcagta cgcgaaatca gttctccttt gatcactgat   1620
cgtgcgttgg atgaagatat aatccgcatt gcggatgcaa ttattaatga tcaacttcct   1680
ctgccagaaa tcatgctgga agaataagct tggcgtaatc atggtcatag ctgtttcctg   1740
tgtgaaattg ttatccgctc acaattccac acaacatacg agccggaagc ataaagtgta   1800
aagcctgggg tgcctaatga gtgagctaac tcacattaat tgcgttgcgc tcactgcccg   1860
ctttccagtc gggaaacctg tcgtgccagc tgcattaatg aatcggccaa cgcgcgggga   1920
gaggcggttt gcgtattggg cgctcttccg cttcctcgct cactgactcg ctgcgctcgg   1980
tcgttcggct gcggcgagcg gtatcagctc actcaaaggc ggtaatacgg ttatccacag   2040
aatcagggga taacgcagga aagaacatgt gagcaaaagg ccagcaaaag gccaggaacc   2100
gtaaaaaggc cgcgttgctg gcgtttttcc ataggctccg cccccctgac gagcatcaca   2160
aaaatcgacg ctcaagtcag aggtggcgaa acccgacagg actataaaga taccaggcgt   2220
ttccccctgg aagctccctc gtgcgctctc ctgttccgac cctgccgctt accggatacc   2280
tgtccgcctt tctcccttcg ggaagcgtgg cgctttctca tagctcacgc tgtaggtatc   2340
tcagttcggt gtaggtcgtt cgctccaagc tgggctgtgt gcacgaaccc cccgttcagc   2400
ccgaccgctg cgccttatcc ggtaactatc gtcttgagtc caacccggta agacacgact   2460
tatcgccact ggcagcagcc actggtaaca ggattagcag agcgaggtat gtaggcggtg   2520
ctacagagtt cttgaagtgg tggcctaact acggctacac tagaagaaca gtatttggta   2580
tctgcgctct gctgaagcca gttaccttcg gaaaaagagt tggtagctct tgatccggca   2640
aacaaaccac cgctggtagc ggtggttttt ttgtttgcaa gcagcagatt acgcgcagaa   2700
aaaaaggatc tcaagaagat cctttgatct tttctacggg gtctgacgct cagtggaacg   2760
aaaactcacg ttaagggatt ttggtcatga gattatcaaa aaggatcttc acctagatcc   2820
ttttaaatta aaaatgaagt tttaaatcaa tctaaagtat atatgagtaa acttggtctg   2880
acagttacca atgcttaatc agtgaggcac ctatctcagc gatctgtcta tttcgttcat   2940
ccatagttgc ctgactcccc gtcgtgtaga taactacgat acgggagggc ttaccatctg   3000
gccccagtgc tgcaatgata ccgcgagacc cacgctcacc ggctccagat ttatcagcaa   3060
taaaccagcc agccggaagg gccgagcgca gaagtggtcc tgcaacttta tccgcctcca   3120
tccagtctat taattgttgc cgggaagcta gagtaagtag ttcgccagtt aatagtttgc   3180
gcaacgttgt tgccattgct acaggcatcg tggtgtcacg ctcgtcgttt ggtatggctt   3240
cattcagctc cggttcccaa cgatcaaggc gagttacatg atcccccatg ttgtgcaaaa   3300
aagcggttag ctccttcggt cctccgatcg ttgtcagaag taagttggcc gcagtgttat   3360
cactcatggt tatggcagca ctgcataatt ctcttactgt catgccatcc gtaagatgct   3420
```

```
tttctgtgac tggtgagtac tcaaccaagt cattctgaga atagtgtatg cggcgaccga   3480

gttgctcttg cccggcgtca atacgggata ataccgcgcc acatagcaga actttaaaag   3540

tgctcatcat tggaaaacgt tcttcggggc gaaaactctc aaggatctta ccgctgttga   3600

gatccagttc gatgtaaccc actcgtgcac ccaactgatc ttcagcatct tttactttca   3660

ccagcgtttc tgggtgagca aaaacaggaa ggcaaaatgc cgcaaaaaag ggaataaggg   3720

cgacacggaa atgttgaata ctcatactct tcctttttca atattattga agcatttatc   3780

agggttattg tctcatgagc ggatacatat ttgaatgtat ttagaaaaat aaacaaatag   3840

gggttccgcg cacatttccc cgaaaagtgc cacctgacgt ctaagaaacc attattatca   3900

tgacattaac ctataaaaat aggcgtatca cgaggccctt tcgtctcgcg cgtttcggtg   3960

atgacggtga aaacctctga cacatgcagc tcccggagac ggtcacagct tgtctgtaag   4020

cggatgccgg gagcagacaa gcccgtcagg gcgcgtcagc gggtgttggc gggtgtcggg   4080

gctggcttaa ctatgcggca tcagagcaga ttgtactgag agtgcaccat atgcggtgtg   4140

aaataccgca cagatgcgta aggagaaaat accgcatcag gcgccattcg ccattcaggc   4200

tgcgcaactg ttgggaaggg cgatcggtgc gggcctcttc gctattacgc cagctggcga   4260

aagggggatg tgctgcaagg cgattaagtt gggtaacgcc agggttttcc cagtcacgac   4320

gtt                                                                 4323
```

<210> SEQ ID NO 24
<211> LENGTH: 5092
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
ctctagaaat aattttgttt aactttaaga aggagatata catatgaaaa cactatcaca     60

ggcccaatct aaaacttctt cacagcaatt cagctttacc gggaactcgt ctgcgaatgt    120

aattatcggc aatcaaaagc tgaccattaa tgatgtagct cgcgttgccc ggaatggcac    180

tttggtgtca ctgacgaaca ataccgacat tctgcaaggt attcaagcta gctgcgatta    240

tatcaataac gccgttgaat ctggcgagcc aatctacggg gtaacaagcg gttttggtgg    300

gatggcgaac gttgccatta gccgtgaaca ggcgagcgaa cttcagacca acctcgtttg    360

gttcctaaag acaggagctg gtaataagtt acctctggct gacgtaagag ccgcgatgct    420

gcttcgcgct aatagtcaca tgcgcggcgc cagtggtatc cgtcttgagc ttatcaagag    480

gatggaaatc ttcctcaacg cgggtgtcac accatatgtt tatgagtttg gtagtatcgg    540

agccagtggt gatcttgttc ccctgagtta tattacgggt tcattgattg gtttagaccc    600

gtcctttaaa gtggatttta acgggaaaga aatggacgcc ccgaccgctt tacgacagct    660

taatctgagc ccacttactt tgctccctaa agaaggtctt gccatgatga atggcacctc    720

tgtgatgact ggaattgccg cgaattgtgt gtatgacacg cagatcctaa cggccattgc    780

catgggtgtt cacgcgttgg acattcaagc cctgaatggt acaaaccagt cgtttcatcc    840

gtttatccat aattcaaaac cccatccggg acagctttgg gctgctgatc agatgatctc    900

actcctggcc aatagtcaac tggttcggga cgagctcgac ggcaaacatg attatcgcga    960

tcatgagctc atccaggacc ggtattcact tcgttgtctc ccacaatacc tggggcctat   1020

cgttgatggt atatctcaaa ttgcgaagca aattgaaatt gagatcaata gcgtaaccga   1080
```

-continued caacccgctt atcgatgttg ataatcaggc ctcttatcac ggtggcaatt ttctgggcca 1140
gtatgttggt atggggatgg atcacctgcg gtactatatt gggcttctgg ctaaacatct 1200
tgatgtgcag attgccttat tagcttcacc agaattttca aatggactgc cgccatcatt 1260
gctcggtaac agagaaagga aagtaaatat gggccttaag ggccttcaga tatgtggtaa 1320
ctcaatcatg cccctcctga ccttttatgg gaactcaatt gctgatcgtt ttccgacaca 1380
tgctgaacag tttaaccaaa acattaactc acagggctat acatccgcga cgttagcgcg 1440
tcggtccgtg gatatcttcc agaattatgt tgctatcgct ctgatgttcg gcgtacaggc 1500
cgttgatttg cgcacttata aaaaaaccgg tcactacgat gctcgggctt gcctgtcgcc 1560
tgccaccgag cggctttata gcgccgtacg tcatgttgtg ggtcagaaac cgacgtcgga 1620
ccgcccctat atttggaatg ataatgaaca agggctggat gaacacatcg cccggatatc 1680
tgccgatatt gccgccggag gtgtcatcgt ccaggcggta caagacatac ttccttgcct 1740
gcattaagct tggcgtaatc atggtcatag ctgtttcctg tgtgaaattg ttatccgctc 1800
acaattccac acaacatacg agccggaagc ataaagtgta aagcctgggg tgcctaatga 1860
gtgagctaac tcacattaat tgcgttgcgc tcactgcccg ctttccagtc gggaaacctg 1920
tcgtgccagc tgcattaatg aatcggccaa cgcgcgggga gaggcggttt gcgtattggg 1980
cgctcttccg cttcctcgct cactgactcg ctgcgctcgg tcgttcggct gcggcgagcg 2040
gtatcagctc actcaaaggc ggtaatacgg ttatccacag aatcagggga taacgcagga 2100
aagaacatgt gagcaaaagg ccagcaaaag gccaggaacc gtaaaaaggc cgcgttgctg 2160
gcgtttttcc ataggctccg cccccctgac gagcatcaca aaaatcgacg ctcaagtcag 2220
aggtggcgaa acccgacagg actataaaga taccaggcgt ttccccctgg aagctccctc 2280
gtgcgctctc ctgttccgac cctgccgctt accggatacc tgtccgcctt tctcccttcg 2340
ggaagcgtgg cgctttctca tagctcacgc tgtaggtatc tcagttcggt gtaggtcgtt 2400
cgctccaagc tgggctgtgt gcacgaaccc cccgttcagc ccgaccgctg cgccttatcc 2460
ggtaactatc gtcttgagtc caacccggta agacacgact tatcgccact ggcagcagcc 2520
actggtaaca ggattagcag agcgaggtat gtaggcggtg ctacagagtt cttgaagtgg 2580
tggcctaact acggctacac tagaagaaca gtatttggta tctgcgctct gctgaagcca 2640
gttaccttcg gaaaaagagt tggtagctct tgatccggca aacaaaccac cgctggtagc 2700
ggtggttttt ttgtttgcaa gcagcagatt acgcgcagaa aaaaaggatc tcaagaagat 2760
cctttgatct tttctacggg gtctgacgct cagtggaacg aaaactcacg ttaagggatt 2820
ttggtcatga gattatcaaa aaggatcttc acctagatcc ttttaaatta aaaatgaagt 2880
tttaaatcaa tctaaagtat atatgagtaa acttggtctg acagttacca atgcttaatc 2940
agtgaggcac ctatctcagc gatctgtcta tttcgttcat ccatagttgc ctgactcccc 3000
gtcgtgtaga taactacgat acgggagggc ttaccatctg gccccagtgc tgcaatgata 3060
ccgcgagacc cacgctcacc ggctccagat ttatcagcaa taaaccagcc agccggaagg 3120
gccgagcgca gaagtggtcc tgcaacttta tccgcctcca tccagtctat taattgttgc 3180
cgggaagcta gagtaagtag ttcgccagtt aatagtttgc gcaacgttgt tgccattgct 3240
acaggcatcg tggtgtcacg ctcgtcgttt ggtatggctt cattcagctc cggttcccaa 3300
cgatcaaggc gagttacatg atcccccatg ttgtgcaaaa aagcggttag ctccttcggt 3360
cctccgatcg ttgtcagaag taagttggcc gcagtgttat cactcatggt tatggcagca 3420
ctgcataatt ctcttactgt catgccatcc gtaagatgct tttctgtgac tggtgagtac 3480
tcaaccaagt cattctgaga atagtgtatg cggcgaccga gttgctcttg cccggcgtca 3540
atacgggata ataccgcgcc acatagcaga actttaaaag tgctcatcat tggaaaacgt 3600
tcttcggggc gaaaactctc aaggatctta ccgctgttga gatccagttc gatgtaaccc 3660
actcgtgcac ccaactgatc ttcagcatct tttactttca ccagcgtttc tgggtgagca 3720
aaaacaggaa ggcaaaatgc cgcaaaaaag ggaataaggg cgacacggaa atgttgaata 3780
ctcatactct tcctttttca atattattga agcatttatc agggttattg tctcatgagc 3840
ggatacatat ttgaatgtat ttagaaaaat aaacaaatag gggttccgcg cacatttccc 3900
cgaaaagtgc cacctgacgt ctaagaaacc attattatca tgacattaac ctataaaaat 3960
aggcgtatca cgaggccctt tcgtctcgcg cgtttcggtg atgacggtga aaacctctga 4020
cacatgcagc tcccggagac ggtcacagct tgtctgtaag cggatgccgg gagcagacaa 4080
gcccgtcagg gcgcgtcagc gggtgttggc gggtgtcggg gctggcttaa ctatgcggca 4140
tcagagcaga ttgtactgag agtgcaccat atgcggtgtg aaataccgca cagatgcgta 4200
aggagaaaat accgcatcag gcgccattcg ccattcaggc tgcgcaactg ttgggaaggg 4260
cgatcggtgc gggcctcttc gctattacgc cagctggcga aagggggatg tgctgcaagg 4320
cgattaagtt gggtaacgcc agggttttcc cagtcacgac gttgtaaaac gacggccagt 4380
gaattcgtta agacccactt tcacatttaa gttgtttttc taatccgcat atgatcaatt 4440
caaggccgaa taagaaggct ggctctgcac cttggtgatc aaataattcg atagcttgtc 4500
gtaataatgg cggcatacta tcagtagtag gtgtttccct ttcttcttta gcgacttgat 4560
gctcttgatc ttccaatacg caacctaaag taaaatgccc cacagcgctg agtgcatata 4620
atgcattctc tagtgaaaaa ccttgttggc ataaaaaggc taattgattt tcgagagttt 4680
catactgttt ttctgtaggc cgtgtaccta aatgtacttt tgctccatcg cgatgactta 4740
gtaaagcaca tctaaaactt ttagcgttat tacgtaaaaa atcttgccag ctttcccctt 4800
ctaaagggca aaagtgagta tggtgcctat ctaacatctc aatggctaag gcgtcgagca 4860
aagcccgctt attttttaca tgccaataca atgtaggctg ctctacacct agcttctggg 4920
cgagtttacg ggttgttaaa ccttcgattc cgacctcatt aagcagctct aatgcgctgt 4980
taatcacttt acttttatct aatctagaca tcattaattc ctaatttttg ttgacactct 5040
atcattgata gagttatttt accactccct atcagtgata gagaaaagtg aa 5092

<210> SEQ ID NO 25
<211> LENGTH: 4987
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
ctctagaaat aattttgttt aactttaaga aggagatata catatgaaag ctaaagatgt 60
tcagccaacc attattatta ataaaaatgg ccttatctct ttggaagata tctatgacat 120
tgcgataaaa caaaaaaaag tagaaatatc aacggagatc actgaacttt tgacgcatgg 180
tcgtgaaaaa ttagaggaaa aattaaattc aggagaggtt atatatggaa tcaatacagg 240
atttggaggg aatgccaatt tagttgtgcc atttgagaaa atcgcagagc atcagcaaaa 300
tctgttaact tttctttctg ctggtactgg ggactatatg tccaaacctt gtattaaagc 360
gtcacaattt actatgttac tttctgtttg caaaggttgg tctgcaacca gaccaattgt 420

```
cgctcaagca attgttgatc atattaatca tgacattgtt cctctggttc ctcgctatgg      480
ctcagtgggt gcaagcggtg atttaattcc tttatcttat attgcacgag cattatgtgg      540
tatcggcaaa gtttattata tgggcgcaga aattgacgct gctgaagcaa ttaaacgtgc      600
agggttgaca ccattatcgt taaaagccaa agaaggtctt gctctgatta acggcacccg      660
ggtaatgtca ggaatcagtg caatcaccgt cattaaactg gaaaaactat ttaaagcctc      720
aatttctgcg attgcccttg ctgttgaagc attacttgca tctcatgaac attatgatgc      780
ccggattcaa caagtaaaaa atcatcctgg tcaaaacgcg gtggcaagtg cattgcgtaa      840
tttattggca ggttcaacgc aggttaatct attatctggg gttaaagaac aagccaataa      900
agcttgtcgt catcaagaaa ttacccaact aaatgatacc ttacaggaag tttattcaat      960
tcgctgtgca ccacaagtat taggtatagt gccagaatct ttagctaccg ctcggaaaat     1020
attggaacgg gaagttatct cagctaatga taatccattg atagatccag aaaatggcga     1080
tgttctacac ggtggaaatt ttatgggca atatgtcgcc cgaacaatgg atgcattaaa      1140
actggatatt gctttaattg ccaatcatct tcacgccatt gtggctctta tgatggataa     1200
ccgtttctct cgtggattac ctaattcact gagtccgaca cccggcatgt atcaaggttt     1260
taaaggcgtc caactttctc aaaccgcttt agttgctgca attcgccatg attgtgctgc     1320
atcaggtatt cataccctcg ccacagaaca atacaatcaa gatattgtca gtttaggtct     1380
gcatgccgct caagatgttt tagagatgga gcagaaatta cgcaatattg tttcaatgac     1440
aattctggta gtttgtcagg ccattcatct tcgcggcaat attagtgaaa ttgcgcctga     1500
aactgctaaa ttttaccatg cagtacgcga aatcagttct cctttgatca ctgatcgtgc     1560
gttggatgaa gatataatcc gcattgcgga tgcaattatt aatgatcaac ttcctctgcc     1620
agaaatcatg ctggaagaat aagcttggcg taatcatggt catagctgtt tcctgtgtga     1680
aattgttatc cgctcacaat tccacacaac atacgagccg gaagcataaa gtgtaaagcc     1740
tggggtgcct aatgagtgag ctaactcaca ttaattgcgt tgcgctcact gcccgctttc     1800
cagtcgggaa acctgtcgtg ccagctgcat taatgaatcg gccaacgcgc ggggagaggc     1860
ggtttgcgta ttgggcgctc ttccgcttcc tcgctcactg actcgctgcg ctcggtcgtt     1920
cggctgcggc gagcggtatc agctcactca aaggcggtaa tacggttatc cacagaatca     1980
ggggataacg caggaaagaa catgtgagca aaaggccagc aaaaggccag gaaccgtaaa     2040
aaggccgcgt tgctggcgtt tttccatagg ctccgccccc ctgacgagca tcacaaaaat     2100
cgacgctcaa gtcagaggtg gcgaaacccg acaggactat aaagatacca ggcgtttccc     2160
cctggaagct ccctcgtgcg ctctcctgtt ccgaccctgc cgcttaccgg atacctgtcc     2220
gcctttctcc cttcgggaag cgtggcgctt tctcatagct cacgctgtag gtatctcagt     2280
tcggtgtagg tcgttcgctc caagctgggc tgtgtgcacg aaccccccgt tcagcccgac     2340
cgctgcgcct tatccggtaa ctatcgtctt gagtccaacc cggtaagaca cgacttatcg     2400
ccactggcag cagccactgg taacaggatt agcagagcga ggtatgtagg cggtgctaca     2460
gagttcttga agtggtggcc taactacggc tacactagaa gaacagtatt tggtatctgc     2520
gctctgctga agccagttac cttcggaaaa agagttggta gctcttgatc cggcaaacaa     2580
accaccgctg gtagcggtgg tttttttgtt tgcaagcagc agattacgcg cagaaaaaaa     2640
ggatctcaag aagatccttt gatcttttct acggggtctg acgctcagtg gaacgaaaac     2700
tcacgttaag ggattttggt catgagatta tcaaaaagga tcttcaccta gatcctttta     2760
```

-continued

```
aattaaaaat gaagttttaa atcaatctaa agtatatatg agtaaacttg gtctgacagt   2820
taccaatgct taatcagtga ggcacctatc tcagcgatct gtctatttcg ttcatccata   2880
gttgcctgac tccccgtcgt gtagataact acgatacggg agggcttacc atctggcccc   2940
agtgctgcaa tgataccgcg agacccacgc tcaccggctc cagatttatc agcaataaac   3000
cagccagccg gaagggccga gcgcagaagt ggtcctgcaa ctttatccgc ctccatccag   3060
tctattaatt gttgccggga agctagagta agtagttcgc cagttaatag tttgcgcaac   3120
gttgttgcca ttgctacagg catcgtggtg tcacgctcgt cgtttggtat ggcttcattc   3180
agctccggtt cccaacgatc aaggcgagtt acatgatccc ccatgttgtg caaaaaagcg   3240
gttagctcct tcggtcctcc gatcgttgtc agaagtaagt tggccgcagt gttatcactc   3300
atggttatgg cagcactgca taattctctt actgtcatgc catccgtaag atgcttttct   3360
gtgactggtg agtactcaac caagtcattc tgagaatagt gtatgcggcg accgagttgc   3420
tcttgcccgg cgtcaatacg ggataatacc gcgccacata gcagaacttt aaaagtgctc   3480
atcattggaa aacgttcttc ggggcgaaaa ctctcaagga tcttaccgct gttgagatcc   3540
agttcgatgt aacccactcg tgcacccaac tgatcttcag catcttttac tttcaccagc   3600
gtttctgggt gagcaaaaac aggaaggcaa aatgccgcaa aaaagggaat aagggcgaca   3660
cggaaatgtt gaatactcat actcttcctt tttcaatatt attgaagcat ttatcagggt   3720
tattgtctca tgagcggata catatttgaa tgtatttaga aaaataaaca aataggggtt   3780
ccgcgcacat ttccccgaaa agtgccacct gacgtctaag aaaccattat tatcatgaca   3840
ttaacctata aaaataggcg tatcacgagg ccctttcgtc tcgcgcgttt cggtgatgac   3900
ggtgaaaacc tctgacacat gcagctcccg gagacggtca cagcttgtct gtaagcggat   3960
gccgggagca gacaagcccg tcagggcgcg tcagcgggtg ttggcgggtg tcggggctgg   4020
cttaactatg cggcatcaga gcagattgta ctgagagtgc accatatgcg gtgtgaaata   4080
ccgcacagat gcgtaaggag aaaataccgc atcaggcgcc attcgccatt caggctgcgc   4140
aactgttggg aagggcgatc ggtgcgggcc tcttcgctat tacgccagct ggcgaaaggg   4200
ggatgtgctg caaggcgatt aagttgggta acgccagggt tttcccagtc acgacgttgt   4260
aaaacgacgg ccagtgaatt cgttaagacc cactttcaca tttaagttgt ttttctaatc   4320
cgcatatgat caattcaagg ccgaataaga aggctggctc tgcaccttgg tgatcaaata   4380
attcgatagc ttgtcgtaat aatggcggca tactatcagt agtaggtgtt tccctttctt   4440
ctttagcgac ttgatgctct tgatcttcca atacgcaacc taaagtaaaa tgccccacag   4500
cgctgagtgc atataatgca ttctctagtg aaaaaccttg ttggcataaa aaggctaatt   4560
gattttcgag agtttcatac tgtttttctg taggccgtgt acctaaatgt acttttgctc   4620
catcgcgatg acttagtaaa gcacatctaa aacttttagc gttattacgt aaaaaatctt   4680
gccagctttc cccttctaaa gggcaaaagt gagtatggtg cctatctaac atctcaatgg   4740
ctaaggcgtc gagcaaagcc cgcttatttt ttacatgcca atacaatgta ggctgctcta   4800
cacctagctt ctgggcgagt ttacgggttg ttaaaccttc gattccgacc tcattaagca   4860
gctctaatgc gctgttaatc actttacttt tatctaatct agacatcatt aattcctaat   4920
ttttgttgac actctatcat tgatagagtt attttaccac tccctatcag tgatagagaa   4980
aagtgaa                                                             4987
```

<210> SEQ ID NO 26
<211> LENGTH: 5962

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
ctcttgatcg ttatcaattc ccacgctgtt tcagagcgtt accttgccct taaacattag 60
caatgtcgat ttatcagagg gccgacaggc tcccacagga gaaaaccgat gaaaacacta 120
tcacaggccc aatctaaaac ttcttcacag caattcagct ttaccgggaa ctcgtctgcg 180
aatgtaatta tcggcaatca aaagctgacc attaatgatg tagctcgcgt tgcccggaat 240
ggcactttgg tgtcactgac gaacaatacc gacattctgc aaggtattca agctagctgc 300
gattatatca ataacgccgt tgaatctggc gagccaatct acggggtaac aagcggtttt 360
ggtgggatgg cgaacgttgc cattagccgt gaacaggcga gcgaacttca gaccaacctc 420
gtttggttcc taaagacagg agctggtaat aagttacctc tggctgacgt aagagccgcg 480
atgctgcttc gcgctaatag tcacatgcgc ggcgccagtg gtatccgtct tgagcttatc 540
aagaggatgg aaatcttcct caacgcgggt gtcacaccat atgtttatga gtttggtagt 600
atcggagcca gtggtgatct tgttcccctg agttatatta cgggttcatt gattggttta 660
gacccgtcct ttaaagtgga ttttaacggg aaagaaatgg acgccccgac cgctttacga 720
cagcttaatc tgagcccact tactttgctc cctaaagaag gtcttgccat gatgaatggc 780
acctctgtga tgactggaat tgccgcgaat tgtgtgtatg acacgcagat cctaacggcc 840
attgccatgg gtgttcacgc gttggacatt caagccctga atggtacaaa ccagtcgttt 900
catccgttta tccataattc aaaaccccat ccgggacagc tttgggctgc tgatcagatg 960
atctcactcc tggccaatag tcaactggtt cgggacgagc tcgacggcaa acatgattat 1020
cgcgatcatg agctcatcca ggaccggtat tcacttcgtt gtctcccaca atacctgggg 1080
cctatcgttg atggtatatc tcaaattgcg aagcaaattg aaattgagat caatagcgta 1140
accgacaacc cgcttatcga tgttgataat caggcctctt atcacggtgg caattttctg 1200
ggccagtatg ttggtatggg gatggatcac ctgcggtact atattgggct tctggctaaa 1260
catcttgatg tgcagattgc cttattagct tcaccagaat tttcaaatgg actgccgcca 1320
tcattgctcg gtaacagaga aaggaaagta aatatgggcc ttaagggcct tcagatatgt 1380
ggtaactcaa tcatgcccct cctgaccttt tatgggaact caattgctga tcgttttccg 1440
acacatgctg aacagtttaa ccaaaacatt aactcacagg gctatacatc cgcgacgtta 1500
gcgcgtcggt ccgtggatat cttccagaat tatgttgcta tcgctctgat gttcggcgta 1560
caggccgttg atttgcgcac ttataaaaaa accggtcact acgatgctcg ggcttgcctg 1620
tcgcctgcca ccgagcggct ttatagcgcc gtacgtcatg ttgtgggtca gaaaccgacg 1680
tcggaccgcc cctatatttg gaatgataat gaacaagggc tggatgaaca catcgcccgg 1740
atatctgccg atattgccgc cggaggtgtc atcgtccagg cggtacaaga catacttcct 1800
tgcctgcatt aagcttggcg taatcatggt catagctgtt tcctgtgtga aattgttatc 1860
cgctcacaat tccacacaac atacgagccg gaagcataaa gtgtaaagcc tggggtgcct 1920
aatgagtgag ctaactcaca ttaattgcgt tgcgctcact gcccgctttc cagtcgggaa 1980
acctgtcgtg ccagctgcat taatgaatcg gccaacgcgc ggggagaggc ggtttgcgta 2040
ttgggcgctc ttccgcttcc tcgctcactg actcgctgcg ctcggtcgtt cggctgcggc 2100
gagcggtatc agctcactca aaggcggtag tacgggtttt gctgcccgca aacgggctgt 2160

```
tctggtgttg ctagtttgtt atcagaatcg cagatccggc ttcaggtttg ccggctgaaa   2220
gcgctatttc ttccagaatt gccatgattt tttccccacg ggaggcgtca ctggctcccg   2280
tgttgtcggc agctttgatt cgataagcag catcgcctgt ttcaggctgt ctatgtgtga   2340
ctgttgagct gtaacaagtt gtctcaggtg ttcaatttca tgttctagtt gctttgtttt   2400
actggtttca cctgttctat taggtgttac atgctgttca tctgttacat tgtcgatctg   2460
ttcatggtga acagctttaa atgcaccaaa aactcgtaaa agctctgatg tatctatctt   2520
ttttacaccg ttttcatctg tgcatatgga cagttttccc tttgatatct aacggtgaac   2580
agttgttcta cttttgtttg ttagtcttga tgcttcactg atagatacaa gagccataag   2640
aacctcagat ccttccgtat ttagccagta tgttctctag tgtggttcgt tgtttttgcg   2700
tgagccatga gaacgaacca ttgagatcat gcttactttg catgtcactc aaaaattttg   2760
cctcaaaact ggtgagctga atttttgcag ttaaagcatc gtgtagtgtt tttcttagtc   2820
cgttacgtag gtaggaatct gatgtaatgg ttgttggtat tttgtcacca ttcattttta   2880
tctggttgtt ctcaagttcg gttacgagat ccatttgtct atctagttca acttggaaaa   2940
tcaacgtatc agtcgggcgg cctcgcttat caaccaccaa tttcatattg ctgtaagtgt   3000
ttaaatcttt acttattggt ttcaaaaccc attggttaag ccttttaaac tcatggtagt   3060
tattttcaag cattaacatg aacttaaatt catcaaggct aatctctata tttgccttgt   3120
gagttttctt ttgtgttagt tcttttaata accactcata aatcctcata gagtatttgt   3180
tttcaaaaga cttaacatgt tccagattat attttatgaa tttttttaac tggaaaagat   3240
aaggcaatat ctcttcacta aaaactaatt ctaatttttc gcttgagaac ttggcatagt   3300
ttgtccactg gaaaatctca aagcctttaa ccaaaggatt cctgatttcc acagttctcg   3360
tcatcagctc tctggttgct ttagctaata caccataagc attttcccta ctgatgttca   3420
tcatctgagc gtattggtta taagtgaacg ataccgtccg ttctttcctt gtagggtttt   3480
caatcgtggg gttgagtagt gccacacagc ataaaattag cttggtttca tgctccgtta   3540
agtcatagcg actaatcgct agttcatttg ctttgaaaac aactaattca gacatacatc   3600
tcaattggtc taggtgattt taatcactat accaattgag atgggctagt caatgataat   3660
tactagtcct tttcctttga gttgtgggta tctgtaaatt ctgctagacc tttgctggaa   3720
aacttgtaaa ttctgctaga ccctctgtaa attccgctag acctttgtgt gttttttttg   3780
tttatattca agtggttata atttatagaa taaagaaaga ataaaaaaag ataaaaagaa   3840
tagatcccag ccctgtgtat aactcactac tttagtcagt tccgcagtat tacaaaagga   3900
tgtcgcaaac gctgtttgct cctctacaaa acagacctta aaaccctaaa ggcttaagta   3960
gcaccctcgc aagctcgggc aaatcgctga atattccttt tgtctccgac catcaggcac   4020
ctgagtcgct gtctttttcg tgacattcag ttcgctgcgc tcacggctct ggcagtgaat   4080
gggggtaaat ggcactacag gcgcctttta tggattcatg caaggaaact acccataata   4140
caagaaaagc ccgtcacggg cttctcaggg cgttttatgg cgggtctgct atgtggtgct   4200
atctgacttt ttgctgttca gcagttcctg ccctctgatt ttccagtctg accacttcgg   4260
attatcccgt gacaggtcat tcagactggc taatgcaccc agtaaggcag cggtatcatc   4320
aacaggctta cccgtcttac tgtcttttct acggggtctg acgctcagtg gaacgaaaac   4380
tcacgttaag ggattttggt catgagatta tcaaaaagga tcttcaccta gatcctttta   4440
aattaaaaat gaagttttaa atcaatctaa agtatatatg agtaaacttg gtctgacagt   4500
```

-continued

```
taccaatgct taatcagtga ggcacctatc tcagcgatct gtctatttcg ttcatccata   4560

gttgcctgac tccccgtcgt gtagataact acgatacggg agggcttacc atctggcccc   4620

agtgctgcaa tgataccgcg agacccacgc tcaccggctc cagatttatc agcaataaac   4680

cagccagccg gaagggccga gcgcagaagt ggtcctgcaa ctttatccgc ctccatccag   4740

tctattaatt gttgccggga agctagagta agtagttcgc cagttaatag tttgcgcaac   4800

gttgttgcca ttgctacagg catcgtggtg tcacgctcgt cgtttggtat ggcttcattc   4860

agctccggtt cccaacgatc aaggcgagtt acatgatccc ccatgttgtg caaaaaagcg   4920

gttagctcct tcggtcctcc gatcgttgtc agaagtaagt tggccgcagt gttatcactc   4980

atggttatgg cagcactgca taattctctt actgtcatgc catccgtaag atgcttttct   5040

gtgactggtg agtactcaac caagtcattc tgagaatagt gtatgcggcg accgagttgc   5100

tcttgcccgg cgtcaatacg ggataatacc gcgccacata gcagaacttt aaaagtgctc   5160

atcattggaa aacgttcttc ggggcgaaaa ctctcaagga tcttaccgct gttgagatcc   5220

agttcgatgt aacccactcg tgcacccaac tgatcttcag catcttttac tttcaccagc   5280

gtttctgggt gagcaaaaac aggaaggcaa aatgccgcaa aaaagggaat aagggcgaca   5340

cggaaatgtt gaatactcat actcttcctt tttcaatatt attgaagcat ttatcagggt   5400

tattgtctca tgagcggata catatttgaa tgtatttaga aaaataaaca aataggggtt   5460

ccgcgcacat ttccccgaaa agtgccacct gacgtctaag aaaccattat tatcatgaca   5520

ttaacctata aaaataggcg tatcacgagg ccctttcgtc tcgcgcgttt cggtgatgac   5580

ggtgaaaacc tctgacacat gcagctcccg gagacggtca cagcttgtct gtaagcggat   5640

gccgggagca gacaagcccg tcagggcgcg tcagcgggtg ttggcgggtg tcggggctgg   5700

cttaactatg cggcatcaga gcagattgta ctgagagtgc accatatgcg gtgtgaaata   5760

ccgcacagat gcgtaaggag aaaataccgc atcaggcgcc attcgccatt caggctgcgc   5820

aactgttggg aagggcgatc ggtgcgggcc tcttcgctat tacgccagct ggcgaaaggg   5880

ggatgtgctg caaggcgatt aagttgggta acgccagggt tttcccagtc acgacgttgt   5940

aaaacgacgg ccagtgaatt cg                                            5962


<210> SEQ ID NO 27
<211> LENGTH: 5857
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

ctcttgatcg ttatcaattc ccacgctgtt tcagagcgtt accttgccct taaacattag     60

caatgtcgat ttatcagagg gccgacaggc tcccacagga gaaaaccgat gaaagctaaa    120

gatgttcagc caaccattat tattaataaa aatggcctta tctctttgga agatatctat    180

gacattgcga taaaacaaaa aaaagtagaa atatcaacgg agatcactga acttttgacg    240

catggtcgtg aaaaattaga ggaaaaatta aattcaggag aggttatata tggaatcaat    300

acaggatttg gagggaatgc caatttagtt gtgccatttg agaaaatcgc agagcatcag    360

caaaatctgt taacttttct ttctgctggt actggggact atatgtccaa accttgtatt    420

aaagcgtcac aatttactat gttactttct gtttgcaaag gttggtctgc aaccagacca    480

attgtcgctc aagcaattgt tgatcatatt aatcatgaca ttgttcctct ggttcctcgc    540
```

-continued

```
tatggctcag tgggtgcaag cggtgattta attcctttat cttatattgc acgagcatta    600
tgtggtatcg gcaaagttta ttatatgggc gcagaaattg acgctgctga agcaattaaa    660
cgtgcagggt tgacaccatt atcgttaaaa gccaaagaag gtcttgctct gattaacggc    720
acccgggtaa tgtcaggaat cagtgcaatc accgtcatta aactggaaaa actatttaaa    780
gcctcaattt ctgcgattgc ccttgctgtt gaagcattac ttgcatctca tgaacattat    840
gatgcccgga ttcaacaagt aaaaaatcat cctggtcaaa acgcggtggc aagtgcattg    900
cgtaatttat tggcaggttc aacgcaggtt aatctattat ctggggttaa agaacaagcc    960
aataaagctt gtcgtcatca agaaattacc caactaaatg ataccttaca ggaagtttat   1020
tcaattcgct gtgcaccaca agtattaggt atagtgccag aatctttagc taccgctcgg   1080
aaaatattgg aacgggaagt tatctcagct aatgataatc cattgataga tccagaaaat   1140
ggcgatgttc tacacggtgg aaattttatg ggcaatatg tcgcccgaac aatggatgca    1200
ttaaaactgg atattgcttt aattgccaat catcttcacg ccattgtggc tcttatgatg   1260
gataaccgtt tctctcgtgg attacctaat tcactgagtc cgacacccgg catgtatcaa   1320
ggttttaaag gcgtccaact ttctcaaacc gctttagttg ctgcaattcg ccatgattgt   1380
gctgcatcag gtattcatac cctcgccaca gaacaataca atcaagatat tgtcagttta   1440
ggtctgcatg ccgctcaaga tgttttagag atggagcaga aattacgcaa tattgtttca   1500
atgacaattc tggtagtttg tcaggccatt catcttcgcg gcaatattag tgaaattgcg   1560
cctgaaactg ctaaatttta ccatgcagta cgcgaaatca gttctccttt gatcactgat   1620
cgtgcgttgg atgaagatat aatccgcatt gcggatgcaa ttattaatga tcaacttcct   1680
ctgccagaaa tcatgctgga agaataagct tggcgtaatc atggtcatag ctgtttcctg   1740
tgtgaaattg ttatccgctc acaattccac acaacatacg agccggaagc ataaagtgta   1800
aagcctgggg tgcctaatga gtgagctaac tcacattaat tgcgttgcgc tcactgcccg   1860
ctttccagtc gggaaacctg tcgtgccagc tgcattaatg aatcggccaa cgcgcgggga   1920
gaggcggttt gcgtattggg cgctcttccg cttcctcgct cactgactcg ctgcgctcgg   1980
tcgttcggct gcggcgagcg gtatcagctc actcaaaggc ggtagtacgg gttttgctgc   2040
ccgcaaacgg gctgttctgg tgttgctagt ttgttatcag aatcgcagat ccggcttcag   2100
gtttgccggc tgaaagcgct atttcttcca gaattgccat gatttttttcc ccacgggagg  2160
cgtcactggc tcccgtgttg tcggcagctt tgattcgata agcagcatcg cctgtttcag   2220
gctgtctatg tgtgactgtt gagctgtaac aagttgtctc aggtgttcaa tttcatgttc   2280
tagttgcttt gttttactgg tttcacctgt tctattaggt gttacatgct gttcatctgt   2340
tacattgtcg atctgttcat ggtgaacagc tttaaatgca ccaaaaactc gtaaaagctc   2400
tgatgtatct atcttttta caccgttttc atctgtgcat atggacagtt ttccctttga    2460
tatctaacgg tgaacagttg ttctactttt gtttgttagt cttgatgctt cactgataga   2520
tacaagagcc ataagaacct cagatccttc cgtatttagc cagtatgttc tctagtgtgg   2580
ttcgttgttt ttgcgtgagc catgagaacg aaccattgag atcatgctta ctttgcatgt   2640
cactcaaaaa ttttgcctca aaactggtga gctgaatttt tgcagttaaa gcatcgtgta   2700
gtgtttttct tagtccgtta cgtaggtagg aatctgatgt aatggttgtt ggtattttgt   2760
caccattcat ttttatctgg ttgttctcaa gttcggttac gagatccatt tgtctatcta   2820
gttcaacttg gaaaatcaac gtatcagtcg ggcggcctcg cttatcaacc accaatttca   2880
tattgctgta agtgtttaaa tctttactta ttggtttcaa aacccattgg ttaagccttt   2940
```

```
taaactcatg gtagttattt tcaagcatta acatgaactt aaattcatca aggctaatct   3000
ctatatttgc cttgtgagtt ttcttttgtg ttagttcttt taataaccac tcataaatcc   3060
tcatagagta tttgttttca aaagacttaa catgttccag attatatttt atgaattttt   3120
ttaactggaa aagataaggc aatatctctt cactaaaaac taattctaat ttttcgcttg   3180
agaacttggc atagtttgtc cactggaaaa tctcaaagcc tttaaccaaa ggattcctga   3240
tttccacagt tctcgtcatc agctctctgg ttgctttagc taatacacca taagcatttt   3300
ccctactgat gttcatcatc tgagcgtatt ggttataagt gaacgatacc gtccgttctt   3360
tccttgtagg gttttcaatc gtggggttga gtagtgccac acagcataaa attagcttgg   3420
tttcatgctc cgttaagtca tagcgactaa tcgctagttc atttgctttg aaaacaacta   3480
attcagacat acatctcaat tggtctaggt gattttaatc actataccaa ttgagatggg   3540
ctagtcaatg ataattacta gtccttttcc tttgagttgt gggtatctgt aaattctgct   3600
agacctttgc tggaaaactt gtaaattctg ctagaccctc tgtaaattcc gctagacctt   3660
tgtgtgtttt ttttgtttat attcaagtgg ttataattta tagaataaag aaagaataaa   3720
aaaagataaa aagaatagat cccagccctg tgtataactc actactttag tcagttccgc   3780
agtattacaa aaggatgtcg caaacgctgt ttgctcctct acaaaacaga ccttaaaacc   3840
ctaaaggctt aagtagcacc ctcgcaagct cgggcaaatc gctgaatatt ccttttgtct   3900
ccgaccatca ggcacctgag tcgctgtctt tttcgtgaca ttcagttcgc tgcgctcacg   3960
gctctggcag tgaatggggg taaatggcac tacaggcgcc ttttatggat tcatgcaagg   4020
aaactaccca taatacaaga aaagcccgtc acgggcttct cagggcgttt tatggcgggt   4080
ctgctatgtg gtgctatctg actttttgct gttcagcagt tcctgccctc tgattttcca   4140
gtctgaccac ttcggattat cccgtgacag gtcattcaga ctggctaatg cacccagtaa   4200
ggcagcggta tcatcaacag gcttacccgt cttactgtct tttctacggg gtctgacgct   4260
cagtggaacg aaaactcacg ttaagggatt ttggtcatga gattatcaaa aaggatcttc   4320
acctagatcc ttttaaatta aaaatgaagt tttaaatcaa tctaaagtat atatgagtaa   4380
acttggtctg acagttacca atgcttaatc agtgaggcac ctatctcagc gatctgtcta   4440
tttcgttcat ccatagttgc ctgactcccc gtcgtgtaga taactacgat acgggagggc   4500
ttaccatctg gccccagtgc tgcaatgata ccgcgagacc cacgctcacc ggctccagat   4560
ttatcagcaa taaaccagcc agccggaagg gccgagcgca gaagtggtcc tgcaacttta   4620
tccgcctcca tccagtctat taattgttgc cgggaagcta gagtaagtag ttcgccagtt   4680
aatagtttgc gcaacgttgt tgccattgct acaggcatcg tggtgtcacg ctcgtcgttt   4740
ggtatggctt cattcagctc cggttcccaa cgatcaaggc gagttacatg atcccccatg   4800
ttgtgcaaaa aagcggttag ctccttcggt cctccgatcg ttgtcagaag taagttggcc   4860
gcagtgttat cactcatggt tatggcagca ctgcataatt ctcttactgt catgccatcc   4920
gtaagatgct tttctgtgac tggtgagtac tcaaccaagt cattctgaga atagtgtatg   4980
cggcgaccga gttgctcttg cccggcgtca atacgggata ataccgcgcc acatagcaga   5040
actttaaaag tgctcatcat tggaaaacgt tcttcggggc gaaaactctc aaggatctta   5100
ccgctgttga gatccagttc gatgtaaccc actcgtgcac ccaactgatc ttcagcatct   5160
tttactttca ccagcgtttc tgggtgagca aaaacaggaa ggcaaaatgc cgcaaaaaag   5220
ggaataaggg cgacacggaa atgttgaata ctcatactct tcctttttca atattattga   5280
```

agcatttatc agggttattg tctcatgagc ggatacatat ttgaatgtat ttagaaaaat 5340
aaacaaatag gggttccgcg cacatttccc cgaaaagtgc cacctgacgt ctaagaaacc 5400
attattatca tgacattaac ctataaaaat aggcgtatca cgaggccctt tcgtctcgcg 5460
cgtttcggtg atgacggtga aaacctctga cacatgcagc tcccggagac ggtcacagct 5520
tgtctgtaag cggatgccgg gagcagacaa gcccgtcagg gcgcgtcagc gggtgttggc 5580
gggtgtcggg gctggcttaa ctatgcggca tcagagcaga ttgtactgag agtgcaccat 5640
atgcggtgtg aaataccgca cagatgcgta aggagaaaat accgcatcag gcgccattcg 5700
ccattcaggc tgcgcaactg ttgggaaggg cgatcggtgc gggcctcttc gctattacgc 5760
cagctggcga aagggggatg tgctgcaagg cgattaagtt gggtaacgcc agggttttcc 5820
cagtcacgac gttgtaaaac gacggccagt gaattcg 5857

<210> SEQ ID NO 28
<211> LENGTH: 6602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
accactccct atcagtgata gagaaaagtg aactctagaa ataattttgt ttaactttaa 60
gaaggagata tacatatgaa aacactatca caggcccaat ctaaaacttc ttcacagcaa 120
ttcagcttta ccgggaactc gtctgcgaat gtaattatcg gcaatcaaaa gctgaccatt 180
aatgatgtag ctcgcgttgc ccggaatggc actttggtgt cactgacgaa caataccgac 240
attctgcaag gtattcaagc tagctgcgat tatatcaata acgccgttga atctggcgag 300
ccaatctacg gggtaacaag cggttttggt gggatggcga acgttgccat tagccgtgaa 360
caggcgagcg aacttcagac caacctcgtt tggttcctaa agacaggagc tggtaataag 420
ttacctctgg ctgacgtaag agccgcgatg ctgcttcgcg ctaatagtca catgcgcggc 480
gccagtggta tccgtcttga gcttatcaag aggatggaaa tcttcctcaa cgcgggtgtc 540
acaccatatg tttatgagtt tggtagtatc ggagccagtg gtgatcttgt tcccctgagt 600
tatattacgg gttcattgat tggtttagac ccgtccttta aagtggattt taacgggaaa 660
gaaatggacg ccccgaccgc tttacgacag cttaatctga gcccacttac tttgctccct 720
aaagaaggtc ttgccatgat gaatggcacc tctgtgatga ctggaattgc cgcgaattgt 780
gtgtatgaca cgcagatcct aacggccatt gccatgggtg ttcacgcgtt ggacattcaa 840
gccctgaatg gtacaaacca gtcgtttcat ccgtttatcc ataattcaaa accccatccg 900
ggacagcttt gggctgctga tcagatgatc tcactcctgg ccaatagtca actggttcgg 960
gacgagctcg acggcaaaca tgattatcgc gatcatgagc tcatccagga ccggtattca 1020
cttcgttgtc tcccacaata cctggggcct atcgttgatg gtatatctca aattgcgaag 1080
caaattgaaa ttgagatcaa tagcgtaacc gacaacccgc ttatcgatgt tgataatcag 1140
gcctcttatc acggtggcaa ttttctgggc cagtatgttg gtatggggat ggatcacctg 1200
cggtactata ttgggcttct ggctaaacat cttgatgtgc agattgcctt attagcttca 1260
ccagaatttt caaatggact gccgccatca ttgctcggta acagagaaag gaaagtaaat 1320
atgggcctta agggccttca gatatgtggt aactcaatca tgcccctcct gaccttttat 1380
gggaactcaa ttgctgatcg ttttccgaca catgctgaac agtttaacca aaacattaac 1440

```
tcacagggct atacatccgc gacgttagcg cgtcggtccg tggatatctt ccagaattat   1500
gttgctatcg ctctgatgtt cggcgtacag gccgttgatt tgcgcactta taaaaaaacc   1560
ggtcactacg atgctcgggc ttgcctgtcg cctgccaccg agcggcttta tagcgccgta   1620
cgtcatgttg tgggtcagaa accgacgtcg gaccgcccct atatttggaa tgataatgaa   1680
caagggctgg atgaacacat cgcccggata tctgccgata ttgccgccgg aggtgtcatc   1740
gtccaggcgg tacaagacat acttccttgc ctgcattaag cttggcgtaa tcatggtcat   1800
agctgtttcc tgtgtgaaat tgttatccgc tcacaattcc acacaacata cgagccggaa   1860
gcataaagtg taaagcctgg ggtgcctaat gagtgagcta actcacatta attgcgttgc   1920
gctcactgcc cgctttccag tcgggaaacc tgtcgtgcca gctgcattaa tgaatcggcc   1980
aacgcgcggg gagaggcggt ttgcgtattg ggcgctcttc cgcttcctcg ctcactgact   2040
cgctgcgctc ggtcgttcgg ctgcggcgag cggtatcagc tcactcaaag gcggtagtac   2100
gggttttgct gcccgcaaac gggctgttct ggtgttgcta gtttgttatc agaatcgcag   2160
atccggcttc aggtttgccg gctgaaagcg ctatttcttc cagaattgcc atgatttttt   2220
ccccacggga ggcgtcactg gctcccgtgt tgtcggcagc tttgattcga taagcagcat   2280
cgcctgtttc aggctgtcta tgtgtgactg ttgagctgta acaagttgtc tcaggtgttc   2340
aatttcatgt tctagttgct ttgttttact ggtttcacct gttctattag gtgttacatg   2400
ctgttcatct gttacattgt cgatctgttc atggtgaaca gctttaaatg caccaaaaac   2460
tcgtaaaagc tctgatgtat ctatcttttt tacaccgttt tcatctgtgc atatggacag   2520
ttttcccttt gatatctaac ggtgaacagt tgttctactt ttgtttgtta gtcttgatgc   2580
ttcactgata gatacaagag ccataagaac ctcagatcct tccgtattta gccagtatgt   2640
tctctagtgt ggttcgttgt ttttgcgtga gccatgagaa cgaaccattg agatcatgct   2700
tactttgcat gtcactcaaa aattttgcct caaaactggt gagctgaatt tttgcagtta   2760
aagcatcgtg tagtgttttt cttagtccgt tacgtaggta ggaatctgat gtaatggttg   2820
ttggtatttt gtcaccattc atttttatct ggttgttctc aagttcggtt acgagatcca   2880
tttgtctatc tagttcaact tggaaaatca acgtatcagt cgggcggcct cgcttatcaa   2940
ccaccaattt catattgctg taagtgttta aatctttact tattggtttc aaaacccatt   3000
ggttaagcct tttaaactca tggtagttat tttcaagcat taacatgaac ttaaattcat   3060
caaggctaat ctctatattt gccttgtgag ttttcttttg tgttagttct tttaataacc   3120
actcataaat cctcatagag tatttgtttt caaaagactt aacatgttcc agattatatt   3180
ttatgaattt ttttaactgg aaaagataag gcaatatctc ttcactaaaa actaattcta   3240
atttttcgct tgagaacttg gcatagtttg tccactggaa aatctcaaag cctttaacca   3300
aaggattcct gatttccaca gttctcgtca tcagctctct ggttgcttta gctaatacac   3360
cataagcatt ttccctactg atgttcatca tctgagcgta ttggttataa gtgaacgata   3420
ccgtccgttc tttccttgta gggttttcaa tcgtggggtt gagtagtgcc acacagcata   3480
aaattagctt ggtttcatgc tccgttaagt catagcgact aatcgctagt tcatttgctt   3540
tgaaaacaac taattcagac atacatctca attggtctag gtgattttaa tcactatacc   3600
aattgagatg ggctagtcaa tgataattac tagtcctttt cctttgagtt gtgggtatct   3660
gtaaattctg ctagaccttt gctggaaaac ttgtaaattc tgctagaccc tctgtaaatt   3720
ccgctagacc tttgtgtgtt ttttttgttt atattcaagt ggttataatt tatagaataa   3780
agaaagaata aaaaaagata aaaagaatag atcccagccc tgtgtataac tcactacttt   3840
```

agtcagttcc gcagtattac aaaaggatgt cgcaaacgct gtttgctcct ctacaaaaca 3900
gaccttaaaa ccctaaaggc ttaagtagca ccctcgcaag ctcgggcaaa tcgctgaata 3960
ttccttttgt ctccgaccat caggcacctg agtcgctgtc tttttcgtga cattcagttc 4020
gctgcgctca cggctctggc agtgaatggg ggtaaatggc actacaggcg ccttttatgg 4080
attcatgcaa ggaaactacc cataatacaa gaaaagcccg tcacgggctt ctcagggcgt 4140
tttatggcgg gtctgctatg tggtgctatc tgactttttg ctgttcagca gttcctgccc 4200
tctgattttc cagtctgacc acttcggatt atcccgtgac aggtcattca gactggctaa 4260
tgcacccagt aaggcagcgg tatcatcaac aggcttaccc gtcttactgt cttttctacg 4320
gggtctgacg ctcagtggaa cgaaaactca cgttaaggga ttttggtcat gagattatca 4380
aaaaggatct tcacctagat ccttttaaat taaaaatgaa gttttaaatc aatctaaagt 4440
atatatgagt aaacttggtc tgacagttac caatgcttaa tcagtgaggc acctatctca 4500
gcgatctgtc tatttcgttc atccatagtt gcctgactcc ccgtcgtgta gataactacg 4560
atacgggagg gcttaccatc tggccccagt gctgcaatga taccgcgaga cccacgctca 4620
ccggctccag atttatcagc aataaaccag ccagccggaa gggccgagcg cagaagtggt 4680
cctgcaactt tatccgcctc catccagtct attaattgtt gccgggaagc tagagtaagt 4740
agttcgccag ttaatagttt gcgcaacgtt gttgccattg ctacaggcat cgtggtgtca 4800
cgctcgtcgt ttggtatggc ttcattcagc tccggttccc aacgatcaag gcgagttaca 4860
tgatccccca tgttgtgcaa aaaagcggtt agctccttcg gtcctccgat cgttgtcaga 4920
agtaagttgg ccgcagtgtt atcactcatg gttatggcag cactgcataa ttctcttact 4980
gtcatgccat ccgtaagatg cttttctgtg actggtgagt actcaaccaa gtcattctga 5040
gaatagtgta tgcggcgacc gagttgctct tgcccggcgt caatacggga taataccgcg 5100
ccacatagca gaactttaaa agtgctcatc attggaaaac gttcttcggg gcgaaaactc 5160
tcaaggatct taccgctgtt gagatccagt tcgatgtaac ccactcgtgc acccaactga 5220
tcttcagcat cttttacttt caccagcgtt tctgggtgag caaaaacagg aaggcaaaat 5280
gccgcaaaaa agggaataag ggcgacacgg aaatgttgaa tactcatact cttccttttt 5340
caatattatt gaagcattta tcagggttat tgtctcatga gcggatacat atttgaatgt 5400
atttagaaaa ataaacaaat aggggttccg cgcacatttc cccgaaaagt gccacctgac 5460
gtctaagaaa ccattattat catgacatta acctataaaa ataggcgtat cacgaggccc 5520
tttcgtctcg cgcgtttcgg tgatgacggt gaaaacctct gacacatgca gctcccggag 5580
acggtcacag cttgtctgta agcggatgcc gggagcagac aagcccgtca gggcgcgtca 5640
gcgggtgttg gcgggtgtcg gggctggctt aactatgcgg catcagagca gattgtactg 5700
agagtgcacc atatgcggtg tgaaataccg cacagatgcg taaggagaaa ataccgcatc 5760
aggcgccatt cgccattcag gctgcgcaac tgttgggaag ggcgatcggt gcgggcctct 5820
tcgctattac gccagctggc gaaaggggga tgtgctgcaa ggcgattaag ttgggtaacg 5880
ccagggtttt cccagtcacg acgttgtaaa acgacggcca gtgaattcgt taagacccac 5940
tttcacattt aagttgtttt tctaatccgc atatgatcaa ttcaaggccg aataagaagg 6000
ctggctctgc accttggtga tcaaataatt cgatagcttg tcgtaataat ggcggcatac 6060
tatcagtagt aggtgtttcc ctttcttctt tagcgacttg atgctcttga tcttccaata 6120
cgcaacctaa agtaaaatgc cccacagcgc tgagtgcata taatgcattc tctagtgaaa 6180
aaccttgttg gcataaaaag gctaattgat tttcgagagt ttcatactgt ttttctgtag 6240
gccgtgtacc taaatgtact tttgctccat cgcgatgact tagtaaagca catctaaaac 6300
ttttagcgtt attacgtaaa aaatcttgcc agctttcccc ttctaaaggg caaaagtgag 6360
tatggtgcct atctaacatc tcaatggcta aggcgtcgag caaagcccgc ttattttta 6420 catgccaata caatgtaggc tgctctacac ctagcttctg ggcgagttta cgggttgtta 6480
aaccttcgat tccgacctca ttaagcagct ctaatgcgct gttaatcact ttacttttat 6540
ctaatctaga catcattaat tcctaatttt tgttgacact ctatcattga tagagttatt 6600
tt 6602

<210> SEQ ID NO 29
<211> LENGTH: 6497
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29
accactccct atcagtgata gagaaaagtg aactctagaa ataattttgt ttaactttaa 60
gaaggagata tacatatgaa agctaaagat gttcagccaa ccattattat taataaaaat 120
ggccttatct ctttggaaga tatctatgac attgcgataa aacaaaaaaa agtagaaata 180
tcaacggaga tcactgaact tttgacgcat ggtcgtgaaa aattagagga aaaattaaat 240
tcaggagagg ttatatatgg aatcaataca ggatttggag ggaatgccaa tttagttgtg 300
ccatttgaga aaatcgcaga gcatcagcaa aatctgttaa cttttctttc tgctggtact 360
ggggactata tgtccaaacc ttgtattaaa gcgtcacaat ttactatgtt actttctgtt 420
tgcaaaggtt ggtctgcaac cagaccaatt gtcgctcaag caattgttga tcatattaat 480
catgacattg ttcctctggt tcctcgctat ggctcagtgg gtgcaagcgg tgatttaatt 540
cctttatctt atattgcacg agcattatgt ggtatcggca aagtttatta tatgggcgca 600
gaaattgacg ctgctgaagc aattaaacgt gcagggttga caccattatc gttaaaagcc 660
aaagaaggtc ttgctctgat taacggcacc cgggtaatgt caggaatcag tgcaatcacc 720
gtcattaaac tggaaaaact atttaaagcc tcaatttctg cgattgccct tgctgttgaa 780
gcattacttg catctcatga acattatgat gcccggattc aacaagtaaa aaatcatcct 840
ggtcaaaacg cggtggcaag tgcattgcgt aatttattgg caggttcaac gcaggttaat 900
ctattatctg ggggttaaaga acaagccaat aaagcttgtc gtcatcaaga aattacccaa 960
ctaaatgata ccttacagga agtttattca attcgctgtg caccacaagt attaggtata 1020
gtgccagaat ctttagctac cgctcggaaa atattggaac gggaagttat ctcagctaat 1080
gataatccat tgatagatcc agaaaatggc gatgttctac acggtggaaa ttttatgggg 1140
caatatgtcg cccgaacaat ggatgcatta aaactggata ttgctttaat tgccaatcat 1200
cttcacgcca ttgtggctct tatgatggat aaccgtttct ctcgtggatt acctaattca 1260
ctgagtccga cacccggcat gtatcaaggt tttaaaggcg tccaactttc tcaaaccgct 1320
ttagttgctg caattcgcca tgattgtgct gcatcaggta ttcataccct cgccacagaa 1380
caatacaatc aagatattgt cagtttaggt ctgcatgccg ctcaagatgt tttagagatg 1440
gagcagaaat tacgcaatat tgtttcaatg acaattctgg tagtttgtca ggccattcat 1500
cttcgcggca atattagtga aattgcgcct gaaactgcta aattttacca tgcagtacgc 1560

-continued gaaatcagtt ctcctttgat cactgatcgt gcgttggatg aagatataat ccgcattgcg 1620
gatgcaatta ttaatgatca acttcctctg ccagaaatca tgctggaaga ataagcttgg 1680
cgtaatcatg gtcatagctg tttcctgtgt gaaattgtta tccgctcaca attccacaca 1740
acatacgagc cggaagcata aagtgtaaag cctggggtgc ctaatgagtg agctaactca 1800
cattaattgc gttgcgctca ctgcccgctt tccagtcggg aaacctgtcg tgccagctgc 1860
attaatgaat cggccaacgc gcggggagag gcggtttgcg tattgggcgc tcttccgctt 1920
cctcgctcac tgactcgctg cgctcggtcg ttcggctgcg gcgagcggta tcagctcact 1980
caaaggcggt agtacgggtt ttgctgcccg caaacgggct gttctggtgt tgctagtttg 2040
ttatcagaat cgcagatccg gcttcaggtt tgccggctga aagcgctatt tcttccagaa 2100
ttgccatgat tttttcccca cgggaggcgt cactggctcc cgtgttgtcg gcagctttga 2160
ttcgataagc agcatcgcct gtttcaggct gtctatgtgt gactgttgag ctgtaacaag 2220
ttgtctcagg tgttcaattt catgttctag ttgctttgtt ttactggttt cacctgttct 2280
attaggtgtt acatgctgtt catctgttac attgtcgatc tgttcatggt gaacagcttt 2340
aaatgcacca aaaactcgta aaagctctga tgtatctatc ttttttacac cgttttcatc 2400
tgtgcatatg gacagttttc cctttgatat ctaacggtga acagttgttc tacttttgtt 2460
tgttagtctt gatgcttcac tgatagatac aagagccata agaacctcag atccttccgt 2520
atttagccag tatgttctct agtgtggttc gttgtttttg cgtgagccat gagaacgaac 2580
cattgagatc atgcttactt tgcatgtcac tcaaaaattt tgcctcaaaa ctggtgagct 2640
gaatttttgc agttaaagca tcgtgtagtg tttttcttag tccgttacgt aggtaggaat 2700
ctgatgtaat ggttgttggt attttgtcac cattcatttt tatctggttg ttctcaagtt 2760
cggttacgag atccatttgt ctatctagtt caacttggaa aatcaacgta tcagtcgggc 2820
ggcctcgctt atcaaccacc aatttcatat tgctgtaagt gtttaaatct ttacttattg 2880
gtttcaaaac ccattggtta agccttttaa actcatggta gttattttca agcattaaca 2940
tgaacttaaa ttcatcaagg ctaatctcta tatttgcctt gtgagttttc ttttgtgtta 3000
gttcttttaa taaccactca taaatcctca tagagtattt gttttcaaaa gacttaacat 3060
gttccagatt atattttatg aattttttta actggaaaag ataaggcaat atctcttcac 3120
taaaaactaa ttctaatttt tcgcttgaga acttggcata gtttgtccac tggaaaatct 3180
caaagccttt aaccaaagga ttcctgattt ccacagttct cgtcatcagc tctctggttg 3240
ctttagctaa tacaccataa gcattttccc tactgatgtt catcatctga gcgtattggt 3300
tataagtgaa cgataccgtc cgttctttcc ttgtagggtt ttcaatcgtg gggttgagta 3360
gtgccacaca gcataaaatt agcttggttt catgctccgt taagtcatag cgactaatcg 3420
ctagttcatt tgctttgaaa acaactaatt cagacataca tctcaattgg tctaggtgat 3480
tttaatcact ataccaattg agatgggcta gtcaatgata attactagtc cttttccttt 3540
gagttgtggg tatctgtaaa ttctgctaga cctttgctgg aaaacttgta aattctgcta 3600
gaccctctgt aaattccgct agacctttgt gtgttttttt tgtttatatt caagtggtta 3660
taatttatag aataaagaaa gaataaaaaa agataaaaag aatagatccc agccctgtgt 3720
ataactcact actttagtca gttccgcagt attacaaaag gatgtcgcaa acgctgtttg 3780
ctcctctaca aaacagacct taaaacccta aaggcttaag tagcaccctc gcaagctcgg 3840
gcaaatcgct gaatattcct tttgtctccg accatcaggc acctgagtcg ctgtcttttt 3900
cgtgacattc agttcgctgc gctcacggct ctggcagtga atgggggtaa atggcactac 3960

-continued

```
aggcgccttt tatggattca tgcaaggaaa ctacccataa tacaagaaaa gcccgtcacg   4020
ggcttctcag ggcgttttat ggcgggtctg ctatgtggtg ctatctgact ttttgctgtt   4080
cagcagttcc tgccctctga ttttccagtc tgaccacttc ggattatccc gtgacaggtc   4140
attcagactg gctaatgcac ccagtaaggc agcggtatca tcaacaggct tacccgtctt   4200
actgtctttt ctacggggtc tgacgctcag tggaacgaaa actcacgtta agggattttg   4260
gtcatgagat tatcaaaaag gatcttcacc tagatccttt taaattaaaa atgaagtttt   4320
aaatcaatct aaagtatata tgagtaaact tggtctgaca gttaccaatg cttaatcagt   4380
gaggcaccta tctcagcgat ctgtctattt cgttcatcca tagttgcctg actccccgtc   4440
gtgtagataa ctacgatacg ggagggctta ccatctggcc ccagtgctgc aatgataccg   4500
cgagacccac gctcaccggc tccagattta tcagcaataa accagccagc cggaagggcc   4560
gagcgcagaa gtggtcctgc aactttatcc gcctccatcc agtctattaa ttgttgccgg   4620
gaagctagag taagtagttc gccagttaat agtttgcgca acgttgttgc cattgctaca   4680
ggcatcgtgg tgtcacgctc gtcgtttggt atggcttcat tcagctccgg ttcccaacga   4740
tcaaggcgag ttacatgatc ccccatgttg tgcaaaaaag cggttagctc cttcggtcct   4800
ccgatcgttg tcagaagtaa gttggccgca gtgttatcac tcatggttat ggcagcactg   4860
cataattctc ttactgtcat gccatccgta agatgctttt ctgtgactgg tgagtactca   4920
accaagtcat tctgagaata gtgtatgcgg cgaccgagtt gctcttgccc ggcgtcaata   4980
cgggataata ccgcgccaca tagcagaact ttaaaagtgc tcatcattgg aaaacgttct   5040
tcggggcgaa aactctcaag gatcttaccg ctgttgagat ccagttcgat gtaacccact   5100
cgtgcaccca actgatcttc agcatctttt actttcacca gcgtttctgg gtgagcaaaa   5160
acaggaaggc aaaatgccgc aaaaaaggga ataagggcga cacggaaatg ttgaatactc   5220
atactcttcc tttttcaata ttattgaagc atttatcagg gttattgtct catgagcgga   5280
tacatatttg aatgtattta gaaaaataaa caaatagggg ttccgcgcac atttccccga   5340
aaagtgccac ctgacgtcta agaaaccatt attatcatga cattaaccta taaaaatagg   5400
cgtatcacga ggccctttcg tctcgcgcgt ttcggtgatg acggtgaaaa cctctgacac   5460
atgcagctcc cggagacggt cacagcttgt ctgtaagcgg atgccgggag cagacaagcc   5520
cgtcagggcg cgtcagcggg tgttggcggg tgtcggggct ggcttaacta tgcggcatca   5580
gagcagattg tactgagagt gcaccatatg cggtgtgaaa taccgcacag atgcgtaagg   5640
agaaaatacc gcatcaggcg ccattcgcca ttcaggctgc gcaactgttg ggaagggcga   5700
tcggtgcggg cctcttcgct attacgccag ctggcgaaag ggggatgtgc tgcaaggcga   5760
ttaagttggg taacgccagg gttttcccag tcacgacgtt gtaaaacgac ggccagtgaa   5820
ttcgttaaga cccactttca catttaagtt gtttttctaa tccgcatatg atcaattcaa   5880
ggccgaataa gaaggctggc tctgcacctt ggtgatcaaa taattcgata gcttgtcgta   5940
ataatggcgg catactatca gtagtaggtg tttccctttc ttctttagcg acttgatgct   6000
cttgatcttc caatacgcaa cctaaagtaa aatgccccac agcgctgagt gcatataatg   6060
cattctctag tgaaaaacct tgttggcata aaaaggctaa ttgattttcg agagtttcat   6120
actgtttttc tgtaggccgt gtacctaaat gtacttttgc tccatcgcga tgacttagta   6180
aagcacatct aaaactttta gcgttattac gtaaaaaatc ttgccagctt tccccttcta   6240
aagggcaaaa gtgagtatgg tgcctatcta acatctcaat ggctaaggcg tcgagcaaag   6300
```

cccgcttatt ttttacatgc caatacaatg taggctgctc tacacctagc ttctgggcga 6360
gtttacgggt tgttaaacct tcgattccga cctcattaag cagctctaat gcgctgttaa 6420
tcactttact tttatctaat ctagacatca ttaattccta atttttgttg acactctatc 6480
attgatagag ttatttt 6497

<210> SEQ ID NO 30
<211> LENGTH: 2137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 30
ccagtgaatt cgttaagacc cactttcaca tttaagttgt ttttctaatc cgcatatgat 60
caattcaagg ccgaataaga aggctggctc tgcaccttgg tgatcaaata attcgatagc 120
ttgtcgtaat aatggcggca tactatcagt agtaggtgtt tccctttctt ctttagcgac 180
ttgatgctct tgatcttcca atacgcaacc taaagtaaaa tgccccacag cgctgagtgc 240
atataatgca ttctctagtg aaaaaccttg ttggcataaa aaggctaatt gattttcgag 300
agtttcatac tgtttttctg taggccgtgt acctaaatgt acttttgctc catcgcgatg 360
acttagtaaa gcacatctaa aacttttagc gttattacgt aaaaaatctt gccagctttc 420
cccttctaaa gggcaaaagt gagtatggtg cctatctaac atctcaatgg ctaaggcgtc 480
gagcaaagcc cgcttatttt ttacatgcca atacaatgta ggctgctcta cacctagctt 540
ctgggcgagt ttacgggttg ttaaaccttc gattccgacc tcattaagca gctctaatgc 600
gctgttaatc actttacttt tatctaatct agacatcatt aattcctaat ttttgttgac 660
actctatcat tgatagagtt attttaccac tccctatcag tgatagagaa aagtgaactc 720
tagaaataat tttgtttaac tttaagaagg agatatacat atgaaaaacg cgtcaaccgt 780
atcggaagat actgcgtcga atcaagagcc gacgcttcat cgcggattac ataaccgtca 840
tattcaactg attgcgttgg gtggcgcaat tggtactggt ctgtttcttg gcattggccc 900
ggcgattcag atggcgggtc cggctgtatt gctgggctac ggcgtcgccg ggatcatcgc 960
tttcctgatt atgcgccagc ttggcgaaat ggtggttgag gagccggtat ccggttcatt 1020
tgcccacttt gcctataaat actggggacc gtttgcgggc ttcctctctg gctggaacta 1080
ctgggtaatg ttcgtgctgg tgggaatggc agagctgacc gctgcgggca tctatatgca 1140
gtactggttc ccggatgttc caacgtggat ttgggctgcc gccttcttta ttatcatcaa 1200
cgccgttaac ctggtgaacg tgcgcttata tggcgaaacc gagttctggt ttgcgttgat 1260
taaagtgctg gcaatcatcg gtatgatcgg ctttggcctg tggctgctgt tttctggtca 1320
cggcggcgag aaagccagta tcgacaacct ctggcgctac ggtggtttct tcgccaccgg 1380
ctggaatggg ctgattttgt cgctggcggt aattatgttc tccttcggcg gtctggagct 1440
gattgggatt actgccgctg aagcgcgcga tccggaaaaa agcattccaa aagcggtaaa 1500
tcaggtggtg tatcgcatcc tgctgtttta catcggttca ctggtggttt tactggcgct 1560
ctatccgtgg gtggaagtga aatccaacag tagcccgttt gtgatgattt tccataatct 1620
cgacagcaac gtggtagctt ctgcgctgaa cttcgtcatt ctggtagcat cgctgtcagt 1680
gtataacagc ggggtttact ctaacagccg catgctgttt ggcctttctg tgcagggtaa 1740
tgcgccgaag tttttgactc gcgtcagccg tcgcggtgtg ccgattaact cgctgatgct 1800
ttccggagcg atcacttcgc tggtggtgtt aatcaactat ctgctgccgc aaaaagcgtt 1860
tggtctgctg atggcgctgg tggtagcaac gctgctgttg aactggatta tgatctgtct 1920
ggcgcatctg cgttttcgtg cagcgatgcg acgtcagggg cgtgaaacac agtttaaggc 1980
gctgctctat ccgttcggca actatctctg cattgccttc ctcggcatga ttttgctgct 2040
gatgtgcacg atggatgata tgcgcttgtc agcgatcctg ctgccggtgt ggattgtatt 2100
cctgtttatg gcatttaaaa cgctgcgtcg gaaataa 2137

<210> SEQ ID NO 31
<211> LENGTH: 3383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31
ggtaccgtca gcataacacc ctgacctctc attaattgtt catgccgggc ggcactatcg 60
tcgtccggcc ttttcctctc ttactctgct acgtacatct atttctataa atccgttcaa 120
tttgtctgtt ttttgcacaa acatgaaata tcagacaatt ccgtgactta agaaaattta 180
tacaaatcag caatataccc cttaaggagt atataaaggt gaatttgatt tacatcaata 240
agcggggttg ctgaatcgtt aaggtaggcg gtaatagaaa agaaatcgag gcaaaaatga 300
gcaaagtcag actcgcaatt atggatcctc tggccgtcgt attacaacgt cgtgactggg 360
aaaaccctgg cgttacccaa cttaatcgcc ttgcggcaca tccccctttc gccagctggc 420
gtaatagcga agaggcccgc accgatcgcc cttcccaaca gttgcgcagc ctgaatggcg 480
aatggcgctt tgcctggttt ccggcaccag aagcggtgcc ggaaagctgg ctggagtgcg 540
atcttcctga cgccgatact gtcgtcgtcc cctcaaactg gcagatgcac ggttacgatg 600
cgcctatcta caccaacgtg acctatccca ttacggtcaa tccgccgttt gttcccgcgg 660
agaatccgac aggttgttac tcgctcacat ttaatattga tgaaagctgg ctacaggaag 720
gccagacgcg aattattttt gatggcgtta actcggcgtt tcatctgtgg tgcaacgggc 780
gctgggtcgg ttacggccag gacagccgtt tgccgtctga atttgacctg agcgcatttt 840
tacgcgccgg agaaaaccgc ctcgcggtga tggtgctgcg ctggagtgac ggcagttatc 900
tggaagatca ggatatgtgg cggatgagcg gcattttccg tgacgtctcg ttgctgcata 960
aaccgaccac gcaaatcagc gatttccaag ttaccactct ctttaatgat gatttcagcc 1020
gcgcggtact ggaggcagaa gttcagatgt acggcgagct gcgcgatgaa ctgcgggtga 1080
cggtttcttt gtggcagggt gaaacgcagg tcgccagcgg caccgcgcct ttcggcggtg 1140
aaattatcga tgagcgtggc ggttatgccg atcgcgtcac actacgcctg aacgttgaaa 1200
atccggaact gtggagcgcc gaaatcccga atctctatcg tgcagtggtt gaactgcaca 1260
ccgccgacgg cacgctgatt gaagcagaag cctgcgacgt cggtttccgc gaggtgcgga 1320
ttgaaaatgg tctgctgctg ctgaacggca agccgttgct gattcgcggc gttaaccgtc 1380
acgagcatca tcctctgcat ggtcaggtca tggatgagca gacgatggtg caggatatcc 1440
tgctgatgaa gcagaacaac tttaacgccg tgcgctgttc gcattatccg aaccatccgc 1500
tgtggtacac gctgtgcgac cgctacggcc tgtatgtggt ggatgaagcc aatattgaaa 1560
cccacggcat ggtgccaatg aatcgtctga ccgatgatcc gcgctggcta cccgcgatga 1620
gcgaacgcgt aacgcggatg gtgcagcgcg atcgtaatca cccgagtgtg atcatctggt 1680
cgctggggaa tgaatcaggc cacggcgcta atcacgacgc gctgtatcgc tggatcaaat 1740
ctgtcgatcc ttcccgcccg gtacagtatg aaggcggcgg agccgacacc acggccaccg 1800
atattatttg cccgatgtac gcgcgcgtgg atgaagacca gcccttcccg gcggtgccga 1860
aatggtccat caaaaaatgg ctttcgctgc ctggagaaat gcgcccgctg atcctttgcg 1920
aatatgccca cgcgatgggt aacagtcttg gcggcttcgc taaatactgg caggcgtttc 1980
gtcagtaccc ccgtttacag ggcggcttcg tctgggactg ggtggatcag tcgctgatta 2040
aatatgatga aaacggcaac ccgtggtcgg cttacggcgg tgattttggc gatacgccga 2100
acgatcgcca gttctgtatg aacggtctgg tctttgccga ccgcacgccg catccggcgc 2160
tgacggaagc aaaacaccaa cagcagtatt tccagttccg tttatccggg cgaaccatcg 2220
aagtgaccag cgaatacctg ttccgtcata gcgataacga gttcctgcac tggatggtgg 2280
cactggatgg caagccgctg gcaagcggtg aagtgcctct ggatgttggc ccgcaaggta 2340
agcagttgat tgaactgcct gaactgccgc agccggagag cgccggacaa ctctggctaa 2400
cggtacgcgt agtgcaacca aacgcgaccg catggtcaga agccggacac atcagcgcct 2460
ggcagcaatg gcgtctggcg gaaaacctca gcgtgacact cccctccgcg tcccacgcca 2520
tccctcaact gaccaccagc ggaacggatt tttgcatcga gctgggtaat aagcgttggc 2580
aatttaaccg ccagtcaggc tttctttcac agatgtggat tggcgatgaa aaacaactgc 2640
tgaccccgct gcgcgatcag ttcacccgtg cgccgctgga taacgacatt ggcgtaagtg 2700
aagcgacccg cattgaccct aacgcctggg tcgaacgctg gaaggcggcg ggccattacc 2760
aggccgaagc ggcgttgttg cagtgcacgg cagatacact tgccgacgcg gtgctgatta 2820
caaccgccca cgcgtggcag catcagggga aaaccttatt tatcagccgg aaaacctacc 2880
ggattgatgg gcacggtgag atggtcatca atgtggatgt tgcggtggca agcgatacac 2940
cgcatccggc gcggattggc ctgacctgcc agctggcgca ggtctcagag cgggtaaact 3000
ggctcggcct ggggccgcaa gaaaactatc ccgaccgcct tactgcagcc tgttttgacc 3060
gctgggatct gccattgtca gacatgtata ccccgtacgt cttcccgagc gaaaacggtc 3120
tgcgctgcgg gacgcgcgaa ttgaattatg gcccacacca gtggcgcggc gacttccagt 3180
tcaacatcag ccgctacagc caacaacaac tgatggaaac cagccatcgc catctgctgc 3240
acgcggaaga aggcacatgg ctgaatatcg acggtttcca tatggggatt ggtggcgacg 3300
actcctggag cccgtcagta tcggcggaat tccagctgag cgccggtcgc taccattacc 3360
agttggtctg gtgtcaaaaa taa 3383

<210> SEQ ID NO 32
<211> LENGTH: 3258
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
ggtacccatt tcctctcatc ccatccgggg tgagagtctt ttcccccgac ttatggctca 60
tgcatgcatc aaaaaagatg tgagcttgat caaaaacaaa aaatatttca ctcgacagga 120
gtatttatat tgcgcccgtt acgtgggctt cgactgtaaa tcagaaagga gaaaacacct 180
atgacgacct acgatcggga tcctctggcc gtcgtattac aacgtcgtga ctgggaaaac 240
cctggcgtta cccaacttaa tcgccttgcg gcacatcccc ctttcgccag ctggcgtaat 300

-continued

```
agcgaagagg cccgcaccga tcgcccttcc caacagttgc gcagcctgaa tggcgaatgg    360
cgctttgcct ggtttccggc accagaagcg gtgccggaaa gctggctgga gtgcgatctt    420
cctgacgccg atactgtcgt cgtcccctca aactggcaga tgcacggtta cgatgcgcct    480
atctacacca acgtgaccta tcccattacg gtcaatccgc cgtttgttcc cgcggagaat    540
ccgacaggtt gttactcgct cacatttaat attgatgaaa gctggctaca ggaaggccag    600
acgcgaatta tttttgatgg cgttaactcg gcgtttcatc tgtggtgcaa cgggcgctgg    660
gtcggttacg gccaggacag ccgtttgccg tctgaatttg acctgagcgc atttttacgc    720
gccggagaaa accgcctcgc ggtgatggtg ctgcgctgga gtgacggcag ttatctggaa    780
gatcaggata tgtggcggat gagcggcatt ttccgtgacg tctcgttgct gcataaaccg    840
accacgcaaa tcagcgattt ccaagttacc actctcttta atgatgattt cagccgcgcg    900
gtactggagg cagaagttca gatgtacggc gagctgcgcg atgaactgcg ggtgacggtt    960
tctttgtggc agggtgaaac gcaggtcgcc agcggcaccg cgcctttcgg cggtgaaatt   1020
atcgatgagc gtggcggtta tgccgatcgc gtcacactac gcctgaacgt tgaaaatccg   1080
gaactgtgga gcgccgaaat cccgaatctc tatcgtgcag tggttgaact gcacaccgcc   1140
gacggcacgc tgattgaagc agaagcctgc gacgtcggtt tccgcgaggt gcggattgaa   1200
aatggtctgc tgctgctgaa cggcaagccg ttgctgattc gcggcgttaa ccgtcacgag   1260
catcatcctc tgcatggtca ggtcatggat gagcagacga tggtgcagga tatcctgctg   1320
atgaagcaga acaactttaa cgccgtgcgc tgttcgcatt atccgaacca tccgctgtgg   1380
tacacgctgt gcgaccgcta cggcctgtat gtggtggatg aagccaatat tgaaacccac   1440
ggcatggtgc caatgaatcg tctgaccgat gatccgcgct ggctacccgc gatgagcgaa   1500
cgcgtaacgc ggatggtgca gcgcgatcgt aatcacccga gtgtgatcat ctggtcgctg   1560
gggaatgaat caggccacgg cgctaatcac gacgcgctgt atcgctggat caaatctgtc   1620
gatccttccc gcccggtaca gtatgaaggc ggcggagccg acaccacggc caccgatatt   1680
atttgcccga tgtacgcgcg cgtggatgaa gaccagccct tcccggcggt gccgaaatgg   1740
tccatcaaaa aatggctttc gctgcctgga gaaatgcgcc cgctgatcct ttgcgaatat   1800
gcccacgcga tgggtaacag tcttggcggc ttcgctaaat actggcaggc gtttcgtcag   1860
tacccccgtt tacagggcgg cttcgtctgg gactgggtgg atcagtcgct gattaaatat   1920
gatgaaaacg gcaacccgtg gtcggcttac ggcggtgatt ttggcgatac gccgaacgat   1980
cgccagttct gtatgaacgg tctggtcttt gccgaccgca cgccgcatcc ggcgctgacg   2040
gaagcaaaac accaacagca gtatttccag ttccgtttat ccgggcgaac catcgaagtg   2100
accagcgaat acctgttccg tcatagcgat aacgagttcc tgcactggat ggtggcactg   2160
gatggcaagc cgctggcaag cggtgaagtg cctctggatg ttggcccgca aggtaagcag   2220
ttgattgaac tgcctgaact gccgcagccg gagagcgccg gacaactctg gctaacggta   2280
cgcgtagtgc aaccaaacgc gaccgcatgg tcagaagccg gacacatcag cgcctggcag   2340
caatggcgtc tggcggaaaa cctcagcgtg acactcccct ccgcgtccca cgccatccct   2400
caactgacca ccagcggaac ggatttttgc atcgagctgg gtaataagcg ttggcaattt   2460
aaccgccagt caggctttct ttcacagatg tggattggcg atgaaaaaca actgctgacc   2520
ccgctgcgcg atcagttcac ccgtgcgccg ctggataacg acattggcgt aagtgaagcg   2580
acccgcattg accctaacgc ctgggtcgaa cgctggaagg cggcgggcca ttaccaggcc   2640
gaagcggcgt tgttgcagtg cacggcagat acacttgccg acgcggtgct gattacaacc   2700
```

```
gcccacgcgt ggcagcatca ggggaaaacc ttatttatca gccggaaaac ctaccggatt   2760

gatgggcacg gtgagatggt catcaatgtg gatgttgcgg tggcaagcga tacaccgcat   2820

ccggcgcgga ttggcctgac ctgccagctg gcgcaggtct cagagcgggt aaactggctc   2880

ggcctggggc cgcaagaaaa ctatcccgac cgccttactg cagcctgttt tgaccgctgg   2940

gatctgccat tgtcagacat gtataccccg tacgtcttcc cgagcgaaaa cggtctgcgc   3000

tgcgggacgc gcgaattgaa ttatggccca caccagtggc gcggcgactt ccagttcaac   3060

atcagccgct acagccaaca acaactgatg gaaaccagcc atcgccatct gctgcacgcg   3120

gaagaaggca catggctgaa tatcgacggt ttccatatgg ggattggtgg cgacgactcc   3180

tggagcccgt cagtatcggc ggaattccag ctgagcgccg gtcgctacca ttaccagttg   3240

gtctggtgtc aaaaataa                                                 3258
```

<210> SEQ ID NO 33
<211> LENGTH: 3386
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33

```
ggtaccgtca gcataacacc ctgacctctc attaattgtt catgccgggc ggcactatcg     60

tcgtccggcc ttttcctctc ttactctgct acgtacatct atttctataa atccgttcaa    120

tttgtctgtt ttttgcacaa acatgaaata tcagacaatt ccgtgactta agaaaattta    180

tacaaatcag caatataccc cttaaggagt atataaaggt gaatttgatt tacatcaata    240

agcggggttg ctgaatcgtt aaggatccct ctagaaataa ttttgtttaa ctttaagaag    300

gagatataca tatgactatg attacggatt ctctggccgt cgtattacaa cgtcgtgact    360

gggaaaaccc tggcgttacc caacttaatc gccttgcggc acatccccct ttcgccagct    420

ggcgtaatag cgaagaggcc cgcaccgatc gcccttccca acagttgcgc agcctgaatg    480

gcgaatggcg ctttgcctgg tttccggcac cagaagcggt gccggaaagc tggctggagt    540

gcgatcttcc tgacgccgat actgtcgtcg tcccctcaaa ctggcagatg cacggttacg    600

atgcgcctat ctacaccaac gtgacctatc ccattacggt caatccgccg tttgttcccg    660

cggagaatcc gacaggttgt tactcgctca catttaatat tgatgaaagc tggctacagg    720

aaggccagac gcgaattatt tttgatggcg ttaactcggc gtttcatctg tggtgcaacg    780

ggcgctgggt cggttacggc caggacagcc gtttgccgtc tgaatttgac ctgagcgcat    840

ttttacgcgc cggagaaaac cgcctcgcgg tgatggtgct gcgctggagt gacggcagtt    900

atctggaaga tcaggatatg tggcggatga gcggcatttt ccgtgacgtc tcgttgctgc    960

ataaaccgac cacgcaaatc agcgatttcc aagttaccac tctctttaat gatgatttca   1020

gccgcgcggt actggaggca gaagttcaga tgtacggcga gctgcgcgat gaactgcggg   1080

tgacggtttc tttgtggcag ggtgaaacgc aggtcgccag cggcaccgcg cctttcggcg   1140

gtgaaattat cgatgagcgt ggcggttatg ccgatcgcgt cacactacgc ctgaacgttg   1200

aaaatccgga actgtggagc gccgaaatcc cgaatctcta tcgtgcagtg gttgaactgc   1260

acaccgccga cggcacgctg attgaagcag aagcctgcga cgtcggtttc cgcgaggtgc   1320

ggattgaaaa tggtctgctg ctgctgaacg gcaagccgtt gctgattcgc ggcgttaacc   1380

gtcacgagca tcatcctctg catggtcagg tcatggatga gcagacgatg gtgcaggata   1440
```

```
tcctgctgat gaagcagaac aactttaacg ccgtgcgctg ttcgcattat ccgaaccatc   1500
cgctgtggta cacgctgtgc gaccgctacg gcctgtatgt ggtggatgaa gccaatattg   1560
aaacccacgg catggtgcca atgaatcgtc tgaccgatga tccgcgctgg ctacccgcga   1620
tgagcgaacg cgtaacgcgg atggtgcagc gcgatcgtaa tcacccgagt gtgatcatct   1680
ggtcgctggg gaatgaatca ggccacggcg ctaatcacga cgcgctgtat cgctggatca   1740
aatctgtcga tccttcccgc ccggtacagt atgaaggcgg cggagccgac accacggcca   1800
ccgatattat ttgcccgatg tacgcgcgcg tggatgaaga ccagcccttc ccggcggtgc   1860
cgaaatggtc catcaaaaaa tggctttcgc tgcctggaga aatgcgcccg ctgatccttt   1920
gcgaatatgc ccacgcgatg ggtaacagtc ttggcggctt cgctaaatac tggcaggcgt   1980
ttcgtcagta cccccgttta cagggcggct tcgtctggga ctgggtggat cagtcgctga   2040
ttaaatatga tgaaaacggc aacccgtggt cggcttacgg cggtgatttt ggcgatacgc   2100
cgaacgatcg ccagttctgt atgaacggtc tggtctttgc cgaccgcacg ccgcatccgg   2160
cgctgacgga agcaaaacac caacagcagt atttccagtt ccgtttatcc gggcgaacca   2220
tcgaagtgac cagcgaatac ctgttccgtc atagcgataa cgagttcctg cactggatgg   2280
tggcactgga tggcaagccg ctggcaagcg gtgaagtgcc tctggatgtt ggcccgcaag   2340
gtaagcagtt gattgaactg cctgaactgc cgcagccgga gagcgccgga caactctggc   2400
taacggtacg cgtagtgcaa ccaaacgcga ccgcatggtc agaagccgga cacatcagcg   2460
cctggcagca atggcgtctg gcggaaaacc tcagcgtgac actcccctcc gcgtcccacg   2520
ccatccctca actgaccacc agcggaacgg atttttgcat cgagctgggt aataagcgtt   2580
ggcaatttaa ccgccagtca ggctttcttt cacagatgtg gattggcgat gaaaaacaac   2640
tgctgacccc gctgcgcgat cagttcaccc gtgcgccgct ggataacgac attggcgtaa   2700
gtgaagcgac ccgcattgac cctaacgcct gggtcgaacg ctggaaggcg gcgggccatt   2760
accaggccga agcggcgttg ttgcagtgca cggcagatac acttgccgac gcggtgctga   2820
ttacaaccgc ccacgcgtgg cagcatcagg ggaaaacctt atttatcagc cggaaaacct   2880
accggattga tgggcacggt gagatggtca tcaatgtgga tgttgcggtg gcaagcgata   2940
caccgcatcc ggcgcggatt ggcctgacct gccagctggc gcaggtctca gagcgggtaa   3000
actggctcgg cctggggccg caagaaaact atcccgaccg ccttactgca gcctgttttg   3060
accgctggga tctgccattg tcagacatgt ataccccgta cgtcttcccg agcgaaaacg   3120
gtctgcgctg cgggacgcgc gaattgaatt atggcccaca ccagtggcgc ggcgacttcc   3180
agttcaacat cagccgctac agccaacaac aactgatgga aaccagccat cgccatctgc   3240
tgcacgcgga agaaggcaca tggctgaata tcgacggttt ccatatgggg attggtggcg   3300
acgactcctg gagcccgtca gtatcggcgg aattccagct gagcgccggt cgctaccatt   3360
accagttggt ctggtgtcaa aaataa                                        3386
```

<210> SEQ ID NO 34
<211> LENGTH: 3261
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
ggtacccatt tcctctcatc ccatccgggg tgagagtctt ttcccccgac ttatggctca     60
```

-continued

```
tgcatgcatc aaaaaagatg tgagcttgat caaaaacaaa aaatatttca ctcgacagga    120
gtatttatat tgcgcccgga tccctctaga aataattttg tttaacttta agaaggagat    180
atacatatga ctatgattac ggattctctg gccgtcgtat tacaacgtcg tgactgggaa    240
aaccctggcg ttacccaact taatcgcctt gcggcacatc ccccttcgc cagctggcgt    300
aatagcgaag aggcccgcac cgatcgccct tcccaacagt tgcgcagcct gaatggcgaa    360
tggcgctttg cctggtttcc ggcaccagaa gcggtgccgg aaagctggct ggagtgcgat    420
cttcctgacg ccgatactgt cgtcgtcccc tcaaactggc agatgcacgg ttacgatgcg    480
cctatctaca ccaacgtgac ctatcccatt acggtcaatc cgccgtttgt tcccgcggag    540
aatccgacag gttgttactc gctcacattt aatattgatg aaagctggct acaggaaggc    600
cagacgcgaa ttatttttga tggcgttaac tcggcgtttc atctgtggtg caacgggcgc    660
tgggtcggtt acggccagga cagccgtttg ccgtctgaat ttgacctgag cgcattttta    720
cgcgccggag aaaaccgcct cgcggtgatg gtgctgcgct ggagtgacgg cagttatctg    780
gaagatcagg atatgtggcg gatgagcggc attttccgtg acgtctcgtt gctgcataaa    840
ccgaccacgc aaatcagcga tttccaagtt accactctct ttaatgatga tttcagccgc    900
gcggtactgg aggcagaagt tcagatgtac ggcgagctgc gcgatgaact gcgggtgacg    960
gtttctttgt ggcagggtga aacgcaggtc gccagcggca ccgcgccttt cggcggtgaa   1020
attatcgatg agcgtggcgg ttatgccgat cgcgtcacac tacgcctgaa cgttgaaaat   1080
ccggaactgt ggagcgccga aatcccgaat ctctatcgtg cagtggttga actgcacacc   1140
gccgacggca cgctgattga agcagaagcc tgcgacgtcg gtttccgcga ggtgcggatt   1200
gaaaatggtc tgctgctgct gaacggcaag ccgttgctga ttcgcggcgt taaccgtcac   1260
gagcatcatc ctctgcatgg tcaggtcatg gatgagcaga cgatggtgca ggatatcctg   1320
ctgatgaagc agaacaactt taacgccgtg cgctgttcgc attatccgaa ccatccgctg   1380
tggtacacgc tgtgcgaccg ctacggcctg tatgtggtgg atgaagccaa tattgaaacc   1440
cacggcatgg tgccaatgaa tcgtctgacc gatgatccgc gctggctacc cgcgatgagc   1500
gaacgcgtaa cgcggatggt gcagcgcgat cgtaatcacc cgagtgtgat catctggtcg   1560
ctggggaatg aatcaggcca cggcgctaat cacgacgcgc tgtatcgctg gatcaaatct   1620
gtcgatcctt cccgcccggt acagtatgaa ggcggcggag ccgacaccac ggccaccgat   1680
attatttgcc cgatgtacgc gcgcgtggat gaagaccagc ccttcccggc ggtgccgaaa   1740
tggtccatca aaaaatggct ttcgctgcct ggagaaatgc gcccgctgat cctttgcgaa   1800
tatgcccacg cgatgggtaa cagtcttggc ggcttcgcta aatactggca ggcgtttcgt   1860
cagtaccccc gtttacaggg cggcttcgtc tgggactggg tggatcagtc gctgattaaa   1920
tatgatgaaa acggcaaccc gtggtcggct tacggcggtg attttggcga tacgccgaac   1980
gatcgccagt tctgtatgaa cggtctggtc tttgccgacc gcacgccgca tccggcgctg   2040
acggaagcaa aacaccaaca gcagtatttc cagttccgtt tatccgggcg aaccatcgaa   2100
gtgaccagcg aatacctgtt ccgtcatagc gataacgagt tcctgcactg gatggtggca   2160
ctggatggca agccgctggc aagcggtgaa gtgcctctgg atgttggccc gcaaggtaag   2220
cagttgattg aactgcctga actgccgcag ccggagagcg ccggacaact ctggctaacg   2280
gtacgcgtag tgcaaccaaa cgcgaccgca tggtcagaag ccggacacat cagcgcctgg   2340
cagcaatggc gtctggcgga aaacctcagc gtgacactcc cctccgcgtc ccacgccatc   2400
```

```
cctcaactga ccaccagcgg aacggatttt tgcatcgagc tgggtaataa gcgttggcaa   2460

tttaaccgcc agtcaggctt tctttcacag atgtggattg gcgatgaaaa acaactgctg   2520

accccgctgc gcgatcagtt cacccgtgcg ccgctggata acgacattgg cgtaagtgaa   2580

gcgacccgca ttgaccctaa cgcctgggtc gaacgctgga aggcggcggg ccattaccag   2640

gccgaagcgg cgttgttgca gtgcacggca gatacacttg ccgacgcggt gctgattaca   2700

accgcccacg cgtggcagca tcaggggaaa accttattta tcagccggaa aacctaccgg   2760

attgatgggc acggtgagat ggtcatcaat gtggatgttg cggtggcaag cgatacaccg   2820

catccggcgc ggattggcct gacctgccag ctggcgcagg tctcagagcg ggtaaactgg   2880

ctcggcctgg ggccgcaaga aaactatccc gaccgcctta ctgcagcctg ttttgaccgc   2940

tgggatctgc cattgtcaga catgtatacc ccgtacgtct tcccgagcga aaacggtctg   3000

cgctgcggga cgcgcgaatt gaattatggc ccacaccagt ggcgcggcga cttccagttc   3060

aacatcagcc gctacagcca acaacaactg atggaaacca gccatcgcca tctgctgcac   3120

gcggaagaag gcacatggct gaatatcgac ggtttccata tggggattgg tggcgacgac   3180

tcctggagcc cgtcagtatc ggcggaattc cagctgagcg ccggtcgcta ccattaccag   3240

ttggtctggt gtcaaaaata a                                              3261
```

<210> SEQ ID NO 35
<211> LENGTH: 3279
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ggtaccagtt gttcttattg gtggtgttgc tttatggttg catcgtagta aatggttgta     60

acaaaagcaa tttttccggc tgtctgtata caaaaacgcc gtaaagtttg agcgaagtca    120

ataaactctc tacccattca gggcaatatc tctcttggat ccctctagaa ataattttgt    180

ttaactttaa gaaggagata tacatatgct atgattacgg attctctggc cgtcgtatta    240

caacgtcgtg actgggaaaa ccctggcgtt acccaactta atcgccttgc ggcacatccc    300

cctttcgcca gctggcgtaa tagcgaagag gcccgcaccg atcgcccttc ccaacagttg    360

cgcagcctga atggcgaatg gcgctttgcc tggtttccgg caccagaagc ggtgccggaa    420

agctggctgg agtgcgatct tcctgacgcc gatactgtcg tcgtcccctc aaactggcag    480

atgcacggtt acgatgcgcc tatctacacc aacgtgacct atcccattac ggtcaatccg    540

ccgtttgttc ccgcggagaa tccgacaggt tgttactcgc tcacatttaa tattgatgaa    600

agctggctac aggaaggcca gacgcgaatt atttttgatg gcgttaactc ggcgtttcat    660

ctgtggtgca acgggcgctg ggtcggttac ggccaggaca gccgtttgcc gtctgaattt    720

gacctgagcg catttttacg cgccggagaa aaccgcctcg cggtgatggt gctgcgctgg    780

agtgacggca gttatctgga agatcaggat atgtggcgga tgagcggcat tttccgtgac    840

gtctcgttgc tgcataaacc gaccacgcaa atcagcgatt tccaagttac cactctcttt    900

aatgatgatt tcagccgcgc ggtactggag gcagaagttc agatgtacgg cgagctgcgc    960

gatgaactgc gggtgacggt ttctttgtgg cagggtgaaa cgcaggtcgc cagcggcacc   1020

gcgcctttcg gcggtgaaat tatcgatgag cgtggcggtt atgccgatcg cgtcacacta   1080

cgcctgaacg ttgaaaatcc ggaactgtgg agcgccgaaa tcccgaatct ctatcgtgca   1140
```

-continued

```
gtggttgaac tgcacaccgc cgacggcacg ctgattgaag cagaagcctg cgacgtcggt   1200
ttccgcgagg tgcggattga aaatggtctg ctgctgctga acggcaagcc gttgctgatt   1260
cgcggcgtta accgtcacga gcatcatcct ctgcatggtc aggtcatgga tgagcagacg   1320
atggtgcagg atatcctgct gatgaagcag aacaacttta acgccgtgcg ctgttcgcat   1380
tatccgaacc atccgctgtg gtacacgctg tgcgaccgct acggcctgta tgtggtggat   1440
gaagccaata ttgaaaccca cggcatggtg ccaatgaatc gtctgaccga tgatccgcgc   1500
tggctacccg cgatgagcga acgcgtaacg cggatggtgc agcgcgatcg taatcacccg   1560
agtgtgatca tctggtcgct ggggaatgaa tcaggccacg gcgctaatca cgacgcgctg   1620
tatcgctgga tcaaatctgt cgatccttcc cgcccggtac agtatgaagg cggcggagcc   1680
gacaccacgg ccaccgatat tatttgcccg atgtacgcgc gcgtggatga agaccagccc   1740
ttcccggcgg tgccgaaatg gtccatcaaa aaatggcttt cgctgcctgg agaaatgcgc   1800
ccgctgatcc tttgcgaata tgcccacgcg atgggtaaca gtcttggcgg cttcgctaaa   1860
tactggcagg cgtttcgtca gtacccccgt ttacagggcg gcttcgtctg ggactgggtg   1920
gatcagtcgc tgattaaata tgatgaaaac ggcaacccgt ggtcggctta cggcggtgat   1980
tttggcgata cgccgaacga tcgccagttc tgtatgaacg gtctggtctt tgccgaccgc   2040
acgccgcatc cggcgctgac ggaagcaaaa caccaacagc agtatttcca gttccgttta   2100
tccgggcgaa ccatcgaagt gaccagcgaa tacctgttcc gtcatagcga taacgagttc   2160
ctgcactgga tggtggcact ggatggcaag ccgctggcaa gcggtgaagt gcctctggat   2220
gttggcccgc aaggtaagca gttgattgaa ctgcctgaac tgccgcagcc ggagagcgcc   2280
ggacaactct ggctaacggt acgcgtagtg caaccaaacg cgaccgcatg gtcagaagcc   2340
ggacacatca gcgcctggca gcaatggcgt ctggcggaaa acctcagcgt gacactcccc   2400
tccgcgtccc acgccatccc tcaactgacc accagcggaa cggatttttg catcgagctg   2460
ggtaataagc gttggcaatt taaccgccag tcaggctttc tttcacagat gtggattggc   2520
gatgaaaaac aactgctgac cccgctgcgc gatcagttca cccgtgcgcc gctggataac   2580
gacattggcg taagtgaagc gacccgcatt gaccctaacg cctgggtcga acgctggaag   2640
gcggcgggcc attaccaggc cgaagcggcg ttgttgcagt gcacggcaga tacacttgcc   2700
gacgcggtgc tgattacaac cgcccacgcg tggcagcatc aggggaaaac cttatttatc   2760
agccggaaaa cctaccggat tgatgggcac ggtgagatgg tcatcaatgt ggatgttgcg   2820
gtggcaagcg atacaccgca tccggcgcgg attggcctga cctgccagct ggcgcaggtc   2880
tcagagcggg taaactggct cggcctgggg ccgcaagaaa actatcccga ccgccttact   2940
gcagcctgtt ttgaccgctg ggatctgcca ttgtcagaca tgtatacccc gtacgtcttc   3000
ccgagcgaaa acggtctgcg ctgcgggacg cgcgaattga attatggccc acaccagtgg   3060
cgcggcgact tccagttcaa catcagccgc tacagccaac aacaactgat ggaaaccagc   3120
catcgccatc tgctgcacgc ggaagaaggc acatggctga atatcgacgg tttccatatg   3180
gggattggtg gcgacgactc ctggagcccg tcagtatcgg cggaattcca gctgagcgcc   3240
ggtcgctacc attaccagtt ggtctggtgt caaaaataa                          3279
```

<210> SEQ ID NO 36
<211> LENGTH: 1910
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36
ggtaccgtca gcataacacc ctgacctctc attaattgtt catgccgggc ggcactatcg 60
tcgtccggcc ttttcctctc ttactctgct acgtacatct atttctataa atccgttcaa 120
tttgtctgtt ttttgcacaa acatgaaata tcagacaatt ccgtgactta agaaaattta 180
tacaaatcag caatataccc cttaaggagt atataaaggt gaatttgatt tacatcaata 240
agcggggttg ctgaatcgtt aaggatccct ctagaaataa ttttgtttaa ctttaagaag 300
gagatataca tatgaaagct aaagatgttc agccaaccat tattattaat aaaaatggcc 360
ttatctcttt ggaagatatc tatgacattg cgataaaaca aaaaaaagta gaaatatcaa 420
cggagatcac tgaacttttg acgcatggtc gtgaaaaatt agaggaaaaa ttaaattcag 480
gagaggttat atatggaatc aatacaggat ttggagggaa tgccaattta gttgtgccat 540
ttgagaaaat cgcagagcat cagcaaaatc tgttaacttt tctttctgct ggtactgggg 600
actatatgtc caaaccttgt attaaagcgt cacaatttac tatgttactt tctgtttgca 660
aaggttggtc tgcaaccaga ccaattgtcg ctcaagcaat tgttgatcat attaatcatg 720
acattgttcc tctggttcct cgctatggct cagtgggtgc aagcggtgat ttaattcctt 780
tatcttatat tgcacgagca ttatgtggta tcggcaaagt ttattatatg ggcgcagaaa 840
ttgacgctgc tgaagcaatt aaacgtgcag ggttgacacc attatcgtta aaagccaaag 900
aaggtcttgc tctgattaac ggcacccggg taatgtcagg aatcagtgca atcaccgtca 960
ttaaactgga aaaactattt aaagcctcaa tttctgcgat tgcccttgct gttgaagcat 1020
tacttgcatc tcatgaacat tatgatgccc ggattcaaca agtaaaaaat catcctggtc 1080
aaaacgcggt ggcaagtgca ttgcgtaatt tattggcagg ttcaacgcag gttaatctat 1140
tatctggggt taaagaacaa gccaataaag cttgtcgtca tcaagaaatt acccaactaa 1200
atgatacctt acaggaagtt tattcaattc gctgtgcacc acaagtatta ggtatagtgc 1260
cagaatcttt agctaccgct cggaaaatat tggaacggga agttatctca gctaatgata 1320
atccattgat agatccagaa aatggcgatg ttctacacgg tggaaatttt atggggcaat 1380
atgtcgcccg aacaatggat gcattaaaac tggatattgc tttaattgcc aatcatcttc 1440
acgccattgt ggctcttatg atggataacc gtttctctcg tggattacct aattcactga 1500
gtccgacacc cggcatgtat caaggtttta aaggcgtcca actttctcaa accgctttag 1560
ttgctgcaat tcgccatgat tgtgctgcat caggtattca taccctcgcc acagaacaat 1620
acaatcaaga tattgtcagt ttaggtctgc atgccgctca agatgtttta gagatggagc 1680
agaaattacg caatattgtt tcaatgacaa ttctggtagt ttgtcaggcc attcatcttc 1740
gcggcaatat tagtgaaatt gcgcctgaaa ctgctaaatt ttaccatgca gtacgcgaaa 1800
tcagttctcc tttgatcact gatcgtgcgt tggatgaaga tataatccgc attgcggatg 1860
caattattaa tgatcaactt cctctgccag aaatcatgct ggaagaataa 1910

<210> SEQ ID NO 37
<211> LENGTH: 1785
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37

-continued

```
ggtacccatt tcctctcatc ccatccgggg tgagagtctt ttcccccgac ttatggctca     60
tgcatgcatc aaaaaagatg tgagcttgat caaaaacaaa aaatatttca ctcgacagga    120
gtatttatat tgcgcccgga tccctctaga aataattttg tttaacttta agaaggagat    180
atacatatga aagctaaaga tgttcagcca accattatta ttaataaaaa tggccttatc    240
tctttggaag atatctatga cattgcgata aaacaaaaaa aagtagaaat atcaacggag    300
atcactgaac ttttgacgca tggtcgtgaa aaattagagg aaaaattaaa ttcaggagag    360
gttatatatg gaatcaatac aggatttgga gggaatgcca atttagttgt gccatttgag    420
aaaatcgcag agcatcagca aaatctgtta actttttcttt ctgctggtac tggggactat    480
atgtccaaac cttgtattaa agcgtcacaa tttactatgt tactttctgt ttgcaaaggt    540
tggtctgcaa ccagaccaat tgtcgctcaa gcaattgttg atcatattaa tcatgacatt    600
gttcctctgg ttcctcgcta tggctcagtg ggtgcaagcg gtgatttaat tcctttatct    660
tatattgcac gagcattatg tggtatcggc aaagtttatt atatgggcgc agaaattgac    720
gctgctgaag caattaaacg tgcagggttg acaccattat cgttaaaagc caaagaaggt    780
cttgctctga ttaacggcac ccgggtaatg tcaggaatca gtgcaatcac cgtcattaaa    840
ctggaaaaac tatttaaagc ctcaatttct gcgattgccc ttgctgttga agcattactt    900
gcatctcatg aacattatga tgcccggatt caacaagtaa aaaatcatcc tggtcaaaac    960
gcggtggcaa gtgcattgcg taatttattg gcaggttcaa cgcaggttaa tctattatct   1020
ggggttaaag aacaagccaa taaagcttgt cgtcatcaag aaattaccca actaaatgat   1080
accttacagg aagtttattc aattcgctgt gcaccacaag tattaggtat agtgccagaa   1140
tctttagcta ccgctcggaa aatattggaa cgggaagtta tctcagctaa tgataatcca   1200
ttgatagatc cagaaaatgg cgatgttcta cacggtggaa attttatggg gcaatatgtc   1260
gcccgaacaa tggatgcatt aaaactggat attgctttaa ttgccaatca tcttcacgcc   1320
attgtggctc ttatgatgga taaccgtttc tctcgtggat tacctaattc actgagtccg   1380
acacccggca tgtatcaagg ttttaaaggc gtccaacttt ctcaaaccgc tttagttgct   1440
gcaattcgcc atgattgtgc tgcatcaggt attcataccc tcgccacaga acaatacaat   1500
caagatattg tcagtttagg tctgcatgcc gctcaagatg ttttagagat ggagcagaaa   1560
ttacgcaata ttgtttcaat gacaattctg gtagtttgtc aggccattca tcttcgcggc   1620
aatattagtg aaattgcgcc tgaaactgct aaattttacc atgcagtacg cgaaatcagt   1680
tctcctttga tcactgatcg tgcgttggat gaagatataa tccgcattgc ggatgcaatt   1740
attaatgatc aacttcctct gccagaaatc atgctggaag aataa                   1785
```

<210> SEQ ID NO 38
<211> LENGTH: 1804
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38

```
ggtaccagtt gttcttattg gtggtgttgc tttatggttg catcgtagta aatggttgta     60
acaaaagcaa tttttccggc tgtctgtata caaaaacgcc gtaaagtttg agcgaagtca    120
ataaactctc tacccattca gggcaatatc tctcttggat ccctctagaa ataattttgt    180
ttaactttaa gaaggagata tacatatgaa agctaaagat gttcagccaa ccattattat    240
```

```
taataaaaat ggccttatct ctttggaaga tatctatgac attgcgataa aacaaaaaaa    300

agtagaaata tcaacggaga tcactgaact tttgacgcat ggtcgtgaaa aattagagga    360

aaaattaaat tcaggagagg ttatatatgg aatcaataca ggatttggag ggaatgccaa    420

tttagttgtg ccatttgaga aaatcgcaga gcatcagcaa aatctgttaa cttttctttc    480

tgctggtact ggggactata tgtccaaacc ttgtattaaa gcgtcacaat ttactatgtt    540

actttctgtt tgcaaaggtt ggtctgcaac cagaccaatt gtcgctcaag caattgttga    600

tcatattaat catgacattg ttcctctggt tcctcgctat ggctcagtgg gtgcaagcgg    660

tgatttaatt cctttatctt atattgcacg agcattatgt ggtatcggca aagtttatta    720

tatgggcgca gaaattgacg ctgctgaagc aattaaacgt gcagggttga caccattatc    780

gttaaaagcc aaagaaggtc ttgctctgat taacggcacc cgggtaatgt caggaatcag    840

tgcaatcacc gtcattaaac tggaaaaact atttaaagcc tcaatttctg cgattgccct    900

tgctgttgaa gcattacttg catctcatga acattatgat gcccggattc aacaagtaaa    960

aaatcatcct ggtcaaaacg cggtggcaag tgcattgcgt aatttattgg caggttcaac   1020

gcaggttaat ctattatctg ggttaaaga acaagccaat aaagcttgtc gtcatcaaga   1080

aattacccaa ctaaatgata ccttacagga agtttattca attcgctgtg caccacaagt   1140

attaggtata gtgccagaat ctttagctac cgctcggaaa atattggaac gggaagttat   1200

ctcagctaat gataatccat tgatagatcc agaaaatggc gatgttctac acggtggaaa   1260

ttttatgggg caatatgtcg cccgaacaat ggatgcatta aaactggata ttgctttaat   1320

tgccaatcat cttcacgcca ttgtggctct tatgatggat aaccgtttct ctcgtggatt   1380

acctaattca ctgagtccga cacccggcat gtatcaaggt tttaaaggcg tccaactttc   1440

tcaaaccgct ttagttgctg caattcgcca tgattgtgct gcatcaggta ttcataccct   1500

cgccacagaa caatacaatc aagatattgt cagtttaggt ctgcatgccg ctcaagatgt   1560

tttagagatg gagcagaaat tacgcaatat tgtttcaatg acaattctgg tagtttgtca   1620

ggccattcat cttcgcggca atattagtga aattgcgcct gaaactgcta aattttacca   1680

tgcagtacgc gaaatcagtt ctcctttgat cactgatcgt gcgttggatg aagatataat   1740

ccgcattgcg gatgcaatta ttaatgatca acttcctctg ccagaaatca tgctggaaga   1800

ataa                                                                1804
```

<210> SEQ ID NO 39
<211> LENGTH: 2170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
ttaagaccca ctttcacatt taagttgttt ttctaatccg catatgatca attcaaggcc     60

gaataagaag gctggctctg caccttggtg atcaaataat tcgatagctt gtcgtaataa    120

tggcggcata ctatcagtag taggtgtttc cctttcttct ttagcgactt gatgctcttg    180

atcttccaat acgcaaccta aagtaaaatg ccccacagcg ctgagtgcat ataatgcatt    240

ctctagtgaa aaaccttgtt ggcataaaaa ggctaattga ttttcgagag tttcatactg    300

tttttctgta ggccgtgtac ctaaatgtac ttttgctcca tcgcgatgac ttagtaaagc    360

acatctaaaa cttttagcgt tattacgtaa aaaatcttgc cagctttccc cttctaaagg    420
```

-continued gcaaaagtga gtatggtgcc tatctaacat ctcaatggct aaggcgtcga gcaaagcccg 480
cttatttttt acatgccaat acaatgtagg ctgctctaca cctagcttct gggcgagttt 540
acgggttgtt aaaccttcga ttccgacctc attaagcagc tctaatgcgc tgttaatcac 600
tttactttta tctaatctag acatcattaa ttcctaattt ttgttgacac tctatcattg 660
atagagttat tttaccactc cctatcagtg atagagaaaa gtgaactcta gaaataattt 720
tgtttaactt taagaaggag atatacatat gaacatttca aggagaaagc tacttttagg 780
tgttggtgct gcgggcgttt tagcaggtgg tgcggcttta gttccaatgg ttcgccgtga 840
cggcaaattt gtggaagcta aatcaagagc atcatttgtt gaaggtacgc aaggggctct 900
tcctaaagaa gcagatgtag tgattattgg tgccggtatt caagggatca tgaccgctat 960
taaccttgct gaacgtggta tgagtgtcac tatcttagaa aagggtcaga ttgccggtga 1020
gcaatcaggc cgtgcataca gccaaattat tagttaccaa acatcgccag aaatcttccc 1080
attacaccat tatgggaaaa tattatggcg tggcatgaat gagaaaattg gtgcggatac 1140
cagttatcgt actcaaggtc gtgtagaagc gctggcagat gaaaaagcat tagataaagc 1200
tcaagcgtgg atcaaaacag ctaaagaagc ggcaggtttt gatacaccat taaatactcg 1260
catcattaaa ggtgaagagc tatcaaatcg cttagtcggt gctcaaacgc catggactgt 1320
tgctgcattt gaagaagatt caggctctgt tgatcctgaa acaggcacac ctgcactcgc 1380
tcgttatgcc aaacaaatcg gtgtgaaaat ttataccaac tgtgcagtaa gaggtattga 1440
aactgcgggt ggtaaaatct ctgatgtggt gagtgagaaa ggggcgatta aaacgtctca 1500
agttgtactc gctgggggta tctggtcgcg tttatttatg ggcaatatgg gtattgatat 1560
cccaacgctc aatgtatatc tatcacaaca acgtgtctca ggggttcctg gtgcaccacg 1620
tggtaatgtg catttaccta atggtattca tttccgcgaa caagcggatg gtacttatgc 1680
cgttgcacca cgtatcttta cgagttcaat agtcaaagat agcttcctgc tagggcctaa 1740
atttatgcac ttattaggtg gcggagagtt accgttggaa ttctctattg gtgaagatct 1800
atttaattca tttaaaatgc cgacctcttg gaatttagat gaaaaaacac cattcgaaca 1860
attccgagtt gccacggcaa cacaaaatac gcaacactta gatgctgttt tccaaagaat 1920
gaaaacagaa ttcccagtat ttgaaaaatc agaagttgtt gaacgttggg gtgccgttgt 1980
gagtccaaca tttgatgaat tacctatcat ttctgaggtc aaagaatacc caggcttagt 2040
gattaacacg gcaacagtgt ggggtatgac agaaggcccg gcagcgggtg aagtgaccgc 2100
tgatattgtc atgggcaaga aacctgttat tgatccaacg ccgtttagtt tggatcgttt 2160
taagaagtaa 2170

<210> SEQ ID NO 40
<211> LENGTH: 2624
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
ttattcacaa cctgccctaa actcgctcgg actcgccccg gtgcattttt taaatactcg 60
cgagaaatag agttgatcgt caaaaccgac attgcgaccg acggtggcga taggcatccg 120
ggtggtgctc aaaagcagct tcgcctgact gatgcgctgg tcctcgcgcc agcttaatac 180
gctaatccct aactgctggc ggaacaaatg cgacagacgc gacggcgaca ggcagacatg 240

-continued

```
ctgtgcgacg ctggcgatat caaaattact gtctgccagg tgatcgctga tgtactgaca    300
agcctcgcgt acccgattat ccatcggtgg atggagcgac tcgttaatcg cttccatgcg    360
ccgcagtaac aattgctcaa gcagatttat cgccagcaat tccgaatagc gcccttcccc    420
ttgtccggca ttaatgattt gcccaaacag gtcgctgaaa tgcggctggt gcgcttcatc    480
cgggcgaaag aaaccggtat tggcaaatat cgacggccag ttaagccatt catgccagta    540
ggcgcgcgga cgaaagtaaa cccactggtg ataccattcg tgagcctccg gatgacgacc    600
gtagtgatga atctctccag gcgggaacag caaaatatca cccggtcggc agacaaattc    660
tcgtccctga tttttcacca ccccctgacc gcgaatggtg agattgagaa tataaccttt    720
cattcccagc ggtcggtcga taaaaaaatc gagataaccg ttggcctcaa tcggcgttaa    780
acccgccacc agatgggcgt taaacgagta tcccggcagc aggggatcat tttgcgcttc    840
agccatactt ttcatactcc cgccattcag agaagaaacc aattgtccat attgcatcag    900
acattgccgt cactgcgtct tttactggct cttctcgcta acccaaccgg taaccccgct    960
tattaaaagc attctgtaac aaagcgggac caaagccatg acaaaaacgc gtaacaaaag   1020
tgtctataat cacggcagaa aagtccacat tgattatttg cacggcgtca cactttgcta   1080
tgccatagca tttttatcca taagattagc ggatccagcc tgacgctttt tttcgcaact   1140
ctctactgtt tctccatacc tctagaaata attttgttta actttaagaa ggagatatac   1200
atatgaacat ttcaaggaga aagctacttt taggtgttgg tgctgcgggc gttttagcag   1260
gtggtgcggc tttagttcca atggttcgcc gtgacggcaa atttgtggaa gctaaatcaa   1320
gagcatcatt tgttgaaggt acgcaagggg ctcttcctaa agaagcagat gtagtgatta   1380
ttggtgccgg tattcaaggg atcatgaccg ctattaacct tgctgaacgt ggtatgagtg   1440
tcactatctt agaaaagggt cagattgccg gtgagcaatc aggccgtgca tacagccaaa   1500
ttattagtta ccaaacatcg ccagaaatct tcccattaca ccattatggg aaaatattat   1560
ggcgtggcat gaatgagaaa attggtgcgg ataccagtta tcgtactcaa ggtcgtgtag   1620
aagcgctggc agatgaaaaa gcattagata aagctcaagc gtggatcaaa acagctaaag   1680
aagcggcagg ttttgataca ccattaaata ctcgcatcat taaaggtgaa gagctatcaa   1740
atcgcttagt cggtgctcaa acgccatgga ctgttgctgc atttgaagaa gattcaggct   1800
ctgttgatcc tgaaacaggc acacctgcac tcgctcgtta tgccaaacaa atcggtgtga   1860
aaatttatac caactgtgca gtaagaggta ttgaaactgc gggtggtaaa atctctgatg   1920
tggtgagtga gaaaggggcg attaaaacgt ctcaagttgt actcgctggg ggtatctggt   1980
cgcgtttatt tatgggcaat atgggtattg atatcccaac gctcaatgta tatctatcac   2040
aacaacgtgt ctcaggggtt cctggtgcac cacgtggtaa tgtgcattta cctaatggta   2100
ttcatttccg cgaacaagcg gatggtactt atgccgttgc accacgtatc tttacgagtt   2160
caatagtcaa agatagcttc ctgctagggc ctaaatttat gcacttatta ggtggcggag   2220
agttaccgtt ggaattctct attggtgaag atctatttaa ttcatttaaa atgccgacct   2280
cttggaattt agatgaaaaa acaccattcg aacaattccg agttgccacg gcaacacaaa   2340
atacgcaaca cttagatgct gttttccaaa gaatgaaaac agaattccca gtatttgaaa   2400
aatcagaagt tgttgaacgt tggggtgccg ttgtgagtcc aacatttgat gaattaccta   2460
tcatttctga ggtcaaagaa tacccaggct tagtgattaa cacggcaaca gtgtggggta   2520
tgacagaagg cccggcagcg ggtgaagtga ccgctgatat tgtcatgggc aagaaacctg   2580
ttattgatcc aacgccgttt agtttggatc gttttaagaa gtaa                    2624
```

<210> SEQ ID NO 41
<211> LENGTH: 3206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41
ggtaccagtt gttcttattg gtggtgttgc tttatggttg catcgtagta aatggttgta 60
acaaaagcaa tttttccggc tgtctgtata caaaaacgcc gcaaagtttg agcgaagtca 120
ataaactctc tacccattca gggcaatatc tctcttggat ccaaagtgaa ctctagaaat 180
aattttgttt aactttaaga aggagatata catatgaaag ctaaagatgt tcagccaacc 240
attattatta ataaaaatgg ccttatctct ttggaagata tctatgacat tgcgataaaa 300
caaaaaaaag tagaaatatc aacggagatc actgaacttt tgacgcatgg tcgtgaaaaa 360
ttagaggaaa aattaaattc aggagaggtt atatatggaa tcaatacagg atttggaggg 420
aatgccaatt tagttgtgcc atttgagaaa atcgcagagc atcagcaaaa tctgttaact 480
tttctttctg ctggtactgg ggactatatg tccaaacctt gtattaaagc gtcacaattt 540
actatgttac tttctgtttg caaaggttgg tctgcaacca gaccaattgt cgctcaagca 600
attgttgatc atattaatca tgacattgtt cctctggttc ctcgctatgg ctcagtgggt 660
gcaagcggtg atttaattcc tttatcttat attgcacgag cattatgtgg tatcggcaaa 720
gtttattata tgggcgcaga aattgacgct gctgaagcaa ttaaacgtgc agggttgaca 780
ccattatcgt taaaagccaa agaaggtctt gctctgatta acggcacccg ggtaatgtca 840
ggaatcagtg caatcaccgt cattaaactg gaaaaactat ttaaagcctc aatttctgcg 900
attgcccttg ctgttgaagc attacttgca tctcatgaac attatgatgc ccggattcaa 960
caagtaaaaa atcatcctgg tcaaaacgcg gtggcaagtg cattgcgtaa tttattggca 1020
ggttcaacgc aggttaatct attatctggg gttaaagaac aagccaataa agcttgtcgt 1080
catcaagaaa ttacccaact aaatgatacc ttacaggaag tttattcaat tcgctgtgca 1140
ccacaagtat taggtatagt gccagaatct ttagctaccg ctcggaaaat attggaacgg 1200
gaagttatct cagctaatga taatccattg atagatccag aaaatggcga tgttctacac 1260
ggtggaaatt ttatggggca atatgtcgcc cgaacaatgg atgcattaaa actggatatt 1320
gctttaattg ccaatcatct tcacgccatt gtggctctta tgatggataa ccgtttctct 1380
cgtggattac ctaattcact gagtccgaca cccggcatgt atcaaggttt taaaggcgtc 1440
caactttctc aaaccgcttt agttgctgca attcgccatg attgtgctgc atcaggtatt 1500
cataccctcg ccacagaaca atacaatcaa gatattgtca gtttaggtct gcatgccgct 1560
caagatgttt tagagatgga gcagaaatta cgcaatattg tttcaatgac aattctggta 1620
gtttgtcagg ccattcatct tcgcggcaat attagtgaaa ttgcgcctga aactgctaaa 1680
ttttaccatg cagtacgcga aatcagttct cctttgatca ctgatcgtgc gttggatgaa 1740
gatataatcc gcattgcgga tgcaattatt aatgatcaac ttcctctgcc agaaatcatg 1800
ctggaagaat aaaagaagga gatatacata tgaaaaacgc gtcaaccgta tcggaagata 1860
ctgcgtcgaa tcaagagccg acgcttcatc gcggattaca taaccgtcat attcaactga 1920
ttgcgttggg tggcgcaatt ggtactggtc tgtttcttgg cattggcccg gcgattcaga 1980
tggcgggtcc ggctgtattg ctgggctacg gcgtcgccgg gatcatcgct ttcctgatta 2040

-continued tgcgccagct tggcgaaatg gtggttgagg agccggtatc cggttcattt gcccactttg 2100
cctataaata ctggggaccg tttgcgggct tcctctctgg ctggaactac tgggtaatgt 2160
tcgtgctggt gggaatggca gagctgaccg ctgcgggcat ctatatgcag tactggttcc 2220
cggatgttcc aacgtggatt tgggctgccg ccttctttat tatcatcaac gccgttaacc 2280
tggtgaacgt gcgcttatat ggcgaaaccg agttctggtt tgcgttgatt aaagtgctgg 2340
caatcatcgg tatgatcggc tttggcctgt ggctgctgtt ttctggtcac ggcggcgaga 2400
aagccagtat cgacaacctc tggcgctacg gtggtttctt cgccaccggc tggaatgggc 2460
tgattttgtc gctggcggta attatgttct ccttcggcgg tctggagctg attgggatta 2520
ctgccgctga agcgcgcgat ccggaaaaaa gcattccaaa agcggtaaat caggtggtgt 2580
atcgcatcct gctgttttac atcggttcac tggtggtttt actggcgctc tatccgtggg 2640
tggaagtgaa atccaacagt agcccgtttg tgatgatttt ccataatctc gacagcaacg 2700
tggtagcttc tgcgctgaac ttcgtcattc tggtagcatc gctgtcagtg tataacagcg 2760
gggtttactc taacagccgc atgctgtttg gcctttctgt gcagggtaat gcgccgaagt 2820
ttttgactcg cgtcagccgt cgcggtgtgc cgattaactc gctgatgctt tccggagcga 2880
tcacttcgct ggtggtgtta atcaactatc tgctgccgca aaaagcgttt ggtctgctga 2940
tggcgctggt ggtagcaacg ctgctgttga actggattat gatctgtctg gcgcatctgc 3000
gttttcgtgc agcgatgcga cgtcaggggc gtgaaacaca gtttaaggcg ctgctctatc 3060
cgttcggcaa ctatctctgc attgccttcc tcggcatgat tttgctgctg atgtgcacga 3120
tggatgatat gcgcttgtca gcgatcctgc tgccggtgtg gattgtattc ctgtttatgg 3180
catttaaaac gctgcgtcgg aaataa 3206

<210> SEQ ID NO 42
<211> LENGTH: 3741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
ttaggtacgg gctgcccatt tgattttaac gcgttcatca ccatcaaacg gacgaccacg 60
ctggcctttt gcaacccaaa tttcatcgat gcaggtatca ataattgcat tacgcatggt 120
cggggttgca cgcagccaca gttcttcata atcgctgcta tcaacaatcc agctaacatc 180
aactgctgcg cttgcgctgc tttcgctaac tgcatctttg gctgcctgca gggtgctcag 240
tgcttcttga tatgcagggg caaaaaactg ttctgccgga ccatcataaa caccattctg 300
acgatcacgc agcaggcgac ccagattttt ttcggcttca cgaactgcgg cttttgcata 360
cttttcatct tcgcttgcct gcggatgggt cagtgctgcc cagcgatctg caactgcaat 420
aacaaacgga tcatccggtt cgcttgctgc taattttgct gcccaacgaa atgcaacata 480
ttcttcaacg cttttacgtg caacataggt cggtgccgga caaccacctt tcacactgct 540
acgccaacaa cgataaccat taccgctata gctacagcta ccaccacaac ccggacaacg 600
catacgaccg ctcagcagat gtttgcgacg ggtatcatga tcgctaccat ccagcggaac 660
accaacacca tcttcacctt taacggctgc ttttgcggct tcttgttctt catcggtcac 720
cagcggagga ccatgcataa cgctaacacg tttaccttca ccgttataaa aggtcagacg 780
acgctgttta ccatcctgac gacctgtggt ctgccaaccc gcatatgccg gattctgaat 840
catatcacgc acggtaactg caatccacgg accaccggtc gggctcggaa tttcacgggt 900
attcattgca tgtgcggtgc ctgcatagct cagacgatcg gtaaccggca gggtaaaaac 960
cagacgggct gcttctgctt tggtcagacc atcaggacca cccgcatctt catcatctgc 1020
tgccagttta cgttcatcat attcatcacc ctcttcatca ctaacggtaa ccagaacaac 1080
acgcagacca tacggtgcac gggcattaac ccattcacca ttttcacgct gatgtgcttt 1140
ggtatcacga acacgttcgc tcagtttttc tgcttcttcg cgtgcttctt ctgcacgacg 1200
aatcagttca ccgcgatcac gtttattggt gctatccaga accggacgac cggtatcttc 1260
atcccaacca aacagcagac gacgaggcat accatcttcc ggttcgataa ttttcagaat 1320
tgcaccggca ccaccacgat cccaacgatc cagacgataa caccacagtg caccaacttc 1380
accgctttcc agggctttca gtgctttgct ctgatcatca cgtgctttac ctttacgaaa 1440
acggcttgcg ctaccaactt ctttccaaac atgacgaacc tgcataccca gcagtgctgc 1500
aactttacga cccagggttt cttgtgctgc aatgctaatt tcttgtttac gacgctgacc 1560
tgcaccattt gcacggcttt taactgcttt gcttttacga caaaacaggt caatcagacc 1620
tgcaggatcc ggaccggttt cggtggtcat accaggcata tgtatatctc cttcttaaag 1680
ttaaacaaaa ttatttctag agttcacttt ggatccaaga gagatattgc cctgaatggg 1740
tagagagttt attgacttcg ctcaaacttt gcggcgtttt tgtatacaga cagccggaaa 1800
aattgctttt gttacaacca tttactacga tgcaaccata aagcaacacc accaataaga 1860
acaactggta ccggatattc atatggacca tggcagctag ccctgcaggg tgcactcaga 1920
aaattatttt aaatttcctc ttgtcaggcc ggaataactc cctataatgc gccaccacga 1980
gcgccggatc agggagtgga cggcctggga gcgctacacg ctgtggctgc ggtcggtgct 2040
tattcttcca gcatgatttc tggcagagga agttgatcat taataattgc atccgcaatg 2100
cggattatat cttcatccaa cgcacgatca gtgatcaaag gagaactgat ttcgcgtact 2160
gcatggtaaa atttagcagt ttcaggcgca atttcactaa tattgccgcg aagatgaatg 2220
gcctgacaaa ctaccagaat tgtcattgaa acaatattgc gtaatttctg ctccatctct 2280
aaaacatctt gagcggcatg cagacctaaa ctgacaatat cttgattgta ttgttctgtg 2340
gcgagggtat gaatacctga tgcagcacaa tcatggcgaa ttgcagcaac taaagcggtt 2400
tgagaaagtt ggacgccttt aaaaccttga tacatgccgg gtgtcggact cagtgaatta 2460
ggtaatccac gagagaaacg gttatccatc ataagagcca caatggcgtg aagatgattg 2520
gcaattaaag caatatccag ttttaatgca tccattgttc gggcgacata ttgccccata 2580
aaatttccac cgtgtagaac atcgccattt tctggatcta tcaatggatt atcattagct 2640
gagataactt cccgttccaa tattttccga gcggtagcta aagattctgg cactatacct 2700
aatacttgtg gtgcacagcg aattgaataa acttcctgta aggtatcatt tagttgggta 2760
atttcttgat gacgacaagc tttattggct tgttctttaa ccccagataa tagattaacc 2820
tgcgttgaac ctgccaataa attacgcaat gcacttgcca ccgcgttttg accaggatga 2880
tttttttactt gttgaatccg ggcatcataa tgttcatgag atgcaagtaa tgcttcaaca 2940
gcaagggcaa tcgcagaaat tgaggcttta aatagttttt ccagtttaat gacggtgatt 3000
gcactgattc ctgacattac ccgggtgccg ttaatcagag caagaccttc tttggctttt 3060
aacgataatg gtgtcaaccc tgcacgttta attgcttcag cagcgtcaat ttctgcgccc 3120
atataataaa ctttgccgat accacataat gctcgtgcaa tataagataa aggaattaaa 3180

-continued

```
tcaccgcttg cacccactga gccatagcga ggaaccagag gaacaatgtc atgattaata   3240

tgatcaacaa ttgcttgagc gacaattggt ctggttgcag accaaccttt gcaaacagaa   3300

agtaacatag taaattgtga cgctttaata caaggtttgg acatatagtc cccagtacca   3360

gcagaaagaa aagttaacag attttgctga tgctctgcga ttttctcaaa tggcacaact   3420

aaattggcat tccctccaaa tcctgtattg attccatata taacctctcc tgaatttaat   3480

ttttcctcta atttttcacg accatgcgtc aaaagttcag tgatctccgt tgatatttct   3540

actttttttt gttttatcgc aatgtcatag atatcttcca aagagataag gccattttta   3600

ttaataataa tggttggctg aacatcttta gctttcatat gtatatctcc ttcttaaagt   3660

taaacaaaat tatttctaga gcagatcagg gtgcgcaagt tgtcaacgct cccaggagag   3720

ttatcgactt gcgtattagg g                                             3741
```

<210> SEQ ID NO 43
<211> LENGTH: 4794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
ttaggtacgg gctgcccatt tgattttaac gcgttcatca ccatcaaacg gacgaccacg     60

ctggcctttt gcaacccaaa tttcatcgat gcaggtatca ataattgcat tacgcatggt    120

cggggttgca cgcagccaca gttcttcata atcgctgcta tcaacaatcc agctaacatc    180

aactgctgcg cttgcgctgc tttcgctaac tgcatctttg gctgcctgca gggtgctcag    240

tgcttcttga tatgcagggg caaaaaactg ttctgccgga ccatcataaa caccattctg    300

acgatcacgc agcaggcgac ccagattttt ttcggcttca cgaactgcgg cttttgcata    360

cttttcatct tcgcttgcct gcggatgggt cagtgctgcc cagcgatctg caactgcaat    420

aacaaacgga tcatccggtt cgcttgctgc taattttgct gcccaacgaa atgcaacata    480

ttcttcaacg cttttacgtg caacataggt cggtgccgga caaccacctt tcacactgct    540

acgccaacaa cgataaccat taccgctata gctacagcta ccaccacaac ccggacaacg    600

catacgaccg ctcagcagat gtttgcgacg ggtatcatga tcgctaccat ccagcggaac    660

accaacacca tcttcacctt taacggctgc ttttgcggct tcttgttctt catcggtcac    720

cagcggagga ccatgcataa cgctaacacg tttaccttca ccgttataaa aggtcagacg    780

acgctgttta ccatcctgac gacctgtggt ctgccaaccc gcatatgccg gattctgaat    840

catatcacgc acggtaactg caatccacgg accaccggtc gggctcggaa tttcacgggt    900

attcattgca tgtgcggtgc ctgcatagct cagacgatcg gtaaccggca gggtaaaaac    960

cagacgggct gcttctgctt tggtcagacc atcaggacca cccgcatctt catcatctgc   1020

tgccagttta cgttcatcat attcatcacc ctcttcatca ctaacggtaa ccagaacaac   1080

acgcagacca tacggtgcac gggcattaac ccattcacca ttttcacgct gatgtgcttt   1140

ggtatcacga acacgttcgc tcagtttttc tgcttcttcg cgtgcttctt ctgcacgacg   1200

aatcagttca ccgcgatcac gtttattggt gctatccaga accggacgac cggtatcttc   1260

atcccaacca aacagcagac gacgaggcat accatcttcc ggttcgataa ttttcagaat   1320

tgcaccggca ccaccacgat cccaacgatc cagacgataa caccacagtg caccaacttc   1380

accgctttcc agggctttca gtgctttgct ctgatcatca cgtgctttac ctttacgaaa   1440
```

acggcttgcg ctaccaactt ctttccaaac atgacgaacc tgcataccca gcagtgctgc 1500
aactttacga cccagggttt cttgtgctgc aatgctaatt tcttgtttac gacgctgacc 1560
tgcaccattt gcacggcttt taactgcttt gcttttacga caaaacaggt caatcagacc 1620
tgcaggatcc ggaccggttt cggtggtcat accaggcata tgtatatctc cttcttaaag 1680
ttaaacaaaa ttatttctag agttcacttt ggatccaaga gagatattgc cctgaatggg 1740
tagagagttt attgacttcg ctcaaacttt gcggcgtttt tgtatacaga cagccggaaa 1800
aattgctttt gttacaacca tttactacga tgcaaccata aagcaacacc accaataaga 1860
acaactggta ccggatattc atatggacca tggcagctag ccctgcaggg tgcactcaga 1920
aaattatttt aaatttcctc ttgtcaggcc ggaataactc cctataatgc gccaccacga 1980
gcgccggatc agggagtgga cggcctggga gcgctacacg ctgtggctgc ggtcggtgct 2040
tacgcgaacg cgaagtccga ctctaagatg tcacggaggt tcaagttacc tttagccgga 2100
agtgctggca ttttgtccaa ttgagactcg tgcaactggt cagcgaactg gtcgtagaaa 2160
tcagccagta catcacaaga ctcatatgtg tcaaccatag tttcgcgcac tgctttgaac 2220
aggttcgcag cgtcagccgg aatggtaccg aaggagtcgt gaatcagtgc aaaagattcg 2280
attccgtact tctcgtgtgc ccacactaca gtcttacgaa ggtggctacc gtcttggctg 2340
tgtacaaagt taggagcgat accagactcc tgtttgtgtg catcaatctc gctatctttg 2400
ttggtgttaa tggtaggctg taagcggaac tgaccgagga acatcaggtt caagcgcgtc 2460
tgaataggct tcttgtattc ctgccacaca gggaaaccat caggagttac ccaatgcaca 2520
gcgcaacgct tgcgaagaat ctctccagtc ttcttatctt tgacctcagc agccagcagc 2580
ttagcagcag acttaagcca gttcattgct tcaaccgcag ctaccaccgt cacgctcaca 2640
gattcccaaa tcagcttagc catgtatcca gcagcctgat tcggctgagt gaacatcaga 2700
cccttgccgg aatcaatagc tggctgaatg gtatcttcca gcacttgttg acggaagccg 2760
aactctttgg acccgtaagc cagcgtcatg actgaacgct tagtcacact gcgagtaaca 2820
ccgtaagcca gccattgacc agccagtgcc ttagtgccca gcttgacttt ctcagagatt 2880
tcaccagtgt tctcatcggt cacggtaact acttcgttat cggtcccatt gattgcgtct 2940
gcttgtagaa tctcgttgac tttcttagca acaatcccgt agatgtcctg aacggtttca 3000
ctaggaagca agttaaccgc gcgaccacct acctcatctc ggagcatcgc ggagaagtgc 3060
tggatgccag agcaagaccc gtcaaacgcc agcggaaggg agcagttata gctcaggccg 3120
tggtgctgta ccccagcgta ctcaaagcag aacgcaagga agcagaacgg agaatcttgc 3180
tcagcccacc aagtgttctc cagtggagac ttagcgcaag ccatgatgtt ctcgtggttt 3240
tcctcaatga acttgatgcg ctcagggaac ggaaccttat cgacacccgc acagtttgca 3300
ccgtggattt tcagccagta gtaaccttcc ttaccgattg gtttaccttt cgccagcgta 3360
agcagtcctt tggtcatatc gttaccttgc gggttgaaca ttgacacagc gtaaacacga 3420
ccgcgccagt ccatgttgta agggaaccag atggccttat ggttagcaaa cttattggct 3480
tgctcaagca tgaactcaag gctgatacgg cgagacttgc gagccttgtc cttgcggtac 3540
acagcagcgg cagcacgttt ccacgcggtg agagcctcag gattcatgtc gatgtcttcc 3600
ggtttcatcg ggagttcttc acgctcaatc gcagggatgt cctcgaccgg acaatgcttc 3660
cacttggtga ttacgttggc gaccgctagg actttcttgt tgattttcca tgcggtgttt 3720
tgcgcaatgt taatcgcttt gtacacctca ggcatgtaaa cgtcttcgta gcgcatcagt 3780
gctttcttac tgtgagtacg caccagcgcc agaggacgac gaccgttagc ccaatagcca 3840
ccaccagtaa tgccagtcca cggcttagga ggaactacgc aaggttggaa catcggagag 3900
atgccagcca gcgcacctgc acgggttgcg atagcctcag cgtattcagg tgcgagttcg 3960
atagtctcag agtcttgacc tactacgcca gcattttggc ggtgtaagct aaccattccg 4020
gttgactcaa tgagcatctc gatgcagcgt actcctacat gaatagagtc ttccttatgc 4080
cacgaagacc acgcctcgcc accgagtaga cccttagaga gcatgtcagc ctcgacaact 4140
tgcataaatg ctttcttgta gacgtgccct acgcgcttgt tgagttgttc ctcaacgttt 4200
ttcttgaagt gcttagcttc aaggtcacgg atacgaccga agcgagcctc gtcctcaatg 4260
gcccgaccga ttgcgcttgc tacagcctga acggttgtat tgtcagcact ggttaggcaa 4320
gccagagtgg tcttaatggt gatgtacgct acggcttccg gcttgatttc ttgcaggaac 4380
tggaaggctg tcgggcgctt gccgcgctta gctttcactt cctcaaacca gtcgttgatg 4440
cgtgcaatca tcttagggag tagggtagtg atgagaggct tggcggcagc gttatccgca 4500
acctcaccag ctttaagttg acgctcaaac atcttgcgga agcgtgcttc acccatctcg 4560
taagactcat gctcaagggc caactgttcg cgagctaaac gctcaccgta atggtcagcc 4620
agagtgttga acgggatagc agccagttcg atgtcagaga agtcgttctt agcgatgtta 4680
atcgtgttca tatgtatatc tccttcttaa agttaaacaa aattatttct agagcagatc 4740
agggtgcgca agttgtcaac gctcccagga gagttatcga cttgcgtatt aggg 4794

<210> SEQ ID NO 44
<211> LENGTH: 1672
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
taatacgact cactataggg agaaagtgaa ctctagaaat aattttgttt aactttaaga 60
aggagatata catatgaaag ctaaagatgt tcagccaacc attattatta ataaaaatgg 120
ccttatctct ttggaagata tctatgacat tgcgataaaa caaaaaaaag tagaaatatc 180
aacggagatc actgaacttt tgacgcatgg tcgtgaaaaa ttagaggaaa aattaaattc 240
aggagaggtt atatatggaa tcaatacagg atttggaggg aatgccaatt tagttgtgcc 300
atttgagaaa atcgcagagc atcagcaaaa tctgttaact tttctttctg ctggtactgg 360
ggactatatg tccaaacctt gtattaaagc gtcacaattt actatgttac tttctgtttg 420
caaaggttgg tctgcaacca gaccaattgt cgctcaagca attgttgatc atattaatca 480
tgacattgtt cctctggttc ctcgctatgg ctcagtgggt gcaagcggtg atttaattcc 540
tttatcttat attgcacgag cattatgtgg tatcggcaaa gtttattata tgggcgcaga 600
aattgacgct gctgaagcaa ttaaacgtgc agggttgaca ccattatcgt taaaagccaa 660
agaaggtctt gctctgatta acggcacccg ggtaatgtca ggaatcagtg caatcaccgt 720
cattaaactg gaaaaactat ttaaagcctc aatttctgcg attgcccttg ctgttgaagc 780
attacttgca tctcatgaac attatgatgc ccggattcaa caagtaaaaa atcatcctgg 840
tcaaaacgcg gtggcaagtg cattgcgtaa tttattggca ggttcaacgc aggttaatct 900
attatctggg gttaaagaac aagccaataa agcttgtcgt catcaagaaa ttacccaact 960
aaatgatacc ttacaggaag tttattcaat tcgctgtgca ccacaagtat taggtatagt 1020
gccagaatct ttagctaccg ctcggaaaat attggaacgg gaagttatct cagctaatga 1080
taatccattg atagatccag aaaatggcga tgttctacac ggtggaaatt ttatggggca 1140
atatgtcgcc cgaacaatgg atgcattaaa actggatatt gctttaattg ccaatcatct 1200
tcacgccatt gtggctctta tgatggataa ccgtttctct cgtggattac ctaattcact 1260
gagtccgaca cccggcatgt atcaaggttt taaaggcgtc caactttctc aaaccgcttt 1320
agttgctgca attcgccatg attgtgctgc atcaggtatt cataccctcg ccacagaaca 1380
atacaatcaa gatattgtca gtttaggtct gcatgccgct caagatgttt tagagatgga 1440
gcagaaatta cgcaatattg tttcaatgac aattctggta gtttgtcagg ccattcatct 1500
tcgcggcaat attagtgaaa ttgcgcctga aactgctaaa ttttaccatg cagtacgcga 1560
aatcagttct cctttgatca ctgatcgtgc gttggatgaa gatataatcc gcattgcgga 1620
tgcaattatt aatgatcaac ttcctctgcc agaaatcatg ctggaagaat aa 1672

<210> SEQ ID NO 45
<211> LENGTH: 2861
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
ttattcacaa cctgccctaa actcgctcgg actcgccccg gtgcattttt taaatactcg 60
cgagaaatag agttgatcgt caaaaccgac attgcgaccg acggtggcga taggcatccg 120
ggtggtgctc aaaagcagct tcgcctgact gatgcgctgg tcctcgcgcc agcttaatac 180
gctaatccct aactgctggc ggaacaaatg cgacagacgc gacggcgaca ggcagacatg 240
ctgtgcgacg ctggcgatat caaaattact gtctgccagg tgatcgctga tgtactgaca 300
agcctcgcgt acccgattat ccatcggtgg atggagcgac tcgttaatcg cttccatgcg 360
ccgcagtaac aattgctcaa gcagatttat cgccagcaat tccgaatagc gcccttcccc 420
ttgtccggca ttaatgattt gcccaaacag gtcgctgaaa tgcggctggt gcgcttcatc 480
cgggcgaaag aaaccggtat tggcaaatat cgacggccag ttaagccatt catgccagta 540
ggcgcgcgga cgaaagtaaa cccactggtg ataccattcg tgagcctccg gatgacgacc 600
gtagtgatga atctctccag gcgggaacag caaaatatca cccggtcggc agacaaattc 660
tcgtccctga tttttcacca ccccctgacc gcgaatggtg agattgagaa tataaccttt 720
cattcccagc ggtcggtcga taaaaaaatc gagataaccg ttggcctcaa tcggcgttaa 780
acccgccacc agatgggcgt taaacgagta tcccggcagc aggggatcat tttgcgcttc 840
agccatactt ttcatactcc cgccattcag agaagaaacc aattgtccat attgcatcag 900
acattgccgt cactgcgtct tttactggct cttctcgcta acccaaccgg taaccccgct 960
tattaaaagc attctgtaac aaagcgggac caaagccatg acaaaaacgc gtaacaaaag 1020
tgtctataat cacggcagaa aagtccacat tgattatttg cacggcgtca cactttgcta 1080
tgccatagca tttttatcca taagattagc ggatccagcc tgacgctttt tttcgcaact 1140
ctctactgtt tctccatacc tctagaaata attttgttta actttaagaa ggagatatac 1200
atatgcctgg tatgaccacc gaaaccggtc cggatcctgc aggtctgatt gacctgtttt 1260
gtcgtaaaag caaagcagtt aaaagccgtg caaatggtgc aggtcagcgt cgtaaacaag 1320
aaattagcat tgcagcacaa gaaaccctgg gtcgtaaagt tgcagcactg ctgggtatgc 1380
aggttcgtca tgtttggaaa gaagttggta gcgcaagccg ttttcgtaaa ggtaaagcac 1440
gtgatgatca gagcaaagca ctgaaagccc tggaaagcgg tgaagttggt gcactgtggt 1500
gttatcgtct ggatcgttgg gatcgtggtg gtgccggtgc aattctgaaa attatcgaac 1560
cggaagatgg tatgcctcgt cgtctgctgt ttggttggga tgaagatacc ggtcgtccgg 1620
ttctggatag caccaataaa cgtgatcgcg gtgaactgat tcgtcgtgca gaagaagcac 1680
gcgaagaagc agaaaaactg agcgaacgtg ttcgtgatac caaagcacat cagcgtgaaa 1740
atggtgaatg ggttaatgcc cgtgcaccgt atggtctgcg tgttgttctg gttaccgtta 1800
gtgatgaaga gggtgatgaa tatgatgaac gtaaactggc agcagatgat gaagatgcgg 1860
gtggtcctga tggtctgacc aaagcagaag cagcccgtct ggtttttacc ctgccggtta 1920
ccgatcgtct gagctatgca ggcaccgcac atgcaatgaa tacccgtgaa attccgagcc 1980
cgaccggtgg tccgtggatt gcagttaccg tgcgtgatat gattcagaat ccggcatatg 2040
cgggttggca gaccacaggt cgtcaggatg gtaaacagcg tcgtctgacc ttttataacg 2100
gtgaaggtaa acgtgttagc gttatgcatg gtcctccgct ggtgaccgat gaagaacaag 2160
aagccgcaaa agcagccgtt aaaggtgaag atggtgttgg tgttccgctg gatggtagcg 2220
atcatgatac ccgtcgcaaa catctgctga gcggtcgtat gcgttgtccg ggttgtggtg 2280
gtagctgtag ctatagcggt aatggttatc gttgttggcg tagcagtgtg aaaggtggtt 2340
gtccggcacc gacctatgtt gcacgtaaaa gcgttgaaga atatgttgca tttcgttggg 2400
cagcaaaatt agcagcaagc gaaccggatg atccgtttgt tattgcagtt gcagatcgct 2460
gggcagcact gacccatccg caggcaagcg aagatgaaaa gtatgcaaaa gccgcagttc 2520
gtgaagccga aaaaaatctg ggtcgcctgc tgcgtgatcg tcagaatggt gtttatgatg 2580
gtccggcaga acagtttttt gcccctgcat atcaagaagc actgagcacc ctgcaggcag 2640
ccaaagatgc agttagcgaa agcagcgcaa gcgcagcagt tgatgttagc tggattgttg 2700
atagcagcga ttatgaagaa ctgtggctgc gtgcaacccc gaccatgcgt aatgcaatta 2760
ttgatacctg catcgatgaa atttgggttg caaaaggcca gcgtggtcgt ccgtttgatg 2820
gtgatgaacg cgttaaaatc aaatgggcag cccgtaccta a 2861

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tagaactgat gcaaaaagtg ctcgacgaag gcacacagat gtgtaggctg gagctgcttc 60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gtttcgtaat tagatagcca ccggcgcttt aatgcccgga catatgaata tcctccttag 60

<210> SEQ ID NO 48
<211> LENGTH: 52
<212> TYPE: DNA

<213> ORGANISM: Artificial Sequence
<220> FEATURE:
<223> OTHER INFORMATION: Description of Artificial Sequence: Synthetic
primer

<400> SEQUENCE: 48
caacacgttt cctgaggaac catgaaacag tatttagaac tgatgcaaaa ag 52

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
cgcacactgg cgtcggctct ggcaggatgt ttcgtaatta gatagc 46

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
atatcgtcgc agcccacagc aacacgtttc ctgagg 36

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
aagaatttaa cggagggcaa aaaaaaccga cgcacactgg cgtcggc 47

<210> SEQ ID NO 52
<211> LENGTH: 52
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

```
Leu Asn Pro Leu Ile Asn Glu Ile Ser Lys Ile Ile Ser Ala Ala Gly
1               5                   10                  15

Asn Phe Asp Val Lys Glu Glu Arg Ala Ala Ala Ser Leu Leu Gln Leu
            20                  25                  30

Ser Gly Asn Ala Ser Asp Phe Ser Tyr Gly Arg Asn Ser Ile Thr Leu
        35                  40                  45

Thr Ala Ser Ala
    50
```

<210> SEQ ID NO 53
<211> LENGTH: 584
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Met Lys Ala Lys Asp Val Gln Pro Thr Ile Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Ser Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp His Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
    210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
    290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
    370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu

```
                405                 410                 415

Val Ala Ala Ile Arg His Asp Cys Ala Ala Ser Gly Ile His Thr Leu
            420                 425                 430

Ala Thr Glu Gln Tyr Asn Gln Asp Ile Val Ser Leu Gly Leu His Ala
        435                 440                 445

Ala Gln Asp Val Leu Glu Met Glu Gln Lys Leu Arg Asn Ile Val Ser
    450                 455                 460

Met Thr Ile Leu Val Val Cys Gln Ala Ile His Leu Arg Gly Asn Ile
465                 470                 475                 480

Ser Glu Ile Ala Pro Glu Thr Ala Lys Phe Tyr His Ala Val Arg Glu
                485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
        515                 520                 525

Met Leu Glu Glu Leu Asn Pro Leu Ile Asn Glu Ile Ser Lys Ile Ile
    530                 535                 540

Ser Ala Ala Gly Asn Phe Asp Val Lys Glu Glu Arg Ala Ala Ala Ser
545                 550                 555                 560

Leu Leu Gln Leu Ser Gly Asn Ala Ser Asp Phe Ser Tyr Gly Arg Asn
                565                 570                 575

Ser Ile Thr Leu Thr Ala Ser Ala
            580


<210> SEQ ID NO 54
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95

Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175
```

```
Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys Leu Asn Pro Leu Ile Asn Glu
465                 470                 475                 480

Ile Ser Lys Ile Ile Ser Ala Ala Gly Asn Phe Asp Val Lys Glu Glu
                485                 490                 495

Arg Ala Ala Ala Ser Leu Leu Gln Leu Ser Gly Asn Ala Ser Asp Phe
            500                 505                 510

Ser Tyr Gly Arg Asn Ser Ile Thr Leu Thr Ala Ser Ala
        515                 520                 525
```

<210> SEQ ID NO 55
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Cys Thr Thr Ala Ala Thr Cys Cys Ala Thr Thr Ala Ala Thr Thr Ala
1               5                   10                  15
```

-continued

```
Ala Thr Gly Ala Ala Ala Thr Cys Ala Gly Cys Ala Ala Ala Ala Thr
            20                  25                  30

Cys Ala Thr Thr Thr Cys Ala Gly Cys Thr Gly Cys Ala Gly Gly Thr
        35                  40                  45

Ala Ala Thr Thr Thr Thr Gly Ala Thr Gly Thr Thr Ala Ala Ala Gly
    50                  55                  60

Ala Gly Gly Ala Ala Ala Gly Ala Gly Cys Thr Gly Cys Ala Gly Cys
65                  70                  75                  80

Thr Thr Cys Thr Thr Thr Ala Thr Thr Gly Cys Ala Gly Thr Thr Gly
                85                  90                  95

Thr Cys Cys Gly Gly Thr Ala Ala Thr Gly Cys Cys Ala Gly Thr Gly
            100                 105                 110

Ala Thr Thr Thr Thr Thr Cys Ala Thr Ala Thr Gly Gly Ala Cys Gly
        115                 120                 125

Gly Ala Ala Cys Thr Cys Ala Ala Thr Ala Ala Cys Thr Thr Thr Gly
    130                 135                 140

Ala Cys Ala Gly Cys Ala Thr Cys Ala Gly Cys Ala Thr Ala Ala
145                 150                 155
```

<210> SEQ ID NO 56
<211> LENGTH: 1777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
acttttcata ctcccgccat tcagagaaga aaccaattgt ccatattgca tcagacattg     60

ccgtcactgc gtcttttact ggctcttctc gctaacccaa ccggtaaccc cgcttattaa    120

aagcattctg taacaaagcg ggaccaaagc catgacaaaa acgcgtaaca aaagtgtcta    180

taatcacggc agaaaaatga acatttcaag gagaaagcta cttttaggtg ttggtgctgc    240

gggcgtttta gcaggtggtg cggctttagt tccaatggtt cgccgtgacg gcaaatttgt    300

ggaagctaaa tcaagagcat catttgttga aggtacgcaa ggggctcttc ctaaagaagc    360

agatgtagtg attattggtg ccggtattca agggatcatg accgctatta accttgctga    420

acgtggtatg agtgtcacta tcttagaaaa gggtcagatt gccggtgagc aatcaggccg    480

tgcatacagc caaattatta gttaccaaac atcgccagaa atcttcccat tacaccatta    540

tgggaaaata ttatggcgtg gcatgaatga gaaaattggt gcggatacca gttatcgtac    600

tcaaggtcgt gtagaagcgc tggcagatga aaaagcatta gataaagctc aagcgtggat    660

caaaacagct aaagaagcgg caggttttga tacaccatta aatactcgca tcattaaagg    720

tgaagagcta tcaaatcgct tagtcggtgc tcaaacgcca tggactgttg ctgcatttga    780

agaagattca ggctctgttg atcctgaaac aggcacacct gcactcgctc gttatgccaa    840

acaaatcggt gtgaaaattt ataccaactg tgcagtaaga ggtattgaaa ctgcgggtgg    900

taaaatctct gatgtggtga gtgagaaagg ggcgattaaa acgtctcaag ttgtactcgc    960

tgggggtatc tggtcgcgtt tatttatggg caatatgggt attgatatcc caacgctcaa   1020

tgtatatcta tcacaacaac gtgtctcagg ggttcctggt gcaccacgtg gtaatgtgca   1080

tttacctaat ggtattcatt tccgcgaaca agcggatggt acttatgccg ttgcaccacg   1140

tatctttacg agttcaatag tcaaagatag cttcctgcta gggcctaaat ttatgcactt   1200
```

```
attaggtggc ggagagttac cgttggaatt ctctattggt gaagatctat ttaattcatt   1260

taaaatgccg acctcttgga atttagatga aaaaacacca ttcgaacaat tccgagttgc   1320

cacggcaaca caaaatacgc aacacttaga tgctgttttc caaagaatga aaacagaatt   1380

cccagtattt gaaaaatcag aagttgttga acgttggggt gccgttgtga gtccaacatt   1440

tgatgaatta cctatcattt ctgaggtcaa agaataccca ggcttagtga ttaacacggc   1500

aacagtgtgg ggtatgacag aaggcccggc agcgggtgaa gtgaccgctg atattgtcat   1560

gggcaagaaa cctgttattg atccaacgcc gtttagtttg gatcgtttta agaagtaact   1620

taatccatta attaatgaaa tcagcaaaat catttcagct gcaggtaatt ttgatgttaa   1680

agaggaaaga gctgcagctt ctttattgca gttgtccggt aatgccagtg atttttcata   1740

tggacggaac tcaataactt tgacagcatc agcataa                            1777
```

<210> SEQ ID NO 57
<211> LENGTH: 1963
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57

```
ggtaccagtt gttcttattg gtggtgttgc tttatggttg catcgtagta aatggttgta     60

acaaaagcaa tttttccggc tgtctgtata caaaaacgcc gtaaagtttg agcgaagtca    120

ataaactctc tacccattca gggcaatatc tctcttggat ccctctagaa ataattttgt    180

ttaactttaa gaaggagata tacatatgaa agctaaagat gttcagccaa ccattattat    240

taataaaaat ggccttatct ctttggaaga tatctatgac attgcgataa aacaaaaaaa    300

agtagaaata tcaacggaga tcactgaact tttgacgcat ggtcgtgaaa aattagagga    360

aaaattaaat tcaggagagg ttatatatgg aatcaataca ggatttggag ggaatgccaa    420

tttagttgtg ccatttgaga aaatcgcaga gcatcagcaa aatctgttaa cttttctttc    480

tgctggtact ggggactata tgtccaaacc ttgtattaaa gcgtcacaat ttactatgtt    540

actttctgtt tgcaaaggtt ggtctgcaac cagaccaatt gtcgctcaag caattgttga    600

tcatattaat catgacattg ttcctctggt tcctcgctat ggctcagtgg gtgcaagcgg    660

tgatttaatt cctttatctt atattgcacg agcattatgt ggtatcggca aagtttatta    720

tatgggcgca gaaattgacg ctgctgaagc aattaaacgt gcagggttga caccattatc    780

gttaaaagcc aaagaaggtc ttgctctgat taacggcacc cgggtaatgt caggaatcag    840

tgcaatcacc gtcattaaac tggaaaaact atttaaagcc tcaatttctg cgattgccct    900

tgctgttgaa gcattacttg catctcatga acattatgat gcccggattc aacaagtaaa    960

aaatcatcct ggtcaaaacg cggtggcaag tgcattgcgt aatttattgg caggttcaac   1020

gcaggttaat ctattatctg gggttaaaga acaagccaat aaagcttgtc gtcatcaaga   1080

aattacccaa ctaaatgata ccttacagga agtttattca attcgctgtg caccacaagt   1140

attaggtata gtgccagaat ctttagctac cgctcggaaa atattggaac gggaagttat   1200

ctcagctaat gataatccat tgatagatcc agaaaatggc gatgttctac acggtggaaa   1260

ttttatgggg caatatgtcg cccgaacaat ggatgcatta aaactggata ttgctttaat   1320

tgccaatcat cttcacgcca ttgtggctct tatgatggat aaccgtttct ctcgtggatt   1380

acctaattca ctgagtccga cacccggcat gtatcaaggt tttaaaggcg tccaactttc   1440
```

-continued

```
tcaaaccgct ttagttgctg caattcgcca tgattgtgct gcatcaggta ttcataccct   1500

cgccacagaa caatacaatc aagatattgt cagtttaggt ctgcatgccg ctcaagatgt   1560

tttagagatg gagcagaaat tacgcaatat tgtttcaatg acaattctgg tagtttgtca   1620

ggccattcat cttcgcggca atattagtga aattgcgcct gaaactgcta aattttacca   1680

tgcagtacgc gaaatcagtt ctcctttgat cactgatcgt gcgttggatg aagatataat   1740

ccgcattgcg gatgcaatta ttaatgatca acttcctctg ccagaaatca tgctggaaga   1800

ataacttaat ccattaatta atgaaatcag caaaatcatt tcagctgcag gtaattttga   1860

tgttaaagag gaaagagctg cagcttcttt attgcagttg tccggtaatg ccagtgattt   1920

ttcatatgga cggaactcaa taactttgac agcatcagca taa                     1963
```

```
<210> SEQ ID NO 58
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Asp Ser Cys His Lys Ile Asp Tyr Gly Leu Tyr Ala Leu Glu Ile
1               5                   10                  15

Leu Ala Gln Tyr His Asn Val Ser Val Asn Pro Glu Glu Ile Lys His
            20                  25                  30

Arg Phe Asp Thr Asp Gly Thr Gly Leu Gly Leu Thr Ser Trp Leu Leu
        35                  40                  45

Ala Ala Lys Ser Leu Glu Leu Lys Val Lys Gln Val Lys Lys Thr Ile
    50                  55                  60

Asp Arg Leu Asn Phe Ile Ser Leu Pro Ala Leu Val Trp Arg Glu Asp
65                  70                  75                  80

Gly Arg His Phe Ile Leu Thr Lys Val Ser Lys Glu Ala Asn Arg Tyr
                85                  90                  95

Leu Ile Phe Asp Leu Glu Gln Arg Asn Pro Arg Val Leu Glu Gln Ser
            100                 105                 110

Glu Phe Glu Ala Leu Tyr Gln Gly His Ile Ile Leu Ile Ala Ser Arg
        115                 120                 125

Ser Ser Val Thr Gly Lys Leu Ala Lys Phe Asp Phe Thr Trp Phe Ile
    130                 135                 140

Pro Ala Ile Ile Lys Tyr Arg Lys Ile Phe Ile Glu Thr Leu Val Val
145                 150                 155                 160

Ser Val Phe Leu Gln Leu Phe Ala Leu Ile Thr Pro Leu Phe Phe Gln
                165                 170                 175

Val Val Met Asp Lys Val Leu Val His Arg Gly Phe Ser Thr Leu Asn
            180                 185                 190

Val Ile Thr Val Ala Leu Ser Val Val Val Val Phe Glu Ile Ile Leu
        195                 200                 205

Ser Gly Leu Arg Thr Tyr Ile Phe Ala His Ser Thr Ser Arg Ile Asp
    210                 215                 220

Val Glu Leu Gly Ala Lys Leu Phe Arg His Leu Leu Ala Leu Pro Ile
225                 230                 235                 240

Ser Tyr Phe Glu Ser Arg Arg Val Gly Asp Thr Val Ala Arg Val Arg
                245                 250                 255

Glu Leu Asp Gln Ile Arg Asn Phe Leu Thr Gly Gln Ala Leu Thr Ser
            260                 265                 270
```

-continued

```
Val Leu Asp Leu Leu Phe Ser Phe Ile Phe Phe Ala Val Met Trp Tyr
        275                 280                 285

Tyr Ser Pro Lys Leu Thr Leu Val Ile Leu Phe Ser Leu Pro Cys Tyr
    290                 295                 300

Ala Ala Trp Ser Val Phe Ile Ser Pro Ile Leu Arg Arg Arg Leu Asp
305                 310                 315                 320

Asp Lys Phe Ser Arg Asn Ala Asp Asn Gln Ser Phe Leu Val Glu Ser
                325                 330                 335

Val Thr Ala Ile Asn Thr Ile Lys Ala Met Ala Val Ser Pro Gln Met
            340                 345                 350

Thr Asn Ile Trp Asp Lys Gln Leu Ala Gly Tyr Val Ala Ala Gly Phe
        355                 360                 365

Lys Val Thr Val Leu Ala Thr Ile Gly Gln Gln Gly Ile Gln Leu Ile
    370                 375                 380

Gln Lys Thr Val Met Ile Ile Asn Leu Trp Leu Gly Ala His Leu Val
385                 390                 395                 400

Ile Ser Gly Asp Leu Ser Ile Gly Gln Leu Ile Ala Phe Asn Met Leu
                405                 410                 415

Ala Gly Gln Ile Val Ala Pro Val Ile Arg Leu Ala Gln Ile Trp Gln
            420                 425                 430

Asp Phe Gln Gln Val Gly Ile Ser Val Thr Arg Leu Gly Asp Val Leu
        435                 440                 445

Asn Ser Pro Thr Glu Ser Tyr His Gly Lys Leu Ala Leu Pro Glu Ile
    450                 455                 460

Asn Gly Asn Ile Thr Phe Arg Asn Ile Arg Phe Arg Tyr Lys Pro Asp
465                 470                 475                 480

Ser Pro Val Ile Leu Asp Asn Ile Asn Leu Ser Ile Lys Gln Gly Glu
                485                 490                 495

Val Ile Gly Ile Val Gly Arg Ser Gly Ser Gly Lys Ser Thr Leu Thr
            500                 505                 510

Lys Leu Ile Gln Arg Phe Tyr Ile Pro Glu Asn Gly Gln Val Leu Ile
        515                 520                 525

Asp Gly His Asp Leu Ala Leu Ala Asp Pro Asn Trp Leu Arg Arg Gln
    530                 535                 540

Val Gly Val Val Leu Gln Asp Asn Val Leu Leu Asn Arg Ser Ile Ile
545                 550                 555                 560

Asp Asn Ile Ser Leu Ala Asn Pro Gly Met Ser Val Glu Lys Val Ile
                565                 570                 575

Tyr Ala Ala Lys Leu Ala Gly Ala His Asp Phe Ile Ser Glu Leu Arg
            580                 585                 590

Glu Gly Tyr Asn Thr Ile Val Gly Glu Gln Gly Ala Gly Leu Ser Gly
        595                 600                 605

Gly Gln Arg Gln Arg Ile Ala Ile Ala Arg Ala Leu Val Asn Asn Pro
    610                 615                 620

Lys Ile Leu Ile Phe Asp Glu Ala Thr Ser Ala Leu Asp Tyr Glu Ser
625                 630                 635                 640

Glu His Ile Ile Met Arg Asn Met His Lys Ile Cys Lys Gly Arg Thr
                645                 650                 655

Val Ile Ile Ile Ala His Arg Leu Ser Thr Val Lys Asn Ala Asp Arg
            660                 665                 670

Ile Ile Val Met Glu Lys Gly Lys Ile Val Glu Gln Gly Lys His Lys
        675                 680                 685
```

Glu Leu Leu Ser Glu Pro Glu Ser Leu Tyr Ser Tyr Leu Tyr Gln Leu
690 695 700

Gln Ser Asp
705

<210> SEQ ID NO 59
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Met Lys Thr Trp Leu Met Gly Phe Ser Glu Phe Leu Leu Arg Tyr Lys
1 5 10 15

Leu Val Trp Ser Glu Thr Trp Lys Ile Arg Lys Gln Leu Asp Thr Pro
20 25 30

Val Arg Glu Lys Asp Glu Asn Glu Phe Leu Pro Ala His Leu Glu Leu
35 40 45

Ile Glu Thr Pro Val Ser Arg Arg Pro Arg Leu Val Ala Tyr Phe Ile
50 55 60

Met Gly Phe Leu Val Ile Ala Val Ile Leu Ser Val Leu Gly Gln Val
65 70 75 80

Glu Ile Val Ala Thr Ala Asn Gly Lys Leu Thr Leu Ser Gly Arg Ser
85 90 95

Lys Glu Ile Lys Pro Ile Glu Asn Ser Ile Val Lys Glu Ile Ile Val
100 105 110

Lys Glu Gly Glu Ser Val Arg Lys Gly Asp Val Leu Leu Lys Leu Thr
115 120 125

Ala Leu Gly Ala Glu Ala Asp Thr Leu Lys Thr Gln Ser Ser Leu Leu
130 135 140

Gln Thr Arg Leu Glu Gln Thr Arg Tyr Gln Ile Leu Ser Arg Ser Ile
145 150 155 160

Glu Leu Asn Lys Leu Pro Glu Leu Lys Leu Pro Asp Glu Pro Tyr Phe
165 170 175

Gln Asn Val Ser Glu Glu Glu Val Leu Arg Leu Thr Ser Leu Ile Lys
180 185 190

Glu Gln Phe Ser Thr Trp Gln Asn Gln Lys Tyr Gln Lys Glu Leu Asn
195 200 205

Leu Asp Lys Lys Arg Ala Glu Arg Leu Thr Ile Leu Ala Arg Ile Asn
210 215 220

Arg Tyr Glu Asn Leu Ser Arg Val Glu Lys Ser Arg Leu Asp Asp Phe
225 230 235 240

Arg Ser Leu Leu His Lys Gln Ala Ile Ala Lys His Ala Val Leu Glu
245 250 255

Gln Glu Asn Lys Tyr Val Glu Ala Ala Asn Glu Leu Arg Val Tyr Lys
260 265 270

Ser Gln Leu Glu Gln Ile Glu Ser Glu Ile Leu Ser Ala Lys Glu Glu
275 280 285

Tyr Gln Leu Val Thr Gln Leu Phe Lys Asn Glu Ile Leu Asp Lys Leu
290 295 300

Arg Gln Thr Thr Asp Asn Ile Glu Leu Leu Thr Leu Glu Leu Glu Lys
305 310 315 320

Asn Glu Glu Arg Gln Gln Ala Ser Val Ile Arg Ala Pro Val Ser Gly
325 330 335

Lys Val Gln Gln Leu Lys Val His Thr Glu Gly Gly Val Val Thr Thr
340 345 350

Ala Glu Thr Leu Met Val Ile Val Pro Glu Asp Asp Thr Leu Glu Val
355 360 365

Thr Ala Leu Val Gln Asn Lys Asp Ile Gly Phe Ile Asn Val Gly Gln
370 375 380

Asn Ala Ile Ile Lys Val Glu Ala Phe Pro Tyr Thr Arg Tyr Gly Tyr
385 390 395 400

Leu Val Gly Lys Val Lys Asn Ile Asn Leu Asp Ala Ile Glu Asp Gln
405 410 415

Lys Leu Gly Leu Val Phe Asn Val Ile Val Ser Val Glu Glu Asn Asp
420 425 430

Leu Ser Thr Gly Asn Lys His Ile Pro Leu Ser Ser Gly Met Ala Val
435 440 445

Thr Ala Glu Ile Lys Thr Gly Met Arg Ser Val Ile Ser Tyr Leu Leu
450 455 460

Ser Pro Leu Glu Glu Ser Val Thr Glu Ser Leu His Glu Arg
465 470 475

<210> SEQ ID NO 60
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Met Lys Asn Ala Ser Thr Val Ser Glu Asp Thr Ala Ser Asn Gln Glu
1 5 10 15

Pro Thr Leu His Arg Gly Leu His Asn Arg His Ile Gln Leu Ile Ala
20 25 30

Leu Gly Gly Ala Ile Gly Thr Gly Leu Phe Leu Gly Ile Gly Pro Ala
35 40 45

Ile Gln Met Ala Gly Pro Ala Val Leu Leu Gly Tyr Gly Val Ala Gly
50 55 60

Ile Ile Ala Phe Leu Ile Met Arg Gln Leu Gly Glu Met Val Val Glu
65 70 75 80

Glu Pro Val Ser Gly Ser Phe Ala His Phe Ala Tyr Lys Tyr Trp Gly
85 90 95

Pro Phe Ala Gly Phe Leu Ser Gly Trp Asn Tyr Trp Val Met Phe Val
100 105 110

Leu Val Gly Met Ala Glu Leu Thr Ala Ala Gly Ile Tyr Met Gln Tyr
115 120 125

Trp Phe Pro Asp Val Pro Thr Trp Ile Trp Ala Ala Ala Phe Phe Ile
130 135 140

Ile Ile Asn Ala Val Asn Leu Val Asn Val Arg Leu Tyr Gly Glu Thr
145 150 155 160

Glu Phe Trp Phe Ala Leu Ile Lys Val Leu Ala Ile Ile Gly Met Ile
165 170 175

Gly Phe Gly Leu Trp Leu Leu Phe Ser Gly His Gly Gly Glu Lys Ala
180 185 190

Ser Ile Asp Asn Leu Trp Arg Tyr Gly Gly Phe Phe Ala Thr Gly Trp
195 200 205

Asn Gly Leu Ile Leu Ser Leu Ala Val Ile Met Phe Ser Phe Gly Gly

```
    210                 215                 220

Leu Glu Leu Ile Gly Ile Thr Ala Ala Glu Ala Arg Asp Pro Glu Lys
225                 230                 235                 240

Ser Ile Pro Lys Ala Val Asn Gln Val Val Tyr Arg Ile Leu Leu Phe
                245                 250                 255

Tyr Ile Gly Ser Leu Val Val Leu Leu Ala Leu Tyr Pro Trp Val Glu
            260                 265                 270

Val Lys Ser Asn Ser Ser Pro Phe Val Met Ile Phe His Asn Leu Asp
        275                 280                 285

Ser Asn Val Val Ala Ser Ala Leu Asn Phe Val Ile Leu Val Ala Ser
    290                 295                 300

Leu Ser Val Tyr Asn Ser Gly Val Tyr Ser Asn Ser Arg Met Leu Phe
305                 310                 315                 320

Gly Leu Ser Val Gln Gly Asn Ala Pro Lys Phe Leu Thr Arg Val Ser
                325                 330                 335

Arg Arg Gly Val Pro Ile Asn Ser Leu Met Leu Ser Gly Ala Ile Thr
            340                 345                 350

Ser Leu Val Val Leu Ile Asn Tyr Leu Leu Pro Gln Lys Ala Phe Gly
        355                 360                 365

Leu Leu Met Ala Leu Val Val Ala Thr Leu Leu Leu Asn Trp Ile Met
    370                 375                 380

Ile Cys Leu Ala His Leu Arg Phe Arg Ala Ala Met Arg Arg Gln Gly
385                 390                 395                 400

Arg Glu Thr Gln Phe Lys Ala Leu Leu Tyr Pro Phe Gly Asn Tyr Leu
                405                 410                 415

Cys Ile Ala Phe Leu Gly Met Ile Leu Leu Leu Met Cys Thr Met Asp
            420                 425                 430

Asp Met Arg Leu Ser Ala Ile Leu Leu Pro Val Trp Ile Val Phe Leu
        435                 440                 445

Phe Met Ala Phe Lys Thr Leu Arg Arg Lys
    450                 455


<210> SEQ ID NO 61
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Glu Gly Gln Gln His Gly Glu Gln Leu Lys Arg Gly Leu Lys Asn
1               5                   10                  15

Arg His Ile Gln Leu Ile Ala Leu Gly Gly Ala Ile Gly Thr Gly Leu
            20                  25                  30

Phe Leu Gly Ser Ala Ser Val Ile Gln Ser Ala Gly Pro Gly Ile Ile
        35                  40                  45

Leu Gly Tyr Ala Ile Ala Gly Phe Ile Ala Phe Leu Ile Met Arg Gln
    50                  55                  60

Leu Gly Glu Met Val Val Glu Glu Pro Val Ala Gly Ser Phe Ser His
65                  70                  75                  80

Phe Ala Tyr Lys Tyr Trp Gly Ser Phe Ala Gly Phe Ala Ser Gly Trp
                85                  90                  95

Asn Tyr Trp Val Leu Tyr Val Leu Val Ala Met Ala Glu Leu Thr Ala
            100                 105                 110
```

-continued

```
Val Gly Lys Tyr Ile Gln Phe Trp Tyr Pro Glu Ile Pro Thr Trp Val
        115                 120                 125

Ser Ala Ala Val Phe Phe Val Val Ile Asn Ala Ile Asn Leu Thr Asn
    130                 135                 140

Val Lys Val Phe Gly Glu Met Glu Phe Trp Phe Ala Ile Ile Lys Val
145                 150                 155                 160

Ile Ala Val Val Ala Met Ile Ile Phe Gly Ala Trp Leu Leu Phe Ser
                165                 170                 175

Gly Asn Gly Gly Pro Gln Ala Ser Val Ser Asn Leu Trp Asp Gln Gly
            180                 185                 190

Gly Phe Leu Pro His Gly Phe Thr Gly Leu Val Met Met Met Ala Ile
        195                 200                 205

Ile Met Phe Ser Phe Gly Gly Leu Glu Leu Val Gly Ile Thr Ala Ala
    210                 215                 220

Glu Ala Asp Asn Pro Glu Gln Ser Ile Pro Lys Ala Thr Asn Gln Val
225                 230                 235                 240

Ile Tyr Arg Ile Leu Ile Phe Tyr Ile Gly Ser Leu Ala Val Leu Leu
                245                 250                 255

Ser Leu Met Pro Trp Thr Arg Val Thr Ala Asp Thr Ser Pro Phe Val
            260                 265                 270

Leu Ile Phe His Glu Leu Gly Asp Thr Phe Val Ala Asn Ala Leu Asn
        275                 280                 285

Ile Val Val Leu Thr Ala Ala Leu Ser Val Tyr Asn Ser Cys Val Tyr
    290                 295                 300

Cys Asn Ser Arg Met Leu Phe Gly Leu Ala Gln Gln Gly Asn Ala Pro
305                 310                 315                 320

Lys Ala Leu Ala Ser Val Asp Lys Arg Gly Val Pro Val Asn Thr Ile
                325                 330                 335

Leu Val Ser Ala Leu Val Thr Ala Leu Cys Val Leu Ile Asn Tyr Leu
            340                 345                 350

Ala Pro Glu Ser Ala Phe Gly Leu Leu Met Ala Leu Val Val Ser Ala
        355                 360                 365

Leu Val Ile Asn Trp Ala Met Ile Ser Leu Ala His Met Lys Phe Arg
    370                 375                 380

Arg Ala Lys Gln Glu Gln Gly Val Val Thr Arg Phe Pro Ala Leu Leu
385                 390                 395                 400

Tyr Pro Leu Gly Asn Trp Val Cys Leu Leu Phe Met Ala Ala Val Leu
                405                 410                 415

Val Ile Met Leu Met Thr Pro Gly Met Ala Ile Ser Val Tyr Leu Ile
            420                 425                 430

Pro Val Trp Leu Ile Val Leu Gly Ile Gly Tyr Leu Phe Lys Glu Lys
        435                 440                 445

Thr Ala Lys Ala Val Lys Ala His
    450                 455
```

<210> SEQ ID NO 62
<211> LENGTH: 1582
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62
ggtaccagtt gttcttattg gtggtgttgc tttatggttg catcgtagta aatggttgta 60

-continued

```
acaaaagcaa tttttccggc tgtctgtata caaaaacgcc gtaaagtttg agcgaagtca    120

ataaactctc tacccattca gggcaatatc tctcttggat ccctctagaa ataattttgt    180

ttaactttaa gaaggagata tacatatgaa aaacgcgtca accgtatcgg aagatactgc    240

gtcgaatcaa gagccgacgc ttcatcgcgg attacataac cgtcatattc aactgattgc    300

gttgggtggc gcaattggta ctggtctgtt tcttggcatt ggcccggcga ttcagatggc    360

gggtccggct gtattgctgg gctacggcgt cgccgggatc atcgctttcc tgattatgcg    420

ccagcttggc gaaatggtgg ttgaggagcc ggtatccggt tcatttgccc actttgccta    480

taaatactgg ggaccgtttg cgggcttcct ctctggctgg aactactggg taatgttcgt    540

gctggtggga atggcagagc tgaccgctgc gggcatctat atgcagtact ggttcccgga    600

tgttccaacg tggatttggg ctgccgcctt ctttattatc atcaacgccg ttaacctggt    660

gaacgtgcgc ttatatggcg aaaccgagtt ctggtttgcg ttgattaaag tgctggcaat    720

catcggtatg atcggctttg gcctgtggct gctgttttct ggtcacggcg gcgagaaagc    780

cagtatcgac aacctctggc gctacggtgg tttcttcgcc accggctgga atgggctgat    840

tttgtcgctg gcggtaatta tgttctcctt cggcggtctg gagctgattg ggattactgc    900

cgctgaagcg cgcgatccgg aaaaaagcat tccaaaagcg gtaaatcagg tggtgtatcg    960

catcctgctg ttttacatcg gttcactggt ggttttactg gcgctctatc cgtgggtgga   1020

agtgaaatcc aacagtagcc cgtttgtgat gattttccat aatctcgaca gcaacgtggt   1080

agcttctgcg ctgaacttcg tcattctggt agcatcgctg tcagtgtata acagcggggt   1140

ttactctaac agccgcatgc tgtttggcct ttctgtgcag ggtaatgcgc cgaagttttt   1200

gactcgcgtc agccgtcgcg gtgtgccgat taactcgctg atgctttccg gagcgatcac   1260

ttcgctggtg gtgttaatca actatctgct gccgcaaaaa gcgtttggtc tgctgatggc   1320

gctggtggta gcaacgctgc tgttgaactg gattatgatc tgtctggcgc atctgcgttt   1380

tcgtgcagcg atgcgacgtc aggggcgtga aacacagttt aaggcgctgc tctatccgtt   1440

cggcaactat ctctgcattg ccttcctcgg catgattttg ctgctgatgt gcacgatgga   1500

tgatatgcgc ttgtcagcga tcctgctgcc ggtgtggatt gtattcctgt ttatggcatt   1560

taaaacgctg cgtcggaaat aa                                            1582
```

<210> SEQ ID NO 63
<211> LENGTH: 1573
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
ggtaccagtt gttcttattg gtggtgttgc tttatggttg catcgtagta aatggttgta     60

acaaaagcaa tttttccggc tgtctgtata caaaaacgcc gtaaagtttg agcgaagtca    120

ataaactctc tacccattca gggcaatatc tctcttggat ccctctagaa ataattttgt    180

ttaactttaa gaaggagata tacatatgga ggggcagcag catggggagc aactgaagcg    240

cgggttaaaa aatcgtcaca ttcaattaat cgcgctgggc ggagcaattg gtacgggatt    300

gttcctgggt tcagcgagcg tcatccaatc ggcaggtcca gggatcatct tgggatatgc    360

gatcgcaggc tttatcgctt ttcttattat gcgccaatta ggtgagatgg tggtcgagga    420

gcctgtagct ggctccttct cacatttcgc gtacaagtat tggggatcct ttgcgggatt    480
```

```
tgcttctggt tggaactatt gggttcttta tgtcctggtg gccatggcgg agctgaccgc    540

ggttggaaaa tatatccagt tctggtaccc cgagatcccg acgtgggtct cagccgcggt    600

attctttgtt gttatcaatg caatcaattt aaccaacgta aaagtatttg gtgaaatgga    660

gttctggttc gcgattatca aagtaattgc cgtagttgct atgattattt ttggggcatg    720

gttgcttttc tcaggaaatg gcggaccaca agcgtcggtt tcaaacctgt gggatcaagg    780

gggattcctg ccgcacggat ttacgggctt ggtgatgatg atggctatca ttatgttttc    840

tttcggtggt cttgaattag tgggtattac cgcagcagag gcagataatc ccgaacaaag    900

catcccaaaa gctactaacc aagttattta ccgtatcctg atttttttata ttggttctct    960

ggcagtcctg ctttccttaa tgccctggac acgtgtaacg gccgatacat ccccttttgt   1020

acttatcttt cacgaactgg gagacacgtt cgtcgccaat gcattaaaca ttgttgtgct   1080

gacagctgcc ttatctgtgt ataatagctg cgtttattgc aattcacgta tgttattcgg   1140

gcttgctcag cagggtaacg cgccaaaggc gttggcctca gtagataagc gcggagtgcc   1200

tgtaaataca attttggtca gcgcattagt cacggctctt tgcgttctga ttaactatct   1260

ggctcctgaa agcgcattcg gattacttat ggccctggtt gtttccgccc tggttatcaa   1320

ttgggcaatg attagtttgg cacatatgaa gttccgccgt gctaaacaag aacaaggtgt   1380

cgtaactcgt ttccctgcct tattgtatcc gctggggaat tgggtatgcc ttcttttat    1440

ggccgcagta ctggtaatta tgttgatgac gcccggcatg gctattagtg tatatacctat   1500

tccggtatgg ttaatcgtct tgggtatcgg ctacttattt aaagaaaaaa cagcaaaagc   1560

cgtaaaggct cat                                                      1573
```

<210> SEQ ID NO 64
<211> LENGTH: 967
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
caaatatcac ataatcttaa catatcaata aacacagtaa agtttcatgt gaaaaacatc     60

aaacataaaa tacaagctcg gaatacgaat cacgctatac acattgctaa caggaatgag    120

attatctaaa tgaggattga tatattaatt ggacatacta gtttttttca tcaaaccagt    180

agagataact tccttcacta tctcaatgag gaagaaataa aacgctatga tcagtttcat    240

tttgtgagtg ataaagaact ctatatttta agccgtatcc tgctcaaaac agcactaaaa    300

agatatcaac ctgatgtctc attacaatca tggcaattta gtacgtgcaa atatggcaaa    360

ccatttatag tttttcctca gttggcaaaa aagatttttt ttaacctttc ccatactata    420

gatacagtag ccgttgctat tagttctcac tgcgagcttg gtgtcgatat tgaacaaata    480

agagatttag acaactctta tctgaatatc agtcagcatt tttttactcc acaggaagct    540

actaacatag tttcacttcc tcgttatgaa ggtcaattac ttttttggaa aatgtggacg    600

ctcaaagaag cttacatcaa atatcgaggt aaaggcctat ctttaggact ggattgtatt    660

gaatttcatt taacaaataa aaaactaact tcaaaatata gaggttcacc tgtttatttc    720

tctcaatgga aaatatgtaa ctcatttctc gcattagcct ctccactcat cacccctaaa    780

ataactattg agctatttcc tatgcagtcc caactttatc accacgacta tcagctaatt    840

cattcgtcaa atgggcagaa ttgaatcgcc acggataatc tagacacttc tgagccgtcg    900
```

-continued

```
ataatattga ttttcatatt ccgtcggtgg tgtaagtatc ccgcataatc gtgccattca    960

catttag                                                              967


<210> SEQ ID NO 65
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

ggatgggggg aaacatggat aagttcaaag aaaaaaaccc gttatctctg cgtgaaagac     60

aagtattgcg catgctggca caaggtgatg agtactctca aatatcacat aatcttaaca    120

tatcaataaa cacagtaaag tttcatgtga aaaacatcaa acataaaata caagctcgga    180

atacgaatca cgctatacac attgctaaca ggaatgagat tatctaaatg aggattgatg    240

tgtaggctgg agctgcttcg aagttcctat actttctaga gaataggaac ttcggaatag    300

gaacttcgga ataggaacta aggaggatat tcatatgtcg tcaaatgggc agaattgaat    360

cgccacggat aatctagaca cttctgagcc gtcgataata ttgattttca tattccgtcg    420

gtgg                                                                 424


<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (6)..(9)
<223> OTHER INFORMATION: a, c, t, g, unknown or other

<400> SEQUENCE: 66

ttgatnnnna tcaa                                                       14
```

BACTERIA ENGINEERED TO REDUCE HYPERPHENYLALANINEMIA

The present application is a Division of U.S. patent application Ser. No. 15/154,934, filed May 13, 2016, issued as U.S. Pat. No. 10,610,546 on April 7, 202, which claims the benefit of priority to U.S. Provisional Patent Application No. 62/161,137, filed May 13, 2015, and U.S. Provisional Patent Application No. 62/256,052, filed Nov. 16, 2015, the contents of which are hereby incorporated by reference herein in their entirety.

The instant application contains a Sequence Listing which has been submitted electronically in ASCII format and is hereby incorporated by reference in its entirety. Said ASCII copy, created on Jun. 23, 2016, is named 12671_0009-00000_SL.txt and is 207,920 bytes in size.

This disclosure relates to compositions and therapeutic methods for reducing hyperphenylalaninemia. In certain aspects, the disclosure relates to genetically engineered bacteria that are capable of reducing hyperphenylalaninemia in a mammal. In certain aspects, the compositions and methods disclosed herein may be used for treating diseases associated with hyperphenylalaninemia, e.g., phenylketonuria.

Phenylalanine is an essential amino acid primarily found in dietary protein. Typically, a small amount is utilized for protein synthesis, and the remainder is hydroxylated to tyrosine in an enzymatic pathway that requires phenylalanine hydroxylase (PAH) and the cofactor tetrahydrobiopterin. Hyperphenylalaninemia is a group of diseases associated with excess levels of phenylalanine, which can be toxic and cause brain damage. Primary hyperphenylalaninemia is caused by deficiencies in PAH activity that result from mutations in the PAH gene and/or a block in cofactor metabolism.

Phenylketonuria (PKU) is a severe form of hyperphenylalaninemia caused by mutations in the PAH gene. PKU is an autosomal recessive genetic disease that ranks as the most common inborn error of metabolism worldwide (1 in 3,000 births), and affects approximately 13,000 patients in the United States. More than 400 different PAH gene mutations have been identified (Hoeks et al., 2009). Current PKU therapies require substantially modified diets consisting of protein restriction. Treatment from birth generally reduces brain damage and mental retardation (Hoeks et al., 2009; Sarkissian et al., 1999). However, the protein-restricted diet must be carefully monitored, and essential amino acids as well as vitamins must be supplemented in the diet. Furthermore, access to low protein foods is a challenge as they are more costly than their higher protein, nonmodified counterparts (Vockley et al., 2014).

In children with PKU, growth retardation is common on a low-phenylalanine diet (Dobbelaere et al., 2003). In adulthood, new problems such as osteoporosis, maternal PKU, and vitamin deficiencies may occur (Hoeks et al., 2009). Excess levels of phenylalanine in the blood, which can freely penetrate the blood-brain barrier, can also lead to neurological impairment, behavioral problems (e.g., irritability, fatigue), and/or physical symptoms (e.g., convulsions, skin rashes, musty body odor). International guidelines recommend lifelong dietary phenylalanine restriction, which is widely regarded as difficult and unrealistic (Sarkissian et al., 1999), and "continued efforts are needed to overcome the biggest challenge to living with PKU—lifelong adherence to the low-phe diet" (Macleod et al., 2010).

In a subset of patients with residual PAH activity, oral administration of the cofactor tetrahydrobiopterin (also referred to as THB, BH4, Kuvan, or sapropterin) may be used together with dietary restriction to lower blood phenylalanine levels. However, cofactor therapy is costly and only suitable for mild forms of phenylketonuria. The annual cost of Kuvan, for example, may be as much as $57,000 per patient. Additionally, the side effects of Kuvan can include gastritis and severe allergic reactions (e.g., wheezing, lightheadedness, nausea, flushing of the skin).

The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. Studies of oral enzyme therapy using PAL have been conducted, but "human and even the animal studies were not continued because PAL was not available in sufficient amounts at reasonable cost" (Sarkissian et al., 1999). A pegylated form of recombinant PAL (PEG-PAL) is also in development as an injectable form of treatment. However, most subjects dosed with PEG-PAL have suffered from injection site reactions and/or developed antibodies to this therapeutic enzyme (Longo et al., 2014). Thus, there is significant unmet need for effective, reliable, and/or long-term treatment for diseases associated with hyperphenylalaninemia, including PKU.

L-amino acid deaminase (LAAD) catalyzes oxidative deamination of phenylalanine to generate phenylpyruvate, and trace amounts of ammonia and hydrogen peroxide. Phenylpyruvic acid (PPA) is widely used in the pharmaceutical, food, and chemical industries, and PPA is the starting material for the synthesis of D-phenylalanine, a raw intermediate in the production of many chiral drugs and food additives. LAAD has therefore been studied in the context of industrial PPA production (Hou et al. 2015, Appl Microbiol Biotechnol. 2015 October; 99(20):8391-402; "Production of phenylpyruvic acid from L-phenylalanine using an L-amino acid deaminase from *Proteus mirabilis*: comparison of enzymatic and whole-cell biotransformation approaches"). Phenylpyruvate is unable to cross the blood brain barrier (Steele, Fed Proc. 1986 June; 45(7):2060-4; "Blood-brain barrier transport of the alpha-keto acid analogs of amino acids," indicating that this conversion is useful in controlling the neurological phenotypes of PKU.

In some embodiments, the disclosure provides genetically engineered bacteria that encode and express a phenylalanine metabolizing enzyme (PME). In some embodiments, the disclosure provides genetically engineered bacteria that encode and express phenylalanine ammonia lyase and/or phenylalanine hydroxylase and/or L-aminoacid deaminase and are capable of reducing hyperphenylalaninemia.

In certain embodiments, the genetically engineered bacteria are non-pathogenic and may be introduced into the gut in order to reduce toxic levels of phenylalanine. In certain embodiments, the phenylalanine ammonia lyase and/or phenylalanine hydroxylase and/or L-aminoacid deaminase is stably produced by the genetically engineered bacteria, and/or the genetically engineered bacteria are stably maintained in vivo and/or in vitro. In certain embodiments, the genetically engineered bacteria further comprise a phenylalanine transporter gene to increase their uptake of phenylalanine. The invention also provides pharmaceutical compositions comprising the genetically engineered bacteria, and methods of modulating and treating disorders associated with hyperphenylalaninemia.

BRIEF DESCRIPTION OF THE FIGURES

FIG. 13A depicts phenylalanine degradation components integrated into the *E. coli* Nissle chromosome. In some embodiments, engineered plasmid-free bacterial strains are used to prevent plasmid conjugation in vivo. In some embodiments, multiple insertions of the PAL gene result in increased copy number and/or increased phenylalanine degradation activity. In some embodiments, a copy of the endogenous *E. coli* high affinity phenylalanine transporter, pheP, is driven by the PfnrS promoter and is inserted into the lacZ locus. FIG. 13B depicts a schematic diagram of one non-limiting embodiment of the disclosure, wherein the *E. coli* Nissle chromosome is engineered to contain four copies of PfnrS-PAL inserted at four different insertion sites across the genome (malE/K, yicS/nepI, agaI/rsmI, and cea), and one copy of a phenylalanine transporter gene inserted at a different insertion site (lacZ). In this embodiment, the PAL gene is PAL3 derived from *P. luminescens*, and the phenylalanine transporter gene is pheP derived from *E. coli*. In one embodiment, the strain is SYN-PKU511. FIG. 13C depicts a schematic diagram of one preferred embodiment of the disclosure, wherein the *E. coli* Nissle chromosome is engineered to contain five copies of PAL under the control of an oxygen level-dependent promoter (e.g., PfnrS-PAL3) inserted at different integration sites on the chromosome (malE/K, yicS/nepI, malP/T, agaI/rsmI, and cea), and one copy of a phenylalanine transporter gene under the control of an oxygen level-dependent promoter (e.g., PfnrS-pheP) inserted at a different integration site on the chromosome (lacZ). The genome is further engineered to include a thyA auxotrophy, in which the thyA gene is deleted and/or replaced with an unrelated gene, as well as a kanamycin resistance gene.

FIG. 17A depicts relatively low PAL and PheP production under aerobic conditions due to oxygen ($O_2$) preventing FNR from dimerizing and activating PAL and/or pheP gene expression. FIG. 17B depicts up-regulated PAL and PheP production under anaerobic conditions due to FNR dimerizing and inducing FNR promoter-mediated expression of PAL and pheP (squiggle above "PAL" and "pheP"). Arrows adjacent to a single rectangle, or a cluster of rectangles, depict the promoter responsible for driving transcription (in the direction of the arrow) of such gene(s). Arrows above each rectangle depict the expression product of each gene.

FIG. 25A depicts phenylalanine concentrations under aerobic conditions using two cell densities. A and B are duplicates under the same experimental conditions. The activity in aerobic conditions is ~50 umol/hr./1e9 cells. FIG. 25B depicts phenylalanine concentrations of aerobically, microaerobically, or anaerobically grown cells.

FIGS. 27A and 27B show blood phenylalanine concentrations at 2 hrs and 4 hrs post-phenylalanine injection, respectively. These data indicate that oral administration of the engineered probiotic strain SYN-PKU303 significantly reduces blood phenylalanine levels in mice, compared to mice administered mock treatment ($H_2O$) or the parental strain (SYN-PKU901) (*, $p<0.05$; *, $p<0.001$; **, $p<0.00001$). SYN-PKU303 is capable of intercepting enterorecirculating phenylalanine.

FIGS. 29A and 29B show blood phenylalanine concentrations at 2 hrs and 4 hrs post-phenylalanine injection, respectively. These data indicate that oral administration of engineered probiotic strains SYN-PKU303 and SYN-PKU304 significantly reduces blood phenylalanine levels in mice compared to mice administered mock treatment (H2O) or the parental strain (SYN-PKU901) (*, $p<0.05$; , $p<0.01$; *, $p<0.001$; **, $p<0.0001$).

FIGS. 30A and 30B show a dose-dependent decrease in blood phenylalanine levels in SYN-PKU304-treated mice compared to mice administered mock treatment (H2O) or the parental strain (SYN-PKU901) (*30% decrease; $p<0.05$). This experiment represents one of eight studies of this same design, and each one shows that SYN-PKU304 is capable of intercepting enterorecirculating phenylalanine.

FIG. 31A depicts a schematic of the conversion of phenylalanine to phenylpyruvic acid and phenyllactic acid in the absence of functional PAH. FIG. 31B depicts a schematic of the conversion of phenylalanine to trans-cinnamic acid by PAL3, which is further metabolized to hippuric acid by liver enzymes. These metabolites can be detected by mass spectrometry as described in Examples 24-26 or by other means.

FIG. 32A depicts blood phenylalanine concentrations relative to baseline; total metabolic activity for SYN-PKU304 was calculated as 81.2 umol/hr. and the total reduction in Δphe was 45% relative to SYN-PKU901 ($P<0.05$). FIG. 32B depicts the blood phenylalanine concentration at 0 and 4 hours post phenylalanine injection. FIG. 32C depicts the blood phenylpyruvate concentration at 0 and 4 hours post phenylalanine injection. FIG. 32D depicts the blood phenyllactate concentration at 0 and 4 hours post phenylalanine injection. FIG. 32E depicts the blood t-cinnamic acid concentration at 0 and 4 hours post phenylalanine injection. FIG. 32F depicts the blood hippuric acid concentration at 0 and 4 hours post phenylalanine injection.

FIG. 33A depicts blood phenylalanine concentrations relative to baseline; total metabolic activity for SYN-PKU517 was calculated as 39.6 umol/hr. and the total reduction in Δphe was 17% relative to SYN-PKU801 ($P<0.05$). FIG. 33B depicts the blood phenylalanine concentration at 0 and 4 hours post phenylalanine injection. FIG. 33C depicts the blood phenylpyruvate concentration at 0 and 4 hours post phenylalanine injection. FIG. 33D depicts the blood phenyllactate concentration at 0 and 4 hours post phenylalanine injection. FIG. 33E depicts the blood t-cinnamic acid concentration at 0 and 4 hours post phenylalanine injection. FIG. 33F depicts the blood hippuric acid concentration at 0 and 4 hours post phenylalanine injection.

FIG. 34A depicts blood phenylalanine concentrations relative to baseline; total metabolic activity for SYN-PKU705 was calculated as 133.2 umol/hr. and the total reduction in Δphe was 30% relative to SYN-PKU901 ($P<0.05$). FIG. 34B depicts the blood phenylalanine concentration at 0 and 4 hours post phenylalanine injection. FIG. 34C depicts the blood phenylpyruvate concentration at 0 and 4 hours post phenylalanine injection. FIG. 34D depicts the blood phenyllactate concentration at 0 and 4 hours post phenylalanine injection. FIG. 34E depicts the blood t-cinnamic acid concentration at 0 and 4 hours post phenylalanine injection. FIG. 34F depicts the blood hippuric acid concentration at 0 and 4 hours post phenylalanine injection.

FIG. 35 depicts phenylalanine and 2 toxic analogs, p-fluoro-DL-phenylalanine, and o-fluoro-DL-phenylalanine, which are useful for an untargeted approach to select PAL enzymes with increased activity. P-fluoro-DL-phenylalanine, and o-fluoro-DL-phenylalanine are incorporated into cellular protein in the place of phenylalanine, resulting in cell death. Since these compounds are readily taken up by PheP, and can act as a substrate for PAL as shown below, they can be employed in genetic selection and screening for the identification of strains with improved Phe consumption activity. Mutations allowing more efficient PAL metabolism may prevent the incorporation of the phenylalanine analog into cellular protein, therefore allowing growth under higher concentrations of the analog.

FIG. 42A depicts a schematic diagram of the PAL3 gene, flanked by Int5 sites, in the OFF orientation (3' to 5'). When Int5 gene expression is activated under anaerobic conditions, recombinatorial flipping of PAL3 to the ON orientation (5' to 3'; FIG. 42B) leads to the production of PAL3 and to phenylalanine metabolism. Any strong constitutive promoter sequence may be used.

FIG. 43A depicts a schematic diagram of the T7 RNA polymerase gene, flanked by Int5 sites, in the OFF orientation. When Int5 gene expression is activated under anaerobic conditions, the T7 RNA polymerase gene is flipped to the ON orientation (FIG. 43B). In engineered bacterial strains comprising a copy of PAL3 under the control of a T7-driven promoter ($P_{T7}$; FIG. 43C), T7 RNA polymerase expression leads to the production of PAL3 and to phenylalanine metabolism.

FIG. 46A also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the araBAD promoter, which induces expression of the essential gene and maintains viability of the bacterial cell.

FIG. 49 depicts exemplary sequences of a wild-type clbA construct and a clbA knockout construct.

FIG. 55A depicts the parameters for starter culture 1 (SC1): loop full—glycerol stock, duration overnight, temperature 37° C., shaking at 250 rpm.

DESCRIPTION OF EMBODIMENTS

Figure 1:
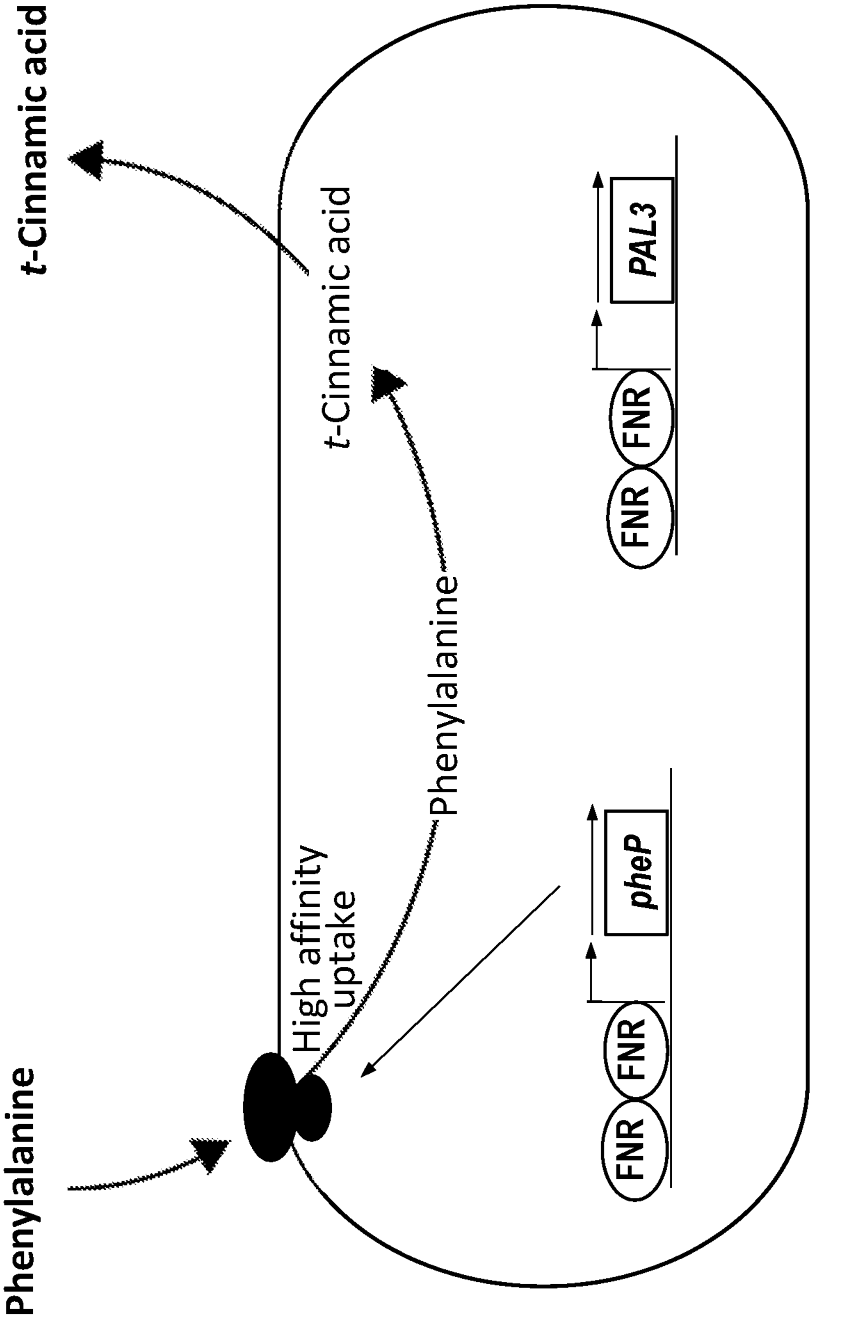
FIG. 1 depicts a synthetic biotic for treating phenylketonuria (PKU) and disorders characterized by hyperphenylalaninemia.
Figure 2A:
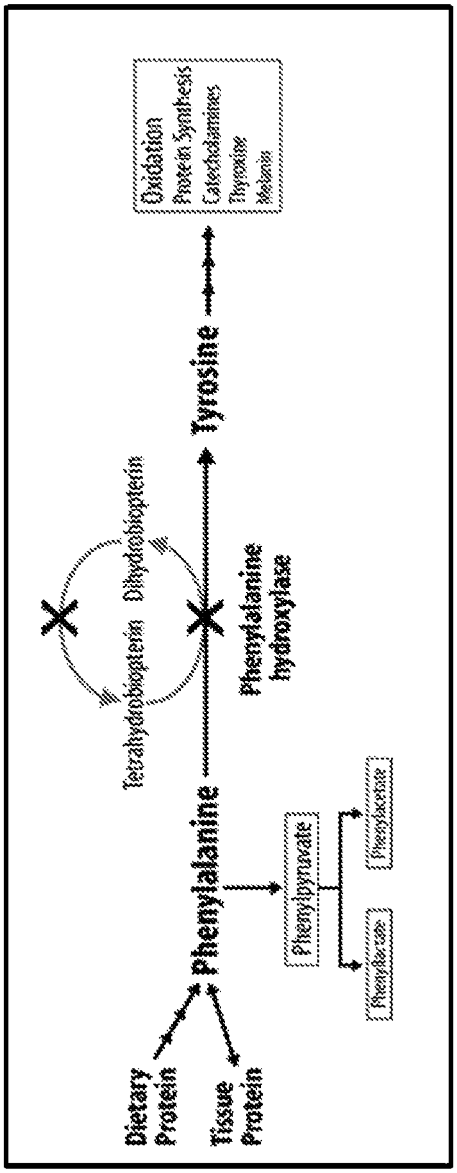
FIG. 2A depicts a schematic of phenylalanine hydroxylase action in phenylketonuria (PKU).
Figure 2B:
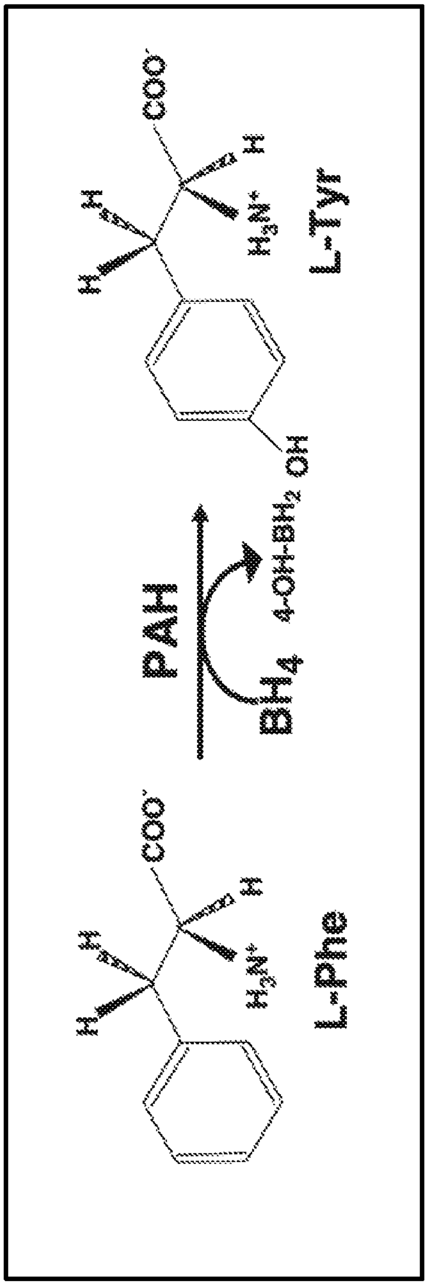
FIG. 2B depicts a schematic of phenylalanine hydroxylase (PAH) action.
Figure 2C:
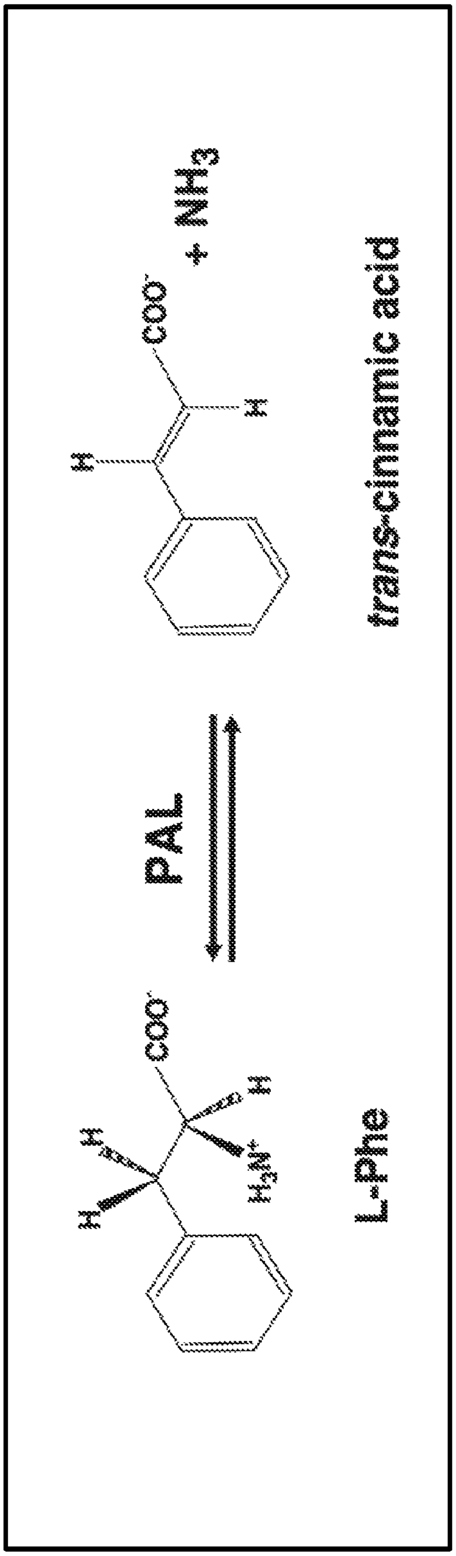
FIG. 2C depicts a schematic of phenylalanine ammonia lyase (PAL) action.
Figure 2D:
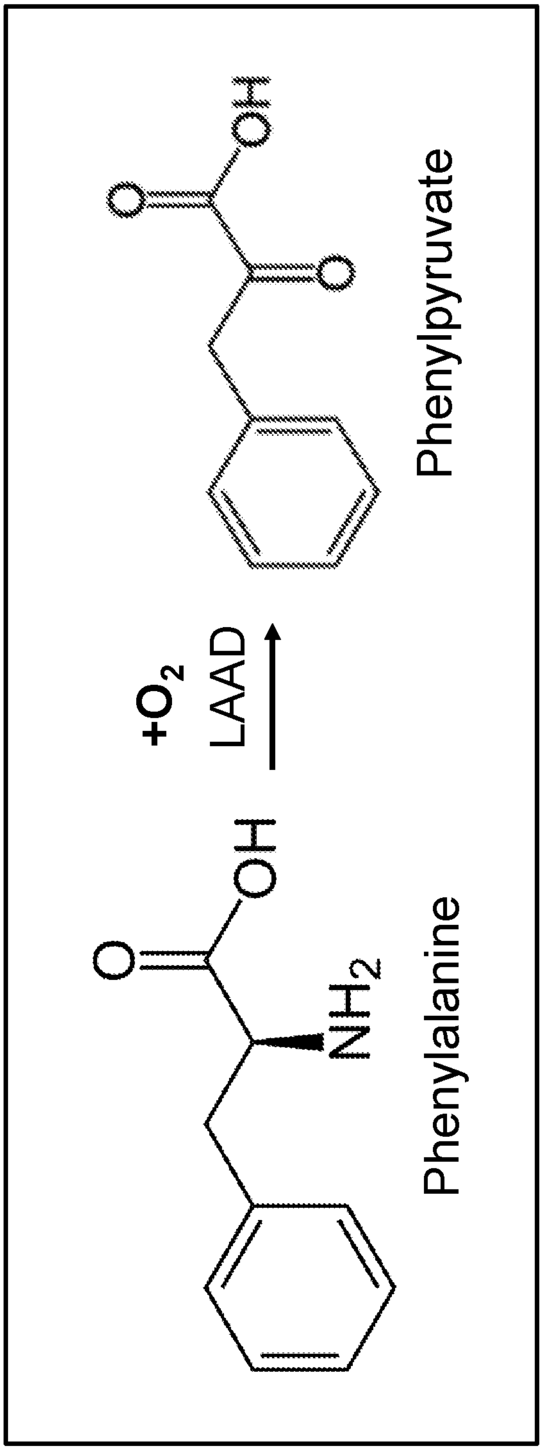
FIG. 2D depicts a schematic of L-amino acid deaminase (LAAD; e.g., from *Proteus mirabilis*) action.
Figure 3:
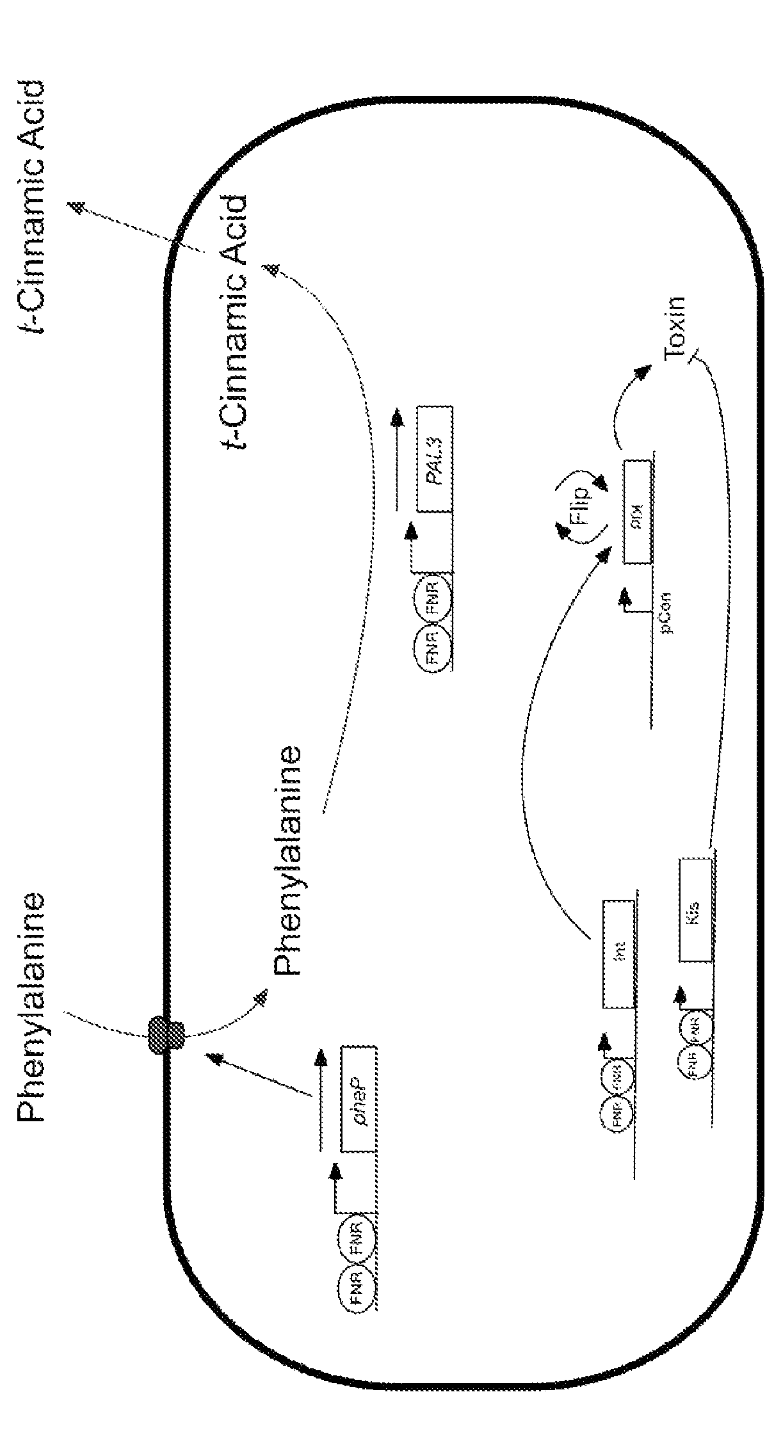
FIG. 3 depicts a synthetic biotic for treating phenylketonuria (PKU) and disorders characterized by hyperphenylalaninemia.
Figure 4:
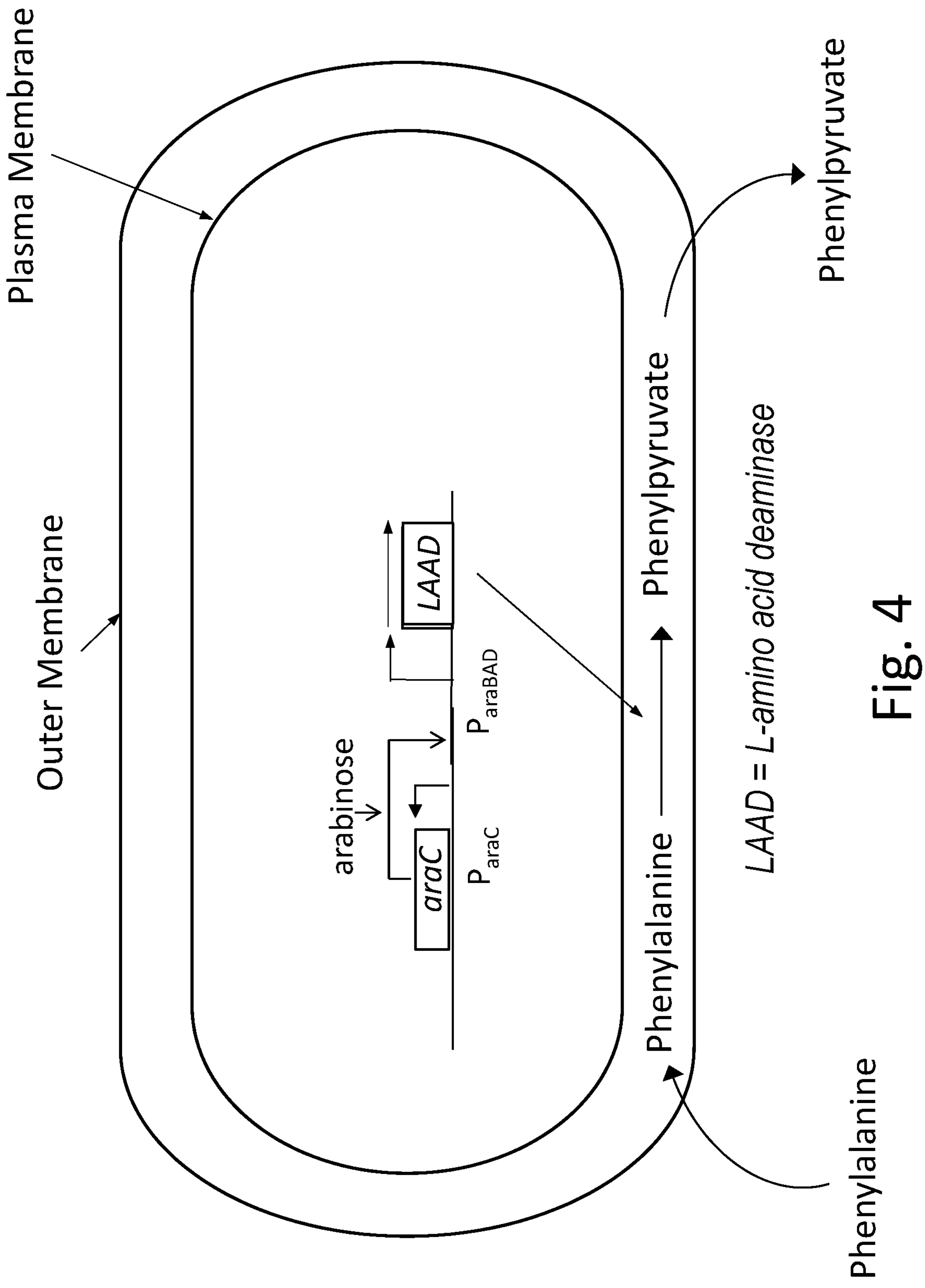
FIG. 4 depicts a synthetic biotic for treating phenylketonuria (PKU) and disorders characterized by hyperphenylalaninemia.
Figure 5:
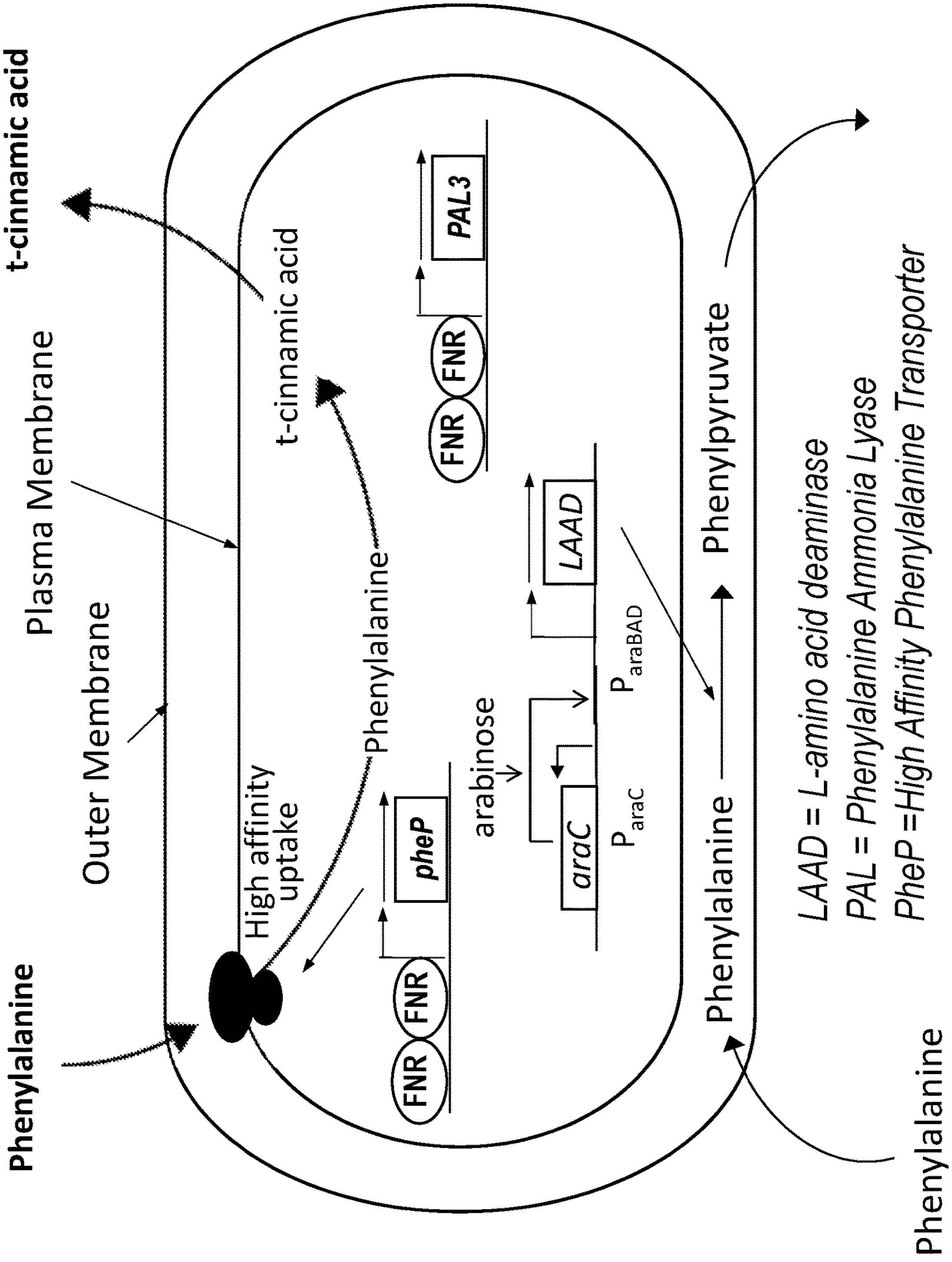
FIG. 5 depicts a synthetic biotic for treating phenylketonuria (PKU) and disorders characterized by hyperphenylalaninemia.
Figure 6:
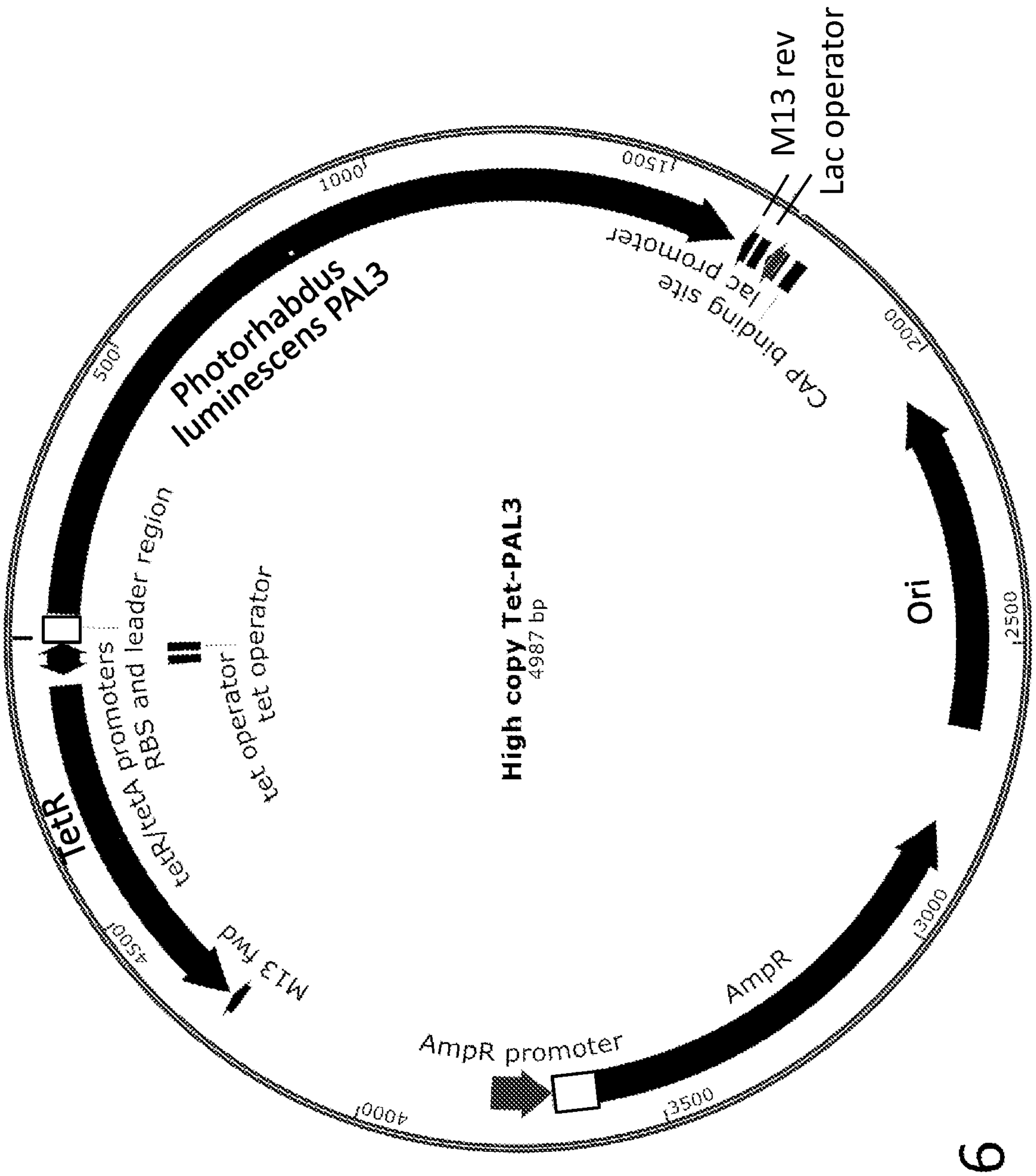
FIG. 6 depicts the gene organization of an exemplary construct comprising a gene encoding PAL3 and a Tet promoter sequence on a high-copy plasmid e.g., as comprised in SYN-PKU202, SYN-PKU303.
Figure 7:
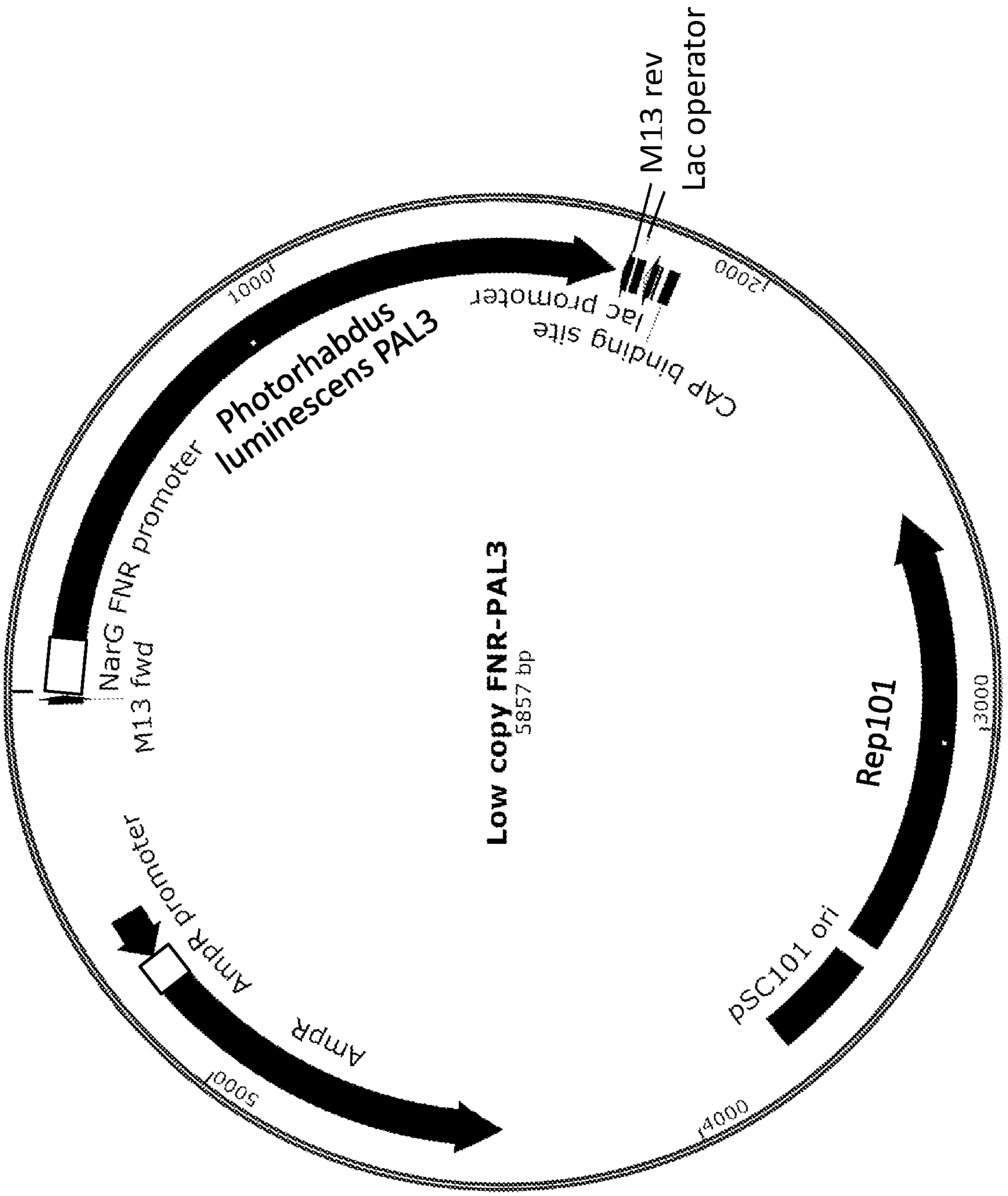
FIG. 7 depicts the gene organization of an exemplary construct comprising a gene encoding PAL3 and an FNR promoter sequence on a low-copy plasmid, e.g., as comprised in SYN-PKU304, SYN-PKU307, SYN-PKU305, SYN-PKU306.
Figure 8:
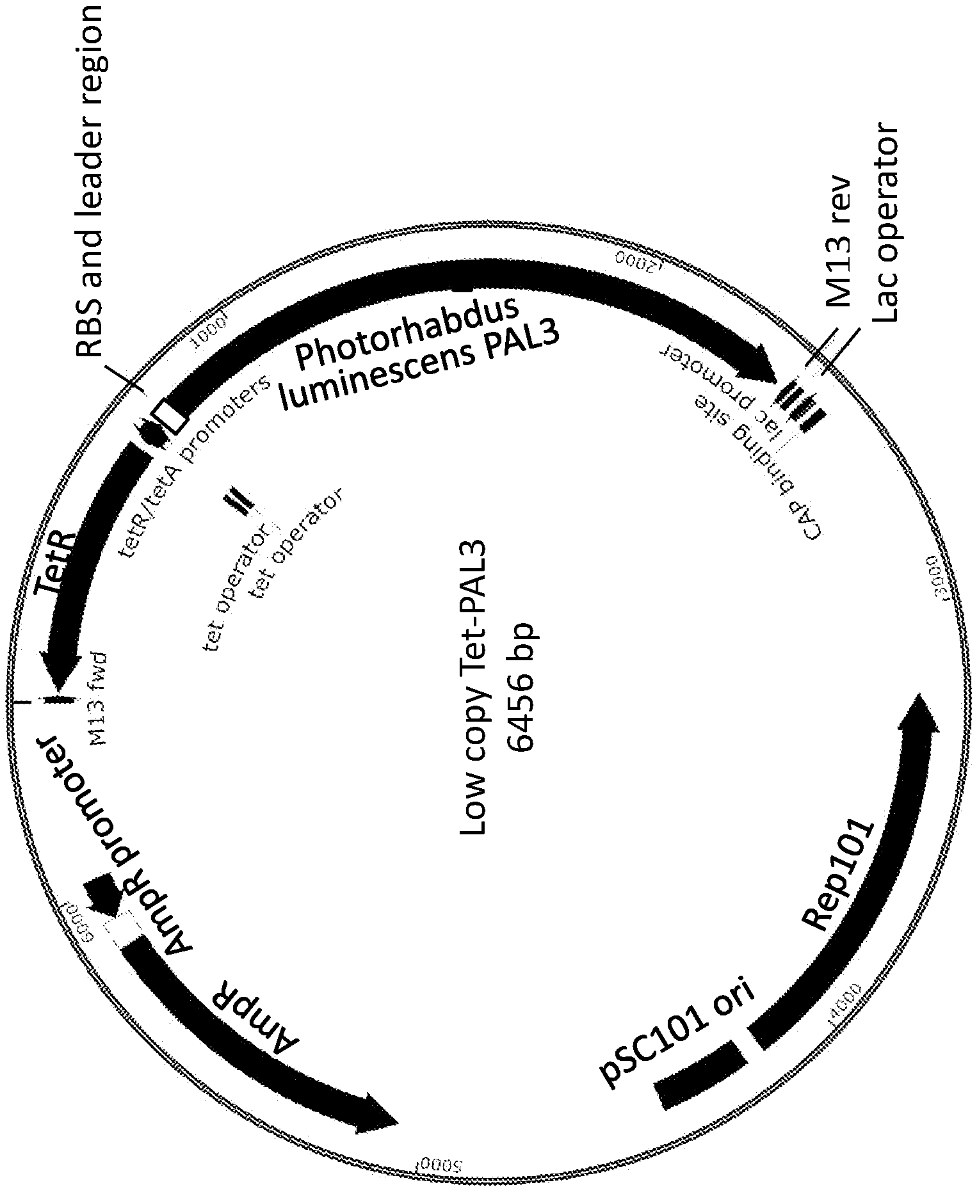
FIG. 8 depicts the gene organization of an exemplary construct comprising a gene encoding PAL3 and a Tet promoter sequence on a low-copy plasmid, e.g., SYN-PKU302, SYN-PKU201.
Figure 9:
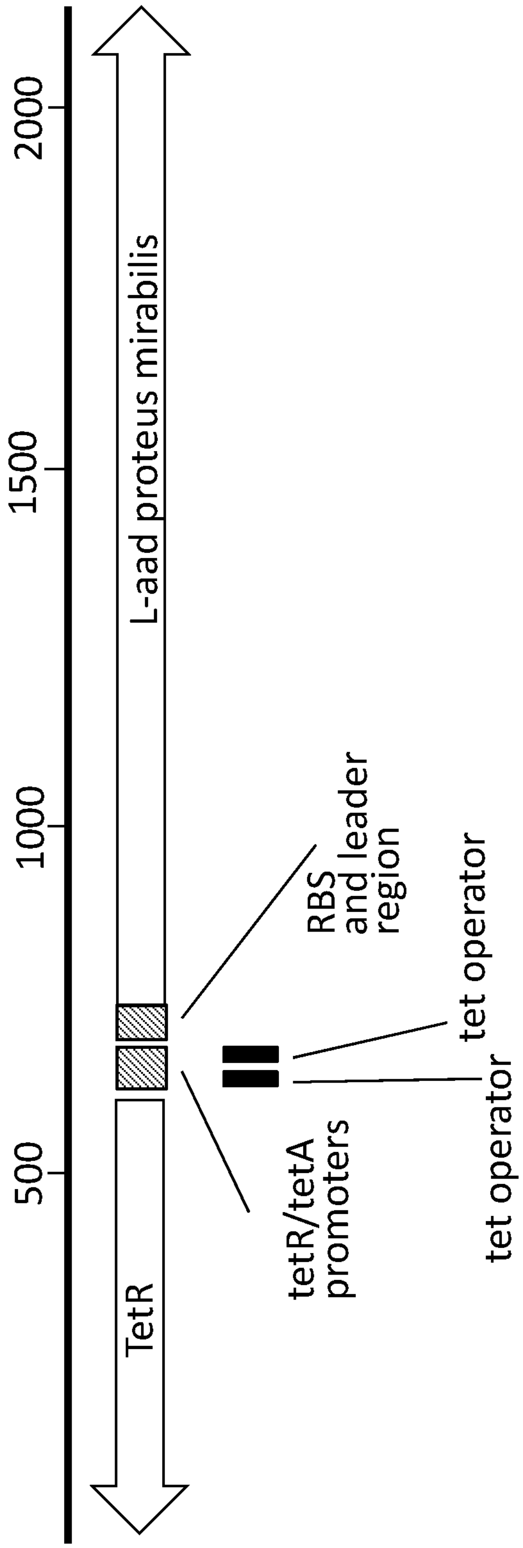
FIG. 9 depicts the gene organization of an exemplary construct, e.g., comprised in SYN-PKU401, comprising a cloned LAAD gene under the control of a Tet promoter sequence and a Tet repressor gene.

The present disclosure includes genetically engineered bacteria, pharmaceutical compositions thereof, and methods of modulating and treating disorders associated with hyperphenylalaninemia. In some embodiments, the genetically engineered bacteria comprise a gene encoding non-native phenylalanine ammonia lyase (PAL) and are capable of processing and reducing phenylalanine in a mammal. Thus, the genetically engineered bacteria and pharmaceutical compositions comprising those bacteria may be used to metabolize phenylalanine in the body into non-toxic molecules in order to treat and/or prevent conditions associated with hyperphenylalaninemia, including PKU. In certain aspects, the compositions comprising the genetically engineered bacteria may be used in the methods of the disclosure to treat and/or prevent disorders associated with hyperphenylalaninemia.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperphenylalaninemia," "hyperphenylalaninemic," and "excess phenylalanine" are used interchangeably herein to refer to increased or abnormally high concentrations of phenylalanine in the body. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL. As used herein, diseases associated with hyperphenylalaninemia include, but are not limited to, phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. Affected individuals can suffer progressive and irreversible neurological deficits, mental retardation, encephalopathy, epilepsy, eczema, reduced growth, microcephaly, tremor, limb spasticity, and/or hypopigmentation (Leonard 2006). Hyperphenylalaninemia can also be secondary to other conditions, e.g., liver diseases.

"Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., *Rhodosporidium toruloides* (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"Phenylalanine hydroxylase" and "PAH" are used to refer to an enzyme that catalyzes the hydroxylation of the aromatic side chain of phenylalanine to create tyrosine in the human body in conjunction with the cofactor tetrahydrobiopterin. The human gene encoding PAH is located on the long (q) arm of chromosome 12 between positions 22 and 24.2. The amino acid sequence of PAH is highly conserved among mammals. Nucleic acid sequences for human and mammalian PAH are well known and widely available. The full-length human cDNA sequence for PAH was reported in 1985 (Kwok et al. 1985). Active fragments of PAH are also well known (e.g., Kobe et al. 1997).

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability.

In some embodiments, the genetically engineered bacteria comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the genetically engineered bacteria is localized to the plasma membrane, facing into the periplasmic space and with the catalytic activity occurring in the periplasmic space.

"Phenylalanine metabolizing enzyme" or "PME" are used to refer to an enzyme which is able to degrade phenylalanine. Any phenylalanine metabolizing enzyme known in the art may be encoded by the genetically engineered bacteria. PMEs include, but are not limited to, phenylalanine hydroxylase (PAH), phenylalanine ammonia lyase (PAL), aminotransferase, L-amino acid deaminase (L-AAD), and phenylalanine dehydrogenases.

Reactions with phenylalanine hydroxylases, phenylalanine dehydrogenases or aminotransferases require cofactors, while L-AAD and PAL do not require any additional cofactors. In some embodiments, the PME encoded by the genetically engineered bacteria requires a cofactor. In some embodiments, this cofactor is provided concurrently or sequentially with the administration of the genetically engineered bacteria. In other embodiments, the genetically engineered bacteria can produce the cofactor. In some embodiments, the genetically engineered bacteria encode a phenylalanine hydroxylase. In some embodiments, the genetically engineered bacteria encode a phenylalanine dehydrogenase. In some embodiments, the genetically engineered bacteria encode an aminotransferase. In some embodiments, the PME encoded by the genetically engineered bacteria does not require a cofactor. Without wishing to be bound by theory, the lack of need for a cofactor means that the rate of phenylalanine degradation by the enzyme is dependent on the availability of the substrate and is not limited by the availability of the cofactor. In some embodiments, the PME produced by the genetically engineered bacteria is PAL. In some embodiments, the PME produced by the genetically engineered bacteria is LAAD. In some embodiments, the genetically engineered bacteria encode combinations of PMEs.

In some embodiments, the catalytic activity of the PME is dependent on oxygen levels. In some embodiments, the PME is catalytically active under microaerobic conditions. As a non-limiting example, LAAD catalytic activity is dependent on oxygen. In some embodiments, LAAD is active under low oxygen conditions, such as microaerobic conditions. In some embodiments, of the invention, the PME functions at very low levels of oxygen or in the absence of oxygen, e.g. as found in the colon. As a non-limiting example, PAL activity is not dependent on the presence of oxygen.

In certain embodiments, new or improved PMEs can be identified according to methods known in the art or described herein, and are encoded by the genetically engineered bacteria. In some embodiments, the enzyme encoded by the genetically engineered bacteria is a wild type enzyme isolated from a viral, prokaryotic or eukaryotic organism. In some embodiments, the enzyme sequence has been further modified or mutated to increase one or more specific properties of the enzyme, such as stability or catalytic activity.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the genetically engineered bacteria encoding a PME.

In some embodiments, the phenylalanine metabolite results directly or indirectly from PAH activity, e.g., from PAH produced by the genetically engineered bacteria. In some embodiments, the metabolite is tyrosine. In some embodiments, the phenylalanine metabolite accumulates in the blood or the urine of a PKU patient, due to defective PAH activity. Non-limiting examples of such PKU metabolites are phenylpyruvic acid and phenyl-lactic acid. Other examples include phenylacetate, phenylethylamine, and phenylacetyl glutamine.

In some embodiments, the phenylalanine metabolite results directly or indirectly from PAL action, e.g., from PAL produced by the genetically engineered bacteria. Non-limiting examples of such PAL metabolites are trans-cinnamic acid and hippuric acid. In some embodiments, the phenylalanine metabolite results directly or indirectly from LAAD action, e.g., from LAAD produced by the genetically engineered bacteria. Examples of such LAAD metabolites are phenylpyruvate and phenyllactic acid.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by apheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region.

A "directly inducible promoter" refers to a regulatory region, wherein the regulatory region is operably linked to a gene encoding a phenylalanine-metabolizing enzyme, e.g., PAL; in the presence of an inducer of said regulatory region, the phenylalanine-metabolizing enzyme is expressed. An "indirectly inducible promoter" refers to a regulatory system comprising two or more regulatory regions, for example, a first regulatory region that is operably linked to a gene encoding a first molecule, e.g., a transcriptional regulator, which is capable of regulating a second regulatory region that is operably linked to a gene encoding a phenylalanine-metabolizing enzyme. In the presence of an inducer of the first regulatory region, the second regulatory region may be activated or repressed, thereby activating or repressing expression of the phenylalanine-metabolizing enzyme. Both a directly inducible promoter and an indirectly inducible promoter are encompassed by "inducible promoter."

"Exogenous environmental conditions" refer to settings or circumstances under which the promoter described above is directly or indirectly induced. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, exogenous environmental conditions refer to the presence of molecules or metabolites that are specific to the mammalian gut in a healthy or disease state, e.g., propionate. In some embodiments, the exogenous environmental conditions are low-oxygen, microaerobic, or anaerobic conditions, such as the environment of the mammalian gut.

"Exogenous environmental condition(s)" refer to setting(s) or circumstance(s) under which the promoter described herein is induced. The phrase "exogenous environmental conditions" is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic conditions by the global transcriptional regulator FNR that is naturally found in Nissle. Under anaerobic conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

Examples of transcription factors and responsive genes and regulatory regions

| Transcription factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions. In some embodiments, the genetically engineered bacteria of the invention comprise a gene encoding a phenylalanine-metabolizing enzyme that is operably linked to a directly or indirectly inducible promoter that is not associated with said gene in nature, e.g., an FNR promoter operably linked to a gene encoding PAL or a ParaBAD promoter operably linked to LAAD.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), PliaG (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, *Bifidobacteria, Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a PAL gene, which is incorporated into the host genome or propagated on a self-replicating extra-chromosomal plasmid, such that the non-native genetic material is retained, expressed, and/or propagated. The stable bacterium is capable of survival and/or growth in vitro, e.g., in medium, and/or in vivo, e.g., in the gut. For example, the stable bacterium may be a genetically modified bacterium comprising a PAL gene, in which the plasmid or chromosome carrying the PAL gene is stably maintained in the host cell, such that PAL can be expressed in the host cell, and the host cell is capable of survival and/or growth in vitro and/or in vivo. In some embodiments, copy number affects the stability of expression of the non-native genetic material, e.g., a PAL gene or a PAH gene. In some embodiments, copy number affects the level of expression of the non-native genetic material, e.g., a PAL gene or a PAH gene.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Primary hyperphenylalaninemia, e.g., PKU, is caused by inborn genetic mutations for which there are no known cures. Hyperphenylalaninemia can also be secondary to other conditions, e.g., liver diseases. Treating hyperphenylalaninemia may encompass reducing or eliminating excess phenylalanine and/or associated symptoms, and does not necessarily encompass the elimination of the underlying disease.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperphenylalaninemia. A therapeutically effective amount may, for example, be sufficient to treat, prevent, reduce the severity, delay the onset, and/or reduce the risk of occurrence of one or more symptoms of a disease or condition associated with excess phenylalanine levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids, "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism.

Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein(s) of interest or therapeutic protein(s) from the microbial, e.g., bacterial cytoplasm. The secretion system may comprise a single protein or may comprise two or more proteins assembled in a complex e.g., HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the proteins of interest include a "secretion tag" of either RNA or peptide origin to direct the protein(s) of interest or therapeutic protein(s) to specific secretion systems. In some embodiments, the secretion system is able to remove this tag before secreting the protein(s) of interest from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the protein(s) of interest into the extracellular milieu.]]

As used herein, the term "transporter" is meant to refer to a mechanism, e.g., protein or proteins, for importing a molecule, e.g., amino acid, toxin, metabolite, substrate, etc. into the microorganism from the extracellular milieu.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

The genetically engineered bacteria of the invention are capable of reducing excess phenylalanine. In some embodiments, the genetically engineered bacteria are non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E.*

*coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic (Sonnenborn et al., 2009). As early as in 1917, *E. coli* Nissle was packaged into medicinal capsules, called Mutaflor, for therapeutic use. It is commonly accepted that *E. coli* Nissle's therapeutic efficacy and safety have convincingly been proven (Ukena et al., 2007).

One of ordinary skill in the art would appreciate that the genetic modifications disclosed herein may be adapted for other species, strains, and subtypes of bacteria. Furthermore, genes from one or more different species can be introduced into one another, e.g., the PAL gene from *Rhodosporidium toruloides* can be expressed in *Escherichia coli* (Sarkissian et al., 1999), and it is known that prokaryotic and eukaryotic phenylalanine ammonia lyases share sequence homology (Xiang and Moore, 2005).

Unmodified *E. coli* Nissle and the genetically engineered bacteria of the invention may be destroyed, e.g., by defense factors in the gut or blood serum (Sonnenborn et al., 2009) or by activation of a kill switch, several hours or days after administration. Thus, the genetically engineered bacteria may require continued administration. In some embodiments, the residence time is calculated for a human subject. Residence time in vivo may be calculated for the genetically engineered bacteria of the invention (see, e.g., FIG. 38).

In some embodiments, the genetically engineered bacteria of the invention comprise a gene encoding PAL, wherein the PAL gene is operably linked to a directly or indirectly inducible promoter. In some embodiments, the bacteria comprise a non-native PAL gene. In some embodiments, the bacteria comprise additional copies of a native PAL gene. In some embodiments, the promoter is not associated with the PAL gene in nature. In some embodiments, the genetically engineered bacteria of the invention comprise a gene encoding PAH, wherein the PAH gene is operably linked to a directly or indirectly inducible promoter. In some embodiments, the bacteria comprise a non-native PAH gene. In some embodiments, the bacteria comprise additional copies of a native PAH gene. In some embodiments, the promoter is not associated with the PAH gene in nature.

The genetically engineered bacteria further comprise a gene encoding a phenylalanine transporter (PheP). In certain embodiments, the bacteria comprise additional copies of a native gene encoding a phenylalanine transporter, wherein the phenylalanine transporter gene is operably linked to a directly or indirectly inducible promoter. In alternate embodiments, the bacteria comprise a gene encoding a non-native phenylalanine transporter, wherein the phenylalanine transporter gene is operably linked to a directly or indirectly inducible promoter. Both embodiments are encompassed by the term "non-native" phenylalanine transporter. In some embodiments, the promoter is not associated with the pheP gene in nature. In some embodiments, the same promoter controls expression of PheP and PAL or PAH.

In some embodiments, the promoter that is operably linked to PAL, PAH, and/or pheP is directly or indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by the presence of molecules or metabolites that are specific to the gut of a mammal, e.g., propionate. In some embodiments, the promoter is directly or indirectly induced by exposure to tetracycline. In some embodiments, the promoter is directly or indirectly induced by a molecule that is co-administered with the genetically engineered bacteria of the invention.

Reducing Hyperphenylalaninemia

The genetically engineered bacteria of the invention comprise a gene encoding a phenylalanine-metabolizing enzyme (PME) and are capable of reducing hyperphenylalaninemia.

Examples of phenylalanine metabolizing enzymes include, but are not limited to, phenylalanine hydroxylase (PAH), phenylalanine ammonia lyase (PAL), aminotransferases, L-amino acid deaminase (L-AAD), and phenylalanine dehydrogenases. Reactions with phenylalanine hydroxylases, phenylalanine dehydrogenases or aminotransferases require cofactors, while L-AAD and PAL do not require any extra cofactor. Without wishing to be bound by theory, the lack of need for a cofactor means that phenylalanine degradation by the enzyme encoded by the genetically engineered bacteria is dependent on the availability of the substrate and is not limited by the availability of the cofactor.

Phenylalanine ammonia lyase (PAL; EC 4.3.1.24) is an enzyme that catalyzes a reaction converting L-phenylalanine to ammonia and trans-cinnamic acid. Phenylalanine ammonia lyase is specific for L-Phe, and to a lesser extent, L-Tyrosine. The reaction catalyzed by PAL is the spontaneous, non-oxidative deamination of L-phenylalanine to yield trans-cinnamic acid and ammonia. Unlike the mammalian enzyme (PAH), PAL is a monomer and requires no cofactors (MacDonald et al., Biochem Cell Biol 2007; 85:273-82. A modern view of phenylalanine ammonia lyase). In microorganisms, it has a catabolic role, allowing them to utilize L-phenylalanine (L-Phe) as a sole source of carbon and nitrogen. In one embodiment, the genetically engineered bacteria of the invention comprise a PAL gene. PAL is capable of converting phenylalanine to non-toxic levels of transcinnamic acid and ammonia. Trans-cinnamic acid (TCA) can further be converted to TCA metabolites benzoic and hippuric acids (Sarkissian et al., J Mass Spectrom. 2007 June; 42(6):811-7; Quantitation of phenylalanine and its trans-cinnamic, benzoic and hippuric acid metabolites in biological fluids in a single GC-MS analysis). PAL enzyme activity does not require THB cofactor activity.

In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, the bacterial species is *Photorhabdus luminescens*. In some embodiments, the bacterial species is *Anabaena variabilis*. In some embodiments, PAL is encoded by a PAL gene derived from a eukaryotic species, e.g., a yeast species, a plant species. Multiple distinct PAL proteins are known in the art. The genetically engineered bacteria convert more phenylalanine when the PAL gene is expressed than unmodified bacteria of the same bacterial subtype under the same conditions. Thus, the genetically engineered bacteria comprising PAL may be used to metabolize phenylalanine in the body into non-toxic molecules in order to treat conditions associated with hyperphenylalaninemia, including PKU. In some embodiments, the genetically engineered bacteria express *Anabaena variabilis* PAL ("PAL1"). In some embodiments, the genetically engineered bacteria express *Photorhabdus luminescens* PAL ("PAL3"). Non-limiting examples of PAL sequences of interest are shown in Table 2.

LAAD catalyzes the stereospecific oxidative, i.e., oxygen consuming, deamination of L-amino acids to α-keto acids along with the production of ammonia and hydrogen peroxide via an imino acid intermediate. L-AADs are found in snake venoms, and in many bacteria (Bifulco et al. 2013), specifically in the cytomembranes of the *Proteus, Providencia*, and *Morganella* bacteria. L-AADs (EC 1.4.3.2) are flavoenzymes with a dimeric structure. Each subunit contains a non-covalently-bound flavin adenine dinucleotide (FAD) cofactor) and do not require any external cofactors. *Proteus mirabilis* contains two types of L-AADs (Duerre and Chakrabarty 1975). One has broad substrate specificity and catalyzes the oxidation of aliphatic and aromatic L-amino acids to keto acids, typically L-phenylalanine (GenBank: U35383.1) (Baek et al., Journal of Basic Microbiology 2011, 51, 129-135; "Expression and characterization of a second L-amino acid deaminase isolated from *Proteus mirabilis* in *Escherichia coli*"). The other type acts mainly on basic L-amino acids (GenBank: EU669819.1). LAADs from bacterial, fungal, and plant sources appear to be involved in the utilization of L-amino acids (i.e., ammonia produced by the enzymatic activity) as a nitrogen source. Most eukaryotic and prokaryotic L-amino acid deaminases are extracellularly secreted, with the exception of from *Proteus* species LAADs, which are membrane-bound. In *Proteus mirabilis*, L-AADs have been reported to be located in the plasma membrane, facing outward into the periplasmic space, in which the enzymatic activity resides (Pelmont J et al., (1972) "L-amino acid oxidases of *Proteus mirabilis*: general properties" Biochimie 54: 1359-1374).

In one embodiment, the genetically engineered bacteria of the invention comprise a LAAD gene. LAAD is capable of converting phenylalanine to non-toxic levels of phenylpyruvate, which can also further be degraded, e.g., by liver enzymes, to phenyllactate. Phenylpyruvate cannot cross the blood brain barrier, which allows LAAD to reduce the levels of phenylalanine in the brain without allowing the accumulation of another potentially toxic metabolite. In some embodiments, LAAD is encoded by a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the genetically engineered bacteria express *Proteus mirabilis* LAAD enzyme GenBank: U35383.1. Non-limiting examples of LAAD sequences of interest are shown in Table 2. In some embodiments, the LAAD enzyme is derived from snake venom. According to the invention, genetically engineered bacteria convert more phenylalanine when the LAAD gene is expressed than unmodified bacteria of the same bacterial subtype under the same conditions. Thus, the genetically engineered bacteria comprising LAAD may be used to metabolize phenylalanine in the body into non-toxic molecules in order to treat conditions associated with hyperphenylalaninemia, including PKU.

In some embodiments, the genetically engineered bacteria encode a wild type enzyme as it occurs in nature. In some embodiments, the genetically engineered bacteria encode an enzyme which comprises mutations relative to the wild type sequence. In some embodiments, the mutations increase stability of the enzyme. In some embodiments, the mutations increase the catalytic activity of the enzyme. In some embodiments, the genetically engineered bacteria comprise a gene encoding one or more of the proteins listed in Table 2. In some embodiments, the genetically engineered bacteria comprise gene sequence(s) encoding one or more of the polypeptides comprising sequence of any of SEQ ID Nos: 1-8. In some embodiments, the genetically engineered bacteria comprise gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 1-8. In some embodiments, the genetically engineered bacteria encode one or more enzymes from Table 2, which comprise a mutation. In some embodiments, the genetically engineered bacteria comprise a gene encoding wild type PAH. In some embodiments, the genetically engineered bacteria encode a mutated PAH with increased stability and/or activity. In some embodiments, the genetically engineered bacteria comprise a gene encoding wild type PAL. In some embodiments, the genetically engineered bacteria encode a mutated PAL with increased stability and/or activity. In some embodiments, the genetically engineered bacteria comprise a gene encoding wild type LAAD. In some embodiments, the genetically engineered bacteria encode a mutated LAAD with increased stability and/or activity. Methods for screening for enzymes with desirable properties are known in the art and described herein.

TABLE 2

Sequences of Phenylalanine Metabolizing Enzymes

| Description | Sequence | SEQ ID NO |
|---|---|---|
| Phenylalanine ammonia-lyase (*Anabaena variabilis*) Acc. No.: Q3M5Z3.1 | MKTLSQAQSKTSSQQFSFTGNSSANVIIGNQKLTIN DVARVARNGTLVSLTNNTDILQGIQASCDYINNAV ESGEPIYGVTSGFGGMANVAISREQASELQTNLVW FLKTGAGNKLPLADVRAAMLLRANSHMRGASGIR LELIKRMEIFLNAGVTPYVYEFGSIGASGDLVPLSYI TGSLIGLDPSFKVDFNGKEMDAPTALRQLNLSPLTL LPKEGLAMMNGTSVMTGIAANCVYDTQILTAIAM GVHALDIQALNGTNQSFHPFIHNSKPHPGQLWAAD QMISLLANSQLVRDELDGKHDYRDHELIQDRYSLR CLPQYLGPIVDGISQIAKQIEIEINSVTDNPLIDVDNQ ASYHGGNFLGQYVGMGMDHLRYYIGLLAKHLDV QIALLASPEFSNGLPPSLLGNRERKVNMGLKGLQIC GNSIMPLLTFYGNSIADRFPTHAEQFNQNINSQGYT SATLARRSVDIFQNYVAIALMFGVQAVDLRTYKKT GHYDARACLSPATERLYSAVRHVVGQKPTSDRPYI WNDNEQGLDEHIARISADIAAGGVIVQAVQDILPCL H | SEQ ID NO: 1 |

TABLE 2-continued

| Sequences of Phenylalanine Metabolizing Enzymes | | |
|---|---|---|
| Description | Sequence | SEQ ID NO |
| histidine ammonia-lyase *Anabaena variabilis* ATCC 294131 (Acc. NO. ABA23593.1) | MKTLSQAQSKTSSQQFSFTGNSSANVIIGNQKLTIN DVARVARNGTLVSLTNNTDILQGIQASCDYINNAV ESGEPIYGVTSGFGGMANVAISREQASELQTNLVW FLKTGAGNKLPLADVRAAMLLRANSHMRGASGIR LELIKRMEIFLNAGVTPYVYEFGSIGASGDLVPLSYI TGSLIGLDPSFKVDFNGKEMDAPTALRQLNLSPLTL LPKEGLAMMNGTSVMTGIAANCVYDTQILTAIAM GVHALDIQALNGTNQSFHPFIHNSKPHPGQLWAAD QMISLLANSQLVRDELDGKHDYRDHELIQDRYSLR CLPQYLGPIVDGISQIAKQIEIEINSVTDNPLIDVDNQ ASYHGGNFLGQYVGMGMDHLRYYIGLLAKHLDV QIALLASPEFSNGLPPSLLGNRERKVNMGLKGLQIC GNSIMPLLTFYGNSIADRFPTHAEQFNQNINSQGYT SATLARRSVDIFQNYVAIALMFGVQAVDLRTYKKT GHYDARACLSPATERLYSAVRHVVGQKPTSDRPYI WNDNEQGLDEHIARISADIAAGGVIVQAVQDILPCL H | SEQ ID NO: 2 |
| histidine ammonia-lyase [*Photorhabdus luminescens*] (WP_011146 484) | MKAKDVQPTIIINKNGLISLEDIYDIAIKQKKVEISTE ITELLTHGREKLEEKLNSGEVIYGINTGFGGNANLV VPFEKIAEHQQNLLTFLSAGTGDYMSKPCIKASQFT MLLSVCKGWSATRPIVAQAIVDHINHDIVPLVPRYG SVGASGDLIPLSYIARALCGIGKVYYMGAEIDAAEA IKRAGLTPLSLKAKEGLALINGTRVMSGISAITVIKL EKLFKASISAIALAVEALLASHEHYDARIQQVKNHP GQNAVASALRNLLAGSTQVNLLSGVKEQANKACR HQEITQLNDTLQEVYSIRCAPQVLGIVPESLATARKI LEREVISANDNPLIDPENGDVLHGGNFMGQYVART MDALKLDIALIANHLHAIVALMMDNRFSRGLPNSL SPTPGMYQGFKGVQLSQTALVAAIRHDCAASGIHT LATEQYNQDIVSLGLHAAQDVLEMEQKLRNIVSMT ILVVCQAIHLRGNISEIAPETAKFYHAVREISSPLITD RALDEDIIRIADAIINDQLPLPEIMLEE | SEQ ID NO: 3 |
| Histidine ammonia lyase (*Photorhabdus luminescens*) Acc. NO: CAE15566 | MKQLTIYPGKLTLDELRQVYLQPVKITLDSQIFPAIE RSVECVNAILAENRTAYGINTGFGLLASTRIEEDNL EKLQRSLVVSHAAGVGKALDDNMTRLIMVLKINSL SRGYSGIRLAVIQALIALVNAEIYPHIPCKGSVGASG DLAPLAHMSLLLLGEGQARYQGEWLPAKEALAKA NLQPITLAAKEGLALLNGTQVSTAFALRGLFEAEDL LAAAIVCGSLSVEAALGSRKPFDARVHVVRGQQGQ IDVAALYRHVLEESSELSDSHINCPKVQDPYSLRCQ PQVMGACLTQLRHAADVILTEANAVSDNPLVFAEQ GEVISGGNFHAEPVAMASDNLALVLAEIGALSERRI ALLMDSHMSQLPPFLVENGGVNSGFMIAQVTAAAL ASENKALAHPASVDSLPTSANQEDHVSMAPAAGRR LWEMAENTRGILAIEWLSACQGIDFRNGLKSSPILE EARVILRAKVDYYDQDRFFAPDIDAAVKLLAEQHL SSLLPSGQILQRKNNR | SEQ ID NO: 4 |
| amino acid deaminase (*Proteus mirabilis*) Acc. No: ACD36582 | MAISRRKFILGGTVVAVAAGAGVLTPMLTREGRFV PGTPRHGFVEGTGGPLPKQDDVVVIGAGILGIMTAI NLAERGLSVTIVEKGNIAGEQSSRFYGQAISYKMPD ETFLLHHLGKHRWREMNAKVGIDTTYRTQGRVEV PLDEEDLENVRKWIDAKSKDVGSDIPFRTKMIEGAE LKQRLRGATTDWKIAGFEEDSGSFDPEVATFVMAE YAKKMGIKIFTNCAARGLETQAGVISDVVTEKGPIK TSRVVVAGGVGSRLFMQNLNVDVPTLPAYQSQQLI SAAPNAPGGNVALPGGIFFRDQADGTYATSPRVIVA PVVKESFTYGYKYLPLLALPDFPVHISLNEQLINSFM QSTHWDLNEESPFEKYRDMTALPDLPELNASLEKL KKEFPAFKESTLIDQWSGAMAIAPDENPIISDVKEYP GLVINTATGWGMTESPVSAEITADLLLGKKPVLDA KPFSLYRF | SEQ ID NO: 5 |
| amino acid deaminase [*Proteus mirabilis* HI4320]) Acc. No.: AAA86752.1 | MNISRRKLLLGVGAAGVLAGGAALVPMVRRDGKF VEAKSRASFVEGTQGALPKEADVVIIGAGIQGIMTA INLAERGMSVTILEKGQIAGEQSGRAYSQIISYQTSP EIFPLHHYGKILWRGMNEKIGADTSYRTQGRVEAL ADEKALDKAQAWIKTAKEAAGFDTPLNTRIIKGEE LSNRLVGAQTPWTVAAFEEDSGSVDPETGTPALAR YAKQIGVKIYTNCAVRGIETAGGKISDVVSEKGAIK TSQVVLAGGIWSRLFMGNMGIDIPTLNVYLSQQRV SGVPGAPRGNVHLPNGIHFREQADGTYAVAPRIFTS | SEQ ID NO: 6 |

TABLE 2-continued

Sequences of Phenylalanine Metabolizing Enzymes

| Description | Sequence | SEQ ID NO |
|---|---|---|
| | SIVKDSFLLGPKFMHLLGGGELPLEFSIGEDLFNSFK<br>MPTSWNLDEKTPFEQFRVATATQNTQHLDAVFQR<br>MKTEFPVFEKSEVVERWGAVVSPTFDELPIISEVKE<br>YPGLVINTATVWGMTEGPAAGEVTADIVMGKKPVI<br>DPTPFSLDRFKK | |
| L-AAD from *Proteus vulgaris;* (Acc. NO: BAA90864) | MAISRRKFIIGGTVVAVAAGAGILTPMLTREGRFVP<br>GTPRHGFVEGTEGALPKQADVVVVGAGILGIMTAI<br>NLVERGLSVVIVEKGNIAGEQSSRFYGQAISYKMPD<br>ETFLLHHLGKHRWREMNAKVGIDTTYRTQGRVEV<br>PLDEEDLVNVRKWIDERSKNVGSDIPFKTRIIEGAEL<br>NQRLRGATTDWKIAGFEEDSGSFDPEVATFVMAEY<br>AKKMGVRIYTQCAARGLETQAGVISDVVTEKGAIK<br>TSQVVVAGGVWSRLFMQNLNVDVPTLPAYQSQQL<br>ISGSPTAPGGNVALPGGIFFREQADGTYATSPRVIVA<br>PVVKESFTYGYKYLPLLALPDFPVHISLNEQLINSFM<br>QSTHWNLDEVSPFEQFRNMTALPDLPELNASLEKL<br>KAEFPAFKESKLIDQWSGAMAIAPDENPIISEVKEYP<br>GLVINTATGWGMTESPVSAELTADLLLGKKPVLDP<br>KPFSLYRF | SEQ ID NO: 7 |
| Phenylalanine hydroxylase [*Homo sapiens*] (Acc. No. AAH26251] | MSTAVLENPGLGRKLSDFGQETSYIEDNCNQNGAIS<br>LIFSLKEEVGALAKVLRLFEENDVNLTHIESRPSRLK<br>KDEYEFFTHLDKRSLPALTNIIKILRHDIGATVHELS<br>RDKKKDTVPWFPRTIQELDRFANQILSYGAELDAD<br>HPGFKDPVYRARRKQFADIAYNYRHGQPIPRVEYM<br>EEGKKTWGTVFKTLKSLYKTHACYEYNHIFPLLEK<br>YCGFHEDNIPQLEDVSQFLQTCTGFRLRPVAGLLSS<br>RDFLGGLAFRVFHCTQYIRHGSKPMYTPEPDICHEL<br>LGHVPLFSDRSFAQFSQEIGLASLGAPDEYIEKLATI<br>YWFTVEFGLCKQGDSIKAYGAGLLSSFGELQYCLS<br>EKPKLLPLELEKTAIQNYTVTEFQPLYYVAESFNDA<br>KEKVRNFAATIPRPFSVRYDPYTQRIEVLDNTQQLK<br>ILADSINSEIGILCSALQKIK | SEQ ID NO: 8 |

The PME, e.g., PAL, LAAD, or PAH, gene may be present on a plasmid or chromosome in the genetically engineered bacteria. In some embodiments, the PME gene is expressed under the control of a constitutive promoter. In some embodiments, the PME gene is expressed under the control of a promoter that is directly or indirectly induced by exogenous environmental conditions, as described herein. In some embodiments, the PME gene is expressed under the control of a promoter that is directly or indirectly induced by exogenous environmental conditions, such as in the presence of molecules or metabolites specific to the gut of a mammal. In one embodiment, the PME gene is expressed under the control of a promoter that is directly or indirectly induced by low-oxygen, microaerobic, or anaerobic conditions, wherein expression of the PME gene, e.g., the PAL gene, is activated under low-oxygen or anaerobic environments, such as the environment of the mammalian gut.

In one embodiment, the genetically engineered bacteria encode a PAL gene which is directly or indirectly induced by low-oxygen or anaerobic conditions, such as the mammalian gut. In one embodiment, the genetically engineered bacteria encode a LAAD gene which is directly or indirectly induced by oxygenated, low oxygen, or microaerobic conditions, such as conditions found in the proximal intestine, including but not limited to the stomach, duodenum, and ileum. In other embodiments, the genetically engineered bacteria encode a PME gene which is directly or indirectly induced by an environmental factor that is naturally present in a mammalian gut. In other embodiments, the genetically engineered bacteria encode a PME gene which is directly or indirectly induced by an environmental factor that is not naturally present in a mammalian gut, e.g., arabinose. In other embodiments, the genetically engineered bacteria encode a PME gene which is directly or indirectly induced by an environmental factor that is naturally present in a mammalian gut under inflammatory conditions.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the PME gene is expressed under the control of an oxygen level-dependent promoter. In a more specific aspect, the PAL gene is under the control of an oxygen level-dependent promoter that is activated under low-oxygen or anaerobic environments, such as the environment of the mammalian gut.

In certain embodiments, the genetically engineered bacteria comprise a PME, e.g., PAL, expressed under the control of the fumarate and nitrate reductase regulator (FNR) promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. In some embodiments, multiple distinct FNR nucleic acid sequences are inserted in the genetically engineered bacteria. In alternate embodiments, the genetically engineered bacteria comprise a PME, e.g., PAL, expressed under the control of an alternate oxygen level-dependent promoter, e.g., an ANR promoter (Ray et al., 1997), a DNR promoter (Trunk et al., 2010). In some embodiments, phenylalanine metabolism is particularly activated in a low-oxygen or anaerobic environment, such as in the gut.

In *P. aeruginosa*, the anaerobic regulation of arginine deiminase and nitrate reduction (ANR) transcriptional regulator is "required for the expression of physiological functions which are inducible under oxygen-limiting or anaerobic conditions" (Winteler et al., 1996; Sawers 1991). *P. aeruginosa* ANR is homologous with *E. coli* FNR, and "the consensus FNR site (TTGAT----ATCAA) (SEQ ID NO: 66) was recognized efficiently by ANR and FNR" (Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator which is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

FNR promoter sequences are known in the art, and any suitable FNR promoter sequence(s) may be used in the genetically engineered bacteria of the invention. Any suitable FNR promoter(s) may be combined with any suitable PAL. Non-limiting FNR promoter sequences are provided in Table 3, and non-limiting PAL sequences are also provided herein. In some embodiments, the genetically engineered bacteria of the invention comprise one or more of: SEQ ID NO: 9, SEQ ID NO: 10, nirB1 promoter (SEQ ID NO: 11), nirB2 promoter (SEQ ID NO: 12), nirB3 promoter (SEQ ID NO: 13), ydfZ promoter (SEQ ID NO: 14), nirB promoter fused to a strong ribosome binding site (SEQ ID NO: 15), ydfZ promoter fused to a strong ribosome binding site (SEQ ID NO: 16), fnrS, an anaerobically induced small RNA gene (fnrS1 promoter SEQ ID NO: 9 or fnrS2 promoter SEQ ID NO: 17), nirB promoter fused to a crp binding site (SEQ ID NO: 18), and fnrS fused to a crp binding site (SEQ ID NO: 19).

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 9, 10, 11, 12, 13, 14, 15, 16, 17, 18, 19, or 20 or a functional fragment thereof.

TABLE 3

FNR Sequences

| SEQ ID NO | FNR-responsive regulatory region Sequence |
|---|---|
| SEQ ID NO: 9 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGCT<br>CCCACAGGAGAAAACCG |
| SEQ ID NO: 10 | CTCTTGATCGTTATCAATTCCCACGCTGTTTCAGAGCGTTACCTTGCCCT<br>TAAACATTAGCAATGTCGATTTATCAGAGGGCCGACAGGCTCCCACAGGA<br>GAAAACCG |
| nirB1<br>SEQ ID NO: 11 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| nirB2<br>SEQ ID NO: 12 | CGGCCCGATCGTTGAACATAGCGGTCCGCAGGCGGCACTGCTTACAGCAA<br>ACGGTCTGTACGCTGTCGTCTTTGTGATGTGCTTCCTGTTAGGTTTCGTC<br>AGCCGTCACCGTCAGCATAACACCCTGACCTCTCATTAATTGCTCATGCC<br>GGACGGCACTATCGTCGTCCGGCCTTTTCCTCTCTTCCCCCGCTACGTGC<br>ATCTATTTCTATAAACCCGCTCATTTTGTCTATTTTTTGCACAAACATGA<br>AATATCAGACAATTCCGTGACTTAAGAAAATTTATACAAATCAGCAATAT<br>ACCCATTAAGGAGTATATAAAGGTGAATTTGATTTACATCAATAAGCGGG<br>GTTGCTGAATCGTTAAGGTAGGCGGTAATAGAAAAGAAATCGAGGCAAAA<br>atgtttgtttaactttaagaaggagatatacat |
| nirB3<br>SEQ ID NO: 13 | GTCAGCATAACACCCTGACCTCTCATTAATTGCTCATGCCGGACGGCACT<br>ATCGTCGTCCGGCCTTTTCCTCTCTTCCCCCGCTACGTGCATCTATTTCT<br>ATAAACCCGCTCATTTTGTCTATTTTTTGCACAAACATGAAATATCAGAC<br>AATTCCGTGACTTAAGAAAATTTATACAAATCAGCAATATACCCATTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| ydfZ<br>SEQ ID ID: 14 | ATTTCCTCTCATCCCATCCGGGGTGAGAGTCTTTTCCCCCGACTTATGGC<br>TCATGCATGCATCAAAAAAGATGTGAGCTTGATCAAAAACAAAAAATATT<br>TCACTCGACAGGAGTATTTATATTGCGCCCGTTACGTGGGCTTCGACTGT<br>AATCAGAAAGGAGAAAACACCT |
| nirB + RBS<br>SEQ ID NO: 15 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT |

TABLE 3-continued

| FNR Sequences | |
|---|---|
| SEQ ID NO | FNR-responsive regulatory region Sequence |
| | ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAA**GGATCC**CTCTAGAAATAATTTTGTTTAACTTTAAGAAGGAGATA<br>TACAT |
| ydfZ + RBS<br>SEQ ID NO: 16 | CATTTCCTCTCATCCCATCCGGGGTGAGAGTCTTTTCCCCCGACTTATGG<br>CTCATGCATGCATCAAAAAAGATGTGAGCTTGATCAAAAACAAAAAATAT<br>TTCACTCGACAGGAGTATTTATATTGCGCCC**GGATCC**CTCTAGAAATAAT<br>TTTGTTTAACTTTAAGAAGGAGATATACAT |
| fnrS1<br>SEQ ID NO: 17 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGTAAAG<br>TTTGAGCGAAGTCAATAAACTCTCTACCCATTCAGGGCAATATCTCTCTT<br>**GGATCC**CTCTAGAAATAATTTTGTTTAACTTTAAGAAGGAGATATACAT |
| fnrS2<br>SEQ ID NO: 18 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGCAAAG<br>TTTGAGCGAAGTCAATAAACTCTCTACCCATTCAGGGCAATATCTCTCTT<br>GGATCCAAAGTGAACTCTAGAAATAATTTTGTTTAACTTTAAGAAGGAGA<br>TATACAT |
| nirB + crp<br>SEQ ID NO: 19 | TCGTCTTTGTGATGTGCTTCCTGTTAGGTTTCGTCAGCCGTCACCGTCAG<br>CATAACACCCTGACCTCTCATTAATTGCTCATGCCGGACGGCACTATCGT<br>CGTCCGGCCTTTTCCTCTCTTCCCCCGCTACGTGCATCTATTTCTATAAA<br>CCCGCTCATTTTGTCTATTTTTTGCACAAACATGAAATATCAGACAATTC<br>CGTGACTTAAGAAAATTTATACAAATCAGCAATATACCCATTAAGGAGTA<br>TATAAAGGTGAATTTGATTTACATCAATAAGCGGGGTTGCTGAATCGTTA<br>AGGTAGaaatgtgatctagttcacatttGCGGTAATAGAAAAGAAATCGA<br>GGCAAAA*atgtttgtttaactttaagaaggagatatacat* |
| fnrS + crp<br>SEQ ID NO: 20 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGCAAAG<br>TTTGAGCGAAGTCAATAAACTCTCTACCCATTCAGGGCAATATCTCTCaa<br>atgtgatctagttcacattt*ttgtttaactttaagaaggagatatacat* |

In other embodiments, a PME, e.g., PAL, is expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stülke, 2008). In some embodiments, PME, e.g., PAL, expression is controlled by an oxygen level-dependent promoter fused to a CRP binding site. In some embodiments, PAL expression is controlled by an FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the PME gene, e.g., PAL gene, by recruiting RNA polymerase to the FNR promoter via direct protein-protein interactions. In the presence of glucose, cyclic AMP does not bind to CRP and a PME, e.g., PAL, gene transcription is repressed. In some embodiments, an oxygen level-dependent promoter (e.g., an FNR promoter) fused to a binding site for a transcriptional activator is used to ensure that a PME, e.g., PAL, is not expressed under anaerobic conditions when sufficient amounts of glucose are present, e.g., by adding glucose to growth media in vitro.

In another embodiment, a PME, e.g., LAAD, is expressed under the control of an inducible promoter fused to a binding site for a transcriptional activator, e.g., CRP, such that expression is repressed in the presence of glucose.

In some embodiments, LAAD is not under the control of an FNRs promoter. LAAD requires oxygen to catalyze the degradation of phenylalanine to phenylpyruvate. Therefore, it would not be desirable to induce LAAD expression under strictly anaerobic conditions where it would be minimally active (FIG. 25).

In some embodiments, a PME, e.g., PAL or LAAD, is expressed under the control of an inducible promoter that is responsive to specific molecules or metabolites in the environment, e.g., the mammalian gut. For example, the short-chain fatty acid propionate is a major microbial fermentation metabolite localized to the gut (Hosseini et al., 2011). In one embodiment, PAL gene expression is under the control of a propionate-inducible promoter. In a more specific embodiment, PME gene expression is under the control of a propionate-inducible promoter that is activated by the presence of propionate in the mammalian gut. Any molecule or metabolite found in the mammalian gut, in a healthy and/or disease state, may be used to induce PME gene expression. Non-limiting examples include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, PME, e.g., PAL and/or LAAD, gene expression is under the control of a ParaBAD promoter, which is activated in the presence of the sugar arabinose. In one embodiment, LAAD expression is under the control of the ParaBAD promoter. In one embodiment, expression of LAAD occurs under aerobic or microaerobic conditions.

In some embodiments, the PAL gene is expressed under the control of a promoter that is induced by exposure to tetracycline. In some embodiments, gene expression is further optimized by methods known in the art, e.g., by optimizing ribosomal binding sites, manipulating transcriptional regulators, and/or increasing mRNA stability.

In some embodiments, the genetically engineered bacteria comprise a stably maintained plasmid or chromosome carrying the PAL gene, such that PAL can be expressed in the host cell, and the host cell is capable of survival and/or growth in vitro, e.g., in medium, and/or in vivo, e.g., in the gut. In some embodiments, the genetically engineered bacteria comprise two or more distinct PAL genes. In some embodiments, the genetically engineered bacteria comprise multiple copies of the same PAL gene. In some embodiments, the PAL gene is present on a plasmid and operably linked to a directly or indirectly inducible promoter. In some embodiments, the PAL gene is present on a plasmid and operably linked to a promoter that is induced under low-oxygen or anaerobic conditions. In some embodiments, the PAL gene is present on a chromosome and operably linked to a directly or indirectly inducible promoter. In some embodiments, the PAL gene is present in the chromosome and operably linked to a promoter that is induced under low-oxygen or anaerobic conditions. In some embodiments, the PAL gene is present on a plasmid and operably linked to a promoter that is induced by exposure to tetracycline.

In some embodiments, the genetically engineered bacteria comprise a stably maintained plasmid or chromosome carrying the LAAD gene, such that LAAD can be expressed in the host cell, and the host cell is capable of survival and/or growth in vitro, e.g., in medium, and/or in vivo, e.g., in the gut. In some embodiments, the genetically engineered bacteria comprise two or more distinct LAAD genes. In some embodiments, the genetically engineered bacteria comprise multiple copies of the same LAAD gene. In some embodiments, the LAAD gene is present on a plasmid and operably linked to a directly or indirectly inducible promoter. In some embodiments, the LAAD gene is present on a plasmid and operably linked to a promoter that is inducible, e.g., by arabinose or tetracycline. In some embodiments, the LAAD gene is present on a chromosome and operably linked to a directly or indirectly inducible promoter. In some embodiments, the LAAD gene is present in the chromosome and operably linked to a promoter that is induced, e.g., by arabinose. In some embodiments, the LAAD gene is present on a plasmid and operably linked to a promoter that is induced by exposure to tetracycline.

In some embodiments, the genetically engineered bacteria comprise an oxygen-level dependent transcriptional regulator, e.g., FNR, ANR, or DNR, and corresponding promoter from a different bacterial species. The non-native oxygen-level dependent transcriptional regulator and promoter increase the transcription of genes operably linked to said promoter, e.g., PAL, in a low-oxygen or anaerobic environment, as compared to the native transcriptional regulator and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., PAL, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., PAL, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., 2006).

In some embodiments, the genetically engineered bacteria of the invention comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding PAL are present on different plasmids. In some embodiments, the gene encoding the oxygen level-sensing transcriptional regulator and the gene encoding PAL are present on the same plasmid. In some embodiments, the gene encoding the oxygen level-sensing transcriptional regulator is present on a chromosome. In some embodiments, the gene encoding the oxygen level-sensing transcriptional regulator and the gene encoding PAL are present on different chromosomes. In some embodiments, the gene encoding the oxygen level-sensing transcriptional regulator and the gene encoding PAL are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the phenylalanine-metabolizing enzyme. In some embodiments, expression of the transcriptional regulator is controlled by the same promoter that controls expression of the phenylalanine-metabolizing enzyme. In some embodiments, the transcriptional regulator and the phenylalanine-metabolizing enzyme are divergently transcribed from a promoter region.

Figure 16A:
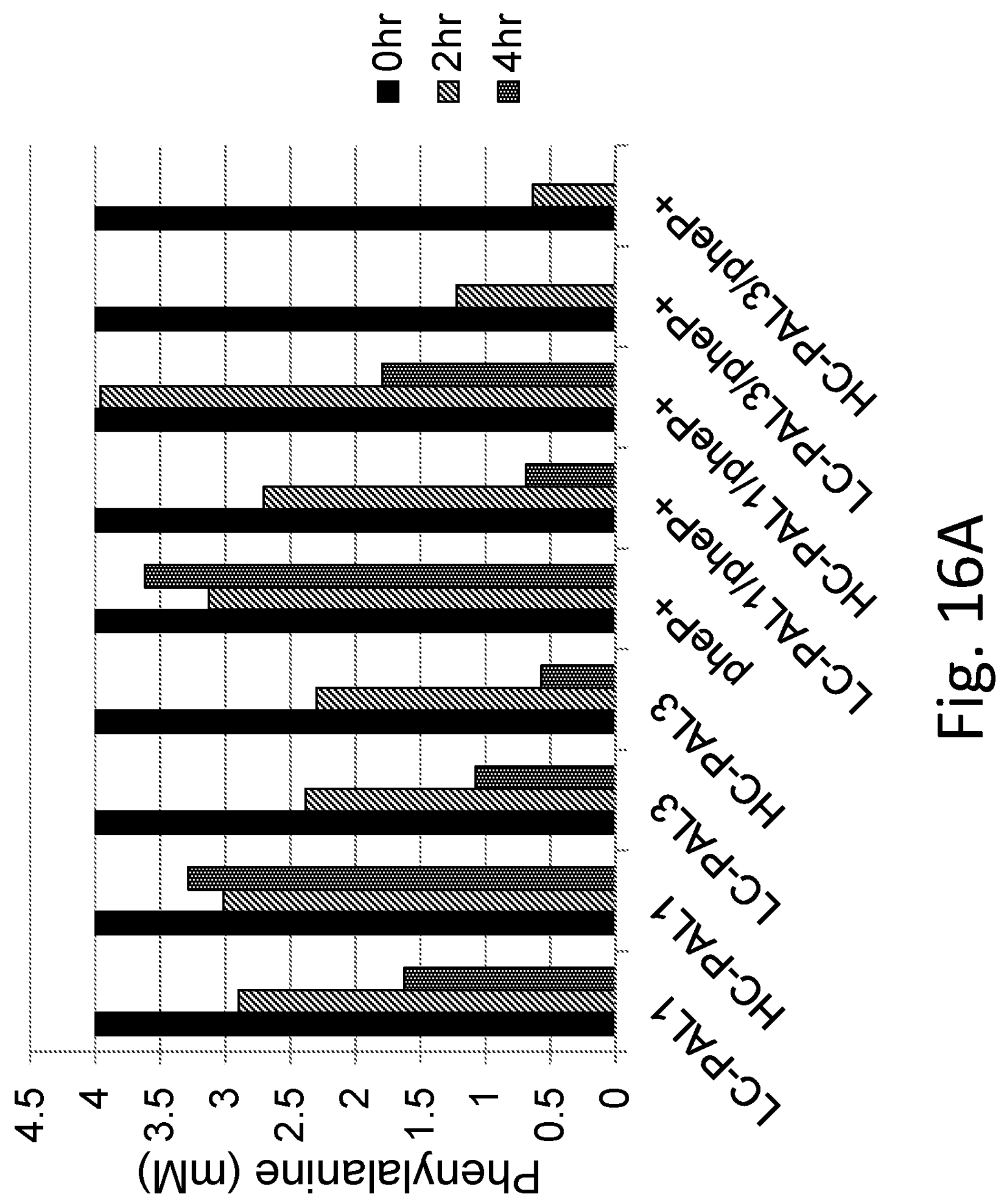
FIG. 16A depicts phenylalanine concentrations in samples comprising bacteria expressing PAL1 or PAL3 on low-copy (LC) or high-copy (HC) plasmids, or further comprising a copy of pheP driven by the Tet promoter integrated into the chromosome. Bacteria were induced with ATC, and then grown in culture medium supplemented with 4 mM (660,000 ng/mL) of phenylalanine to an $OD_{600}$ of 2.0. Samples were removed at 0 hrs, 2 hrs, and 4 hrs post-induction and phenylalanine concentrations were determined by mass spectrometry. Notably, the additional copy of pheP permitted the degradation of phenylalanine (4 mM) in 4 hrs.
Figure 16B:
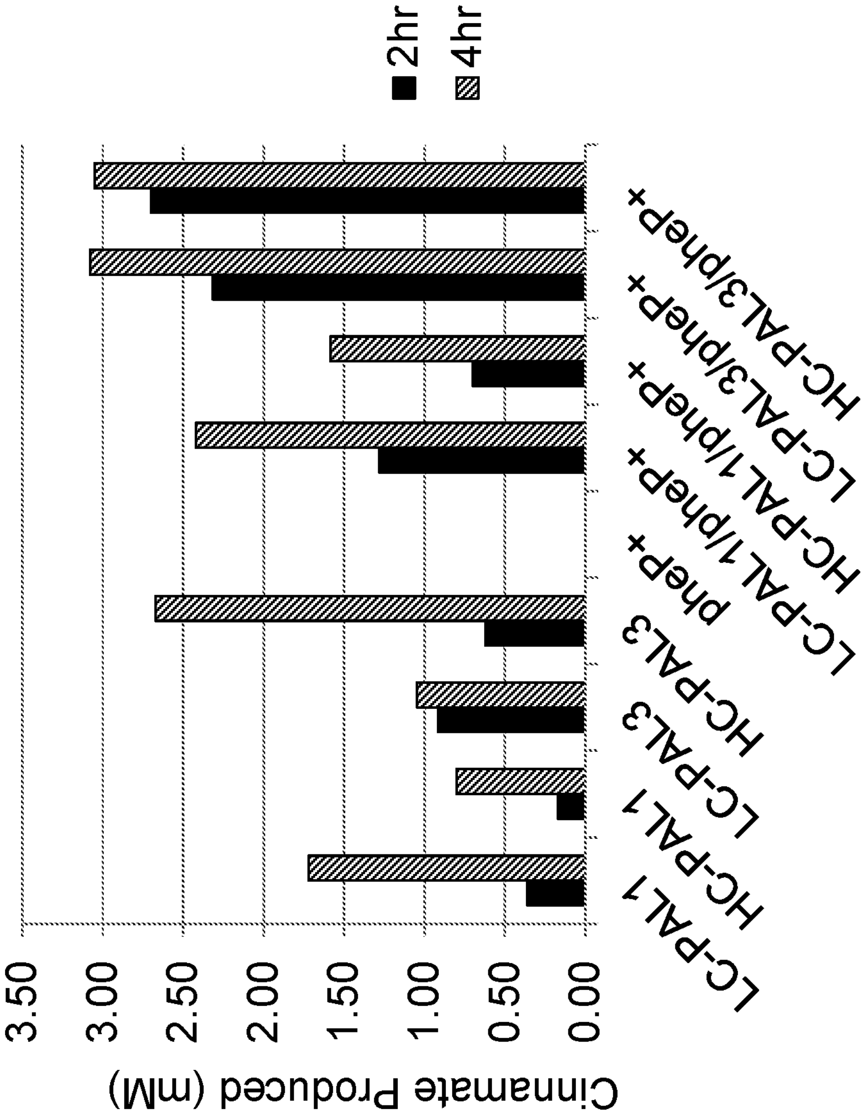
FIG. 16B depicts cinnamate levels in samples at 2 hrs and 4 hrs post-induction. In some embodiments, cinnamate may be used as an alternative biomarker for strain activity. PheP overexpression improves phenylalanine metabolism in engineered bacteria. Strains analyzed in this data set are SYN-PKU101, SYN-PKU102, SYN-PKU202, SYN-PKU201, SYN-PKU401, SYN-PKU402, SYN-PKU203, SYN-PKU302, SYN-PKU303.
Figure 17A:
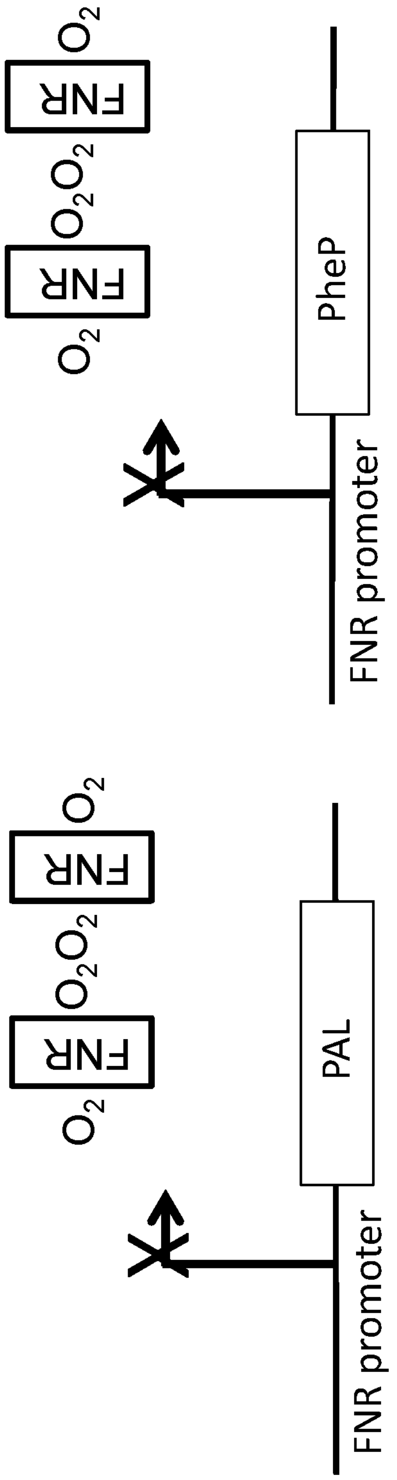
FIGS. 17A and 17B depict the state of one non-limiting embodiment of the PAL construct under non-inducing (FIG. 17A) and inducing (FIG. 17B) conditions.
Figure 17B:
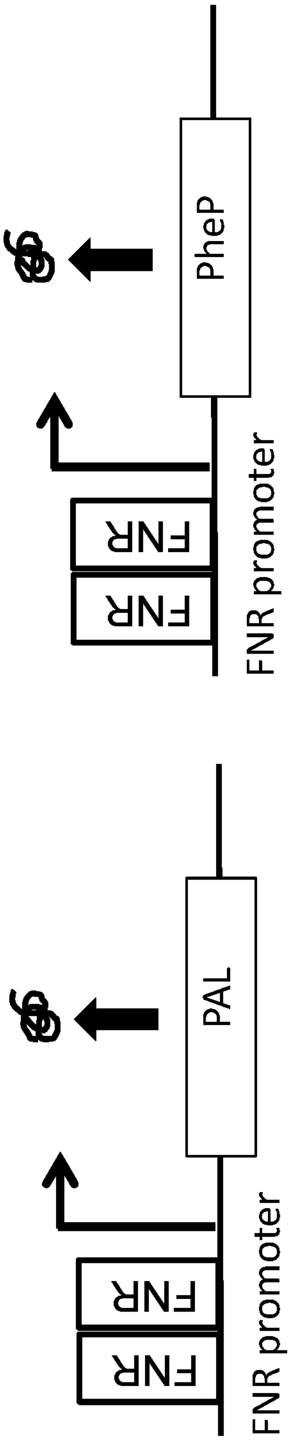

In some embodiments, the genetically engineered bacteria of the invention produce PAL under exogenous environmental conditions, such as the low-oxygen environment of the mammalian gut, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, PAL-mediated processing of phenylalanine will be appreciable under exogenous environmental conditions. Phenylalanine may be measured by methods known in the art, e.g., blood sampling and mass spectrometry. In some embodiments, cinnamate is measured by methods known in the art to assess PAL activity. Cinnamate production is directly correlated with phenylalanine degradation, and in some embodiments, that cinnamate may be used as an alternative biomarker for strain activity (FIG. 16B). Cinnamate can be further degraded to hippuric acid by liver enzymes; both can be measured as described in Example 24-26. In some embodiments, PAL expression is measured by methods known in the art to assess PAL activity.

In some embodiments, the genetically engineered bacteria of the invention produce LAAD, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, LAAD-mediated processing of phenylalanine will be appreciable under exogenous environmental conditions. Phenylalanine may be measured by methods known in the art, e.g., blood sampling and mass spectrometry. Pyruvic acid and phenylpyruvate, the LAAD generated degradation products can be measured using masspectrometry as described in Examples 24-26, and can be used as an additional readout of LAAD activity.

Figure 15A:
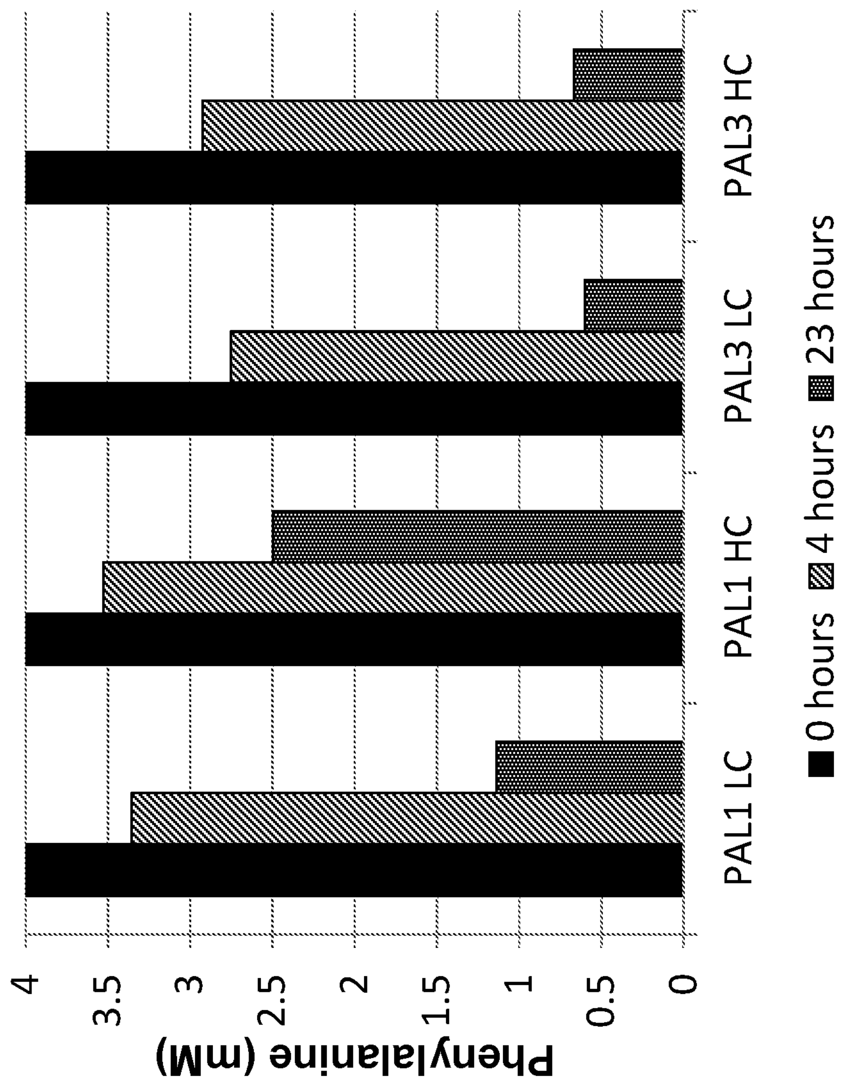
FIG. 15A depicts phenylalanine concentrations in samples comprising bacteria expressing PAL1 or on low-copy (LC; SYN-PKU101) or high-copy (HC; SYN-PKU102) plasmids or PAL3 on low-copy (LC; SYN-PKU201) or high-copy (HC; SYN-PKU202) plasmids, induced with anhydrous tetracycline (ATC), and then grown in culture medium supplemented with 4 mM (660,000 ng/mL) of phenylalanine. Samples were removed at 0 hrs, 4 hrs, and 23 hrs. Phenylalanine concentrations were determined by mass spectrometry.
Figure 15B:
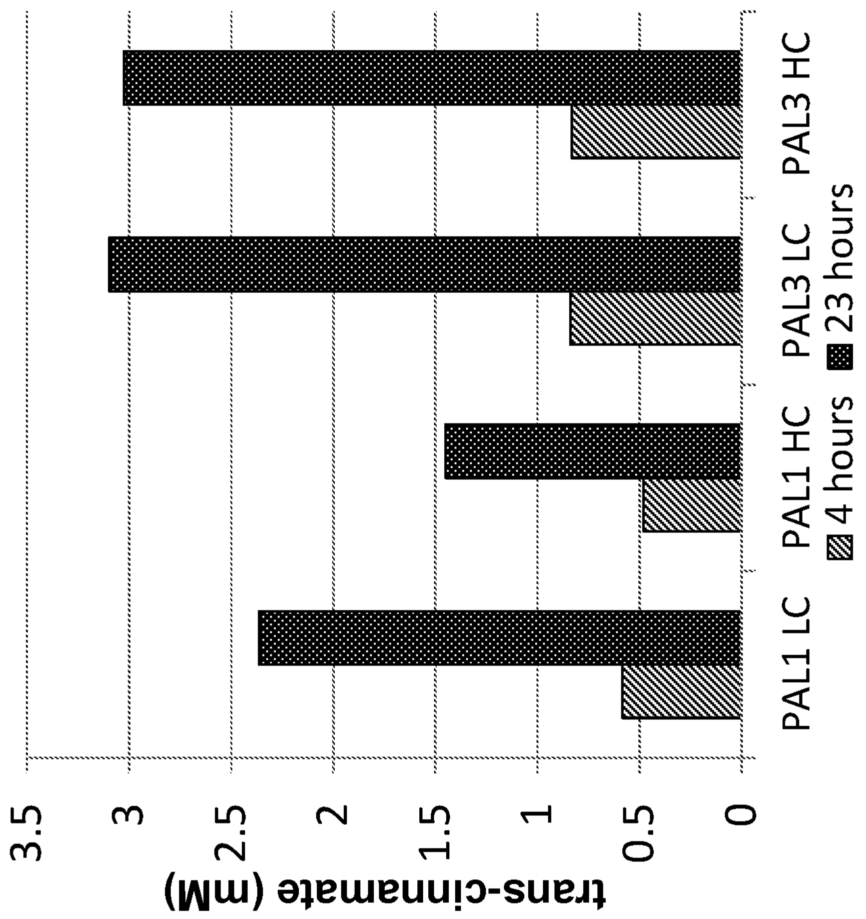
FIG. 15B depicts cinnamate levels in samples at 4 hrs and 23 hrs post-induction. In PAL3-expressing strains, the PAL3 gene is derived from *Photorhabdus luminescens*, an enterobacterium in the same taxonomic subdivision as *Escherichia coli*.

In some embodiments, the PME, e.g., PAL, LAAD, and/or PAH, is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the PME, e.g., PAL, LAAD, and/or PAH, is expressed on a high-copy plasmid. In some embodiments, the high-copy plasmid may be useful for increasing the PME, e.g., PAL, LAAD, and/or PAH, expression, thereby increasing the metabolism of phenylalanine and reducing hyperphenylalaninemia. In some embodiments, a genetically engineered bacterium comprising a the PME, e.g., PAL, LAAD, and/or PAH, expressed on a high-copy plasmid does not increase phenylalanine metabolism or decrease phenylalanine levels as compared to a genetically engineered bacterium comprising the same PME, e.g., PAL, LAAD, and/or PAH, expressed on a low-copy plasmid in the absence of heterologous pheP and additional copies of a native pheP. Genetically engineered bacteria comprising the same the PME gene, e.g., PAL, LAAD, and/or PAH gene on high and low copy plasmids were generated. For example, either PAL1 or PAL3 on a high-copy plasmid and a low-copy plasmid were generated, and each metabolized and reduced phenylalanine to similar levels (FIG. 15). Thus, in some embodiments, the rate-limiting step of phenylalanine metabolism is phenylalanine availability (see, e.g., FIG. 16). In these embodiments, it may be advantageous to increase phenylalanine transport into the cell, thereby enhancing phenylalanine metabolism. In conjunction with pheP, even low-copy PAL plasmids are capable of almost completely eliminating Phe from a test sample (see, e.g., FIG. 16A). Furthermore, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

In some embodiments, a transporter may not increase phenylalanine degradation. For example, *Proteus mirabilis* LAAD is localized to the plasma membrane, with the enzymatic catalysis occurring in the periplasm. Phenylalanine can readily traverse the outer membrane without the need of a transporter. Therefore, in embodiments, in which the genetically engineered bacteria express LAAD, a transporter may not be needed or improve phenylalanine metabolism.

Figure 36:
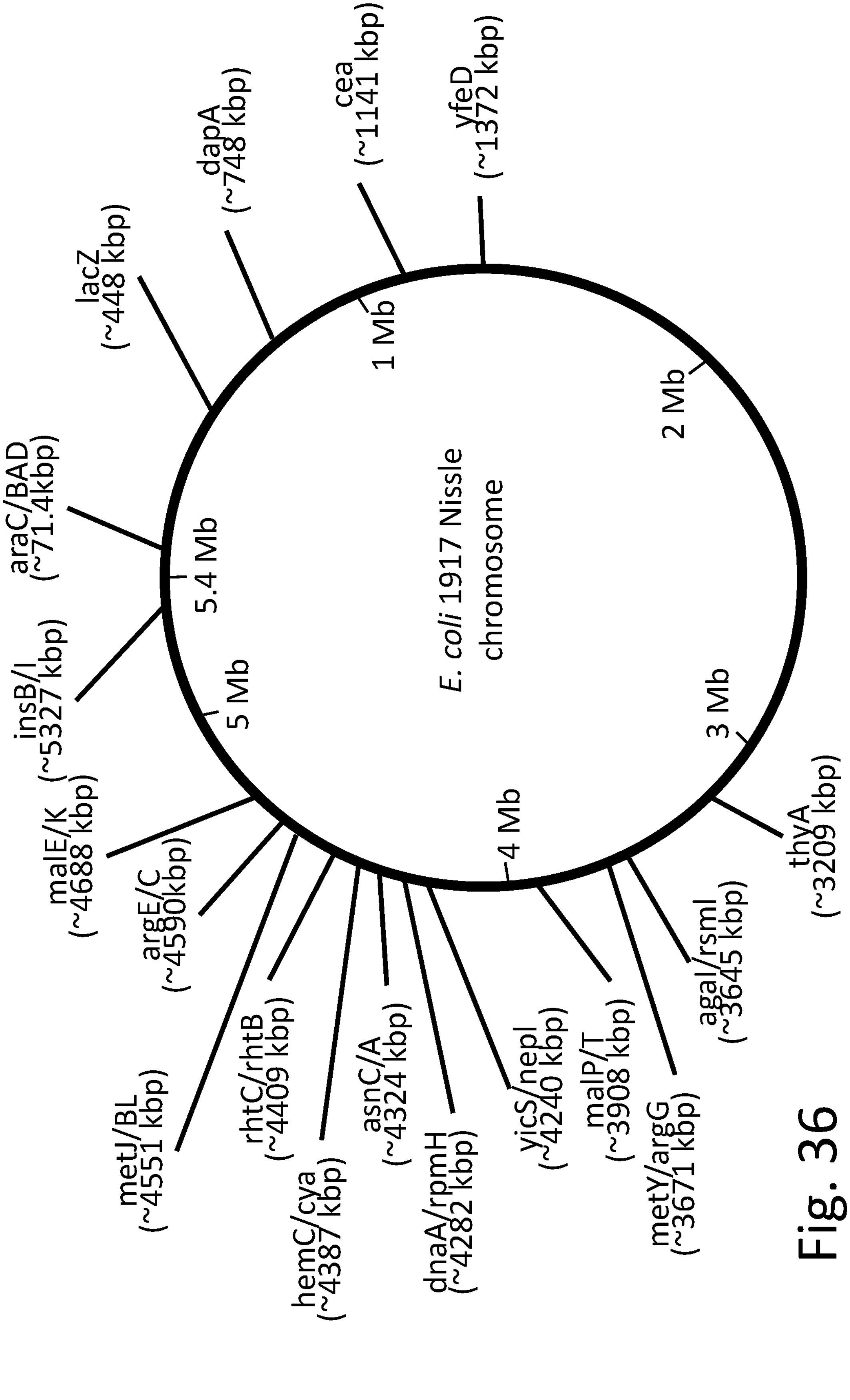
FIG. 36 depicts a map of exemplary integration sites within the *E. coli* 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites.
Figure 37:
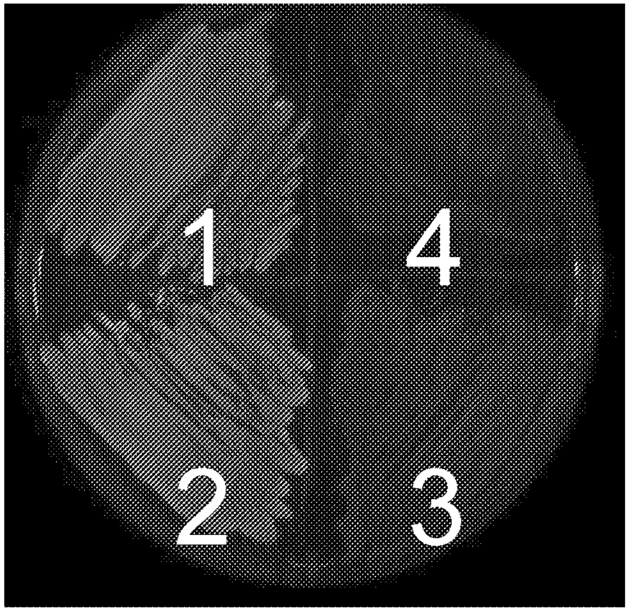
FIG. 37 depicts three bacterial strains which constitutively express red fluorescent protein (RFP). In strains 1-3, the rfp gene has been inserted into different sites within the bacterial chromosome, and results in varying degrees of brightness under fluorescent light. Unmodified *E. coli* Nissle (strain 4) is non-fluorescent.

In some embodiments, the PME, e.g., PAL, LAAD, and/or PAH, gene is expressed on a chromosome. In some embodiments, expression from the chromosome may be useful for increasing stability of expression of the PME. In some embodiments, the PME gene, e.g., PAL, LAAD, and/or PAH gene(s), is integrated into the bacterial chromosome at one or more integration sites in the genetically engineered bacteria. In some embodiments, the PME gene, e.g., PAL, LAAD, and/or PAH gene(s) is inserted into the bacterial genome at one or more of the following insertion sites in *E. coli* Nissle: malE/K, insB/I, araC/BAD, lacZ, agaI/rsmI, thyA, and malP/T. Any suitable insertion site may be used (see, e.g., FIG. 36). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the PME gene, e.g., PAL, PAH, and/or LAAD is integrated into the bacterial chromosome at one or more integration sites in the genetically engineered bacteria. The more than one copy of a PME gene may be more then one copy of the same PME gene or more than one copy of different PME genes.

Exemplary constructs are shown in 4-13 below. Table 4 shows the sequence of an exemplary construct comprising a gene encoding PheP and an FNR promoter sequence for chromosomal insertion (SEQ ID NO: 21), with the pheP sequence underlined and the FNR promoter sequence bolded. Table 5 shows the sequence of an exemplary construct comprising a gene encoding PAL1 and an FNR promoter sequence on a high-copy plasmid (SEQ ID NO: 22), with the PAL1 sequence underlined and the FNR promoter sequence bolded. Table 6 shows the sequence of an exemplary construct comprising a gene encoding PAL3 and an FNR promoter sequence on a high-copy plasmid (SEQ ID NO: 23), with the PAL3 sequence underlined and the FNR promoter sequence bolded. Table 7 shows the sequence of an exemplary construct comprising a gene encoding PAL1 and a Tet promoter sequence on a high-copy plasmid (SEQ ID NO: 24), with the PAL1 sequence underlined and the Tet promoter sequence bolded. Table 8 shows the sequence of an exemplary construct comprising a gene encoding PAL3 and a Tet promoter sequence on a high-copy plasmid (SEQ ID NO: 25), with the PAL3 sequence underlined and the Tet promoter sequence bolded. Table 9 shows the sequence of an exemplary construct comprising a gene encoding PAL1 and an FNR promoter sequence on a low-copy plasmid (SEQ ID NO: 26), with the PAL1 sequence underlined and the FNR promoter sequence bolded. Table 10 shows the sequence of an exemplary construct comprising a gene encoding PAL3 and an FNR promoter sequence on a low-copy plasmid (SEQ ID NO: 27), with the PAL3 sequence underlined and the FNR promoter sequence bolded. Table 11 shows the sequence of an exemplary construct comprising a gene encoding PAL1 and a Tet promoter sequence on a low-copy plasmid (SEQ ID NO: 28), with the PAL1 sequence underlined and the Tet promoter sequence bolded. Table 12 shows the sequence of an exemplary construct comprising a gene encoding PAL3 and a Tet promoter sequence on a low-copy plasmid (SEQ ID NO: 29), with the PAL3 sequence underlined and the Tet promoter sequence bolded. Table 13 shows the sequence of an exemplary construct comprising a gene encoding PheP, a gene coding TetR, and a Tet promoter sequence for chromosomal insertion (SEQ ID NO: 30), with the pheP sequence underlined, the TetR sequence boxed, and the FNR promoter sequence bolded.

TABLE 4

| Nucleotide sequences of FNR promoter-PheP construct (SEQ ID NO: 21) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAAACGCGTCAACCGTATCGGAAGATACTGCGTCGAATCAA |
| GAGCCGACGCTTCATCGCGGATTACATAACCGTCATATTCAACTGATTGCG |
| TTGGGTGGCGCAATTGGTACTGGTCTGTTTCTTGGCATTGGCCCGGCGATT |
| CAGATGGCGGGTCCGGCTGTATTGCTGGGCTACGGCGTCGCCGGGATCATC |
| GCTTTCCTGATTATGCGCCAGCTTGGCGAAATGGTGGTTGAGGAGCCGGTA |
| TCCGGTTCATTTGCCCACTTTGCCTATAAATACTGGGGACCGTTTGCGGGC |
| TTCCTCTCTGGCTGGAACTACTGGGTAATGTTCGTGCTGGTGGGAATGGCA |
| GAGCTGACCGCTGCGGGCATCTATATGCAGTACTGGTTCCCGGATGTTCCA |
| ACGTGGATTTGGGCTGCCGCCTTCTTTATTATCATCAACGCCGTTAACCTG |
| GTGAACGTGCGCTTATATGGCGAAACCGAGTTCTGGTTTGCGTTGATTAAA |
| GTGCTGGCAATCATCGGTATGATCGGCTTTGGCCTGTGGCTGCTGTTTTCT |
| GGTCACGGCGGCGAGAAAGCCAGTATCGACAACCTCTGGCGCTACGGTGGT |
| TTCTTCGCCACCGGCTGGAATGGGCTGATTTTGTCGCTGGCGGTAATTATG |
| TTCTCCTTCGGCGGTCTGGAGCTGATTGGGATTACTGCCGCTGAAGCGCGC |
| GATCCGGAAAAAAGCATTCCAAAAGCGGTAAATCAGGTGGTGTATCGCATC |
| CTGCTGTTTTACATCGGTTCACTGGTGGTTTTACTGGCGCTCTATCCGTGG |
| GTGGAAGTGAAATCCAACAGTAGCCCGTTTGTGATGATTTTCCATAATCTC |
| GACAGCAACGTGGTAGCTTCTGCGCTGAACTTCGTCATTCTGGTAGCATCG |
| CTGTCAGTGTATAACAGCGGGGTTTACTCTAACAGCCGCATGCTGTTTGGC |
| CTTTCTGTGCAGGGTAATGCGCCGAAGTTTTTGACTCGCGTCAGCCGTCGC |
| GGTGTGCCGATTAACTCGCTGATGCTTTCCGGAGCGATCACTTCGCTGGTG |
| GTGTTAATCAACTATCTGCTGCCGCAAAAAGCGTTTGGTCTGCTGATGGCG |

TABLE 4-continued

| Nucleotide sequences of FNR promoter-PheP construct (SEQ ID NO: 21) |
|---|
| CTGGTGGTAGCAACGCTGCTGTTGAACTGGATTATGATCTGTCTGGCGCAT |
| CTGCGTTTTCGTGCAGCGATGCGACGTCAGGGGCGTGAAACACAGTTTAAG |
| GCGCTGCTCTATCCGTTCGGCAACTATCTCTGCATTGCCTTCCTCGGCATG |
| ATTTTGCTGCTGATGTGCACGATGGATGATATGCGCTTGTCAGCGATCCTG |
| CTGCCGGTGTGGATTGTATTCCTGTTTATGGCATTTAAAACGCTGCGTCGG |
| AAATAA |

TABLE 5

| Nucleotide sequences of FNR promoter-PAL1 construct, high-copy (SEQ ID NO: 22) |
|---|
| CTCTTGATCGTTATCAATTCCCACGCTGTTTCAGAGCGTTACCTTGCCCTT |
| AAACATTAGCAATGTCGATTTATCAGAGGGCCGACAGGCTCCCACAGGAGA |
| AAACCGATGAAAACACTATCACAGGCCCAATCTAAAACTTCTTCACAGCAA |
| TTCAGCTTTACCGGGAACTCGTCTGCGAATGTAATTATCGGCAATCAAAAG |
| CTGACCATTAATGATGTAGCTCGCGTTGCCCGGAATGGCACTTTGGTGTCA |
| CTGACGAACAATACCGACATTCTGCAAGGTATTCAAGCTAGCTGCGATTAT |
| ATCAATAACGCCGTTGAATCTGGCGAGCCAATCTACGGGGTAACAAGCGGT |
| TTTGGTGGGATGGCGAACGTTGCCATTAGCCGTGAACAGGCGAGCGAACTT |
| CAGACCAACCTCGTTTGGTTCCTAAAGACAGGAGCTGGTAATAAGTTACCT |
| CTGGCTGACGTAAGAGCCGCGATGCTGCTTCGCGCTAATAGTCACATGCGC |
| GGCGCCAGTGGTATCCGTCTTGAGCTTATCAAGAGGATGGAAATCTTCCTC |
| AACGCGGGTGTCACACCATATGTTTATGAGTTTGGTAGTATCGGAGCCAGT |
| GGTGATCTTGTTCCCCTGAGTTATATTACGGGTTCATTGATTGGTTTAGAC |
| CCGTCCTTTAAAGTGGATTTTAACGGGAAAGAAATGGACGCCCCGACCGCT |
| TTACGACAGCTTAATCTGAGCCCACTTACTTTGCTCCCTAAAGAAGGTCTT |
| GCCATGATGAATGGCACCTCTGTGATGACTGGAATTGCCGCGAATTGTGTG |
| TATGACACGCAGATCCTAACGGCCATTGCCATGGGTGTTCACGCGTTGGAC |
| ATTCAAGCCCTGAATGGTACAAACCAGTCGTTTCATCCGTTTATCCATAAT |
| TCAAAACCCCATCCGGGACAGCTTTGGGCTGCTGATCAGATGATCTCACTC |
| CTGGCCAATAGTCAACTGGTTCGGGACGAGCTCGACGGCAAACATGATTAT |
| CGCGATCATGAGCTCATCCAGGACCGGTATTCACTTCGTTGTCTCCCACAA |
| TACCTGGGGCCTATCGTTGATGGTATATCTCAAATTGCGAAGCAAATTGAA |
| ATTGAGATCAATAGCGTAACCGACAACCCGCTTATCGATGTTGATAATCAG |
| GCCTCTTATCACGGTGGCAATTTTCTGGGCCAGTATGTTGGTATGGGGATG |
| GATCACCTGCGGTACTATATTGGGCTTCTGGCTAAACATCTTGATGTGCAG |
| ATTGCCTTATTAGCTTCACCAGAATTTTCAAATGGACTGCCGCCATCATTG |
| CTCGGTAACAGAGAAAGGAAAGTAAATATGGGCCTTAAGGGCCTTCAGATA |
| TGTGGTAACTCAATCATGCCCCTCCTGACCTTTTATGGGAACTCAATTGCT |

TABLE 5-continued

| Nucleotide sequences of FNR promoter-PAL1 construct, high-copy (SEQ ID NO: 22) |
|---|
| GATCGTTTTCCGACACATGCTGAACAGTTTAACCAAAACATTAACTCACAG |
| GGCTATACATCCGCGACGTTAGCGCGTCGGTCCGTGGATATCTTCCAGAAT |
| TATGTTGCTATCGCTCTGATGTTCGGCGTACAGGCCGTTGATTTGCGCACT |
| TATAAAAAAACCGGTCACTACGATGCTCGGGCTTGCCTGTCGCCTGCCACC |
| GAGCGGCTTTATAGCGCCGTACGTCATGTTGTGGGTCAGAAACCGACGTCG |
| GACCGCCCCTATATTTGGAATGATAATGAACAAGGGCTGGATGAACACATC |
| GCCCGGATATCTGCCGATATTGCCGCCGGAGGTGTCATCGTCCAGGCGGTA |
| CAAGACATACTTCCTTGCCTGCATTAAGCTTGGCGTAATCATGGTCATAGC |
| TGTTTCCTGTGTGAAATTGTTATCCGCTCACAATTCCACACAACATACGAG |
| CCGGAAGCATAAAGTGTAAAGCCTGGGGTGCCTAATGAGTGAGCTAACTCA |
| CATTAATTGCGTTGCGCTCACTGCCCGCTTTCCAGTCGGGAAACCTGTCGT |
| GCCAGCTGCATTAATGAATCGGCCAACGCGCGGGGAGAGGCGGTTTGCGTA |
| TTGGGCGCTCTTCCGCTTCCTCGCTCACTGACTCGCTGCGCTCGGTCGTTC |
| GGCTGCGGCGAGCGGTATCAGCTCACTCAAAGGCGGTAATACGGTTATCCA |
| CAGAATCAGGGGATAACGCAGGAAAGAACATGTGAGCAAAAGGCCAGCAAA |
| AGGCCAGGAACCGTAAAAAGGCCGCGTTGCTGGCGTTTTTCCATAGGCTCC |
| GCCCCCCTGACGAGCATCACAAAAATCGACGCTCAAGTCAGAGGTGGCGAA |
| ACCCGACAGGACTATAAAGATACCAGGCGTTTCCCCCTGGAAGCTCCCTCG |
| TGCGCTCTCCTGTTCCGACCCTGCCGCTTACCGGATACCTGTCCGCCTTTC |
| TCCCTTCGGGAAGCGTGGCGCTTTCTCATAGCTCACGCTGTAGGTATCTCA |
| GTTCGGTGTAGGTCGTTCGCTCCAAGCTGGGCTGTGTGCACGAACCCCCCG |
| TTCAGCCCGACCGCTGCGCCTTATCCGGTAACTATCGTCTTGAGTCCAACC |
| CGGTAAGACACGACTTATCGCCACTGGCAGCAGCCACTGGTAACAGGATTA |
| GCAGAGCGAGGTATGTAGGCGGTGCTACAGAGTTCTTGAAGTGGTGGCCTA |
| ACTACGGCTACACTAGAAGAACAGTATTTGGTATCTGCGCTCTGCTGAAGC |
| CAGTTACCTTCGGAAAAAGAGTTGGTAGCTCTTGATCCGGCAAACAAACCA |
| CCGCTGGTAGCGGTGGTTTTTTTGTTTGCAAGCAGCAGATTACGCGCAGAA |
| AAAAAGGATCTCAAGAAGATCCTTTGATCTTTTCTACGGGGTCTGACGCTC |
| AGTGGAACGAAAACTCACGTTAAGGGATTTTGGTCATGAGATTATCAAAAA |
| GGATCTTCACCTAGATCCTTTTAAATTAAAAATGAAGTTTTAAATCAATCT |
| AAAGTATATATGAGTAAACTTGGTCTGACAGTTACCAATGCTTAATCAGTG |
| AGGCACCTATCTCAGCGATCTGTCTATTTCGTTCATCCATAGTTGCCTGAC |
| TCCCCGTCGTGTAGATAACTACGATACGGGAGGGCTTACCATCTGGCCCCA |
| GTGCTGCAATGATACCGCGAGACCCACGCTCACCGGCTCCAGATTTATCAG |
| CAATAAACCAGCCAGCCGGAAGGGCCGAGCGCAGAAGTGGTCCTGCAACTT |
| TATCCGCCTCCATCCAGTCTATTAATTGTTGCCGGGAAGCTAGAGTAAGTA |
| GTTCGCCAGTTAATAGTTTGCGCAACGTTGTTGCCATTGCTACAGGCATCG |
| TGGTGTCACGCTCGTCGTTTGGTATGGCTTCATTCAGCTCCGGTTCCCAAC |

TABLE 5-continued

| Nucleotide sequences of FNR promoter-PAL1 construct, high-copy (SEQ ID NO: 22) |
|---|
| GATCAAGGCGAGTTACATGATCCCCCATGTTGTGCAAAAAAGCGGTTAGCT |
| CCTTCGGTCCTCCGATCGTTGTCAGAAGTAAGTTGGCCGCAGTGTTATCAC |
| TCATGGTTATGGCAGCACTGCATAATTCTCTTACTGTCATGCCATCCGTAA |
| GATGCTTTTCTGTGACTGGTGAGTACTCAACCAAGTCATTCTGAGAATAGT |
| GTATGCGGCGACCGAGTTGCTCTTGCCCGGCGTCAATACGGGATAATACCG |
| CGCCACATAGCAGAACTTTAAAAGTGCTCATCATTGGAAAACGTTCTTCGG |
| GGCGAAAACTCTCAAGGATCTTACCGCTGTTGAGATCCAGTTCGATGTAAC |
| CCACTCGTGCACCCAACTGATCTTCAGCATCTTTTACTTTCACCAGCGTTT |
| CTGGGTGAGCAAAAACAGGAAGGCAAAATGCCGCAAAAAAGGGAATAAGGG |
| CGACACGGAAATGTTGAATACTCATACTCTTCCTTTTTCAATATTATTGAA |
| GCATTTATCAGGGTTATTGTCTCATGAGCGGATACATATTTGAATGTATTT |
| AGAAAAATAAACAAATAGGGGTTCCGCGCACATTTCCCCGAAAAGTGCCAC |
| CTGACGTCTAAGAAACCATTATTATCATGACATTAACCTATAAAAATAGGC |
| GTATCACGAGGCCCTTTCGTCTCGCGCGTTTCGGTGATGACGGTGAAAACC |
| TCTGACACATGCAGCTCCCGGAGACGGTCACAGCTTGTCTGTAAGCGGATG |
| CCGGGAGCAGACAAGCCCGTCAGGGCGCGTCAGCGGGTGTTGGCGGGTGTC |
| GGGGCTGGCTTAACTATGCGGCATCAGAGCAGATTGTACTGAGAGTGCACC |
| ATATGCGGTGTGAAATACCGCACAGATGCGTAAGGAGAAAATACCGCATCA |
| GGCGCCATTCGCCATTCAGGCTGCGCAACTGTTGGGAAGGGCGATCGGTGC |
| GGGCCTCTTCGCTATTACGCCAGCTGGCGAAAGGGGGATGTGCTGCAAGGC |
| GATTAAGTTGGGTAACGCCAGGGTTTTCCCAGTCACGACGTT |

TABLE 6

| Nucleotide sequences of FNR promoter-PAL3 construct, high-copy (SEQ ID NO: 23) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAGCTAAAGATGTTCAGCCAACCATTATTATTAATAAAAAT |
| GGCCTTATCTCTTTGGAAGATATCTATGACATTGCGATAAAACAAAAAAAA |
| GTAGAAATATCAACGGAGATCACTGAACTTTTGACGCATGGTCGTGAAAAA |
| TTAGAGGAAAAATTAAATTCAGGAGAGGTTATATATGGAATCAATACAGGA |
| TTTGGAGGGAATGCCAATTTAGTTGTGCCATTTGAGAAAATCGCAGAGCAT |
| CAGCAAAATCTGTTAACTTTTCTTTCTGCTGGTACTGGGGACTATATGTCC |
| AAACCTTGTATTAAAGCGTCACAATTTACTATGTTACTTTCTGTTTGCAAA |
| GGTTGGTCTGCAACCAGACCAATTGTCGCTCAAGCAATTGTTGATCATATT |
| AATCATGACATTGTTCCTCTGGTTCCTCGCTATGGCTCAGTGGGTGCAAGC |
| GGTGATTTAATTCCTTTATCTTATATTGCACGAGCATTATGTGGTATCGGC |
| AAAGTTTATTATATGGGCGCAGAAATTGACGCTGCTGAAGCAATTAAACGT |
| GCAGGGTTGACACCATTATCGTTAAAAGCCAAAGAAGGTCTTGCTCTGATT |

TABLE 6-continued

| Nucleotide sequences of FNR promoter-PAL3 construct, high-copy (SEQ ID NO: 23) |
|---|
| AACGGCACCCGGGTAATGTCAGGAATCAGTGCAATCACCGTCATTAAACTG |
| GAAAAACTATTTAAAGCCTCAATTTCTGCGATTGCCCTTGCTGTTGAAGCA |
| TTACTTGCATCTCATGAACATTATGATGCCCGGATTCAACAAGTAAAAAAT |
| CATCCTGGTCAAAACGCGGTGGCAAGTGCATTGCGTAATTTATTGGCAGGT |
| TCAACGCAGGTTAATCTATTATCTGGGGTTAAAGAACAAGCCAATAAAGCT |
| TGTCGTCATCAAGAAATTACCCAACTAAATGATACCTTACAGGAAGTTTAT |
| TCAATTCGCTGTGCACCACAAGTATTAGGTATAGTGCCAGAATCTTTAGCT |
| ACCGCTCGGAAAATATTGGAACGGGAAGTTATCTCAGCTAATGATAATCCA |
| TTGATAGATCCAGAAAATGGCGATGTTCTACACGGTGGAAATTTTATGGGG |
| CAATATGTCGCCCGAACAATGGATGCATTAAAACTGGATATTGCTTTAATT |
| GCCAATCATCTTCACGCCATTGTGGCTCTTATGATGGATAACCGTTTCTCT |
| CGTGGATTACCTAATTCACTGAGTCCGACACCCGGCATGTATCAAGGTTTT |
| AAAGGCGTCCAACTTTCTCAAACCGCTTTAGTTGCTGCAATTCGCCATGAT |
| TGTGCTGCATCAGGTATTCATACCCTCGCCACAGAACAATACAATCAAGAT |
| ATTGTCAGTTTAGGTCTGCATGCCGCTCAAGATGTTTTAGAGATGGAGCAG |
| AAATTACGCAATATTGTTTCAATGACAATTCTGGTAGTTTGTCAGGCCATT |
| CATCTTCGCGGCAATATTAGTGAAATTGCGCCTGAAACTGCTAAATTTTAC |
| CATGCAGTACGCGAAATCAGTTCTCCTTTGATCACTGATCGTGCGTTGGAT |
| GAAGATATAATCCGCATTGCGGATGCAATTATTAATGATCAACTTCCTCTG |
| CCAGAAATCATGCTGGAAGAATAAGCTTGGCGTAATCATGGTCATAGCTGT |
| TTCCTGTGTGAAATTGTTATCCGCTCACAATTCCACACAACATACGAGCCG |
| GAAGCATAAAGTGTAAAGCCTGGGGTGCCTAATGAGTGAGCTAACTCACAT |
| TAATTGCGTTGCGCTCACTGCCCGCTTTCCAGTCGGGAAACCTGTCGTGCC |
| AGCTGCATTAATGAATCGGCCAACGCGCGGGGAGAGGCGGTTTGCGTATTG |
| GGCGCTCTTCCGCTTCCTCGCTCACTGACTCGCTGCGCTCGGTCGTTCGGC |
| TGCGGCGAGCGGTATCAGCTCACTCAAAGGCGGTAATACGGTTATCCACAG |
| AATCAGGGGATAACGCAGGAAAGAACATGTGAGCAAAAGGCCAGCAAAAGG |
| CCAGGAACCGTAAAAAGGCCGCGTTGCTGGCGTTTTTCCATAGGCTCCGCC |
| CCCCTGACGAGCATCACAAAAATCGACGCTCAAGTCAGAGGTGGCGAAACC |
| CGACAGGACTATAAAGATACCAGGCGTTTCCCCCTGGAAGCTCCCTCGTGC |
| GCTCTCCTGTTCCGACCCTGCCGCTTACCGGATACCTGTCCGCCTTTCTCC |
| CTTCGGGAAGCGTGGCGCTTTCTCATAGCTCACGCTGTAGGTATCTCAGTT |
| CGGTGTAGGTCGTTCGCTCCAAGCTGGGCTGTGTGCACGAACCCCCCGTTC |
| AGCCCGACCGCTGCGCCTTATCCGGTAACTATCGTCTTGAGTCCAACCCGG |
| TAAGACACGACTTATCGCCACTGGCAGCAGCCACTGGTAACAGGATTAGCA |
| GAGCGAGGTATGTAGGCGGTGCTACAGAGTTCTTGAAGTGGTGGCCTAACT |
| ACGGCTACACTAGAAGAACAGTATTTGGTATCTGCGCTCTGCTGAAGCCAG |
| TTACCTTCGGAAAAAGAGTTGGTAGCTCTTGATCCGGCAAACAAACCACCG |

TABLE 6-continued

| Nucleotide sequences of FNR promoter-PAL3 construct, high-copy (SEQ ID NO: 23) |
|---|
| CTGGTAGCGGTGGTTTTTTTGTTTGCAAGCAGCAGATTACGCGCAGAAAAA |
| AAGGATCTCAAGAAGATCCTTTGATCTTTTCTACGGGGTCTGACGCTCAGT |
| GGAACGAAAACTCACGTTAAGGGATTTTGGTCATGAGATTATCAAAAAGGA |
| TCTTCACCTAGATCCTTTTAAATTAAAAATGAAGTTTTAAATCAATCTAAA |
| GTATATATGAGTAAACTTGGTCTGACAGTTACCAATGCTTAATCAGTGAGG |
| CACCTATCTCAGCGATCTGTCTATTTCGTTCATCCATAGTTGCCTGACTCC |
| CCGTCGTGTAGATAACTACGATACGGGAGGGCTTACCATCTGGCCCCAGTG |
| CTGCAATGATACCGCGAGACCCACGCTCACCGGCTCCAGATTTATCAGCAA |
| TAAACCAGCCAGCCGGAAGGGCCGAGCGCAGAAGTGGTCCTGCAACTTTAT |
| CCGCCTCCATCCAGTCTATTAATTGTTGCCGGGAAGCTAGAGTAAGTAGTT |
| CGCCAGTTAATAGTTTGCGCAACGTTGTTGCCATTGCTACAGGCATCGTGG |
| TGTCACGCTCGTCGTTTGGTATGGCTTCATTCAGCTCCGGTTCCCAACGAT |
| CAAGGCGAGTTACATGATCCCCCATGTTGTGCAAAAAAGCGGTTAGCTCCT |
| TCGGTCCTCCGATCGTTGTCAGAAGTAAGTTGGCCGCAGTGTTATCACTCA |
| TGGTTATGGCAGCACTGCATAATTCTCTTACTGTCATGCCATCCGTAAGAT |
| GCTTTTCTGTGACTGGTGAGTACTCAACCAAGTCATTCTGAGAATAGTGTA |
| TGCGGCGACCGAGTTGCTCTTGCCCGGCGTCAATACGGGATAATACCGCGC |
| CACATAGCAGAACTTTAAAAGTGCTCATCATTGGAAAACGTTCTTCGGGGC |
| GAAAACTCTCAAGGATCTTACCGCTGTTGAGATCCAGTTCGATGTAACCCA |
| CTCGTGCACCCAACTGATCTTCAGCATCTTTTACTTTCACCAGCGTTTCTG |
| GGTGAGCAAAAACAGGAAGGCAAAATGCCGCAAAAAAGGGAATAAGGGCGA |
| CACGGAAATGTTGAATACTCATACTCTTCCTTTTTCAATATTATTGAAGCA |
| TTTATCAGGGTTATTGTCTCATGAGCGGATACATATTTGAATGTATTTAGA |
| AAAATAAACAAATAGGGGTTCCGCGCACATTTCCCCGAAAAGTGCCACCTG |
| ACGTCTAAGAAACCATTATTATCATGACATTAACCTATAAAAATAGGCGTA |
| TCACGAGGCCCTTTCGTCTCGCGCGTTTCGGTGATGACGGTGAAAACCTCT |
| GACACATGCAGCTCCCGGAGACGGTCACAGCTTGTCTGTAAGCGGATGCCG |
| GGAGCAGACAAGCCCGTCAGGGCGCGTCAGCGGGTGTTGGCGGGTGTCGGG |
| GCTGGCTTAACTATGCGGCATCAGAGCAGATTGTACTGAGAGTGCACCATA |
| TGCGGTGTGAAATACCGCACAGATGCGTAAGGAGAAAATACCGCATCAGGC |
| GCCATTCGCCATTCAGGCTGCGCAACTGTTGGGAAGGGCGATCGGTGCGGG |
| CCTCTTCGCTATTACGCCAGCTGGCGAAAGGGGGATGTGCTGCAAGGCGAT |
| TAAGTTGGGTAACGCCAGGGTTTTCCCAGTCACGACGTT |

TABLE 7

| Nucleotide sequences of Tet promoter-PAL1 construct, high-copy (SEQ ID NO: 24) |
|---|
| CTCTAGAAATAATTTTGTTTAACTTTAAGAAGGAGATATACATATGAAAACACTATCACA |
| GGCCCAATCTAAAACTTCTTCACAGCAATTCAGCTTTACCGGGAACTCGTCTGCGAATGT |
| AATTATCGGCAATCAAAAGCTGACCATTAATGATGTAGCTCGCGTTGCCCGGAATGGCAC |
| TTTGGTGTCACTGACGAACAATACCGACATTCTGCAAGGTATTCAAGCTAGCTGCGATTA |
| TATCAATAACGCCGTTGAATCTGGCGAGCCAATCTACGGGGTAACAAGCGGTTTTGGTGG |
| GATGGCGAACGTTGCCATTAGCCGTGAACAGGCGAGCGAACTTCAGACCAACCTCGTTTG |
| GTTCCTAAAGACAGGAGCTGGTAATAAGTTACCTCTGGCTGACGTAAGAGCCGCGATGCT |
| GCTTCGCGCTAATAGTCACATGCGCGGCGCCAGTGGTATCCGTCTTGAGCTTATCAAGAG |
| GATGGAAATCTTCCTCAACGCGGGTGTCACACCATATGTTTATGAGTTTGGTAGTATCGG |
| AGCCAGTGGTGATCTTGTTCCCCTGAGTTATATTACGGGTTCATTGATTGGTTTAGACCC |
| GTCCTTTAAAGTGGATTTTAACGGGAAAGAAATGGACGCCCCGACCGCTTTACGACAGCT |
| TAATCTGAGCCCACTTACTTTGCTCCCTAAAGAAGGTCTTGCCATGATGAATGGCACCTC |
| TGTGATGACTGGAATTGCCGCGAATTGTGTGTATGACACGCAGATCCTAACGGCCATTGC |
| CATGGGTGTTCACGCGTTGGACATTCAAGCCCTGAATGGTACAAACCAGTCGTTTCATCC |
| GTTTATCCATAATTCAAAACCCCATCCGGGACAGCTTTGGGCTGCTGATCAGATGATCTC |
| ACTCCTGGCCAATAGTCAACTGGTTCGGGACGAGCTCGACGGCAAACATGATTATCGCGA |
| TCATGAGCTCATCCAGGACCGGTATTCACTTCGTTGTCTCCCACAATACCTGGGGCCTAT |
| CGTTGATGGTATATCTCAAATTGCGAAGCAAATTGAAATTGAGATCAATAGCGTAACCGA |
| CAACCCGCTTATCGATGTTGATAATCAGGCCTCTTATCACGGTGGCAATTTTCTGGGCCA |
| GTATGTTGGTATGGGGATGGATCACCTGCGGTACTATATTGGGCTTCTGGCTAAACATCT |
| TGATGTGCAGATTGCCTTATTAGCTTCACCAGAATTTTCAAATGGACTGCCGCCATCATT |
| GCTCGGTAACAGAGAAAGGAAAGTAAATATGGGCCTTAAGGGCCTTCAGATATGTGGTAA |
| CTCAATCATGCCCCTCCTGACCTTTTATGGGAACTCAATTGCTGATCGTTTTCCGACACA |
| TGCTGAACAGTTTAACCAAAACATTAACTCACAGGGCTATACATCCGCGACGTTAGCGCG |
| TCGGTCCGTGGATATCTTCCAGAATTATGTTGCTATCGCTCTGATGTTCGGCGTACAGGC |
| CGTTGATTTGCGCACTTATAAAAAAACCGGTCACTACGATGCTCGGGCTTGCCTGTCGCC |
| TGCCACCGAGCGGCTTTATAGCGCCGTACGTCATGTTGTGGGTCAGAAACCGACGTCGGA |
| CCGCCCCTATATTTGGAATGATAATGAACAAGGGCTGGATGAACACATCGCCCGGATATC |
| TGCCGATATTGCCGCCGGAGGTGTCATCGTCCAGGCGGTACAAGACATACTTCCTTGCCT |
| GCATTAAGCTTGGCGTAATCATGGTCATAGCTGTTTCCTGTGTGAAATTGTTATCCGCTC |
| ACAATTCCACACAACATACGAGCCGGAAGCATAAAGTGTAAAGCCTGGGGTGCCTAATGA |
| GTGAGCTAACTCACATTAATTGCGTTGCGCTCACTGCCCGCTTTCCAGTCGGGAAACCTG |
| TCGTGCCAGCTGCATTAATGAATCGGCCAACGCGCGGGGAGAGGCGGTTTGCGTATTGGG |
| CGCTCTTCCGCTTCCTCGCTCACTGACTCGCTGCGCTCGGTCGTTCGGCTGCGGCGAGCG |
| GTATCAGCTCACTCAAAGGCGGTAATACGGTTATCCACAGAATCAGGGGATAACGCAGGA |
| AAGAACATGTGAGCAAAAGGCCAGCAAAAGGCCAGGAACCGTAAAAAGGCCGCGTTGCTG |
| GCGTTTTTCCATAGGCTCCGCCCCCCTGACGAGCATCACAAAAATCGACGCTCAAGTCAG |
| AGGTGGCGAAACCCGACAGGACTATAAAGATACCAGGCGTTTCCCCCTGGAAGCTCCCTC |
| GTGCGCTCTCCTGTTCCGACCCTGCCGCTTACCGGATACCTGTCCGCCTTTCTCCCTTCG |

TABLE 7-continued

| Nucleotide sequences of Tet promoter-PAL1 construct, high-copy (SEQ ID NO: 24) |
|---|

GGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCAGCC

ACTGGTAACAGGATTAGCAGAGCGAGGTATGTAGGCGGTGCTACAGAGTTCTTGAAGTGG

TGGCCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGTAGC

GGTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGAAGT

TTTAAATCAATCTAAAGTATATATGAGTAAACTTGGTCTGACAGTTACCAATGCTTAATC

AGTGAGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCAATGATA

CCGCGAGACCCACGCTCACCGGCTCCAGATTTATCAGCAATAAACCAGCCAGCCGGAAGG

GCCGAGCGCAGAAGTGGTCCTGCAACTTTATCCGCCTCCATCCAGTCTATTAATTGTTGC

CGGGAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCCAA

CGATCAAGGCGAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTGAGTAC

TCAACCAAGTCATTCTGAGAATAGTGTATGCGGCGACCGAGTTGCTCTTGCCCGGCGTCA

ATACGGGATAATACCGCGCCACATAGCAGAACTTTAAAAGTGCTCATCATTGGAAAACGT

TCTTCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAGCA

AAAACAGGAAGGCAAAATGCCGCAAAAAAGGGAATAAGGGCGACACGGAAATGTTGAATA

CTCATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTTCCC

CGAAAAGTGCCACCTGACGTCTAAGAAACCATTATTATCATGACATTAACCTATAAAAAT

AGGCGTATCACGAGGCCCTTTCGTCTCGCGCGTTTCGGTGATGACGGTGAAAACCTCTGA

CACATGCAGCTCCCGGAGACGGTCACAGCTTGTCTGTAAGCGGATGCCGGGAGCAGACAA

GCCCGTCAGGGCGCGTCAGCGGGTGTTGGCGGGTGTCGGGGCTGGCTTAACTATGCGGCA

TCAGAGCAGATTGTACTGAGAGTGCACCATATGCGGTGTGAAATACCGCACAGATGCGTA

AGGAGAAAATACCGCATCAGGCGCCATTCGCCATTCAGGCTGCGCAACTGTTGGGAAGGG

CGATCGGTGCGGGCCTCTTCGCTATTACGCCAGCTGGCGAAAGGGGGATGTGCTGCAAGG

CGATTAAGTTGGGTAACGCCAGGGTTTTCCCAGTCACGACGTTGTAAAACGACGGCCAGT

GAATTCGTTAAGACCCACTTTCACATTTAAGTTGTTTTTCTAATCCGCATATGATCAATT

CAAGGCCGAATAAGAAGGCTGGCTCTGCACCTTGGTGATCAAATAATTCGATAGCTTGTC

GTAATAATGGCGGCATACTATCAGTAGTAGGTGTTTCCCTTTCTTCTTTAGCGACTTGAT

GCTCTTGATCTTCCAATACGCAACCTAAAGTAAAATGCCCCACAGCGCTGAGTGCATATA

TABLE 7-continued

| Nucleotide sequences of Tet promoter-PAL1 construct, high-copy (SEQ ID NO: 24) |
|---|
| ATGCATTCTCTAGTGAAAAACCTTGTTGGCATAAAAAGGCTAATTGATTTTCGAGAGTTT |
| CATACTGTTTTTCTGTAGGCCGTGTACCTAAATGTACTTTTGCTCCATCGCGATGACTTA |
| GTAAAGCACATCTAAAACTTTTAGCGTTATTACGTAAAAAATCTTGCCAGCTTTCCCCTT |
| CTAAAGGGCAAAAGTGAGTATGGTGCCTATCTAACATCTCAATGGCTAAGGCGTCGAGCA |
| AAGCCCGCTTATTTTTTACATGCCAATACAATGTAGGCTGCTCTACACCTAGCTTCTGGG |
| CGAGTTTACGGGTTGTTAAACCTTCGATTCCGACCTCATTAAGCAGCTCTAATGCGCTGT |
| TAATCACTTTACTTTTATCTAATCTAGACATCATTAATTCCTAATTTTT**GTTGACACTCT** |
| **ATCATTGATAGAGTTATTTTACCACTCCCTATCAGTGATAGAGAA**AAGTGAA |

TABLE 8

| Nucleotide sequences of Tet promoter-PAL3, high-copy construct (SEQ ID NO: 25) |
|---|
| CTCTAGAAATAATTTTGTTTAACTTTAAGAAGGAGATATACATATGAAAGCTAAAGATGT |
| TCAGCCAACCATTATTATTAATAAAAATGGCCTTATCTCTTTGGAAGATATCTATGACAT |
| TGCGATAAAACAAAAAAAAGTAGAAATATCAACGGAGATCACTGAACTTTTGACGCATGG |
| TCGTGAAAAATTAGAGGAAAAATTAAATTCAGGAGAGGTTATATATGGAATCAATACAGG |
| ATTTGGAGGGAATGCCAATTTAGTTGTGCCATTTGAGAAAATCGCAGAGCATCAGCAAAA |
| TCTGTTAACTTTTCTTTCTGCTGGTACTGGGGACTATATGTCCAAACCTTGTATTAAAGC |
| GTCACAATTTACTATGTTACTTTCTGTTTGCAAAGGTTGGTCTGCAACCAGACCAATTGT |
| CGCTCAAGCAATTGTTGATCATATTAATCATGACATTGTTCCTCTGGTTCCTCGCTATGG |
| CTCAGTGGGTGCAAGCGGTGATTTAATTCCTTTATCTTATATTGCACGAGCATTATGTGG |
| TATCGGCAAAGTTTATTATATGGGCGCAGAAATTGACGCTGCTGAAGCAATTAAACGTGC |
| AGGGTTGACACCATTATCGTTAAAAGCCAAAGAAGGTCTTGCTCTGATTAACGGCACCCG |
| GGTAATGTCAGGAATCAGTGCAATCACCGTCATTAAACTGGAAAAACTATTTAAAGCCTC |
| AATTTCTGCGATTGCCCTTGCTGTTGAAGCATTACTTGCATCTCATGAACATTATGATGC |
| CCGGATTCAACAAGTAAAAAATCATCCTGGTCAAAACGCGGTGGCAAGTGCATTGCGTAA |
| TTTATTGGCAGGTTCAACGCAGGTTAATCTATTATCTGGGGTTAAAGAACAAGCCAATAA |
| AGCTTGTCGTCATCAAGAAATTACCCAACTAAATGATACCTTACAGGAAGTTTATTCAAT |
| TCGCTGTGCACCACAAGTATTAGGTATAGTGCCAGAATCTTTAGCTACCGCTCGGAAAAT |
| ATTGGAACGGGAAGTTATCTCAGCTAATGATAATCCATTGATAGATCCAGAAAATGGCGA |
| TGTTCTACACGGTGGAAATTTTATGGGGCAATATGTCGCCCGAACAATGGATGCATTAAA |
| ACTGGATATTGCTTTAATTGCCAATCATCTTCACGCCATTGTGGCTCTTATGATGGATAA |
| CCGTTTCTCTCGTGGATTACCTAATTCACTGAGTCCGACACCCGGCATGTATCAAGGTTT |
| TAAAGGCGTCCAACTTTCTCAAACCGCTTTAGTTGCTGCAATTCGCCATGATTGTGCTGC |
| ATCAGGTATTCATACCCTCGCCACAGAACAATACAATCAAGATATTGTCAGTTTAGGTCT |
| GCATGCCGCTCAAGATGTTTTAGAGATGGAGCAGAAATTACGCAATATTGTTTCAATGAC |
| AATTCTGGTAGTTTGTCAGGCCATTCATCTTCGCGGCAATATTAGTGAAATTGCGCCTGA |
| AACTGCTAAATTTTACCATGCAGTACGCGAAATCAGTTCTCCTTTGATCACTGATCGTGC |
| GTTGGATGAAGATATAATCCGCATTGCGGATGCAATTATTAATGATCAACTTCCTCTGCC |

TABLE 8-continued

| Nucleotide sequences of Tet promoter-PAL3, high-copy construct (SEQ ID NO: 25) |
|---|

AGAAATCATGCTGGAAGAATAAGCTTGGCGTAATCATGGTCATAGCTGTTTCCTGTGTGA

AATTGTTATCCGCTCACAATTCCACACAACATACGAGCCGGAAGCATAAAGTGTAAAGCC

TGGGGTGCCTAATGAGTGAGCTAACTCACATTAATTGCGTTGCGCTCACTGCCCGCTTTC

CAGTCGGGAAACCTGTCGTGCCAGCTGCATTAATGAATCGGCCAACGCGCGGGGAGAGGC

GGTTTGCGTATTGGGCGCTCTTCCGCTTCCTCGCTCACTGACTCGCTGCGCTCGGTCGTT

CGGCTGCGGCGAGCGGTATCAGCTCACTCAAAGGCGGTAATACGGTTATCCACAGAATCA

GGGGATAACGCAGGAAAGAACATGTGAGCAAAAGGCCAGCAAAAGGCCAGGAACCGTAAA

AAGGCCGCGTTGCTGGCGTTTTTCCATAGGCTCCGCCCCCCTGACGAGCATCACAAAAAT

CGACGCTCAAGTCAGAGGTGGCGAAACCCGACAGGACTATAAAGATACCAGGCGTTTCCC

CCTGGAAGCTCCCTCGTGCGCTCTCCTGTTCCGACCCTGCCGCTTACCGGATACCTGTCC

GCCTTTCTCCCTTCGGGAAGCGTGGCGCTTTCTCATAGCTCACGCTGTAGGTATCTCAGT

TCGGTGTAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGACTTATCG

CCACTGGCAGCAGCCACTGGTAACAGGATTAGCAGAGCGAGGTATGTAGGCGGTGCTACA

GAGTTCTTGAAGTGGTGGCCTAACTACGGCTACACTAGAAGAACAGTATTTGGTATCTGC

GCTCTGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAAAAA

GGATCTCAAGAAGATCCTTTGATCTTTTCTACGGGGTCTGACGCTCAGTGGAACGAAAAC

TCACGTTAAGGGATTTTGGTCATGAGATTATCAAAAAGGATCTTCACCTAGATCCTTTTA

AATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGCCCC

AGTGCTGCAATGATACCGCGAGACCCACGCTCACCGGCTCCAGATTTATCAGCAATAAAC

CAGCCAGCCGGAAGGGCCGAGCGCAGAAGTGGTCCTGCAACTTTATCCGCCTCCATCCAG

TCTATTAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTTCT

GTGACTGGTGAGTACTCAACCAAGTCATTCTGAGAATAGTGTATGCGGCGACCGAGTTGC

TCTTGCCCGGCGTCAATACGGGATAATACCGCGCCACATAGCAGAACTTTAAAAGTGCTC

ATCATTGGAAAACGTTCTTCGGGGCGAAAACTCTCAAGGATCTTACCGCTGTTGAGATCC

AGTTCGATGTAACCCACTCGTGCACCCAACTGATCTTCAGCATCTTTTACTTTCACCAGC

GTTTCTGGGTGAGCAAAAACAGGAAGGCAAAATGCCGCAAAAAAGGGAATAAGGGCGACA

CGGAAATGTTGAATACTCATACTCTTCCTTTTTCAATATTATTGAAGCATTTATCAGGGT

TATTGTCTCATGAGCGGATACATATTTGAATGTATTTAGAAAAATAAACAAATAGGGGTT

CCGCGCACATTTCCCCGAAAAGTGCCACCTGACGTCTAAGAAACCATTATTATCATGACA

TTAACCTATAAAAATAGGCGTATCACGAGGCCCTTTCGTCTCGCGCGTTTCGGTGATGAC

TABLE 8-continued

| Nucleotide sequences of Tet promoter-PAL3, high-copy construct (SEQ ID NO: 25) |
|---|
| GGTGAAAACCTCTGACACATGCAGCTCCCGGAGACGGTCACAGCTTGTCTGTAAGCGGAT |
| GCCGGGAGCAGACAAGCCCGTCAGGGCGCGTCAGCGGGTGTTGGCGGGTGTCGGGGCTGG |
| CTTAACTATGCGGCATCAGAGCAGATTGTACTGAGAGTGCACCATATGCGGTGTGAAATA |
| CCGCACAGATGCGTAAGGAGAAAATACCGCATCAGGCGCCATTCGCCATTCAGGCTGCGC |
| AACTGTTGGGAAGGGCGATCGGTGCGGGCCTCTTCGCTATTACGCCAGCTGGCGAAAGGG |
| GGATGTGCTGCAAGGCGATTAAGTTGGGTAACGCCAGGGTTTTCCCAGTCACGACGTTGT |
| AAAACGACGGCCAGTGAATTCGTTAAGACCCACTTTCACATTTAAGTTGTTTTTCTAATC |
| CGCATATGATCAATTCAAGGCCGAATAAGAAGGCTGGCTCTGCACCTTGGTGATCAAATA |
| ATTCGATAGCTTGTCGTAATAATGGCGGCATACTATCAGTAGTAGGTGTTTCCCTTTCTT |
| CTTTAGCGACTTGATGCTCTTGATCTTCCAATACGCAACCTAAAGTAAAATGCCCCACAG |
| CGCTGAGTGCATATAATGCATTCTCTAGTGAAAAACCTTGTTGGCATAAAAAGGCTAATT |
| GATTTTCGAGAGTTTCATACTGTTTTTCTGTAGGCCGTGTACCTAAATGTACTTTTGCTC |
| CATCGCGATGACTTAGTAAAGCACATCTAAAACTTTTAGCGTTATTACGTAAAAAATCTT |
| GCCAGCTTTCCCCTTCTAAAGGGCAAAAGTGAGTATGGTGCCTATCTAACATCTCAATGG |
| CTAAGGCGTCGAGCAAAGCCCGCTTATTTTTTACATGCCAATACAATGTAGGCTGCTCTA |
| CACCTAGCTTCTGGGCGAGTTTACGGGTTGTTAAACCTTCGATTCCGACCTCATTAAGCA |
| GCTCTAATGCGCTGTTAATCACTTTACTTTTATCTAATCTAGACATCATTAATTCCTAAT |
| TTTT**GTTGACACTCTATCATTGATAGAGTTATTTTACCACTCCCTATCAGTGATAGAGAA** |
| AAGTGAA |

TABLE 9

| Nucleotide sequences of FNR promoter-PAL1 construct, low-copy (SEQ ID NO: 26) |
|---|
| **CTCTTGATCGTTATCAATTCCCACGCTGTTTCAGAGCGTTACCTTGCCCTTAAACATTAG** |
| **CAATGTCGATTTATCAGAGGGCCGACAGGCTCCCACAGGAGAAAACCG**ATGAAAACACTA |
| TCACAGGCCCAATCTAAAACTTCTTCACAGCAATTCAGCTTTACCGGGAACTCGTCTGCG |
| AATGTAATTATCGGCAATCAAAAGCTGACCATTAATGATGTAGCTCGCGTTGCCCGGAAT |
| GGCACTTTGGTGTCACTGACGAACAATACCGACATTCTGCAAGGTATTCAAGCTAGCTGC |
| GATTATATCAATAACGCCGTTGAATCTGGCGAGCCAATCTACGGGGTAACAAGCGGTTTT |
| GGTGGGATGGCGAACGTTGCCATTAGCCGTGAACAGGCGAGCGAACTTCAGACCAACCTC |
| GTTTGGTTCCTAAAGACAGGAGCTGGTAATAAGTTACCTCTGGCTGACGTAAGAGCCGCG |
| ATGCTGCTTCGCGCTAATAGTCACATGCGCGGCGCCAGTGGTATCCGTCTTGAGCTTATC |
| AAGAGGATGGAAATCTTCCTCAACGCGGGTGTCACACCATATGTTTATGAGTTTGGTAGT |
| ATCGGAGCCAGTGGTGATCTTGTTCCCCTGAGTTATATTACGGGTTCATTGATTGGTTTA |
| GACCCGTCCTTTAAAGTGGATTTTAACGGGAAAGAAATGGACGCCCCGACCGCTTTACGA |
| CAGCTTAATCTGAGCCCACTTACTTTGCTCCCTAAAGAAGGTCTTGCCATGATGAATGGC |
| ACCTCTGTGATGACTGGAATTGCCGCGAATTGTGTGTATGACACGCAGATCCTAACGGCC |
| ATTGCCATGGGTGTTCACGCGTTGGACATTCAAGCCCTGAATGGTACAAACCAGTCGTTT |
| CATCCGTTTATCCATAATTCAAAACCCCATCCGGGACAGCTTTGGGCTGCTGATCAGATG |

TABLE 9-continued

| Nucleotide sequences of FNR promoter-PAL1 construct, low-copy (SEQ ID NO: 26) |
| --- |
| ATCTCACTCCTGGCCAATAGTCAACTGGTTCGGGACGAGCTCGACGGCAAACATGATTAT |
| CGCGATCATGAGCTCATCCAGGACCGGTATTCACTTCGTTGTCTCCCACAATACCTGGGG |
| CCTATCGTTGATGGTATATCTCAAATTGCGAAGCAAATTGAAATTGAGATCAATAGCGTA |
| ACCGACAACCCGCTTATCGATGTTGATAATCAGGCCTCTTATCACGGTGGCAATTTTCTG |
| GGCCAGTATGTTGGTATGGGGATGGATCACCTGCGGTACTATATTGGGCTTCTGGCTAAA |
| CATCTTGATGTGCAGATTGCCTTATTAGCTTCACCAGAATTTTCAAATGGACTGCCGCCA |
| TCATTGCTCGGTAACAGAGAAAGGAAAGTAAATATGGGCCTTAAGGGCCTTCAGATATGT |
| GGTAACTCAATCATGCCCCTCCTGACCTTTTATGGGAACTCAATTGCTGATCGTTTTCCG |
| ACACATGCTGAACAGTTTAACCAAAACATTAACTCACAGGGCTATACATCCGCGACGTTA |
| GCGCGTCGGTCCGTGGATATCTTCCAGAATTATGTTGCTATCGCTCTGATGTTCGGCGTA |
| CAGGCCGTTGATTTGCGCACTTATAAAAAAACCGGTCACTACGATGCTCGGGCTTGCCTG |
| TCGCCTGCCACCGAGCGGCTTTATAGCGCCGTACGTCATGTTGTGGGTCAGAAACCGACG |
| TCGGACCGCCCCTATATTTGGAATGATAATGAACAAGGGCTGGATGAACACATCGCCCGG |
| ATATCTGCCGATATTGCCGCCGGAGGTGTCATCGTCCAGGCGGTACAAGACATACTTCCT |
| TGCCTGCATTAAGCTTGGCGTAATCATGGTCATAGCTGTTTCCTGTGTGAAATTGTTATC |
| CGCTCACAATTCCACACAACATACGAGCCGGAAGCATAAAGTGTAAAGCCTGGGGTGCCT |
| AATGAGTGAGCTAACTCACATTAATTGCGTTGCGCTCACTGCCCGCTTTCCAGTCGGGAA |
| ACCTGTCGTGCCAGCTGCATTAATGAATCGGCCAACGCGCGGGGAGAGGCGGTTTGCGTA |
| TTGGGCGCTCTTCCGCTTCCTCGCTCACTGACTCGCTGCGCTCGGTCGTTCGGCTGCGGC |
| GAGCGGTATCAGCTCACTCAAAGGCGGTAGTACGGGTTTTGCTGCCCGCAAACGGGCTGT |
| TCTGGTGTTGCTAGTTTGTTATCAGAATCGCAGATCCGGCTTCAGGTTTGCCGGCTGAAA |
| GCGCTATTTCTTCCAGAATTGCCATGATTTTTTCCCCACGGGAGGCGTCACTGGCTCCCG |
| TGTTGTCGGCAGCTTTGATTCGATAAGCAGCATCGCCTGTTTCAGGCTGTCTATGTGTGA |
| CTGTTGAGCTGTAACAAGTTGTCTCAGGTGTTCAATTTCATGTTCTAGTTGCTTTGTTTT |
| ACTGGTTTCACCTGTTCTATTAGGTGTTACATGCTGTTCATCTGTTACATTGTCGATCTG |
| TTCATGGTGAACAGCTTTAAATGCACCAAAAACTCGTAAAAGCTCTGATGTATCTATCTT |
| TTTTACACCGTTTTCATCTGTGCATATGGACAGTTTTCCCTTTGATATCTAACGGTGAAC |
| AGTTGTTCTACTTTTGTTTGTTAGTCTTGATGCTTCACTGATAGATACAAGAGCCATAAG |
| AACCTCAGATCCTTCCGTATTTAGCCAGTATGTTCTCTAGTGTGGTTCGTTGTTTTTGCG |
| TGAGCCATGAGAACGAACCATTGAGATCATGCTTACTTTGCATGTCACTCAAAAATTTTG |
| CCTCAAAACTGGTGAGCTGAATTTTTGCAGTTAAAGCATCGTGTAGTGTTTTTCTTAGTC |
| CGTTACGTAGGTAGGAATCTGATGTAATGGTTGTTGGTATTTTGTCACCATTCATTTTTA |
| TCTGGTTGTTCTCAAGTTCGGTTACGAGATCCATTTGTCTATCTAGTTCAACTTGGAAAA |
| TCAACGTATCAGTCGGGCGGCCTCGCTTATCAACCACCAATTTCATATTGCTGTAAGTGT |
| TTAAATCTTTACTTATTGGTTTCAAAACCCATTGGTTAAGCCTTTTAAACTCATGGTAGT |
| TATTTTCAAGCATTAACATGAACTTAAATTCATCAAGGCTAATCTCTATATTTGCCTTGT |
| GAGTTTTCTTTTGTGTTAGTTCTTTTAATAACCACTCATAAATCCTCATAGAGTATTTGT |
| TTTCAAAAGACTTAACATGTTCCAGATTATATTTTATGAATTTTTTTAACTGGAAAAGAT |

TABLE 9-continued

| Nucleotide sequences of FNR promoter-PAL1 construct, low-copy (SEQ ID NO: 26) |
|---|
| AAGGCAATATCTCTTCACTAAAAACTAATTCTAATTTTTCGCTTGAGAACTTGGCATAGT |
| TTGTCCACTGGAAAATCTCAAAGCCTTTAACCAAAGGATTCCTGATTTCCACAGTTCTCG |
| TCATCAGCTCTCTGGTTGCTTTAGCTAATACACCATAAGCATTTTCCCTACTGATGTTCA |
| TCATCTGAGCGTATTGGTTATAAGTGAACGATACCGTCCGTTCTTTCCTTGTAGGGTTTT |
| CAATCGTGGGGTTGAGTAGTGCCACACAGCATAAAATTAGCTTGGTTTCATGCTCCGTTA |
| AGTCATAGCGACTAATCGCTAGTTCATTTGCTTTGAAAACAACTAATTCAGACATACATC |
| TCAATTGGTCTAGGTGATTTTAATCACTATACCAATTGAGATGGGCTAGTCAATGATAAT |
| TACTAGTCCTTTTCCTTTGAGTTGTGGGTATCTGTAAATTCTGCTAGACCTTTGCTGGAA |
| AACTTGTAAATTCTGCTAGACCCTCTGTAAATTCCGCTAGACCTTTGTGTGTTTTTTTTG |
| TTTATATTCAAGTGGTTATAATTTATAGAATAAAGAAAGAATAAAAAAAGATAAAAAGAA |
| TAGATCCCAGCCCTGTGTATAACTCACTACTTTAGTCAGTTCCGCAGTATTACAAAAGGA |
| TGTCGCAAACGCTGTTTGCTCCTCTACAAAACAGACCTTAAAACCCTAAAGGCTTAAGTA |
| GCACCCTCGCAAGCTCGGGCAAATCGCTGAATATTCCTTTTGTCTCCGACCATCAGGCAC |
| CTGAGTCGCTGTCTTTTTCGTGACATTCAGTTCGCTGCGCTCACGGCTCTGGCAGTGAAT |
| GGGGGTAAATGGCACTACAGGCGCCTTTTATGGATTCATGCAAGGAAACTACCCATAATA |
| CAAGAAAAGCCCGTCACGGGCTTCTCAGGGCGTTTTATGGCGGGTCTGCTATGTGGTGCT |
| ATCTGACTTTTTGCTGTTCAGCAGTTCCTGCCCTCTGATTTTCCAGTCTGACCACTTCGG |
| ATTATCCCGTGACAGGTCATTCAGACTGGCTAATGCACCCAGTAAGGCAGCGGTATCATC |
| AACAGGCTTACCCGTCTTACTGTCTTTTCTACGGGGTCTGACGCTCAGTGGAACGAAAAC |
| TCACGTTAAGGGATTTTGGTCATGAGATTATCAAAAAGGATCTTCACCTAGATCCTTTTA |
| AATTAAAAATGAAGTTTTAAATCAATCTAAAGTATATATGAGTAAACTTGGTCTGACAGT |
| TACCAATGCTTAATCAGTGAGGCACCTATCTCAGCGATCTGTCTATTTCGTTCATCCATA |
| GTTGCCTGACTCCCCGTCGTGTAGATAACTACGATACGGGAGGGCTTACCATCTGGCCCC |
| AGTGCTGCAATGATACCGCGAGACCCACGCTCACCGGCTCCAGATTTATCAGCAATAAAC |
| CAGCCAGCCGGAAGGGCCGAGCGCAGAAGTGGTCCTGCAACTTTATCCGCCTCCATCCAG |
| TCTATTAATTGTTGCCGGGAAGCTAGAGTAAGTAGTTCGCCAGTTAATAGTTTGCGCAAC |
| GTTGTTGCCATTGCTACAGGCATCGTGGTGTCACGCTCGTCGTTTGGTATGGCTTCATTC |
| AGCTCCGGTTCCCAACGATCAAGGCGAGTTACATGATCCCCCATGTTGTGCAAAAAAGCG |
| GTTAGCTCCTTCGGTCCTCCGATCGTTGTCAGAAGTAAGTTGGCCGCAGTGTTATCACTC |
| ATGGTTATGGCAGCACTGCATAATTCTCTTACTGTCATGCCATCCGTAAGATGCTTTTCT |
| GTGACTGGTGAGTACTCAACCAAGTCATTCTGAGAATAGTGTATGCGGCGACCGAGTTGC |
| TCTTGCCCGGCGTCAATACGGGATAATACCGCGCCACATAGCAGAACTTTAAAAGTGCTC |
| ATCATTGGAAAACGTTCTTCGGGGCGAAAACTCTCAAGGATCTTACCGCTGTTGAGATCC |
| AGTTCGATGTAACCCACTCGTGCACCCAACTGATCTTCAGCATCTTTTACTTTCACCAGC |
| GTTTCTGGGTGAGCAAAAACAGGAAGGCAAAATGCCGCAAAAAAGGGAATAAGGGCGACA |
| CGGAAATGTTGAATACTCATACTCTTCCTTTTTCAATATTATTGAAGCATTTATCAGGGT |
| TATTGTCTCATGAGCGGATACATATTTGAATGTATTTAGAAAAATAAACAAATAGGGGTT |
| CCGCGCACATTTCCCCGAAAAGTGCCACCTGACGTCTAAGAAACCATTATTATCATGACA |
| TTAACCTATAAAAATAGGCGTATCACGAGGCCCTTTCGTCTCGCGCGTTTCGGTGATGAC |

TABLE 9-continued

| Nucleotide sequences of FNR promoter-PAL1 construct, low-copy (SEQ ID NO: 26) |
|---|
| GGTGAAAACCTCTGACACATGCAGCTCCCGGAGACGGTCACAGCTTGTCTGTAAGCGGAT |
| GCCGGGAGCAGACAAGCCCGTCAGGGCGCGTCAGCGGGTGTTGGCGGGTGTCGGGGCTGG |
| CTTAACTATGCGGCATCAGAGCAGATTGTACTGAGAGTGCACCATATGCGGTGTGAAATA |
| CCGCACAGATGCGTAAGGAGAAAATACCGCATCAGGCGCCATTCGCCATTCAGGCTGCGC |
| AACTGTTGGGAAGGGCGATCGGTGCGGGCCTCTTCGCTATTACGCCAGCTGGCGAAAGGG |
| GGATGTGCTGCAAGGCGATTAAGTTGGGTAACGCCAGGGTTTTCCCAGTCACGACGTTGT |
| AAAACGACGGCCAGTGAATTCG |

TABLE 10

| Nucleotide sequences of FNR promoter-PAL3 construct, low-copy (SEQ ID NO: 27) |
|---|
| **CTCTTGATCGTTATCAATTCCCACGCTGTTTCAGAGCGTTACCTTGCCCTTAAACATTAG** |
| **CAATGTCGATTTATCAGAGGGCCGACAGGCTCCCACAGGAGAAAACCG**ATGAAAGCTAAA |
| GATGTTCAGCCAACCATTATTATTAATAAAAATGGCCTTATCTCTTTGGAAGATATCTAT |
| GACATTGCGATAAAACAAAAAAAAGTAGAAATATCAACGGAGATCACTGAACTTTTGACG |
| CATGGTCGTGAAAAATTAGAGGAAAAATTAAATTCAGGAGAGGTTATATATGGAATCAAT |
| ACAGGATTTGGAGGGAATGCCAATTTAGTTGTGCCATTTGAGAAAATCGCAGAGCATCAG |
| CAAAATCTGTTAACTTTTCTTTCTGCTGGTACTGGGGACTATATGTCCAAACCTTGTATT |
| AAAGCGTCACAATTTACTATGTTACTTTCTGTTTGCAAAGGTTGGTCTGCAACCAGACCA |
| ATTGTCGCTCAAGCAATTGTTGATCATATTAATCATGACATTGTTCCTCTGGTTCCTCGC |
| TATGGCTCAGTGGGTGCAAGCGGTGATTTAATTCCTTTATCTTATATTGCACGAGCATTA |
| TGTGGTATCGGCAAAGTTTATTATATGGGCGCAGAAATTGACGCTGCTGAAGCAATTAAA |
| CGTGCAGGGTTGACACCATTATCGTTAAAAGCCAAAGAAGGTCTTGCTCTGATTAACGGC |
| ACCCGGGTAATGTCAGGAATCAGTGCAATCACCGTCATTAAACTGGAAAAACTATTTAAA |
| GCCTCAATTTCTGCGATTGCCCTTGCTGTTGAAGCATTACTTGCATCTCATGAACATTAT |
| GATGCCCGGATTCAACAAGTAAAAAATCATCCTGGTCAAAACGCGGTGGCAAGTGCATTG |
| CGTAATTTATTGGCAGGTTCAACGCAGGTTAATCTATTATCTGGGGTTAAAGAACAAGCC |
| AATAAAGCTTGTCGTCATCAAGAAATTACCCAACTAAATGATACCTTACAGGAAGTTTAT |
| TCAATTCGCTGTGCACCACAAGTATTAGGTATAGTGCCAGAATCTTTAGCTACCGCTCGG |
| AAAATATTGGAACGGGAAGTTATCTCAGCTAATGATAATCCATTGATAGATCCAGAAAAT |
| GGCGATGTTCTACACGGTGGAAATTTTATGGGGCAATATGTCGCCCGAACAATGGATGCA |
| TTAAAACTGGATATTGCTTTAATTGCCAATCATCTTCACGCCATTGTGGCTCTTATGATG |
| GATAACCGTTTCTCTCGTGGATTACCTAATTCACTGAGTCCGACACCCGGCATGTATCAA |
| GGTTTTAAAGGCGTCCAACTTTCTCAAACCGCTTTAGTTGCTGCAATTCGCCATGATTGT |
| GCTGCATCAGGTATTCATACCCTCGCCACAGAACAATACAATCAAGATATTGTCAGTTTA |
| GGTCTGCATGCCGCTCAAGATGTTTTAGAGATGGAGCAGAAATTACGCAATATTGTTTCA |
| ATGACAATTCTGGTAGTTTGTCAGGCCATTCATCTTCGCGGCAATATTAGTGAAATTGCG |
| CCTGAAACTGCTAAATTTTACCATGCAGTACGCGAAATCAGTTCTCCTTTGATCACTGAT |

TABLE 10-continued

| Nucleotide sequences of FNR promoter-PAL3 construct, low-copy (SEQ ID NO: 27) |
|---|
| CGTGCGTTGGATGAAGATATAATCCGCATTGCGGATGCAATTATTAATGATCAACTTCCT |
| CTGCCAGAAATCATGCTGGAAGAATAAGCTTGGCGTAATCATGGTCATAGCTGTTTCCTG |
| TGTGAAATTGTTATCCGCTCACAATTCCACACAACATACGAGCCGGAAGCATAAAGTGTA |
| AAGCCTGGGGTGCCTAATGAGTGAGCTAACTCACATTAATTGCGTTGCGCTCACTGCCCG |
| CTTTCCAGTCGGGAAACCTGTCGTGCCAGCTGCATTAATGAATCGGCCAACGCGCGGGGA |
| GAGGCGGTTTGCGTATTGGGCGCTCTTCCGCTTCCTCGCTCACTGACTCGCTGCGCTCGG |
| TCGTTCGGCTGCGGCGAGCGGTATCAGCTCACTCAAAGGCGGTAGTACGGGTTTTGCTGC |
| CCGCAAACGGGCTGTTCTGGTGTTGCTAGTTTGTTATCAGAATCGCAGATCCGGCTTCAG |
| GTTTGCCGGCTGAAAGCGCTATTTCTTCCAGAATTGCCATGATTTTTTCCCCACGGGAGG |
| CGTCACTGGCTCCCGTGTTGTCGGCAGCTTTGATTCGATAAGCAGCATCGCCTGTTTCAG |
| GCTGTCTATGTGTGACTGTTGAGCTGTAACAAGTTGTCTCAGGTGTTCAATTTCATGTTC |
| TAGTTGCTTTGTTTTACTGGTTTCACCTGTTCTATTAGGTGTTACATGCTGTTCATCTGT |
| TACATTGTCGATCTGTTCATGGTGAACAGCTTTAAATGCACCAAAAACTCGTAAAAGCTC |
| TGATGTATCTATCTTTTTTACACCGTTTTCATCTGTGCATATGGACAGTTTTCCCTTTGA |
| TATCTAACGGTGAACAGTTGTTCTACTTTTGTTTGTTAGTCTTGATGCTTCACTGATAGA |
| TACAAGAGCCATAAGAACCTCAGATCCTTCCGTATTTAGCCAGTATGTTCTCTAGTGTGG |
| TTCGTTGTTTTTGCGTGAGCCATGAGAACGAACCATTGAGATCATGCTTACTTTGCATGT |
| CACTCAAAAATTTTGCCTCAAAACTGGTGAGCTGAATTTTTGCAGTTAAAGCATCGTGTA |
| GTGTTTTTCTTAGTCCGTTACGTAGGTAGGAATCTGATGTAATGGTTGTTGGTATTTTGT |
| CACCATTCATTTTTATCTGGTTGTTCTCAAGTTCGGTTACGAGATCCATTTGTCTATCTA |
| GTTCAACTTGGAAAATCAACGTATCAGTCGGGCGGCCTCGCTTATCAACCACCAATTTCA |
| TATTGCTGTAAGTGTTTAAATCTTTACTTATTGGTTTCAAAACCCATTGGTTAAGCCTTT |
| TAAACTCATGGTAGTTATTTTCAAGCATTAACATGAACTTAAATTCATCAAGGCTAATCT |
| CTATATTTGCCTTGTGAGTTTTCTTTTGTGTTAGTTCTTTTAATAACCACTCATAAATCC |
| TCATAGAGTATTTGTTTTCAAAAGACTTAACATGTTCCAGATTATATTTTATGAATTTTT |
| TTAACTGGAAAAGATAAGGCAATATCTCTTCACTAAAAACTAATTCTAATTTTTCGCTTG |
| AGAACTTGGCATAGTTTGTCCACTGGAAAATCTCAAAGCCTTTAACCAAAGGATTCCTGA |
| TTTCCACAGTTCTCGTCATCAGCTCTCTGGTTGCTTTAGCTAATACACCATAAGCATTTT |
| CCCTACTGATGTTCATCATCTGAGCGTATTGGTTATAAGTGAACGATACCGTCCGTTCTT |
| TCCTTGTAGGGTTTTCAATCGTGGGGTTGAGTAGTGCCACACAGCATAAAATTAGCTTGG |
| TTTCATGCTCCGTTAAGTCATAGCGACTAATCGCTAGTTCATTTGCTTTGAAAACAACTA |
| ATTCAGACATACATCTCAATTGGTCTAGGTGATTTTAATCACTATACCAATTGAGATGGG |
| CTAGTCAATGATAATTACTAGTCCTTTTCCTTTGAGTTGTGGGTATCTGTAAATTCTGCT |
| AGACCTTTGCTGGAAAACTTGTAAATTCTGCTAGACCCTCTGTAAATTCCGCTAGACCTT |
| TGTGTGTTTTTTTTGTTTATATTCAAGTGGTTATAATTTATAGAATAAAGAAAGAATAAA |
| AAAAGATAAAAAGAATAGATCCCAGCCCTGTGTATAACTCACTACTTTAGTCAGTTCCGC |
| AGTATTACAAAAGGATGTCGCAAACGCTGTTTGCTCCTCTACAAAACAGACCTTAAAACC |
| CTAAAGGCTTAAGTAGCACCCTCGCAAGCTCGGGCAAATCGCTGAATATTCCTTTTGTCT |
| CCGACCATCAGGCACCTGAGTCGCTGTCTTTTTCGTGACATTCAGTTCGCTGCGCTCACG |

TABLE 10-continued

| Nucleotide sequences of FNR promoter-PAL3 construct, low-copy (SEQ ID NO: 27) |
|---|
| GCTCTGGCAGTGAATGGGGGTAAATGGCACTACAGGCGCCTTTTATGGATTCATGCAAGG |
| AAACTACCCATAATACAAGAAAAGCCCGTCACGGGCTTCTCAGGGCGTTTTATGGCGGGT |
| CTGCTATGTGGTGCTATCTGACTTTTTGCTGTTCAGCAGTTCCTGCCCTCTGATTTTCCA |
| GTCTGACCACTTCGGATTATCCCGTGACAGGTCATTCAGACTGGCTAATGCACCCAGTAA |
| GGCAGCGGTATCATCAACAGGCTTACCCGTCTTACTGTCTTTTCTACGGGGTCTGACGCT |
| CAGTGGAACGAAAACTCACGTTAAGGGATTTTGGTCATGAGATTATCAAAAAGGATCTTC |
| ACCTAGATCCTTTTAAATTAAAAATGAAGTTTTAAATCAATCTAAAGTATATATGAGTAA |
| ACTTGGTCTGACAGTTACCAATGCTTAATCAGTGAGGCACCTATCTCAGCGATCTGTCTA |
| TTTCGTTCATCCATAGTTGCCTGACTCCCCGTCGTGTAGATAACTACGATACGGGAGGGC |
| TTACCATCTGGCCCCAGTGCTGCAATGATACCGCGAGACCCACGCTCACCGGCTCCAGAT |
| TTATCAGCAATAAACCAGCCAGCCGGAAGGGCCGAGCGCAGAAGTGGTCCTGCAACTTTA |
| TCCGCCTCCATCCAGTCTATTAATTGTTGCCGGGAAGCTAGAGTAAGTAGTTCGCCAGTT |
| AATAGTTTGCGCAACGTTGTTGCCATTGCTACAGGCATCGTGGTGTCACGCTCGTCGTTT |
| GGTATGGCTTCATTCAGCTCCGGTTCCCAACGATCAAGGCGAGTTACATGATCCCCCATG |
| TTGTGCAAAAAAGCGGTTAGCTCCTTCGGTCCTCCGATCGTTGTCAGAAGTAAGTTGGCC |
| GCAGTGTTATCACTCATGGTTATGGCAGCACTGCATAATTCTCTTACTGTCATGCCATCC |
| GTAAGATGCTTTTCTGTGACTGGTGAGTACTCAACCAAGTCATTCTGAGAATAGTGTATG |
| CGGCGACCGAGTTGCTCTTGCCCGGCGTCAATACGGGATAATACCGCGCCACATAGCAGA |
| ACTTTAAAAGTGCTCATCATTGGAAAACGTTCTTCGGGGCGAAAACTCTCAAGGATCTTA |
| CCGCTGTTGAGATCCAGTTCGATGTAACCCACTCGTGCACCCAACTGATCTTCAGCATCT |
| TTTACTTTCACCAGCGTTTCTGGGTGAGCAAAAACAGGAAGGCAAAATGCCGCAAAAAAG |
| GGAATAAGGGCGACACGGAAATGTTGAATACTCATACTCTTCCTTTTTCAATATTATTGA |
| AGCATTTATCAGGGTTATTGTCTCATGAGCGGATACATATTTGAATGTATTTAGAAAAAT |
| AAACAAATAGGGGTTCCGCGCACATTTCCCCGAAAAGTGCCACCTGACGTCTAAGAAACC |
| ATTATTATCATGACATTAACCTATAAAAATAGGCGTATCACGAGGCCCTTTCGTCTCGCG |
| CGTTTCGGTGATGACGGTGAAAACCTCTGACACATGCAGCTCCCGGAGACGGTCACAGCT |
| TGTCTGTAAGCGGATGCCGGGAGCAGACAAGCCCGTCAGGGCGCGTCAGCGGGTGTTGGC |
| GGGTGTCGGGGCTGGCTTAACTATGCGGCATCAGAGCAGATTGTACTGAGAGTGCACCAT |
| ATGCGGTGTGAAATACCGCACAGATGCGTAAGGAGAAAATACCGCATCAGGCGCCATTCG |
| CCATTCAGGCTGCGCAACTGTTGGGAAGGGCGATCGGTGCGGGCCTCTTCGCTATTACGC |
| CAGCTGGCGAAAGGGGGATGTGCTGCAAGGCGATTAAGTTGGGTAACGCCAGGGTTTTCC |
| CAGTCACGACGTTGTAAAACGACGGCCAGTGAATTCG |

TABLE 11

| Nucleotide sequences of Tet promoter-PAL1 construct, low-copy (SEQ ID NO: 28) |
|---|
| **ACCACTCCCTATCAGTGATAGAGAA**AAGTGAACTCTAGAAATAATTTTGTTTAACTTTAA |
| GAAGGAGATATACATATGAAAACACTATCACAGGCCCAATCTAAAACTTCTTCACAGCAA |

TABLE 11-continued

| Nucleotide sequences of Tet promoter-PAL1 construct, low-copy (SEQ ID NO: 28) |
|---|
| TTCAGCTTTACCGGGAACTCGTCTGCGAATGTAATTATCGGCAATCAAAAGCTGACCATT |
| AATGATGTAGCTCGCGTTGCCCGGAATGGCACTTTGGTGTCACTGACGAACAATACCGAC |
| ATTCTGCAAGGTATTCAAGCTAGCTGCGATTATATCAATAACGCCGTTGAATCTGGCGAG |
| CCAATCTACGGGGTAACAAGCGGTTTTGGTGGGATGGCGAACGTTGCCATTAGCCGTGAA |
| CAGGCGAGCGAACTTCAGACCAACCTCGTTTGGTTCCTAAAGACAGGAGCTGGTAATAAG |
| TTACCTCTGGCTGACGTAAGAGCCGCGATGCTGCTTCGCGCTAATAGTCACATGCGCGGC |
| GCCAGTGGTATCCGTCTTGAGCTTATCAAGAGGATGGAAATCTTCCTCAACGCGGGTGTC |
| ACACCATATGTTTATGAGTTTGGTAGTATCGGAGCCAGTGGTGATCTTGTTCCCCTGAGT |
| TATATTACGGGTTCATTGATTGGTTTAGACCCGTCCTTTAAAGTGGATTTTAACGGGAAA |
| GAAATGGACGCCCCGACCGCTTTACGACAGCTTAATCTGAGCCCACTTACTTTGCTCCCT |
| AAAGAAGGTCTTGCCATGATGAATGGCACCTCTGTGATGACTGGAATTGCCGCGAATTGT |
| GTGTATGACACGCAGATCCTAACGGCCATTGCCATGGGTGTTCACGCGTTGGACATTCAA |
| GCCCTGAATGGTACAAACCAGTCGTTTCATCCGTTTATCCATAATTCAAAACCCCATCCG |
| GGACAGCTTTGGGCTGCTGATCAGATGATCTCACTCCTGGCCAATAGTCAACTGGTTCGG |
| GACGAGCTCGACGGCAAACATGATTATCGCGATCATGAGCTCATCCAGGACCGGTATTCA |
| CTTCGTTGTCTCCCACAATACCTGGGGCCTATCGTTGATGGTATATCTCAAATTGCGAAG |
| CAAATTGAAATTGAGATCAATAGCGTAACCGACAACCCGCTTATCGATGTTGATAATCAG |
| GCCTCTTATCACGGTGGCAATTTTCTGGGCCAGTATGTTGGTATGGGGATGGATCACCTG |
| CGGTACTATATTGGGCTTCTGGCTAAACATCTTGATGTGCAGATTGCCTTATTAGCTTCA |
| CCAGAATTTTCAAATGGACTGCCGCCATCATTGCTCGGTAACAGAGAAAGGAAAGTAAAT |
| ATGGGCCTTAAGGGCCTTCAGATATGTGGTAACTCAATCATGCCCCTCCTGACCTTTTAT |
| GGGAACTCAATTGCTGATCGTTTTCCGACACATGCTGAACAGTTTAACCAAAACATTAAC |
| TCACAGGGCTATACATCCGCGACGTTAGCGCGTCGGTCCGTGGATATCTTCCAGAATTAT |
| GTTGCTATCGCTCTGATGTTCGGCGTACAGGCCGTTGATTTGCGCACTTATAAAAAAACC |
| GGTCACTACGATGCTCGGGCTTGCCTGTCGCCTGCCACCGAGCGGCTTTATAGCGCCGTA |
| CGTCATGTTGTGGGTCAGAAACCGACGTCGGACCGCCCCTATATTTGGAATGATAATGAA |
| CAAGGGCTGGATGAACACATCGCCCGGATATCTGCCGATATTGCCGCCGGAGGTGTCATC |
| GTCCAGGCGGTACAAGACATACTTCCTTGCCTGCATTAAGCTTGGCGTAATCATGGTCAT |
| AGCTGTTTCCTGTGTGAAATTGTTATCCGCTCACAATTCCACACAACATACGAGCCGGAA |
| GCATAAAGTGTAAAGCCTGGGGTGCCTAATGAGTGAGCTAACTCACATTAATTGCGTTGC |
| GCTCACTGCCCGCTTTCCAGTCGGGAAACCTGTCGTGCCAGCTGCATTAATGAATCGGCC |
| AACGCGCGGGGAGAGGCGGTTTGCGTATTGGGCGCTCTTCCGCTTCCTCGCTCACTGACT |
| CGCTGCGCTCGGTCGTTCGGCTGCGGCGAGCGGTATCAGCTCACTCAAAGGCGGTAGTAC |
| GGGTTTTGCTGCCCGCAAACGGGCTGTTCTGGTGTTGCTAGTTTGTTATCAGAATCGCAG |
| ATCCGGCTTCAGGTTTGCCGGCTGAAAGCGCTATTTCTTCCAGAATTGCCATGATTTTTT |
| CCCCACGGGAGGCGTCACTGGCTCCCGTGTTGTCGGCAGCTTTGATTCGATAAGCAGCAT |
| CGCCTGTTTCAGGCTGTCTATGTGTGACTGTTGAGCTGTAACAAGTTGTCTCAGGTGTTC |
| AATTTCATGTTCTAGTTGCTTTGTTTTACTGGTTTCACCTGTTCTATTAGGTGTTACATG |
| CTGTTCATCTGTTACATTGTCGATCTGTTCATGGTGAACAGCTTTAAATGCACCAAAAAC |

TABLE 11-continued

| Nucleotide sequences of Tet promoter-PAL1 construct, low-copy (SEQ ID NO: 28) |
| --- |

TCGTAAAAGCTCTGATGTATCTATCTTTTTTACACCGTTTTCATCTGTGCATATGGACAG

TTTTCCCTTTGATATCTAACGGTGAACAGTTGTTCTACTTTTGTTTGTTAGTCTTGATGC

TTCACTGATAGATACAAGAGCCATAAGAACCTCAGATCCTTCCGTATTTAGCCAGTATGT

TCTCTAGTGTGGTTCGTTGTTTTTGCGTGAGCCATGAGAACGAACCATTGAGATCATGCT

TACTTTGCATGTCACTCAAAAATTTTGCCTCAAAACTGGTGAGCTGAATTTTTGCAGTTA

AAGCATCGTGTAGTGTTTTTCTTAGTCCGTTACGTAGGTAGGAATCTGATGTAATGGTTG

TTGGTATTTTGTCACCATTCATTTTTATCTGGTTGTTCTCAAGTTCGGTTACGAGATCCA

TTTGTCTATCTAGTTCAACTTGGAAAATCAACGTATCAGTCGGGCGGCCTCGCTTATCAA

CCACCAATTTCATATTGCTGTAAGTGTTTAAATCTTTACTTATTGGTTTCAAAACCCATT

GGTTAAGCCTTTTAAACTCATGGTAGTTATTTTCAAGCATTAACATGAACTTAAATTCAT

CAAGGCTAATCTCTATATTTGCCTTGTGAGTTTTCTTTTGTGTTAGTTCTTTTAATAACC

ACTCATAAATCCTCATAGAGTATTTGTTTTCAAAAGACTTAACATGTTCCAGATTATATT

TTATGAATTTTTTTAACTGGAAAAGATAAGGCAATATCTCTTCACTAAAAACTAATTCTA

ATTTTTCGCTTGAGAACTTGGCATAGTTTGTCCACTGGAAAATCTCAAAGCCTTTAACCA

AAGGATTCCTGATTTCCACAGTTCTCGTCATCAGCTCTCTGGTTGCTTTAGCTAATACAC

CATAAGCATTTTCCCTACTGATGTTCATCATCTGAGCGTATTGGTTATAAGTGAACGATA

CCGTCCGTTCTTTCCTTGTAGGGTTTTCAATCGTGGGGTTGAGTAGTGCCACACAGCATA

AAATTAGCTTGGTTTCATGCTCCGTTAAGTCATAGCGACTAATCGCTAGTTCATTTGCTT

TGAAAACAACTAATTCAGACATACATCTCAATTGGTCTAGGTGATTTTAATCACTATACC

AATTGAGATGGGCTAGTCAATGATAATTACTAGTCCTTTTCCTTTGAGTTGTGGGTATCT

GTAAATTCTGCTAGACCTTTGCTGGAAAACTTGTAAATTCTGCTAGACCCTCTGTAAATT

CCGCTAGACCTTTGTGTGTTTTTTTTGTTTATATTCAAGTGGTTATAATTTATAGAATAA

AGAAAGAATAAAAAAAGATAAAAAGAATAGATCCCAGCCCTGTGTATAACTCACTACTTT

AGTCAGTTCCGCAGTATTACAAAAGGATGTCGCAAACGCTGTTTGCTCCTCTACAAAACA

GACCTTAAAACCCTAAAGGCTTAAGTAGCACCCTCGCAAGCTCGGGCAAATCGCTGAATA

TTCCTTTTGTCTCCGACCATCAGGCACCTGAGTCGCTGTCTTTTTCGTGACATTCAGTTC

GCTGCGCTCACGGCTCTGGCAGTGAATGGGGGTAAATGGCACTACAGGCGCCTTTTATGG

ATTCATGCAAGGAAACTACCCATAATACAAGAAAAGCCCGTCACGGGCTTCTCAGGGCGT

TTTATGGCGGGTCTGCTATGTGGTGCTATCTGACTTTTTGCTGTTCAGCAGTTCCTGCCC

TCTGATTTTCCAGTCTGACCACTTCGGATTATCCCGTGACAGGTCATTCAGACTGGCTAA

TGCACCCAGTAAGGCAGCGGTATCATCAACAGGCTTACCCGTCTTACTGTCTTTTCTACG

GGGTCTGACGCTCAGTGGAACGAAAACTCACGTTAAGGGATTTTGGTCATGAGATTATCA

AAAAGGATCTTCACCTAGATCCTTTTAAATTAAAAATGAAGTTTTAAATCAATCTAAAGT

ATATATGAGTAAACTTGGTCTGACAGTTACCAATGCTTAATCAGTGAGGCACCTATCTCA

GCGATCTGTCTATTTCGTTCATCCATAGTTGCCTGACTCCCCGTCGTGTAGATAACTACG

ATACGGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAGTGGT

CCTGCAACTTTATCCGCCTCCATCCAGTCTATTAATTGTTGCCGGGAAGCTAGAGTAAGT

TABLE 11-continued

Nucleotide sequences of Tet promoter-PAL1 construct,
low-copy (SEQ ID NO: 28)

AGTTCGCCAGTTAATAGTTTGCGCAACGTTGTTGCCATTGCTACAGGCATCGTGGTGTCA
CGCTCGTCGTTTGGTATGGCTTCATTCAGCTCCGGTTCCCAACGATCAAGGCGAGTTACA
TGATCCCCCATGTTGTGCAAAAAAGCGGTTAGCTCCTTCGGTCCTCCGATCGTTGTCAGA
AGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCGCG
CCACATAGCAGAACTTTAAAAGTGCTCATCATTGGAAAACGTTCTTCGGGGCGAAAACTC
TCAAGGATCTTACCGCTGTTGAGATCCAGTTCGATGTAACCCACTCGTGCACCCAACTGA
TCTTCAGCATCTTTTACTTTCACCAGCGTTTCTGGGTGAGCAAAAACAGGAAGGCAAAAT
GCCGCAAAAAAGGGAATAAGGGCGACACGGAAATGTTGAATACTCATACTCTTCCTTTTT
CAATATTATTGAAGCATTTATCAGGGTTATTGTCTCATGAGCGGATACATATTTGAATGT
ATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCC
TTTCGTCTCGCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAGGGCGCGTCA
GCGGGTGTTGGCGGGTGTCGGGGCTGGCTTAACTATGCGGCATCAGAGCAGATTGTACTG
AGAGTGCACCATATGCGGTGTGAAATACCGCACAGATGCGTAAGGAGAAAATACCGCATC
AGGCGCCATTCGCCATTCAGGCTGCGCAACTGTTGGGAAGGGCGATCGGTGCGGGCCTCT
TCGCTATTACGCCAGCTGGCGAAAGGGGGATGTGCTGCAAGGCGATTAAGTTGGGTAACG
CCAGGGTTTTCCCAGTCACGACGTTGTAAAACGACGGCCAGTGAATTCGTTAAGACCCAC
TTTCACATTTAAGTTGTTTTTCTAATCCGCATATGATCAATTCAAGGCCGAATAAGAAGG
CTGGCTCTGCACCTTGGTGATCAAATAATTCGATAGCTTGTCGTAATAATGGCGGCATAC
TATCAGTAGTAGGTGTTTCCCTTTCTTCTTTAGCGACTTGATGCTCTTGATCTTCCAATA
CGCAACCTAAAGTAAAATGCCCCACAGCGCTGAGTGCATATAATGCATTCTCTAGTGAAA
AACCTTGTTGGCATAAAAAGGCTAATTGATTTTCGAGAGTTTCATACTGTTTTTCTGTAG
GCCGTGTACCTAAATGTACTTTTGCTCCATCGCGATGACTTAGTAAAGCACATCTAAAAC
TTTTAGCGTTATTACGTAAAAAATCTTGCCAGCTTTCCCCTTCTAAAGGGCAAAAGTGAG
TATGGTGCCTATCTAACATCTCAATGGCTAAGGCGTCGAGCAAAGCCCGCTTATTTTTTA
CATGCCAATACAATGTAGGCTGCTCTACACCTAGCTTCTGGGCGAGTTTACGGGTTGTTA
AACCTTCGATTCCGACCTCATTAAGCAGCTCTAATGCGCTGTTAATCACTTTACTTTTAT
CTAATCTAGACATCATTAATTCCTAATTTTT**GTTGACACTCTATCATTGATAGAGTTATT
TT**

TABLE 12

Nucleotide sequences of Tet promoter-PAL3 construct,
low-copy (SEQ ID NO: 29)

ACCACTCCCTATCAGTGATAGAGAAAAGTGAACTCTAGAAATAATTTTGTTTAACTTTAA
GAAGGAGATATACAT<u>ATGAAAGCTAAAGATGTTCAGCCAACCATTATTATTAATAAAAAT</u>
<u>GGCCTTATCTCTTTGGAAGATATCTATGACATTGCGATAAAACAAAAAAAAGTAGAAATA</u>

TABLE 12-continued

| Nucleotide sequences of Tet promoter-PAL3 construct, low-copy (SEQ ID NO: 29) |
|---|

TCAACGGAGATCACTGAACTTTTGACGCATGGTCGTGAAAAATTAGAGGAAAAATTAAAT

TCAGGAGAGGTTATATATGGAATCAATACAGGATTTGGAGGGAATGCCAATTTAGTTGTG

CCATTTGAGAAAATCGCAGAGCATCAGCAAAATCTGTTAACTTTTCTTTCTGCTGGTACT

GGGGACTATATGTCCAAACCTTGTATTAAAGCGTCACAATTTACTATGTTACTTTCTGTT

TGCAAAGGTTGGTCTGCAACCAGACCAATTGTCGCTCAAGCAATTGTTGATCATATTAAT

CATGACATTGTTCCTCTGGTTCCTCGCTATGGCTCAGTGGGTGCAAGCGGTGATTTAATT

CCTTTATCTTATATTGCACGAGCATTATGTGGTATCGGCAAAGTTTATTATATGGGCGCA

GAAATTGACGCTGCTGAAGCAATTAAACGTGCAGGGTTGACACCATTATCGTTAAAAGCC

AAAGAAGGTCTTGCTCTGATTAACGGCACCCGGGTAATGTCAGGAATCAGTGCAATCACC

GTCATTAAACTGGAAAAACTATTTAAAGCCTCAATTTCTGCGATTGCCCTTGCTGTTGAA

GCATTACTTGCATCTCATGAACATTATGATGCCCGGATTCAACAAGTAAAAAATCATCCT

GGTCAAAACGCGGTGGCAAGTGCATTGCGTAATTTATTGGCAGGTTCAACGCAGGTTAAT

CTATTATCTGGGGTTAAAGAACAAGCCAATAAAGCTTGTCGTCATCAAGAAATTACCCAA

CTAAATGATACCTTACAGGAAGTTTATTCAATTCGCTGTGCACCACAAGTATTAGGTATA

GTGCCAGAATCTTTAGCTACCGCTCGGAAAATATTGGAACGGGAAGTTATCTCAGCTAAT

GATAATCCATTGATAGATCCAGAAAATGGCGATGTTCTACACGGTGGAAATTTTATGGGG

CAATATGTCGCCCGAACAATGGATGCATTAAAACTGGATATTGCTTTAATTGCCAATCAT

CTTCACGCCATTGTGGCTCTTATGATGGATAACCGTTTCTCTCGTGGATTACCTAATTCA

CTGAGTCCGACACCCGGCATGTATCAAGGTTTTAAAGGCGTCCAACTTTCTCAAACCGCT

TTAGTTGCTGCAATTCGCCATGATTGTGCTGCATCAGGTATTCATACCCTCGCCACAGAA

CAATACAATCAAGATATTGTCAGTTTAGGTCTGCATGCCGCTCAAGATGTTTTAGAGATG

GAGCAGAAATTACGCAATATTGTTTCAATGACAATTCTGGTAGTTTGTCAGGCCATTCAT

CTTCGCGGCAATATTAGTGAAATTGCGCCTGAAACTGCTAAATTTTACCATGCAGTACGC

GAAATCAGTTCTCCTTTGATCACTGATCGTGCGTTGGATGAAGATATAATCCGCATTGCG

GATGCAATTATTAATGATCAACTTCCTCTGCCAGAAATCATGCTGGAAGAATAAGCTTGG

CGTAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAACTCA

CATTAATTGCGTTGCGCTCACTGCCCGCTTTCCAGTCGGGAAACCTGTCGTGCCAGCTGC

ATTAATGAATCGGCCAACGCGCGGGGAGAGGCGGTTTGCGTATTGGGCGCTCTTCCGCTT

CCTCGCTCACTGACTCGCTGCGCTCGGTCGTTCGGCTGCGGCGAGCGGTATCAGCTCACT

CAAAGGCGGTAGTACGGGTTTTGCTGCCCGCAAACGGGCTGTTCTGGTGTTGCTAGTTTG

TTATCAGAATCGCAGATCCGGCTTCAGGTTTGCCGGCTGAAAGCGCTATTTCTTCCAGAA

TTGCCATGATTTTTTCCCCACGGGAGGCGTCACTGGCTCCCGTGTTGTCGGCAGCTTTGA

TTCGATAAGCAGCATCGCCTGTTTCAGGCTGTCTATGTGTGACTGTTGAGCTGTAACAAG

TTGTCTCAGGTGTTCAATTTCATGTTCTAGTTGCTTTGTTTTACTGGTTTCACCTGTTCT

ATTAGGTGTTACATGCTGTTCATCTGTTACATTGTCGATCTGTTCATGGTGAACAGCTTT

AAATGCACCAAAAACTCGTAAAAGCTCTGATGTATCTATCTTTTTTACACCGTTTTCATC

TGTGCATATGGACAGTTTTCCCTTTGATATCTAACGGTGAACAGTTGTTCTACTTTTGTT

TABLE 12-continued

| Nucleotide sequences of Tet promoter-PAL3 construct, low-copy (SEQ ID NO: 29) |
|---|
| TGTTAGTCTTGATGCTTCACTGATAGATACAAGAGCCATAAGAACCTCAGATCCTTCCGT |
| ATTTAGCCAGTATGTTCTCTAGTGTGGTTCGTTGTTTTTGCGTGAGCCATGAGAACGAAC |
| CATTGAGATCATGCTTACTTTGCATGTCACTCAAAAATTTTGCCTCAAAACTGGTGAGCT |
| GAATTTTTGCAGTTAAAGCATCGTGTAGTGTTTTTCTTAGTCCGTTACGTAGGTAGGAAT |
| CTGATGTAATGGTTGTTGGTATTTTGTCACCATTCATTTTTATCTGGTTGTTCTCAAGTT |
| CGGTTACGAGATCCATTTGTCTATCTAGTTCAACTTGGAAAATCAACGTATCAGTCGGGC |
| GGCCTCGCTTATCAACCACCAATTTCATATTGCTGTAAGTGTTTAAATCTTTACTTATTG |
| GTTTCAAAACCCATTGGTTAAGCCTTTTAAACTCATGGTAGTTATTTTCAAGCATTAACA |
| TGAACTTAAATTCATCAAGGCTAATCTCTATATTTGCCTTGTGAGTTTTCTTTTGTGTTA |
| GTTCTTTTAATAACCACTCATAAATCCTCATAGAGTATTTGTTTTCAAAAGACTTAACAT |
| GTTCCAGATTATATTTTATGAATTTTTTTAACTGGAAAAGATAAGGCAATATCTCTTCAC |
| TAAAAACTAATTCTAATTTTTCGCTTGAGAACTTGGCATAGTTTGTCCACTGGAAAATCT |
| CAAAGCCTTTAACCAAAGGATTCCTGATTTCCACAGTTCTCGTCATCAGCTCTCTGGTTG |
| CTTTAGCTAATACACCATAAGCATTTTCCCTACTGATGTTCATCATCTGAGCGTATTGGT |
| TATAAGTGAACGATACCGTCCGTTCTTTCCTTGTAGGGTTTTCAATCGTGGGGTTGAGTA |
| GTGCCACACAGCATAAAATTAGCTTGGTTTCATGCTCCGTTAAGTCATAGCGACTAATCG |
| CTAGTTCATTTGCTTTGAAAACAACTAATTCAGACATACATCTCAATTGGTCTAGGTGAT |
| TTTAATCACTATACCAATTGAGATGGGCTAGTCAATGATAATTACTAGTCCTTTTCCTTT |
| GAGTTGTGGGTATCTGTAAATTCTGCTAGACCTTTGCTGGAAAACTTGTAAATTCTGCTA |
| GACCCTCTGTAAATTCCGCTAGACCTTTGTGTGTTTTTTTTGTTTATATTCAAGTGGTTA |
| TAATTTATAGAATAAAGAAAGAATAAAAAAAGATAAAAAGAATAGATCCCAGCCCTGTGT |
| ATAACTCACTACTTTAGTCAGTTCCGCAGTATTACAAAAGGATGTCGCAAACGCTGTTTG |
| CTCCTCTACAAAACAGACCTTAAAACCCTAAAGGCTTAAGTAGCACCCTCGCAAGCTCGG |
| GCAAATCGCTGAATATTCCTTTTGTCTCCGACCATCAGGCACCTGAGTCGCTGTCTTTTT |
| CGTGACATTCAGTTCGCTGCGCTCACGGCTCTGGCAGTGAATGGGGGTAAATGGCACTAC |
| AGGCGCCTTTTATGGATTCATGCAAGGAAACTACCCATAATACAAGAAAAGCCCGTCACG |
| GGCTTCTCAGGGCGTTTTATGGCGGGTCTGCTATGTGGTGCTATCTGACTTTTTGCTGTT |
| CAGCAGTTCCTGCCCTCTGATTTTCCAGTCTGACCACTTCGGATTATCCCGTGACAGGTC |
| ATTCAGACTGGCTAATGCACCCAGTAAGGCAGCGGTATCATCAACAGGCTTACCCGTCTT |
| ACTGTCTTTTCTACGGGGTCTGACGCTCAGTGGAACGAAAACTCACGTTAAGGGATTTTG |
| GTCATGAGATTATCAAAAAGGATCTTCACCTAGATCCTTTTAAATTAAAAATGAAGTTTT |
| AAATCAATCTAAAGTATATATGAGTAAACTTGGTCTGACAGTTACCAATGCTTAATCAGT |
| GAGGCACCTATCTCAGCGATCTGTCTATTTCGTTCATCCATAGTTGCCTGACTCCCCGTC |
| GTGTAGATAACTACGATACGGGAGGGCTTACCATCTGGCCCCAGTGCTGCAATGATACCG |
| CGAGACCCACGCTCACCGGCTCCAGATTTATCAGCAATAAACCAGCCAGCCGGAAGGGCC |
| GAGCGCAGAAGTGGTCCTGCAACTTTATCCGCCTCCATCCAGTCTATTAATTGTTGCCGG |
| GAAGCTAGAGTAAGTAGTTCGCCAGTTAATAGTTTGCGCAACGTTGTTGCCATTGCTACA |
| GGCATCGTGGTGTCACGCTCGTCGTTTGGTATGGCTTCATTCAGCTCCGGTTCCCAACGA |
| TCAAGGCGAGTTACATGATCCCCCATGTTGTGCAAAAAAGCGGTTAGCTCCTTCGGTCCT |

TABLE 12-continued

| Nucleotide sequences of Tet promoter-PAL3 construct, low-copy (SEQ ID NO: 29) |
|---|
| CCGATCGTTGTCAGAAGTAAGTTGGCCGCAGTGTTATCACTCATGGTTATGGCAGCACTG |
| CATAATTCTCTTACTGTCATGCCATCCGTAAGATGCTTTTCTGTGACTGGTGAGTACTCA |
| ACCAAGTCATTCTGAGAATAGTGTATGCGGCGACCGAGTTGCTCTTGCCCGGCGTCAATA |
| CGGGATAATACCGCGCCACATAGCAGAACTTTAAAAGTGCTCATCATTGGAAAACGTTCT |
| TCGGGGCGAAAACTCTCAAGGATCTTACCGCTGTTGAGATCCAGTTCGATGTAACCCACT |
| CGTGCACCCAACTGATCTTCAGCATCTTTTACTTTCACCAGCGTTTCTGGGTGAGCAAAA |
| ACAGGAAGGCAAAATGCCGCAAAAAAGGGAATAAGGGCGACACGGAAATGTTGAATACTC |
| ATACTCTTCCTTTTTCAATATTATTGAAGCATTTATCAGGGTTATTGTCTCATGAGCGGA |
| TACATATTTGAATGTATTTAGAAAAATAAACAAATAGGGGTTCCGCGCACATTTCCCCGA |
| AAAGTGCCACCTGACGTCTAAGAAACCATTATTATCATGACATTAACCTATAAAAATAGG |
| CGTATCACGAGGCCCTTTCGTCTCGCGCGTTTCGGTGATGACGGTGAAAACCTCTGACAC |
| ATGCAGCTCCCGGAGACGGTCACAGCTTGTCTGTAAGCGGATGCCGGGAGCAGACAAGCC |
| CGTCAGGGCGCGTCAGCGGGTGTTGGCGGGTGTCGGGGCTGGCTTAACTATGCGGCATCA |
| GAGCAGATTGTACTGAGAGTGCACCATATGCGGTGTGAAATACCGCACAGATGCGTAAGG |
| AGAAAATACCGCATCAGGCGCCATTCGCCATTCAGGCTGCGCAACTGTTGGGAAGGGCGA |
| TCGGTGCGGGCCTCTTCGCTATTACGCCAGCTGGCGAAAGGGGGATGTGCTGCAAGGCGA |
| TTAAGTTGGGTAACGCCAGGGTTTTCCCAGTCACGACGTTGTAAAACGACGGCCAGTGAA |
| TTCGTTAAGACCCACTTTCACATTTAAGTTGTTTTTCTAATCCGCATATGATCAATTCAA |
| GGCCGAATAAGAAGGCTGGCTCTGCACCTTGGTGATCAAATAATTCGATAGCTTGTCGTA |
| ATAATGGCGGCATACTATCAGTAGTAGGTGTTTCCCTTTCTTCTTTAGCGACTTGATGCT |
| CTTGATCTTCCAATACGCAACCTAAAGTAAAATGCCCCACAGCGCTGAGTGCATATAATG |
| CATTCTCTAGTGAAAAACCTTGTTGGCATAAAAAGGCTAATTGATTTTCGAGAGTTTCAT |
| ACTGTTTTTCTGTAGGCCGTGTACCTAAATGTACTTTTGCTCCATCGCGATGACTTAGTA |
| AAGCACATCTAAAACTTTTAGCGTTATTACGTAAAAAATCTTGCCAGCTTTCCCCTTCTA |
| AAGGGCAAAAGTGAGTATGGTGCCTATCTAACATCTCAATGGCTAAGGCGTCGAGCAAAG |
| CCCGCTTATTTTTTACATGCCAATACAATGTAGGCTGCTCTACACCTAGCTTCTGGGCGA |
| GTTTACGGGTTGTTAAACCTTCGATTCCGACCTCATTAAGCAGCTCTAATGCGCTGTTAA |
| TCACTTTACTTTTATCTAATCTAGACATCATTAATTCCTAATTTTT**GTTGACACTCTATC** |
| **ATTGATAGAGTTATTTT** |

TABLE 13

| Nucleotide sequences of TetR-PheP construct, low-copy (SEQ ID NO: 30) |
|---|
| ccagtgaattcgttaagacccactttcacatttaagttgtttttctaatccgcatatgat |
| caattcaaggccgaataagaaggctggctctgcaccttggtgatcaaataattcgatagc |
| ttgtcgtaataatggcggcatactatcagtagtaggtgtttccctttcttctttagcgac |
| ttgatgctcttgatcttccaatacgcaacctaaagtaaaatgccccacagcgctgagtgc |

TABLE 13-continued

| Nucleotide sequences of TetR-PheP construct, low-copy (SEQ ID NO: 30) |
|---|
| atataatgcattctctagtgaaaaaccttgttggcataaaaaggctaattgattttcgag |
| agtttcatactgtttttctgtaggccgtgtacctaaatgtacttttgctccatcgcgatg |
| acttagtaaagcacatctaaaacttttagcgttattacgtaaaaaatcttgccagctttc |
| cccttctaaagggcaaaagtgagtatggtgcctatctaacatctcaatggctaaggcgtc |
| gagcaaagcccgcttattttttacatgccaatacaatgtaggctgctctacacctagctt |
| ctgggcgagtttacgggttgttaaaccttcgattccgacctcattaagcagctctaatgc |
| gctgttaatcactttacttttatctaatctagacatcattaattcctaatttttgttgac |
| actctatcattgatagagttattttaccactccctatcagtgatagagaaaagtgaactc |
| tagaaataattttgtttaactttaagaaggagatatacatATGAAAAACGCGTCAACCGT |
| ATCGGAAGATACTGCGTCGAATCAAGAGCCGACGCTTCATCGCGGATTACATAACCGTCA |
| TATTCAACTGATTGCGTTGGGTGGCGCAATTGGTACTGGTCTGTTTCTTGGCATTGGCCC |
| GGCGATTCAGATGGCGGGTCCGGCTGTATTGCTGGGCTACGGCGTCGCCGGGATCATCGC |
| TTTCCTGATTATGCGCCAGCTTGGCGAAATGGTGGTTGAGGAGCCGGTATCCGGTTCATT |
| TGCCCACTTTGCCTATAAATACTGGGGACCGTTTGCGGGCTTCCTCTCTGGCTGGAACTA |
| CTGGGTAATGTTCGTGCTGGTGGGAATGGCAGAGCTGACCGCTGCGGGCATCTATATGCA |
| GTACTGGTTCCCGGATGTTCCAACGTGGATTTGGGCTGCCGCCTTCTTTATTATCATCAA |
| CGCCGTTAACCTGGTGAACGTGCGCTTATATGGCGAAACCGAGTTCTGGTTTGCGTTGAT |
| TAAAGTGCTGGCAATCATCGGTATGATCGGCTTTGGCCTGTGGCTGCTGTTTTCTGGTCA |
| CGGCGGCGAGAAAGCCAGTATCGACAACCTCTGGCGCTACGGTGGTTTCTTCGCCACCGG |
| CTGGAATGGGCTGATTTTGTCGCTGGCGGTAATTATGTTCTCCTTCGGCGGTCTGGAGCT |
| GATTGGGATTACTGCCGCTGAAGCGCGCGATCCGGAAAAAAGCATTCCAAAAGCGGTAAA |
| TCAGGTGGTGTATCGCATCCTGCTGTTTTACATCGGTTCACTGGTGGTTTTACTGGCGCT |
| CTATCCGTGGGTGGAAGTGAAATCCAACAGTAGCCCGTTTGTGATGATTTTCCATAATCT |
| CGACAGCAACGTGGTAGCTTCTGCGCTGAACTTCGTCATTCTGGTAGCATCGCTGTCAGT |
| GTATAACAGCGGGGTTTACTCTAACAGCCGCATGCTGTTTGGCCTTTCTGTGCAGGGTAA |
| TGCGCCGAAGTTTTTGACTCGCGTCAGCCGTCGCGGTGTGCCGATTAACTCGCTGATGCT |
| TTCCGGAGCGATCACTTCGCTGGTGGTGTTAATCAACTATCTGCTGCCGCAAAAAGCGTT |
| TGGTCTGCTGATGGCGCTGGTGGTAGCAACGCTGCTGTTGAACTGGATTATGATCTGTCT |
| GGCGCATCTGCGTTTTCGTGCAGCGATGCGACGTCAGGGGCGTGAAACACAGTTTAAGGC |
| GCTGCTCTATCCGTTCGGCAACTATCTCTGCATTGCCTTCCTCGGCATGATTTTGCTGCT |
| GATGTGCACGATGGATGATATGCGCTTGTCAGCGATCCTGCTGCCGGTGTGGATTGTATT |
| CCTGTTTATGGCATTTAAAACGCTGCGTCGGAAATAA |

In some embodiments, the genetically engineered bacteria contain gene sequence(s) comprising one or more sequence(s) of any of SEQ ID Nos: 21-30. In some embodiments, the genetically engineered bacteria contain gene sequence(s) comprising one or more sequence(s) having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 21-30.

Phenylalanine Transport

Each of PAL1 and PAL3 was expressed on a high-copy plasmid and a low-copy plasmid in genetically engineered *E. coli* Nissle. Surprisingly, each construct metabolized and reduced phenylalanine to similar levels (FIG. 15), and the rate-limiting step of phenylalanine metabolism was phenylalanine availability (FIG. 16). Thus, in some embodiments, it is advantageous to increase phenylalanine transport into the cell, thereby enhancing phenylalanine metabolism. Unexpectedly, even low-copy PAL plasmids are capable of almost completely eliminating Phe from a test sample when expressed in conjunction with pheP (FIG. 16A). Furthermore, there may be additional advantages to using a low-copy PAL-expressing plasmid in conjunction with pheP in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

The genetically engineered bacteria further comprise a gene encoding a phenylalanine transporter. Phenylalanine transporters may be expressed or modified in the genetically engineered bacteria of the invention in order to enhance phenylalanine transport into the cell.

PheP is a membrane transport protein that is capable of transporting phenylalanine into bacterial cells (see, e.g., Pi et al., 1991). In some embodiments, the native pheP gene in the genetically modified bacteria of the invention is not modified. In some embodiments, the genetically engineered bacteria of the invention comprise multiple copies of the native pheP gene. In some embodiments, the genetically engineered bacteria of the invention comprise multiple copies of a non-native pheP gene. In some embodiments, the genetically engineered bacteria of the invention comprise a pheP gene that is controlled by its native promoter, an inducible promoter, a promoter that is stronger than the native promoter, e.g., the GlnRS promoter or the P(Bla) promoter, or a constitutive promoter. In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP gene is isolated and inserted into the genetically engineered bacteria (see, e.g., Pi et al., 1996; Pi et al., 1998). The phenylalanine transporter modifications described herein may be present on a plasmid or chromosome.

In some embodiments, the genetically engineered bacterium is *E. coli* Nissle, and the native pheP gene in *E. coli* Nissle is not modified; one or more additional copies the native *E. coli* Nissle pheP genes are inserted into the *E. coli* Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium is inserted into the *E. coli* Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is *E. coli* Nissle, and the native pheP gene in *E. coli* Nissle is not modified; one or more additional copies the native *E. coli* Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain (ΔaroP ΔpheP Δmtr Δtna ΔtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies of the native *E. coli* Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in *E. coli* Nissle: malE/K, insB/I, araC/BAD, lacZ, agaI/rsmI, thyA, and malP/T. Any suitable insertion site may be used (see, e.g., FIG. 36). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

Multiple Mechanisms of Action

Figure 13A:
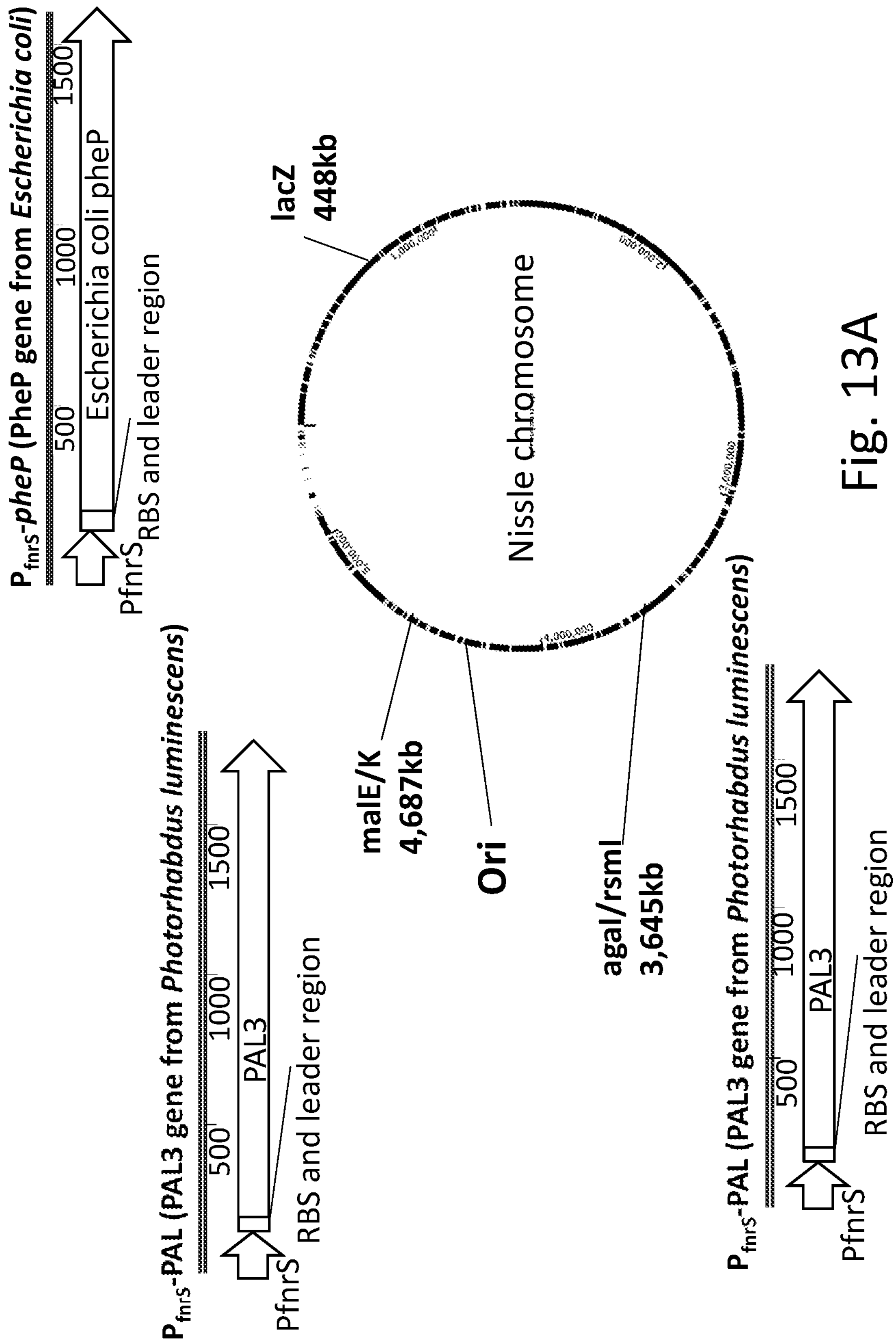
FIGS. 13A, 13B, and 13C depict schematic diagrams of non-limiting embodiments of the disclosure.
Figure 13B:
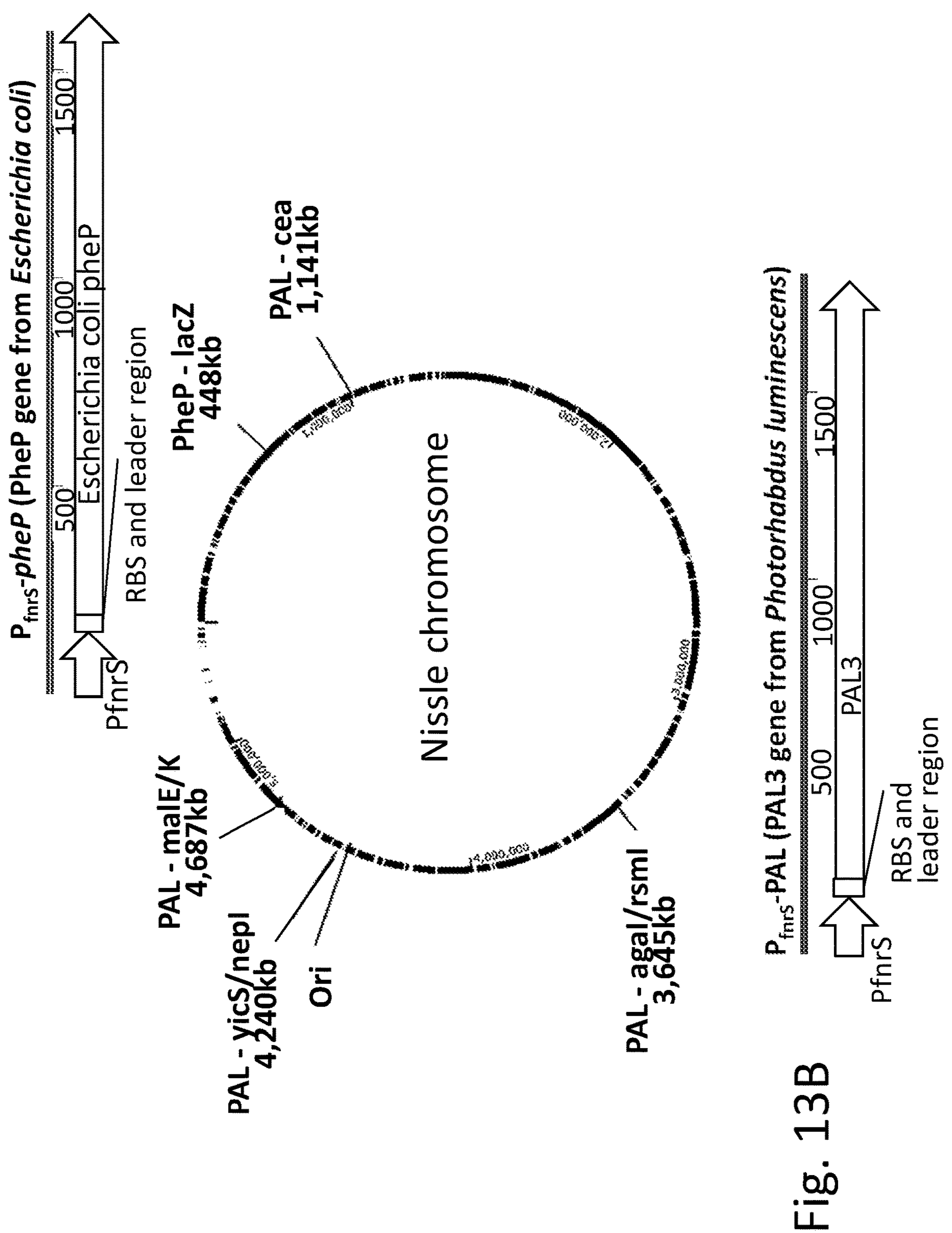
Figure 13C:
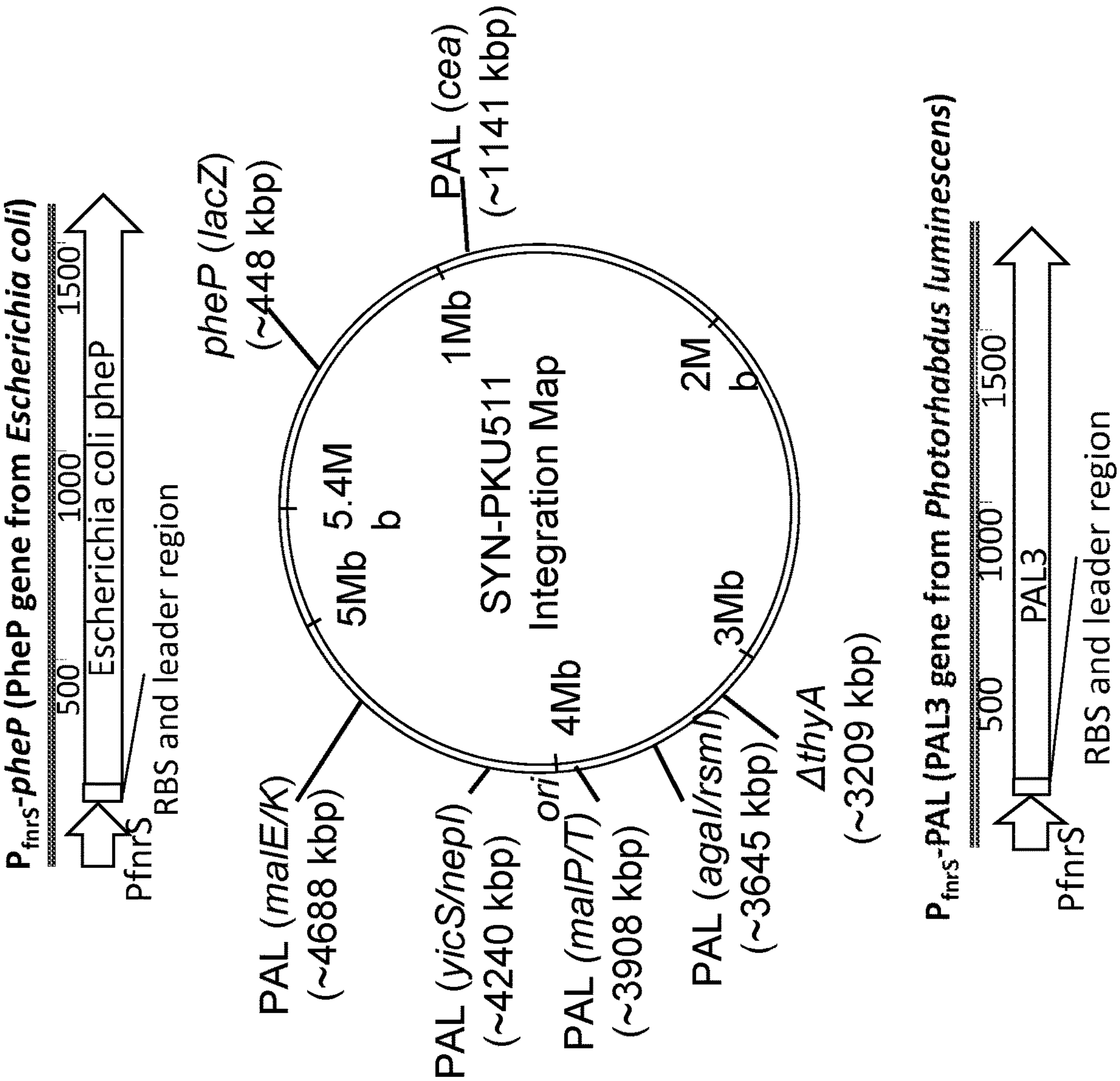
Figure 14:
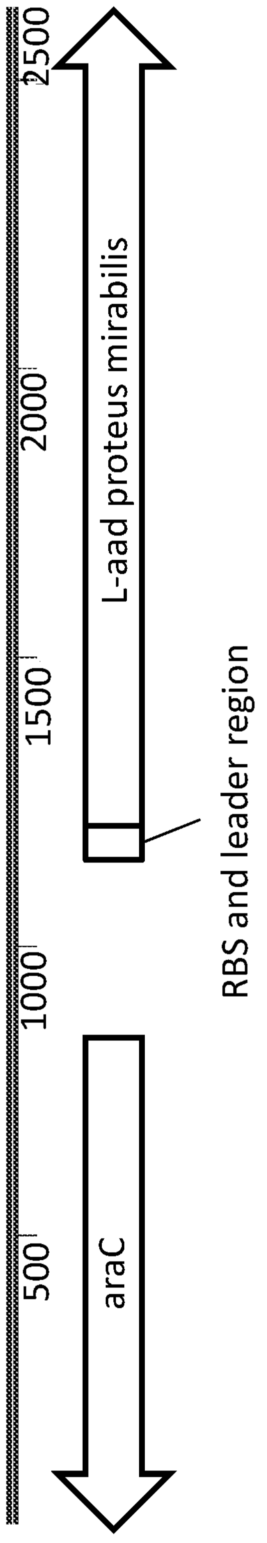
FIG. 14 depicts the gene organization of a non-limiting exemplary construct comprising a gene encoding araC and a gene encoding LAAD from *Proteus mirabilis* and an arabinose inducible promoter (ParaBAD) sequence for chromosomal insertion into the endogenous arabinose operon for chromosomal integration, e.g., as comprised in SYN-PKU705.

In some embodiments, the bacteria are genetically engineered to include multiple mechanisms of action (MoAs), e.g., circuits producing multiple copies of the same product (e.g., to enhance copy number) or circuits performing multiple different functions. Examples of insertion sites include, but are not limited to, malE/K, yicS nepI, insB/I, araC/BAD, lacZ, agaI/rsmI, thyA, malP/T, dapA, and cea, and others shown in FIG. 36. For example, the genetically engineered bacteria may include four copies of PAL inserted at four different insertion sites, e.g., malE/K, insB/I, araC/BAD, and lacZ The genetically engineered bacteria may also include four copies of PAL inserted at four different insertion sites, e.g., malE/K, yicS nepI, agaI/rsmI, and cea, and one copy of a phenylalanine transporter gene inserted at a different insertion site, e.g., lacZ (FIG. 13B). Alternatively, the genetically engineered bacteria may include three copies of PAL inserted at three different insertion sites, e.g., malE/K, insB/I, and lacZ, and three copies of a phenylalanine transporter gene inserted at three different insertion sites, e.g., dapA, cea, and araC/BAD.

In some embodiments, the genetically engineered bacteria comprise one or more of (1) PAL, PAH, LAAD for degradation of phenylalanine, in wild type or in a mutated form (for increased stability or metabolic activity) (2) transporter PheP or AroP for uptake of phenylalanine, in wild type or in mutated form (for increased stability or metabolic activity) (3) PAL, PAH, LAAD, and/or PheP for secretion and extracellular phenylalanine degradation, (4) components of secretion machinery, as described herein (5) Auxotrophy, e.g., deltaThyA (6) antibiotic resistance, including but not limited to, kanamycin or chloramphenicol resistance (7) mutations/deletions in genes involved in oxygen metabolism, as described herein and (8) mutations/deletions in genes of the endogenous Nissle phenylalanine synthesis pathway (e.g., delta PheA for Phe auxotrophy).

In one embodiment, the genetically engineered bacteria comprise one or more copies of PAL3, (e.g., under the control of a Pfnr promoter) and one or more copies of PAL1 (e.g. under the control of a Pfnr promoter). In one embodiment, the genetically engineered bacteria comprise one or more copies of PAL3, (e.g., under the control of a Pfnr promoter) and one or more copies of PAL1 (e.g. under the control of a Pfnr promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of LAAD (e.g., under the control of the ParaBAD promoter). In one embodiment, the genetically engineered bacteria comprise one or more copies of PAL3, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of PAH. In one embodiment, the genetically engineered bacteria comprise one or more copies of PAL3, (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAL1, (e.g., under the control of a Pfnr promoter) and one or more copies of LAAD (e.g., under the control of the ParaBAD promoter). In one embodiment, the genetically engineered bacteria comprise one or more copies of PAL1, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL1 (e.g., under the control of a Pfnr promoter) and one or more copies of PAH. In one embodiment, the genetically engineered bacteria comprise one or more copies of PAL1 (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAH and one or more copies of LAAD (e.g., under the control of the ParaBAD promoter). In one embodiment, the genetically engineered bacteria comprise one or more copies of PAH and one or more copies of LAAD (e.g., under the control of the ParaBAD promoter); and further comprises one or more copies of a phenylalanine transporter (e.g., PheP and/or AroP, e.g., under the control of a Pfnr promoter). PMEs and transporters may be integrated into any of the insertion sites described herein.

In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter); and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH. In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter); and further comprise one or more copies of a phenylalanine transporter (e.g., PheP and/or AroP, e.g., under the control of a Pfnr promoter). PMEs and/or transporters may be integrated into any of the insertion sites described herein. Alternatively, PMEs and/or transporters may be comprised on low or high copy plasmids. PMEs and/or transporters may be integrated into any of the insertion sites described herein in combination with PMEs and/or transporters that are comprised on low or high copy plasmids.

In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). PMEs and transporters may be integrated into any of the insertion sites described herein. Alternatively, PMEs and/or transporters may be comprised on low or high copy plasmids.

In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). PMEs and transporters may be integrated into any of the insertion sites described herein. Alternatively, located PMEs and/or transporters may be comprised on low or high copy plasmids.

In one embodiment, the genetically engineered bacteria comprise two copies of PAL (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and one copy of LAAD (e.g., under the control of the ParaBAD promoter).

In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise one or more PMEs for metabolizing phenylalanine in combination with one or more PMEs for secretion. In one embodiment, the genetically engineered bacteria comprise one or more PMEs for metabolizing phenylalanine and a phenylalanine transporter in combination with one or more PMEs for secretion. In one embodiment, the genetically engineered bacteria comprise one or more PMEs for metabolizing phenylalanine and a phenylalanine transporter in combination with one or more PMEs for secretion, and also include an auxotrophy and/or an antibiotic resistance. Secretion systems described herein are utilized to secrete the PMEs in the genetically engineered bacteria with multiple mechanisms of action.

In one embodiment, the genetically engineered bacteria comprise two additional copies of PheP (in addition to the wild type gene). This provides redundancy, in case one of the PheP genes acquires a mutation. In one embodiment, the PheP genes are inserted at lacZ and agal/rsml. In one embodiment, the two copies of PheP are under the control of the PfnrS promoter. In one embodiment, the genetically engineered bacteria comprise three copies of PAL3. In one embodiment, the genetically engineered bacteria comprise three copies of PAL3, inserted at malEK, malPT, yicS/nepI. In one embodiment, the expression of the three copies of PAL3 is under the control of the PfnrS promoter. In one embodiment, the genetically engineered bacteria comprise one or more copies of LAAD. In one embodiment, the genetically engineered bacteria comprise one copy of LAAD, inserted in the arabinose operon. In one embodiment, LAAD is under the control of the endogenous ParaBAD promoter. In one embodiment, the genetically engineered bacteria comprise an auxotrophy, e.g., deltaThyA. In one embodiment, the genetically engineered bacteria comprise an antibiotic resistance. In one embodiment the genetically engineered bacteria comprise an antibiotic resistance and an auxotrophy, e.g., deltaThyA. In one embodiment, the genetically engineered bacteria do not comprise an auxotrophy, e.g., deltaThyA. In one embodiment, the genetically engineered bacteria do not comprise an antibiotic resistance. In one embodiment the genetically engineered bacteria comprise neither an antibiotic resistance nor an auxotrophy, e.g., deltaThyA.

In one embodiment, the genetically engineered bacteria comprise three copies of PAL, e.g., PAL3, 2 copies of PheP (in addition to the endogenous PheP), and one copy of LAAD. In one embodiment, the genetically engineered bacteria comprise three copies of PAL, e.g., PAL3, 2 copies of PheP (in addition to the endogenous PheP), and one copy of LAAD, and an auxotrophy, e.g., delta ThyA. In one embodiment, the genetically engineered bacteria comprise three copies of PAL, 2 copies of PheP (in addition to the endogenous PheP), and one copy of LAAD, and an antibiotic resistance gene. In one embodiment, the genetically engineered bacteria comprise three copies of PAL, 2 copies of PheP (in addition to the endogenous PheP), and one copy of LAAD, and an antibiotic resistance gene and an auxotrophy, e.g., delta ThyA.

In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter). In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an auxotrophy, e.g., delta ThyA. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance and an auxotrophy, e.g., deltaThyA.

In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agal/rsml sites), and one copy of LAAD (under the control of the endogenous ParaBAD promoter, and inserted in the endogenous arabinose operon). In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agal/rsml sites), and one copy of LAAD (under the control of the endogenous ParaBAD promoter, and inserted in the endogenous arabinose operon), and further comprise an antibiotic resistance. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agal/rsml sites), and one copy of LAAD (under the control of the endogenous ParaBAD promoter, and inserted in the endogenous arabinose operon) and further comprise an auxotrophy, e.g., deltaThyA. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agal/rsml sites), and one copy of LAAD (under the control of the endogenous ParaBAD promoter, and inserted in the endogenous arabinose operon), and further comprise an antibiotic resistance and an auxotrophy, e.g., deltaThyA.

In one embodiment, the genetically engineered bacteria are SYN-PKU705. In one embodiment, SYN-PKU705 further comprises an antibiotic resistance. In one embodiment, SYN-PKU705 further comprises an auxotrophy, e.g., deltaThyA. In one embodiment, SYN-PKU705 further comprises an antibiotic resistance and auxotrophy, e.g., deltaThyA.

Table 14 contains non-limiting examples of the genetically engineered bacteria of the disclosure. In certain embodiments, the genetically engineered bacteria of Table 14 further contain a PME for secretion.

TABLE 14

Non-limiting Examples of Embodiments of the Disclosure

| Strain Name | Genotype |
|---|---|
| | Plasmid -based strains |
| SYN-PKU101 | Low copy pSC101-Ptet::PAL1, ampicillin resistant |
| SYN-PKU102 | High copy pColE1-Ptet::PAL1, ampicillin resistant, |
| SYN-PKU201 | Low copy pSC101-Ptet::PAL3, ampicillin resistant |
| SYN-PKU202 | High copy pColE1-Ptet::PAL3, ampicillin resistant, |
| SYN-PKU203 | lacZ::Ptet-pheP::cam |
| SYN-PKU401 | Low copy pSC101-Ptet::PAL1, ampicillin resistant, chromosomal lacZ::Ptet-pheP::cam |
| SYN-PKU402 | High copy pColE1-Ptet::PAL1, ampicillin resistant, chromosomal lacZ::Ptet-pheP::cam |
| SYN-PKU302 | Low Copy pSC101-Ptet::PAL3, ampicillin resistant; chromosomal lacZ::Ptet-pheP::cam |
| SYN-PKU303 | High copy pColE1-Ptet::PAL3, ampicillin resistant, chromosomal lacZ: :Ptet-pheP::cam |
| SYN-PKU304 | Low Copy pSC101-PfnrS::PAL3, ampicillin resistant; chromosomal lacZ..PfnrS-pheP::cam |
| SYN-PKU305 | Low Copy pSC101-PfnrS::PAL3, kanamycin resistant; chromosomal lacZ::PfnrS-pheP::cam |
| SYN-PKU306 | Low Copy pSC101-PfnrS::PAL3, kanamycin resistant; thyA |
| SYN-PKU307 | Low Copy pSC101-PfnrS::PAL3, ampicillin resistant; |
| SYN-PKU308 | Low Copy pSC101-PfnrS::PAL3, kanamycin resistant; |
| SYN-PKU401 | High Copy pUC57-Ptet::LAAD; kanamycin resistant |
| | Integrated strains |
| SYN-PKU501 | malPT:: PfnrS::PAL3::kan |
| SYN-PKU502 | malPT:: PfnrS::PAL3::kan; bicistronic lacZ:: PfnrS::PAL3-pheP::cam |
| SYN-PKU503 | malEK::PfnrS::PAL3::cam |
| SYN-PKU504 | agaI/rsmI::PfnrS::PAL3 |
| SYN-PKU505 | cea::PfnrS::PAL3 |
| SYN-PKU506 | malEK::PfnrS::PAL3; agaI/rsmI::PfnrS::PAL3; cea::PfnrS::PAL3 |
| SYN-PKU507 | malEK::PfnrS::PAL3; agaI/rsmI::PfnrS::PAL3; cea::PfnrS::PAL3; lacZ::Pfnr-pheP::cam |
| SYN-PKU508 | malEK::PfnrS::PAL3: pheA auxotroph |
| SYN-PKU509 | malEK::PfnrS::PAL3; agaI/rsmI::PfnrS::PAL3; cea::PfnrS::PAL3; lacZ::Pfnr-pheP::cam |
| SYN-PKU601 | malPT::PfnrS-INT5::kan, rrnBUP -[PAL3]; lacZ::Pfnr-pheP::cam (recombinase based strain) |

TABLE 14-continued

Non-limiting Examples of Embodiments of the Disclosure

| Strain Name | Genotype |
|---|---|
| SYN-PKU510 | malEK::PfnrS::PAL3; agaI/rsmI::PfnrS::PAL3; cea::PfnrS::PAL3; |
| SYN-PKU511 | malEK:: PfnrS::PAL3; agaI/rsmI::PfnrS::PAL3; cea::PfnrS::PAL3; yicS/nepI::PfnrS-PAL3::kan; malPT::PfnrS::PAL3; lacZ::Pfnr-pheP; ΔthyA |
| SYN-PKU204 | lacZ::Pfnr-pheP::cam |
| SYN-PKU512 | malEK::PfnrS::PAL3; agaI/rsmI::PfnrS::PAL3; cea::PfnrS::PAL3; malPT::PfnrS::PAL3; lacZ::Pfnr-pheP::cam; ΔthyA |
| SYN-PKU513 | malEK: PfnrS::PAL3; agaI/rsmI::PfhrS::PAL3; cea::PfnrS::PAL3; lacZ::Pfnr-pheP; ΔthyA |
| SYN-PKU514 | malEK: PfnrS::PAL3; agaI/rsmI::PfhrS::PAL3; cea::PfnrS::PAL3; malPT::PfnrS::PAL3; ΔthyA |
| SYN-PKU515 | malEK: PfnrS::PAL3; agaI/rsmI::PfhrS::PAL3; cea::PfnrS::PAL3; ΔthyA |
| SYN-PKU516 | agaI/rsmI::PfnrS::PAL3::kan |
| SYN-PKU517 | malEK:: PfnrS::PAL3::cam; malPT::PfnrS::PAL3::kan; lacZ::PfnrS-pheP; ΔthyA |
| SYN-PKU518 | malEK-PfnrS::PAL3::cam; PfnrS::pheP::kan |
| SYN-PKU519 | ParaBC-PAL3::cam; PfnrS-pheP::kan |
| SYN-PKU520 | agaI/rsmI::PfnrS::PAL3::kan; PfnrS-PheP::cam |
| SYN-PKU801 | ΔargR; thyA::cam |
| SYN-PKU701 | ParaBC-LAAD::cam; malEK-PfnrS-PAL3; malPT::PfnrS-PAL3::kan; PfnrS-pheP |
| SYN-PKU521 | yicS/nepI::PfnrS-PAL3::kan; lacZ::Pfnr-pheP::cam |
| SYN-PKU522 | cea::PfnrS-PAL3::kan; lacZ::Pfnr-pheP::cam |
| SYN-PKU523 | malPT::PfnrS-PAL3::kan; lacZ::Pfnr-pheP::cam |
| SYN-PKU524 | malEK::PfnrS::PAL3; malPT::PfhrS::PAL3; lacZ::Pfnr-pheP |
| SYN-PKU702 | malEK::PfnrS::PAL3; lacZ::Pfnr-pheP; Para::LAAD |
| SYN-PKU703 | malEK:: PfnrS::PAL3; malPT::PfnrS::PAL3; lacZ::Pfnr-pheP; agaI/rsmI::PfnrS::pheP; Para::LAAD |
| SYN-PKU704 | malEK:: PfnrS::PAL3; malPT::PfnrS::PAL3; yicS/nepI::PfnrS-PAL3; lacZ::Pfnr-pheP; Para::LAAD |
| SYN-PKU705 | malEK::PfnrS::PAL3; malPT::PfnrS::PAL3; yicS/nepI::PfnrS-PAL3::kan; lacZ::Pfnr-pheP: agaI/rsmI::PfnrS::pheP Para::LAAD |
| SYN-PKU602 | malEK::PT7::PAL3; Para::INT5::cam (recombinase); lacZ::Pfnr-pheP; malPT::Pconstitutive::T7 polymerase (unflipped); |
| SYN-PKU901 | Nissle with streptomycin resistance |

Secretion

In some embodiments, the genetically engineered bacteria further comprise a native secretion mechanism (e.g., gram positive bacteria) or non-native secretion mechanism (e.g., gram negative bacteria) that is capable of secreting the protein(s) of interest or therapeutic protein(s), e.g., PAH, PAL or LAAD, from the bacterial cytoplasm. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes. In some embodiments, the genetically engineered bacteria further comprise a non-native double membrane-spanning secretion system. Double membrane-spanning secretion systems include, but are not limited to, the type I secretion system (T1SS), the type II secretion system (T2SS), the type III secretion system (T3SS), the type IV secretion system (T4SS), the type VI secretion system (T6SS), and the resistance-nodulation-division (RND) family of multi-drug efflux pumps (Pugsley 1993; Gerlach et al., 2007; Collinson et al., 2015; Costa et al., 2015; Reeves et al., 2015; WO2014138324A1, incorporated herein by reference). Examples of such secretion systems are shown in FIGS. 3-6. Mycobacteria, which have a Gram-negative-like cell envelope, may also encode a type VII secretion system (T7SS) (Stanley et al., 2003). With the exception of the T2SS, double membrane-spanning secretions generally transport substrates from the bacterial cytoplasm directly into the extracellular space or into the target cell. In contrast, the T2SS and secretion systems that span only the outer membrane may use a two-step mechanism, wherein substrates are first translocated to the periplasm by inner membrane-spanning transporters, and then transferred to the outer membrane or secreted into the extracellular space. Outer membrane-spanning secretion systems include, but are not limited to, the type V secretion or autotransporter system (T5SS), the curli secretion system, and the chaperone-usher pathway for pili assembly (Saier, 2006; Costa et al., 2015).

In some embodiments, the genetically engineered bacteria of the invention further comprise a type III or a type III-like secretion system (T3SS) from *Shigella, Salmonella, E. coli, Bivrio, Burkholderia, Yersinia, Chlamydia*, or *Pseudomonas*. The T3SS is capable of transporting a protein from the bacterial cytoplasm to the host cytoplasm through a needle complex. The T3SS may be modified to secrete the molecule from the bacterial cytoplasm, but not inject the molecule into the host cytoplasm. Thus, the molecule is secreted into the gut lumen or other extracellular space. In some embodiments, the genetically engineered bacteria comprise said modified T3SS and are capable of secreting the protein(s) of interest or therapeutic protein(s) from the bacterial cytoplasm. In some embodiments, the secreted molecule, such as a heterologous protein or peptide, e.g., the protein of interest or therapeutic protein e.g., PAH, PAL or LAAD, comprises a type III secretion sequence that allows the protein(s) of interest or therapeutic protein(s) to be secreted from the bacteria.

In some embodiments, a flagellar type III secretion pathway is used to secrete the molecule of interest, e.g., PAH, PAL or LAAD. In some embodiments, an incomplete flagellum is used to secrete a therapeutic peptide of interest, e.g., PAH, PAL or LAAD, by recombinantly fusing the peptide to an N-terminal flagellar secretion signal of a native flagellar component. In this manner, the intracellularly expressed chimeric peptide can be mobilized across the inner and outer membranes into the surrounding host environment.

Figure 10:
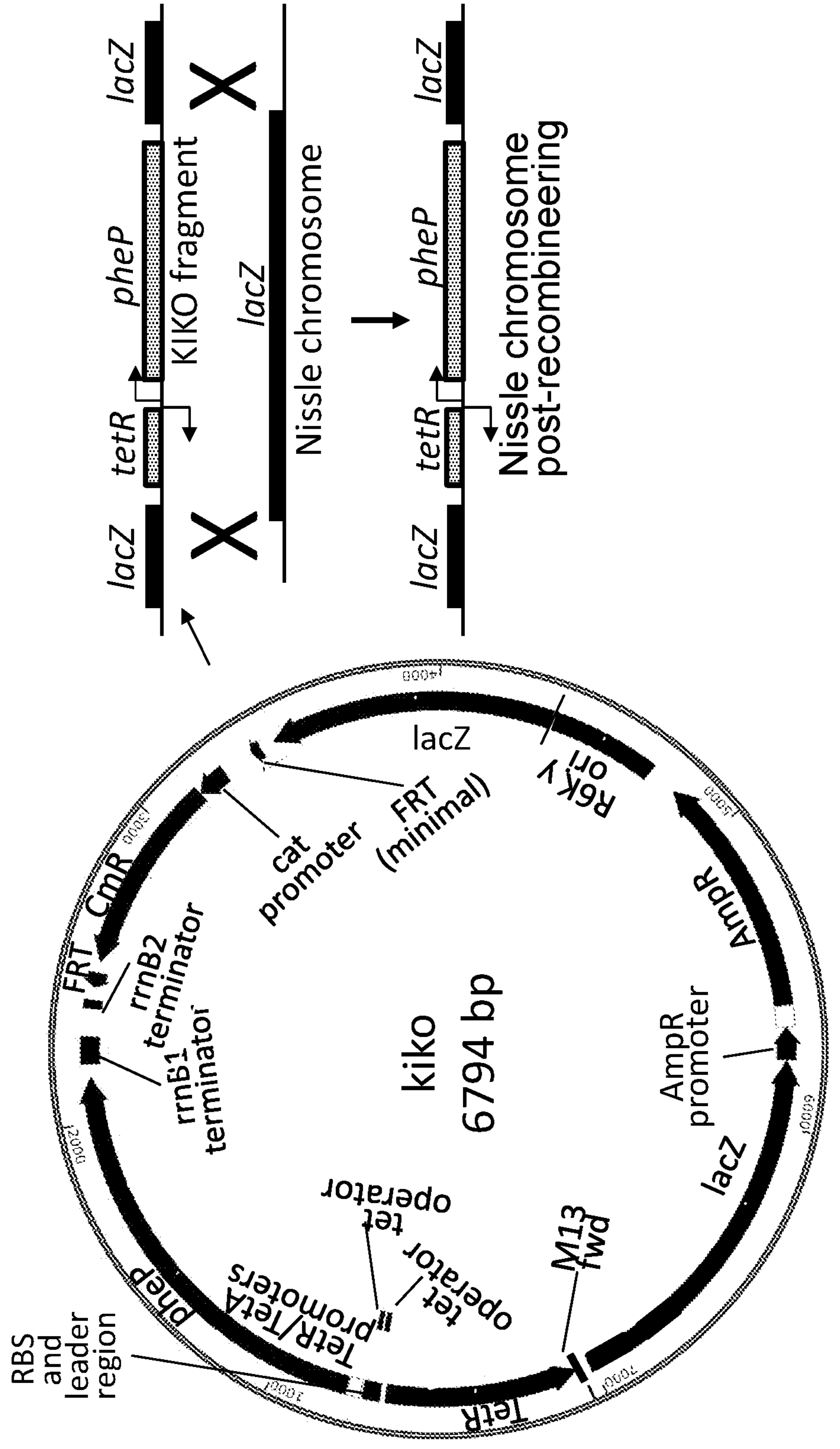
FIG. 10 depicts a schematic representation of the construction of apheP knock-in strain, wherein recombineering is used to insert a second copy of pheP into the Nissle lacZ gene.

In some embodiments, a Type V Autotransporter Secretion System is used to secrete the therapeutic peptide, e.g., PAH, PAL or LAAD. Due to the simplicity of the machinery and capacity to handle relatively large protein fluxes, the Type V secretion system is attractive for the extracellular production of recombinant proteins. As shown in FIG. 10, a therapeutic peptide (star) can be fused to an N-terminal secretion signal, a linker, and the beta-domain of an autotransporter. The N-terminal signal sequence directs the protein to the SecA-YEG machinery which moves the protein across the inner membrane into the periplasm, followed by subsequent cleavage of the signal sequence. The Beta-domain is recruited to the Bam complex ('Beta-barrel assembly machinery') where the beta-domain is folded and inserted into the outer membrane as a beta-barrel structure. The therapeutic peptide, e.g., PAH, PAL or LAAD, is threaded through the hollow pore of the beta-barrel structure ahead of the linker sequence. Once exposed to the extracellular environment, the therapeutic peptide, e.g., PAH, PAL or LAAD, can be freed from the linker system by an autocatalytic cleavage (left side of Bam complex) or by targeting of a membrane-associated peptidase (black scissors; right side of Bam complex) to a complimentary protease cut site in the linker. Thus, in some embodiments, the secreted molecule, such as a heterologous protein or peptide, e.g., the protein of interest or therapeutic protein, comprises an N-terminal secretion signal, a linker, and beta-domain of an autotransporter so as to allow the molecule to be secreted from the bacteria.

Figure 11:
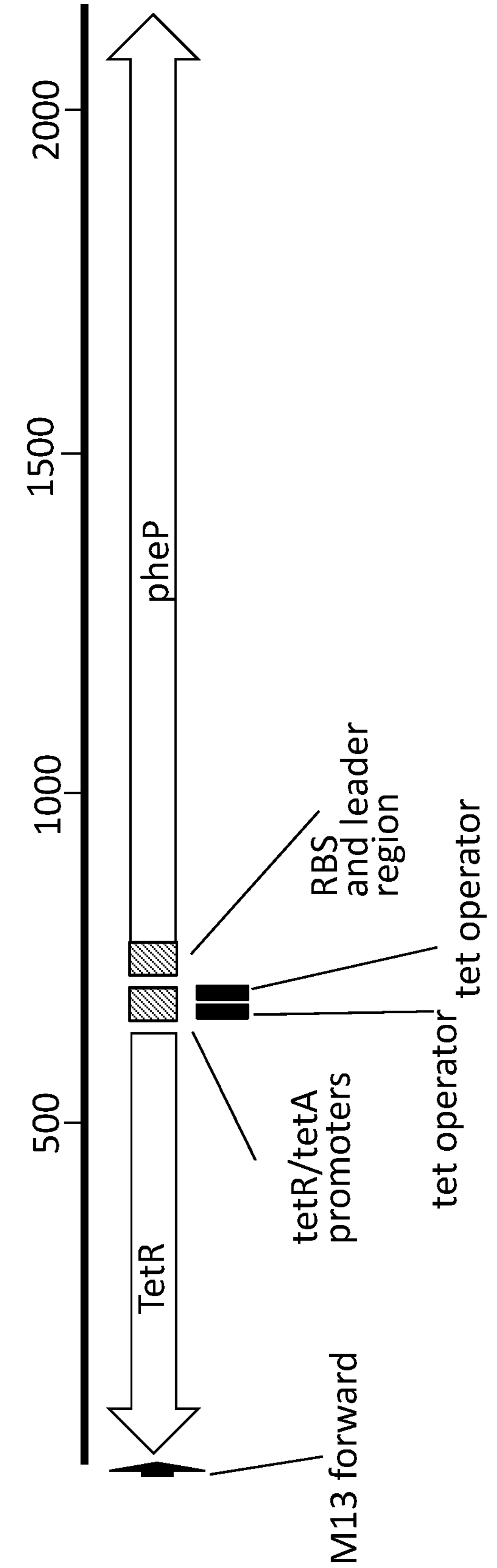
FIG. 11 depicts the gene organization of an exemplary construct comprising a gene encoding PheP, a gene encoding TetR, and a tet promoter sequence for chromosomal insertion e.g., as for example comprised in SYN-PKU203, SYN-PKU401, SYN-PKU402, SYN-PKU302, and SYN-PKU303.
Figure 12A:
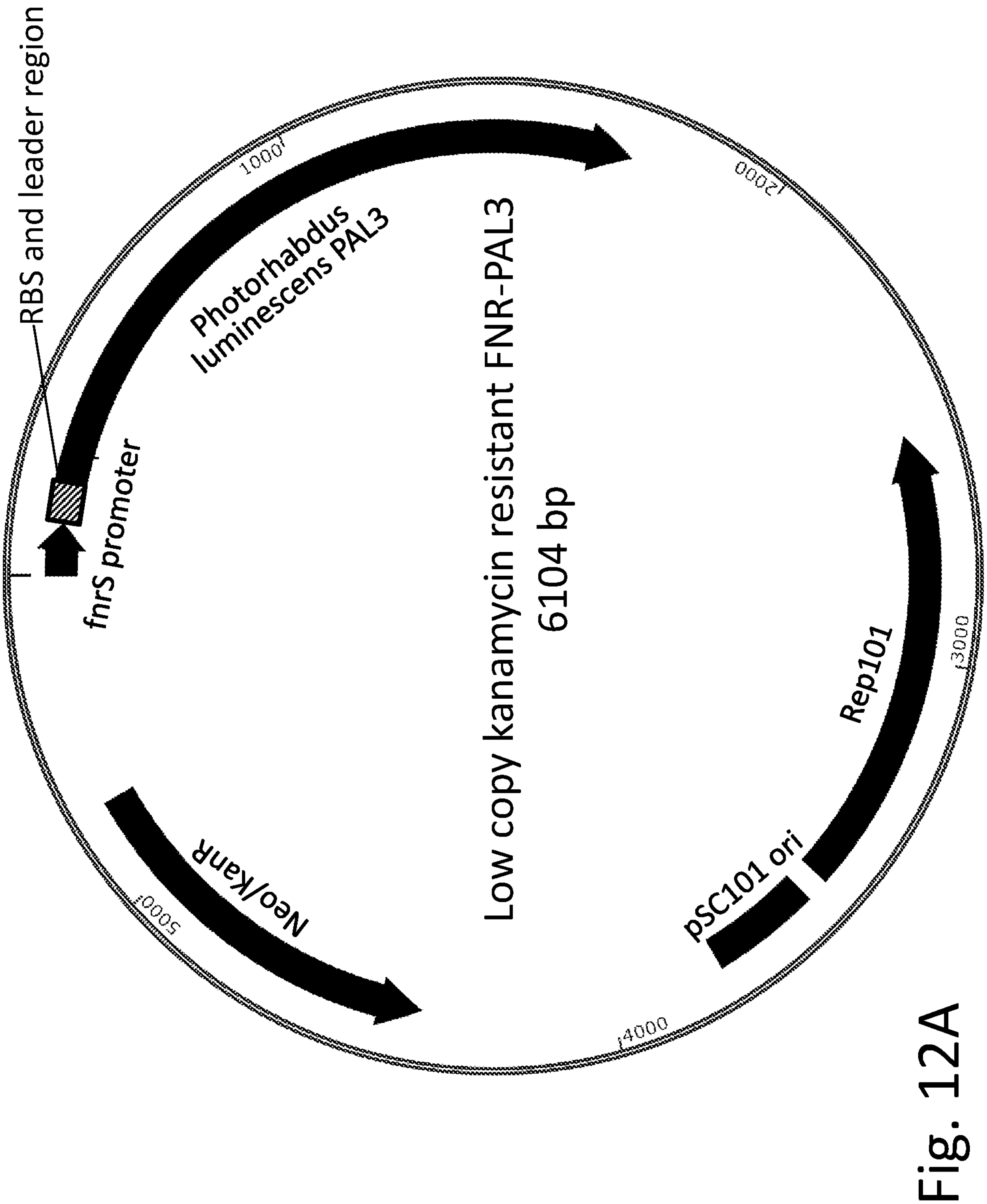
FIG. 12A depicts the gene organization of an exemplary construct, comprising a cloned PAL3 gene under the control of an FNR promoter sequence, on a low-copy, kanamycin-resistant plasmid (pSC101 origin of replication. Under anaerobic conditions, PAL3 degrades phenylalanine to non-toxic trans-cinnamate.
Figure 12B:
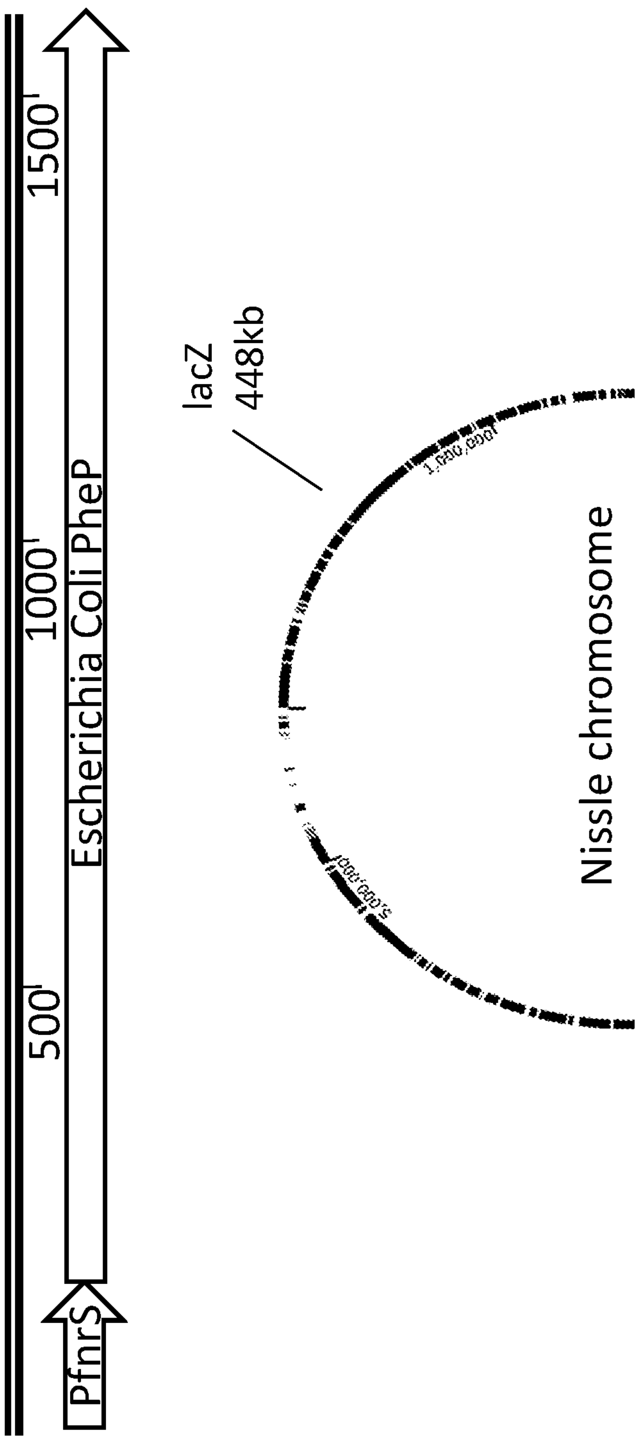
FIG. 12B depicts an additional copy of the endogenous *E. coli* high affinity phenylalanine transporter, pheP, driven by the PfnrS promoter and inserted into the lacZ locus on the Nissle chromosome.

In some embodiments, a Hemolysin-based Secretion System is used to secrete the molecule of interest, e.g., e.g., PAH, PAL or LAAD. Type I Secretion systems offer the advantage of translocating their passenger peptide directly from the cytoplasm to the extracellular space, obviating the two-step process of other secretion types. FIG. 11 shows the alpha-hemolysin (HlyA) of uropathogenic *Escherichia coli*. This pathway uses HlyB, an ATP-binding cassette transporter; HlyD, a membrane fusion protein; and TolC, an outer membrane protein. The assembly of these three proteins forms a channel through both the inner and outer membranes. Natively, this channel is used to secrete HlyA, however, to secrete the therapeutic peptide of the present disclosure, the secretion signal-containing C-terminal portion of HlyA is fused to the C-terminal portion of a therapeutic peptide (star) to mediate secretion of this peptide.

In alternate embodiments, the genetically engineered bacteria further comprise a non-native single membrane-spanning secretion system. Single membrane-spanning exporters may act as a component of a secretion system, or may export substrates independently. Such exporters include, but are not limited to, ATP-binding cassette translocases, flagellum/virulence-related translocases, conjugation-related translocases, the general secretory system (e.g., the SecYEG complex in *E. coli*), the accessory secretory system in mycobacteria and several types of Gram-positive bacteria (e.g., *Bacillus anthracis, Lactobacillus johnsonii, Corynebacterium glutamicum, Streptococcus gordonii, Staphylococcus aureus*), and the twin-arginine translocation (TAT) system (Saier, 2006; Rigel and Braunstein, 2008; Albiniak et al., 2013). It is known that the general secretory and TAT systems can both export substrates with cleavable N-terminal signal peptides into the periplasm, and have been explored in the context of biopharmaceutical production. The TAT system may offer particular advantages, however, in that it is able to transport folded substrates, thus eliminating the potential for premature or incorrect folding. In certain embodiments, the genetically engineered bacteria comprise a TAT or a TAT-like system and are capable of secreting the protein(s) of interest or therapeutic protein(s), e.g., PAH, PAL or LAAD, from the bacterial cytoplasm. One of ordinary skill in the art would appreciate that the secretion systems disclosed herein may be modified to act in different species, strains, and subtypes of bacteria, and/or adapted to deliver different payloads.

In order to translocate a protein, e.g., therapeutic polypeptide, e.g., PAH, PAL or LAAD, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

One way to secrete properly folded proteins in gram-negative bacteria-particularly those requiring disulphide bonds—is to target the periplasm in a bacterium with a destabilized outer membrane. In this manner the protein is mobilized into the oxidizing environment and allowed to fold properly. In contrast to orchestrated extracellular secretion systems, the protein is then able to escape the periplasmic space in a correctly folded form by membrane leakage. These "leaky" gram-negative mutants are therefore capable of secreting bioactive, properly disulphide-bonded polypeptides. In some embodiments, the genetically engineered bacteria have a "leaky" or de-stabilized outer membrane. Destabilizing the bacterial outer membrane to induce leakiness can be accomplished by deleting or mutagenizing genes responsible for tethering the outer membrane to the rigid peptidoglycan skeleton, including for example, lpp, ompC, ompA, ompF, tolA, tolB, pal, degS, degP, and nlpl. Lpp is the most abundant polypeptide in the bacterial cell existing at ~500,000 copies per cell and functions as the primary 'staple' of the bacterial cell wall to the peptidoglycan. Silhavy, T. J., Kahne, D. & Walker, S. The bacterial cell envelope. *Cold Spring Harb Perspect Biol* 2, a000414 (2010). TolA-PAL and OmpA complexes function similarly to Lpp and are other deletion targets to generate a leaky phenotype. Additionally, leaky phenotypes have been observed when periplasmic proteases are deactivated. The periplasm is very densely packed with protein and therefore encode several periplasmic proteins to facilitate protein turnover. Removal of periplasmic proteases such as degS, degP or nlpI can induce leaky phenotypes by promoting an excessive build-up of periplasmic protein. Mutation of the proteases can also preserve the effector polypeptide by preventing targeted degradation by these proteases. Moreover, a combination of these mutations may synergistically enhance the leaky phenotype of the cell without major sacrifices in cell viability. Thus, in some embodiments, the engineered bacteria have one or more deleted or mutated membrane genes. In some embodiments, the engineered bacteria have a deleted or mutated lpp gene. In some embodiments, the engineered bacteria have one or more deleted or mutated gene(s), selected from ompA, ompA, and ompF genes. In some embodiments, the engineered bacteria have one or more deleted or mutated gene(s), selected from tolA, tolB, and pal genes. in some embodiments, the engineered bacteria have one or more deleted or mutated periplasmic protease genes. In some embodiments, the engineered bacteria have one or more deleted or mutated periplasmic protease genes selected from degS, degP, and nlpl. In some embodiments, the engineered bacteria have one or more deleted or mutated gene(s), selected from lpp, ompA, ompA, ompF, tolA, tolB, pal, degS, degP, and nlpl genes.

To minimize disturbances to cell viability, the leaky phenotype can be made inducible by placing one or more membrane or periplasmic protease genes, e.g., selected from lpp, ompA, ompA, ompF, tolA, tolB, pal, degS, degP, and nlpl, under the control of an inducible promoter. For example, expression of lpp or other cell wall stability protein or periplasmic protease can be repressed in conditions where the therapeutic polypeptide needs to be delivered (secreted). For instance, under inducing conditions a transcriptional repressor protein or a designed antisense RNA can be expressed which reduces transcription or translation of a target membrane or periplasmic protease gene. Conversely, overexpression of certain peptides can result in a destabilized phenotype, e.g., overexpression of colicins or the third topological domain of TolA, wherein peptide overexpression can be induced in conditions in which the therapeutic polypeptide needs to be delivered (secreted). These sorts of strategies would decouple the fragile, leaky phenotypes from biomass production. Thus, in some embodiments, the engineered bacteria have one or more membrane and/or periplasmic protease genes under the control of an inducible promoter.

Table 15 and Table 16 list secretion systems for Gram positive bacteria and Gram negative bacteria. These can be used to secrete polypeptides, proteins of interest or therapeutic protein(s) from the engineered bacteria, which are reviewed in Milton H. Saier, Jr. Microbe/Volume 1, Number 9, 2006 “Protein Secretion Systems in Gram-Negative Bacteria Gram-negative bacteria possess many protein secretion-membrane insertion systems that apparently evolved independently”, the contents of which is herein incorporated by reference in its entirety.

TABLE 15

Secretion systems for gram positive bacteria

| Bacterial Strain | Relevant Secretion System |
|---|---|
| *C. novyi*-NT (Gram+) | Sec pathway Twin-arginine (TAT) pathway |
| *C. butryicum* (Gram+) | Sec pathway Twin-arginine (TAT) pathway |
| *Listeria monocytogenes* (Gram+) | Sec pathway Twin-arginine (TAT) pathway |

TABLE 16

Secretion Systems for Gram negative bacteria
Protein secretary pathways (SP) in gram-negative bacteria and their descendants

| Type (Abbreviation) | Name | TC#$^2$ | Bacteria | Archaea | Eukarya | # Proteins/ System | Energy Source |
|---|---|---|---|---|---|---|---|
| IMPS - Gram-negative bacterial inner membrane channel-forming translocases | | | | | | | |
| ABC (SIP) | ATP binding cassette translocase | 3.A.1 | + | + | + | 3-4 | ATP |
| SEC (IISP) | General secretory translocase | 3.A.5 | + | + | + | ~12 | GTP OR ATP + PMF |
| Fla/Path (IIISP) | Flagellum/ virulence-related translocase | 3.A.6 | + | − | − | >10 | ATP |
| Conj (IVSP) | Conjugation-related translocase | 3.A.7 | + | − | − | >10 | ATP |
| Tat (IISP) | Twin-arginine targeting translocase | 2.A.64 | + | + | + (chloroplasts) | 2-4 | PMF |
| Oxal (YidC) | Cytochrome oxidase biogenesis family | 2.A.9 | + | + | + (mitochondria chloroplasts) | 1 | None or PMF |
| MscL | Large conductance mechanosensitive channel family | 1.A.22 | + | + | + | 1 | None |

TABLE 16-continued

| Secretion Systems for Gram negative bacteria<br>Protein secretary pathways (SP) in gram-negative bacteria and their descendants | | | | | | | |
|---|---|---|---|---|---|---|---|
| Type (Abbreviation) | Name | TC#[2] | Bacteria | Archaea | Eukarya | # Proteins/ System | Energy Source |
| Holins | Holin functional superfamily | 1.E.1•21 | + | − | − | 1 | None |
| | | Eukaryotic Organelles | | | | | |
| MPT | Mitochondria 1 protein translocase | 3.A.B | − | − | + (mitochondrial) | >20 | ATP |
| CEPT | Chloroplast envelope protein translocase | 3.A.9 | (+) | − | + (chloroplasts) | ≥3 | GTP |
| Bcl-2 | Eukaryotic Bcl-2 family (programmed cell death) | 1.A.21 | − | − | + | 1? | None |
| | Gram-negative bacterial outer membrane channel-forming translocases | | | | | | |
| MTB (IISP) | Main terminal branch of the general secretory translocase | 3.A.15 | +[b] | − | − | ~14 | ATP; PMF |
| FUP AT-1 | Fimbrial usher protein | 1.B.11 | +[b] | − | − | 1 | None |
| | Autotransporter-1 | 1.B.12 | +[b] | | − | 1 | None |
| AT-2 | Autotransporter-2 | 1.B.40 | +[b] | − | − | 1 | None |
| OMF (ISP) | | 1.B.17 | +[b] | | +(?) | 1 | None |
| TPS | | 1.B.20 | + | − | + | 1 | None |
| Secretin (IISP and IISP) | | 1.B.22 | +[b] | | − | 1 | None |
| OmpIP | Outer membrane insertion porin | 1.B.33 | + | − | + (mitochondria; chloroplasts) | ≥4 | None ? |

In some embodiments, the genetically engineered bacterial comprise a native or non-native secretion system described herein for the secretion of a PME, e.g., PAH, PAL and/or LAAD. In some embodiments, the secretion system is selected from the modified type III flagellar, type I (e.g., hemolysin secretion system), type II, type IV, type V, type VI, and type VII secretion systems, resistance-nodulation-division (RND) multi-drug efflux pumps, a single membrane secretion system, Sec and, TAT secretion systems.

In some embodiments, the PMEs secreted by the genetically engineered bacteria are modified to increase resistance to proteases. For example, in some embodiments, the one or more PME administered is modified as described in Sakissian et al., 2011, Mol Genet Metab. 2011 November; 104(3): 249-254, the contents of which is herein incorporated by reference in its entirety. In some embodiments, the secreted PAL is Av-p.C503S/p.C565S/p.F18A PAL. In some embodiments, the secreted PAL is PEG-Av-p.C503S/p.C565S/p.F18A PAL.

In some embodiments, the one or more PMEs for secretion are under the control of an inducible promoter, as described herein. In one example, the one or more PMEs are under the control of the FNR promoter and are produced and secreted under anaerobic conditions. In some embodiments, the PMEs for secretion are under the control of the ParaBAD promoter. In some embodiments, the PMEs for secretion are under the control of a constitutive promoter.

In some embodiments in which the one or more PMEs are secreted or exported from the microorganism, the engineered microorganism comprises gene sequence(s) that includes a secretion tag. In some embodiments, the PME(s) include a "secretion tag" of either RNA or peptide origin to direct the PME(s) to specific secretion systems. For example, a secretion tag for the Type I Hemolysin secretion system is encoded in the C-terminal 53 amino acids of the alpha hemolysin protein (HlyA). HlyA secretion signal.

HlyB inserts into inner membrane to form a pore, HlyD aligns HlyB with TolC (outer membrane pore) thereby forming a channel through inner and outer membrane. The C-terminal secretion tag can be removed by either an autocatalytic or protease-catalyzed e.g., OmpT cleavage thereby releasing the PME(s) into the extracellular milieu.

The Type V Auto-secretion System utilizes an N-terminal Sec-dependent peptide tag (inner membrane) and C-terminal tag (outer-membrane). This uses Sec-system to get from cytoplasm to periplasm. C-terminal tag then inserts into the outer membrane forming a pore through which the "passenger protein" threads through. Once across the outer membrane, the passenger (anti-cancer molecule) is released from the membrane-embedded C-terminal tag by either an autocatalytic, intein-like mechanism or via a membrane-bound protease (I.e., OmpT). The N-terminal tag is removed by the Sec system. Thus, in some embodiments, the secretion system is able to remove this tag before secreting the PME(s), e.g., PAL, PAH, and/or LAAD from the engineered bacteria. In the Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the anti-cancer molecule(s) into the extracellular milieu.

In the Flagellar modified Type III Secretion, the tag is encoded in 5'untranslated region of the mRNA and thus there is no peptide tag to cleave/remove. This modified system does not contain the "syringe" portion and instead uses the basal body of the flagella structure as the pore to translocate across both membranes and out through the forming flagella. If the fliC/fliD genes (encoding the flagella "tail"/whip) are disrupted the flagella cannot fully form and this promotes overall secretion. In some embodiments, the tail portion can be removed entirely. In the Type III traditional secretion system, the basal body closely resembles the flagella, however, instead of a "tail"/whip, the traditional T3SS has a syringe to inject the passenger proteins into host cells. The secretion tag is encoded by an N-terminal peptide (lengths vary and there are several different tags, see PCT/US14/020972). The N-terminal tag is not removed from the polypeptides in this secretion system.

In some embodiments the PME contains expressed as fusion protein with the 53 amino acids of the C termini of alpha-hemolysin (hlyA) of *E. coli* CFT073 (C terminal secretion tag).

Oxygen Consuming Enzymes

LAAD catalytic activity is dependent on oxygen, and therefore may not be active in anaerobic environments in the intestine, e.g., the colon. Oxygen is present in more proximal compartments of the GI tract.

The oxygen tension as measured in healthy mice is shown in Table 17. He et al., Proc Natl Acad Sci USA. 1999 Apr. 13; 96(8):4586-91; "Noninvasive measurement of anatomic structure and intraluminal oxygenation in the gastrointestinal tract of living mice with spatial and spectral EPR imaging", the contents of which is herein incorporated by reference in its entirety. A marked oxygen gradient from the proximal to the distal GI tract. As noted by He et al., the observed oxygen gradient seen along the GI tract can be explained by a combination of processes. Without wishing to be bound by theory, food, when swallowed, is initially equilibrated with the oxygen tension of ambient room air. On passage to the stomach and later the small intestine, the oxygen levels may fall as oxygen diffuses across the mucosal membrane. A gradual process of equilibration with the capillary levels of oxygen (i.e., 5-10 torr; ref. 9) may occur. On passage to the colon, with its heavy bacterial colonization, further decreases in oxygenation occur. Finally, the lumen of the distal colon displays marked hypoxia, as expected, based on the abundance of anaerobic bacteria at this site.

TABLE 17

Oxygen Tension in Gastrointestinal Tract Compartments

| Compartment | Oxygen Tension |
|---|---|
| Ambient Air | 159 Torr |
| stomach | ~60 torr |
| duodenum and first part of jejunum | (~30 torr); ~20% oxygen in ambient air |
| ileum | (~10 torr); ~6% oxygen in ambient air |
| colon | (<2 torr) |

Figure 25A:
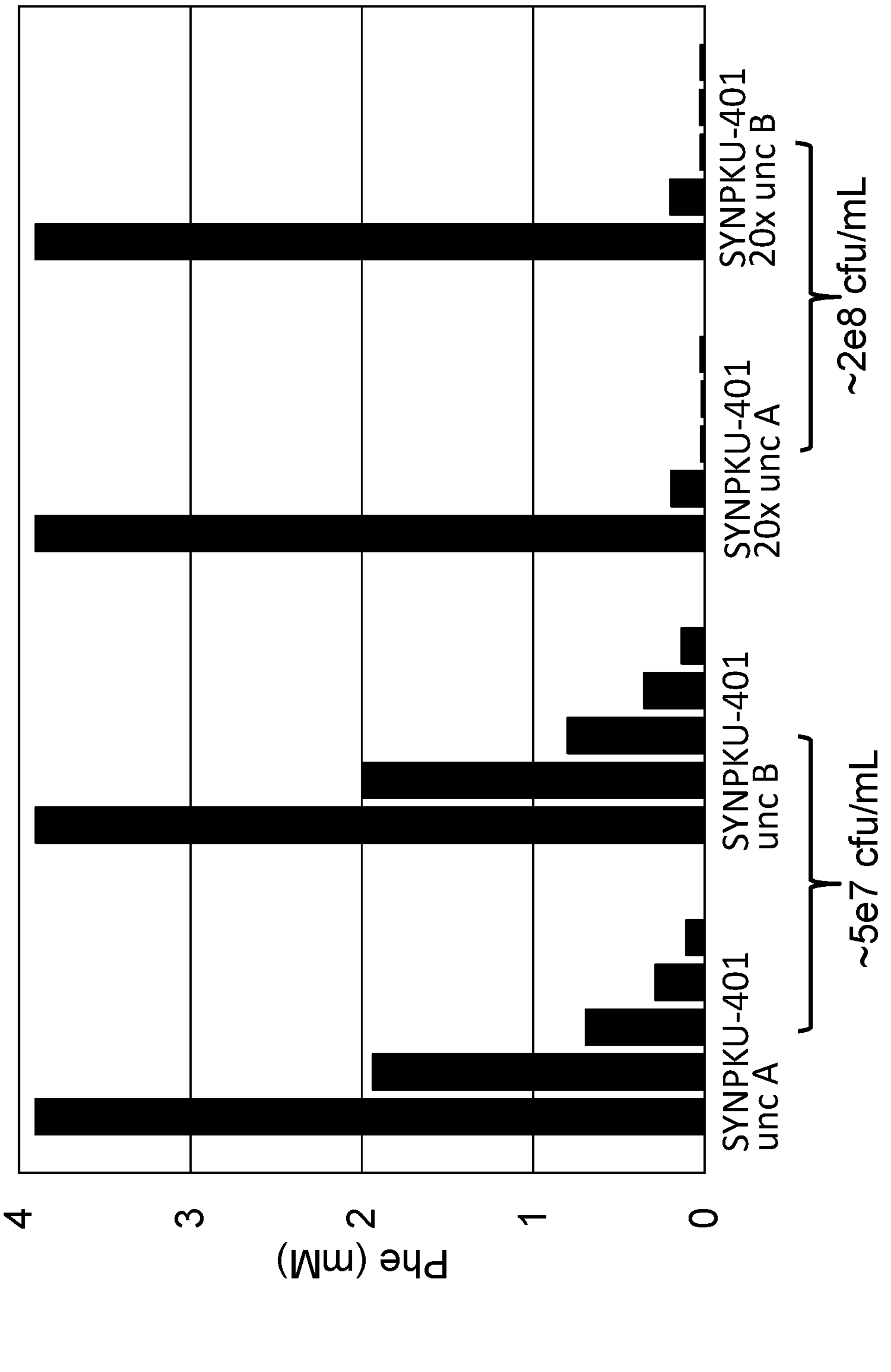
FIGS. 25A and 25B depict phenylalanine concentrations in cultures of a synthetic probiotic strain, SYN-PKU401, which comprises a high copy pUC57-plasmid with LAAD driven by a Tet inducible promoter, cells were grown in flasks shaking at 37 C, and induced with TCA at early log phase for a duration of 2 hours. Cells were spun down and re-suspended in assay buffer containing phenylalanine. Cells were measured at various cell concentrations and at varying oxygen levels. Cells were either incubated aerobically (1 ml) in a 14 ml culture tube, shaking at 250 rpm. For microaerobic conditions, cells (1 ml) were incubated in a 1.7 ml conical tube without shaking. Cells were incubated anaerobically in a Coy anaerobic chamber supplying 90% N2, 5% CO2, and 5% H2. Aliquots were removed from cell assays every 30 min for 2 hrs for phenylalanine quantification by mass spectrometry.
Figure 25B:
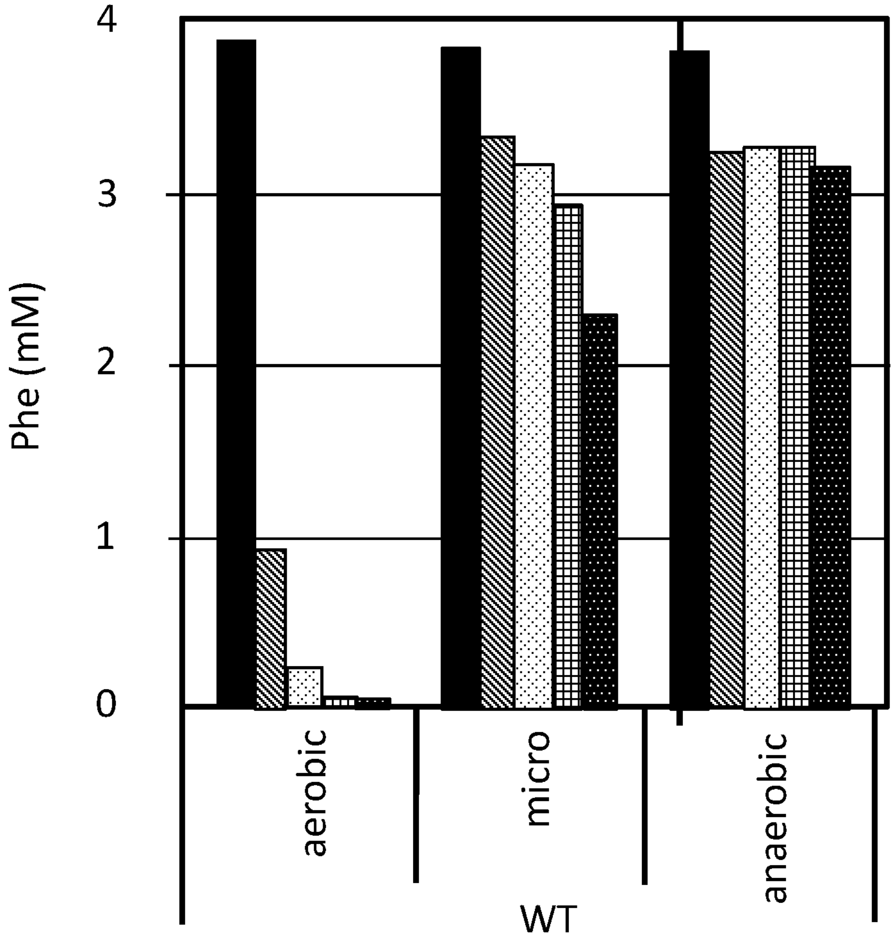

As shown in FIG. 25B, LAAD activity is retained in microaerobic conditions, albeit at lower levels than under aerobic conditions (FIG. 25A and FIG. 25B). LAAD therefore may be active in the more proximal areas of the intestine, such as stomach, duodenum, jejunum, and ileum. It is contemplated as part of this disclosure that LAAD expressed by the genetically engineered bacteria may advantageously be active in a different compartment than PAL, which may be expressed in the colon if under the control of an FNR promoter. In one embodiment, the genetically engineered bacteria express two enzymes, which have different oxygen requirements and/or are induced under different oxygen conditions, such that an PME is expressed and active throughout the entire gastrointestinal system. For example, the first enzyme, e.g., LAAD, which is dependent on the presence of oxygen, is expressed in one or more of stomach, duodenum and ileum under the control of a constitutive or inducible promoter (such as ParaBAD), and the second enzyme, e.g., PAL, is expressed in the colon under the control of an FNR promoter.

Several strategies can be employed to further increase LAAD activity under oxygen limiting conditions. For example, the activity of other enzymes that consume large amounts of oxygen can be reduced or extinguished. One such enzyme is NADH dehydrogenase. *E coli* has two NADH dehydrogenases; nuo and ndh2, and is has been shown that knock out of both of these enzymes reduces oxygen consumption by 80%. In some embodiments, additional measures are taken to conserve limiting oxygen, i.e., to allow LAAD to function under lower exogenous oxygen conditions in the genetically engineered bacteria expressing LAAD. In some embodiments, the genetically engineered bacteria further comprise a mutation in one or more genes involved in oxygen consumption. In some embodiments, one or both *E. coli* NADH dehydrogenases are knocked out. In some embodiments, the knocked out NADH dehydrogenase is nuo. In some embodiments the knocked out NADH dehydrogenase is ndh2. In some embodiments nuo and ndh2 are knocked out. Other enzymes involved in *E. coli* oxygen metabolism may also be knocked out, including enzymes in the respiratory chain, such as cydB (a subunit of high affinity terminal oxidase), cydD (an enzyme required to make cytochrome D), and cyoABC (subunits of low affinity cytochrome oxidase). In some embodiments, the genetically engineered bacteria harbor a knock out mutation/deletion in one more genes selected from cydB, cydD, and cyoABC.

In one embodiment, the one or more PME encoded by the genetically engineered bacteria are expressed and show activity in the stomach. In one embodiment, the one or more PME encoded by the genetically engineered bacteria are expressed and show activity in the duodenum. In one embodiment, the one or more PME encoded by the genetically engineered bacteria are expressed and show activity in the jejunum. In one embodiment, the one or more PME encoded by the genetically engineered bacteria are expressed and show activity in the ileum. In one embodiment, the one or more PME encoded by the genetically engineered bacteria are expressed and show activity in the colon.

Essential Genes and Auxotrophs

As used herein, the term "essential gene" refers to a gene that is necessary for cell growth and/or survival. Bacterial essential genes are well known to one of ordinary skill in the art, and can be identified by directed deletion of genes and/or random mutagenesis and screening (see, e.g., Zhang and Lin, "DEG 5.0, a database of essential genes in both prokaryotes and eukaryotes," Nucl Acids Res, 2009; 37:D455-D458 and Gerdes et al., "Essential genes on metabolic maps," Curr Opin Biotechnol, 2006; 17(5):448-456, the entire contents of each of which are expressly incorporated herein by reference).

An "essential gene" may be dependent on the circumstances and environment in which an organism lives. For example, a mutation of, modification of, or excision of an essential gene may result in the genetically engineered bacteria of the disclosure becoming an auxotroph. An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. Table 18 lists exemplary bacterial genes which may be disrupted or deleted to produce an auxotrophic strain. These include, but are not limited to, genes required for oligonucleotide synthesis, amino acid synthesis, and cell wall synthesis.

TABLE 18

Non-limiting Examples of Bacterial Genes Useful for Generation of an Auxotroph

| Amino Acid | Oligonucleotide | Cell Wall |
|---|---|---|
| cysE | thyA | dapA |
| glnA | uraA | dapB |
| ilvD | | dapD |
| leuB | | dapE |
| lysA | | dapF |
| serA | | |
| metA | | |
| glyA | | |
| hisB | | |
| ilvA | | |
| pheA | | |
| proA | | |
| thrC | | |
| trpC | | |
| tyrA | | |

Table 19 shows the survival of various amino acid auxotrophs in the mouse gut, as detected 24 hrs and 48 hrs post-gavage. These auxotrophs were generated using BW25113, a non-Nissle strain of *E. coli*.

TABLE 19

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/ Isoleucine/ Leucine | Present | Present | Absent |
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro, or in the presence of high uracil levels found naturally in the human gut in vivo. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to, yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, Igt, JbaA, pgk, yqgD, metK, yqgF, plsC, ygiT, pare, ribB, cca, ygjD, tdcF, yraL, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, ispA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def fmt, rplQ, rpoA, rpsD, rpsK, rpsM, entD, mrdB, mrdA, nadD, hlepB, rpoE, pssA, yfiO, rplS, trmD, rpsP, fJh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf pyrH, olA, rlpB, leuS, lnt, glnS, fldA, cydA, infA, cydC, ftsK, lolA, serS, rpsA, msbA, lpxK, kdsB, mukF, mukE, mukB, asnS, fabA, mviN, rne, yceQ, fabD, fabG, acpP, tmk, holB, lolC, lolD, lolE, purB, ymK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson, "Synthetic Auxotrophs with Ligand-Dependent Essential Genes for a BL21 (DE3) Biosafety Strain," ACS Synth Biol 2015; 4(12):1279-1286, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, 149G, and A51C. In some embodiments, the essential gene is adk comprising one or more of the following mutations: I4L, L5I, and L6G. In some embodiments, the essential gene is adk comprising the mutations I4L, L5I, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, 149G, and A51C) are complemented by benzothiazole, indole, 2-aminobenzothiazole, indole-3-butyric acid, indole-3-acetic acid, or L-histidine methyl ester. Bacterial cells comprising mutations in dnaN(H191N, R240C, I317S, F319V, L340T, V347I, and S345C) are complemented by benzothiazole, indole, or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, 149G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 43-47.

In some embodiments, the genetically engineered bacterium of the disclosure is an auxotroph and also comprises kill switch circuitry, such as any of the kill switch components and systems described herein. For example, the genetically engineered bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synth Biol, 2015; 4(3):307-316, the entire contents of which are expressly incorporated herein by reference). In some embodiments, the genetically engineered bacterium of the disclosure is an auxotroph and also comprises kill switch circuitry, such as any of the kill switch components and systems described herein, as well as another biosecurity system, such a conditional origin of replication (Wright et al., 2015).

The addition of a Phe-auxotrophy may also have utility for increasing the rate of phenylalanine degradation. For example, the deletion of the pheA gene confers phenylalanine auxotrophy. By turning off endogenous bacterial phenylalanine production, this may drive increased uptake from the environment and also result in increased degradation of phenylalanine taken up from the environment.

Genetic Regulatory Circuits

In some embodiments, the genetically engineered bacteria comprise multilayered genetic regulatory circuits for expressing the constructs described herein (see, e.g., U.S. Provisional Application No. 62/184,811, incorporated herein by reference in its entirety). The genetic regulatory circuits are useful to screen for mutant bacteria that produce a phenylalanine-metabolizing enzyme or rescue an auxotroph. In certain embodiments, the invention provides methods for selecting genetically engineered bacteria that produce one or more genes of interest.

In some embodiments, the invention provides genetically engineered bacteria comprising a gene or gene cassette for producing a phenylalanine-metabolizing enzyme (e.g., PAL or PAH) and a T7 polymerase-regulated genetic regulatory circuit. For example, the genetically engineered bacteria comprise a first gene encoding a T7 polymerase, wherein the first gene is operably linked to an FNR-responsive promoter; a second gene or gene cassette for producing a phenylalanine-metabolizing enzyme, wherein the second gene or gene cassette is operably linked to a T7 promoter that is induced by the T7 polymerase; and a third gene encoding an inhibitory factor, lysY, that is capable of inhibiting the T7 polymerase. In the presence of oxygen, FNR does not bind the FNR-responsive promoter, and the phenylalanine-metabolizing enzyme is not expressed. LysY is expressed constitutively (P-lac constitutive) and further inhibits T7 polymerase. In the absence of oxygen, FNR dimerizes and binds to the FNR-responsive promoter, T7 polymerase is expressed at a level sufficient to overcome lysY inhibition, and the phenylalanine-metabolizing enzyme is expressed. In some embodiments, the lysY gene is operably linked to an additional FNR binding site. In the absence of oxygen, FNR dimerizes to activate T7 polymerase expression as described above, and also inhibits lysY expression.

In some embodiments, the invention provides genetically engineered bacteria comprising a gene or gene cassette for producing a phenylalanine-metabolizing enzyme (e.g., PAL or PAH) and a protease-regulated genetic regulatory circuit. For example, the genetically engineered bacteria comprise a first gene encoding an mf-lon protease, wherein the first gene is operably linked to an FNR-responsive promoter; a second gene or gene cassette for producing a phenylalanine-metabolizing enzyme operably linked to a Tet regulatory region (TetO); and a third gene encoding an mf-lon degradation signal linked to a Tet repressor (TetR), wherein the TetR is capable of binding to the Tet regulatory region and repressing expression of the second gene or gene cassette. The mf-lon protease is capable of recognizing the mf-lon degradation signal and degrading the TetR. In the presence of oxygen, FNR does not bind the FNR-responsive promoter, the repressor is not degraded, and the phenylalanine-metabolizing enzyme is not expressed. In the absence of oxygen, FNR dimerizes and binds the FNR-responsive promoter, thereby inducing expression of the mf-lon protease. The mf-lon protease recognizes the mf-lon degradation signal and degrades the TetR, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a repressor-regulated genetic regulatory circuit. For example, the genetically engineered bacteria comprise a first gene encoding a first repressor, wherein the first gene is operably linked to an FNR-responsive promoter; a second gene or gene cassette for producing a phenylalanine-metabolizing enzyme operably linked to a first regulatory region comprising a constitutive promoter; and a third gene encoding a second repressor, wherein the second repressor is capable of binding to the first regulatory region and repressing expression of the second gene or gene cassette. The third gene is operably linked to a second regulatory region comprising a constitutive promoter, wherein the first repressor is capable of binding to the second regulatory region and inhibiting expression of the second repressor. In the presence of oxygen, FNR does not bind the FNR-responsive promoter, the first repressor is not expressed, the second repressor is expressed, and the phenylalanine-metabolizing enzyme is not expressed. In the absence of oxygen, FNR dimerizes and binds the FNR-responsive promoter, the first repressor is expressed, the second repressor is not expressed, and the phenylalanine-metabolizing enzyme is expressed.

Examples of repressors useful in these embodiments include, but are not limited to, ArgR, TetR, ArsR, AscG, LacI, CscR, DeoR, DgoR, FruR, GalR, GatR, CI, LexA, RafR, QacR, and PtxS (US20030166191).

In some embodiments, the invention provides genetically engineered bacteria comprising a gene or gene cassette for producing a phenylalanine-metabolizing enzyme (e.g., PAL or PAH) and a regulatory RNA-regulated genetic regulatory circuit. For example, the genetically engineered bacteria comprise a first gene encoding a regulatory RNA, wherein the first gene is operably linked to an FNR-responsive promoter, and a second gene or gene cassette for producing a phenylalanine-metabolizing enzyme. The second gene or gene cassette is operably linked to a constitutive promoter and further linked to a nucleotide sequence capable of producing an mRNA hairpin that inhibits translation of the phenylalanine-metabolizing enzyme. The regulatory RNA is capable of eliminating the mRNA hairpin and inducing translation via the ribosomal binding site. In the presence of oxygen, FNR does not bind the FNR-responsive promoter, the regulatory RNA is not expressed, and the mRNA hairpin prevents the phenylalanine-metabolizing enzyme from being translated. In the absence of oxygen, FNR dimerizes and binds the FNR-responsive promoter, the regulatory RNA is expressed, the mRNA hairpin is eliminated, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a CRISPR-regulated genetic regulatory circuit. For example, the genetically engineered bacteria comprise a Cas9 protein; a first gene encoding a CRISPR guide RNA, wherein the first gene is operably linked to an FNR-responsive promoter; a second gene or gene cassette for producing a phenylalanine-metabolizing enzyme, wherein the second gene or gene cassette is operably linked to a regulatory region comprising a constitutive promoter; and a third gene encoding a repressor operably linked to a constitutive promoter, wherein the repressor is capable of binding to the regulatory region and repressing expression of the second gene or gene cassette. The third gene is further linked to a CRISPR target sequence that is capable of binding to the CRISPR guide RNA, wherein said binding to the CRISPR guide RNA induces cleavage by the Cas9 protein and inhibits expression of the repressor. In the presence of oxygen, FNR does not bind the FNR-responsive promoter, the guide RNA is not expressed, the repressor is expressed, and the phenylalanine-metabolizing enzyme is not expressed. In the absence of oxygen, FNR dimerizes and binds the FNR-responsive promoter, the guide RNA is expressed, the repressor is not expressed, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a recombinase-regulated genetic regulatory circuit. For example, the genetically engineered bacteria comprise a first gene encoding a recombinase, wherein the first gene is operably linked to an FNR-responsive promoter, and a second gene or gene cassette for producing a phenylalanine-metabolizing enzyme operably linked to a constitutive promoter. The second gene or gene cassette is inverted in orientation (3' to 5') and flanked by recombinase binding sites, and the recombinase is capable of binding to the recombinase binding sites to induce expression of the second gene or gene cassette by reverting its orientation (5' to 3'). In the presence of oxygen, FNR does not bind the FNR-responsive promoter, the recombinase is not expressed, the gene or gene cassette remains in the 3' to 5' orientation, and no functional phenylalanine-metabolizing enzyme is produced. In the absence of oxygen, FNR dimerizes and binds the FNR-responsive promoter, the recombinase is expressed, the gene or gene cassette is reverted to the 5' to 3' orientation, and a functional phenylalanine-metabolizing enzyme is produced (see, e.g., FIG. 42).

In some embodiments, the invention provides genetically engineered bacteria comprising a gene or gene cassette for producing a phenylalanine-metabolizing enzyme (e.g., PAL or PAH) and a polymerase- and recombinase-regulated genetic regulatory circuit. For example, the genetically engineered bacteria comprise a first gene encoding a recombinase, wherein the first gene is operably linked to an FNR-responsive promoter; a second gene or gene cassette for producing a phenylalanine-metabolizing enzyme operably linked to a T7 promoter; a third gene encoding a T7 polymerase, wherein the T7 polymerase is capable of binding to the T7 promoter and inducing expression of the phenylalanine-metabolizing enzyme. The third gene encoding the T7 polymerase is inverted in orientation (3' to 5') and flanked by recombinase binding sites, and the recombinase is capable of binding to the recombinase binding sites to induce expression of the T7 polymerase gene by reverting its orientation (5' to 3'). In the presence of oxygen, FNR does not bind the FNR-responsive promoter, the recombinase is not expressed, the T7 polymerase gene remains in the 3' to 5' orientation, and the phenylalanine-metabolizing enzyme is not expressed. In the absence of oxygen, FNR dimerizes and binds the FNR-responsive promoter, the recombinase is expressed, the T7 polymerase gene is reverted to the 5' to 3' orientation, and the phenylalanine-metabolizing enzyme is expressed (see, e.g., FIG. 43).

Synthetic gene circuits expressed on plasmids may function well in the short term but lose ability and/or function in the long term (Danino et al., 2015). In some embodiments, the genetically engineered bacteria comprise stable circuits for expressing genes of interest over prolonged periods. In some embodiments, the genetically engineered bacteria are capable of producing a phenylalanine-metabolizing enzyme (e.g., PAL or PAH) and further comprise a toxin-anti-toxin system that simultaneously produces a toxin (hok) and a short-lived anti-toxin (sok), wherein loss of the plasmid causes the cell to be killed by the long-lived toxin (Danino et al., 2015). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Kill Switch

In some embodiments, the genetically engineered bacteria of the invention also comprise a kill switch (see, e.g., U.S. Provisional Application Nos. 62/183,935 and 62/263,329, incorporated herein by reference in their entireties). The kill switch is intended to actively kill genetically engineered bacteria in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria comprising kill switches have been engineered for in vitro research purposes, e.g., to limit the spread of a biofuel-producing microorganism outside of a laboratory environment. Bacteria engineered for in vivo administration to treat a disease may also be programmed to die at a specific time after the expression and delivery of a heterologous gene or genes, for example, a phenylalanine-metabolizing enzyme, or after the subject has experienced the therapeutic effect. For example, in some embodiments, the kill switch is activated to kill the bacteria after a period of time following oxygen level-dependent expression of the phenylalanine-metabolizing enzyme (e.g., PAL or PAH) and/or the phenylalanine transporter gene. In some embodiments, the kill switch is activated in a delayed fashion following oxygen level-dependent expression of the phenylalanine-metabolizing enzyme and/or phenylalanine transporter gene. Alternatively, the bacteria may be engineered to die after the bacterium has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject). Examples of such toxins that can be used in kill switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl 3-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010).

Kill switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in a low-oxygen environment. In some embodiments, the genetically engineered bacteria of the present disclosure comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill switch systems once the engineered bacterial cell senses the exogenous environmental condition and expresses the heterologous gene of interest, the recombinant bacterial cell is no longer viable.

In another embodiment in which the genetically engineered bacteria of the present disclosure express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int2, Int3, Int4, Int5, Int6, Int7, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

In the above-described kill switch circuits, a toxin is produced in the presence of an environmental factor or signal. In another aspect of kill switch circuitry, a toxin may be repressed in the presence of an environmental factor (i.e., not produced) and then produced once the environmental condition or external signal is no longer present. Such kill switches are called repression-based kill switches and represent systems in which the bacterial cells are viable only in the presence of an external factor or signal, such as arabinose or other sugar. Exemplary kill switch designs in which the toxin is repressed in the presence of an external factor or signal (and activated once the external signal is removed) is shown in FIGS. 43-47. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter (ParaBAD). In the absence of arabinose, the AraC transcription factor adopts a conformation that represses transcription of genes under the control of the araBAD promoter. In the presence of arabinose, the AraC transcription factor undergoes a conformational change that allows it to bind to and activate the araBAD promoter, which induces expression of the desired gene, for example TetR, which represses expression of a toxin gene. In this embodiment, the toxin gene is repressed in the presence of arabinose or other sugar. In an environment where arabinose is not present, the TetR gene is not activated and the toxin is expressed, thereby killing the bacteria. The arabinose system can also be used to express an essential gene, in which the essential gene is only expressed in the presence of arabinose or other sugar and is not expressed when arabinose or other sugar is absent from the environment.

Thus, in some embodiments, in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an anti-toxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and ParaBAD. In one embodiment, the arabinose inducible promoter is from *E. coli*. In some embodiments, the $P_{araC}$ promoter and the ParaBAD promoter operate as a bidirectional promoter, with the ParaBAD promoter controlling expression of a heterologous gene(s) in one direction, and the $P_{araC}$ (in close proximity to, and on the opposite strand from the ParaBAD promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the genetically engineered bacteria of the present disclosure contain a kill switch having at least the following sequences: a ParaBAD promoter operably linked to a heterologous gene encoding a tetracycline repressor (TetR) protein, a $P_{araC}$ promoter operably linked to a heterologous gene encoding the AraC transcription factor, and a heterologous gene encoding a bacterial toxin operably linked to a promoter which is repressed by the TetR protein. In the presence of arabinose, the AraC transcription factor activates the ParaBAD promoter, which activates transcription of the TetR protein which, in turn, represses transcription of the toxin. In the absence of arabinose, however, AraC suppresses transcription from the ParaBAD promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the araC gene encoding the AraC transcription factor is under the control of a constitutive promoter and is therefore constitutively expressed.

In one embodiment of the disclosure, the genetically engineered bacterium further comprises an anti-toxin under the control of a constitutive promoter. In this situation, in the presence of arabinose, the toxin is not expressed due to repression by TetR protein, and the anti-toxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the genetically engineered bacterium further comprises an anti-toxin under the control of the ParaBAD promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the genetically engineered bacteria of the present disclosure contain a kill switch having at least the following sequences: a ParaBAD promoter operably linked to a heterologous gene encoding an essential polypeptide not found in the recombinant bacterial cell (and required for survival), and a $P_{araC}$ promoter operably linked to a heterologous gene encoding the AraC transcription factor. In the presence of arabinose, the AraC transcription factor activates the ParaBAD promoter, which activates transcription of the heterologous gene encoding the essential polypeptide, allowing the recombinant bacterial cell to survive. In the absence of arabinose, however, AraC suppresses transcription from the ParaBAD promoter and the essential protein required for survival is not expressed. In this case, the recombinant bacterial cell dies in the absence of arabinose. In some embodiments, the sequence of ParaBAD promoter operably linked to a heterologous gene encoding an essential polypeptide not found in the recombinant bacterial cell can be present in the bacterial cell in conjunction with the TetR/toxin kill switch system described directly above. In some embodiments, the sequence of ParaBAD promoter operably linked to a heterologous gene encoding an essential polypeptide not found in the recombinant bacterial cell can be present in the bacterial cell in conjunction with the TetR/toxin/anti-toxin kill switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure further comprise the gene(s) encoding the components of any of the above-described kill switch circuits.

In any of the above-described embodiments, the bacterial toxin is selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-C51, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6, colicin E5, colicin D, colicin M, and cloacin DF13, or a biologically active fragment thereof.

In any of the above-described embodiments, the anti-toxin is selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, $MccE^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, the genetically engineered bacterium provided herein is an auxotroph. In one embodiment, the genetically engineered bacterium is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacterium provided herein further comprises a kill switch circuit, such as any of the kill switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin. In some embodiments, the engineered bacteria further comprise one or more genes encoding a toxin under the control of a promoter having a TetR repressor binding site and a gene encoding the TetR under the control of an inducible promoter that is induced by arabinose, such as ParaBAD. In some embodiments, the genetically engineered bacteria further comprise one or more genes encoding an anti-toxin.

In some embodiments, the genetically engineered bacterium is an auxotroph comprising a gene encoding a phenylalanine-metabolizing enzyme and further comprises a kill switch circuit, such as any of the kill switch circuits described herein.

In some embodiments, of the above described genetically engineered bacteria, the gene or gene cassette for producing the phenylalanine-metabolizing enzyme is present on a plasmid in the bacterium and operatively linked on the plasmid to the promoter that is induced under low-oxygen or anaerobic conditions. In other embodiments, the gene or gene cassette for producing the phenylalanine-metabolizing enzyme is present in the bacterial chromosome and is operatively linked in the chromosome to the promoter that is induced under low-oxygen or anaerobic conditions.

Pharmaceutical Compositions and Formulations

Pharmaceutical compositions comprising the genetically engineered bacteria of the invention may be used to treat, manage, ameliorate, and/or prevent diseases associated with hyperphenylalaninemia, e.g., PKU. Pharmaceutical compositions of the invention comprising one or more genetically engineered bacteria, alone or in combination with prophylactic agents, therapeutic agents, and/or and pharmaceutically acceptable carriers are provided. In certain embodiments, the pharmaceutical composition comprises one species, strain, or subtype of bacteria that are engineered to comprise the genetic modifications described herein. In alternate embodiments, the pharmaceutical composition comprises two or more species, strains, and/or subtypes of bacteria that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, PA. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4

(stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the invention provides methods of treating a disease associated with hyperphenylalaninemia or symptom(s) associated with hyperphenylalaninemia. In some embodiments, the disease is selected from the group consisting of: phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

In certain embodiments, the genetically engineered bacteria are capable of metabolizing phenylalanine in the diet in order to treat a disease or disorder associated with hyperphenylalaninemia, e.g., PKU. In some embodiments, the genetically engineered bacteria are delivered simultaneously with dietary protein. In other embodiments, the genetically engineered bacteria are not delivered simultaneously with dietary protein. Studies have shown that pancreatic and other glandular secretions into the intestine contain high levels of proteins, enzymes, and polypeptides, and that the amino acids produced as a result of their catabolism are reabsorbed back into the blood in a process known as "enterorecirculation" (Chang, 2007; Sarkissian et al., 1999). Thus, high intestinal levels of phenylalanine may be partially independent of food intake, and are available for breakdown by PAL. In some embodiments, the genetically engineered bacteria and dietary protein are delivered after a period of fasting or phenylalanine-restricted dieting. In these embodiments, a patient suffering from hyperphenylalaninemia may be able to resume a substantially normal diet, or a diet that is less restrictive than a phenylalanine-free diet. In some embodiments, the genetically engineered bacteria may be capable of metabolizing phenylalanine from additional sources, e.g., the blood, in order to treat a disease associated with hyperphenylalaninemia, e.g., PKU. In these embodiments, the genetically engineered bacteria need not be delivered simultaneously with dietary protein, and a phenylalanine gradient is generated, e.g., from blood to gut, and the genetically engineered bacteria metabolize phenylalanine and reduce phenylalaninemia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, the pharmaceutical composition described herein is administered to reduce phenylalanine levels in a subject. In some embodiments, the methods of the present disclosure reduce the phenylalanine levels in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the phenylalanine level in a subject before and after administration of the pharmaceutical composition. In some embodiments, the method of treating or ameliorating hyperphenylalaninemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, phenylalanine levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce phenylalanine. In some embodiments, the methods may include administration of the compositions of the invention to reduce phenylalanine to undetectable levels in a subject. In some embodiments, the methods may include administration of the compositions of the invention to reduce phenylalanine concentrations to undetectable levels, or to less than about 1%, 2%, 5%, 10%, 20%, 25%, 30%, 40%, 50%, 60%, 70%, 75%, or 80% of the subject's phenylalanine levels prior to treatment.

Figure 38:
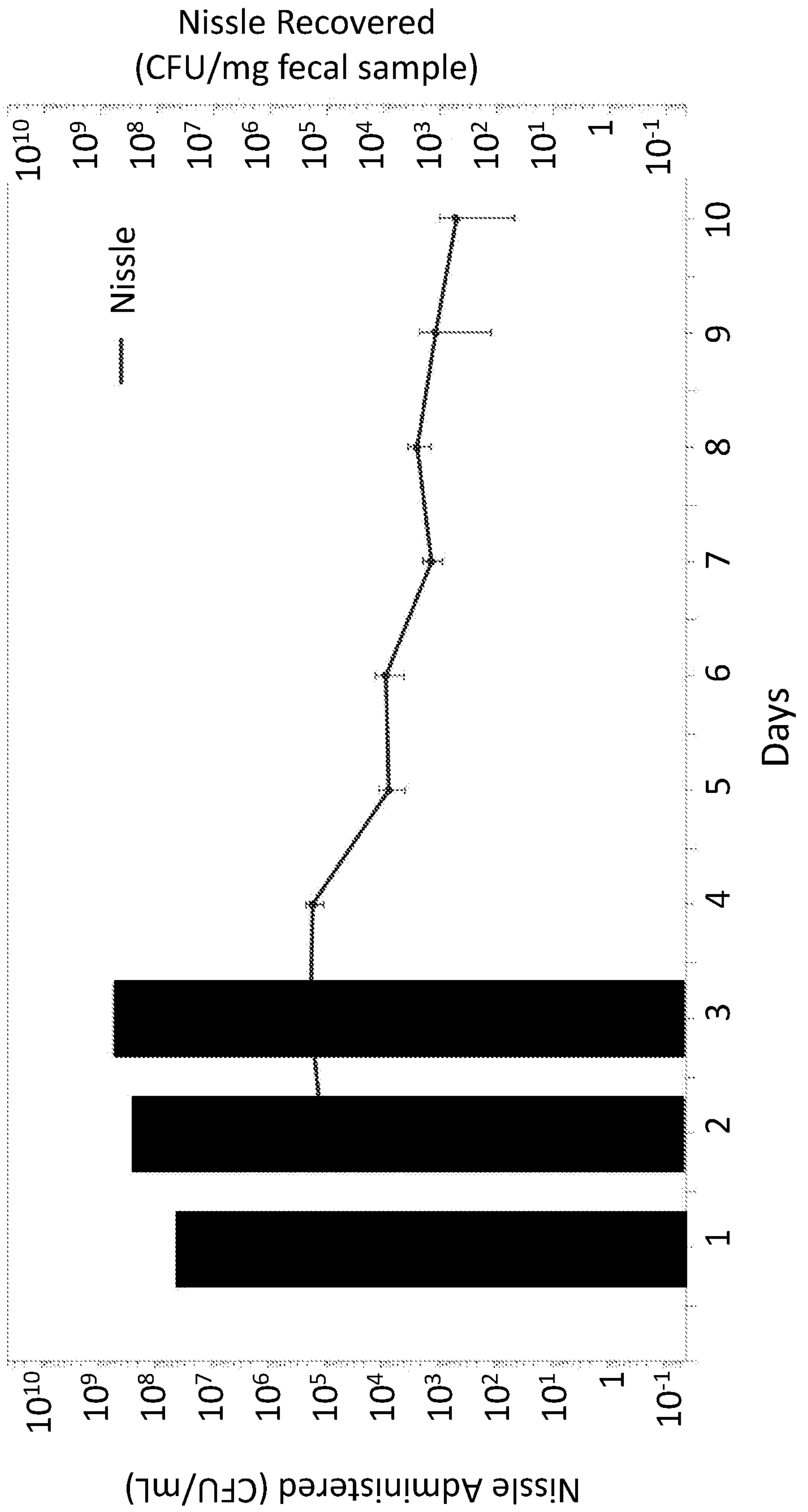
FIG. 38 depicts a graph of Nissle residence in vivo. Streptomycin-resistant Nissle was administered to mice via oral gavage without antibiotic pre-treatment. Fecal pellets from 6 total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

In certain embodiments, the genetically engineered bacteria are *E. coli* Nissle. The genetically engineered bacteria may be destroyed, e.g., by defense factors in the gut or blood serum (Sonnenbom et al., 2009) or by activation of a kill switch, several hours or days after administration. Thus, the pharmaceutical composition comprising the genetically engineered bacteria may be re-administered at a therapeutically effective dose and frequency. Length of Nissle residence in vivo in mice is shown in FIG. 38. In alternate embodiments, the genetically engineered bacteria are not destroyed within hours or days after administration and may propagate and colonize the gut.

The methods of the invention may comprise administration of the pharmaceutical composition alone or in combination with one or more additional therapeutic agents. In some embodiments, the pharmaceutical composition is administered in conjunction with the cofactor tetrahydrobiopterin (e.g., Kuvan/sapropterin), large neutral amino acids (e.g., tyrosine, tryptophan), glycomacropeptides, a probiotic (e.g., VSL3), an enzyme (e.g., pegylated-PAL), and/or other agents used in the treatment of phenylketonuria (Al Hafid and Christodoulou, 2015).

In some embodiments, the genetically engineered bacteria are administered in combination with one or more recombinantly produced PME enzymes, e.g. recombinant PAL, LAAD or PAH. In some embodiments, the recombinant enzymes are further formulated for improved stability and/or delivery. In some embodiments, the one or more PME enzyme administered in combination with the genetically engineered bacteria is peggylated. In some embodiments, the one or more PME enzyme administered in combination with the genetically engineered bacteria is delivered as a fusion protein. A non-limiting example of such a fusion protein is a fusion between a PME and a transduction domain for uptake into cells. A non-limiting example of such transduction domain or cell penetrating peptide is the TAT peptide. In some embodiments, the one or more PME enzyme administered in combination with the genetically engineered bacteria is formulated in a nanoparticle. A non-limiting example of such a nanoparticle is a dextran sulfate/chitosan PME nanoparticle. In some embodiments, the one or more PME enzyme administered in combination with the genetically engineered bacteria is delivered as a PME microsphere. A non-limiting example of such a microsphere is a barium alginate PME microsphere. In some embodiments, the one or more PME enzyme administered in combination with the genetically engineered bacteria is delivered as amorphous silica PME particles.

In some embodiments, the genetically engineered bacteria are administered in combination with PAL. In some embodiments, the genetically engineered bacteria are administered in combination with PAH. In some embodiments, the genetically engineered bacteria are administered in combination with LAAD. In some embodiments, the genetically engineered bacteria are administered in combination with PAL and PAH. In some embodiments, the genetically engineered bacteria are administered in combination with PAL and LAAD. In some embodiments, the genetically engineered bacteria are administered in combination with PAH and LAAD. In some embodiments, the genetically engineered bacteria are administered in combination with PAL, PAH, and LAAD.

In some embodiments, the genetically engineered bacteria are administered in combination with pegylated PAL. In some embodiments, the genetically engineered bacteria are administered in combination with pegylated PAH. In some embodiments, the genetically engineered bacteria are administered in combination with pegylated LAAD. In some embodiments, the genetically engineered bacteria are administered in combination with a PAL fusion protein, e.g., a cell penetrating peptide. In some embodiments, the genetically engineered bacteria are administered in combination with a PAH fusion protein, e.g., a cell penetrating peptide. In some embodiments, the genetically engineered bacteria are administered in combination with a LAAD fusion protein, e.g., a cell penetrating peptide. In some embodiments, the genetically engineered bacteria are administered in combination with PAL-nanoparticles. In some embodiments, the genetically engineered bacteria are administered in combination with PAH-nanoparticles. In some embodiments, the genetically engineered bacteria are administered in combination with LAAD nanoparticles. In some embodiments, the genetically engineered bacteria are administered in combination with PAL-microspheres. In some embodiments, the genetically engineered bacteria are administered in combination with PAH-microspheres. In some embodiments, the genetically engineered bacteria are administered in combination with LAAD-microspheres. In some embodiments, the genetically engineered bacteria are administered in combination with PAL-silica particles. In some embodiments, the genetically engineered bacteria are administered in combination with PAH-silica particles. In some embodiments, the genetically engineered bacteria are administered in combination with LAAD-silica particles.

In some embodiments, a recombinant enzyme replacement therapy or substitution therapy, e.g. PAL, PAH, and/or LAAD is administered without the genetically engineered bacteria.

In some embodiments, the one or more PME administered is PAL. In some embodiments, PAL is modified as described in Sakissian et al., 2011, Mol Genet Metab. 2011 November; 104(3): 249-254, the contents of which is herein incorporated by reference in its entirety. In some embodiments, the PAL is Av-p.C503S/p.C565S/p.F18A PAL. In some embodiments, the PAL is PEG-Av-p.C503S/p.C565S/p.F18A PAL.

In some embodiments, the PAL is PEGylated. In one embodiment, the pegylated PAL is from *Anabaena variabilis*. In one embodiment, the pegylated PAL is from *Photorhabdus luminescens*. In some embodiments, the one or more PME administered is PAH. In one embodiment, PAH is human PAH. In some embodiments, the one or more PME administered is LAAD. In one embodiment, the LAAD protein administered is derived from *Proteus mirabilis*. In some embodiments, the one or more PME administered in combination with PAL and PAH. In some embodiments, the one or more PME administered is PAL and LAAD. In some embodiments, the one or more PME administered is PAH and LAAD. In some embodiments, the one or more PME administered is PAL, PAH, and LAAD.

In some embodiments, the recombinant enzymes are further formulated for improved stability and/or delivery. In some embodiments, the one or more PME enzyme administered is peggylated. In some embodiments, the one or more PME enzyme administered is delivered as a fusion protein. A non-limiting example of such a fusion protein is a fusion between a PME and a transduction domain for uptake into cells. A non-limiting example of such transduction domain or cell penetrating peptide is the TAT peptide. In some embodiments, the one or more PME enzyme administered is formulated in a nanoparticle. A non-limiting example of such a nanoparticle is a dextran sulfate/chitosan PME nanoparticle. In some embodiments, the one or more PME enzyme administered is delivered as a PME microsphere. A non-limiting example of such a microsphere is a barium alginate PME microsphere. In some embodiments, the one or more PME enzyme administered is delivered as amorphous silica PME particles.

In some embodiments, pegylated PAL is administered. In some embodiments, pegylated LAAD is administered. In some embodiments peggylated LAAD from *Proteus mirabilis* is administered. In some embodiments, pegylated PAH is administered.

In one embodiment, a PAL fusion protein, e.g., with a cell penetrating peptide, is administered. In one embodiment, a LAAD fusion protein, e.g., with a cell penetrating peptide, is administered. In one embodiment, a PAH fusion protein, e.g., with a cell penetrating peptide, is administered. In some embodiments, PAL-nanoparticles are administered. In some embodiments, PAH-nanoparticles are administered. In some embodiments, LAAD-nanoparticles are administered. In some embodiments, PAL-microspheres are administered. In some embodiments, PAH-microspheres are administered. In some embodiments, LAAD-microspheres are administered. In some embodiments, PAL-silica particles are administered. In some embodiments, PAH-silica particles are administered. In some embodiments, LAAD-silica particles are administered.

In some embodiments the PME, e.g., PAH, PAL, and/or LAAD is formulated with aprotinin, e.g., 40 mg/ml aprotinin.

In some embodiments the PMEs are delivered as gene therapy. In some embodiments, a CRISPR technology is used. In some embodiments a gene therapy vector is used to deliver the one or more PME, e.g., PAL, LAAD, and/or PAH. Gene therapy vectors are known in the art and include, but are not limited to, retroviral vectors, adenoviral vectors, adeno-associated viral vectors. Alternatively, formulated or naked PME gene DNA or RNA can be delivered.

An important consideration in the selection of the one or more additional therapeutic agents is that the agent(s) should be compatible with the genetically engineered bacteria of the invention, e.g., the agent(s) must not interfere with or kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-phenylalanine diet. The dosage of the pharmaceutical composition and the frequency of administration may be selected based on the severity of the symptoms and the progression of the disease. The appropriate therapeutically effective dose and/or frequency of administration can be selected by a treating clinician.

The methods of the invention also include kits comprising the pharmaceutical composition described herein. The kit can include one or more other elements including, but not limited to: instructions for use; other reagents, e.g., a label, an additional therapeutic agent; devices or materials for measuring phenylalanine levels, or levels of other molecules or metabolites associated with hyperphenylalaninemia, in a subject; devices or other materials for preparing the pharmaceutical composition of the invention for administration; and devices or other materials for administration to a subject. Instructions for use can include guidance for therapeutic application, such as suggested dosages and/or modes of administration, e.g., in a patient with hyperphenylalaninemia. The kit can further contain at least one additional therapeutic agent, and/or one or more additional genetically engineered bacterial strains of the invention, formulated as appropriate, in one or more separate pharmaceutical preparations.

In some embodiments, the kit is used for administration of the pharmaceutical composition to a subject. In some embodiments, the kit is used for administration of the pharmaceutical composition, alone or in combination with one or more additional therapeutic agents, to a subject. In some embodiments, the kit is used for measuring phenylalanine levels (e.g., blood phenylalanine levels) in a subject before, during, or after administration of the pharmaceutical composition to the subject. In certain embodiments, the kit is used for administration and/or re-administration of the pharmaceutical composition, alone or in combination with one or more additional therapeutic agents, when blood phenylalanine levels are increased or abnormally high. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL.

Table 20 shows non-limiting examples of target degradation rates, based on levels of phenylalanine on average in classical PKU patients.

TABLE 20

| Target Degradation Rates | | | | | | | | | |
|---|---|---|---|---|---|---|---|---|---|
| | Age (years) | | | | | | | | |
| | 0-6 months | 7-12 months | 1-3 | 4-8 | 9-13 | 14-18 (M) | 14-18 (F) | >18 (M) | >18 (F) |
| RDA Protein (g/d) | 9.1 | 11 | 13 | 19 | 34 | 52 | 46 | 56 | 46 |
| Daily PHE (mg)-Healthy subject (1 g protein = 47 mg PHE) | 428 | 517 | 611 | 893 | 1598 | 2444 | 2162 | 2632 | 2162 |
| Daily PHE tolerance (mg) (Classical PKU) | 250 | 250 | 250 | 250 | 250 | 250 | 250 | 250 | 250 |
| Target Reduction (mg) | 178 | 267 | 361 | 643 | 1348 | 2194 | 1912 | 2382 | 1912 |
| Target Reduction (mmol) | 1.08 | 1.62 | 2.19 | 3.89 | 8.16 | 13.28 | 11.57 | 14.42 | 11.57 |
| Target degradation rate (μmol/$10^9$ CFUs/hr) (based on $3.10^{11}$ CFUs/day dose) assuming all dose functioning for 24 hours | 0.15 | 0.22 | 0.3 | 0.54 | 1.13 | 1.84 | 1.61 | 2 | 1.61 |
| Target degradation rate 2 hrs transit time (μmol/$10^9$ CFUs/hr) assuming 2 hour transit time per dose | 0.6 | 0.9 | 1.21 | 2.16 | 4.53 | 7.38 | 6.43 | 8.01 | 6.43 |
| Target degradation rate 6 hrs transit time (μmol/$10^9$ CFUs/hr) assuming 6 hour transit time per dose | 0.2 | 0.3 | 0.4 | 0.72 | 1.51 | 2.46 | 2.14 | 2.67 | 2.14 |

In some embodiments, the genetically engineered bacteria achieve a target degradation rate of about 0.15 to about 8.01 μmol/$10^9$ CFUs/hr. In some embodiments, the genetically engineered bacteria achieve a target degradation rate of about 0.15 to about 2 μmol/$10^9$ CFUs/hr. In some embodiments, the genetically engineered bacteria achieve a target degradation rate of about 0.6 to about 8.01 μmol/$10^9$ CFUs/hr. In some embodiments, the genetically engineered bacteria achieve a target degradation rate of about 0.2 to about 2.67 μmol/$10^9$ CFUs/hr.

In some embodiments, the genetically engineered bacteria achieve a target degradation rate of about 0.15 to about 0.6 μmol/$10^9$ CFUs/hr. In some embodiments, the genetically engineered bacteria achieve a target degradation rate of about 0.22 to about 0.9 μmol/$10^9$ CFUs/hr. In some embodiments, the genetically engineered bacteria achieve a target degradation rate of about 0.3 to about 1.21 μmol/$10^9$ CFUs/hr. In some embodiments, the genetically engineered bacteria achieve a target degradation rate of about 0.54 to about 2.16 μmol/$10^9$ CFUs/hr. In some embodiments, the genetically engineered bacteria achieve a target degradation rate of about 1.13 to about 4.53 μmol/$10^9$ CFUs/hr. In some embodiments, the genetically engineered bacteria achieve a target degradation rate of about 1.84 to about 7.38 μmol/$10^9$ CFUs/hr. In some embodiments, the genetically engineered bacteria achieve a target degradation rate of about 1.61 to about 6.43 μmol/$10^9$ CFUs/hr. In some embodiments, the genetically engineered bacteria achieve a target degradation rate of about 2 to about 8.01 μmol/$10^9$ CFUs/hr.

In some embodiments, the genetically engineered bacteria achieve a target degradation rate of about 0.1 to about 1

μmol/$10^9$ CFUs/hr. In some embodiments, the genetically engineered bacteria achieve a target degradation rate of about 1 to about 2 mol/$10^9$ CFUs/hr. In some embodiments, the genetically engineered bacteria achieve a target degradation rate of about 2 to about 3 μmol/$10^9$ CFUs/hr. In some embodiments, the genetically engineered bacteria achieve a target degradation rate of about 3 to about 4 mol/$10^9$ CFUs/hr. In some embodiments, the genetically engineered bacteria achieve a target degradation rate of about 4 to about 5 μmol/$10^9$ CFUs/hr. In some embodiments, the genetically engineered bacteria achieve a target degradation rate of about 5 to about 6 mol/$10^9$ CFUs/hr. In some embodiments, the genetically engineered bacteria achieve a target degradation rate of about 6 to about 7 μmol/$10^9$ CFUs/hr. In some embodiments, the genetically engineered bacteria achieve a target degradation rate of about 7 to about 8 mol/$10^9$ CFUs/hr.

In some embodiments, the genetically engineered bacteria achieve a target reduction rate of less than 0.15 μmol/$10^9$ CFUs/hr. In some embodiments, the genetically engineered bacteria achieve a target degradation rate of greater than 8.01 μmol/$10^9$ CFUs/hr.

In some embodiments, the genetically engineered bacteria achieve a target reduction of between about 178 mg and 2382 mg. In some embodiments, the genetically engineered bacteria achieve a target reduction of 1.08 mmol to 14.42 mmol. In some embodiments, the reduction is less than 1.08 mmol. In some embodiments, the reduction is greater than 14.42 mmol.

In some embodiments, target reduction and target degradation rates are based on classical PKU phenylalanine levels. In some embodiments, the target reduction and target degradation rates are based on phenylalanine levels observed in mild PKU. In some embodiments, target reduction and target degradation rates are based on phenylalanine levels observed in mild hyperphenylalaninemia.

Treatment In Vivo

The genetically engineered bacteria of the invention may be evaluated in vivo, e.g., in an animal model. Any suitable animal model of a disease or condition associated with hyperphenylalaninemia may be used (see, e.g., Sarkissian et al., 1999). In some embodiments, the animal model is a mouse model of PKU. In certain embodiments, the mouse model of PKU is an PAH mutant BTBR mouse (BTBR-$Pah^{enu2}$, Jackson Laboratories). In these embodiments, the mouse model contains a chemically (ENU)-induced homozygous missense mutation (T835C) in exon 7 of the Pah gene, which results in a phenylalanine to serine substitution at amino acid 263 (F263S). This residue is located in the active site of the PAH enzyme, as shown by crystal structure analysis, and results in the complete loss of PAH activity. On normal diets, these mutant mice demonstrate a 10- to 20-fold increase in serum phenylalanine levels compared to unaffected controls. The genetically engineered bacteria of the invention may be administered to the animal, e.g., by oral gavage, and treatment efficacy is determined, e.g., by measuring blood phenylalanine and/or cinnamate before and after treatment. In animal models, it is noted that residence time of the genetically engineered bacteria within the GI tract may be shorter than residence time in humans. The animal may be sacrificed, and tissue samples may be collected and analyzed.

In some embodiments, pharmacokinetics and pharmacodynamic studies may be conducted in non-human primates to determine any potential toxicities arising from administration of the genetically engineered bacteria. the pharmacokinetics and pharmacodynamics of the genetically engineered bacteria. Non-limiting examples of such studies are described in Examples 30 and 31.

In some embodiments, the genetically engineered bacteria expressing LAAD can be specifically detected in the feces and differentiated from other *E. coli* strains. A Phenylalanine Deaminase Test "Phenylalanine Agar Slant" can be used for this purpose. Phenylalanine agar used to determine whether the microbe can use phenylalanine and convert it to phenyl pyruvate. When the test chemicals are added to the tube containing the sample on the phenylalanine agar, phenylpyruvate is converted to a green compound, indicating a positive test. Wild type *E. coli* does not produce phenylpyruvate, since they do not encode an enzyme, which can produce phenylpyruvate from phenylalanine, allowing differentiation from other *E coli* strains. The genetically engineered bacteria can be differentiated from other bacterial species which are able to produce phenylpyruvate by PCR-based tests known in the art. For example, species specific sequences can be amplified. For example, universal PCR that amplifies conserved regions in various bacteria is ideal to detect any pathogen in screening of specimens. For this purpose, the conserved region of the 16S rRNA gene can be used as a target gene for the universal PCR; the 16S rRNA gene contains species-specific regions by which a large number of bacterial species can be differentiated.

In some embodiments, the Phenylalanine Deaminase Test can be used to detect the genetically engineered bacteria in a feces sample. In some embodiments, PCR-based tests can be conducted to differentiate the genetically engineered bacteria from other bacterial species.

Screening Methods

In some embodiments, of the disclosure a genetically engineered strain may be improved upon by using screening and selection methods, e.g., to increase PME enzymatic activity or to increase the ability of a strain to take up phenylalanine. In some embodiments, the screen serves to generate a bacterial strain with improved PME activity. In some embodiments, the screen serves to generate a bacterial strain which has improved phenylalanine uptake ability. In some embodiments, the screen may identify a bacterial strain with both improved PME activity and enhanced substrate import. Non-limiting examples of methods of screening which can be used are described herein.

Generation of Bacterial Strains with Enhance Ability to Transport Biomolecules

Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing an amino acid is disrupted a strain capable of high-affinity capture of said amino acid can be evolved via ALE. First, the strain is grown in varying concentrations of the auxotrophic amino acid, until a minimum concentration to support growth is established. The strain is then passaged at that concentration, and diluted into lowering concentrations of the amino acid at regular intervals. Over time, cells that are most competitive for the amino acid—at growth-limiting concentrations—will come to dominate the population. These strains will likely have mutations in their amino acid-transporters resulting in increased ability to import the essential and limiting amino acid.

Similarly, by using an auxotroph that cannot use an upstream metabolite to form an amino acid, a strain can be evolved that not only can more efficiently import the upstream metabolite, but also convert the metabolite into the essential downstream metabolite. These strains will also evolve mutations to increase import of the upstream metabolite, but may also contain mutations which increase expression or reaction kinetics of downstream enzymes, or that reduce competitive substrate utilization pathways.

In the previous examples, a metabolite innate to the microbe was made essential via mutational auxotrophy and selection was applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate. Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD[1]. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. Ø. Cumulative Number of Cell Divisions as a Meaningful Timescale for Adaptive Laboratory Evolution of *Escherichia coli*. *PLoS ONE* 6, e26172 (2011).

In some embodiments, the ALE method can be used to identify genetically engineered bacteria with improved phenylalanine uptake.

Specific Screen to Improve PME Activity

Screens using genetic selection are conducted to improve phenylalanine consumption in the genetically engineered bacteria. Toxic phenylalanine analogs exert their mechanism of action (MOA) by being incorporated into cellular protein, causing cell death. These compounds, such as paralog p-fluoro-DL-phenylalanine and ortholog o-fluoro-DL-phenylalanine have utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds, and can be screened for and selected on this basis.

REFERENCES

Al Hafid N, Christodoulou J. Phenylketonuria: a review of current and future treatments. Transl Pediatr. 2015 October; 4(4):304-317. PMID: 26835392;

Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098;

Andersen et al. Uracil uptake in *Escherichia coli* K-12: isolation of uraA mutants and cloning of the gene. J Bacteriol. 1995 April; 177(8):2008-2013. PMID: 7721693;

Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887;

Arthur et al. Intestinal inflammation targets cancer-inducing activity of the microbiota. Science. 2012 Oct. 5; 338 (6103):120-123. PMID: 22903521;
Callura et al. Tracking, Tuning and terminating microbial physiology using synthetic riboregulators. Proc Natl Acad Sci USA. 2010; 27(36): 15898-15903. PMID: 20713708;
Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-2844. PMID: 19477902;
Chang, ed. (2007) "Use of Enzyme Artificial Cells for Genetic Enzyme Defects." In Artificial Cells: Biotechnology, Nanomedicine, Regenerative Medicine, Blood Substitutes, Bioencapsulation, and Cell/Stem Cell Therapy. World Scientific Publishing, pp. 147-159;
Clarkson et al. Diaminopimelic acid and lysine auxotrophs of *Pseudomonas aeruginosa* 8602. J Gen Microbiol. 1971 May; 66(2):161-169. PMID: 4999073;
Cuevas-Ramos et al. *Escherichia coli* induces DNA damage in vivo and triggers genomic instability in mammalian cells. Proc Natl Acad Sci USA. 2010 Jun. 22; 107(25): 11537-11542. PMID: 20534522;
Danino et al. Programmable probiotics for detection of cancer in urine. Sci Transl Med. 2015 May 27; 7(289): 289ra84. PMID: 26019220;
Deutscher. The mechanisms of carbon catabolite repression in bacteria. Curr Opin Microbiol. 2008 April; 11(2):87-93. PMID: 18359269;
Dinleyici et al. *Saccharomyces boulardii* CNCM 1-745 in different clinical conditions. Expert Opin Biol Ther. 2014 November; 14(11): 1593-1609. PMID: 24995675;
Dobbelaere et al. Evaluation of nutritional status and pathophysiology of growth retardation in patients with phenylketonuria. J Inherit Metab Dis. 2003; 26(1):1-11. PMID: 12872834;
Eiglmeier et al. Molecular genetic analysis of FNR-dependent promoters. Mol Microbiol. 1989 July; 3(7):869-878. PMID: 2677602;
Estrem et al. Identification of an UP element consensus sequence for bacterial promoters. Proc Natl Acad Sci USA. 1998 Aug. 18; 95(17):9761-9766. PMID: 9707549;
Galimand et al. Positive FNR-like control of anaerobic arginine degradation and nitrate respiration in *Pseudomonas aeruginosa*. J Bacteriol. 1991 March; 173(5):1598-1606. PMID: 1900277;
Gardner et al. Construction of a genetic toggle switch in *Escherichia coli*. Nature. 2000; 403:339-342. PMID: 10659857;
Gerdes et al. Essential genes on metabolic maps. Curr Opin Biotechnol. 2006 October; 17(5):448-456. PMID: 16978855;
Gilbert et al. Molecular cloning of the phenylalanine ammonia lyase gene from *Rhodosporidium toruloides* in *Escherichia coli* K-12. J Bacteriol. 1985 January; 161(1): 314-320. PMID: 2981805;
Görke B, Stülke J. Carbon catabolite repression in bacteria: many ways to make the most out of nutrients. Nat Rev Microbiol. 2008 August; 6(8):613-624. PMID: 18628769;
Hasegawa et al. Activation of a consensus FNR-dependent promoter by DNR of *Pseudomonas aeruginosa* in response to nitrite. FEMS Microbiol Lett. 1998 Sep. 15; 166(2):213-217. PMID: 9770276;
Hoeks et al. Adult issues in phenylketonuria. Neth J Med. 2009 January; 67(1):2-7. PMID: 19155540;
Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476;
Hosseini et al. Propionate as a health-promoting microbial metabolite in the human gut. Nutr Rev. 2011 May; 69(5): 245-258. PMID: 21521227;
Isabella et al. Deep sequencing-based analysis of the anaerobic stimulon in *Neisseria gonorrhoeae*. BMC Genomics. 2011 Jan. 20; 12:51. PMID: 21251255;
Ivanovska et al. Pediatric drug formulations: a review of challenges and progress. Pediatrics. 2014 August; 134(2): 361-372. PMID: 25022739; Kobe et al. Regulation and crystallization of phosphorylated and dephosphorylated forms of truncated dimeric phenylalanine hydroxylase. Protein Sci. 1997 June; 6(6):1352-1357. PMID: 9194198;
Kwok et al. Nucleotide sequence of a full-length complementary DNA clone and amino acid sequence of human phenylalanine hydroxylase. Biochemistry 1985 Jan. 29; 24(3):556-561. PMID: 2986678;
Leonard J V (2006). Disorders of the urea cycle and related enzymes. *Inborn Metabolic Diseases,* 4$^{th}$ ed (pp. 263-272). Springer Medizin Verlag Heidelberg;
Longo et al. Phase 1 Trial of Subcutaneous rAvPAL-PEG in Subjects with Phenylketonuria. Lancet. 2014 Jul. 5; 384 (9937):37-44;
Lopez G, Anderson J C. Synthetic Auxotrophs with Ligand-Dependent Essential Genes for a BL21(DE3) Biosafety Strain. ACS Synth Biol. 2015 Dec. 18; 4(12):1279-1286. PMID: 26072987;
Macleod et al. Nutritional Management of Phenylketonuria. Ann Nestle Eng. 2010 June; 68(2):58-69. PMID: 22475869;
Meadow et al. Biosynthesis of diaminopimelic acid and lysine in *Escherichia coli*. Biochem J. 1959 July; 72(3): 396-400. PMID: 16748796;
Miller (1972) Experiments in Molecular Genetics. Cold Spring Harbor Laboratory Press, Cold Spring Harbor, NY;
Moffitt et al. Discovery of two cyanobacterial phenylalanine ammonia lyases: kinetic and structural characterization. Biochemistry. 2007 Jan. 30; 46(4): 1004-1012. PMID: 17240984;
Moore et al. Regulation of FNR dimerization by subunit charge repulsion. J Biol Chem. 2006 Nov. 3; 281(44): 33268-33275. PMID: 16959764;
Nougayrede et al. *Escherichia coli* induces DNA double-strand breaks in eukaryotic cells. Science. 2006 Aug. 11; 313(5788):848-51. PMID: 16902142;
Olier et al. Genotoxicity of *Escherichia coli* Nissle 1917 strain cannot be dissociated from its probiotic activity. Gut Microbes. 2012 November-December; 3(6):501-509. PMID: 22895085;
Pi et al. Cloning and sequencing of the pheP gene, which encodes the phenylalanine-specific transport system of *Escherichia coli*. J Bacteriol. 1991 June; 173(12):3622-3629. PMID: 1711024;
Pi et al. Topology of the phenylalanine-specific permease of *Escherichia coli*. J Bacteriol. 1996 May; 178(9):2650-2655. PMID: 8626334;
Pi et al. Functional consequences of changing proline residues in the phenylalanine-specific permease of *Escherichia coli*. J Bacteriol. 1998 November; 180(21):5515-5519. PMID: 9791098;
Purcell et al. Towards a whole-cell modeling approach for synthetic biology. Chaos. 2013 June; 23(2):025112. PMID: 23822510;

Ray et al. The effects of mutation of the anr gene on the aerobic respiratory chain of *Pseudomonas aeruginosa*. FEMS Microbiol Lett. 1997 Nov. 15; 156(2):227-232. PMID: 9513270;

Reister et al. Complete genome sequence of the Gram-negative probiotic *Escherichia coli* strain Nissle 1917. J Biotechnol. 2014 Oct. 10; 187:106-107. PMID: 25093936;

Rembacken et al. Non-pathogenic *Escherichia coli* versus mesalazine for the treatment of ulcerative colitis: a randomised trial. Lancet. 1999 Aug. 21; 354(9179):635-639. PMID: 10466665;

Remington's Pharmaceutical Sciences (2012), $22^{nd}$ ed. Mack Publishing Co, Easton, PA.

Salmon et al. Global gene expression profiling in *Escherichia coli* K12. The effects of oxygen availability and FNR. J Biol Chem. 2003 Aug. 8; 278(32):29837-29855. PMID: 12754220;

Sarkissian et al. A different approach to treatment of phenylketonuria: phenylalanine degradation with recombinant phenylalanine ammonia lyase. Proc Natl Acad Sci USA. 1999 Mar. 2; 96(5):2339-2344. PMID: 10051643;

Sat et al. The *Escherichia coli* mazEF suicide module mediates thymineless death. J Bacteriol. 2003 March; 185(6):1803-1807. PMID: 12618443;

Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-1481. PMID: 1787797;

Schultz. Clinical use of *E. coli* Nissle 1917 in inflammatory bowel disease. Inflamm Bowel Dis. 2008 July; 14(7): 1012-1018. PMID: 18240278;

Sonnenborn et al. The non-pathogenic *Escherichia coli* strain Nissle 1917—features of a versatile probiotic. Microbial Ecology in Health and Disease. 2009; 21:122-158;

Trunk et al. Anaerobic adaptation in *Pseudomonas aeruginosa*: definition of the Anr and Dnr regulons. Environ Microbiol. 2010 June; 12(6):1719-1733. PMID: 20553552;

Ukena et al. Probiotic *Escherichia coli* Nissle 1917 inhibits leaky gut by enhancing mucosal integrity. PLoS One. 2007 Dec. 12; 2(12):e1308. PMID: 18074031;

Unden et al. Alternative respiratory pathways of *Escherichia coli*: energetics and transcriptional regulation in response to electron acceptors. Biochim Biophys Acta. 1997 Jul. 4; 1320(3):217-234. PMID: 9230919;

Vockley et al. Phenylalanine hydroxylase deficiency: diagnosis and management guideline. Genet Med. 2014 February; 16(2):188-200. PMID: 24385074;

Wanner et al. The phenylalanine ammonia-lyase gene family in *Arabidopsis thaliana*. Plant Mol Biol. 1995 January; 27(2):327-338. PMID: 7888622;

Williams et al. The gene stlA encodes a phenylalanine ammonia-lyase that is involved in the production of a stilbene antibiotic in *Photorhabdus luminescens* TT01. Microbiology. 2005 August; 151(Pt 8):2543-2550. PMID: 16079333.

Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-693. PMID: 8868444;

Wright et al. GeneGuard: A Modular Plasmid System Designed for Biosafety. ACS Synth Biol. 2015 Mar. 20; 4(3):307-316. PMID: 24847673;

Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598;

Xiang L, Moore B S. Biochemical characterization of a prokaryotic phenylalanine ammonia lyase. J Bacteriol. 2005 June; 187(12):4286-4289. PMID: 15937191;

Zhang R, Lin Y. DEG 5.0, a database of essential genes in both prokaryotes and eukaryotes. Nucleic Acids Res. 2009 January; 37(Database issue):D455-D458. PMID: 18974178;

Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-1490. PMID: 1787798.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Example 1. Construction of PAL Plasmids

To facilitate inducible production of PAL in *Escherichia coli* Nissle, the PAL gene of *Anabaena variabilis* ("PAL1") or *Photorhabdus luminescens* ("PAL3"), as well as transcriptional and translational elements, were synthesized (Gen9, Cambridge, MA) and cloned into vector pBR322. The PAL gene was placed under the control of an inducible promoter. Low-copy and high-copy plasmids were generated for each of PAL1 and PAL3 under the control of an inducible FNR promoter or a Tet promoter. Exemplary FNR promoters are shown in Table 3. Organization and nucleotide sequences of these constructs are shown in FIGS. 6-9. However, as noted above, other promoters may be used to drive expression of the PAL gene, other PAL genes may be used, and other phenylalanine metabolism-regulating genes may be used.

Example 2. Transforming *E. coli*

Each of the plasmids described herein was transformed into *E. coli* Nissle for the studies described herein according to the following steps. All tubes, solutions, and cuvettes were pre-chilled to 4° C. An overnight culture of *E. coli* Nissle was diluted 1:100 in 5 mL of lysogeny broth (LB) containing ampicillin and grown until it reached an $OD_{600}$ of 0.4-0.6. The *E. coli* cells were then centrifuged at 2,000 rpm for 5 min at 4° C., the supernatant was removed, and the cells were resuspended in 1 mL of 4° C. water. The *E. coli* were again centrifuged at 2,000 rpm for 5 min at 4° C., the supernatant was removed, and the cells were resuspended in 0.5 mL of 4° C. water. The *E. coli* were again centrifuged at 2,000 rpm for 5 min at 4° C., the supernatant was removed, and the cells were finally resuspended in 0.1 mL of 4° C. water. The electroporator was set to 2.5 kV. Plasmid (0.5 μg) was added to the cells, mixed by pipetting, and pipetted into a sterile, chilled cuvette. The dry cuvette was placed into the sample chamber, and the electric pulse was applied. One mL of room-temperature SOC media was added immediately, and the mixture was transferred to a culture tube and incubated at 37° C. for 1 hr. The cells were spread out on an LB plate containing ampicillin and incubated overnight.

Example 3. Comparison of Phenylalanine Metabolism Between High-Copy and Low Copy Plasmids Expressing PAL1 and PAL2

Genetically engineered bacteria comprising the same PAL gene, either PAL3 on a low-copy plasmid or high copy plasmid (SYN-PKU101 and SYN-PKU102) or PAL3 on a low-copy plasmid or a high copy plasmid (SYN-PKU201 and SYN-PKU202) were assayed for phenylalanine metabolism in vitro.

Engineered bacteria were induced with anhydrous tetracycline (ATC), and then grown in culture medium supplemented with 4 mM (660,000 ng/mL) of phenylalanine for 2 hours. Samples were removed at 0 hrs, 4 hrs, and 23 hrs, and phenylalanine (FIG. 15A) and trans-cinnamic acid (TCA) (FIG. 15B) concentrations were determined by mass spectrometry as described in Examples 24-26.

High copy plasmids and low copy plasmid strains were found to metabolize and reduce phenylalanine to similar levels (FIG. 15). A greater reduction in phenylalanine levels and increase in TCA levels was observed in the strains expressing PAL3.

Example 4. Phenylalanine Transporter—Integration of PheP into the Bacterial Chromosome In some embodiments, it may be advantageous to increase phenylalanine transport into the cell, thereby enhancing phenylalanine metabolism. Therefore, a second copy of the native high affinity phenylalanine transporter, PheP, driven by an inducible promoter, was inserted into the Nissle genome through homologous recombination. Organization of the construct is shown in FIG. 11. The pheP gene was placed downstream of the $P_{tet}$ promoter, and the tetracycline repressor, TetR, was divergently transcribed (see, e.g., FIG. 11). This sequence was synthesized by Genewiz (Cambridge, MA). To create a vector capable of integrating the synthesized TetR-PheP construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome (FIG. 10). Gibson assembly was used to clone the TetR-PheP fragment between these arms. PCR was used to amplify the region from this plasmid containing the entire sequence of the homology arms, as well as the pheP sequence between them. This PCR fragment was used to transform electrocompetent Nissle-pKD46, a strain that contains a temperature-sensitive plasmid encoding the lambda red recombinase genes. After transformation, cells were grown for 2 hrs before plating on chloramphenicol at 20 μg/mL at 37° C. Growth at 37° C. cures the pKD46 plasmid. Transformants containing anhydrous tetracycline (ATC)-inducible pheP were lac-minus (lac-) and chloramphenicol resistant.

Example 5. Effect of the Phenylalanine Transporter on Phenylalanine Degradation

To determine the effect of the phenylalanine transporter on phenylalanine degradation, phenylalanine degradation and trans-cinnamate accumulation achieved by genetically engineered bacteria expressing PAL1 or PAL3 on low-copy (LC) or high-copy (HC) plasmids in the presence or absence of a copy of pheP driven by the Tet promoter integrated into the chromosome was assessed.

For in vitro studies, all incubations were performed at 37° C. Cultures of *E. coli* Nissle transformed with a plasmid comprising the PAL gene driven by the Tet promoter were grown overnight and then diluted 1:100 in LB. The cells were grown with shaking (200 rpm) to early log phase. Anhydrous tetracycline (ATC) was added to cultures at a concentration of 100 ng/mL to induce expression of PAL, and bacteria were grown for another 2 hrs. Bacteria were then pelleted, washed, and resuspended in minimal media, and supplemented with 4 mM phenylalanine. Aliquots were removed at 0 hrs, 2 hrs, and 4 hrs for phenylalanine quantification (FIG. 16A), and at 2 hrs and 4 hrs for cinnamate quantification (FIG. 16B), by mass spectrometry, as described in Examples 24-26. As shown in FIG. 16, expression of pheP in conjunction with PAL significantly enhances the degradation of phenylalanine as compared to PAL alone or pheP alone. Notably, the additional copy of pheP permitted the complete degradation of phenylalanine (4 mM) in 4 hrs (FIG. 16A). FIG. 16B depicts cinnamate levels in samples at 2 hrs and 4 hrs post-induction. Since cinnamate production is directly correlated with phenylalanine degradation, these data suggest that phenylalanine disappearance is due to phenylalanine catabolism, and that cinnamate may be used as an alternative biomarker for strain activity. PheP overexpression improves phenylalanine metabolism in engineered bacteria.

In conclusion, in conjunction with pheP, even low-copy PAL-expressing plasmids are capable of almost completely eliminating phenylalanine from a test sample (FIGS. 16A and 16B). Furthermore, without wishing to be bound by theory, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with a high-copy PAL-expressing plasmid.

Example 6. FNR Promoter Activity

Figure 18:
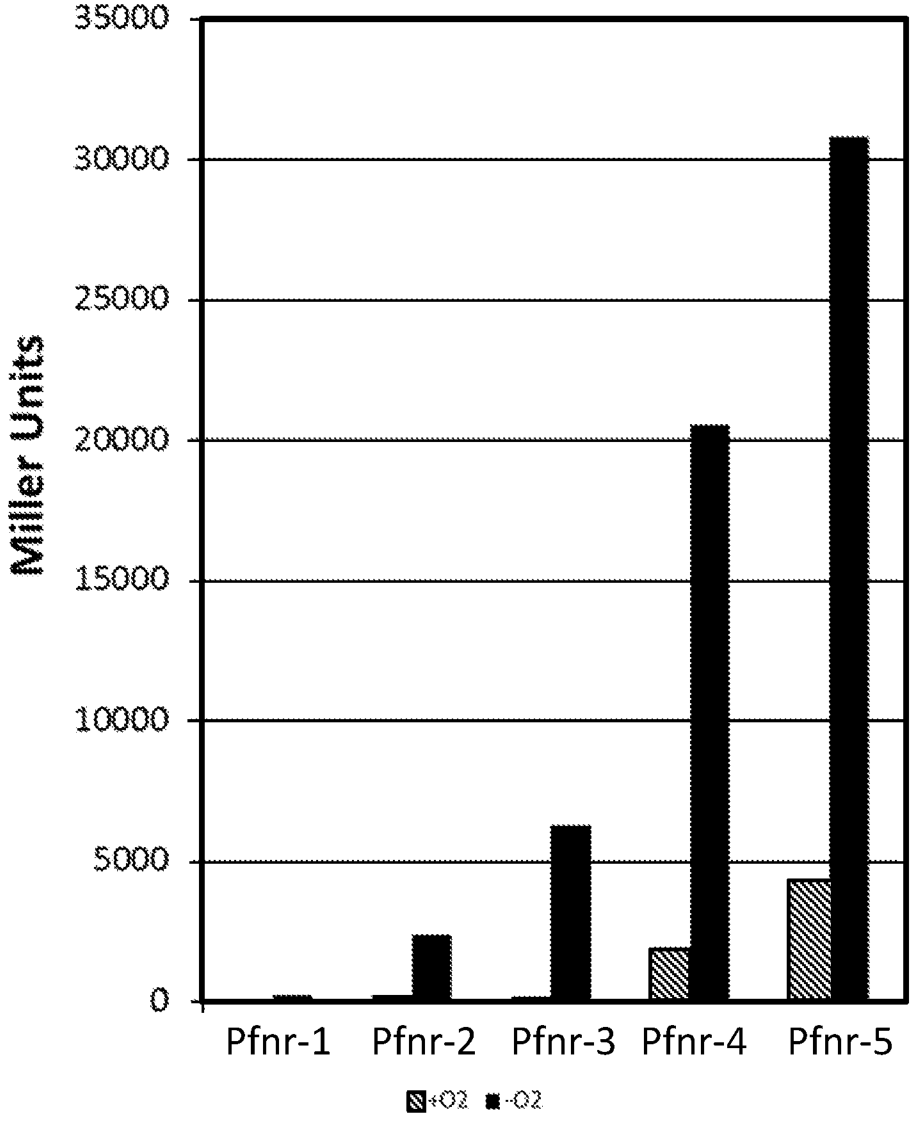
FIG. 18 depicts β-galactosidase levels in samples comprising bacteria harboring a low-copy plasmid expressing lacZ from an FNR-responsive promoter selected from the exemplary FNR promoters shown Table 3 (Pfnr1-5). Different FNR-responsive promoters were used to create a library of anaerobic-inducible reporters with a variety of expression levels and dynamic ranges. These promoters included strong ribosome binding sites. Bacterial cultures were grown in either aerobic ($+O_2$) or anaerobic conditions ($-O_2$). Samples were removed at 4 hrs and the promoter activity based on β-galactosidase levels was analyzed by performing standard β-galactosidase colorimetric assays.

In order to measure the promoter activity of different FNR promoters, the lacZ gene, as well as transcriptional and translational elements, were synthesized (Gen9, Cambridge, MA) and cloned into vector pBR322. The lacZ gene was placed under the control of any of the exemplary FNR promoter sequences disclosed in Table 3. The nucleotide sequences of these constructs are shown in Tables 21-28 (SEQ ID NOs 31-38). However, as noted above, the lacZ gene may be driven by other inducible promoters in order to analyze activities of those promoters, and other genes may be used in place of the lacZ gene as a readout for promoter activity. Alternatively, beta-galactosidase may be used as a reporter, exemplary results are shown in FIG. 18.

Table 21 shows the nucleotide sequence of an exemplary construct comprising a gene encoding lacZ, and an exemplary FNR promoter, $P_{fnr1}$ (SEQ ID NO: 3). The construct comprises a translational fusion of the Nissle nirB1 gene and the lacZ gene, in which the translational fusions are fused in frame to the $8^{th}$ codon of the lacZ coding region. The $P_{fnr1}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 22 shows the nucleotide sequence of an exemplary construct comprising a gene encoding lacZ, and an exemplary FNR promoter, $P_{fnr2}$ (SEQ ID NO: 6). The construct comprises a translational fusion of the Nissle ydfZ gene and the lacZ gene, in which the translational fusions are fused in frame to the $8^{th}$ codon of the lacZ coding region. The $P_{fnr2}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 23 shows the nucleotide sequence of an exemplary construct comprising a gene encoding lacZ, and an exemplary FNR promoter, $P_{fnr3}$ (SEQ ID NO: 7). The construct comprises a transcriptional fusion of the Nissle nirB gene and the lacZ gene, in which the transcriptional fusions use only the promoter region fused to a strong ribosomal binding site. The $P_{fnr3}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 24 shows the nucleotide sequence of an exemplary construct comprising a gene encoding lacZ, and an exemplary FNR promoter, $P_{fnr4}$ (SEQ ID NO: 8). The construct comprises a transcriptional fusion of the Nissle ydfZ gene and the lacZ gene. The $P_{fnr4}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 25 shows the nucleotide sequence of an exemplary construct comprising a gene encoding lacZ, and an exemplary FNR promoter, PfnrS (SEQ ID NO: 9). The construct comprises a transcriptional fusion of the anaerobically induced small RNA gene, fnrS1, fused to lacZ. The $P_{fnrs}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 26 shows the nucleotide sequence of an exemplary construct comprising a gene encoding PAL3, and an exemplary FNR promoter, $P_{fnr3}$ (SEQ ID NO: 7). The construct comprises a transcriptional fusion of the Nissle nirB gene and the PAL3 gene, in which the transcriptional fusions use only the promoter region fused to a strong ribosomal binding site. The $P_{fnr3}$ sequence is bolded lower case, and the predicted ribosome binding site within the promoter is underlined. The PAL3 sequence is underlined upper case. ATG site is bolded upper case, and the cloning sites used to synthesize the construct are shown in regular upper case.

Table 27 shows the nucleotide sequences of an exemplary construct comprising a gene encoding PAL3, and an exemplary FNR promoter, $P_{fnr4}$ (SEQ ID NO: 8). The construct comprises a transcriptional fusion of the Nissle ydfZ gene and the PAL3 gene. The $P_{fnr4}$ sequence is bolded lower case, and the predicted ribosome binding site within the promoter is underlined. The PAL3 sequence is underlined upper case. ATG site is bolded upper case, and the cloning sites used to synthesize the construct are shown in regular upper case.

Table 28 shows the nucleotide sequences of an exemplary construct comprising a gene encoding PAL3, and an exemplary FNR promoter, $P_{fnrs}$ (SEQ ID NO: 9). The construct comprises a transcriptional fusion of the anaerobically induced small RNA gene, fnrS1, fused to PAL3. The Pfnrs sequence is bolded lower case, and the predicted ribosome binding site within the promoter is underlined. The PAL3 sequence is underlined upper case. ATG site is bolded upper case, and the cloning sites used to synthesize the construct are shown in regular upper case.

TABLE 21

| Nucleotide sequences of Pfnr1-lacZ construct, low-copy (SEQ ID NO: 31) |
|---|
| GGTACC**gtcagcataacaccctgacctctcattaattgttcatgccgg** |
| **gcggcactatcgtcgtccggccttttcctctcttactctgctacgtac** |
| **atctatttctataaatccgttcaatttgtctgtttttttgcacaaacat** |
| **gaaatatcagacaattccgtgacttaagaaaatttatacaaatcagca** |
| **atataccccttaaggagtatataaaggtgaatttgatttacatcaata** |
| **agcggggttgctgaatcgttaaggtaggcggtaatagaaaagaaatcg** |
| **aggcaaaaATGagcaaagtcagactcgcaattat**GGATCCTCTGGCCG |
| TCGTATTACAACGTCGTGACTGGGAAAACCCTGGCGTTACCCAACTTA |
| ATCGCCTTGCGGCACATCCCCCTTTCGCCAGCTGGCGTAATAGCGAAG |
| AGGCCCGCACCGATCGCCCTTCCCAACAGTTGCGCAGCCTGAATGGCG |
| AATGGCGCTTTGCCTGGTTTCCGGCACCAGAAGCGGTGCCGGAAAGCT |
| GGCTGGAGTGCGATCTTCCTGACGCCGATACTGTCGTCGTCCCCTCAA |
| ACTGGCAGATGCACGGTTACGATGCGCCTATCTACACCAACGTGACCT |
| ATCCCATTACGGTCAATCCGCCGTTTGTTCCCGCGGAGAATCCGACAG |
| GTTGTTACTCGCTCACATTTAATATTGATGAAAGCTGGCTACAGGAAG |
| GCCAGACGCGAATTATTTTTGATGGCGTTAACTCGGCGTTTCATCTGT |
| GGTGCAACGGGCGCTGGGTCGGTTACGGCCAGGACAGCCGTTTGCCGT |
| CTGAATTTGACCTGAGCGCATTTTTACGCGCCGGAGAAAACCGCCTCG |
| CGGTGATGGTGCTGCGCTGGAGTGACGGCAGTTATCTGGAAGATCAGG |
| ATATGTGGCGGATGAGCGGCATTTTCCGTGACGTCTCGTTGCTGCATA |
| AACCGACCACGCAAATCAGCGATTTCCAAGTTACCACTCTCTTTAATG |
| ATGATTTCAGCCGCGCGGTACTGGAGGCAGAAGTTCAGATGTACGGCG |
| AGCTGCGCGATGAACTGCGGGTGACGGTTTCTTTGTGGCAGGGTGAAA |
| CGCAGGTCGCCAGCGGCACCGCGCCTTTCGGCGGTGAAATTATCGATG |
| AGCGTGGCGGTTATGCCGATCGCGTCACACTACGCCTGAACGTTGAAA |
| ATCCGGAACTGTGGAGCGCCGAAATCCCGAATCTCTATCGTGCAGTGG |
| TTGAACTGCACACCGCCGACGGCACGCTGATTGAAGCAGAAGCCTGCG |
| ACGTCGGTTTCCGCGAGGTGCGGATTGAAAATGGTCTGCTGCTGCTGA |
| ACGGCAAGCCGTTGCTGATTCGCGGCGTTAACCGTCACGAGCATCATC |
| CTCTGCATGGTCAGGTCATGGATGAGCAGACGATGGTGCAGGATATCC |
| TGCTGATGAAGCAGAACAACTTTAACGCCGTGCGCTGTTCGCATTATC |
| CGAACCATCCGCTGTGGTACACGCTGTGCGACCGCTACGGCCTGTATG |
| TGGTGGATGAAGCCAATATTGAAACCCACGGCATGGTGCCAATGAATC |
| GTCTGACCGATGATCCGCGCTGGCTACCCGCGATGAGCGAACGCGTAA |

TABLE 21-continued

| Nucleotide sequences of Pfnr1-lacZ construct, low-copy (SEQ ID NO: 31) |
|---|
| CGCGGATGGTGCAGCGCGATCGTAATCACCCGAGTGTGATCATCTGGT |
| CGCTGGGGAATGAATCAGGCCACGGCGCTAATCACGACGCGCTGTATC |
| GCTGGATCAAATCTGTCGATCCTTCCCGCCCGGTACAGTATGAAGGCG |
| GCGGAGCCGACACCACGGCCACCGATATTATTTGCCCGATGTACGCGC |
| GCGTGGATGAAGACCAGCCCTTCCCGGCGGTGCCGAAATGGTCCATCA |
| AAAAATGGCTTTCGCTGCCTGGAGAAATGCGCCCGCTGATCCTTTGCG |
| AATATGCCCACGCGATGGGTAACAGTCTTGGCGGCTTCGCTAAATACT |
| GGCAGGCGTTTCGTCAGTACCCCCGTTTACAGGGCGGCTTCGTCTGGG |
| ACTGGGTGGATCAGTCGCTGATTAAATATGATGAAAACGGCAACCCGT |
| GGTCGGCTTACGGCGGTGATTTTGGCGATACGCCGAACGATCGCCAGT |
| TCTGTATGAACGGTCTGGTCTTTGCCGACCGCACGCCGCATCCGGCGC |
| TGACGGAAGCAAAACACCAACAGCAGTATTTCCAGTTCCGTTTATCCG |
| GGCGAACCATCGAAGTGACCAGCGAATACCTGTTCCGTCATAGCGATA |
| ACGAGTTCCTGCACTGGATGGTGGCACTGGATGGCAAGCCGCTGGCAA |
| GCGGTGAAGTGCCTCTGGATGTTGGCCCGCAAGGTAAGCAGTTGATTG |
| AACTGCCTGAACTGCCGCAGCCGGAGAGCGCCGGACAACTCTGGCTAA |
| CGGTACGCGTAGTGCAACCAAACGCGACCGCATGGTCAGAAGCCGGAC |
| ACATCAGCGCCTGGCAGCAATGGCGTCTGGCGGAAAACCTCAGCGTGA |
| CACTCCCCTCCGCGTCCCACGCCATCCCTCAACTGACCACCAGCGGAA |
| CGGATTTTTGCATCGAGCTGGGTAATAAGCGTTGGCAATTTAACCGCC |
| AGTCAGGCTTTCTTTCACAGATGTGGATTGGCGATGAAAAACAACTGC |
| TGACCCCGCTGCGCGATCAGTTCACCCGTGCGCCGCTGGATAACGACA |
| TTGGCGTAAGTGAAGCGACCCGCATTGACCCTAACGCCTGGGTCGAAC |
| GCTGGAAGGCGGCGGGCCATTACCAGGCCGAAGCGGCGTTGTTGCAGT |
| GCACGGCAGATACACTTGCCGACGCGGTGCTGATTACAACCGCCCACG |
| CGTGGCAGCATCAGGGGAAAACCTTATTTATCAGCCGGAAAACCTACC |
| GGATTGATGGGCACGGTGAGATGGTCATCAATGTGGATGTTGCGGTGG |
| CAAGCGATACACCGCATCCGGCGCGGATTGGCCTGACCTGCCAGCTGG |
| CGCAGGTCTCAGAGCGGGTAAACTGGCTCGGCCTGGGGCCGCAAGAAA |
| ACTATCCCGACCGCCTTACTGCAGCCTGTTTTGACCGCTGGGATCTGC |
| CATTGTCAGACATGTATACCCCGTACGTCTTCCCGAGCGAAAACGGTC |
| TGCGCTGCGGGACGCGCGAATTGAATTATGGCCCACACCAGTGGCGCG |
| GCGACTTCCAGTTCAACATCAGCCGCTACAGCCAACAACAACTGATGG |
| AAACCAGCCATCGCCATCTGCTGCACGCGGAAGAAGGCACATGGCTGA |
| ATATCGACGGTTTCCATATGGGGATTGGTGGCGACGACTCCTGGAGCC |
| CGTCAGTATCGGCGGAATTCCAGCTGAGCGCCGGTCGCTACCATTACC |
| AGTTGGTCTGGTGTCAAAAATAA |

TABLE 22

| Nucleotide sequences of Pfnr2-lacZ construct, low-copy (SEQ ID NO: 32) |
|---|
| GGTACC**catttcctctcatcccatccggggtgagagtcttttccccg** |
| **acttatggctcatgcatgcatcaaaaaagatgtgagcttgatcaaaaa** |
| **caaaaaatatttcactcgacaggagtatttatattgcgcccgttacgt** |
| **gggcttcgactgtaaatcagaaaggagaaaacacctATGacgacctac** |
| **gatcg**GGATCCTCTGGCCGTCGTATTACAACGTCGTGACTGGGAAAAC |
| CCTGGCGTTACCCAACTTAATCGCCTTGCGGCACATCCCCCTTTCGCC |
| AGCTGGCGTAATAGCGAAGAGGCCCGCACCGATCGCCCTTCCCAACAG |
| TTGCGCAGCCTGAATGGCGAATGGCGCTTTGCCTGGTTTCCGGCACCA |
| GAAGCGGTGCCGGAAAGCTGGCTGGAGTGCGATCTTCCTGACGCCGAT |
| ACTGTCGTCGTCCCCTCAAACTGGCAGATGCACGGTTACGATGCGCCT |
| ATCTACACCAACGTGACCTATCCCATTACGGTCAATCCGCCGTTTGTT |
| CCCGCGGAGAATCCGACAGGTTGTTACTCGCTCACATTTAATATTGAT |
| GAAAGCTGGCTACAGGAAGGCCAGACGCGAATTATTTTTGATGGCGTT |
| AACTCGGCGTTTCATCTGTGGTGCAACGGGCGCTGGGTCGGTTACGGC |
| CAGGACAGCCGTTTGCCGTCTGAATTTGACCTGAGCGCATTTTTACGC |
| GCCGGAGAAAACCGCCTCGCGGTGATGGTGCTGCGCTGGAGTGACGGC |
| AGTTATCTGGAAGATCAGGATATGTGGCGGATGAGCGGCATTTTCCGT |
| GACGTCTCGTTGCTGCATAAACCGACCACGCAAATCAGCGATTTCCAA |
| GTTACCACTCTCTTTAATGATGATTTCAGCCGCGCGGTACTGGAGGCA |
| GAAGTTCAGATGTACGGCGAGCTGCGCGATGAACTGCGGGTGACGGTT |
| TCTTTGTGGCAGGGTGAAACGCAGGTCGCCAGCGGCACCGCGCCTTTC |
| GGCGGTGAAATTATCGATGAGCGTGGCGGTTATGCCGATCGCGTCACA |
| CTACGCCTGAACGTTGAAAATCCGGAACTGTGGAGCGCCGAAATCCCG |
| AATCTCTATCGTGCAGTGGTTGAACTGCACACCGCCGACGGCACGCTG |
| ATTGAAGCAGAAGCCTGCGACGTCGGTTTCCGCGAGGTGCGGATTGAA |
| AATGGTCTGCTGCTGCTGAACGGCAAGCCGTTGCTGATTCGCGGCGTT |
| AACCGTCACGAGCATCATCCTCTGCATGGTCAGGTCATGGATGAGCAG |
| ACGATGGTGCAGGATATCCTGCTGATGAAGCAGAACAACTTTAACGCC |
| GTGCGCTGTTCGCATTATCCGAACCATCCGCTGTGGTACACGCTGTGC |
| GACCGCTACGGCCTGTATGTGGTGGATGAAGCCAATATTGAAACCCAC |
| GGCATGGTGCCAATGAATCGTCTGACCGATGATCCGCGCTGGCTACCC |
| GCGATGAGCGAACGCGTAACGCGGATGGTGCAGCGCGATCGTAATCAC |
| CCGAGTGTGATCATCTGGTCGCTGGGGAATGAATCAGGCCACGGCGCT |
| AATCACGACGCGCTGTATCGCTGGATCAAATCTGTCGATCCTTCCCGC |
| CCGGTACAGTATGAAGGCGGCGGAGCCGACACCACGGCCACCGATATT |
| ATTTGCCCGATGTACGCGCGCGTGGATGAAGACCAGCCCTTCCCGGCG |
| GTGCCGAAATGGTCCATCAAAAAATGGCTTTCGCTGCCTGGAGAAATG |
| CGCCCGCTGATCCTTTGCGAATATGCCCACGCGATGGGTAACAGTCTT |
| GGCGGCTTCGCTAAATACTGGCAGGCGTTTCGTCAGTACCCCCGTTTA |

TABLE 22-continued

| Nucleotide sequences of Pfnr2-lacZ construct, low-copy (SEQ ID NO: 32) |
|---|
| CAGGGCGGCTTCGTCTGGGACTGGGTGGATCAGTCGCTGATTAAATAT |
| GATGAAAACGGCAACCCGTGGTCGGCTTACGGCGGTGATTTTGGCGAT |
| ACGCCGAACGATCGCCAGTTCTGTATGAACGGTCTGGTCTTTGCCGAC |
| CGCACGCCGCATCCGGCGCTGACGGAAGCAAAACACCAACAGCAGTAT |
| TTCCAGTTCCGTTTATCCGGGCGAACCATCGAAGTGACCAGCGAATAC |
| CTGTTCCGTCATAGCGATAACGAGTTCCTGCACTGGATGGTGGCACTG |
| GATGGCAAGCCGCTGGCAAGCGGTGAAGTGCCTCTGGATGTTGGCCCG |
| CAAGGTAAGCAGTTGATTGAACTGCCTGAACTGCCGCAGCCGGAGAGC |
| GCCGGACAACTCTGGCTAACGGTACGCGTAGTGCAACCAAACGCGACC |
| GCATGGTCAGAAGCCGGACACATCAGCGCCTGGCAGCAATGGCGTCTG |
| GCGGAAAACCTCAGCGTGACACTCCCCTCCGCGTCCCACGCCATCCCT |
| CAACTGACCACCAGCGGAACGGATTTTTGCATCGAGCTGGGTAATAAG |
| CGTTGGCAATTTAACCGCCAGTCAGGCTTTCTTTCACAGATGTGGATT |
| GGCGATGAAAAACAACTGCTGACCCCGCTGCGCGATCAGTTCACCCGT |
| GCGCCGCTGGATAACGACATTGGCGTAAGTGAAGCGACCCGCATTGAC |
| CCTAACGCCTGGGTCGAACGCTGGAAGGCGGCGGGCCATTACCAGGCC |
| GAAGCGGCGTTGTTGCAGTGCACGGCAGATACACTTGCCGACGCGGTG |
| CTGATTACAACCGCCCACGCGTGGCAGCATCAGGGGAAAACCTTATTT |
| ATCAGCCGGAAAACCTACCGGATTGATGGCACGGTGAGATGGTCATC |
| AATGTGGATGTTGCGGTGGCAAGCGATACACCGCATCCGGCGCGGATT |
| GGCCTGACCTGCCAGCTGGCGCAGGTCTCAGAGCGGGTAAACTGGCTC |
| GGCCTGGGGCCGCAAGAAAACTATCCCGACCGCCTTACTGCAGCCTGT |
| TTTGACCGCTGGGATCTGCCATTGTCAGACATGTATACCCCGTACGTC |
| TTCCCGAGCGAAAACGGTCTGCGCTGCGGGACGCGCGAATTGAATTAT |
| GGCCCACACCAGTGGCGCGGCGACTTCCAGTTCAACATCAGCCGCTAC |
| AGCCAACAACAACTGATGGAAACCAGCCATCGCCATCTGCTGCACGCG |
| GAAGAAGGCACATGGCTGAATATCGACGGTTTCCATATGGGGATTGGT |
| GGCGACGACTCCTGGAGCCCGTCAGTATCGGCGGAATTCCAGCTGAGC |
| GCCGGTCGCTACCATTACCAGTTGGTCTGGTGTCAAAAATAA |

TABLE 23

| Nucleotide sequences of Pfnr3-lacZ construct, low-copy (SEQ ID NO: 33) |
|---|
| GGTACC**gtcagcataacaccctgacctctcattaattgttcatgccgg** |
| **gcggcactatcgtcgtccggccttttcctctcttactctgctacgtac** |
| **atctatttctataaatccgttcaatttgtctgtttttttgcacaaacat** |
| **gaaatatcagacaattccgtgacttaagaaaatttatacaaatcagca** |
| **atataccccttaaggagtatataaaggtgaatttgatttacatcaata** |

TABLE 23-continued

| Nucleotide sequences of Pfnr3-lacZ construct, low-copy (SEQ ID NO: 33) |
|---|
| **agcggggttgctgaatcgttaa**GGATCC**ctctagaaataattttgttt** |
| **aactttaagaaggagatatacatATG**ACTATGATTACGGATTCTCTGG |
| CCGTCGTATTACAACGTCGTGACTGGGAAAACCCTGGCGTTACCCAAC |
| TTAATCGCCTTGCGGCACATCCCCCTTTCGCCAGCTGGCGTAATAGCG |
| AAGAGGCCCGCACCGATCGCCCTTCCCAACAGTTGCGCAGCCTGAATG |
| GCGAATGGCGCTTTGCCTGGTTTCCGGCACCAGAAGCGGTGCCGGAAA |
| GCTGGCTGGAGTGCGATCTTCCTGACGCCGATACTGTCGTCGTCCCCT |
| CAAACTGGCAGATGCACGGTTACGATGCGCCTATCTACACCAACGTGA |
| CCTATCCCATTACGGTCAATCCGCCGTTTGTTCCCGCGGAGAATCCGA |
| CAGGTTGTTACTCGCTCACATTTAATATTGATGAAAGCTGGCTACAGG |
| AAGGCCAGACGCGAATTATTTTTGATGGCGTTAACTCGGCGTTTCATC |
| TGTGGTGCAACGGGCGCTGGGTCGGTTACGGCCAGGACAGCCGTTTGC |
| CGTCTGAATTTGACCTGAGCGCATTTTTACGCGCCGGAGAAAACCGCC |
| TCGCGGTGATGGTGCTGCGCTGGAGTGACGGCAGTTATCTGGAAGATC |
| AGGATATGTGGCGGATGAGCGGCATTTTCCGTGACGTCTCGTTGCTGC |
| ATAAACCGACCACGCAAATCAGCGATTTCCAAGTTACCACTCTCTTTA |
| ATGATGATTTCAGCCGCGCGGTACTGGAGGCAGAAGTTCAGATGTACG |
| GCGAGCTGCGCGATGAACTGCGGGTGACGGTTTCTTTGTGGCAGGGTG |
| AAACGCAGGTCGCCAGCGGCACCGCGCCTTTCGGCGGTGAAATTATCG |
| ATGAGCGTGGCGGTTATGCCGATCGCGTCACACTACGCCTGAACGTTG |
| AAAATCCGGAACTGTGGAGCGCCGAAATCCCGAATCTCTATCGTGCAG |
| TGGTTGAACTGCACACCGCCGACGGCACGCTGATTGAAGCAGAAGCCT |
| GCGACGTCGGTTTCCGCGAGGTGCGGATTGAAAATGGTCTGCTGCTGC |
| TGAACGGCAAGCCGTTGCTGATTCGCGGCGTTAACCGTCACGAGCATC |
| ATCCTCTGCATGGTCAGGTCATGGATGAGCAGACGATGGTGCAGGATA |
| TCCTGCTGATGAAGCAGAACAACTTTAACGCCGTGCGCTGTTCGCATT |
| ATCCGAACCATCCGCTGTGGTACACGCTGTGCGACCGCTACGGCCTGT |
| ATGTGGTGGATGAAGCCAATATTGAAACCCACGGCATGGTGCCAATGA |
| ATCGTCTGACCGATGATCCGCGCTGGCTACCCGCGATGAGCGAACGCG |
| TAACGCGGATGGTGCAGCGCGATCGTAATCACCCGAGTGTGATCATCT |
| GGTCGCTGGGGAATGAATCAGGCCACGGCGCTAATCACGACGCGCTGT |
| ATCGCTGGATCAAATCTGTCGATCCTTCCCGCCCGGTACAGTATGAAG |
| GCGGCGGAGCCGACACCACGGCCACCGATATTATTTGCCCGATGTACG |
| CGCGCGTGGATGAAGACCAGCCCTTCCCGGCGGTGCCGAAATGGTCCA |
| TCAAAAAATGGCTTTCGCTGCCTGGAGAAATGCGCCCGCTGATCCTTT |
| GCGAATATGCCCACGCGATGGGTAACAGTCTTGGCGGCTTCGCTAAAT |
| ACTGGCAGGCGTTTCGTCAGTACCCCCGTTTACAGGGCGGCTTCGTCT |
| GGGACTGGGTGGATCAGTCGCTGATTAAATATGATGAAAACGGCAACC |
| CGTGGTCGGCTTACGGCGGTGATTTTGGCGATACGCCGAACGATCGCC |

TABLE 23-continued

| Nucleotide sequences of Pfnr3-lacZ construct, low-copy (SEQ ID NO: 33) |
|---|
| AGTTCTGTATGAACGGTCTGGTCTTTGCCGACCGCACGCCGCATCCGG |
| CGCTGACGGAAGCAAAACACCAACAGCAGTATTTCCAGTTCCGTTTAT |
| CCGGGCGAACCATCGAAGTGACCAGCGAATACCTGTTCCGTCATAGCG |
| ATAACGAGTTCCTGCACTGGATGGTGGCACTGGATGGCAAGCCGCTGG |
| CAAGCGGTGAAGTGCCTCTGGATGTTGGCCCGCAAGGTAAGCAGTTGA |
| TTGAACTGCCTGAACTGCCGCAGCCGGAGAGCGCCGGACAACTCTGGC |
| TAACGGTACGCGTAGTGCAACCAAACGCGACCGCATGGTCAGAAGCCG |
| GACACATCAGCGCCTGGCAGCAATGGCGTCTGGCGGAAAACCTCAGCG |
| TGACACTCCCCTCCGCGTCCCACGCCATCCCTCAACTGACCACCAGCG |
| GAACGGATTTTTGCATCGAGCTGGGTAATAAGCGTTGGCAATTTAACC |
| GCCAGTCAGGCTTTCTTTCACAGATGTGGATTGGCGATGAAAAACAAC |
| TGCTGACCCCGCTGCGCGATCAGTTCACCCGTGCGCCGCTGGATAACG |
| ACATTGGCGTAAGTGAAGCGACCCGCATTGACCCTAACGCCTGGGTCG |
| AACGCTGGAAGGCGGCGGGCCATTACCAGGCCGAAGCGGCGTTGTTGC |
| AGTGCACGGCAGATACACTTGCCGACGCGGTGCTGATTACAACCGCCC |
| ACGCGTGGCAGCATCAGGGGAAAACCTTATTTATCAGCCGGAAAACCT |
| ACCGGATTGATGGGCACGGTGAGATGGTCATCAATGTGGATGTTGCGG |
| TGGCAAGCGATACACCGCATCCGGCGCGGATTGGCCTGACCTGCCAGC |
| TGGCGCAGGTCTCAGAGCGGGTAAACTGGCTCGGCCTGGGGCCGCAAG |
| AAAACTATCCCGACCGCCTTACTGCAGCCTGTTTTGACCGCTGGGATC |
| TGCCATTGTCAGACATGTATACCCCGTACGTCTTCCCGAGCGAAAACG |
| GTCTGCGCTGCGGGACGCGCGAATTGAATTATGGCCCACACCAGTGGC |
| GCGGCGACTTCCAGTTCAACATCAGCCGCTACAGCCAACAACAACTGA |
| TGGAAACCAGCCATCGCCATCTGCTGCACGCGGAAGAAGGCACATGGC |
| TGAATATCGACGGTTTCCATATGGGGATTGGTGGCGACGACTCCTGGA |
| GCCCGTCAGTATCGGCGGAATTCCAGCTGAGCGCCGGTCGCTACCATT |
| ACCAGTTGGTCTGGTGTCAAAAATAA |

TABLE 24

| Nucleotide sequences of Pfnr4-lacZ construct, low-copy (SEQ ID NO: 34) |
|---|
| GGTACCc**atttcctctcatcccatccggggtgagagtcttttcccccgac** |
| **ttatggctcatgcatgcatcaaaaaagatgtgagcttgatcaaaaacaaa** |
| **aaatatttcactcgacaggagtatttatattgcgccc**GGATCC**ctctaga** |
| **aataattttgtttaactttaagaaggagatatacatATG**ACTATGATTAC |
| GGATTCTCTGGCCGTCGTATTACAACGTCGTGACTGGGAAAACCCTGGCG |
| TTACCCAACTTAATCGCCTTGCGGCACATCCCCCTTTCGCCAGCTGGCGT |
| AATAGCGAAGAGGCCCGCACCGATCGCCCTTCCCAACAGTTGCGCAGCCT |

TABLE 24-continued

| Nucleotide sequences of Pfnr4-lacZ construct, low-copy (SEQ ID NO: 34) |
|---|
| GAATGGCGAATGGCGCTTTGCCTGGTTTCCGGCACCAGAAGCGGTGCCGG |
| AAAGCTGGCTGGAGTGCGATCTTCCTGACGCCGATACTGTCGTCGTCCCC |
| TCAAACTGGCAGATGCACGGTTACGATGCGCCTATCTACACCAACGTGAC |
| CTATCCCATTACGGTCAATCCGCCGTTTGTTCCCGCGGAGAATCCGACAG |
| GTTGTTACTCGCTCACATTTAATATTGATGAAAGCTGGCTACAGGAAGGC |
| CAGACGCGAATTATTTTTGATGGCGTTAACTCGGCGTTTCATCTGTGGTG |
| CAACGGGCGCTGGGTCGGTTACGGCCAGGACAGCCGTTTGCCGTCTGAAT |
| TTGACCTGAGCGCATTTTTACGCGCCGGAGAAAACCGCCTCGCGGTGATG |
| GTGCTGCGCTGGAGTGACGGCAGTTATCTGGAAGATCAGGATATGTGGCG |
| GATGAGCGGCATTTTCCGTGACGTCTCGTTGCTGCATAAACCGACCACGC |
| AAATCAGCGATTTCCAAGTTACCACTCTCTTTAATGATGATTTCAGCCGC |
| GCGGTACTGGAGGCAGAAGTTCAGATGTACGGCGAGCTGCGCGATGAACT |
| GCGGGTGACGGTTTCTTTGTGGCAGGGTGAAACGCAGGTCGCCAGCGGCA |
| CCGCGCCTTTCGGCGGTGAAATTATCGATGAGCGTGGCGGTTATGCCGAT |
| CGCGTCACACTACGCCTGAACGTTGAAAATCCGGAACTGTGGAGCGCCGA |
| AATCCCGAATCTCTATCGTGCAGTGGTTGAACTGCACACCGCCGACGGCA |
| CGCTGATTGAAGCAGAAGCCTGCGACGTCGGTTTCCGCGAGGTGCGGATT |
| GAAAATGGTCTGCTGCTGCTGAACGGCAAGCCGTTGCTGATTCGCGGCGT |
| TAACCGTCACGAGCATCATCCTCTGCATGGTCAGGTCATGGATGAGCAGA |
| CGATGGTGCAGGATATCCTGCTGATGAAGCAGAACAACTTTAACGCCGTG |
| CGCTGTTCGCATTATCCGAACCATCCGCTGTGGTACACGCTGTGCGACCG |
| CTACGGCCTGTATGTGGTGGATGAAGCCAATATTGAAACCCACGGCATGG |
| TGCCAATGAATCGTCTGACCGATGATCCGCGCTGGCTACCCGCGATGAGC |
| GAACGCGTAACGCGGATGGTGCAGCGCGATCGTAATCACCCGAGTGTGAT |
| CATCTGGTCGCTGGGGAATGAATCAGGCCACGGCGCTAATCACGACGCGC |
| TGTATCGCTGGATCAAATCTGTCGATCCTTCCCGCCCGGTACAGTATGAA |
| GGCGGCGGAGCCGACACCACGGCCACCGATATTATTTGCCCGATGTACGC |
| GCGCGTGGATGAAGACCAGCCCTTCCCGGCGGTGCCGAAATGGTCCATCA |
| AAAAATGGCTTTCGCTGCCTGGAGAAATGCGCCCGCTGATCCTTTGCGAA |
| TATGCCCACGCGATGGGTAACAGTCTTGGCGGCTTCGCTAAATACTGGCA |
| GGCGTTTCGTCAGTACCCCCGTTTACAGGGCGGCTTCGTCTGGGACTGGG |
| TGGATCAGTCGCTGATTAAATATGATGAAAACGGCAACCCGTGGTCGGCT |
| TACGGCGGTGATTTTGGCGATACGCCGAACGATCGCCAGTTCTGTATGAA |
| CGGTCTGGTCTTTGCCGACCGCACGCCGCATCCGGCGCTGACGGAAGCAA |
| AACACCAACAGCAGTATTTCCAGTTCCGTTTATCCGGGCGAACCATCGAA |
| GTGACCAGCGAATACCTGTTCCGTCATAGCGATAACGAGTTCCTGCACTG |
| GATGGTGGCACTGGATGGCAAGCCGCTGGCAAGCGGTGAAGTGCCTCTGG |
| ATGTTGGCCCGCAAGGTAAGCAGTTGATTGAACTGCCTGAACTGCCGCAG |
| CCGGAGAGCGCCGGACAACTCTGGCTAACGGTACGCGTAGTGCAACCAAA |

TABLE 24-continued

| Nucleotide sequences of Pfnr4-lacZ construct, low-copy (SEQ ID NO: 34) |
|---|
| CGCGACCGCATGGTCAGAAGCCGGACACATCAGCGCCTGGCAGCAATGGC |
| GTCTGGCGGAAAACCTCAGCGTGACACTCCCCTCCGCGTCCCACGCCATC |
| CCTCAACTGACCACCAGCGGAACGGATTTTTGCATCGAGCTGGGTAATAA |
| GCGTTGGCAATTTAACCGCCAGTCAGGCTTTCTTTCACAGATGTGGATTG |
| GCGATGAAAAACAACTGCTGACCCCGCTGCGCGATCAGTTCACCCGTGCG |
| CCGCTGGATAACGACATTGGCGTAAGTGAAGCGACCCGCATTGACCCTAA |
| CGCCTGGGTCGAACGCTGGAAGGCGGCGGGCCATTACCAGGCCGAAGCGG |
| CGTTGTTGCAGTGCACGGCAGATACACTTGCCGACGCGGTGCTGATTACA |
| ACCGCCCACGCGTGGCAGCATCAGGGGAAAACCTTATTTATCAGCCGGAA |
| AACCTACCGGATTGATGGGCACGGTGAGATGGTCATCAATGTGGATGTTG |
| CGGTGGCAAGCGATACACCGCATCCGGCGCGGATTGGCCTGACCTGCCAG |
| CTGGCGCAGGTCTCAGAGCGGGTAAACTGGCTCGGCCTGGGGCCGCAAGA |
| AAACTATCCCGACCGCCTTACTGCAGCCTGTTTTGACCGCTGGGATCTGC |
| CATTGTCAGACATGTATACCCCGTACGTCTTCCCGAGCGAAAACGGTCTG |
| CGCTGCGGGACGCGCGAATTGAATTATGGCCCACACCAGTGGCGCGGCGA |
| CTTCCAGTTCAACATCAGCCGCTACAGCCAACAACAACTGATGGAAACCA |
| GCCATCGCCATCTGCTGCACGCGGAAGAAGGCACATGGCTGAATATCGAC |
| GGTTTCCATATGGGGATTGGTGGCGACGACTCCTGGAGCCCGTCAGTATC |
| GGCGGAATTCCAGCTGAGCGCCGGTCGCTACCATTACCAGTTGGTCTGGT |
| GTCAAAAATAA |

TABLE 25

| Nucleotide sequences of Pfnrs-lacZ construct, low-copy (SEQ ID NO: 35) |
|---|
| GGTACC**agttgttcttattggtggtgttgctttatggttgcatcgtagta** |
| **aatggttgtaacaaaagcaatttttccggctgtctgtatacaaaaacgcc** |
| **gtaaagtttgagcgaagtcaataaactctctacccattcagggcaatatc** |
| **tctctt**GGATCC**ctctagaaataattttgtttaactttaagaaggagata** |
| **tacatATG**CTATGATTACGGATTCTCTGGCCGTCGTATTACAACGTCGTG |
| ACTGGGAAAACCCTGGCGTTACCCAACTTAATCGCCTTGCGGCACATCCC |
| CCTTTCGCCAGCTGGCGTAATAGCGAAGAGGCCCGCACCGATCGCCCTTC |
| CCAACAGTTGCGCAGCCTGAATGGCGAATGGCGCTTTGCCTGGTTTCCGG |
| CACCAGAAGCGGTGCCGGAAAGCTGGCTGGAGTGCGATCTTCCTGACGCC |
| GATACTGTCGTCGTCCCCTCAAACTGGCAGATGCACGGTTACGATGCGCC |
| TATCTACACCAACGTGACCTATCCCATTACGGTCAATCCGCCGTTTGTTC |
| CCGCGGAGAATCCGACAGGTTGTTACTCGCTCACATTTAATATTGATGAA |
| AGCTGGCTACAGGAAGGCCAGACGCGAATTATTTTTGATGGCGTTAACTC |
| GGCGTTTCATCTGTGGTGCAACGGGCGCTGGGTCGGTTACGGCCAGGACA |

TABLE 25-continued

| Nucleotide sequences of Pfnrs-lacZ construct, low-copy (SEQ ID NO: 35) |
|---|
| GCCGTTTGCCGTCTGAATTTGACCTGAGCGCATTTTTACGCGCCGGAGAA |
| AACCGCCTCGCGGTGATGGTGCTGCGCTGGAGTGACGGCAGTTATCTGGA |
| AGATCAGGATATGTGGCGGATGAGCGGCATTTTCCGTGACGTCTCGTTGC |
| TGCATAAACCGACCACGCAAATCAGCGATTTCCAAGTTACCACTCTCTTT |
| AATGATGATTTCAGCCGCGCGGTACTGGAGGCAGAAGTTCAGATGTACGG |
| CGAGCTGCGCGATGAACTGCGGGTGACGGTTTCTTTGTGGCAGGGTGAAA |
| CGCAGGTCGCCAGCGGCACCGCGCCTTTCGGCGGTGAAATTATCGATGAG |
| CGTGGCGGTTATGCCGATCGCGTCACACTACGCCTGAACGTTGAAAATCC |
| GGAACTGTGGAGCGCCGAAATCCCGAATCTCTATCGTGCAGTGGTTGAAC |
| TGCACACCGCCGACGGCACGCTGATTGAAGCAGAAGCCTGCGACGTCGGT |
| TTCCGCGAGGTGCGGATTGAAAATGGTCTGCTGCTGCTGAACGGCAAGCC |
| GTTGCTGATTCGCGGCGTTAACCGTCACGAGCATCATCCTCTGCATGGTC |
| AGGTCATGGATGAGCAGACGATGGTGCAGGATATCCTGCTGATGAAGCAG |
| AACAACTTTAACGCCGTGCGCTGTTCGCATTATCCGAACCATCCGCTGTG |
| GTACACGCTGTGCGACCGCTACGGCCTGTATGTGGTGGATGAAGCCAATA |
| TTGAAACCCACGGCATGGTGCCAATGAATCGTCTGACCGATGATCCGCGC |
| TGGCTACCCGCGATGAGCGAACGCGTAACGCGGATGGTGCAGCGCGATCG |
| TAATCACCCGAGTGTGATCATCTGGTCGCTGGGGAATGAATCAGGCCACG |
| GCGCTAATCACGACGCGCTGTATCGCTGGATCAAATCTGTCGATCCTTCC |
| CGCCCGGTACAGTATGAAGGCGGCGGAGCCGACACCACGGCCACCGATAT |
| TATTTGCCCGATGTACGCGCGCGTGGATGAAGACCAGCCCTTCCCGGCGG |
| TGCCGAAATGGTCCATCAAAAAATGGCTTTCGCTGCCTGGAGAAATGCGC |
| CCGCTGATCCTTTGCGAATATGCCCACGCGATGGGTAACAGTCTTGGCGG |
| CTTCGCTAAATACTGGCAGGCGTTTCGTCAGTACCCCCGTTTACAGGGCG |
| GCTTCGTCTGGGACTGGGTGGATCAGTCGCTGATTAAATATGATGAAAAC |
| GGCAACCCGTGGTCGGCTTACGGCGGTGATTTTGGCGATACGCCGAACGA |
| TCGCCAGTTCTGTATGAACGGTCTGGTCTTTGCCGACCGCACGCCGCATC |
| CGGCGCTGACGGAAGCAAAACACCAACAGCAGTATTTCCAGTTCCGTTTA |
| TCCGGGCGAACCATCGAAGTGACCAGCGAATACCTGTTCCGTCATAGCGA |
| TAACGAGTTCCTGCACTGGATGGTGGCACTGGATGGCAAGCCGCTGGCAA |
| GCGGTGAAGTGCCTCTGGATGTTGGCCCGCAAGGTAAGCAGTTGATTGAA |
| CTGCCTGAACTGCCGCAGCCGGAGAGCGCCGGACAACTCTGGCTAACGGT |
| ACGCGTAGTGCAACCAAACGCGACCGCATGGTCAGAAGCCGGACACATCA |
| GCGCCTGGCAGCAATGGCGTCTGGCGGAAAACCTCAGCGTGACACTCCCC |
| TCCGCGTCCCACGCCATCCCTCAACTGACCACCAGCGGAACGGATTTTTG |
| CATCGAGCTGGGTAATAAGCGTTGGCAATTTAACCGCCAGTCAGGCTTTC |
| TTTCACAGATGTGGATTGGCGATGAAAAACAACTGCTGACCCCGCTGCGC |
| GATCAGTTCACCCGTGCGCCGCTGGATAACGACATTGGCGTAAGTGAAGC |
| GACCCGCATTGACCCTAACGCCTGGGTCGAACGCTGGAAGGCGGCGGGCC |

TABLE 25-continued

| Nucleotide sequences of Pfnrs-lacZ construct, low-copy (SEQ ID NO: 35) |
|---|
| ATTACCAGGCCGAAGCGGCGTTGTTGCAGTGCACGGCAGATACACTTGCC |
| GACGCGGTGCTGATTACAACCGCCCACGCGTGGCAGCATCAGGGGAAAAC |
| CTTATTTATCAGCCGGAAAACCTACCGGATTGATGGCACGGTGAGATGG |
| TCATCAATGTGGATGTTGCGGTGGCAAGCGATACACCGCATCCGGCGCGG |
| ATTGGCCTGACCTGCCAGCTGGCGCAGGTCTCAGAGCGGGTAAACTGGCT |
| CGGCCTGGGGCCGCAAGAAAACTATCCCGACCGCCTTACTGCAGCCTGTT |
| TTGACCGCTGGGATCTGCCATTGTCAGACATGTATACCCCGTACGTCTTC |
| CCGAGCGAAAACGGTCTGCGCTGCGGGACGCGCGAATTGAATTATGGCCC |
| ACACCAGTGGCGCGGCGACTTCCAGTTCAACATCAGCCGCTACAGCCAAC |
| AACAACTGATGGAAACCAGCCATCGCCATCTGCTGCACGCGGAAGAAGGC |
| ACATGGCTGAATATCGACGGTTTCCATATGGGGATTGGTGGCGACGACTC |
| CTGGAGCCCGTCAGTATCGGCGGAATTCCAGCTGAGCGCCGGTCGCTACC |
| ATTACCAGTTGGTCTGGTGTCAAAAATAA |

TABLE 26

| Nucleotide sequences of Pfnr3-PAL3 construct, low-copy (SEQ ID NO: 36) |
|---|
| GGTACC**gtcagcataacaccctgacctctcattaattgttcatgccgggc** |
| **ggcactatcgtcgtccggccttttcctctcttactctgctacgtacatct** |
| **atttctataaatccgttcaatttgtctgtttttttgcacaaacatgaaata** |
| **tcagacaattccgtgacttaagaaaatttatacaaatcagcaatataccc** |
| **cttaaggagtatataaaggtgaatttgatttacatcaataagcggggttg** |
| **ctgaatcgttaa**GGATCC**ctctagaaataattttgtttaactttaagaag** |
| **gagatatacatATG**AAAGCTAAAGATGTTCAGCCAACCATTATTATTAAT |
| AAAAATGGCCTTATCTCTTTGGAAGATATCTATGACATTGCGATAAAACA |
| AAAAAAAGTAGAAATATCAACGGAGATCACTGAACTTTTGACGCATGGTC |
| GTGAAAAATTAGAGGAAAAATTAAATTCAGGAGAGGTTATATATGGAATC |
| AATACAGGATTTGGAGGGAATGCCAATTTAGTTGTGCCATTTGAGAAAAT |
| CGCAGAGCATCAGCAAAATCTGTTAACTTTTCTTTCTGCTGGTACTGGGG |
| ACTATATGTCCAAACCTTGTATTAAAGCGTCACAATTTACTATGTTACTT |
| TCTGTTTGCAAAGGTTGGTCTGCAACCAGACCAATTGTCGCTCAAGCAAT |
| TGTTGATCATATTAATCATGACATTGTTCCTCTGGTTCCTCGCTATGGCT |
| CAGTGGGTGCAAGCGGTGATTTAATTCCTTTATCTTATATTGCACGAGCA |
| TTATGTGGTATCGGCAAAGTTTATTATATGGGCGCAGAAATTGACGCTGC |
| TGAAGCAATTAAACGTGCAGGGTTGACACCATTATCGTTAAAAGCCAAAG |
| AAGGTCTTGCTCTGATTAACGGCACCCGGGTAATGTCAGGAATCAGTGCA |
| ATCACCGTCATTAAACTGGAAAAACTATTTAAAGCCTCAATTTCTGCGAT |
| TGCCCTTGCTGTTGAAGCATTACTTGCATCTCATGAACATTATGATGCCC |

TABLE 26-continued

| Nucleotide sequences of Pfnr3-PAL3 construct, low-copy (SEQ ID NO: 36) |
|---|
| GGATTCAACAAGTAAAAAATCATCCTGGTCAAAACGCGGTGGCAAGTGCA |
| TTGCGTAATTTATTGGCAGGTTCAACGCAGGTTAATCTATTATCTGGGGT |
| TAAAGAACAAGCCAATAAAGCTTGTCGTCATCAAGAAATTACCCAACTAA |
| ATGATACCTTACAGGAAGTTTATTCAATTCGCTGTGCACCACAAGTATTA |
| GGTATAGTGCCAGAATCTTTAGCTACCGCTCGGAAAATATTGGAACGGGA |
| AGTTATCTCAGCTAATGATAATCCATTGATAGATCCAGAAAATGGCGATG |
| TTCTACACGGTGGAAATTTTATGGGGCAATATGTCGCCCGAACAATGGAT |
| GCATTAAAACTGGATATTGCTTTAATTGCCAATCATCTTCACGCCATTGT |
| GGCTCTTATGATGGATAACCGTTTCTCTCGTGGATTACCTAATTCACTGA |
| GTCCGACACCCGGCATGTATCAAGGTTTTAAAGGCGTCCAACTTTCTCAA |
| ACCGCTTTAGTTGCTGCAATTCGCCATGATTGTGCTGCATCAGGTATTCA |
| TACCCTCGCCACAGAACAATACAATCAAGATATTGTCAGTTTAGGTCTGC |
| ATGCCGCTCAAGATGTTTTAGAGATGGAGCAGAAATTACGCAATATTGTT |
| TCAATGACAATTCTGGTAGTTTGTCAGGCCATTCATCTTCGCGGCAATAT |
| TAGTGAAATTGCGCCTGAAACTGCTAAATTTTACCATGCAGTACGCGAAA |
| TCAGTTCTCCTTTGATCACTGATCGTGCGTTGGATGAAGATATAATCCGC |
| ATTGCGGATGCAATTATTAATGATCAACTTCCTCTGCCAGAAATCATGCT |
| GGAAGAATAA |

TABLE 27

| Nucleotide sequences of Pfnr4-PAL3 construct, low-copy (SEQ ID NO: 37) |
|---|
| GGTACC**catttcctctcatcccatccggggtgagagtcttttcccccgac** |
| **ttatggctcatgcatgcatcaaaaaagatgtgagcttgatcaaaaacaaa** |
| **aaatatttcactcgacaggagtatttatattgcgccc**GGATCC**ctctaga** |
| **aataattttgtttaactttaagaaggagatatacatATG**AAAGCTAAAGA |
| TGTTCAGCCAACCATTATTATTAATAAAAATGGCCTTATCTCTTTGGAAG |
| ATATCTATGACATTGCGATAAAACAAAAAAAAGTAGAAATATCAACGGAG |
| ATCACTGAACTTTTGACGCATGGTCGTGAAAAATTAGAGGAAAAATTAAA |
| TTCAGGAGAGGTTATATATGGAATCAATACAGGATTTGGAGGGAATGCCA |
| ATTTAGTTGTGCCATTTGAGAAAATCGCAGAGCATCAGCAAAATCTGTTA |
| ACTTTTCTTTCTGCTGGTACTGGGGACTATATGTCCAAACCTTGTATTAA |
| AGCGTCACAATTTACTATGTTACTTTCTGTTTGCAAAGGTTGGTCTGCAA |
| CCAGACCAATTGTCGCTCAAGCAATTGTTGATCATATTAATCATGACATT |
| GTTCCTCTGGTTCCTCGCTATGGCTCAGTGGGTGCAAGCGGTGATTTAAT |
| TCCTTTATCTTATATTGCACGAGCATTATGTGGTATCGGCAAAGTTTATT |
| ATATGGGCGCAGAAATTGACGCTGCTGAAGCAATTAAACGTGCAGGGTTG |
| ACACCATTATCGTTAAAAGCCAAAGAAGGTCTTGCTCTGATTAACGGCAC |
| CCGGGTAATGTCAGGAATCAGTGCAATCACCGTCATTAAACTGGAAAAAC |

TABLE 27-continued

| Nucleotide sequences of Pfnr4-PAL3 construct, low-copy (SEQ ID NO: 37) |
| --- |
| TATTTAAAGCCTCAATTTCTGCGATTGCCCTTGCTGTTGAAGCATTACTT |
| GCATCTCATGAACATTATGATGCCCGGATTCAACAAGTAAAAAATCATCC |
| TGGTCAAAACGCGGTGGCAAGTGCATTGCGTAATTTATTGGCAGGTTCAA |
| CGCAGGTTAATCTATTATCTGGGGTTAAAGAACAAGCCAATAAAGCTTGT |
| CGTCATCAAGAAATTACCCAACTAAATGATACCTTACAGGAAGTTTATTC |
| AATTCGCTGTGCACCACAAGTATTAGGTATAGTGCCAGAATCTTTAGCTA |
| CCGCTCGGAAAATATTGGAACGGGAAGTTATCTCAGCTAATGATAATCCA |
| TTGATAGATCCAGAAAATGGCGATGTTCTACACGGTGGAAATTTTATGGG |
| GCAATATGTCGCCCGAACAATGGATGCATTAAAACTGGATATTGCTTTAA |
| TTGCCAATCATCTTCACGCCATTGTGGCTCTTATGATGGATAACCGTTTC |
| TCTCGTGGATTACCTAATTCACTGAGTCCGACACCCGGCATGTATCAAGG |
| TTTTAAAGGCGTCCAACTTTCTCAAACCGCTTTAGTTGCTGCAATTCGCC |
| ATGATTGTGCTGCATCAGGTATTCATACCCTCGCCACAGAACAATACAAT |
| CAAGATATTGTCAGTTTAGGTCTGCATGCCGCTCAAGATGTTTTAGAGAT |
| GGAGCAGAAATTACGCAATATTGTTTCAATGACAATTCTGGTAGTTTGTC |
| AGGCCATTCATCTTCGCGGCAATATTAGTGAAATTGCGCCTGAAACTGCT |
| AAATTTTACCATGCAGTACGCGAAATCAGTTCTCCTTTGATCACTGATCG |
| TGCGTTGGATGAAGATATAATCCGCATTGCGGATGCAATTATTAATGATC |
| AACTTCCTCTGCCAGAAATCATGCTGGAAGAATAA |

TABLE 28

| Nucleotide sequences of PfnrS-PAL3 construct, low-copy (SEQ ID NO: 38) |
| --- |
| GGTACC**agttgttcttattggtggtgttgctttatggttgcatcgtagta** |
| **aatggttgtaacaaaagcaatttttccggctgtctgtatacaaaaacgcc** |
| **gtaaagtttgagcgaagtcaataaactctctacccattcagggcaatatc** |
| **tctctt**GGATCC**ctctagaaataattttgtttaactttaagaaggagata** |
| **tacatATG**AAAGCTAAAGATGTTCAGCCAACCATTATTATTAATAAAAAT |
| GGCCTTATCTCTTTGGAAGATATCTATGACATTGCGATAAAACAAAAAAA |
| AGTAGAAATATCAACGGAGATCACTGAACTTTTGACGCATGGTCGTGAAA |
| AATTAGAGGAAAAATTAAATTCAGGAGAGGTTATATATGGAATCAATACA |
| GGATTTGGAGGGAATGCCAATTTAGTTGTGCCATTTGAGAAAATCGCAGA |
| GCATCAGCAAAATCTGTTAACTTTTCTTTCTGCTGGTACTGGGGACTATA |
| TGTCCAAACCTTGTATTAAAGCGTCACAATTTACTATGTTACTTTCTGTT |
| TGCAAAGGTTGGTCTGCAACCAGACCAATTGTCGCTCAAGCAATTGTTGA |
| TCATATTAATCATGACATTGTTCCTCTGGTTCCTCGCTATGGCTCAGTGG |
| GTGCAAGCGGTGATTTAATTCCTTTATCTTATATTGCACGAGCATTATGT |
| GGTATCGGCAAAGTTTATTATATGGGCGCAGAAATTGACGCTGCTGAAGC |

TABLE 28-continued

| Nucleotide sequences of PfnrS-PAL3 construct, low-copy (SEQ ID NO: 38) |
| --- |
| AATTAAACGTGCAGGGTTGACACCATTATCGTTAAAAGCCAAAGAAGGTC |
| TTGCTCTGATTAACGGCACCCGGGTAATGTCAGGAATCAGTGCAATCACC |
| GTCATTAAACTGGAAAAACTATTTAAAGCCTCAATTTCTGCGATTGCCCT |
| TGCTGTTGAAGCATTACTTGCATCTCATGAACATTATGATGCCCGGATTC |
| AACAAGTAAAAAATCATCCTGGTCAAAACGCGGTGGCAAGTGCATTGCGT |
| AATTTATTGGCAGGTTCAACGCAGGTTAATCTATTATCTGGGGTTAAAGA |
| ACAAGCCAATAAAGCTTGTCGTCATCAAGAAATTACCCAACTAAATGATA |
| CCTTACAGGAAGTTTATTCAATTCGCTGTGCACCACAAGTATTAGGTATA |
| GTGCCAGAATCTTTAGCTACCGCTCGGAAAATATTGGAACGGGAAGTTAT |
| CTCAGCTAATGATAATCCATTGATAGATCCAGAAAATGGCGATGTTCTAC |
| ACGGTGGAAATTTTATGGGGCAATATGTCGCCCGAACAATGGATGCATTA |
| AAACTGGATATTGCTTTAATTGCCAATCATCTTCACGCCATTGTGGCTCT |
| TATGATGGATAACCGTTTCTCTCGTGGATTACCTAATTCACTGAGTCCGA |
| CACCCGGCATGTATCAAGGTTTTAAAGGCGTCCAACTTTCTCAAACCGCT |
| TTAGTTGCTGCAATTCGCCATGATTGTGCTGCATCAGGTATTCATACCCT |
| CGCCACAGAACAATACAATCAAGATATTGTCAGTTTAGGTCTGCATGCCG |
| CTCAAGATGTTTTAGAGATGGAGCAGAAATTACGCAATATTGTTTCAATG |
| ACAATTCTGGTAGTTTGTCAGGCCATTCATCTTCGCGGCAATATTAGTGA |
| AATTGCGCCTGAAACTGCTAAATTTTACCATGCAGTACGCGAAATCAGTT |
| CTCCTTTGATCACTGATCGTGCGTTGGATGAAGATATAATCCGCATTGCG |
| GATGCAATTATTAATGATCAACTTCCTCTGCCAGAAATCATGCTGGAAGA |
| ATAA |

Each of the plasmids was transformed into *E. coli* Nissle, as described above. Cultures of transformed *E. coli* Nissle were grown overnight and then diluted 1:200 in LB. The cells were grown with shaking at 250 rpm either aerobically or anaerobically in a Coy anaerobic chamber supplied with 90% $N_2$, 5% $CO_2$, and 5% $H_2$. After 4-6 hrs of incubation, samples were collected, and promoter activity was analyzed by performing β-galactosidase assays (Miller, 1972). As shown in FIG. 20, the activities of the FNR promoters were greatly enhanced under anaerobic conditions compared to aerobic conditions.

Example 7. Measuring the Activity of an FNR Promoter

Figure 19A:
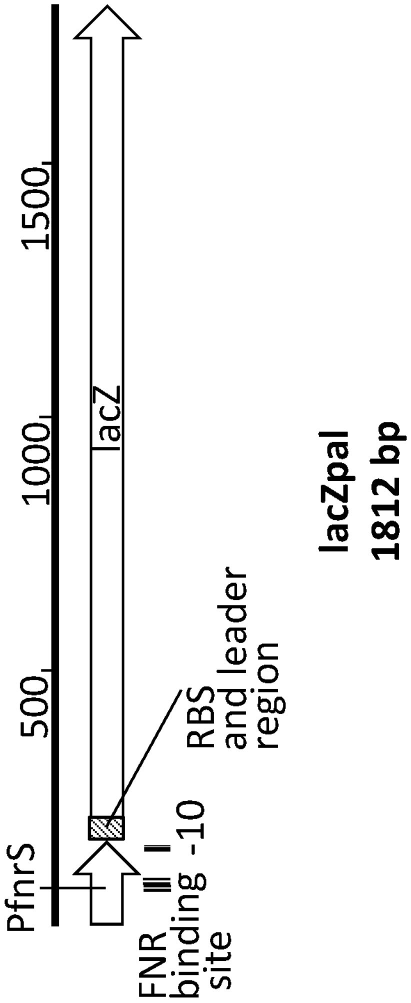
FIG. 19A depicts a schematic representation of the lacZ gene under the control of an exemplary FNR promoter ($P_{fnrS}$). LacZ encodes the β-galactosidase enzyme and is a common reporter gene in bacteria.
Figure 19B:
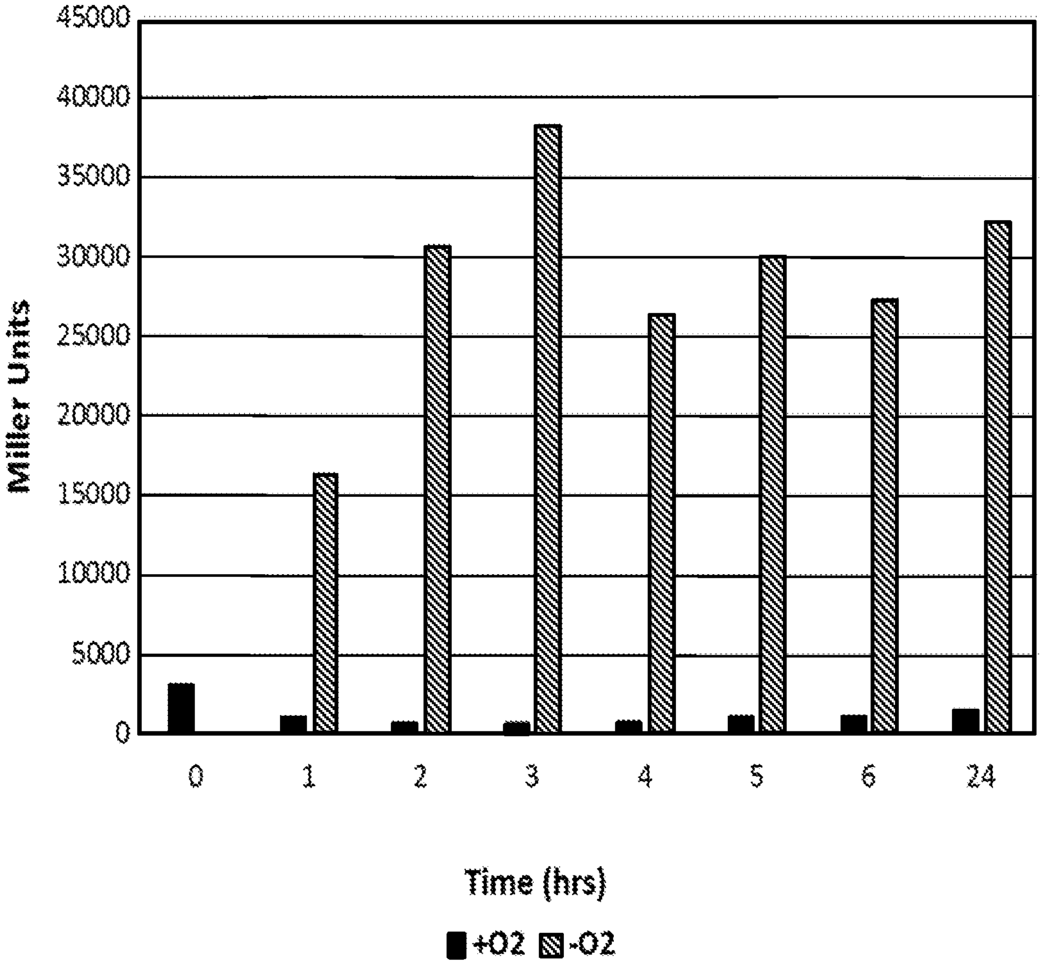
FIG. 19B depicts FNR promoter activity as a function of β-galactosidase activity in SYN-PKU904. SYN-PKU904, an engineered bacterial strain harboring a low-copy fnrS-lacZ fusion gene, was grown in the presence or absence of oxygen. Values for standard β-galactosidase colorimetric assays are expressed in Miller units (Miller, 1972). These data suggest that the fnrS promoter begins to drive high-level gene expression within 1 hr. under anaerobic conditions.
Figure 19C:
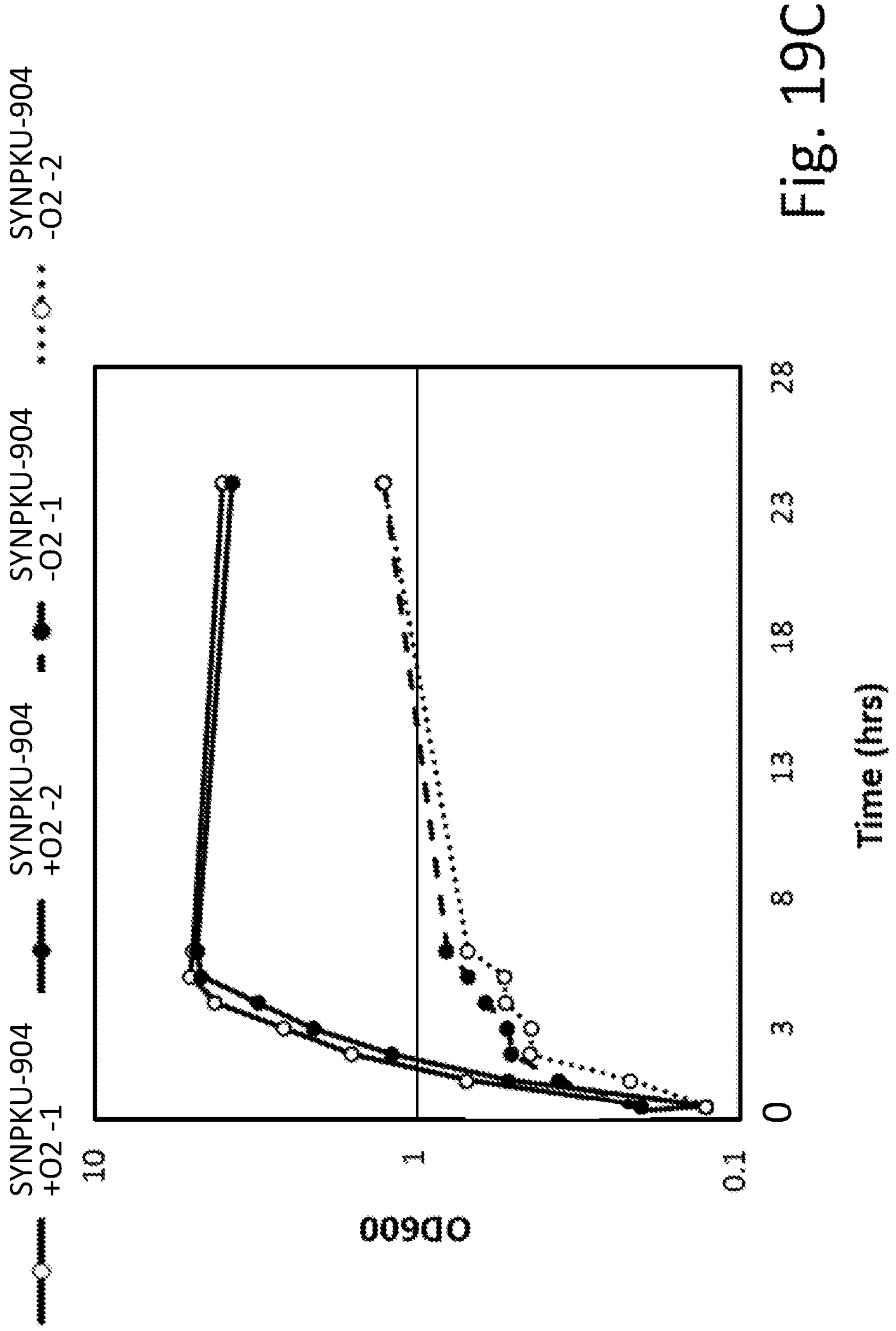
FIG. 19C depicts the growth of bacterial cell cultures expressing lacZ over time, both in the presence and absence of oxygen.

To determine the kinetics of FNR promoter-driven gene expression, *E. coli* strains harboring a low-copy fnrS-lacZ fusion gene (FIG. 19A) were grown aerobically with shaking at 250 rpm. Cultures were split after 1 hr., and then incubated either aerobically or anaerobically in a Coy anaerobic chamber (supplying 90% $N_2$, 5% $CO_2$, and 5% $H_2$) at 37° C. Promoter activity was measured as a function of 0-galactosidase activity using a standard colorimetric assay (Miller, 1972). FIG. 19B demonstrates that the fnrS promoter begins to drive high-level gene expression within 1 hr. under anaerobic conditions. Growth curves of bacterial cell cultures expressing lacZ are shown in FIG. 19C, both in the presence and absence of oxygen.

Example 8. Production of PAL from FNR Promoter in Recombinant *E. coli*

Figure 20A:
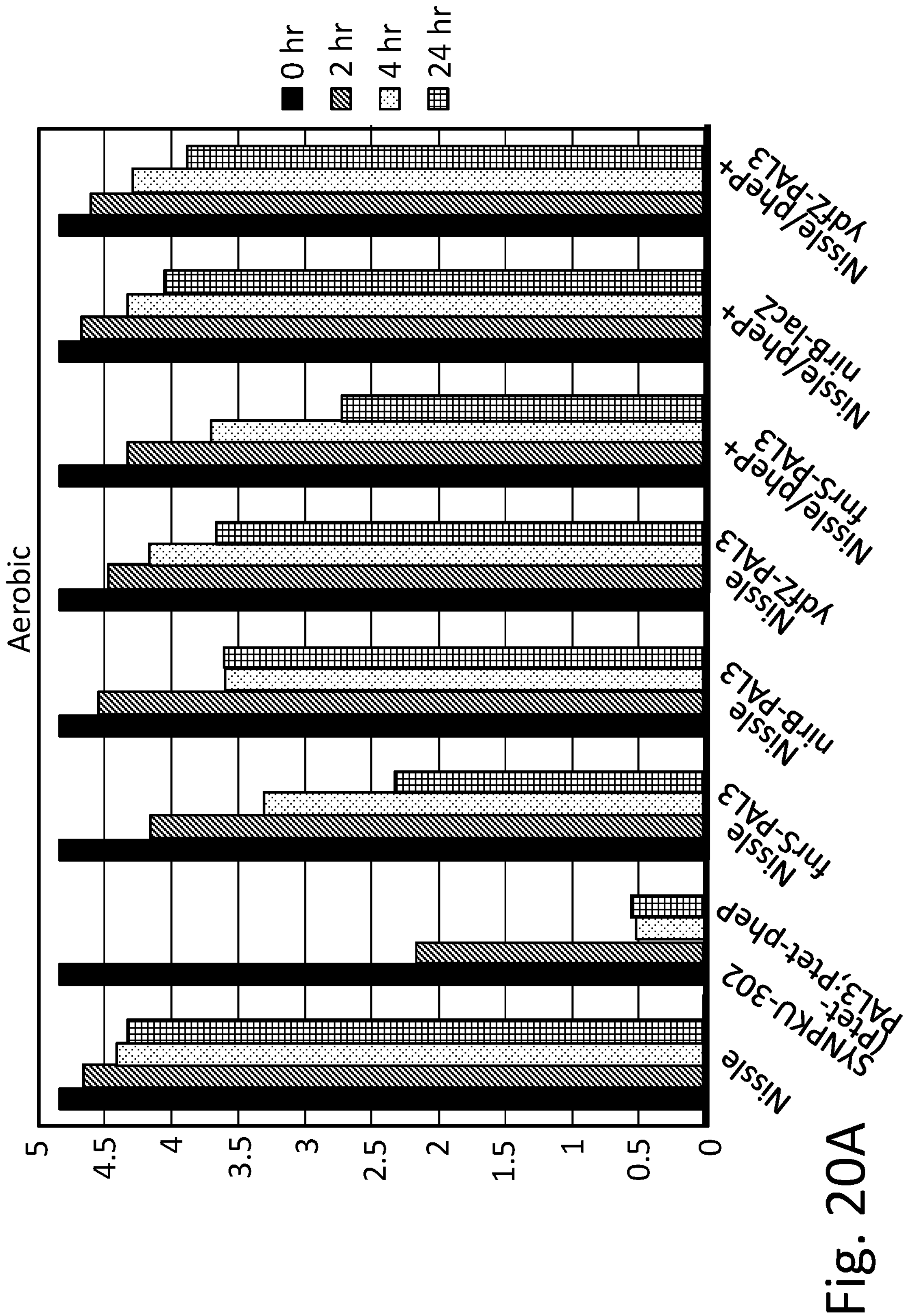
FIGS. 20A and 20B depict phenylalanine levels produced under aerobic (FIG. 20A) or anaerobic conditions (FIG. 20B) in samples of wild-type Nissle, samples of bacteria comprising a low-copy plasmid expressing PAL3 from the Tet promoter or exemplary FNR promoters, or further comprising a copy of pheP driven by the Tet promoter and integrated into the chromosome. Samples were incubated in culture medium supplemented with ATC and 4 mM (660,000 ng/mL) of phenylalanine. Samples were removed at 0 hrs, 2 hrs, 4 hrs, and 24 hrs. Phenylalanine concentration was determined by mass spectrometry. These data suggest that the FNR-responsive fnrS promoter is as effective at activating PAL3 expression as a tetracycline-inducible promoter under anaerobic conditions.
Figure 20B:
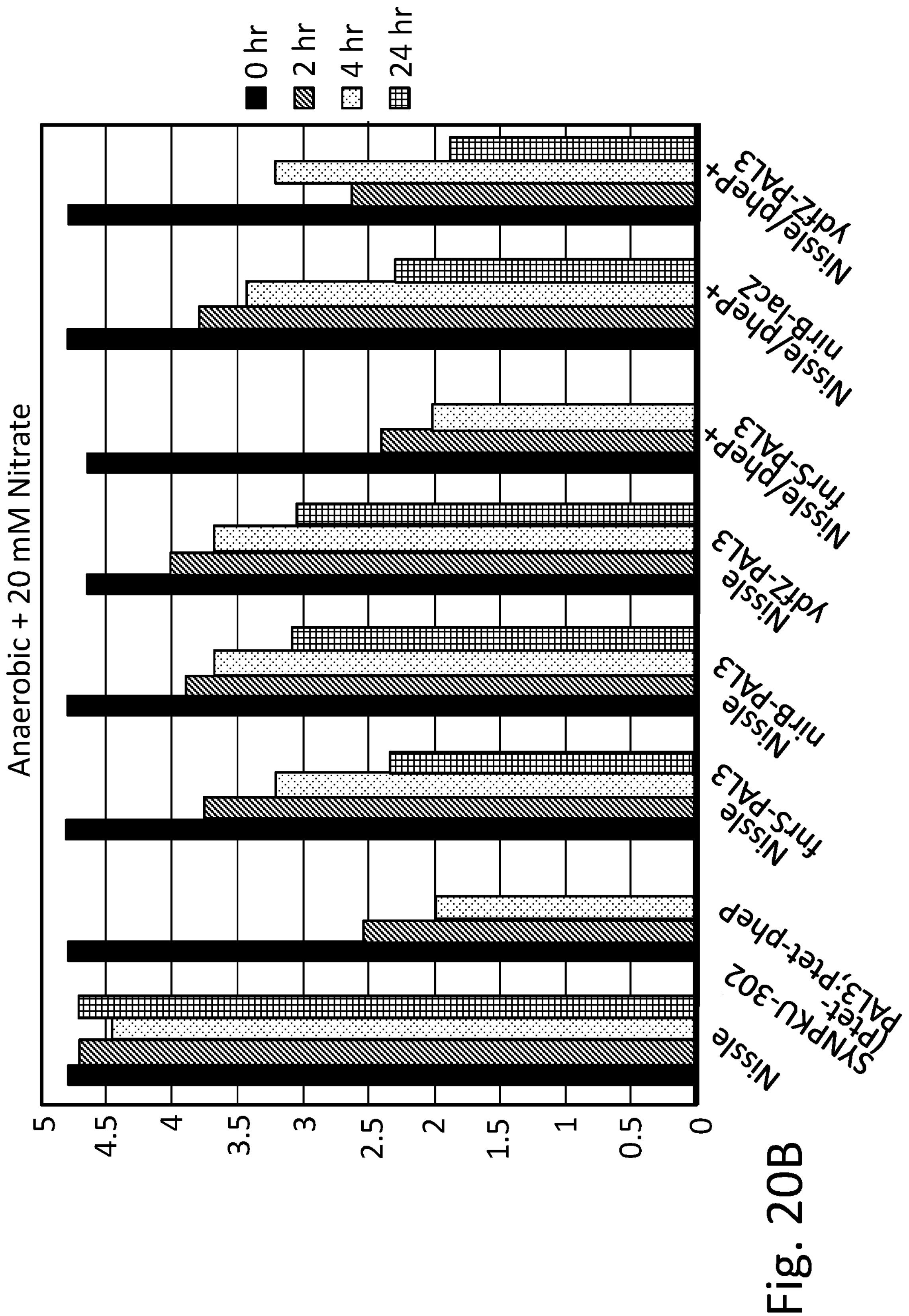

Cultures of *E. coli* Nissle transformed with a plasmid comprising the PAL gene driven by any of the exemplary FNR promoters were grown overnight and then diluted 1:200 in LB. The bacterial cells may further comprise the pheP gene driven by the Tet promoter and incorporated into the chromosome. ATC was added to cultures at a concentration of 100 ng/mL to induce expression of pheP, and the cells were grown with shaking at 250 rpm either aerobically or anaerobically in a Coy anaerobic chamber supplied with 90% $N_2$, 5% $CO_2$, and 5% $H_2$. After 4 hrs of incubation, cells were pelleted down, washed, and resuspended in M9 minimal medium supplemented with 0.5% glucose and 4 mM phenylalanine. Aliquots were collected at 0 hrs, 2 hrs, 4 hrs, and 24 hrs for phenylalanine quantification (FIG. 20). As shown in FIG. 20B, the genetically engineered bacteria expressing PAL3 driven by the FNR promoter are more efficient at removing phenylalanine from culture medium under anaerobic conditions, compared to aerobic conditions (FIG. 20A). The expression of pheP in conjunction with PAL3 further decreased levels of phenylalanine.

Example 9. Phenylalanine Degradation in Recombinant *E. coli* with and without pheP Overexpression The SYN-PKU304 and SYN-PKU305 strains contain low-copy plasmids harboring the PAL3 gene, and a copy of pheP integrated at the lacZ locus. The SYN-PKU308 and SYN-PKU307 strains also contain low-copy plasmids harboring the PAL3 gene, but lack a copy of pheP integrated at the lacZ locus. In all four strains, expression of PAL3 and pheP (when applicable) is controlled by an oxygen level-dependent promoter.

To determine rates of phenylalanine degradation in engineered *E. coli* Nissle with and without pheP on the chromosome, overnight cultures of SYN-PKU304 and SYN-PKU307 were diluted 1:100 in LB containing ampicillin, and overnight cultures of SYN-PKU308 and SYN-PKU305 were diluted 1:100 in LB containing kanamycin. All strains were grown for 1.5 hrs before cultures were placed in a Coy anaerobic chamber supplying 90% $N_2$, 5% $CO_2$, and 5% $H_2$. After 4 hrs of induction, bacteria were pelleted, washed in PBS, and resuspended in 1 mL of assay buffer. Assay buffer contained M9 minimal media supplemented with 0.5% glucose, 8.4% sodium bicarbonate, and 4 mM of phenylalanine.

Figure 21:
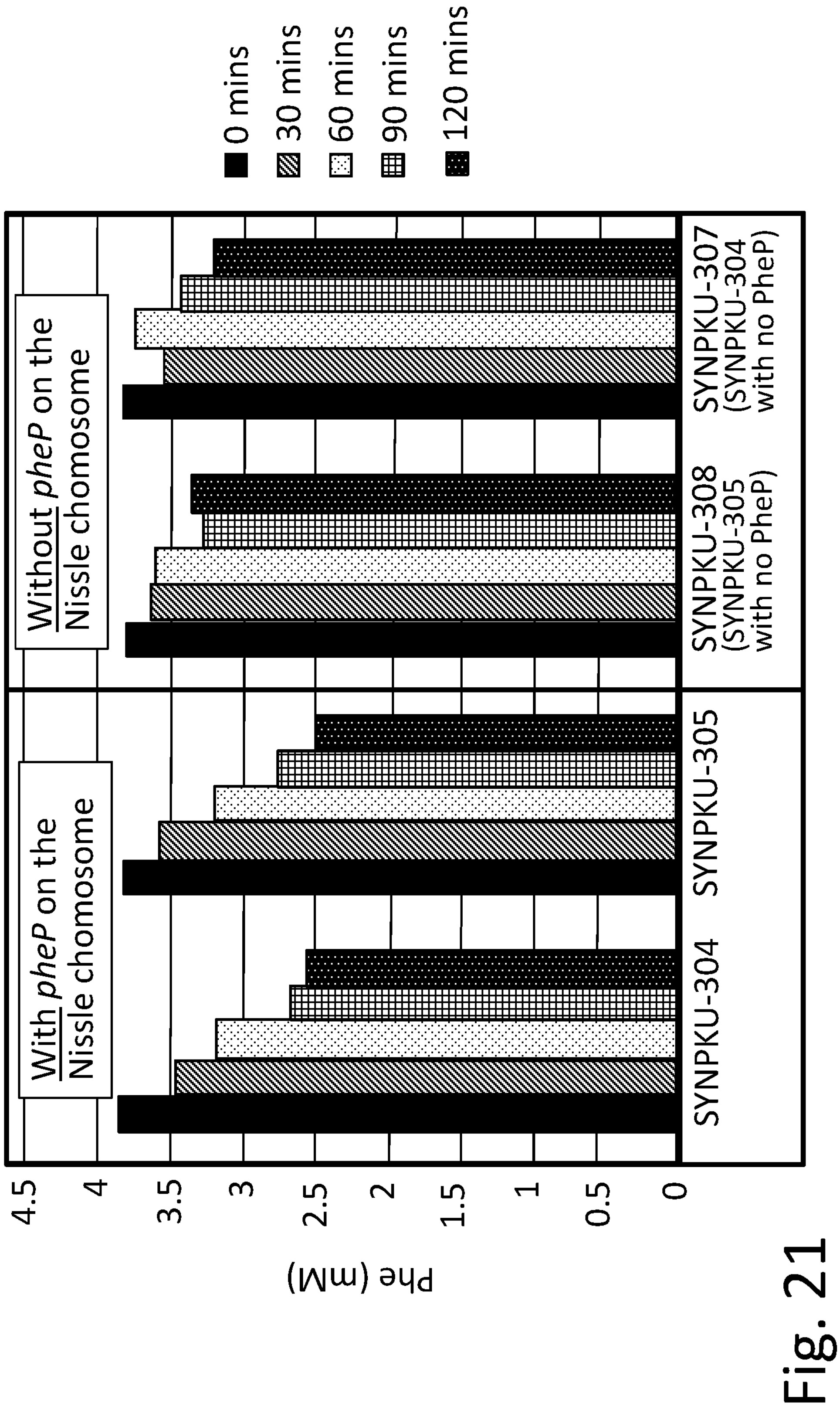
FIG. 21 depicts phenylalanine concentrations in cultures of synthetic probiotic strains, with and without an additional copy of pheP inserted on the chromosome. After 1.5 hrs of growth, cultures were placed in Coy anaerobic chamber supplying 90% $N_2$, 5% $CO_2$, and 5% $H_2$. After 4 hrs of induction, bacteria were resuspended in assay buffer containing 4 mM phenylalanine. Aliquots were removed from cell assays every 30 min for 3 hrs for phenylalanine quantification by mass spectrometry. Phenylalanine degradation rates in strains comprising an additional copy of pheP (SYN-PKU304 and SYN-PKU305; left) were higher than strains lacking an additional copy of pheP (SYN-PKU308 and SYN-PKU307; right).

For the activity assay, starting counts of colony-forming units (cfu) were quantified using serial dilution and plating. Aliquots were removed from each cell assay every 30 min for 3 hrs for phenylalanine quantification by mass spectrometry. Specifically, 150 µL of bacterial cells were pelleted and the supernatant was harvested for LC-MS analysis, with assay media without cells used as the zero-time point. FIG. 21 shows the observed phenylalanine degradation for strains with pheP on the chromosome (SYN-PKU304 and SYN-PKU305; left), as well as strains lacking pheP on the chromosome (SYN-PKU308 and SYN-PKU307; right). These data show that pheP overexpression is important in order to increase rates of phenylalanine degradation in synthetic probiotics.

Example 10. Activity of Strains with Single and Multiple Chromosomal PAL3 Insertions To assess the effect of insertion site and number of insertions on the activity of the genetically engineered bacteria, in vitro activity of strains with different single insertions of PAL3 at various chromosomal locations and with multiple PAL3 insertions was measured.

Figure 22:
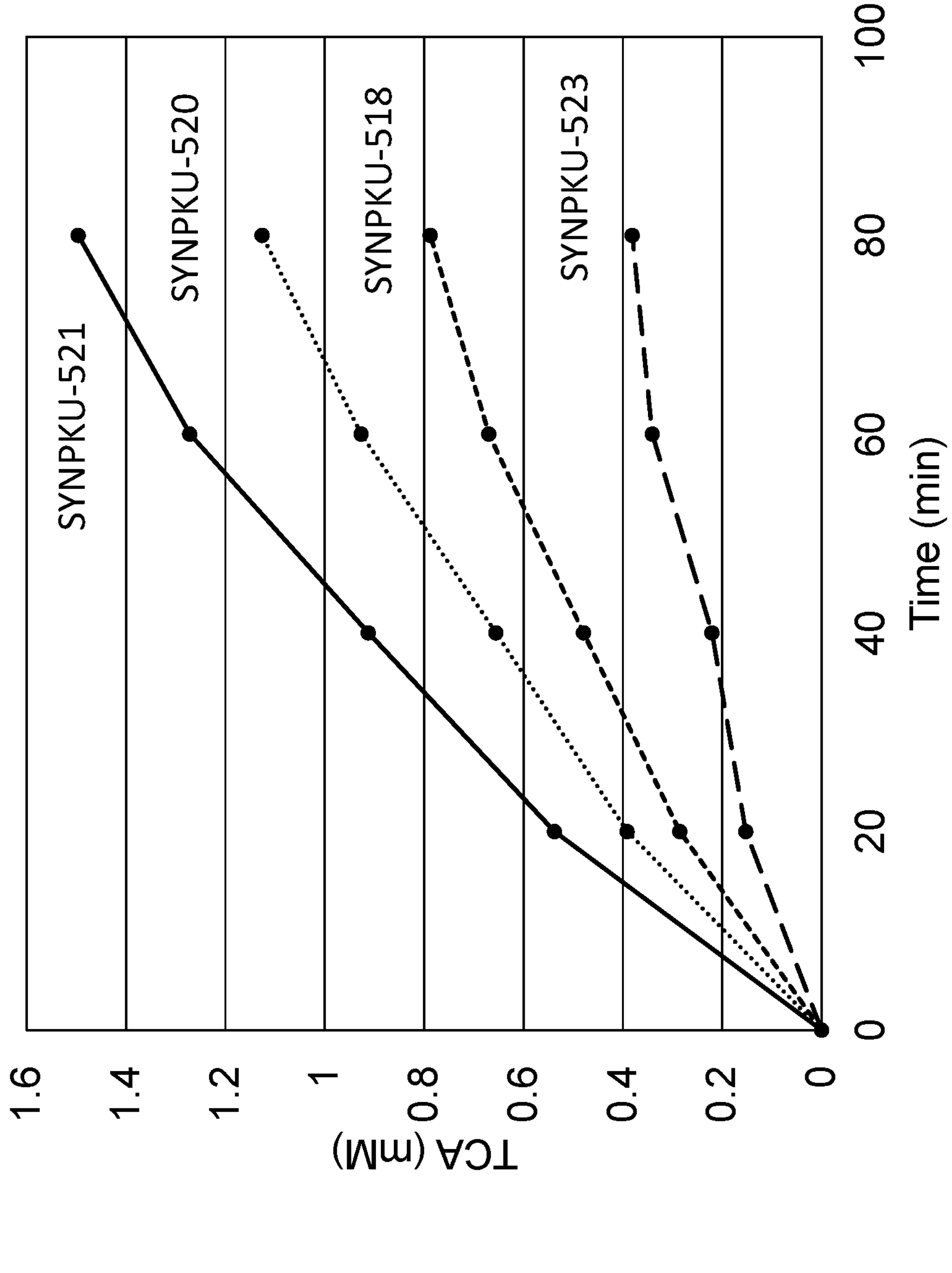
FIG. 22 depicts trans-cinnamate concentrations (PAL activity) for strains comprising single PAL3 insertions at various locations on the chromosome.
Figure 23:
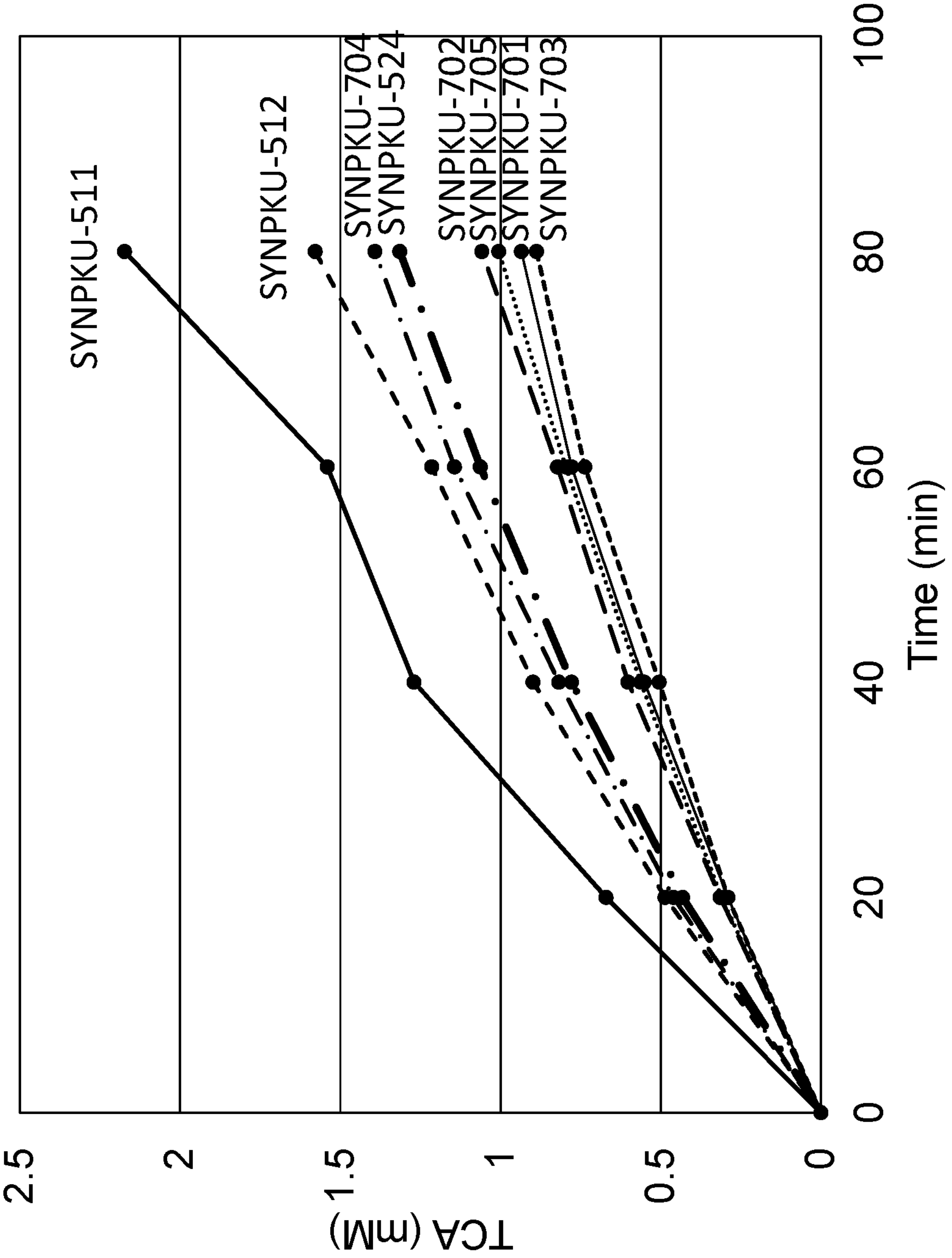
FIG. 23 depicts trans-cinnamate concentrations (PAL activity) for strains comprising multiple PAL3 insertions at various locations on the chromosome.

Cells were grown overnight in LB and diluted 1:100. After 1.5 hrs of growth, cultures were placed in Coy anaerobic chamber supplying 90% $N_2$, 5% $CO_2$, and 5% $H_2$. After 4 hrs of induction, bacteria were resuspended in assay buffer containing 50 mM phenylalanine. Aliquots were removed from cell assays every 20 min for 1.5 hrs for trans-cinnamate quantification by absorbance at 290 nm. Results are shown in FIGS. 22 and 23 and Table 39 and Table 40. FIG. 22 depicts trans-cinnamate concentrations (PAL activity) for strains comprising single PAL3 insertions at various locations on the chromosome. FIG. 23 depicts trans-cinnamate concentrations (PAL activity) for strains comprising multiple PAL3 insertions at various locations on the chromosome.

TABLE 39

Activity of various strains comprising a single PAL3 chromosomal insertion at various sites

| Insertion: | Strain: | rate (umol/hr./1e9 cells): |
|---|---|---|
| agaI/rsmI | SYN-PKU520 | 1.97 |
| yicS/nepI | SYN-PKU521 | 2.44 |
| cea | SYN-PKU522 | ND |
| malEK | SYN-PKU518 | 1.66 |
| malPT | SYN-PKU523 | 0.47 |

TABLE 40

In vitro activity of various strains comprising one or more chromosomal PAL3 insertions

| Genotypes: | Strain | Rate (umol/hr./1e9 cells) |
|---|---|---|
| agaI:PAL, cea:PAL, matPT:PAL, malEK:PAL, lacZ:pheP, thyA- | SYN-PKU512 | 6.76 |
| agaI:PAL, yicS:PAL, cea:PAL, matPT:PAL, malEK:PAL, lacZ:pheP, thyA- | SYN-PKU511 | 7.65 |
| malPT:PAL, malEK:PAL, lacZ:pheP | SYN-PKU524 | 2.89 |
| malEK:PAL, lacZ:pheP, ara-LAAD | SYN-PKU702 | 1.53 |
| malPT:PAL, malEK:PAL, lacZ:pheP, ara-LAAD | SYN-PKU701 | 2.65 |
| malPT:PAL, malEK:PAL, lacZ:pheP, agaI:pheP. ara-LAAD | SYN-PKU703 | 3.14 |
| yicS:PAL, malPT:PAL, malEK:PAL lacZ:pheP. ara-LAAD | SYN-PKU704 | 3.47 |
| yicS:PAL, malPT:PAL, malEK:PAL, lacZ:pheP, agaI:pheP, ara-LAAD | SYN-PKU705 | 3.74 |

Example 11. Activity of a Strain with Five Chromosomal Copies of PAL3

The activity of a strain SYN-PKU511, a strain comprising five integrated copies of an anaerobically (FNR) controlled PAL3 and an anaerobically controlled pheP integrated in the lacZ locus, was assessed.

Figure 24:
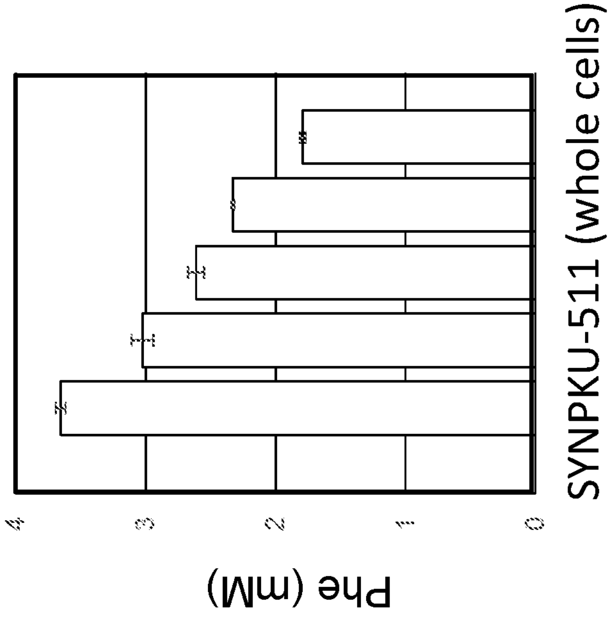
FIG. 24 depicts phenylalanine concentrations in cultures of synthetic probiotic strain SYN-PKU511 over time. After 2.5 hrs of growth, cultures were placed in Coy anaerobic chamber supplying 90% N2, 5% CO2, and 5% H2. After 3.5 hrs of induction in phenylalanine containing medium, whole cell extracts were prepared every 30 min for 3 hrs and phenylalanine was quantified by mass spectrometry. SYN-PKU511 comprises 5 integrated copies of an anaerobically (FNR) controlled gene encoding phenylalanine ammonia lyase (PAL) at 5 chromosomal locations and an anaerobically controlled gene encoding a high affinity Phe transporter (pheP) integrated in the lacZ locus.

The genetically engineered bacteria were grown overnight, diluted and allowed to grow for another 2.5 hours. Cultures were then placed in Coy anaerobic chamber supplying 90% $N_2$, 5% $CO_2$, and 5% H2. After 3.5 hrs of induction in phenylalanine containing medium (4 mM phenylalanine), whole cell extracts were prepared every 30 min for 3 hrs and phenylalanine was quantified by mass spectrometry. Results are shown in FIG. 24. The in vitro activity of the cells was 8 umol/hr./1e9 cells. Phenylalanine levels drop to about half of the original levels after 2 hours.

Example 12. Activity of a Strain Expressing LAAD

To assess whether LAAD expression can be used as an alternative, additional or complementary phenylalanine degradation means to PAL3, the ability of genetically engineered strain SYN-PKU401, which contains a high copy plasmid expressing LAAD driven by a Tet-inducible promoter, was measured at various cell concentrations and at varying oxygen levels.

Overnight cultures of SYN-PKU401 were diluted 1:100 and grown to early log phase before induction with ATC (100 ng/ml) for 2 hours. Cells were spun down and incubated as follows.

Cells (1 ml) were incubated aerobically in a 14 ml culture tube, shaking at 250 rpm (FIGS. 25 A and B). For microaerobic conditions, cells (1 ml) were incubated in a 1.7 ml conical tube without shaking. Cells were incubated anaerobically in a Coy anaerobic chamber supplying 90% $N_2$, 5% $CO_2$, and 5% H2 (FIG. 25B). Aliquots were removed from cell assays every 30 min for 2 hrs for phenylalanine quantification by mass spectrometry, and results are shown in FIGS. 25A and 25B. FIG. 25A shows cell concentration dependent aerobic activity. The activity in aerobic conditions is ~50 umol/hr./1e9 cells, and some activity is retained under microaerobic conditions, which may allow for activity in environments with oxygen concentrations less than ambient air. The activity of SYN-PKU401 under microaerobic conditions is comparable to SYN-PKU304 under anaerobic conditions, however, activity seems to be dependent on cell density.

Table 41 and Table 42 contain LAAD constructs of interest. Table 41 shows the sequence of an exemplary construct comprising a gene encoding LAAD from *Proteus mirabilis* and a Tet repressor gene and a Tet promoter sequence and RBS and leader region, on a plasmid SEQ ID NO: 39, with the LAAD sequence underlined the TetR sequence in italics and the Tet promoter sequence bolded and the RBS and leader region underlined and italics. Table 42 shows the sequence of an exemplary construct comprising a gene encoding araC and a gene encoding LAAD from *Proteus mirabilis* and an arabinose inducible promoter (ParaBAD) sequence for chromosomal insertion into the endogenous arabinose operon (SEQ ID NO: 40), with the araC sequence underlined and the ParaBAD promoter sequence bolded and the LAAD sequence in italics and the RBS and leader region underlined and in italics.

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 20-42, or a functional fragment thereof.

TABLE 41

| LAAD driven by a Tet inducible promoter on a plasmid Nucleotide sequences of TetR-LAAD plasmid construct (SEQ ID NO: 39) |
|---|
| *Ttaagacccactttcacatttaagttgtttttctaatccgcatatgatca* |
| *attcaaggccgaataagaaggctggctctgcaccttggtgatcaaataat* |
| *tcgatagcttgtcgtaataatggcggcatactatcagtagtaggtgtttc* |
| *cctttcttctttagcgacttgatgctcttgatcttccaatacgcaaccta* |
| *aagtaaaatgccccacagcgctgagtgcatataatgcattctctagtgaa* |
| *aaaccttgttggcataaaaaggctaattgattttcgagagtttcatactg* |
| *tttttctgtaggccgtgtacctaaatgtacttttgctccatcgcgatgac* |
| *ttagtaaagcacatctaaaacttttagcgttattacgtaaaaaatcttgc* |
| *cagctttccccttctaaagggcaaaagtgagtatggtgcctatctaacat* |
| *ctcaatggctaaggcgtcgagcaaagcccgcttattttttacatgccaat* |
| *acaatgtaggctgctctacacctagcttctgggcgagtttacgggttgtt* |
| *aaaccttcgattccgacctcattaagcagctctaatgcgctgttaatcac* |
| *tttacttttatctaatctagacatcattaattcctaattttt***gttgacac** |
| **tctatcattgatagagttattttaccactccctatcagtgatagagaa**aa |
| gtgaa*ctctagaaataattttgtttaactttaagaaggagatatacatat* |
| gaacatttcaaggagaaagctacttttaggtgttggtgctgcgggcgttt |
| tagcaggtggtgcggctttagttccaatggttcgccgtgacggcaaattt |
| gtggaagctaaatcaagagcatcatttgttgaaggtacgcaaggggctct |
| tcctaaagaagcagatgtagtgattattggtgccggtattcaagggatca |
| tgaccgctattaaccttgctgaacgtggtatgagtgtcactatcttagaa |
| aagggtcagattgccggtgagcaatcaggccgtgcatacagccaaattat |
| tagttaccaaacatcgccagaaatcttcccattacaccattatgggaaaa |
| tattatggcgtggcatgaatgagaaaattggtgcggataccagttatcgt |
| actcaaggtcgtgtagaagcgctggcagatgaaaaagcattagataaagc |
| tcaagcgtggatcaaaacagctaaagaagcggcaggttttgatacaccat |
| taaatactcgcatcattaaaggtgaagagctatcaaatcgcttagtcggt |
| gctcaaacgccatggactgttgctgcatttgaagaagattcaggctctgt |
| tgatcctgaaacaggcacacctgcactcgctcgttatgccaaacaaatcg |
| gtgtgaaaatttataccaactgtgcagtaagaggtattgaaactgcgggt |
| ggtaaaatctctgatgtggtgagtgagaaaggggcgattaaaacgtctca |
| agttgtactcgctgggggtatctggtcgcgtttatttatgggcaatatgg |
| gtattgatatcccaacgctcaatgtatatctatcacaacaacgtgtctca |
| ggggttcctggtgcaccacgtggtaatgtgcatttacctaatggtattca |
| tttccgcgaacaagcggatggtacttatgccgttgcaccacgtatcttta |
| cgagttcaatagtcaaagatagcttcctgctagggcctaaatttatgcac |
| ttattaggtggcggagagttaccgttggaattctctattggtgaagatct |

TABLE 41-continued

| LAAD driven by a Tet inducible promoter on a plasmid<br>Nucleotide sequences of TetR-LAAD plasmid construct (SEQ ID NO: 39) |
|---|
| atttaattcatttaaaatgccgacctcttggaatttagatgaaaaaacac |
| cattcgaacaattccgagttgccacggcaacacaaaatacgcaacactta |
| gatgctgttttccaaagaatgaaaacagaattcccagtatttgaaaaatc |
| agaagttgttgaacgttggggtgccgttgtgagtccaacatttgatgaat |
| tacctatcatttctgaggtcaaagaatacccaggcttagtgattaacacg |
| gcaacagtgtggggtatgacagaaggcccggcagcgggtgaagtgaccgc |
| tgatattgtcatgggcaagaaacctgttattgatccaacgccgtttagtt |
| tggatcgttttaagaagtaa |

TABLE 42

| LAAD sequence driven by the AraBAD promoter for insertion into the Ara operon<br>Nucleotide sequences of AraC-ARABAD promoter-LAAD construct (SEQ ID NO: 40) |
|---|
| Ttattcacaacctgccctaaactcgctcggactcgccccggtgcatttttt |
| taaatactcgcgagaaatagagttgatcgtcaaaaccgacattgcgaccg |
| acggtggcgataggcatccgggtggtgctcaaaagcagcttcgcctgact |
| gatgcgctggtcctcgcgccagcttaatacgctaatccctaactgctggc |
| ggaacaaatgcgacagacgcgacggcgacaggcagacatgctgtgcgacg |
| ctggcgatatcaaaattactgtctgccaggtgatcgctgatgtactgaca |
| agcctcgcgtacccgattatccatcggtggatggagcgactcgttaatcg |
| cttccatgcgccgcagtaacaattgctcaagcagatttatcgccagcaat |
| tccgaatagcgcccttccccttgtccggcattaatgatttgcccaaacag |
| gtcgctgaaatgcggctggtgcgcttcatccgggcgaaagaaaccggtat |
| tggcaaatatcgacggccagttaagccattcatgccagtaggcgcgcgga |
| cgaaagtaaacccactggtgataccattcgtgagcctccggatgacgacc |
| gtagtgatgaatctctccaggcgggaacagcaaaatatcacccggtcggc |
| agacaaattctcgtccctgatttttcaccaccccctgaccgcgaatggtg |
| agattgagaatataacctttcattcccagcggtcggtcgataaaaaaatc |
| gagataaccgttggcctcaatcggcgttaaacccgccaccagatgggcgt |
| taaacgagtatcccggcagcaggggatcattttgcgcttcagccatactt |
| ttcatactcccgccattcagagaagaaaccaattgtccatattgcatcag |
| acattgccgtcactgcgtcttttactggctcttctcgctaacccaaccgg |
| taaccccgcttattaaaagcattctgtaacaaagcgggaccaaagccatg |
| acaaaaacgcgtaacaaaagtgtctataatcacggcagaaaagtccacat |
| tgattatttgcacggcgtcacactttgctatgccatagcatttttatcca |
| taagattagcggatccagcctgacgctttttttcgcaactctctactgtt |
| tctccatAcctctagaaataattttgtttaactttaagaaggagatatac |

TABLE 42-continued

| LAAD sequence driven by the AraBAD promoter for insertion into the Ara operon<br>Nucleotide sequences of AraC-ARABAD promoter-LAAD construct (SEQ ID NO: 40) |
|---|
| atatgaacatttcaaggagaaagctacttttaggtgttggtgctgcgggc |
| gttttagcaggtggtgcggctttagttccaatggttcgccgtgacggcaa |
| atttgtggaagctaaatcaagagcatcatttgttgaaggtacgcaagggg |
| ctcttcctaaagaagcagatgtagtgattattggtgccggtattcaaggg |
| atcatgaccgctattaaccttgctgaacgtggtatgagtgtcactatctt |
| agaaaagggtcagattgccggtgagcaatcaggccgtgcatacagccaaa |
| ttattagttaccaaacatcgccagaaatcttcccattacaccattatggg |
| aaaatattatggcgtggcatgaatgagaaaattggtgcggataccagtta |
| tcgtactcaaggtcgtgtagaagcgctggcagatgaaaaagcattagata |
| aagctcaagcgtggatcaaaacagctaaagaagcggcaggttttgataca |
| ccattaaatactcgcatcattaaaggtgaagagctatcaaatcgcttagt |
| cggtgctcaaacgccatggactgttgctgcatttgaagaagattcaggct |
| ctgttgatcctgaaacaggcacacctgcactcgctcgttatgccaaacaa |
| atcggtgtgaaaatttataccaactgtgcagtaagaggtattgaaactgc |
| gggtggtaaaatctctgatgtggtgagtgagaaaggggcgattaaaacgt |
| ctcaagttgtactcgctgggggtatctggtcgcgtttatttatgggcaat |
| atgggtattgatatcccaacgctcaatgtatatctatcacaacaacgtgt |
| ctcaggggttcctggtgcaccacgtggtaatgtgcatttacctaatggta |
| ttcatttccgcgaacaagcggatggtacttatgccgttgcaccacgtatc |
| tttacgagttcaatagtcaaagatagcttcctgctagggcctaaatttat |
| gcacttattaggtggcggagagttaccgttggaattctctattggtgaag |
| atctatttaattcatttaaaatgccgacctcttggaatttagatgaaaaa |
| acaccattcgaacaattccgagttgccacggcaacacaaaatacgcaaca |
| cttagatgctgttttccaaagaatgaaaacagaattcccagtatttgaaa |
| aatcagaagttgttgaacgttggggtgccgttgtgagtccaacatttgat |
| gaattacctatcatttctgaggtcaaagaatacccaggcttagtgattaa |
| cacggcaacagtgtggggtatgacagaaggcccggcagcgggtgaagtga |
| ccgctgatattgtcatgggcaagaaacctgttattgatccaacgccgttt |
| agtttggatcgttttaagaagtaa |

Example 13. Efficacy of PAL-Expressing Bacteria in a Mouse Model of PKU

For in vivo studies, BTBR-Pah$^{enu2}$ mice were obtained from Jackson Laboratory and bred to homozygosity for use as a model of PKU. Bacteria harboring a low-copy pSC101 origin plasmid expressing PAL3 from the Tet promoter, as well as a copy of pheP driven by the Tet promoter integrated into the genome (SYN-PKU302), were grown. SYN-PKU1 was induced by ATC for 2 hrs prior to administration. Bacteria were resuspended in phosphate buffered saline (PBS) and $10^9$ ATC-induced SYN-PKU302 or control Nissle bacteria were administered to mice by oral gavage.

At the beginning of the study, mice were given water that was supplemented with 100 micrograms/mL ATC and 5% sucrose. Mice were fasted by removing chow overnight (10 hrs), and blood samples were collected by mandibular bleeding the next morning in order to determine baseline phenylalanine levels. Blood samples were collected in heparinized tubes and spun at 2G for 20 min to produce plasma, which was then removed and stored at −80° C. Mice were given chow again, and were gavaged after 1 hr. with 100 μL ($5\times10^9$ CFU) of bacteria that had previously been induced for 2 hrs with ATC. Mice were put back on chow for 2 hrs. Plasma samples were prepared as described above.

Figure 26A:
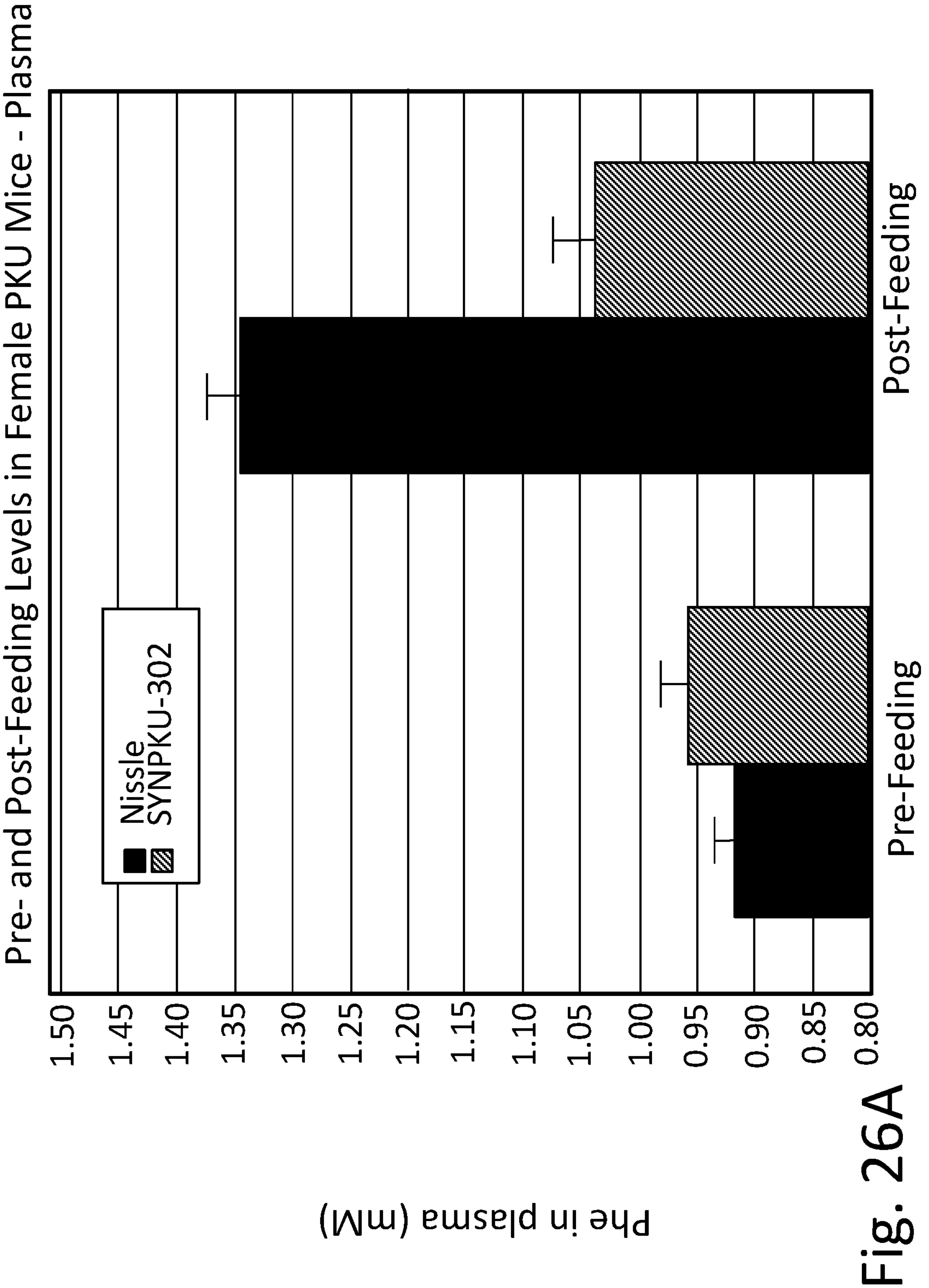
FIG. 26A shows phenylalanine concentrations before and after feeding in an in vivo mouse model of PKU. At the beginning of the study, homozygous BTBR-$Pah^{enu2}$ mice were given water supplemented with 100 micrograms/mL ATC and 5% sucrose. Mice were fasted by removing chow overnight (10 hrs), and blood samples were collected by mandibular bleeding the next morning in order to determine baseline phenylalanine levels. Mice were given chow again, gavaged with 100 microliters ($5\times10^9$ CFU) of bacteria (SYN-PKU302 or control Nissle) after 1 hr., and allowed to feed for another 2 hrs. Serum phenylalanine concentrations were determined 2 hrs post-gavage.
Figure 26B:
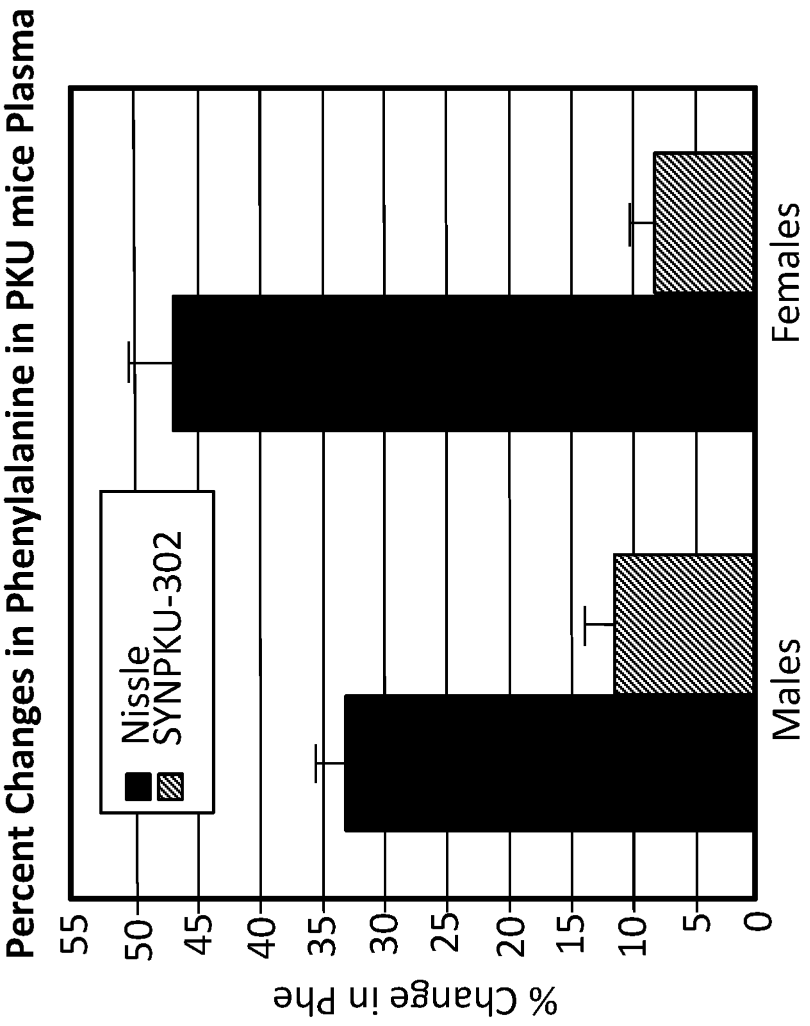
FIG. 26B shows the percent (%) change in blood phenylalanine concentrations before and after feeding as a male or female group average ($p<0.01$).

FIG. 26A shows phenylalanine levels before and after feeding, and FIG. 26B shows the percent (%) change in blood phenylalanine levels before and after feeding as a male or female group average ($p<0.01$). As shown in FIG. 26, PKU mice treated with SYN-PKU1 exhibit a significantly reduced post-feeding rise in serum phenylalanine levels compared to controls.

Example 14. Efficacy of PAL-Expressing Bacteria Following Subcutaneous Phenylalanine Challenge Streptomycin-resistant *E. coli* Nissle (SYN-PKU901) was grown from frozen stocks to a density of $10^{10}$ cells/mL. Bacteria containing a copy of pheP under the control of a Tet promoter integrated into the lacZ locus, as well as a high-copy plasmid expressing PAL3 under the control of a Tet promoter (SYN-PKU303) were grown to an $A_{600}$ of 0.25 and then induced by ATC (100 ng/mL) for 4 hrs. Bacteria were centrifuged, washed, and resuspended in bicarbonate buffer at density of $1\times10^{10}$ cells/mL before freezing at −80° C.

Beginning at least 3 days prior to the study (i.e., Days −6 to −3), homozygous BTBR-$Pah^{enu2}$ mice (approx. 6-12 weeks of age) were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, 200 μL of $H_2O$ (n=30), SYN-PKU901 (n=33), or SYN-PKU303 (n=34) were administered to mice by oral gavage. Blood samples were collected at 2 hrs and 4 hrs following phenylalanine challenge, and phenylalanine levels in the blood were measured using mass spectrometry.

Figure 27A:
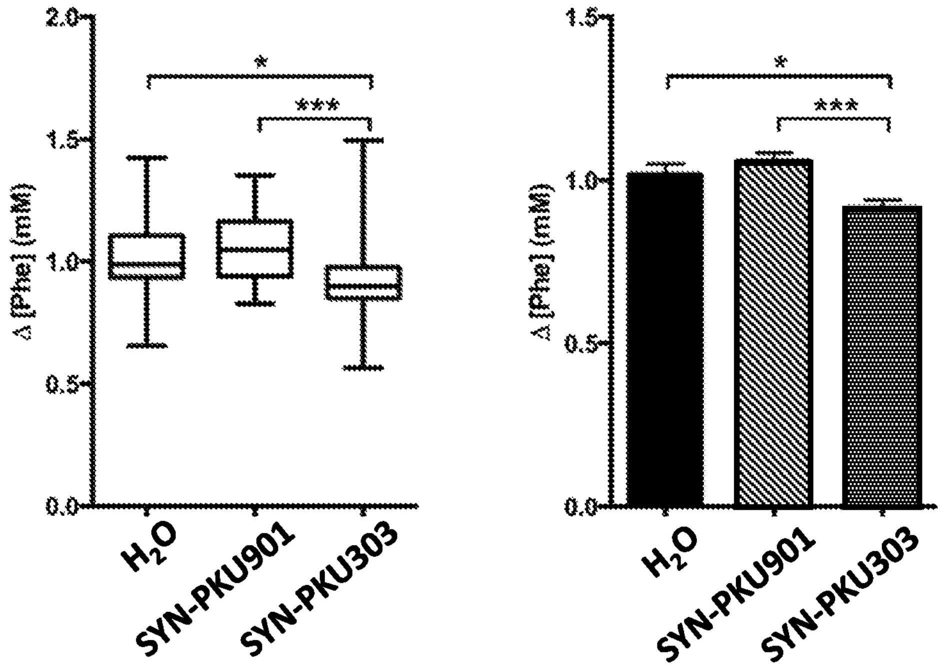
FIGS. 27A and 27B depict blood phenylalanine concentrations relative to baseline following subcutaneous phenylalanine challenge in an in vivo mouse model of PKU. Mice were orally gavaged with 200 μL of $H_2O$ (n=30), SYN-PKU901 (n=33), or SYN-PKU303 (n=34) at 30 and 90 minutes post-phenylalanine injection (0.1 mg/gram of average group body weight).
Figure 27B:
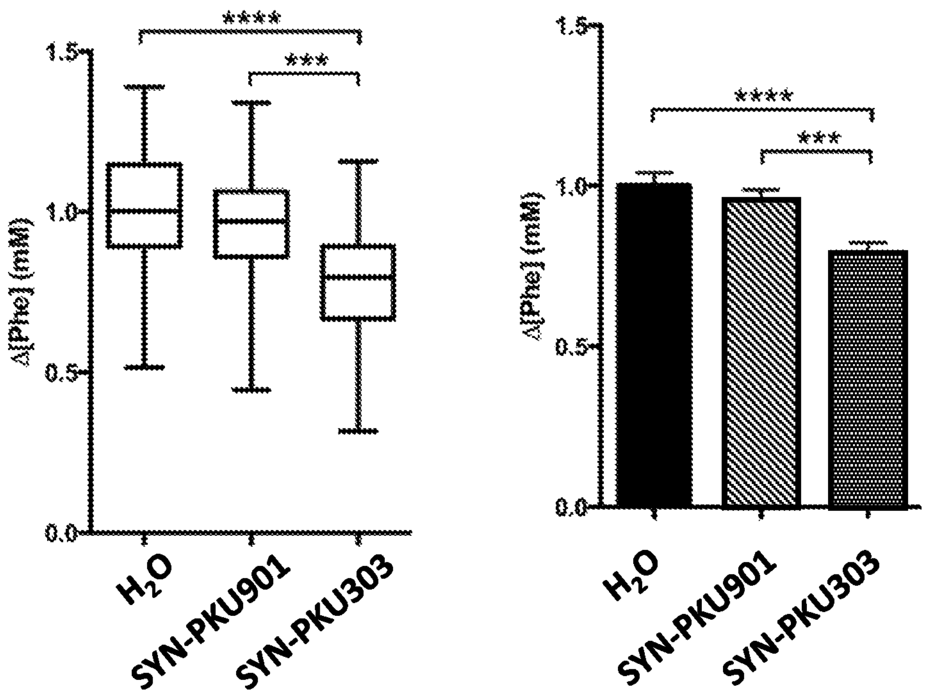
Figure 28:
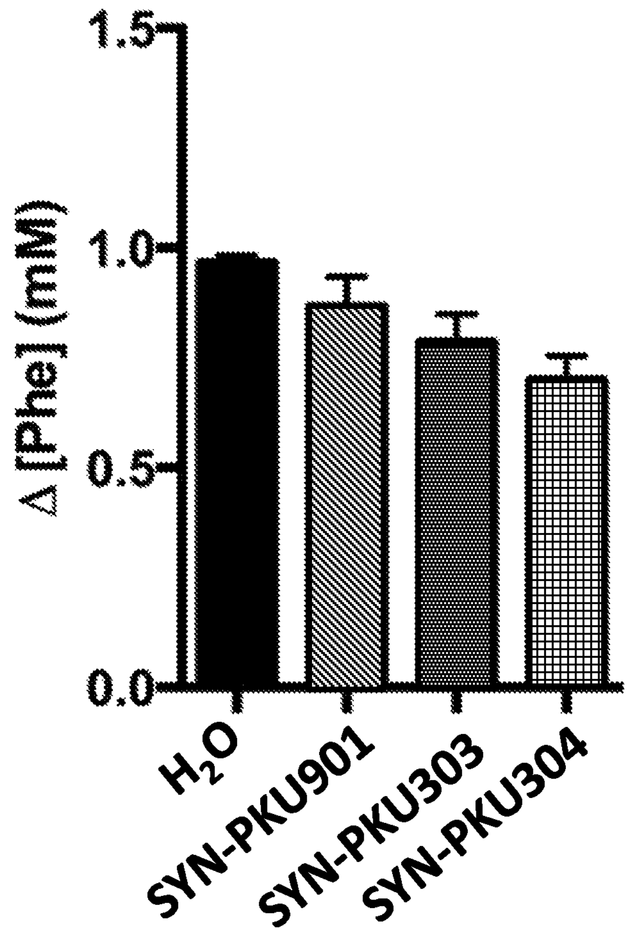
FIG. 28 depicts blood phenylalanine concentrations relative to baseline following subcutaneous phenylalanine challenge in an in vivo mouse model of PKU. Mice were orally gavaged with 200 μL of $H_2O$ (n=30), SYN-PKU901 (n=33), SYN-PKU303 (n=34), or SYN-PKU304 (n=34) at 30 and 90 minutes post-phenylalanine injection (0.1 mg/gram of average group body weight). Blood phenylalanine concentrations post phenylalanine injection indicate that SYN-PKU304 (low copy plasmid containing fnrS-PAL) is at least as effective as SYN-PKU303 (high copy plasmid containing Tet-PAL) in reducing circulating Phe levels in the entero-recirculation model.
Figure 29A:
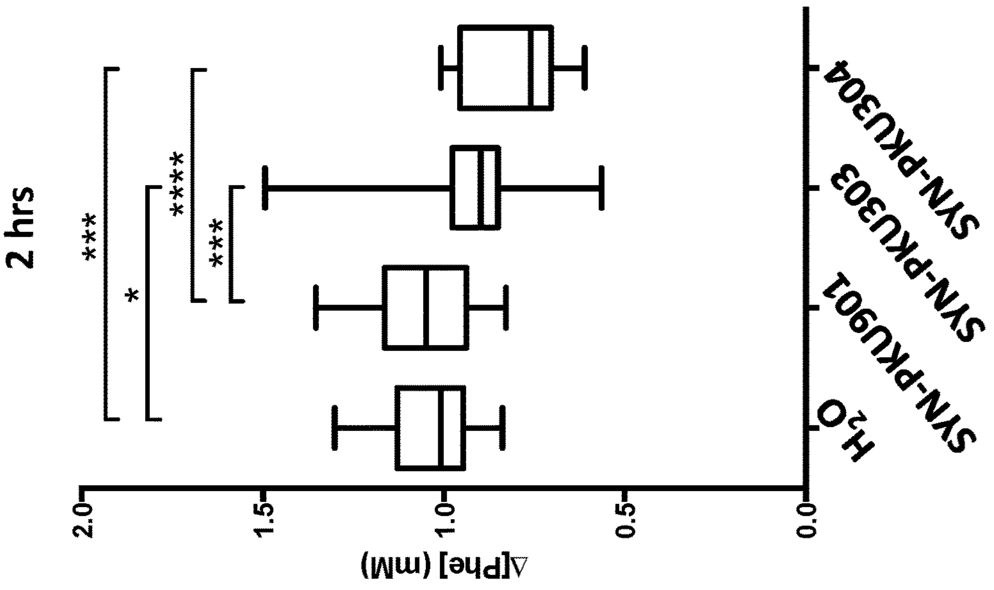
FIGS. 29A and 29B depict blood phenylalanine concentrations relative to baseline following subcutaneous phenylalanine challenge in an in vivo mouse model of PKU. Mice were orally gavaged with H2O, SYN-PKU901, SYN-PKU303, or SYN-PKU304 at 30 and 90 minutes post-phenylalanine injection (0.1 mg/gram of average group body weight).
Figure 29B:
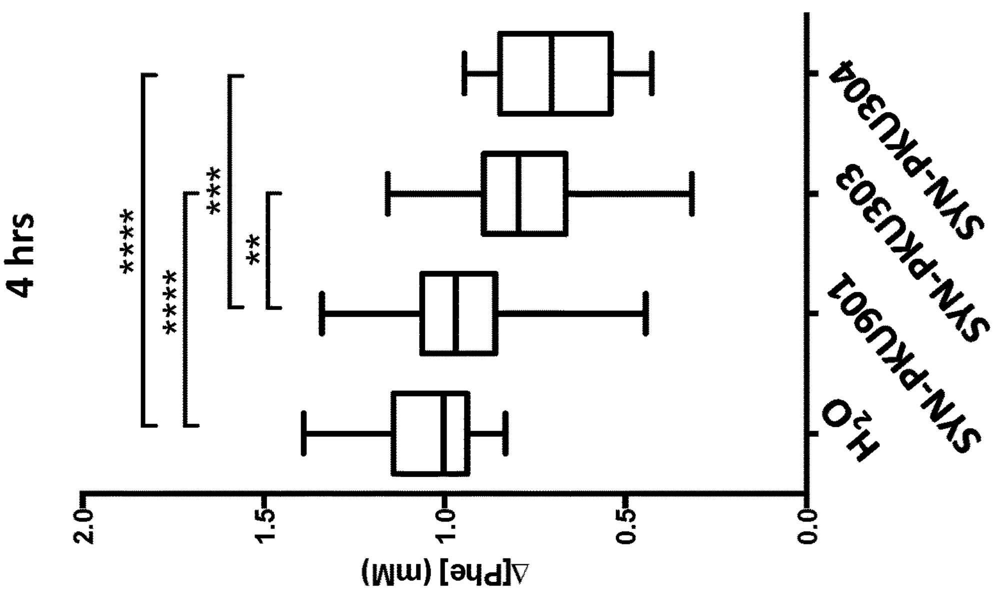
Figure 29D:
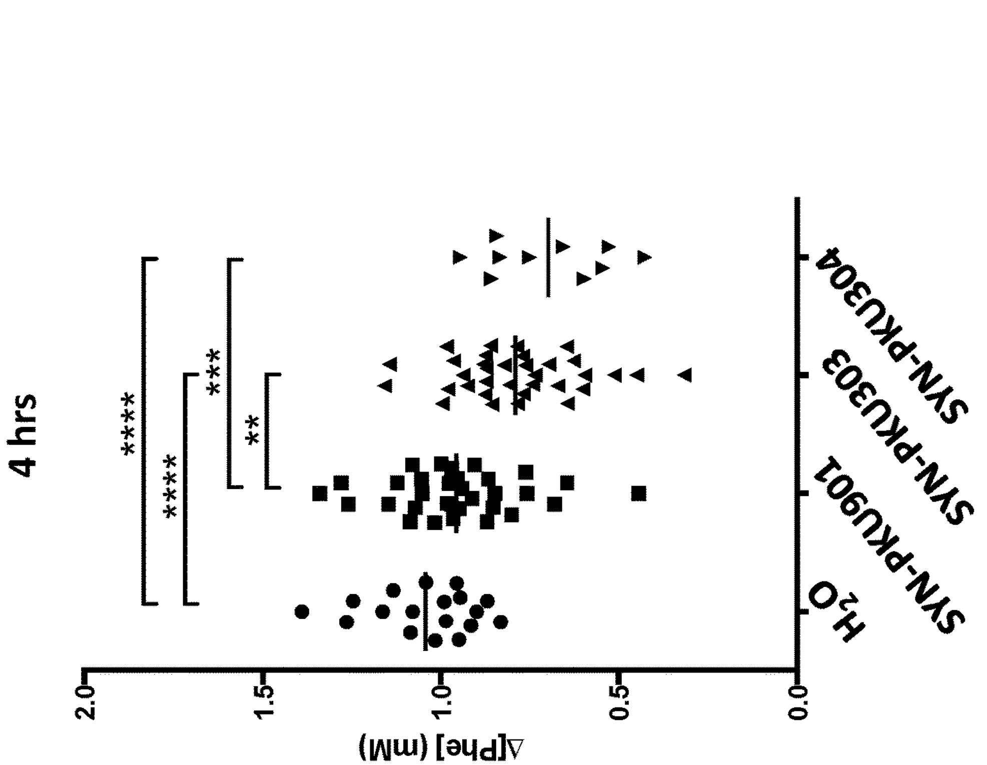
FIGS. 29C and 29D depict scatter plots of the data shown in FIGS. 29A and 29**B.
Figure 29C:
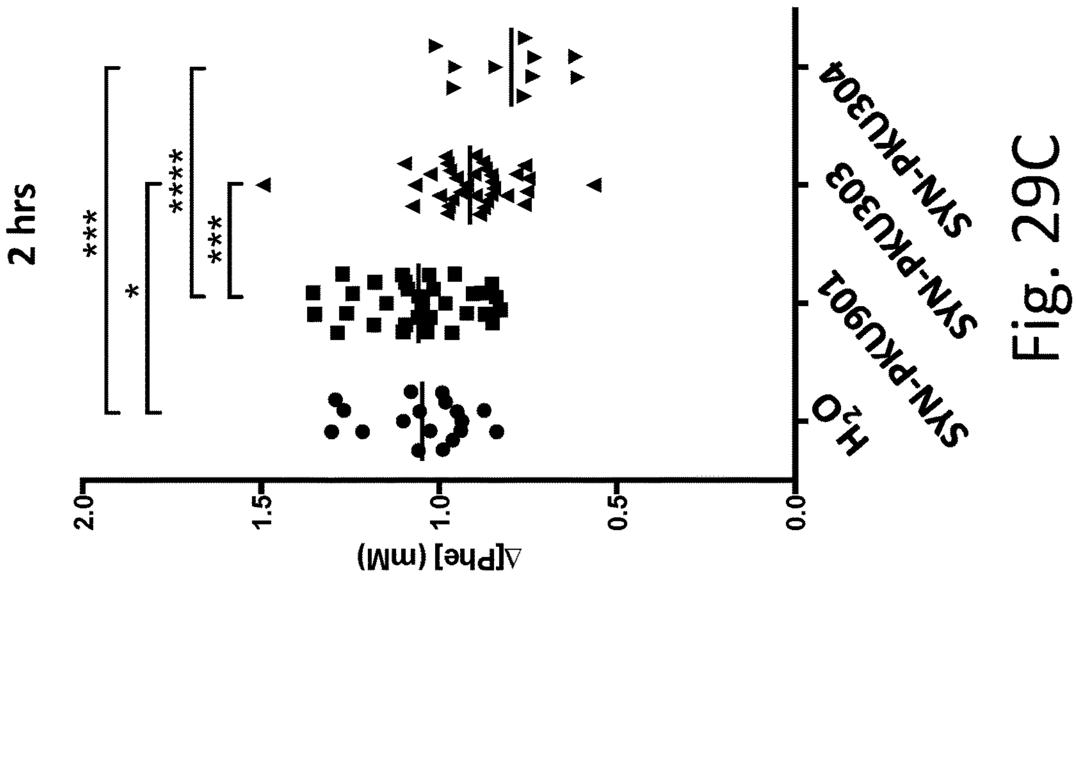

FIG. 27 shows phenylalanine blood concentrations relative to baseline concentrations at 2 hrs (FIG. 27A) and 4 hrs (FIG. 27B) post-phenylalanine injection. These data suggest that subcutaneous injection of phenylalanine causes hyperphenylalanemia in homozygous enu2/enu2 mice, and that oral administration of SYN-PKU303 significantly reduces blood phenylalanine levels following phenylalanine challenge, compared to control groups ($p<0.00001$ at 4 hrs). Moreover, these results confirm that the orally-administered engineered bacteria, and not the non-engineered Nissle parent, can significantly impact blood-phenylalanine levels independent of dietary exposure. Thus, a PKU-specific probiotic may not need to be co-administered in conjunction with diet.

Example 15. Dose-Response Activity of PAL-Expressing Bacteria on Systemic Phenylalanine Streptomycin-resistant *E. coli* Nissle (SYN-PKU901) were grown from frozen stocks to a density of $10^{10}$ cells/mL. Bacteria containing a copy of pheP under the control of a $P_{fnrS}$ promoter integrated into the lacZ locus, as well as a low-copy plasmid expressing PAL3 under the control of a $P_{fnrS}$ promoter (SYN-PKU304) were grown to an $A_{600}$ of 0.25 and then induced anaerobically by purging the bacterial fermenter with nitrogen for 4 hrs. Bacteria were centrifuged, washed, and resuspended in bicarbonate buffer at density of $5\times10^9$ cells/mL before freezing at −80° C.

Beginning at least 3 days prior to the study (i.e., Days −6 to −3), mice were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, 200 μL of $H_2O$ (n=12), 200 μL of SYN-PKU901 (n=12), or 100 μL, 200 μL, or 400 μL of SYN-PKU304 (n=12 in each dose group) were administered to mice by oral gavage. Blood samples were collected at 2 hrs and 4 hrs following phenylalanine challenge, and phenylalanine levels in the blood were measured using mass spectrometry.

Figure 30B:
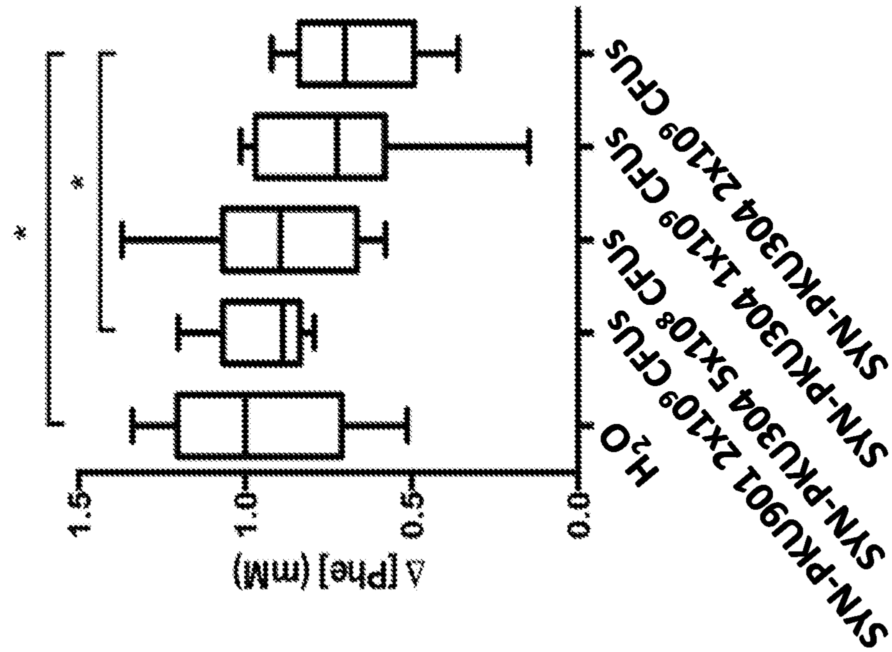
FIGS. 30A and 30B depict blood phenylalanine concentrations relative to baseline following subcutaneous phenylalanine challenge in an in vivo mouse model of PKU. Mice were orally gavaged with 200 μL of H2O (n=12), 200 μL of SYN-PKU901 (n=12), or 100, 200, or 400 μL of SYN-PKU304 (n=12 in each dose group) at 30 and 90 minutes post-phenylalanine injection (0.1 mg/gram of average group body weight).
Figure 30A:
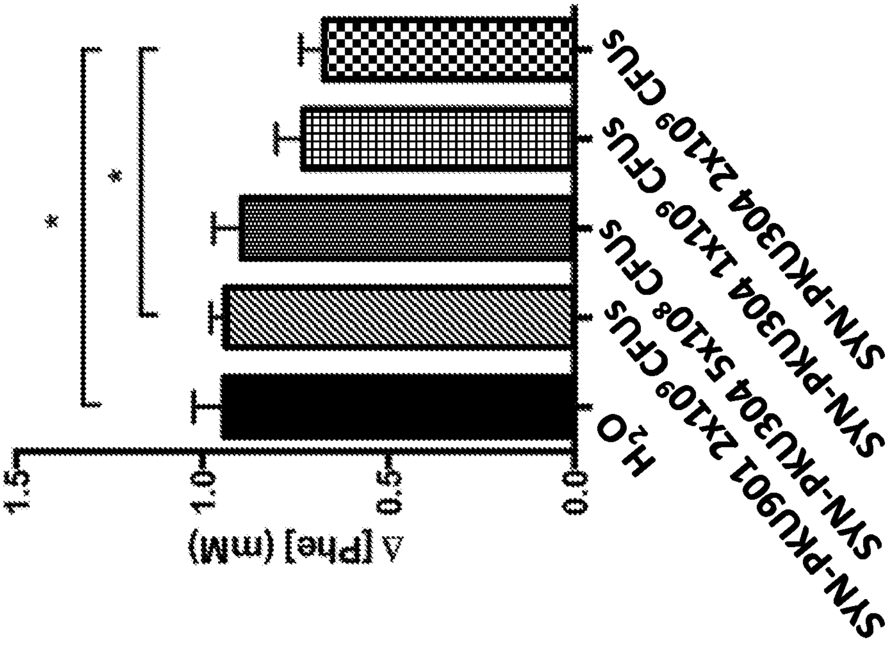
Figures 31A, 31B:
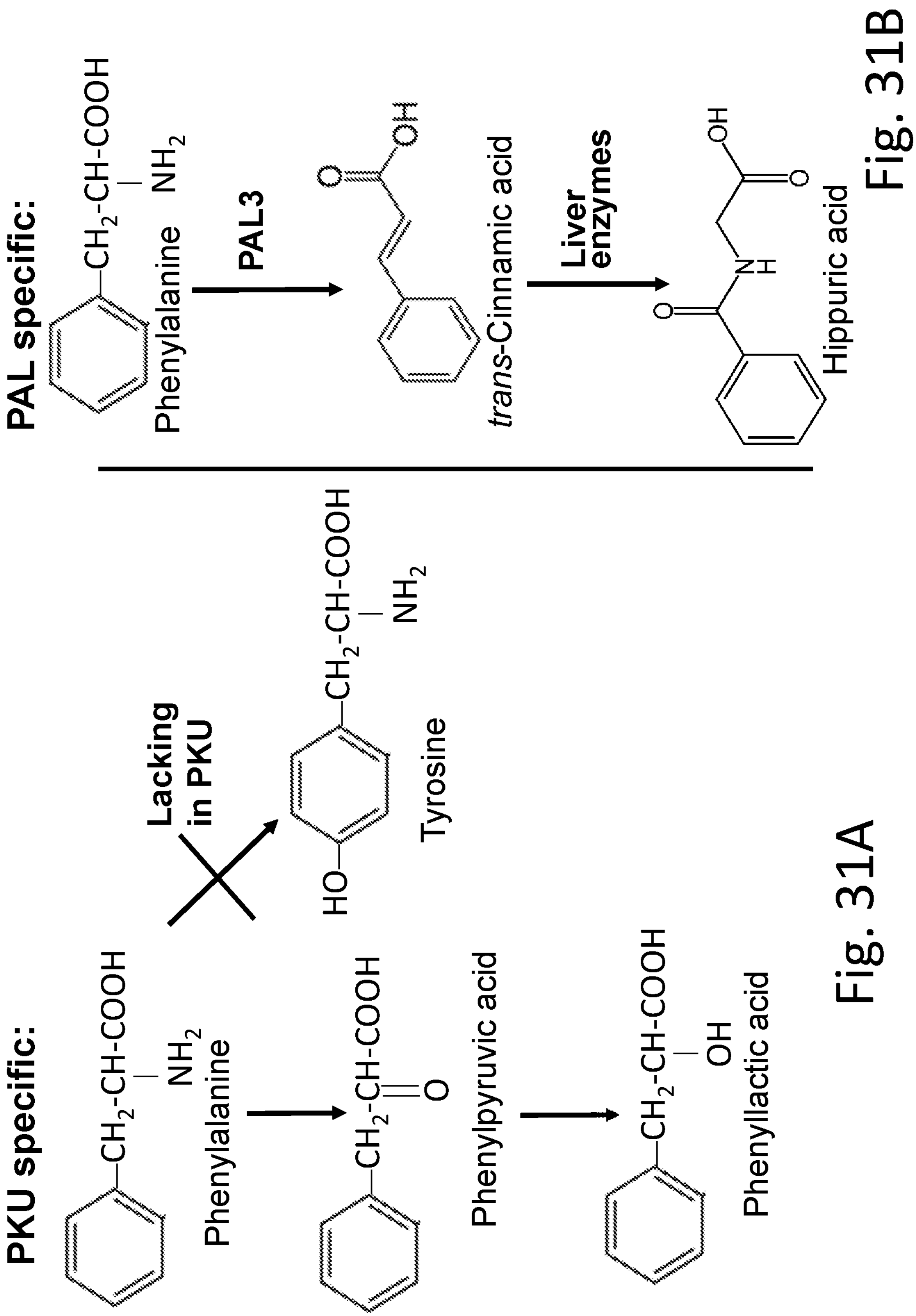
FIGS. 31A and 31B depicts a schematic of PKU specific and PAL specific phenylalanine metabolites.
Figure 32A:
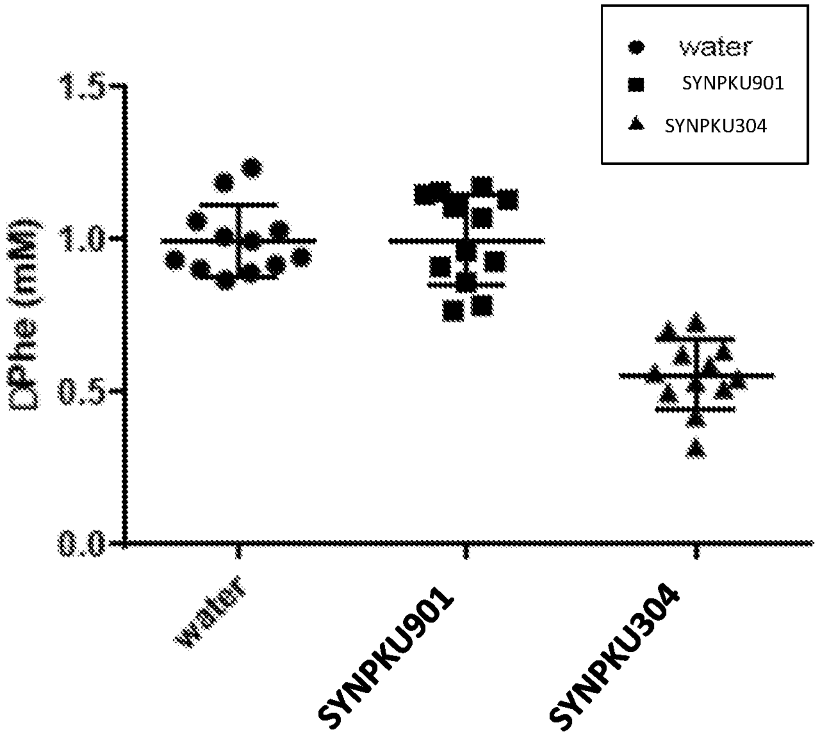
FIGS. 32A, 32B, 32C, 32D, 32E, and 32F depict blood phenylalanine concentrations relative to baseline and concentrations of phenylalanine (FIG. 32A), and absolute values of phenylalanine and PKU specific and PAL specific metabolites (FIGS. 32B, 32C, 32D, 32E, and 32F) following subcutaneous phenylalanine challenge in an in vivo mouse model of PKU. Mice were orally gavaged with a total of 800 μL of H2O (n=12), SYN-PKU901 (n=12), or 800 μL of SYN-PKU304 (n=12) (2.9e10 cfu/mouse) at 30 and 90 minutes post-phenylalanine injection.
Figure 32B:
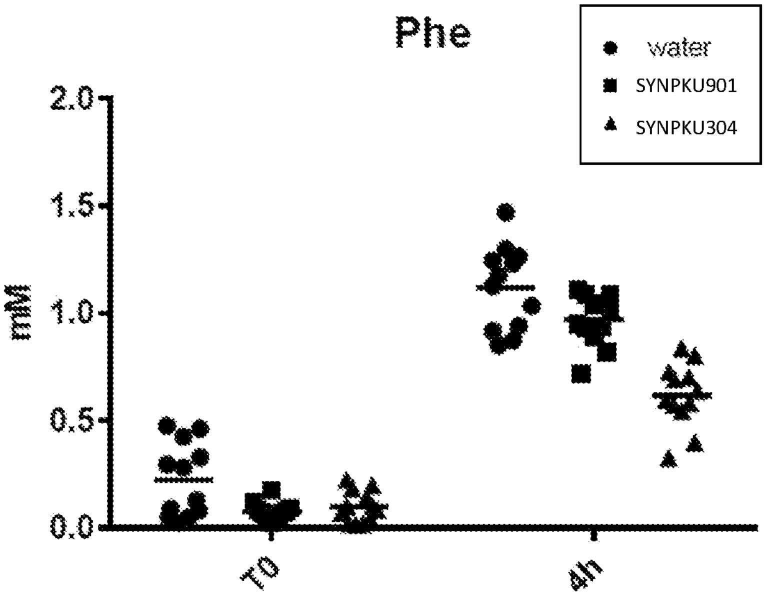
Figure 32C:
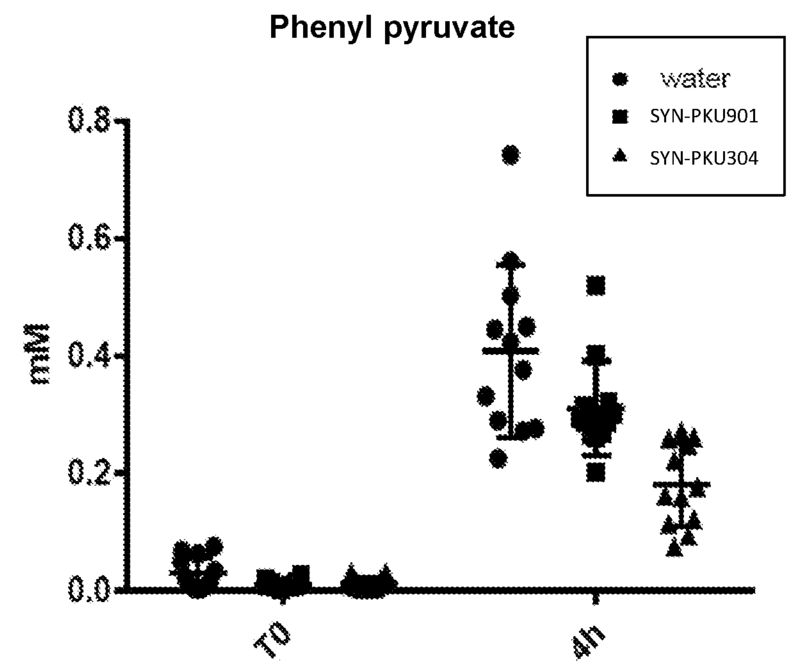
Figure 32D:
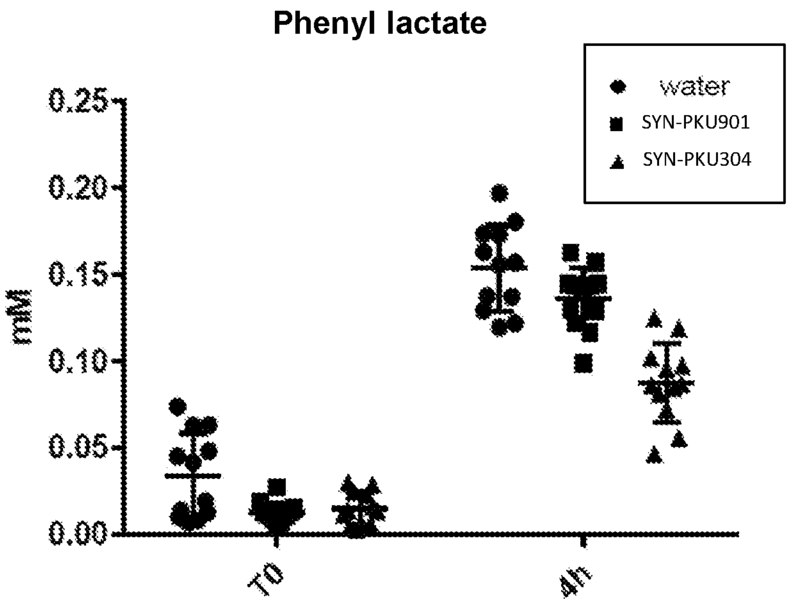
Figure 32E:
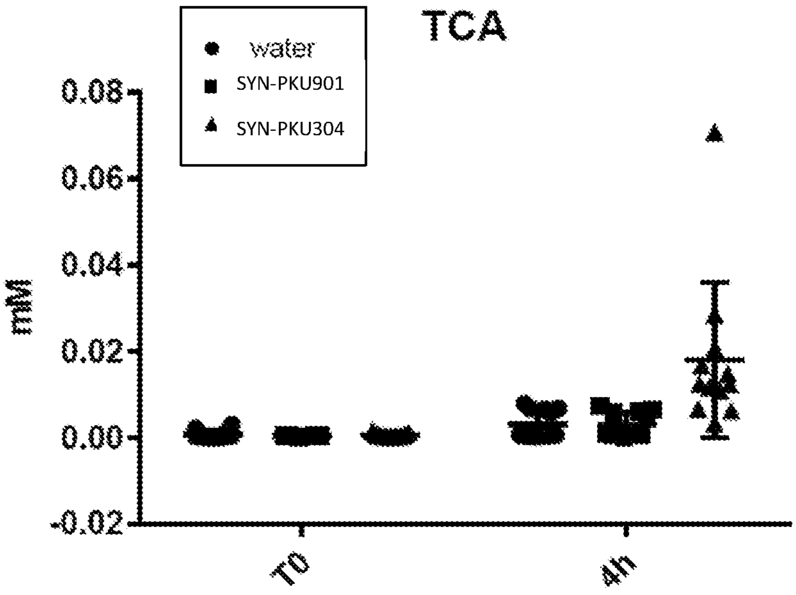
Figure 32F:
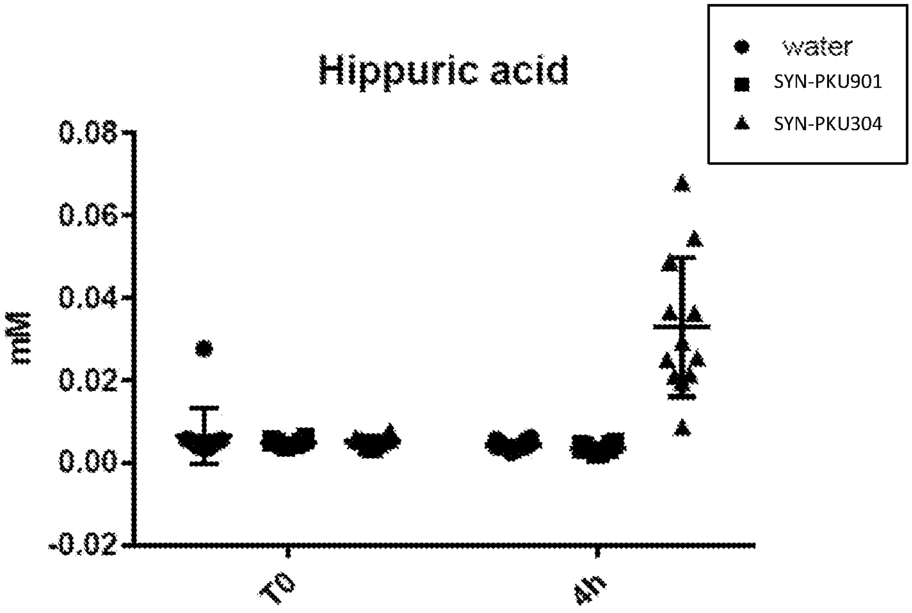

FIG. 30 shows phenylalanine blood concentrations relative to baseline concentrations post-phenylalanine injection. These data demonstrate a dose-dependent decrease in blood phenylalanine levels in SYN-PKU304-treated mice compared to mock treatment ($H_2O$) or administration of the parental strain (SYN-PKU901), following subcutaneous injection of phenylalanine (*30% decrease; $p<0.05$).

Example 16. Phenylalanine Degradation Activity In Vivo (PAL)

To compare the correlation between in vivo and in vitro phenylalanine activity, SYN-PKU304 (containing a low copy plasmin expressing PAL3 with a chromosomal insertion of PfnrS-pheP at the LacZ locus, was compared to SYN-PKU901, a control Nissle strain with streptomycin resistance in vivo).

Beginning at least 3 days prior to the study (i.e., Days −6 to −3), homozygous BTBR-$Pah^{enu2}$ mice (approx. 6-12 weeks of age) were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, the bacteria were administered to mice by oral gavage.

To prepare the cells, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 4e10 cfu/mL and mixed 9:1 in 1M bicarbonate. Each mouse gavaged 800 uL total, or 2.9e10 cfu/mouse.

Blood samples were collected at 2 hrs and 4 hrs following phenylalanine challenge, and phenylalanine levels in the blood were measured using mass spectrometry, and the change in Phenylalanine concentration per hour was calculated. Results are shown in FIG. 32. The total metabolic activity measured was 81.2 umol/hr. and the total reduction in change in phenylalanine was 45% (P<0.05). These same cells showed an in vitro activity of 2.8 umol/hr./1e9 cells.

Additionally, various metabolites were measured to determine whether secondary metabolites can be used as an additional parameter to assess the rate of phenylalanine consumption of the engineered bacteria. When PAH activity is reduced in PKU, the accumulated phenylalanine is converted into PKU specific metabolites phenylpyruvate, which can be further converted into phenyllactic acid. In the presence of the genetically engineered bacteria, phenylalanine is converted by PAL to PAL specific metabolites trans-cinnamic acid, which then can be further converted by liver enzymes to hippuric acid (FIG. 32). Blood samples were analyzed for phenylpyruvate, phenyllactate, trans-cinnamic acid, and hippuric acid as described in Example 24-26. Results are shown in FIGS. 32C, 32D, 32E, and 32F and are consistent with the phenylalanine degradation shown in FIGS. 32A and 32B. For SYN-PKU304, PAL specific metabolites are detected at 4 hours, and moreover, lower levels of PKU specific metabolites are observed as compared to SYN-PKU901, indicating that PAL phenylalanine degradation may cause a shift away from PKU specific metabolites in favor or PAL specific metabolites.

Example 17. Phenylalanine Degradation Activity In Vivo (PAL)

SYN-PKU517 (comprising 2 chromosomal insertions of PAL (2×fnrS-PAL (malEK, malPT)), and a chromosomal insertion of pheP (fnrS-pheP (lacZ)), thyA auxotrophy (kan/cm)) was compared to SYN-PKU901.

Mice were maintained, fed, and administered phenylalanine as described above. To prepare the bacterial cells for gavage, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 4e10 cfu/mL was mixed 9:1 in 1M bicarbonate. Each mouse gavaged 800 uL total, or 3.6e10 cfu/mouse.

Figure 33A:
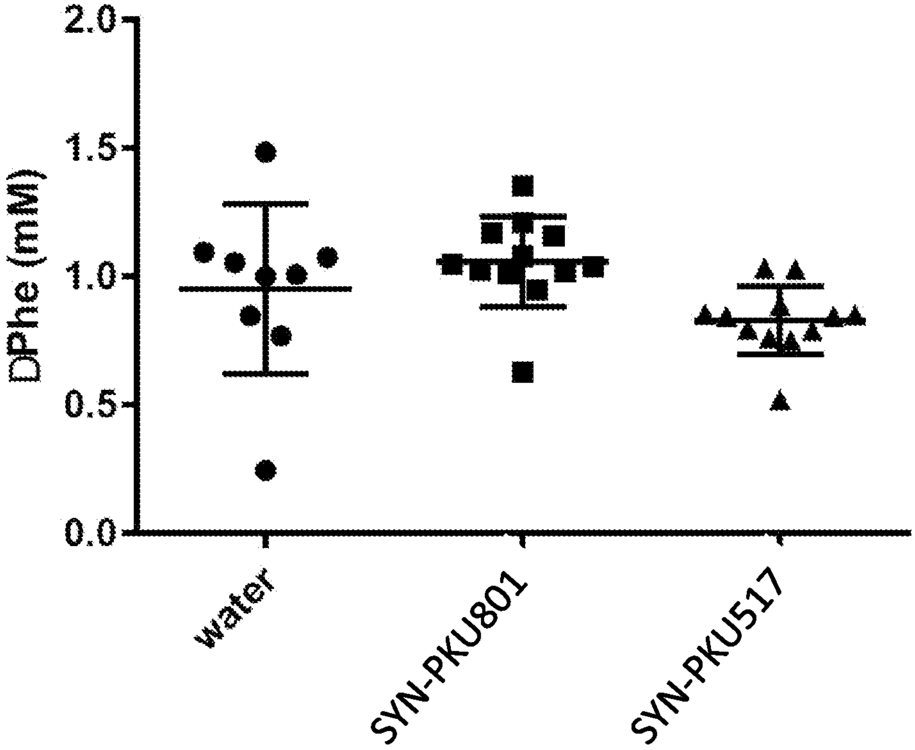
FIGS. 33A, 33B, 33C, 33D, 33E, and 33F depict blood phenylalanine concentrations relative to baseline and concentrations of phenylalanine (FIG. 33A), and absolute values of phenylalanine and PKU specific and PAL specific metabolites (FIGS. 33B, 33C, 33D, 33E, and 33F) following subcutaneous phenylalanine challenge in an in vivo mouse model of PKU. Mice were orally gavaged with a total of 800 μL of H2O (n=9]), SYN-PKU801 (n=12), or 800 μL of SYN-PKU517 (n=12) (3.6e10 cfu/mouse) at 30 and 90 minutes post-phenylalanine injection.
Figure 33B:
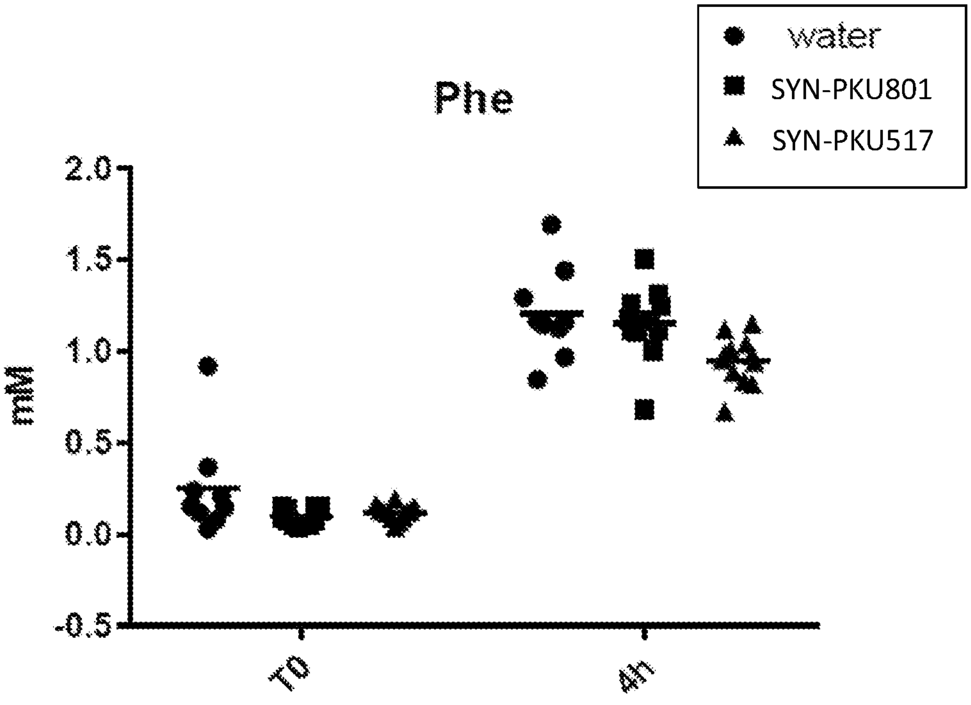
Figure 33C:
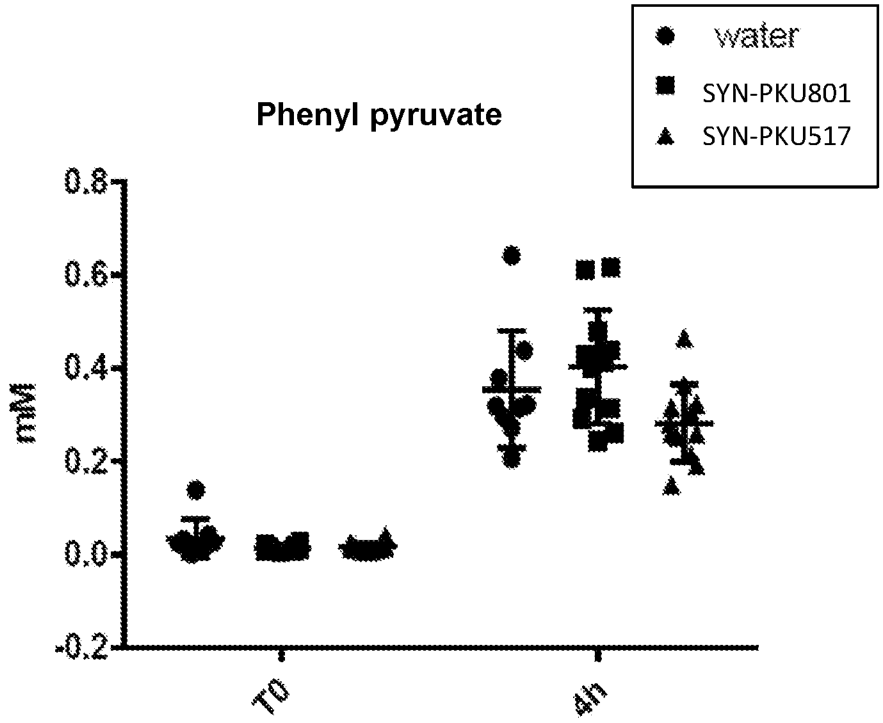
Figure 33D:
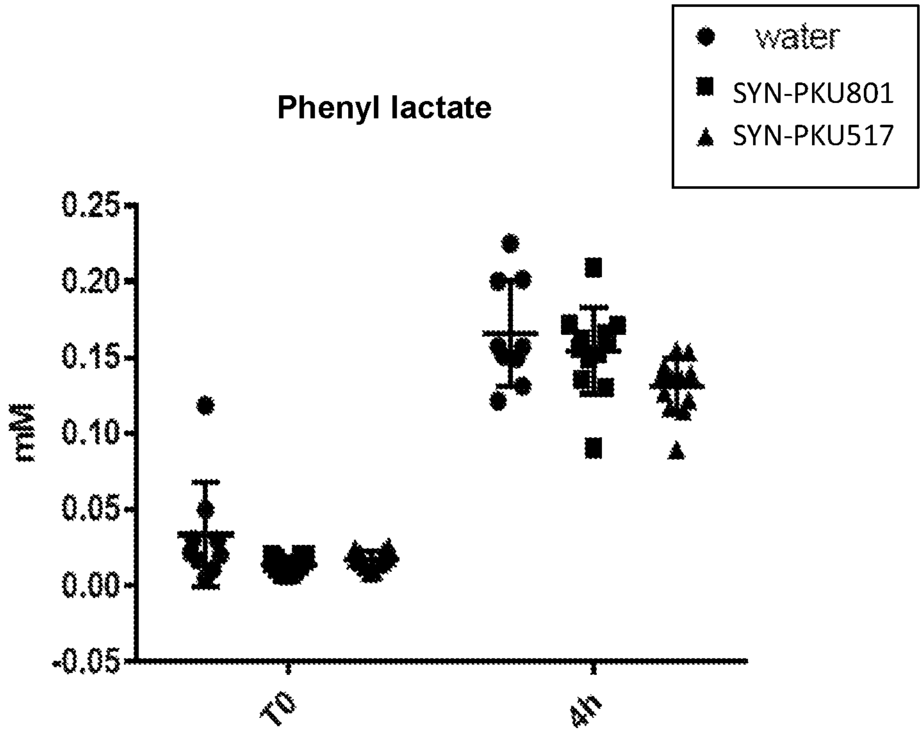
Figure 33E:
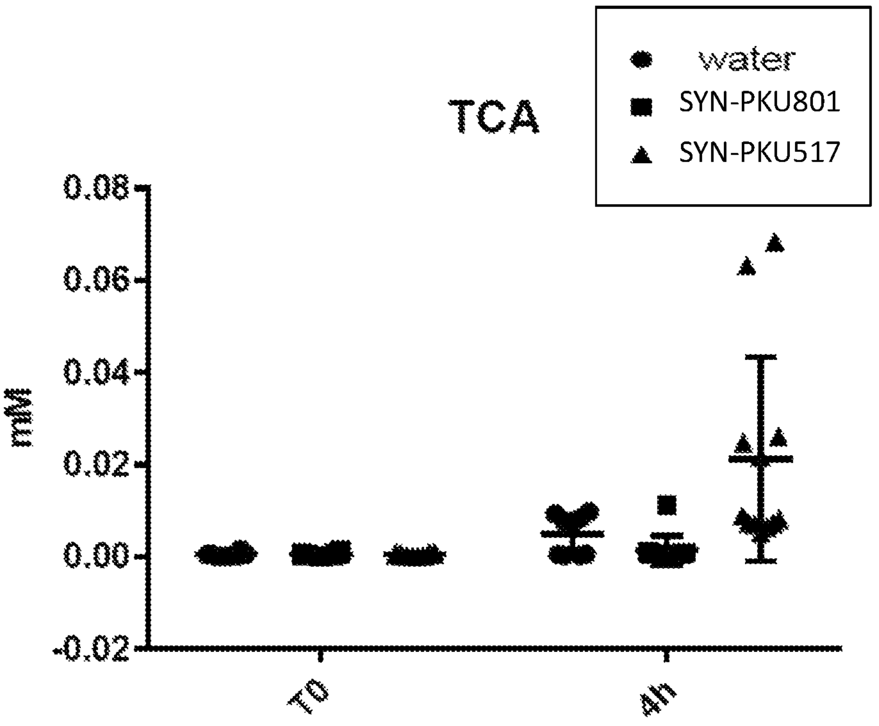
Figure 33F:
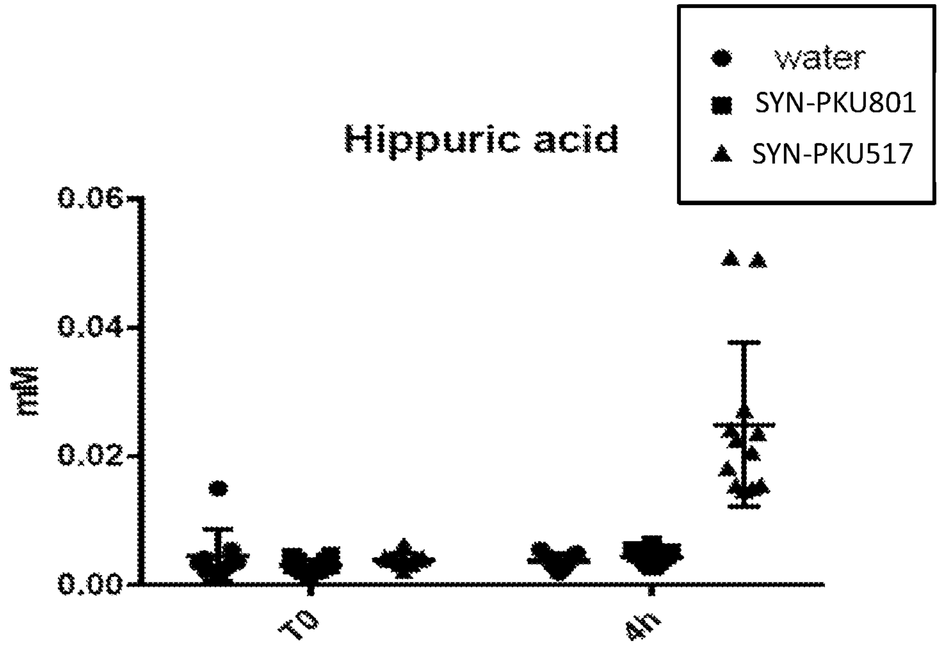

As described above, blood samples were collected, and the change in phenylalanine concentration as compared to baseline was calculated. Results are shown in FIGS. 33A and 33B. The total metabolic activity measured was 39.6 umol/hr. and the total reduction in change in phenylalanine was 17% (P<0.05). These same cells showed an in vitro activity of 1.1 umol/hr./1e9 cells.

Absolute levels of phenylalanine and of PKU and PAL metabolites are shown in FIGS. 33C, 33D, 33E, and 33F and are consistent with the phenylalanine degradation shown in FIGS. 33A and 33B. For SYN-PKU517, PAL specific metabolites were detected at 4 hours, and moreover, lower levels of PKU specific metabolites were observed as compared to SYN-PKU901, indicating that PAL phenylalanine degradation may cause a shift away from PKU specific metabolites in favor or PAL specific metabolites.

In some embodiments, urine is collected at predetermined time points, and analyzed for phenylalanine levels and levels of PAL and PKU metabolites.

Example 18. Phenylalanine Degradation Activity In Vivo (PAL)

SYN-PKU705 (comprising 3 chromosomal insertions of PAL (3×fnrS-PAL (malEK, malPT, yicS/nepI)), and 2 chromosomal insertions of pheP (2×fnrS-pheP (lacZ, agal/rsml)), and LAAD (driven by the ParaBAD promoter integrated within the endogenous arabinose operon) was compared to SYN-PKU901.

Figure 34A:
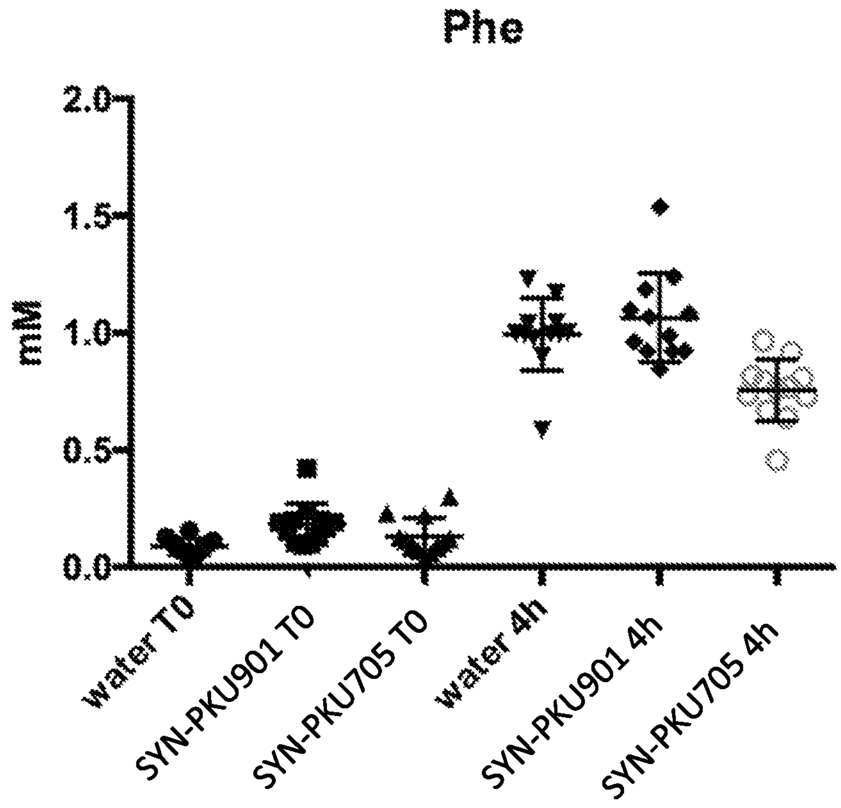
FIGS. 34A, 34B, 34C, 34D, 34E, and 34F depict blood phenylalanine concentrations relative to baseline and concentrations of phenylalanine (FIG. 34A), and absolute values of phenylalanine and PKU specific and PAL specific metabolites (FIGS. 34B, 34C, 34D, 34E, and 34F) following subcutaneous phenylalanine challenge in an in vivo mouse model of PKU. Mice were orally gavaged with a total of 800 μL of H2O (n=12), SYN-PKU901 (n=12), or 800 μL of SYN-PKU705 (n=12) (3.6e10 cfu/mouse) at 30 and 90 minutes post-phenylalanine injection.

Mice were maintained, fed, and administered phenylalanine as described above. To prepare the bacterial cells for gavage, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 5e10 cfu/mL was mixed 9:1 in 1M bicarbonate. Each mouse gavaged 800 uL total, or 3.6e10 cfu/mouse. Note: Though this strain contains the LAAD gene, it was not induced in this study As described above, blood samples were collected, and the change in phenylalanine concentration as compared to baseline was calculated. Results are shown in FIG. 34A. The total metabolic activity measured was 133.2 umol/hr. and the total reduction in change in phenylalanine was 30% (P<0.05). These same cells showed an in vitro activity of 3.7 umol/hr./1e9 cells.

Figure 34B:
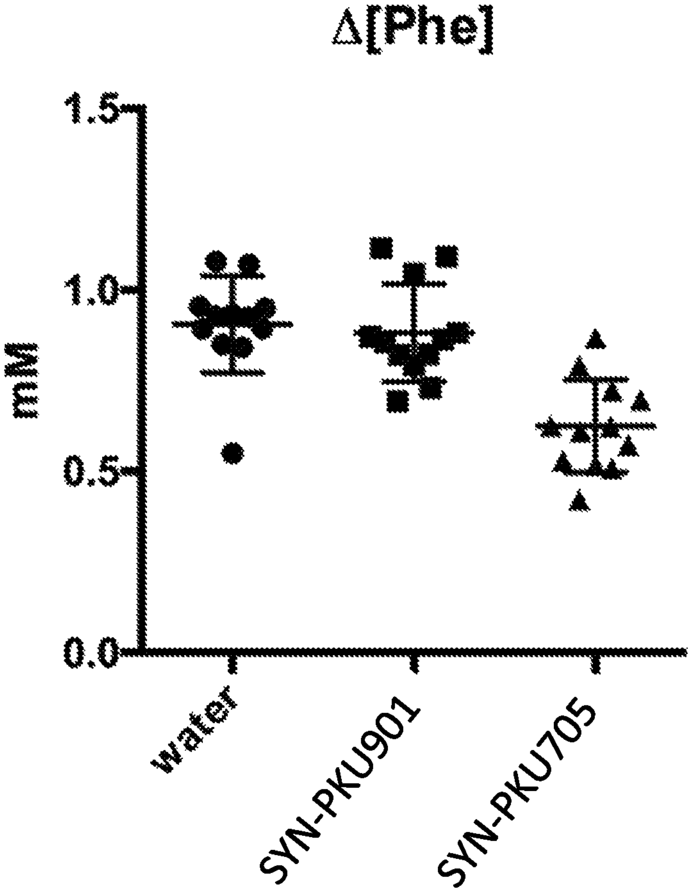
Figure 34C:
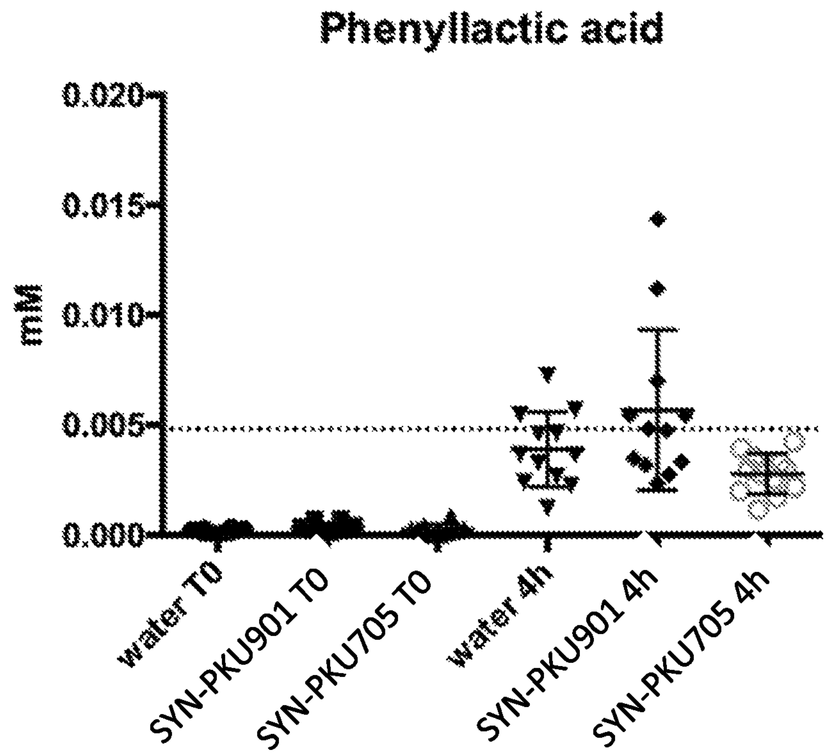
Figure 34D:
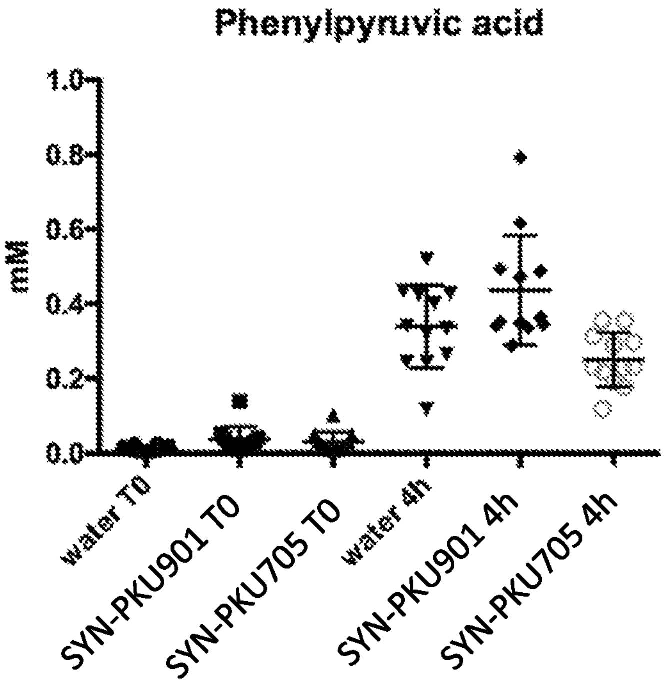
Figure 34E:
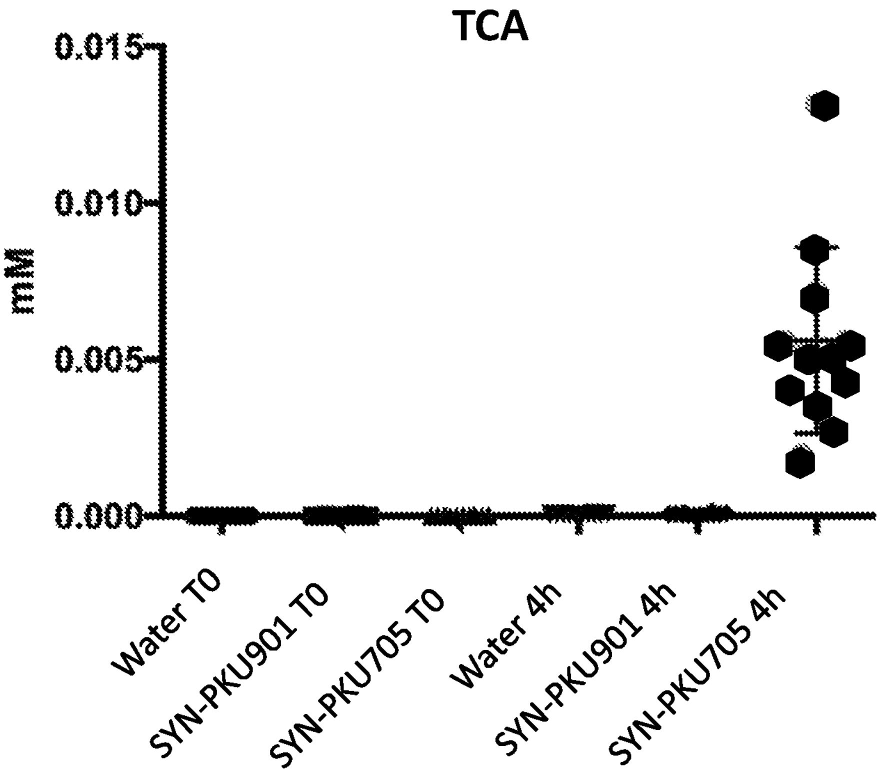
Figure 34F:
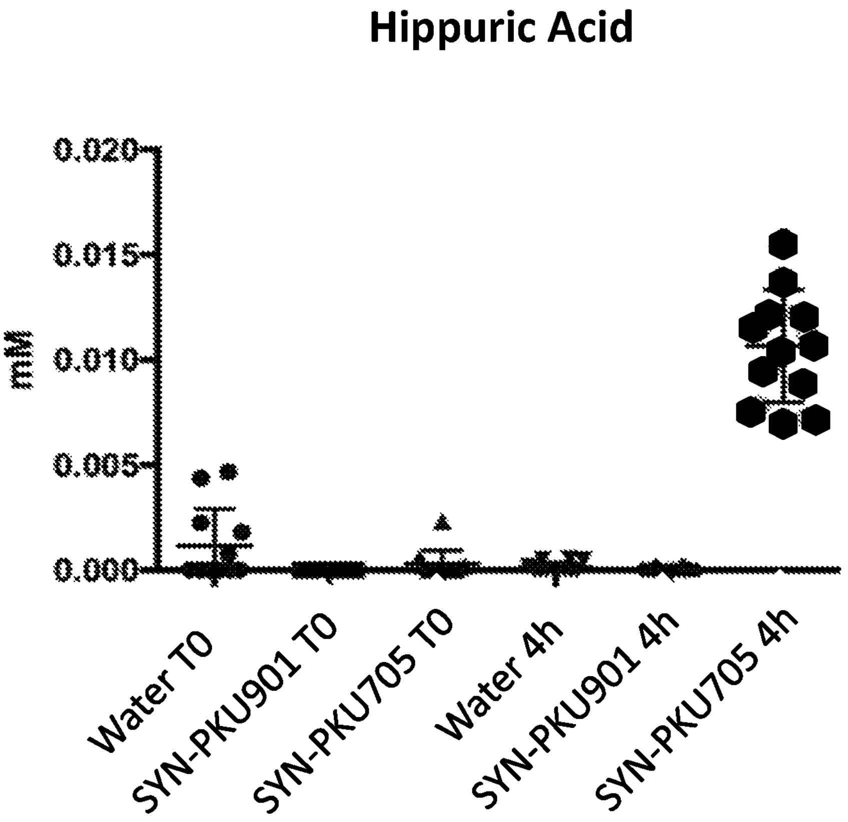

Absolute levels of phenylalanine and of PKU and PAL metabolites are shown in FIGS. 34C, 34D, 34E, and 34F and are consistent with the phenylalanine degradation shown in FIGS. 34A and 34B. PAL specific metabolites were detected at 4 hours, and moreover, lower levels of PKU specific metabolites were observed as compared to SYN-PKU901, indicating that PAL phenylalanine degradation may cause a shift away from PKU specific metabolites in favor or PAL specific metabolites. total metabolic activity measured activity was greater than the total metabolic activity measured of the PAL3 plasmid-based strain SYN-PKU304 and the total reduction in phenylalanine approached that of SYN-PKU304 (30% as compared to 45%).

In some embodiments, urine is collected at predetermined time points, and analyzed for phenylalanine levels and levels of PAL and PKU metabolites.

Example 19. Phenylalanine Degradation Activity In Vivo (PAL) LAAD

The suitability of *P. proteus* LAAD for phenylalanine degradation by the genetically engineered bacteria is further assessed in vivo. Bacterial strain SYN-PKU401 (comprising a high copy plasmid comprising LAAD driven by a Tet-inducible promoter is compared to SYN-PKU901.

Mice are maintained, fed, and administered phenylalanine as described above. To prepare the bacterial cells for gavage, cells are diluted 1:100 in LB (2 L), grown for 1.5 h aerobically, then ATC is added and the cells are grown for another 2 hours. Prior to administration, cells are concentrated 200× and frozen for storage. Cells are thawed on ice, and resuspended. Cells are mixed 9:1 in 1M bicarbonate. Each mouse is gavaged four times with 800 uL total volume, or with a total of bacteria ranging from $2 \times 10^9$ to $1 \times 10^{10}$. Blood samples are collected from the mice described in the previous examples and are analyzed for phenylalanine, phenylpyruvate, phenyllactate, trans-cinnamic acid, and hippuric acid levels. Total reduction in phenylalanine and total metabolic activity are calculated.

Example 20. Effect of pH on Phenylalanine Degradation in Recombinant *E. coli*

Figure 39A:
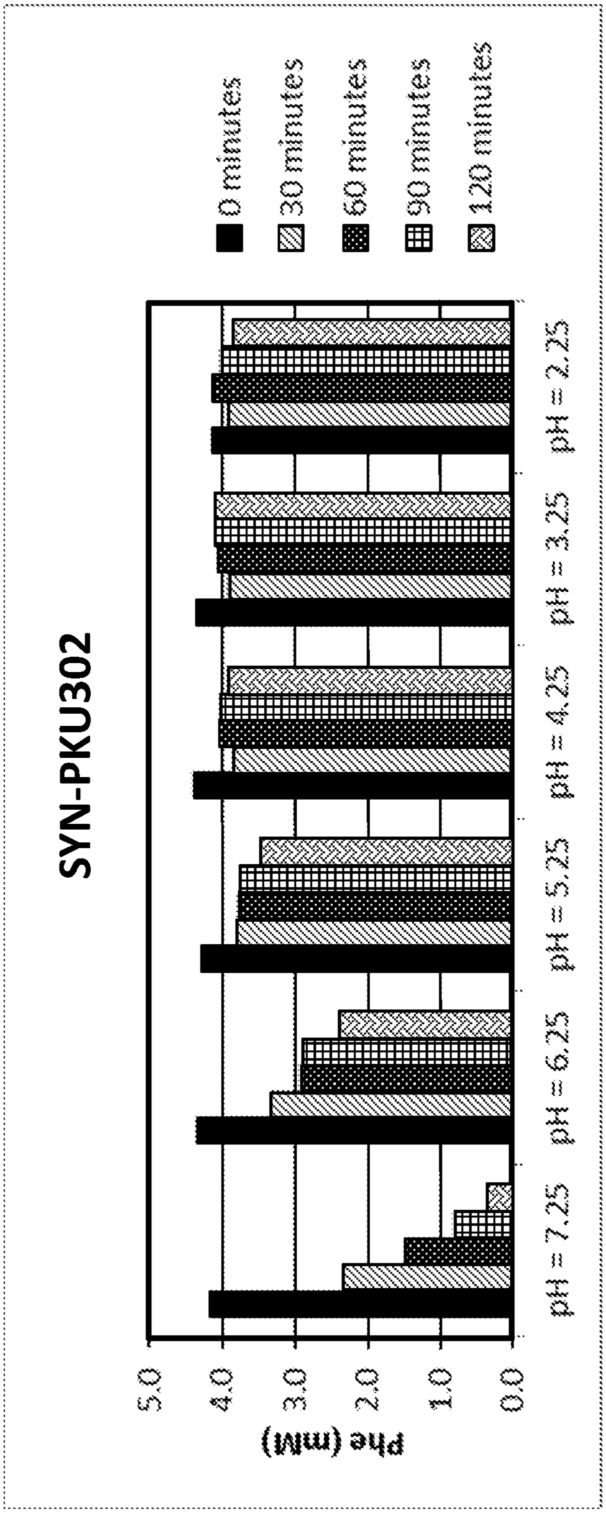
FIGS. 39A and 39B depict phenylalanine concentrations in SYN-PKU302 cultures over time. After 1.5 hrs of growth, ATC was added to cultures of SYN-PKU302, and SYN-PKU304 cultures were placed in Coy anaerobic chamber supplying 90% $N_2$, 5% $CO_2$, and 5% $H_2$. After 4 hrs of induction, bacteria were resuspended in assay buffer containing 4 mM phenylalanine and at different pH (pH range 7.25-2.25). Aliquots were removed from cell assays every 30 min for 2 hrs for phenylalanine quantification by mass spectrometry. Phenylalanine degradation rates decreased as pH of the assay buffer decreased in both strains, SYN-PKU302 (FIG. 39A) and SYN-PKU304 (FIG. 39B).
Figure 39B:
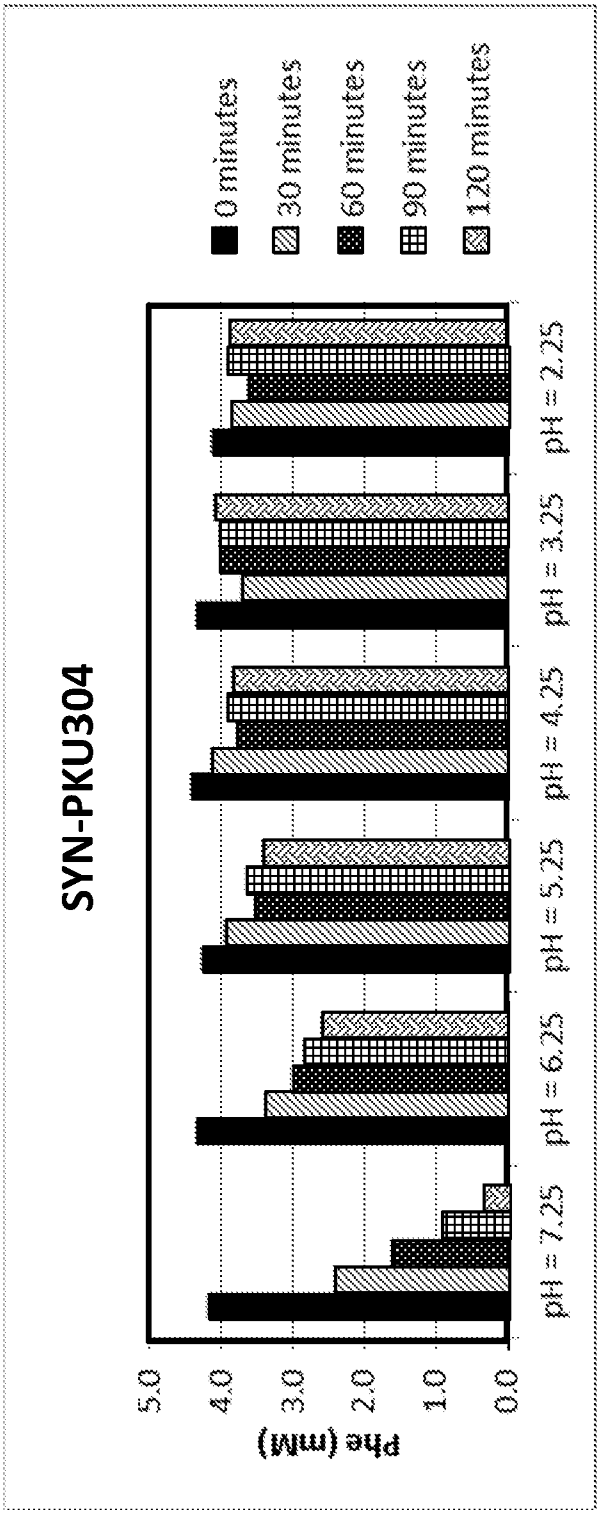
Figure 40:
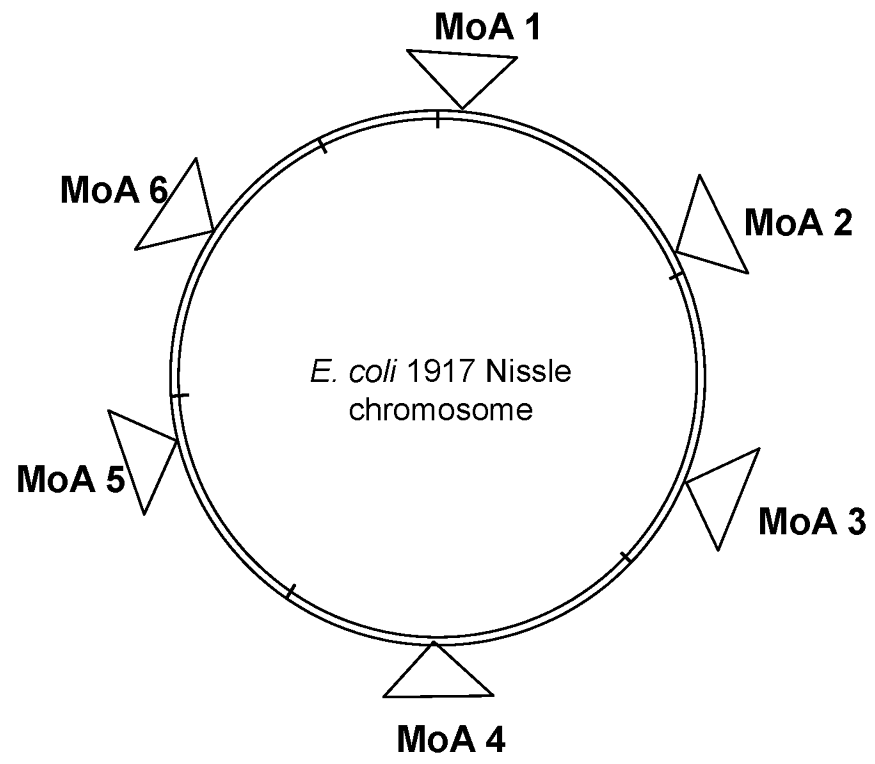
FIG. 40 depicts an exemplary schematic of the *E. coli* 1917 Nissle chromosome comprising multiple mechanisms of action (MoAs).

To determine whether the rates of phenylalanine degradation in SYN-PKU304 and SYN-PKU302 are affected by low pH, overnight cultures of both strains were diluted 1:100 in LB and grown with shaking (250 rpm) at 37° C. After 1.5 hrs of growth, ATC (100 ng/mL) was added to cultures of SYN-PKU302, and SYN-PKU304 cultures were placed in a Coy anaerobic chamber (supplying 90% $N_2$, 5% $CO_2$, and 5% $H_2$). After 4 hrs of induction, bacteria were pelleted, washed in PBS, and resuspended in assay buffer (M9 minimal media with 0.5% glucose, 8.4% sodium bicarbonate, and 4 mM Phe) to a concentration of 5e9 cells/mL. Assay buffer was prepared with incrementally decreasing values of pH, ranging from 7.25-2.25, using 1M HCl. Aliquots were removed from the cell assay every 30 min for 2 hrs for phenylalanine quantification by mass spectrometry. As shown in FIG. 39, phenylalanine degradation rates decreased as pH of the assay buffer decreased in both strains, SYN-PKU302 (FIG. 39A) and SYN-PKU304 (FIG. 39B).

Example 21. Degradation of Dipeptides and Tripeptides

Overnight strains of SYN-PKU304, and SYN-PKU705 were diluted 1:100 and grown to early log before shifting to anaerobic conditions for induction of PAL and pheP. One culture of SYN-PKU705 was also induced with arabinose to induce the LAAD protein. The focus of this study was to determine if PKU strains could degrade Phe when sequestered in the form of di and tripeptides. After strain induction Cells were spun down and resuspended in assay buffer containing M9 minimal media, 0.5% glucose, 50 mM MOPS, and 50 mM of Phe or Phe-containing di- or tripeptide. Supernatant samples were removed every 20 minutes for a total of 80 minutes, and supernatant was analyzed on a UV-Vis spectrophotometer to measure absorbance at 290 nm (the absorption peak for trans-cinnamic acid). Results are shown in Table 43 indicated that PKU strains were capable of degrading Phe rapidly even in the form of di- and tri-peptides.

TABLE 43

Dipeptide and Tripeptide Degradation Rates

| | Rate (umol TCA produced/hr./1e9 cfu) | | | | | |
|---|---|---|---|---|---|---|
| | Phe | Phe-Val | Phe-Ala | Gly-Phe | Phe-Pro | Phe-Gly-Gly |
| SYN-PKU304 | 4.1 | 3.9 | 3.5 | 1.7 | 1.1 | 2.0 |
| SYN-PKU705 | 6.9 | 5.8 | 5.0 | 4.1 | 1.3 | 4.5 |
| SYN-PKU705 + ara | 4.8 | 5.8 | 4.2 | 2.0 | 1.4 | 3.3 |

Example 22. Engineering Bacterial Strains Using Chromosomal Insertions

Bacterial strains, in which the pheP and/or PAL3 genes are integrated directly into the *E. coli* Nissle genome under the control of an FNR-responsive promoter, were constructed. The methods described below may be used for engineering bacterial strains comprising chromosomal insertions (e.g., SYN-PKU902 and/or any of the integrated strains listed in Table 14.

Figure 41:
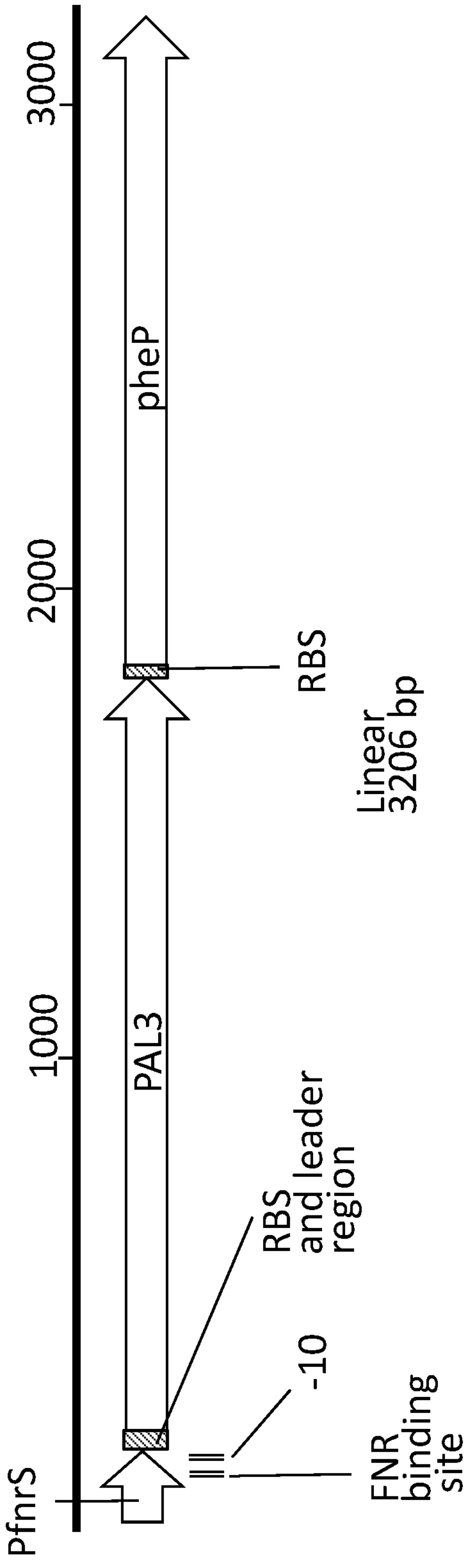
FIG. 41 depicts the gene organization of an exemplary construct in which the PAL3 and pheP genes are co-transcribed under the control of an exemplary FNR promoter ($P_{fnrS}$).

The SYN-PKU902 strain (lacZ::$P_{fnrS}$-PAL3-pheP) contains a copy of PAL3 and a copy of pheP integrated at the lacZ locus, with both genes operatively linked to a single fnrS promoter and co-transcribed in a bicistronic message (FIG. 41). Table 21 shows the sequence of an exemplary construct in which the PAL3 and pheP genes are co-transcribed under the control of an exemplary FNR promoter (SEQ ID NO: 31), with the FNR promoter sequence bolded, the PAL3 sequence boxed, the pheP sequence underlined, and ribosomal binding sites highlighted.

To create a vector capable of integrating the $P_{fnrS}$-PAL3-pheP sequence into the chromosome, Gibson assembly was used to add 1000 bp sequences of DNA homologous to the Nissle lacZ locus to both sides of a flippase recombination target (FRT) site-flanked chloramphenicol resistance ($cm^R$) cassette on a knock-in knock-out (KIKO) plasmid. Gibson assembly was then used to clone the $P_{fnrS}$-PAL3-pheP DNA sequence between these homology arms, adjacent to the FRT-$cm^R$-FRT site. Successful insertion of the fragment was validated by sequencing. PCR was used to amplify the entire lacZ::FRT-$cm^R$-FRT::$P_{fnrs}$-PAL3-pheP::lacZ region. This knock-in PCR fragment was used to transform an electrocompetent Nissle strain that contains a temperature-sensitive plasmid encoding the lambda red recombinase genes. After transformation, cells were grown for 2 hrs at 37° C. Growth at 37° C. cured the temperature-sensitive plasmid. Transformants with successful chromosomal integration of the fragment were selected on chloramphenicol at 20 µg/mL.

The SYN-PKU501 strain (malPT::$P_{fnrS}$-PAL3, lacZ::$P_{fnrS}$-pheP) contains a copy of PAL3 integrated at the malP/T locus, and a copy of pheP integrated at the lacZ locus, with both genes operatively linked to separate fnrS promoters (see Table 28; SEQ ID NO: 38). The SYN-PKU502 strain (malPT::$P_{fnrS}$-PAL3, lacZ::$P_{fnrS}$-PAL3-pheP) contains a copy of PAL3 integrated at the malP/T locus under the control of an fnrS promoter (see Table 28; SEQ ID NO: 38), as well as a PAL3-pheP construct integrated at the lacZ locus, wherein both genes at the lacZ locus are operatively linked to a single fnrS promoter and co-transcribed in a bicistronic message (see Table 21; SEQ ID NO: 31).

To create a vector capable of integrating the $P_{fnrS}$-PAL3 sequence (SEQ ID NO: 38) into the *E. coli* Nissle chromosome in SYN-PKU501 and SYN-PKU502, Gibson assembly was used to add 1000 bp sequences of DNA homologous to the Nissle malP and malT loci on either side of an FRT site-flanked kanamycin resistance ($kn^R$) cassette on a KIKO plasmid. Gibson assembly was then used to clone the $P_{fnrS}$-PAL3 DNA sequence between these homology arms, adjacent to the FRT-$kn^R$-FRT site. Successful insertion of the fragment was validated by sequencing. PCR was used to amplify the entire malP::FRT-$kn^R$-FRT::$P_{fnrS}$-PAL3::malT region. This knock-in PCR fragment was used to transform an electrocompetent Nissle strain already containing $P_{fnrS}$-pheP or bicistronic $P_{fnrS}$-PAL3-pheP in the lacZ locus, and expressing the lambda red recombinase genes. After transformation, cells were grown for 2 hrs at 37° C. Transformants with successful integration of the fragment were selected on kanamycin at 50 µg/mL. These same methods may be used to create a vector capable of integrating the $P_{fnrS}$-PAL3 sequence (SEQ ID NO: 38) at the malE/K insertion site in SYN-PKU506 and SYN-PKU507.

Figure 42A:
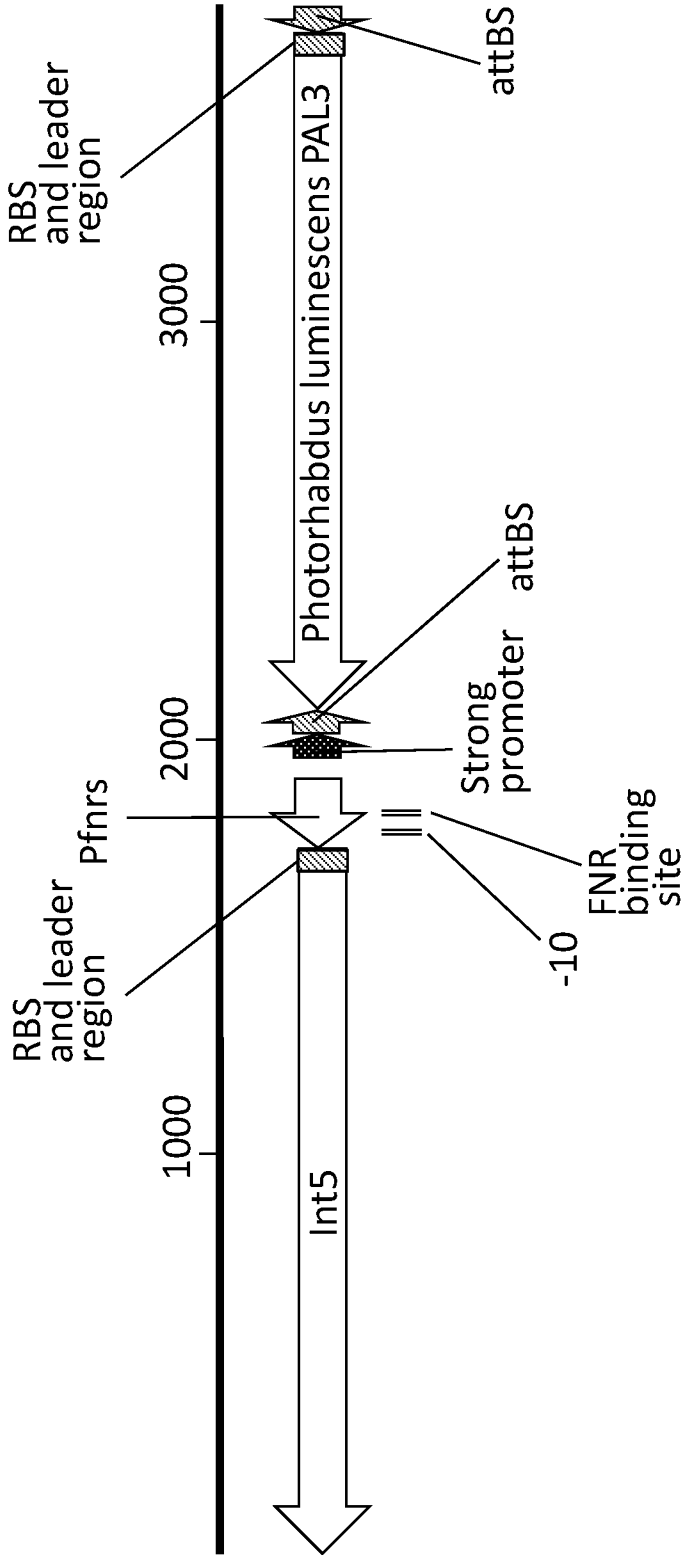
FIGS. 42A and 42B depict the gene organization of an exemplary construct in which the Int5 recombinase gene is operably linked to an exemplary FNR promoter ($P_{fnrS}$), and the PAL3 gene is operably linked to a strong constitutive promoter.
Figure 42B:
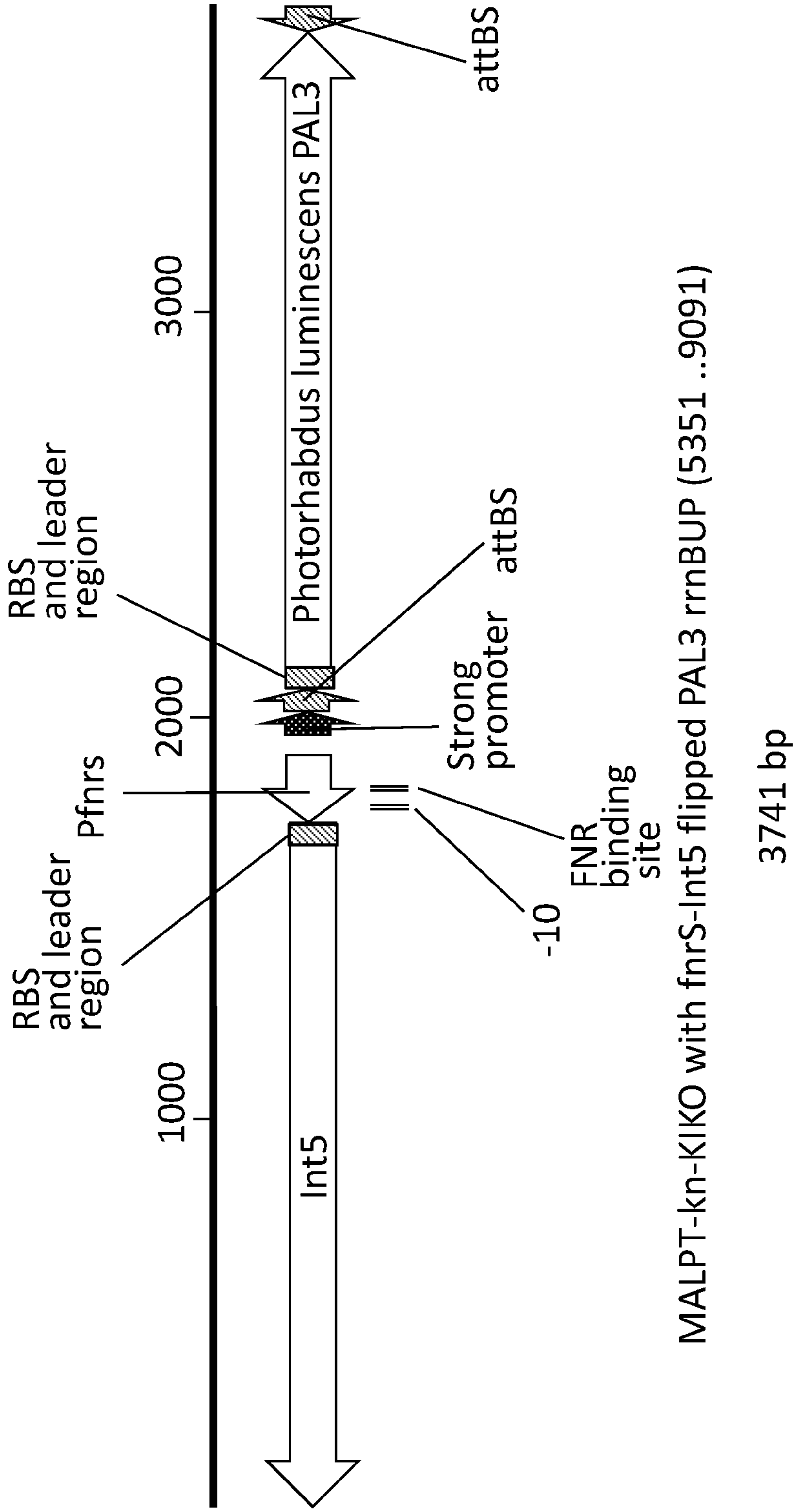
Figure 43A:
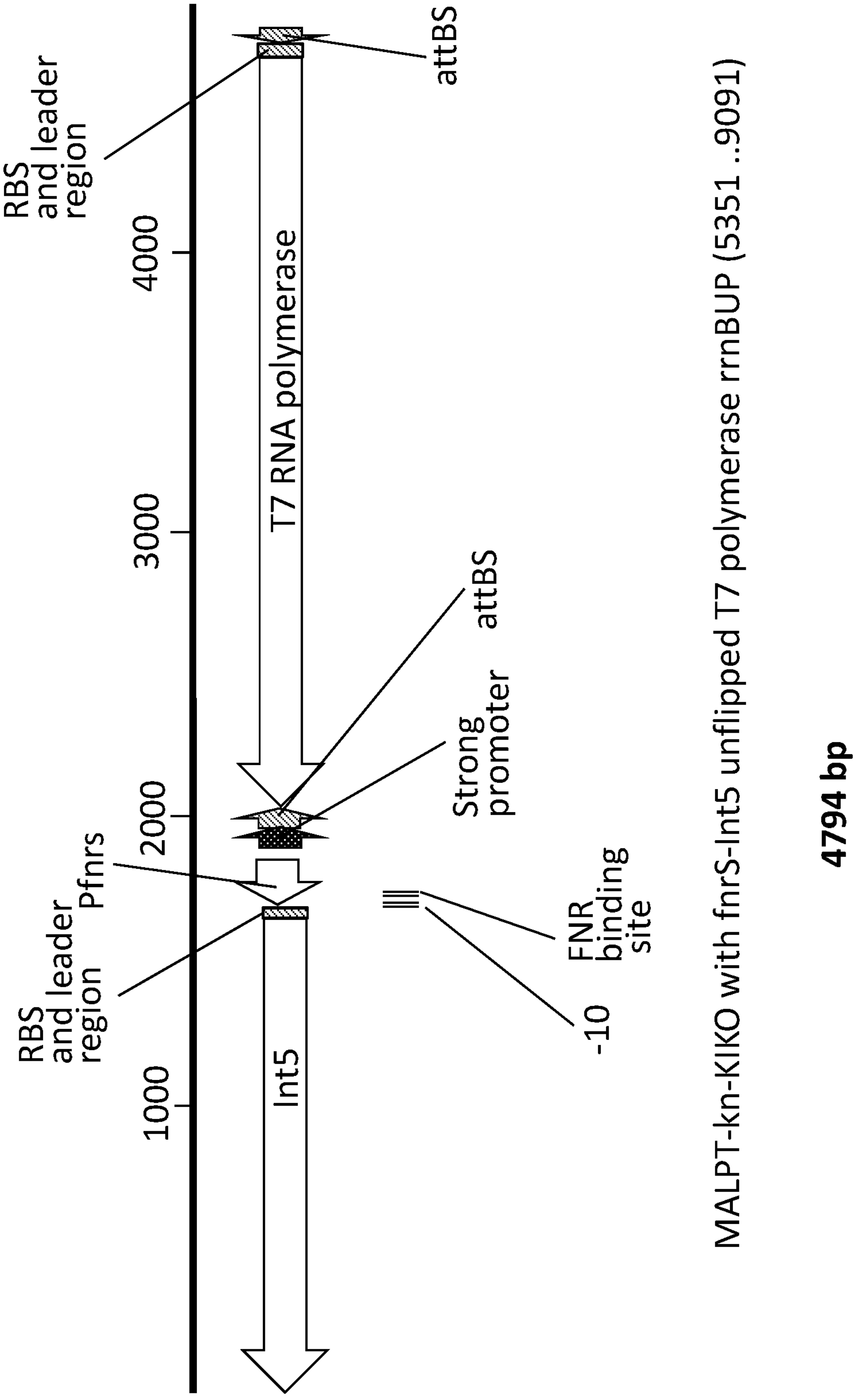
FIGS. 43A, 43B, and 43C depict the gene organization of an exemplary construct in which the Int5 recombinase gene is operably linked to an FNR promoter ($P_{fnrS}$), and the gene encoding T7 RNA polymerase is flanked by recombinase sites and operably linked to a strong constitutive promoter.
Figure 43B:
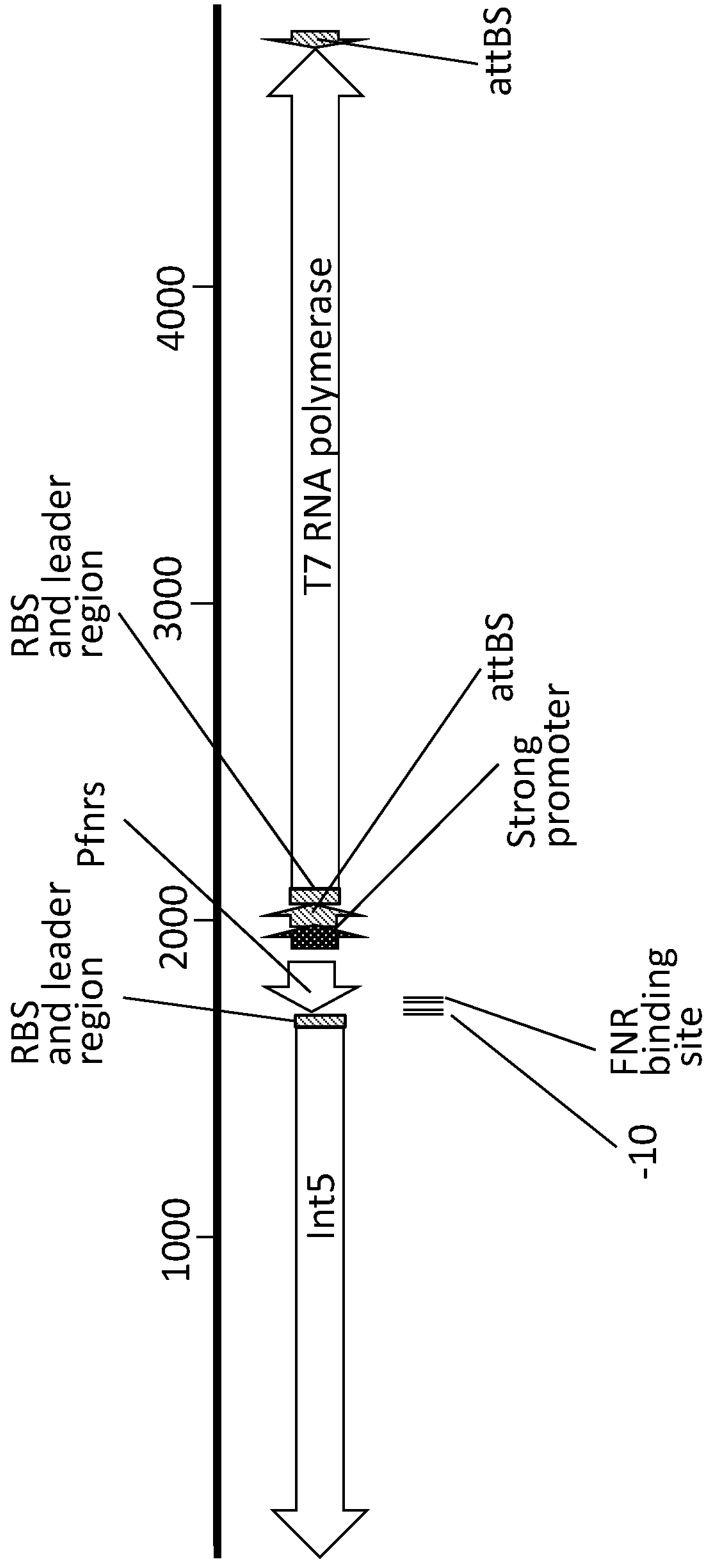
Figure 43C:
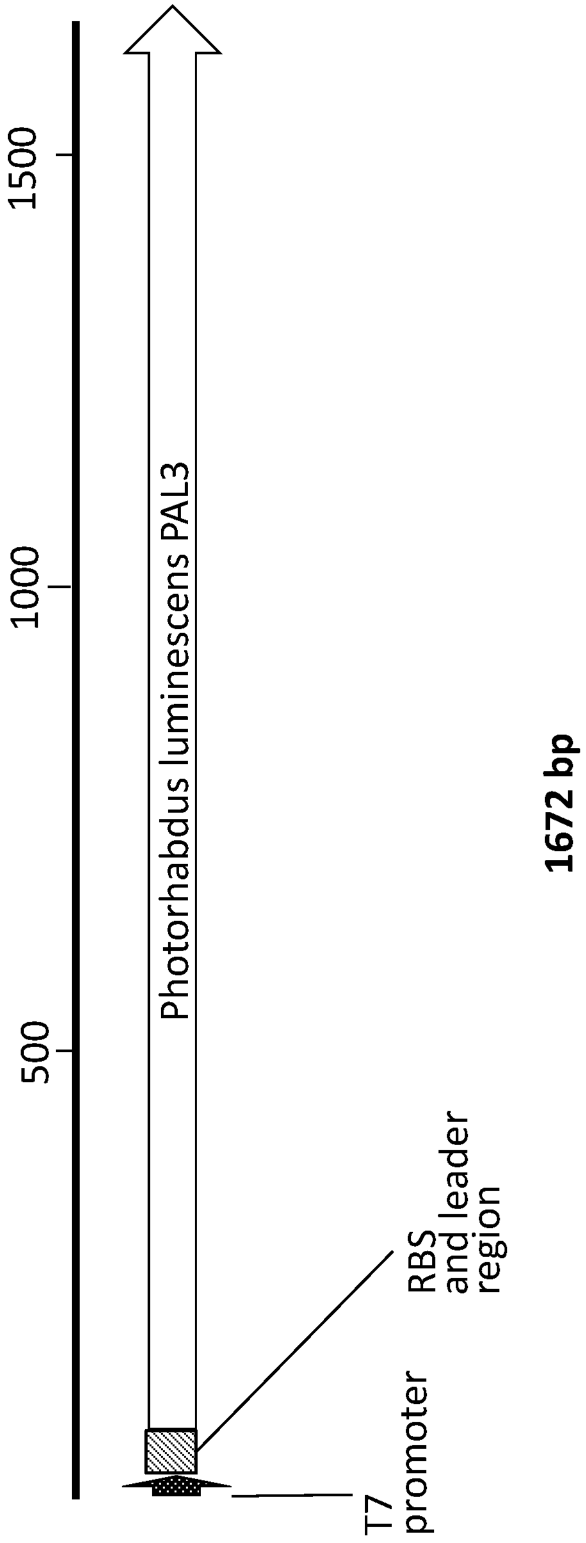
Figure 44A:
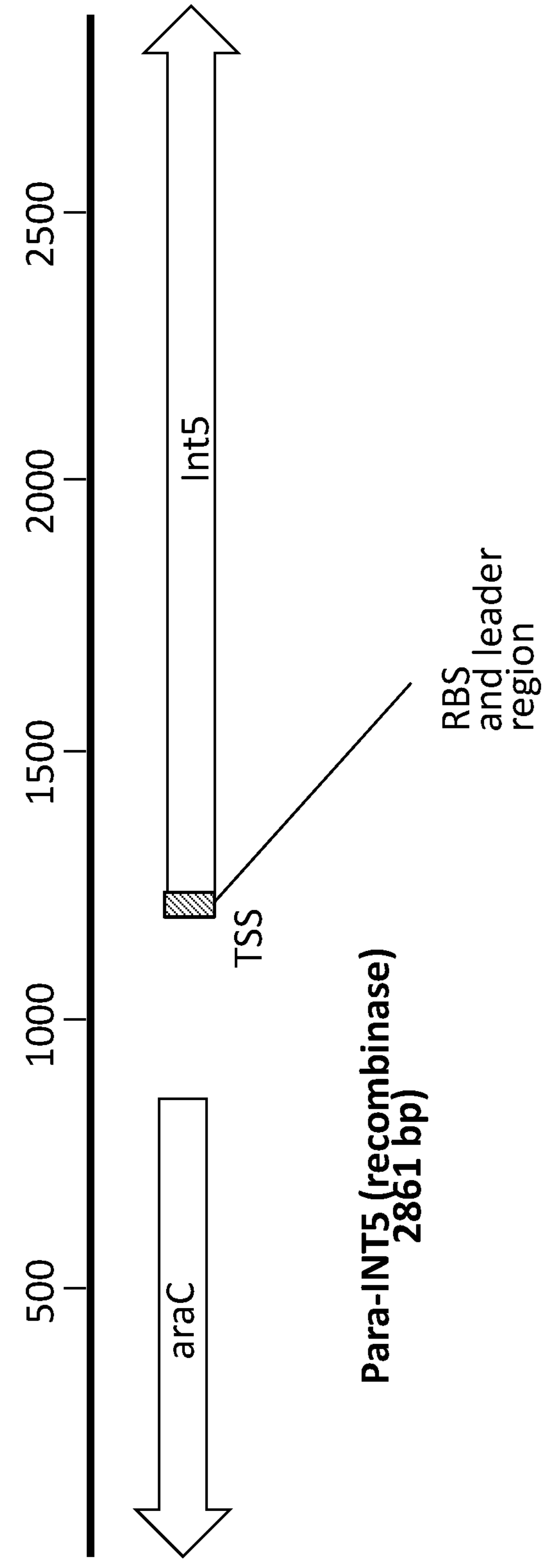
FIGS. 44A and 44B depict the gene organization of an exemplary construct in which the Int5 recombinase gene is operably linked to an ParaBAD promoter (ParaBAD), and the gene encoding T7 RNA polymerase is flanked by recombinase sites and operably linked to a strong constitutive promoter.
Figure 44B:
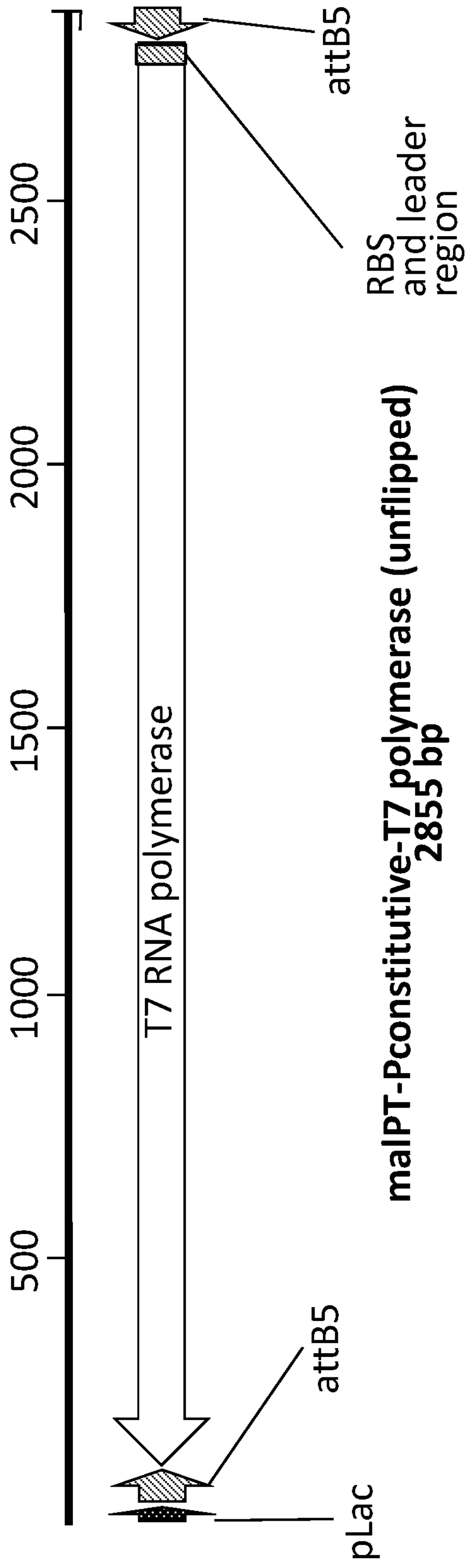
Figure 45B:
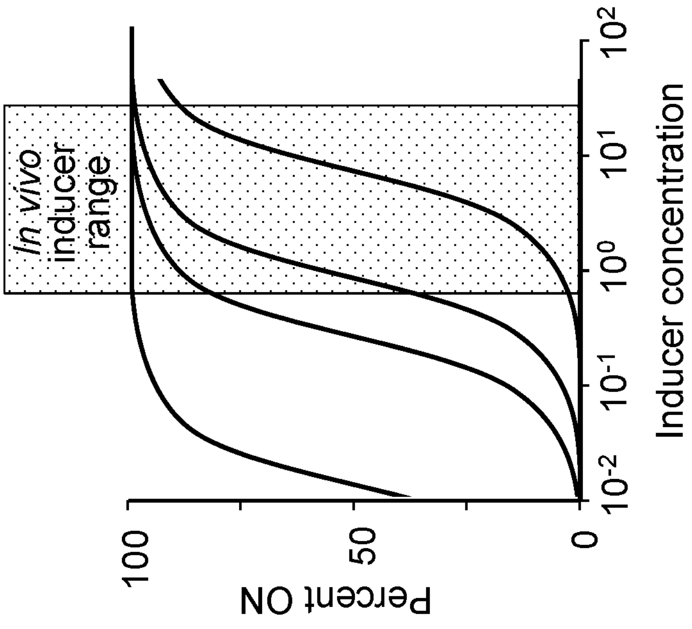
FIG. 45B depicts the relationship between the concentration of an inducer and the percentage of PAL3-containing constructs in the ON orientation. The shaded area shows the predicted efficacy range of the inducer in vivo.
Figure 45A:
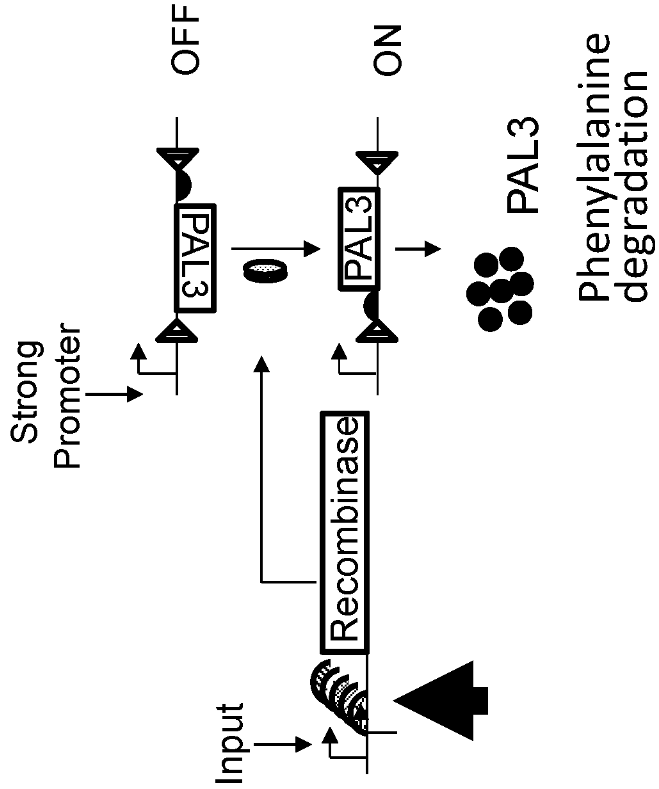
FIG. 45A depicts a schematic of a recombinase-based switch to activate PAL3 expression using different inducible promoters and ribosome binding sites. Recombinase expression causes recombinatorial flipping of the PAL3 gene to the ON orientation, leading to the production of PAL3 and to the degradation of phenylalanine. In some embodiments, recombinase-based switches are tuned to respond to specific levels of an inducer.
Figure 46A:
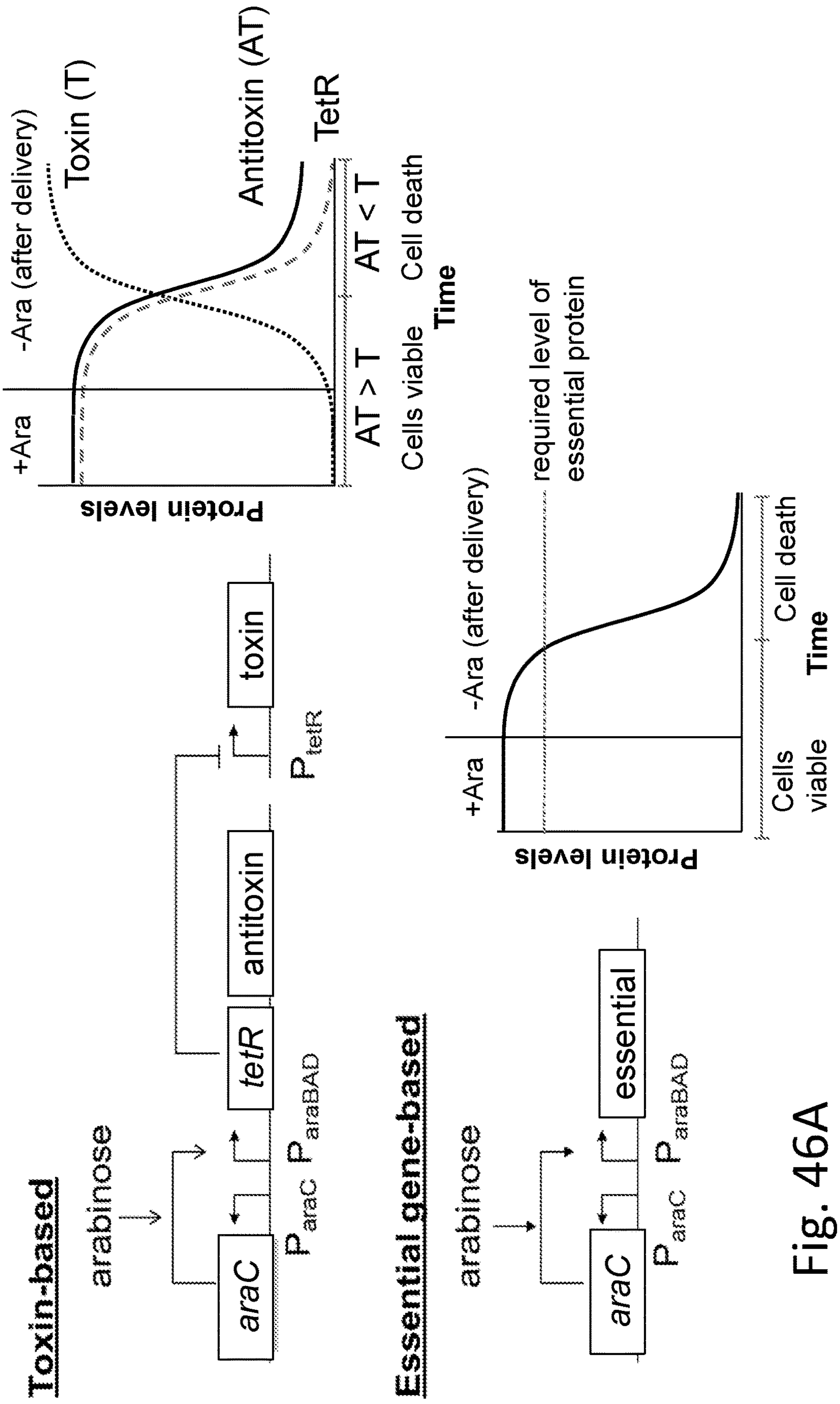
FIG. 46A depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the ParaBAD promoter (ParaBAD), which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell.
Figure 46B:
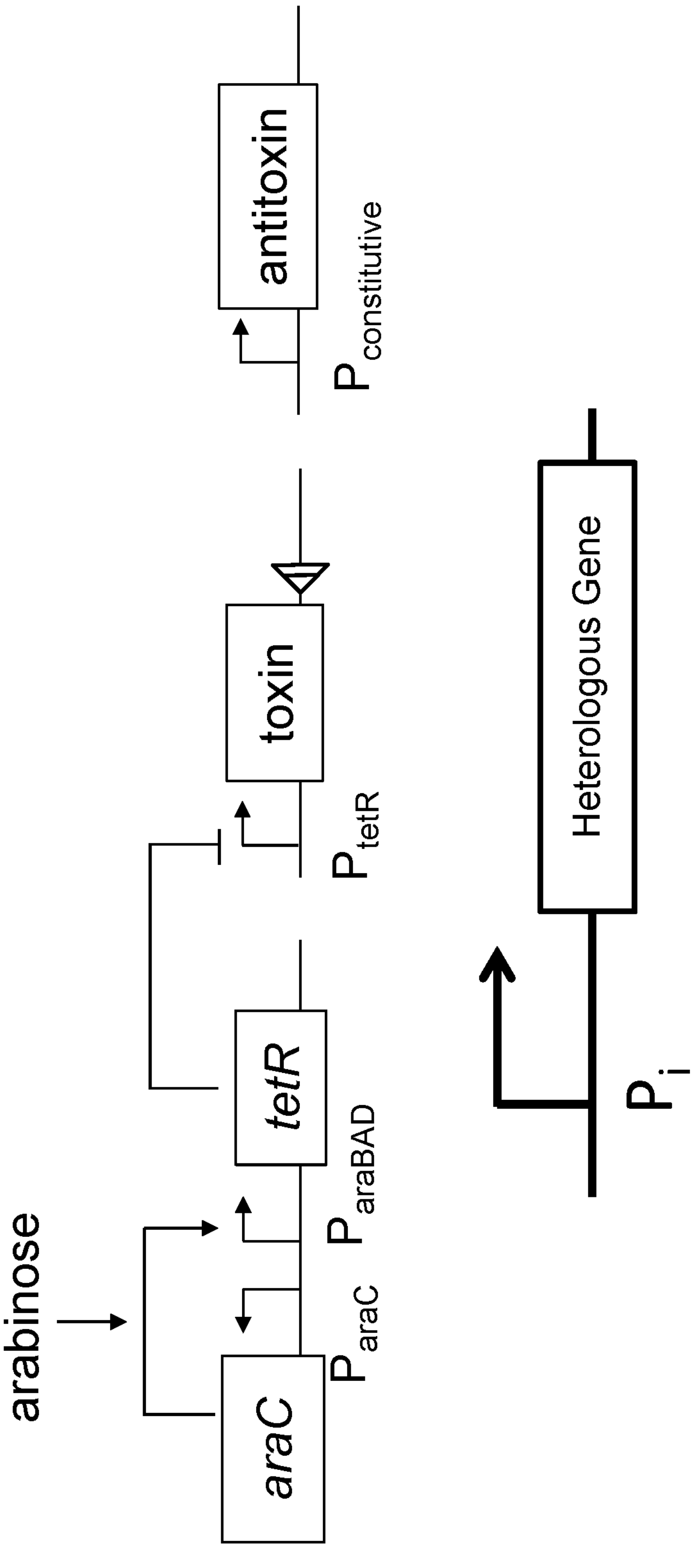
FIG. 46B depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR, thus preventing expression of a toxin. However, when arabinose is not present, TetR is not expressed, and the toxin is expressed, eventually overcoming the anti-toxin and killing the cell. The constitutive promoter regulating expression of the anti-toxin should be a weaker promoter than the promoter driving expression of the toxin. The araC gene is under the control of a constitutive promoter in this circuit.
Figure 46C:
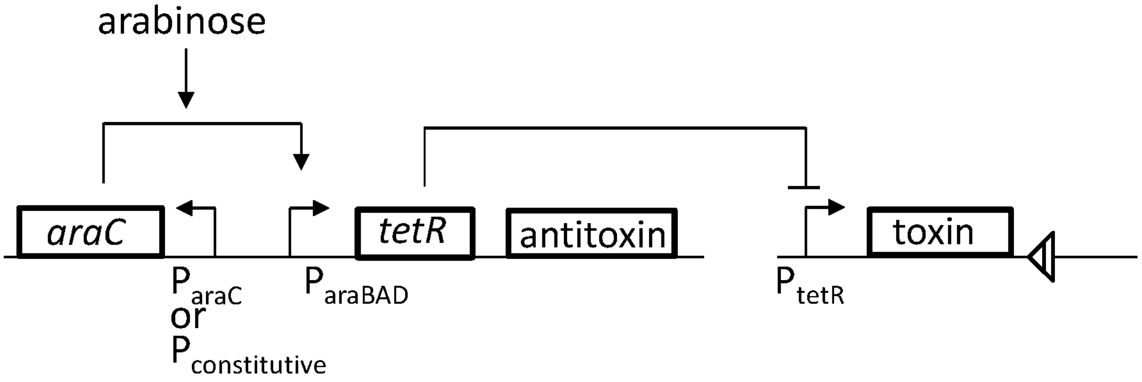
FIG. 46C depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. The araC gene is either under the control of a constitutive promoter or an inducible promoter (e.g., AraC promoter) in this circuit.
Figure 47:
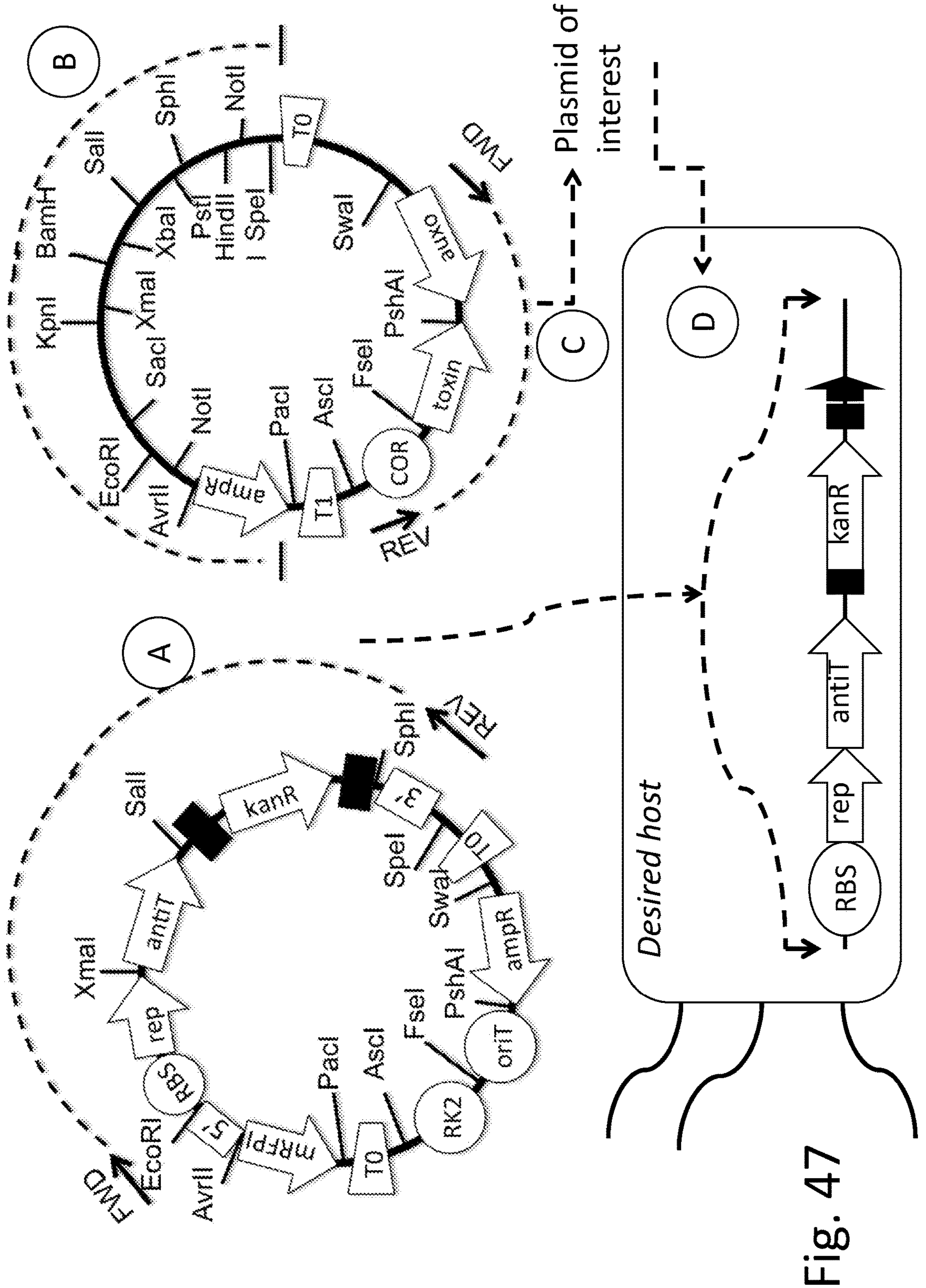
FIG. 47 depicts the use of GeneGuards as an engineered safety component. All engineered DNA is present on a plasmid which can be conditionally destroyed. See, e.g., Wright et al., 2015.
Figure 48A:
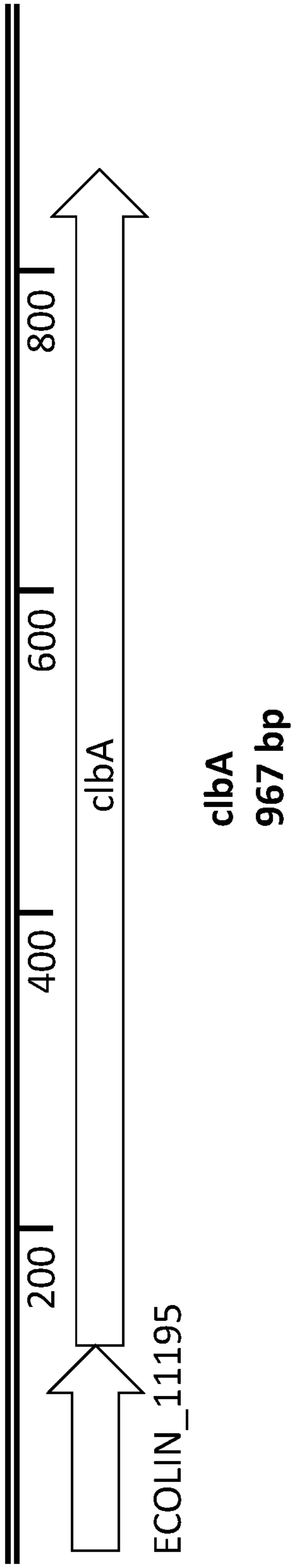
FIG. 48A depicts a schematic diagram of a wild-type clbA construct.
Figure 48B:
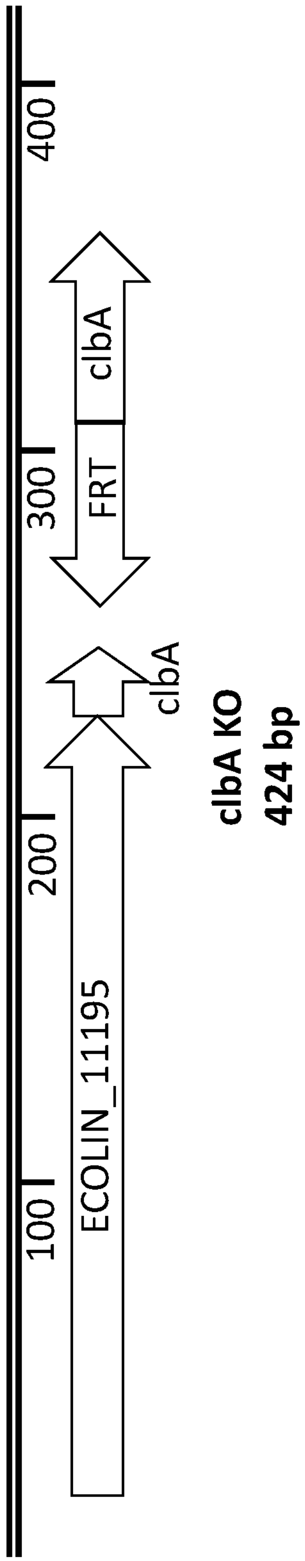
FIG. 48B depicts a schematic diagram of a clbA knockout construct.
Figure 50:
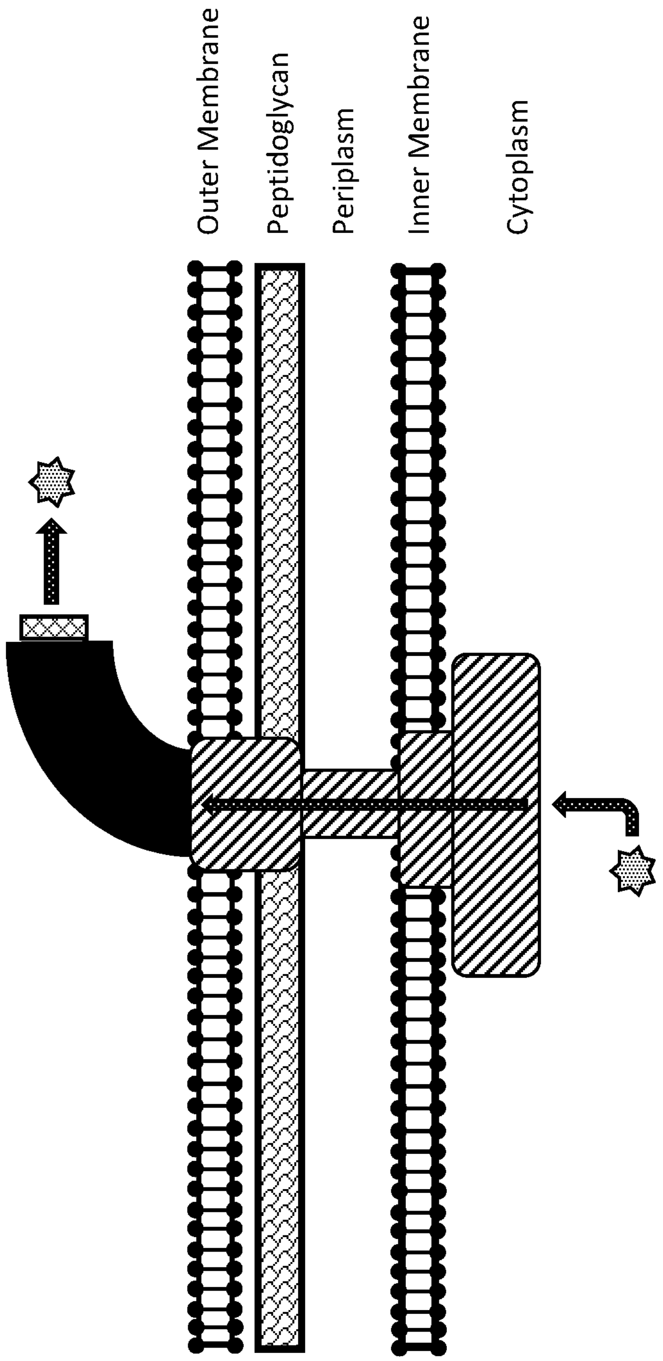
FIG. 50 depicts a schematic of a secretion system based on the flagellar type III secretion in which a modified flagellum is used to secrete a therapeutic peptide of interest by recombinantly fusing the peptide to an N-terminal flagellar secretion signal of a native flagellar component so that the intracellularly expressed chimeric peptide can be mobilized across the inner and outer membranes into the surrounding host environment.
Figure 51:
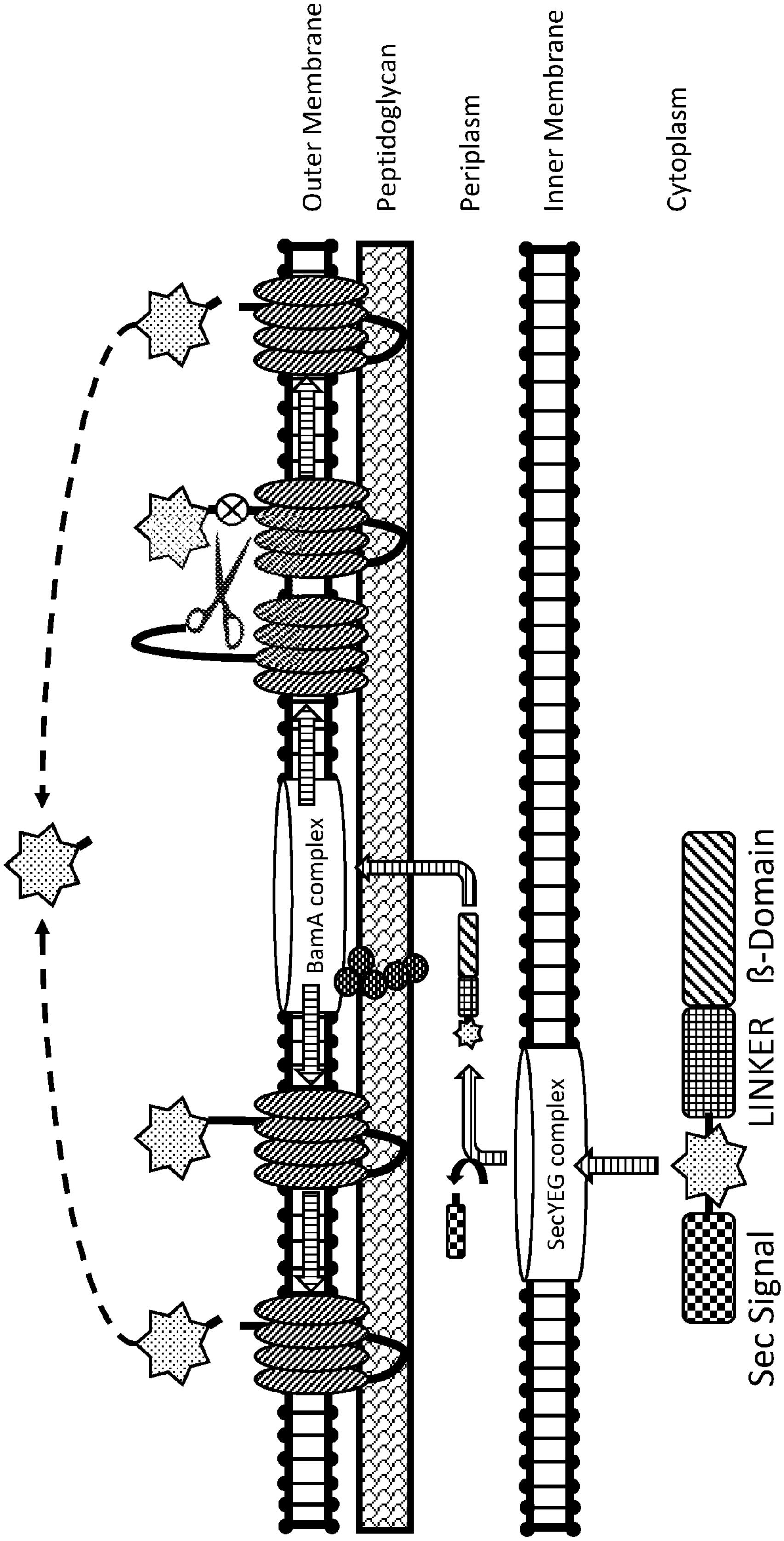
FIG. 51 depicts a schematic of a type V secretion system for the extracellular production of recombinant proteins in which a therapeutic peptide (star) can be fused to an N-terminal secretion signal, a linker and the beta-domain of an auto-secreter. In this system, the N-terminal signal sequence directs the protein to the SecA-YEG machinery, which moves the protein across the inner membrane into the periplasm, followed by subsequent cleavage of the signal sequence. The beta-domain is recruited to the Bam complex where the beta-domain is folded and inserted into the outer membrane as a beta-barrel structure. The therapeutic peptide is then threaded through the hollow pore of the beta-barrel structure ahead of the linker sequence. The therapeutic peptide is freed from the linker system by an autocatalytic cleavage or by targeting of a membrane-associated peptidase (scissors) to a complementary protease cut site in the linker.
Figure 52:
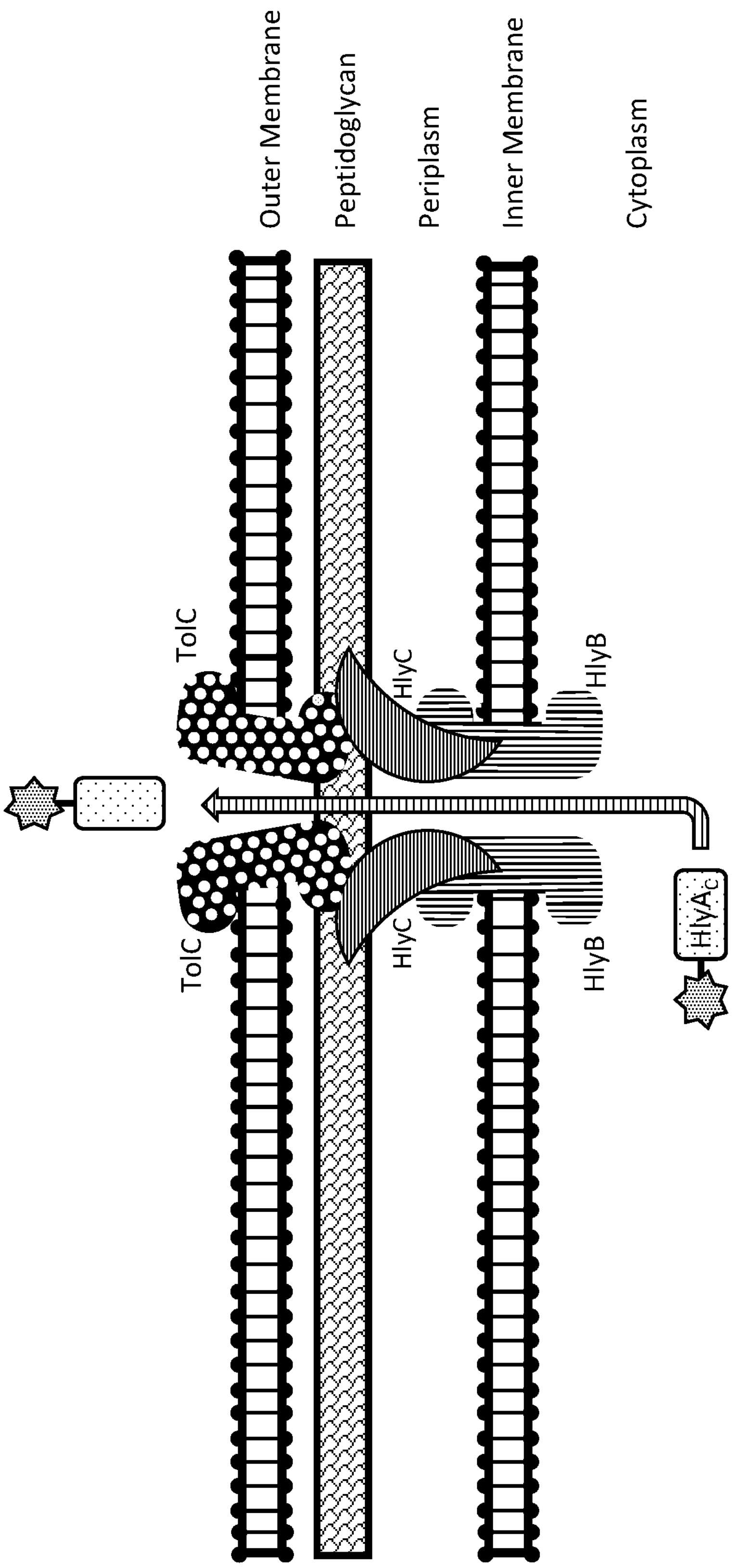
FIG. 52 depicts a schematic of a type I secretion system, which translocates a passenger peptide directly from the cytoplasm to the extracellular space using HlyB (an ATP-binding cassette secreter; HlyD (a membrane fusion protein); and TolC (an outer membrane protein) which form a channel through both the inner and outer membranes. The secretion signal-containing C-terminal portion of HlyA is fused to the C-terminal portion of a therapeutic peptide (star) to mediate secretion of this peptide.
Figure 53:
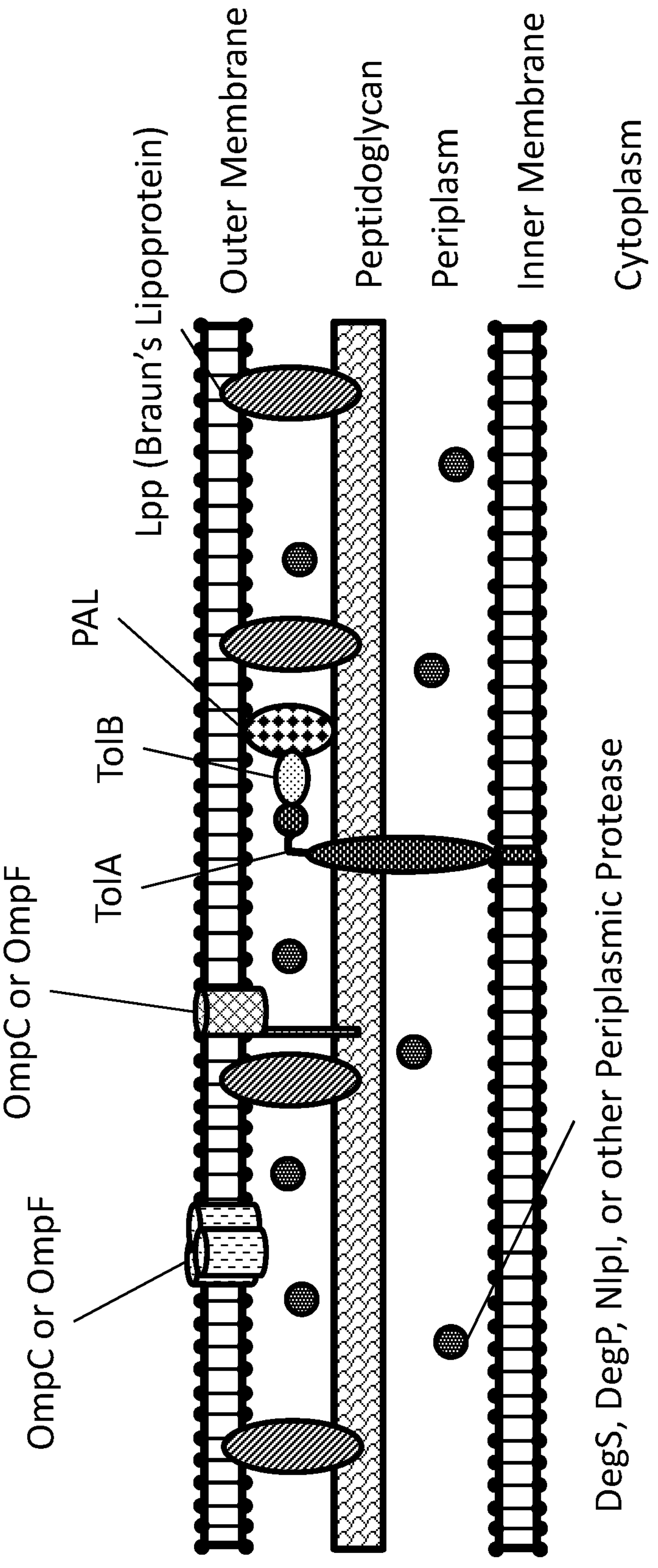
FIG. 53 depicts a schematic of the outer and inner membranes of a gram-negative bacterium, and several deletion targets for generating a leaky or destabilized outer membrane, thereby facilitating the translocation of a therapeutic polypeptides to the extracellular space, e.g., therapeutic polypeptides of eukaryotic origin containing disulphide bonds. Deactivating mutations of one or more genes encoding a protein that tethers the outer membrane to the peptidoglycan skeleton, e.g., lpp, ompC, ompA, ompF, tolA, tolB, pal, and/or one or more genes encoding a periplasmic protease, e.g., degS, degP, nlpl, generates a leaky phenotype. Combinations of mutations may synergistically enhance the leaky phenotype.
Figure 54:
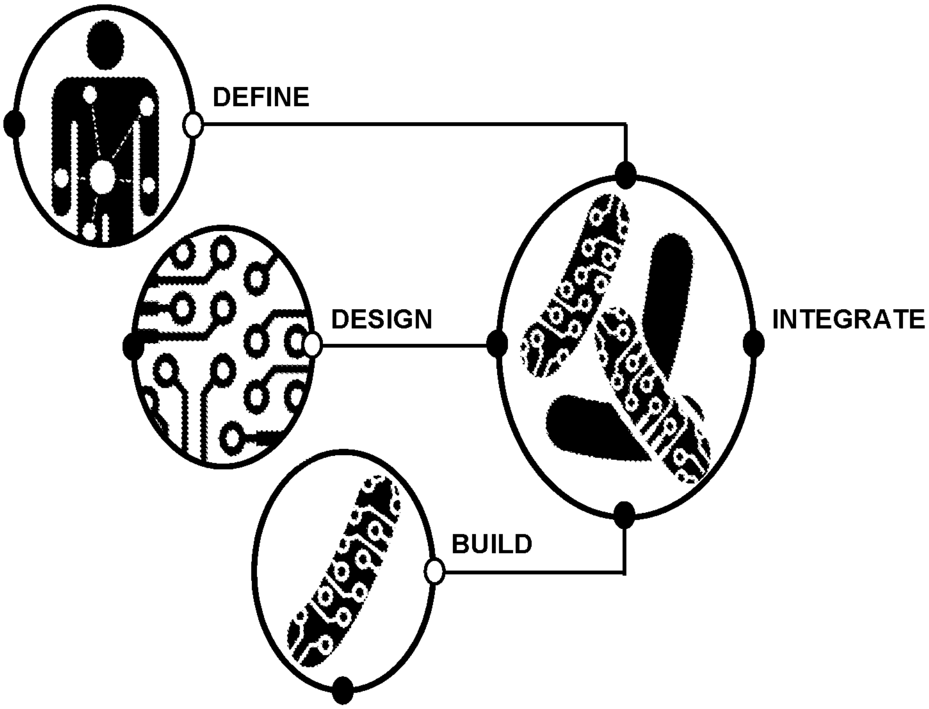
FIG. 54 depicts a schematic of non-limiting processes for designing and producing the genetically engineered bacteria of the present disclosure.
Figures 55A, 55B, 55C, 55D, 55E:
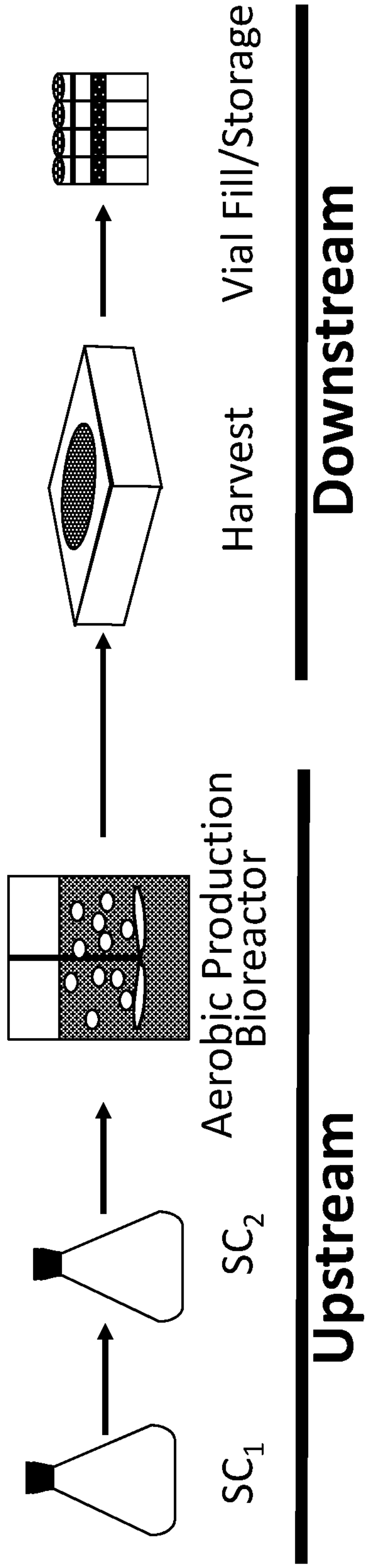
FIGS. 55A, B, C, D, and E depict a schematic of non-limiting manufacturing processes for upstream and downstream production of the genetically engineered bacteria of the present disclosure.
FIG. 55B depicts the parameters for starter culture 2 (SC2): 1/100 dilution from SC1, duration 1.5 hours, temperature 37° C., shaking at 250 rpm.
FIG. 55C depicts the parameters for the production bioreactor: inoculum—SC2, temperature 37° C., pH set point 7.00, pH dead band 0.05, dissolved oxygen set point 50%, dissolved oxygen cascade agitation/gas FLO, agitation limits 300-1200 rpm, gas FLO limits 0.5-20 standard liters per minute, duration 24 hours.
FIG. 55D depicts the parameters for harvest: centrifugation at speed 4000 rpm and duration 30 minutes, wash 1×10% glycerol/PBS, centrifugation, re-suspension 10% glycerol/PBS.
FIG. 55E depicts the parameters for vial fill/storage: 1-2 mL aliquots, −80° C.

In some embodiments, recombinase-based switches may be used to activate PAL3 expression. The SYN-PKU601 strain (malPT::$P_{fnrS}$-Int5, rrnBUP-PAL3; lacZ::$P_{fnrS}$-pheP) contains the Int5 recombinase operably linked to a $P_{fnrS}$ promoter, as well as a copy of PAL3 under the control of a strong constitutive promoter, integrated at the mal/T locus (FIG. 42). Table 45 shows the sequence of an exemplary $P_{fnrS}$-Int5, rrnBUP-PAL3 construct (SEQ ID NO: 42), wherein $P_{fnrS}$, Int5, and PAL3 are in reverse orientation. The Int5 sequence is bolded, the $P_{fnrS}$ sequence is boxed, the PAL3 sequence is underlined, and recombinase sites are bolded and underlined. Ribosomal binding sites are highlighted, and the rrnBUP constitutive promoter sequence is boxed. The UP element-containing *E. coli* rrnBUP promoter was selected to yield high PAL3 expression (Estrem et al., 1998), although any strong promoter may be used. SYN-PKU601 also contains a copy of pheP integrated at the lacZ locus.

To construct the SYN-PKU601 strain, the $P_{fnrS}$-driven Int5 gene and the rrnBUP-driven, recombinase site-flanked PAL3 gene sequences were synthesized by Genewiz (Cambridge, MA). Gibson assembly was used to add 1000 bp sequences of DNA homologous to the Nissle malP and malT loci on either side of the $P_{fnrS}$-Int5, rrnBUP-PAL3 DNA sequence and to clone this sequence between the homology arms. Successful insertion of the fragment into a KIKO plasmid was validated by sequencing. PCR was used to amplify the entire $P_{fnrS}$-Int5, rrnBUP-PAL3 region. This knock-in PCR fragment was used to transform an electrocompetent Nissle strain already containing $P_{fnrS}$-pheP in the lacZ locus, and expressing the lambda red recombinase genes. After transformation, cells were grown for 2 hrs at 37° C. Transformants with successful integration of the $P_{fnrS}$-PAL3 fragment at the malPT intergenic region were selected on kanamycin at 50 μg/mL. This strategy may also be used to construct a recombinase-based strain requiring T7 polymerase activity for PAL3 expression (FIG. 43). [Table 46 shows the sequence of an exemplary $P_{fnrS}$-Int5, rrnBUP-T7 construct (SEQ ID NO: 43), wherein $P_{fnrS}$, Int5, and the T7 polymerase gene are in reverse orientation. The Int5 sequence is bolded, the $P_{fnrS}$ sequence is boxed, the T7 polymerase sequence is underlined, and recombinase sites are bolded and underlined. Ribosomal binding sites are highlighted, and the rrnBUP constitutive promoter sequence is boxed. Table 44 shows the sequence of an exemplary $P_{T7}$-PAL3 construct, with the $P_{T7}$ sequence highlighted, the ribosome binding site underlined, and the PAL3 sequence bolded.

TABLE 44

| Nucleotide sequences of FNR promoter-PAL3-pheP construct (SEQ ID NO: 41) |
|---|
| **ggtaccAGTTGTTCTTATTGGTGGTGTTGCTTTATGGTTGCATCGTAGTAAATGGTTGT** |
| **AACAAAAGCAATTTTTCCGGCTGTCTGTATACAAAAACGCCGCAAAGTTTGAGCGAAGT** |
| **CAATAAACTCTCTACCCATTCAGGGCAATATCTCTCTT**ggatccaaagtgaactctaga |
| aataattttgtttaactttaagaaggagatatacatATGAAAGCTAAAGATGTTCAGCC |
| AACCATTATTATTAATAAAAATGGCCTTATCTCTTTGGAAGATATCTATGACATTGCGA |
| TAAAACAAAAAAAAGTAGAAATATCAACGGAGATCACTGAACTTTTGACGCATGGTCGT |
| GAAAAATTAGAGGAAAAATTAAATTCAGGAGAGGTTATATATGGAATCAATACAGGATT |
| TGGAGGGAATGCCAATTTAGTTGTGCCATTTGAGAAAATCGCAGAGCATCAGCAAAATC |
| TGTTAACTTTTCTTTCTGCTGGTACTGGGGACTATATGTCCAAACCTTGTATTAAAGCG |
| TCACAATTTACTATGTTACTTTCTGTTTGCAAAGGTTGGTCTGCAACCAGACCAATTGT |
| CGCTCAAGCAATTGTTGATCATATTAATCATGACATTGTTCCTCTGGTTCCTCGCTATG |
| GCTCAGTGGGTGCAAGCGGTGATTTAATTCCTTTATCTTATATTGCACGAGCATTATGT |
| GGTATCGGCAAAGTTTATTATATGGGCGCAGAAATTGACGCTGCTGAAGCAATTAAACG |
| TGCAGGGTTGACACCATTATCGTTAAAAGCCAAAGAAGGTCTTGCTCTGATTAACGGCA |
| CCCGGGTAATGTCAGGAATCAGTGCAATCACCGTCATTAAACTGGAAAAACTATTTAAA |
| GCCTCAATTTCTGCGATTGCCCTTGCTGTTGAAGCATTACTTGCATCTCATGAACATTA |
| TGATGCCCGGATTCAACAAGTAAAAAATCATCCTGGTCAAAACGCGGTGGCAAGTGCAT |
| TGCGTAATTTATTGGCAGGTTCAACGCAGGTTAATCTATTATCTGGGGTTAAAGAACAA |
| GCCAATAAAGCTTGTCGTCATCAAGAAATTACCCAACTAAATGATACCTTACAGGAGGT |
| TTATTCAATTCGCTGTGCACCACAAGTATTAGGTATAGTGCCAGAATCTTTAGCTACCG |
| CTCGGAAAATATTGGAACGGGAAGTTATCTCAGCTAATGATAATCCATTGATAGATCCA |
| GAAAATGGCGATGTTCTACACGGTGGAAATTTTATGGGGCAATATGTCGCCCGAACAAT |

TABLE 44-continued

| Nucleotide sequences of FNR promoter-PAL3-pheP construct (SEQ ID NO: 41) |
| --- |
| GGATGCATTAAAACTGGATATTGCTTTAATTGCCAATCATCTTCACGCCATTGTGGCTC |
| TTATGATGGATAACCGTTTCTCTCGTGGATTACCTAATTCACTGAGTCCGACACCCGGC |
| ATGTATCAAGGTTTTAAAGGCGTCCAACTTTCTCAAACCGCTTTAGTTGCTGCAATTCG |
| CCATGATTGTGCTGCATCAGGTATTCATACCCTCGCCACAGAACAATACAATCAAGATA |
| TTGTCAGTTTAGGTCTGCATGCCGCTCAAGATGTTTTAGAGATGGAGCAGAAATTACGC |
| AATATTGTTTCAATGACAATTCTGGTAGTTTGTCAGGCCATTCATCTTCGCGGCAATAT |
| TAGTGAAATTGCGCCTGAAACTGCTAAATTTTACCATGCAGTACGCGAAATCAGTTCTC |
| CTTTGATCACTGATCGTGCGTTGGATGAAGATATAATCCGCATTGCGGATGCAATTATT |
| AATGATCAACTTCCTCTGCCAGAAATCATGCTGGAAGAATAAaagaaggagatatacat |
| atgAAAAACGCGTCAACCGTATCGGAAGATACTGCGTCGAATCAAGAGCCGACGCTTCA |
| TCGCGGATTACATAACCGTCATATTCAACTGATTGCGTTGGGTGGCGCAATTGGTACTG |
| GTCTGTTTCTTGGCATTGGCCCGGCGATTCAGATGGCGGGTCCGGCTGTATTGCTGGGC |
| TACGGCGTCGCCGGGATCATCGCTTTCCTGATTATGCGCCAGCTTGGCGAAATGGTGGT |
| TGAGGAGCCGGTATCCGGTTCATTTGCCCACTTTGCCTATAAATACTGGGGACCGTTTG |
| CGGGCTTCCTCTCTGGCTGGAACTACTGGGTAATGTTCGTGCTGGTGGGAATGGCAGAG |
| CTGACCGCTGCGGGCATCTATATGCAGTACTGGTTCCCGGATGTTCCAACGTGGATTTG |
| GGCTGCCGCCTTCTTTATTATCATCAACGCCGTTAACCTGGTGAACGTGCGCTTATATG |
| GCGAAACCGAGTTCTGGTTTGCGTTGATTAAAGTGCTGGCAATCATCGGTATGATCGGC |
| TTTGGCCTGTGGCTGCTGTTTTCTGGTCACGGCGGCGAGAAAGCCAGTATCGACAACCT |
| CTGGCGCTACGGTGGTTTCTTCGCCACCGGCTGGAATGGGCTGATTTTGTCGCTGGCGG |
| TAATTATGTTCTCCTTCGGCGGTCTGGAGCTGATTGGGATTACTGCCGCTGAAGCGCGC |
| GATCCGGAAAAAAGCATTCCAAAAGCGGTAAATCAGGTGGTGTATCGCATCCTGCTGTT |
| TTACATCGGTTCACTGGTGGTTTTACTGGCGCTCTATCCGTGGGTGGAAGTGAAATCCA |
| ACAGTAGCCCGTTTGTGATGATTTTCCATAATCTCGACAGCAACGTGGTAGCTTCTGCG |
| CTGAACTTCGTCATTCTGGTAGCATCGCTGTCAGTGTATAACAGCGGGGTTTACTCTAA |
| CAGCCGCATGCTGTTTGGCCTTTCTGTGCAGGGTAATGCGCCGAAGTTTTTGACTCGCG |
| TCAGCCGTCGCGGTGTGCCGATTAACTCGCTGATGCTTTCCGGAGCGATCACTTCGCTG |
| GTGGTGTTAATCAACTATCTGCTGCCGCAAAAAGCGTTTGGTCTGCTGATGGCGCTGGT |
| GGTAGCAACGCTGCTGTTGAACTGGATTATGATCTGTCTGGCGCATCTGCGTTTTCGTG |
| CAGCGATGCGACGTCAGGGGCGTGAAACACAGTTTAAGGCGCTGCTCTATCCGTTCGGC |
| AACTATCTCTGCATTGCCTTCCTCGGCATGATTTTGCTGCTGATGTGCACGATGGATGA |
| TATGCGCTTGTCAGCGATCCTGCTGCCGGTGTGGATTGTATTCCTGTTTATGGCATTTA |
| AAACGCTGCGTCGGAAAtaa |

TABLE 45

| Nucleotide sequences of FNR promoter-Int5, rrnBUP-PAL3 construct (SEQ ID NO: 42) |
|---|
| ttaggtacgggctgcccatttgattttaacgcgttcatcaccatcaaacggacgaccac |
| gctggccttttgcaacccaaatttcatcgatgcaggtatcaataattgcattacgcatg |
| gtcggggttgcacgcagccacagttcttcataatcgctgctatcaacaatccagctaac |
| atcaactgctgcgcttgcgctgctttcgctaactgcatctttggctgcctgcagggtgc |
| tcagtgcttcttgatatgcaggggcaaaaaactgttctgccggaccatcataaacacca |
| ttctgacgatcacgcagcaggcgacccagatttttttcggcttcacgaactgcggcttt |
| tgcatacttttcatcttcgcttgcctgcggatgggtcagtgctgcccagcgatctgcaa |
| ctgcaataacaaacggatcatccggttcgcttgctgctaattttgctgcccaacgaaat |
| gcaacatattcttcaacgcttttacgtgcaacataggtcggtgccggacaaccaccttt |
| cacactgctacgccaacaacgataaccattaccgctatagctacagctaccaccacaac |
| ccggacaacgcatacgaccgctcagcagatgtttgcgacgggtatcatgatcgctacca |
| tccagcggaacaccaacaccatcttcacctttaacggctgcttttgcggcttcttgttc |
| ttcatcggtcaccagcggaggaccatgcataacgctaacacgtttaccttcaccgttat |
| aaaaggtcagacgacgctgtttaccatcctgacgacctgtggtctgccaacccgcatat |
| gccggattctgaatcatatcacgcacggtaactgcaatccacggaccaccggtcgggct |
| cggaatttcacgggtattcattgcatgtgcggtgcctgcatagctcagacgatcggtaa |
| ccggcagggtaaaaaccagacgggctgcttctgctttggtcagaccatcaggaccaccc |
| gcatcttcatcatctgctgccagtttacgttcatcatattcatcaccctcttcatcact |
| aacggtaaccagaacaacacgcagaccatacggtgcacgggcattaacccattcaccat |
| tttcacgctgatgtgctttggtatcacgaacacgttcgctcagtttttctgcttcttcg |
| cgtgcttcttctgcacgacgaatcagttcaccgcgatcacgtttattggtgctatccag |
| aaccggacgaccggtatcttcatcccaaccaaacagcagacgacgaggcataccatctt |
| ccggttcgataattttcagaattgcaccggcaccaccacgatcccaacgatccagacga |
| taacaccacagtgcaccaacttcaccgctttccagggctttcagtgctttgctctgatc |
| atcacgtgctttacctttacgaaaacggcttgcgctaccaacttctttccaaacatgac |
| gaacctgcatacccagcagtgctgcaactttacgacccagggtttcttgtgctgcaatg |
| ctaatttcttgtttacgacgctgacctgcaccatttgcacggcttttaactgctttgct |
| tttacgacaaaacaggtcaatcagacctgcaggatccggaccggtttcggtggtcatac |
| caggcatatgtatatctccttcttaaagttaaacaaaattatttctagagttcactttg |
| gatccAAGAGAGATATTGCCCTGAATGGGTAGAGAGTTTATTGACTTCGCTCAAACTTT |
| GCGGCGTTTTTGTATACAGACAGCCGGAAAAATTGCTTTTGTTACAACCATTTACTACG |
| ATGCAACCATAAAGCAACACCACCAATAAGAACAACTggtaccGGATATTCATATGGAC |
| CATGGCAGCTAGCCCTGCAGGGTGCACTCAGAAAATTATTTTAAATTTCCTCTTGTCA |
| GGCCGGAATAACTCCCTATAATGCGCCACCACgagcgccggatcagggagtggacggc |
| ctgggagcgctacacgctgtggctgcggtcggtgcTTATTCTTCCAGCATGATTTCTGG |
| CAGAGGAAGTTGATCATTAATAATTGCATCCGCAATGCGGATTATATCTTCATCCAACG |
| CACGATCAGTGATCAAAGGAGAACTGATTTCGCGTACTGCATGGTAAAATTTAGCAGTT |

TABLE 45-continued

| Nucleotide sequences of FNR promoter-Int5, rrnBUP-PAL3 construct (SEQ ID NO: 42) |
|---|
| TCAGGCGCAATTTCACTAATATTGCCGCGAAGATGAATGGCCTGACAAACTACCAGAAT |
| TGTCATTGAAACAATATTGCGTAATTTCTGCTCCATCTCTAAAACATCTTGAGCGGCAT |
| GCAGACCTAAACTGACAATATCTTGATTGTATTGTTCTGTGGCGAGGGTATGAATACCT |
| GATGCAGCACAATCATGGCGAATTGCAGCAACTAAAGCGGTTTGAGAAAGTTGGACGCC |
| TTTAAAACCTTGATACATGCCGGGTGTCGGACTCAGTGAATTAGGTAATCCACGAGAGA |
| AACGGTTATCCATCATAAGAGCCACAATGGCGTGAAGATGATTGGCAATTAAAGCAATA |
| TCCAGTTTTAATGCATCCATTGTTCGGGCGACATATTGCCCCATAAAATTTCCACCGTG |
| TAGAACATCGCCATTTTCTGGATCTATCAATGGATTATCATTAGCTGAGATAACTTCCC |
| GTTCCAATATTTTCCGAGCGGTAGCTAAAGATTCTGGCACTATACCTAATACTTGTGGT |
| GCACAGCGAATTGAATAAACTTCCTGTAAGGTATCATTTAGTTGGGTAATTTCTTGATG |
| ACGACAAGCTTTATTGGCTTGTTCTTTAACCCCAGATAATAGATTAACCTGCGTTGAAC |
| CTGCCAATAAATTACGCAATGCACTTGCCACCGCGTTTTGACCAGGATGATTTTTTACT |
| TGTTGAATCCGGGCATCATAATGTTCATGAGATGCAAGTAATGCTTCAACAGCAAGGGC |
| AATCGCAGAAATTGAGGCTTTAAATAGTTTTTCCAGTTTAATGACGGTGATTGCACTGA |
| TTCCTGACATTACCCGGGTGCCGTTAATCAGAGCAAGACCTTCTTTGGCTTTTAACGAT |
| AATGGTGTCAACCCTGCACGTTTAATTGCTTCAGCAGCGTCAATTTCTGCGCCCATATA |
| ATAAACTTTGCCGATACCACATAATGCTCGTGCAATATAAGATAAAGGAATTAAATCAC |
| CGCTTGCACCCACTGAGCCATAGCGAGGAACCAGAGGAACAATGTCATGATTAATATGA |
| TCAACAATTGCTTGAGCGACAATTGGTCTGGTTGCAGACCAACCTTTGCAAACAGAAAG |
| TAACATAGTAAATTGTGACGCTTTAATACAAGGTTTGGACATATAGTCCCCAGTACCAG |
| CAGAAAGAAAAGTTAACAGATTTTGCTGATGCTCTGCGATTTTCTCAAATGGCACAACT |
| AAATTGGCATTCCCTCCAAATCCTGTATTGATTCCATATATAACCTCTCCTGAATTTAA |
| TTTTTCCTCTAATTTTTCACGACCATGCGTCAAAAGTTCAGTGATCTCCGTTGATATTT |
| CTACTTTTTTTTGTTTTATCGCAATGTCATAGATATCTTCCAAAGAGATAAGGCCATTT |
| TTATTAATAATAATGGTTGGCTGAACATCTTTAGCTTTCATatgtatatctccttctta |
| aagttaaacaaaattatttctagag**cagatcagggtgcgcaagttgtcaacgctcccag** |
| **gagagttatcgacttgcgtattaggg** |

TABLE 46

| Nucleotide sequences of FNR promoter-Int5, rrnBUP-T7 construct (SEQ ID NO: 43) |
|---|
| **ttaggtacgggctgcccatttgattttaacgcgttcatcaccatcaaacggacgaccac** |
| **gctggccttttgcaacccaaatttcatcgatgcaggtatcaataattgcattacgcatg** |
| **gtcggggttgcacgcagccacagttcttcataatcgctgctatcaacaatccagctaac** |
| **atcaactgctgcgcttgcgctgctttcgctaactgcatctttggctgcctgcagggtgc** |
| **tcagtgcttcttgatatgcaggggcaaaaaactgttctgccggaccatcataaacacca** |
| **ttctgacgatcacgcagcaggcgacccagatttttttcggcttcacgaactgcggcttt** |
| **tgcatacttttcatcttcgcttgcctgcggatgggtcagtgctgcccagcgatctgcaa** |

TABLE 46-continued

| Nucleotide sequences of FNR promoter-Int5, rrnBUP-T7 construct (SEQ ID NO: 43) |
|---|
| **ctgcaataacaaacggatcatccggttcgcttgctgctaattttgctgcccaacgaaat** |
| **gcaacatattcttcaacgcttttacgtgcaacataggtcggtgccggacaaccaccttt** |
| **cacactgctacgccaacaacgataaccattaccgctatagctacagctaccaccacaac** |
| **ccggacaacgcatacgaccgctcagcagatgtttgcgacgggtatcatgatcgctacca** |
| **tccagcggaacaccaacaccatcttcacctttaacggctgcttttgcggcttcttgttc** |
| **ttcatcggtcaccagcggaggaccatgcataacgctaacacgtttaccttcaccgttat** |
| **aaaaggtcagacgacgctgtttaccatcctgacgacctgtggtctgccaacccgcatat** |
| **gccggattctgaatcatatcacgcacggtaactgcaatccacggaccaccggtcgggct** |
| **cggaatttcacgggtattcattgcatgtgcggtgcctgcatagctcagacgatcggtaa** |
| **ccggcagggtaaaaaccagacgggctgcttctgctttggtcagaccatcaggaccaccc** |
| **gcatcttcatcatctgctgccagtttacgttcatcatattcatcaccctcttcatcact** |
| **aacggtaaccagaacaacacgcagaccatacggtgcacgggcattaacccattcaccat** |
| **tttcacgctgatgtgctttggtatcacgaacacgttcgctcagtttttctgcttcttcg** |
| **cgtgcttcttctgcacgacgaatcagttcaccgcgatcacgtttattggtgctatccag** |
| **aaccggacgaccggtatcttcatcccaaccaaacagcagacgacgaggcataccatctt** |
| **ccggttcgataattttcagaattgcaccggcaccaccacgatcccaacgatccagacga** |
| **taacaccacagtgcaccaacttcaccgctttccagggctttcagtgctttgctctgatc** |
| **atcacgtgctttacctttacgaaaacggcttgcgctaccaacttctttccaaacatgac** |
| **gaacctgcatacccagcagtgctgcaactttacgacccagggtttcttgtgctgcaatg** |
| **ctaatttcttgtttacgacgctgacctgcaccatttgcacggcttttaactgctttgct** |
| **tttacgacaaaacaggtcaatcagacctgcaggatccggaccggtttcggtggtcatac** |
| **caggcat**atgtatatctccttcttaaagttaaacaaaattatttctagagttcactttg |
| gatccAAGAGAGATATTGCCCTGAATGGGTAGAGAGTTTATTGACTTCGCTCAAACTTT |
| GCGGCGTTTTTGTATACAGACAGCCGGAAAAATTGCTTTTGTTACAACCATTTACTACG |
| ATGCAACCATAAAGCAACACCACCAATAAGAACAACTggtaccGGATATTCATATGGAC |
| CATGGCAGCTAGCCCTGCAGGGTGCAGTCAGAAAATTATTTTAAATTTCCTCTTGTCA |
| GGCCGGAATAACTCCCTATAATGCGCCACCAC**gagcgccggatcagggagtggacggc** |
| **ctgggagcgctacacgctgtggctgcggtcggtgc**ttacgcgaacgcgaagtccgactc |
| taagatgtcacggaggttcaagttacctttagccggaagtgctggcattttgtccaatt |
| gagactcgtgcaactggtcagcgaactggtcgtagaaatcagccagtacatcacaagac |
| tcatatgtgtcaaccatagtttcgcgcactgctttgaacaggttcgcagcgtcagccgg |
| aatggtaccgaaggagtcgtgaatcagtgcaaaagattcgattccgtacttctcgtgtg |
| cccacactacagtcttacgaaggtggctaccgtcttggctgtgtacaaagttaggagcg |
| ataccagactcctgtttgtgtgcatcaatctcgctatctttgttggtgttaatggtagg |
| ctgtaagcggaactgaccgaggaacatcaggttcaagcgcgtctgaataggcttcttgt |
| attcctgccacacagggaaaccatcaggagttacccaatgcacagcgcaacgcttgcga |
| agaatctctccagtcttcttatctttgacctcagcagccagcagcttagcagcagactt |

TABLE 46-continued

| Nucleotide sequences of FNR promoter-Int5, rrnBUP-T7 construct (SEQ ID NO: 43) |
|---|
| aagccagttcattgcttcaaccgcagctaccaccgtcacgctcacagattcccaaatca |
| gcttagccatgtatccagcagcctgattcggctgagtgaacatcagacccttgccggaa |
| tcaatagctggctgaatggtatcttccagcacttgttgacggaagccgaactctttgga |
| cccgtaagccagcgtcatgactgaacgcttagtcacactgcgagtaacaccgtaagcca |
| gccattgaccagccagtgccttagtgcccagcttgactttctcagagatttcaccagtg |
| ttctcatcggtcacggtaactacttcgttatcggtcccattgattgcgtctgcttgtag |
| aatctcgttgactttcttagcaacaatcccgtagatgtcctgaacggtttcactaggaa |
| gcaagttaaccgcgcgaccacctacctcatctcggagcatcgcggagaagtgctggatg |
| ccagagcaagacccgtcaaacgccagcggaagggagcagttatagctcaggccgtggtg |
| ctgtaccccagcgtactcaaagcagaacgcaaggaagcagaacggagaatcttgctcag |
| cccaccaagtgttctccagtggagacttagcgcaagccatgatgttctcgtggttttcc |
| tcaatgaacttgatgcgctcagggaacggaaccttatcgacacccgcacagtttgcacc |
| gtggattttcagccagtagtaaccttccttaccgattggtttacctttcgccagcgtaa |
| gcagtcctttggtcatatcgttaccttgcgggttgaacattgacacagcgtaaacacga |
| ccgcgccagtccatgttgtaagggaaccagatggccttatggttagcaaacttattggc |
| ttgctcaagcatgaactcaaggctgatacggcgagacttgcgagccttgtccttgcggt |
| acacagcagcggcagcacgtttccacgcggtgagagcctcaggattcatgtcgatgtct |
| tccggtttcatcgggagttcttcacgctcaatcgcagggatgtcctcgaccggacaatg |
| cttccacttggtgattacgttggcgaccgctaggactttcttgttgattttccatgcgg |
| tgttttgcgcaatgttaatcgctttgtacacctcaggcatgtaaacgtcttcgtagcgc |
| atcagtgctttcttactgtgagtacgcaccagcgccagaggacgacgaccgttagccca |
| atagccaccaccagtaatgccagtccacggcttaggaggaactacgcaaggttggaaca |
| tcggagagatgccagccagcgcacctgcacgggttgcgatagcctcagcgtattcaggt |
| gcgagttcgatagtctcagagtcttgacctactacgccagcattttggcggtgtaagct |
| aaccattccggttgactcaatgagcatctcgatgcagcgtactcctacatgaatagagt |
| cttccttatgccacgaagaccacgcctcgccaccgagtagacccttagagagcatgtca |
| gcctcgacaacttgcataaatgctttcttgtagacgtgccctacgcgcttgttgagttg |
| ttcctcaacgtttttcttgaagtgcttagcttcaaggtcacggatacgaccgaagcgag |
| cctcgtcctcaatggcccgaccgattgcgcttgctacagcctgaacggttgtattgtca |
| gcactggttaggcaagccagagtggtcttaatggtgatgtacgctacggcttccggctt |
| gatttcttgcaggaactggaaggctgtcgggcgcttgccgcgcttagctttcacttcct |
| caaaccagtcgttgatgcgtgcaatcatcttagggagtagggtagtgatgagaggcttg |
| gcggcagcgttatccgcaacctcaccagctttaagttgacgctcaaacatcttgcggaa |
| gcgtgcttcacccatctcgtaagactcatgctcaagggccaactgttcgcgagctaaac |
| gctcaccgtaatggtcagccagagtgttgaacgggatagcagccagttcgatgtcagag |
| aagtcgttcttagcgatgttaatcgtgttcatatgtatatctccttcttaaagttaaac |

TABLE 46-continued

| Nucleotide sequences of FNR promoter-Int5, rrnBUP-T7 construct (SEQ ID NO: 43) |
|---|
| aaaattatttctagag**cagatcagggtgcgcaagttgtcaacgctcccaggagagttat** |
| **cgacttgcgtattaggg** |

TABLE 47

| Nucleotide sequences of T7 promoter-PAL3 construct (SEQ ID NO: 44) |
|---|
| taatacgactcactatagggagaaagtgaactctagaaataattttgtttaactttaag |
| aaggagatatacat**ATGAAAGCTAAAGATGTTCAGCCAACCATTATTATTAATAAAAAT** |
| **GGCCTTATCTCTTTGGAAGATATCTATGACATTGCGATAAAACAAAAAAAAGTAGAAAT** |
| **ATCAACGGAGATCACTGAACTTTTGACGCATGGTCGTGAAAAATTAGAGGAAAAATTAA** |
| **ATTCAGGAGAGGTTATATATGGAATCAATACAGGATTTGGAGGGAATGCCAATTTAGTT** |
| **GTGCCATTTGAGAAAATCGCAGAGCATCAGCAAAATCTGTTAACTTTTCTTTCTGCTGG** |
| **TACTGGGGACTATATGTCCAAACCTTGTATTAAAGCGTCACAATTTACTATGTTACTTT** |
| **CTGTTTGCAAAGGTTGGTCTGCAACCAGACCAATTGTCGCTCAAGCAATTGTTGATCAT** |
| **ATTAATCATGACATTGTTCCTCTGGTTCCTCGCTATGGCTCAGTGGGTGCAAGCGGTGA** |
| **TTTAATTCCTTTATCTTATATTGCACGAGCATTATGTGGTATCGGCAAAGTTTATTATA** |
| **TGGGCGCAGAAATTGACGCTGCTGAAGCAATTAAACGTGCAGGGTTGACACCATTATCG** |
| **TTAAAAGCCAAAGAAGGTCTTGCTCTGATTAACGGCACCCGGGTAATGTCAGGAATCAG** |
| **TGCAATCACCGTCATTAAACTGGAAAAACTATTTAAAGCCTCAATTTCTGCGATTGCCC** |
| **TTGCTGTTGAAGCATTACTTGCATCTCATGAACATTATGATGCCCGGATTCAACAAGTA** |
| **AAAAATCATCCTGGTCAAAACGCGGTGGCAAGTGCATTGCGTAATTTATTGGCAGGTTC** |
| **AACGCAGGTTAATCTATTATCTGGGGTTAAAGAACAAGCCAATAAAGCTTGTCGTCATC** |
| **AAGAAATTACCCAACTAAATGATACCTTACAGGAAGTTTATTCAATTCGCTGTGCACCA** |
| **CAAGTATTAGGTATAGTGCCAGAATCTTTAGCTACCGCTCGGAAAATATTGGAACGGGA** |
| **AGTTATCTCAGCTAATGATAATCCATTGATAGATCCAGAAAATGGCGATGTTCTACACG** |
| **GTGGAAATTTTATGGGGCAATATGTCGCCCGAACAATGGATGCATTAAAACTGGATATT** |
| **GCTTTAATTGCCAATCATCTTCACGCCATTGTGGCTCTTATGATGGATAACCGTTTCTC** |
| **TCGTGGATTACCTAATTCACTGAGTCCGACACCCGGCATGTATCAAGGTTTTAAAGGCG** |
| **TCCAACTTTCTCAAACCGCTTTAGTTGCTGCAATTCGCCATGATTGTGCTGCATCAGGT** |
| **ATTCATACCCTCGCCACAGAACAATACAATCAAGATATTGTCAGTTTAGGTCTGCATGC** |
| **CGCTCAAGATGTTTTAGAGATGGAGCAGAAATTACGCAATATTGTTTCAATGACAATTC** |
| **TGGTAGTTTGTCAGGCCATTCATCTTCGCGGCAATATTAGTGAAATTGCGCCTGAAACT** |
| **GCTAAATTTTACCATGCAGTACGCGAAATCAGTTCTCCTTTGATCACTGATCGTGCGTT** |
| **GGATGAAGATATAATCCGCATTGCGGATGCAATTATTAATGATCAACTTCCTCTGCCAG** |
| **AAATCATGCTGGAAGAATAA** |

To construct the SYN-PKU602 strain comprising $P_{ARA}$-Int5 construct, $P_{T7}$-PAL3 construct, and $P_{Lac}$-T7 polymerase construct (FIG. 44), Gibson assembly was used essentially as described above.

Table 48 shows the sequence of an exemplary $P_{ARA}$-Int5 construct (SEQ ID NO: 45), for integration at the Ara locus. The Int5 sequence is bolded, the $P_{ara}$ sequence containing TSS and RBS sites is underlined, and AraC sequence is in italics.

TABLE 48

| Nucleotide Sequence of $P_{ARA}$-Int5 construct; SEQ ID NO: 45 |
|---|
| *TTATTCACAACCTGCCCTAAACTCGCTCGGACTCGCCCCGGTGCATTTTT* |
| *TAAATACTCGCGAGAAATAGAGTTGATCGTCAAAACCGACATTGCGACCG* |
| *ACGGTGGCGATAGGCATCCGGGTGGTGCTCAAAAGCAGCTTCGCCTGACT* |
| *GATGCGCTGGTCCTCGCGCCAGCTTAATACGCTAATCCCTAACTGCTGGC* |
| *GGAACAAATGCGACAGACGCGACGGCGACAGGCAGACATGCTGTGCGACG* |
| *CTGGCGATATCAAAATTACTGTCTGCCAGGTGATCGCTGATGTACTGACA* |
| *AGCCTCGCGTACCCGATTATCCATCGGTGGATGGAGCGACTCGTTAATCG* |
| *CTTCCATGCGCCGCAGTAACAATTGCTCAAGCAGATTTATCGCCAGCAAT* |
| *TCCGAATAGCGCCCTTCCCCTTGTCCGGCATTAATGATTTGCCCAAACAG* |
| *GTCGCTGAAATGCGGCTGGTGCGCTTCATCCGGGCGAAAGAAACCGGTAT* |
| *TGGCAAATATCGACGGCCAGTTAAGCCATTCATGCCAGTAGGCGCGCGGA* |
| *CGAAAGTAAACCCACTGGTGATACCATTCGTGAGCCTCCGGATGACGACC* |
| *GTAGTGATGAATCTCTCCAGGCGGGAACAGCAAAATATCACCCGGTCGGC* |
| *AGACAAATTCTCGTCCCTGATTTTTCACCACCCCCTGACCGCGAATGGTG* |
| *AGATTGAGAATATAACCTTTCATTCCCAGCGGTCGGTCGATAAAAAAATC* |
| *GAGATAACCGTTGGCCTCAATCGGCGTTAAACCCGCCACCAGATGGGCGT* |
| *TAAACGAGTATCCCGGCAGCAGGGGATCATTTTGCGCTTCAGCCAT*ACTT |
| TTCATACTCCCGCCATTCAGAGAAGAAACCAATTGTCCATATTGCATCAG |
| ACATTGCCGTCACTGCGTCTTTTACTGGCTCTTCTCGCTAACCCAACCGG |
| TAACCCCGCTTATTAAAAGCATTCTGTAACAAAGCGGGACCAAAGCCATG |
| ACAAAAACGCGTAACAAAAGTGTCTATAATCACGGCAGAAAAGTCCACAT |
| TGATTATTTGCACGGCGTCACACTTTGCTATGCCATAGCATTTTTATCCA |
| TAAGATTAGCGGATCCAGCCTGACGCTTTTTTTCGCAACTCTCTACTGTT |
| TCTCCATACCTCTAGAAATAATTTTGTTTAACTTTAAGAAGGAGATATAC |
| AT**ATGCCTGGTATGACCACCGAAACCGGTCCGGATCCTGCAGGTCTGATT** |
| **GACCTGTTTTGTCGTAAAAGCAAAGCAGTTAAAAGCCGTGCAAATGGTGC** |
| **AGGTCAGCGTCGTAAACAAGAAATTAGCATTGCAGCACAAGAAACCCTGG** |
| **GTCGTAAAGTTGCAGCACTGCTGGGTATGCAGGTTCGTCATGTTTGGAAA** |
| **GAAGTTGGTAGCGCAAGCCGTTTTCGTAAAGGTAAAGCACGTGATGATCA** |
| **GAGCAAAGCACTGAAAGCCCTGGAAAGCGGTGAAGTTGGTGCACTGTGGT** |
| **GTTATCGTCTGGATCGTTGGGATCGTGGTGGTGCCGGTGCAATTCTGAAA** |
| **ATTATCGAACCGGAAGATGGTATGCCTCGTCGTCTGCTGTTTGGTTGGGA** |
| **TGAAGATACCGGTCGTCCGGTTCTGGATAGCACCAATAAACGTGATCGCG** |
| **GTGAACTGATTCGTCGTGCAGAAGAAGCACGCGAAGAAGCAGAAAAACTG** |
| **AGCGAACGTGTTCGTGATACCAAAGCACATCAGCGTGAAAATGGTGAATG** |
| **GGTTAATGCCCGTGCACCGTATGGTCTGCGTGTTGTTCTGGTTACCGTTA** |
| **GTGATGAAGAGGGTGATGAATATGATGAACGTAAACTGGCAGCAGATGAT** |
| **GAAGATGCGGGTGGTCCTGATGGTCTGACCAAAGCAGAAGCAGCCCGTCT** |
| GGTTTTTACCCTGCCGGTTACCGATCGTCTGAGCTATGCAGGCACCGCAC |
| **ATGCAATGAATACCCGTGAAATTCCGAGCCCGACCGGTGGTCCGTGGATT** |
| **GCAGTTACCGTGCGTGATATGATTCAGAATCCGGCATATGCGGGTTGGCA** |
| **GACCACAGGTCGTCAGGATGGTAAACAGCGTCGTCTGACCTTTTATAACG** |
| **GTGAAGGTAAACGTGTTAGCGTTATGCATGGTCCTCCGCTGGTGACCGAT** |
| **GAAGAACAAGAAGCCGCAAAAGCAGCCGTTAAAGGTGAAGATGGTGTTGG** |
| **TGTTCCGCTGGATGGTAGCGATCATGATACCCGTCGCAAACATCTGCTGA** |
| **GCGGTCGTATGCGTTGTCCGGGTTGTGGTGGTAGCTGTAGCTATAGCGGT** |
| **AATGGTTATCGTTGTTGGCGTAGCAGTGTGAAAGGTGGTTGTCCGGCACC** |
| GACCTATGTTGCACGTAAAAGCGTTGAAGAATATGTTGCATTTCGTTGGG |
| **CAGCAAAATTAGCAGCAAGCGAACCGGATGATCCGTTTGTTATTGCAGTT** |
| **GCAGATCGCTGGGCAGCACTGACCCATCCGCAGGCAAGCGAAGATGAAAA** |
| **GTATGCAAAAGCCGCAGTTCGTGAAGCCGAAAAAAATCTGGGTCGCCTGC** |
| **TGCGTGATCGTCAGAATGGTGTTTATGATGGTCCGGCAGAACAGTTTTTT** |
| **GCCCCTGCATATCAAGAAGCACTGAGCACCCTGCAGGCAGCCAAAGATGC** |
| **AGTTAGCGAAAGCAGCGCAAGCGCAGCAGTTGATGTTAGCTGGATTGTTG** |
| **ATAGCAGCGATTATGAAGAACTGTGGCTGCGTGCAACCCCGACCATGCGT** |
| **AATGCAATTATTGATACCTGCATCGATGAAATTTGGGTTGCAAAAGGCCA** |
| **GCGTGGTCGTCCGTTTGATGGTGATGAACGCGTTAAAATCAAATGGGCAG** |
| **CCCGTACCTAA** |

Example 23. Generation of DeltaThyA

An auxotrophic mutation causes bacteria to die in the absence of an exogenously added nutrient essential for survival or growth because they lack the gene(s) necessary to produce that essential nutrient. In order to generate genetically engineered bacteria with an auxotrophic modification, the thyA, a gene essential for oligonucleotide synthesis was deleted. Deletion of the thyA gene in *E. coli* Nissle yields a strain that cannot form a colony on LB plates unless they are supplemented with thymidine.

A thyA::cam PCR fragment was amplified using 3 rounds of PCR as follows. Sequences of the primers used at a 100 um concentration are found in Table 49.

TABLE 49

| Primer Sequences | | | |
|---|---|---|---|
| Name | Sequence | Description | SEQ ID NO |
| SR36 | tagaactgatgcaaaaagtgctcgacgaaggcacacagaTGTGTAG GCTGGAGCTGCTTC | Round 1: binds on pKD3 | SEQ ID NO: 46 |
| SR38 | gtttcgtaattagatagccaccggcgctttaatgcccggaCATATGAA TATCCTCCTTAG | Round 1: binds on pKD3 | SEQ ID NO: 47 |
| SR33 | caacacgtacctgaggaaccatgaaacagtatttagaactgatgcaaaaag | Round 2: binds to round 1 PCR product | SEQ ID NO: 48 |
| SR34 | cgcacactggcgtcggctctggcaggatgtttcgtaattagatagc | Round 2: binds to round 1 PCR product | SEQ ID NO: 49 |
| SR43 | atatcgtcgcagcccacagcaacacgtttcctgagg | Round 3: binds to round 2 PCR product | SEQ ID NO: 50 |
| SR44 | aagaatttaacggagggcaaaaaaaaccgacgcacactggcgtcggc | Round 3: binds to round 2 PCR product | SEQ ID NO: 51 |

For the first PCR round, 4×50 ul PCR reactions containing 1 ng pKD3 as template, 25 ul 2×phusion, 0.2 ul primer SR36 and SR38, and either 0, 0.2, 0.4 or 0.6 ul DMSO were brought up to 50 ul volume with nuclease free water and amplified under the following cycle conditions:

step1: 98c for 30 s
step2: 98c for 10 s
step3: 55c for 15 s
step4: 72c for 20 s
repeat step 2-4 for 30 cycles
step5: 72c for 5 min Subsequently, 5 ul of each PCR reaction was run on an agarose gel to confirm PCR product of the appropriate size. The PCR product was purified from the remaining PCR reaction using a Zymoclean gel DNA recovery kit according to the manufacturer's instructions and eluted in 30 ul nuclease free water.

For the second round of PCR, 1 ul purified PCR product from round 1 was used as template, in 4×50 ul PCR reactions as described above except with 0.2 ul of primers SR33 and SR34. Cycle conditions were the same as noted above for the first PCR reaction. The PCR product run on an agarose gel to verify amplification, purified, and eluted in 30 ul as described above.

For the third round of PCR, 1 ul of purified PCR product from round 2 was used as template in 4×50 ul PCR reactions as described except with primer SR43 and SR44. Cycle conditions were the same as described for rounds 1 and 2. Amplification was verified, the PCR product purified, and eluted as described above. The concentration and purity was measured using a spectrophotometer. The resulting linear DNA fragment, which contains 92 bp homologous to upstream of thyA, the chloramphenicol cassette flanked by frt sites, and 98 bp homologous to downstream of the thyA gene, was transformed into a *E. coli* Nissle 1917 strain containing pKD46 grown for recombineering. Following electroporation, 1 ml SOC medium containing 3 mM thymidine was added, and cells were allowed to recover at 37 C for 2 h with shaking. Cells were then pelleted at 10,000×g for 1 minute, the supernatant was discarded, and the cell pellet was resuspended in 100 ul LB containing 3 mM thymidine and spread on LB agar plates containing 3 mM thy and 20 ug/ml chloramphenicol. Cells were incubated at 37 C overnight. Colonies that appeared on LB plates were restreaked. +cam 20 ug/ml + or −thy 3 mM. (thyA auxotrophs will only grow in media supplemented with thy 3 mM).

Next, the antibiotic resistance was removed with pCP20 transformation. pCP20 has the yeast Flp recombinase gene, FLP, chloramphenicol and ampicillin resistant genes, and temperature sensitive replication. Bacteria were grown in LB media containing the selecting antibiotic at 37° C. until OD600=0.4-0.6. 1 mL of cells were washed as follows: cells were pelleted at 16,000×g for 1 minute. The supernatant was discarded and the pellet was resuspended in 1 mL ice-cold 10% glycerol. This wash step was repeated 3× times. The final pellet was resuspended in 70 ul ice-cold 10% glycerol. Next, cells were electroporated with 1 ng pCP20 plasmid DNA, and 1 mL SOC supplemented with 3 mM thymidine was immediately added to the cuvette. Cells were resuspended and transferred to a culture tube and grown at 30° C. for 1 hours. Cells were then pelleted at 10,000×g for 1 minute, the supernatant was discarded, and the cell pellet was resuspended in 100 ul LB containing 3 mM thymidine and spread on LB agar plates containing 3 mM thy and 100 ug/ml carbenicillin and grown at 30° C. for 16-24 hours. Next, transformants were colony purified non-selectively (no antibiotics) at 42° C.

To test the colony-purified transformants, a colony was picked from the 42° C. plate with a pipette tip and resuspended in 10 μL LB. 3 μL of the cell suspension was pipetted onto a set of 3 plates: Cam, (37° C.; tests for the presence/absence of CamR gene in the genome of the host strain), Amp, (30° C., tests for the presence/absence of AmpR from the pCP20 plasmid) and LB only (desired cells that have lost the chloramphenicol cassette and the pCP20 plasmid), 37° C. Colonies were considered cured if there is no growth in neither the Cam or Amp plate, picked, and re-streaked on an LB plate to get single colonies, and grown overnight at 37° C.

Example 24. Phenylalanine Quantification (Dansyl-Chloride Derivatization)

For in vitro and in vivo assays described herein, which assess the ability of the genetically engineered bacteria to degrade phenylalanine and which require quantification of phenylalanine levels in the sample, a dansyl-chloride derivatization protocol was employed as follows.

Sample Preparation

Phenylalanine standards (1000, 500, 250, 100, 20, 4 and 0.8 g/mL in water) were prepared. On ice, 10 μL of sample was pipetted into a V-bottom polypropylene 96-well plate, and 190 μL of 60% acetonitrile with 1 ug/mL of L-Phenyl-$d_5$-alanine internal standard was added. The plate was heat sealed, mixed well, and centrifuged at 4000 rpm for 5 min. Next, 5 L of diluted samples were added to 95 μL of derivatization mix (85 L 10 mM $NaHCO_3$ pH 9.7 and 10 μL 10 mg/mL dansyl-chloride (diluted in acetonitrile)) in a V-bottom 96-well polypropylene plate, and the plate was heat-sealed and mixed well. The samples were incubated at 60° C. for 45 min for derivatization and then centrifuged at 4000 rpm for 5 minutes. Next, 20 μL of the derivatized samples were added to 180 μL of water with 0.1% formic acid in a round-bottom 96-well plate, plates were heat-sealed and mixed well.

LC-MS/MS Method

Phenylalanine was measured by liquid chromatography coupled to tandem mass spectrometry (LC-MS/MS) using a Thermo TSQ Quantum Max triple quadrupole mass spectrometer. HPLC Method details are described in Table 50 and Table 51. Tandem Mass Spectrometry details are described in Table 52.

TABLE 50

| HPLC Method Details | |
|---|---|
| Column | Luna C18(2) column, 5 μm (50 × 2.1 mm) |
| Mobile Phase A | 100% H2O, 0.1% Formic Acid |
| Mobile Phase B | 100% ACN, 0.1% Formic Acid |
| Injection volume | 10 uL |

TABLE 51

HPLC Method Details

| Total Time (min) | Flow Rate (μL/min) | A % | B % |
|---|---|---|---|
| 0 | 400 | 90 | 10 |
| 0.5 | 400 | 90 | 10 |
| 0.6 | 400 | 10 | 90 |
| 2 | 400 | 10 | 90 |
| 2.01 | 400 | 90 | 10 |
| 3 | 400 | 90 | 10 |

TABLE 52

| Tandem Mass Spectrometry Details | |
|---|---|
| Ion Source | HESI-II |
| Polarity | Positive |
| SRM transitions | |
| L-Phenylalanine | 399.1/170.1 |
| L-Phenyl-d5-alanine | 404.1/170.1 |

Example 25 Trans-Cinnamic Acid Quantification (Trifluoroethylamine Derivatization)

For in vitro and in vivo assays described herein, which assess the ability of the genetically engineered bacteria to degrade phenylalanine and which require quantification of Trans-cinnamic acid levels in the sample, a trifluoroethylamine derivatization protocol was employed as follows.

Sample Preparation

Trans-cinnamic acid standard (500, 250, 100, 20, 4 and 0.8 g/mL in water) were prepared. On ice, 10 μL of sample was pipetted into a V-bottom polypropylene 96-well plate. Next, 30 μL of 80% acetonitrile with 2 ug/mL of trans-cinnamic acid-d7 internal standard was added, and the plate was heat sealed, mixed well, and centrifuged at 4000 rpm for 5 minutes. Next, 20 μL of diluted samples were added to 180 μL of 10 mM MES pH4, 20 mM N-(3-Dimethylaminopropyl)-N'-ethylcarbodiimide (EDC), 20 mM trifluoroethylamine in a round-bottom 96-well polypropylene plate. The plate was heat-sealed, mixed well, and samples were incubated at room temperature for 1 hour.

LC-MS/MS Method

Trans-cinnamic acid was measured by liquid chromatography coupled to tandem mass spectrometry (LC-MS/MS) using a Thermo TSQ Quantum Max triple quadrupole mass spectrometer. HPLC Method details are described in Table 53 and Table 54. Tandem Mass Spectrometry details are described in Table 55.

TABLE 53

| HPLC Method Details | |
|---|---|
| Column | Thermo Aquasil C18 column, 5 μm (50 × 2.1 mm) |
| Mobile Phase A | 100% H2O, 0.1% Formic Acid |
| Mobile Phase B | 100% ACN, 0.1% Formic Acid |
| Injection volume | 10 uL |

TABLE 54

HPLC Method Details

| Total Time (min) | Flow Rate (μL/min) | A % | B % |
|---|---|---|---|
| 0 | 500 | 100 | 0 |
| 1 | 500 | 100 | 0 |
| 2 | 500 | 10 | 90 |
| 4 | 500 | 10 | 90 |
| 4.01 | 500 | 100 | 0 |
| 5 | 500 | 100 | 0 |

TABLE 55

| Tandem Mass Spectrometry Details | |
|---|---|
| Ion Source: | HESI-II |
| Polarity | Positive |
| SRM transitions | |
| Trans-cinnamic acid: | 230.1/131.1 |
| Trans-cinnamic acid-d7 | 237.1/137.2 |

Example 26. Phenylalanine, Trans-Cinnamic Acid, Phenylacetic Acid, Phenylpyruvic Acid, Phenyllactic Acid, Hippuric Acid and Benzoic Acid Quantification (2-Hydrazinoquinoline Derivatization)

For in vitro and in vivo assays described herein, which assess the ability of the genetically engineered bacteria to degrade phenylalanine and which require quantification of phenylalanine, trans-cinnamic acid, phenylacetic acid, phenylpyruvic acid, phenyllactic acid, hippuric acid, and benzoic acid levels in the sample, a 2-Hydrazinoquinoline derivatization protocol was employed as follows Sample Preparation Standard solutions containing 250, 100, 20, 4, 0.8, 0.16 and 0.032 μg/mL of each standard in water were prepared. On ice, 10 μL of sample was pipetted into a V-bottom polypropylene 96-well plate, and 90 μL of the derivatizing solution containing 50 mM of 2-Hydrazinoquinoline (2-HQ), dipyridyl disulfide, and triphenylphospine in acetonitrile with 1 ug/mL of L-Phenyl-$d_5$-alanine, 1 ug/mL of hippuric acid-d5 and 0.25 ug/mL trans-cinnamic acid-d7 internal standards was added. The plate was heat-sealed, mixed well, and samples were incubated at 60° C. for 1 hour for derivatization, and then centrifuged at 4000 rpm for 5 min. In a round-bottom 96-well plate, 20 μL of the derivatized samples were added to 180 μL of water with 0.1% formic acid. Plates were heat-sealed and mixed well.

LC-MS/MS Method

Metabolites derivatized by 2-HQ were measured by liquid chromatography coupled to tandem mass spectrometry (LC-MS/MS) using a Thermo TSQ Quantum Max triple quadrupole mass spectrometer. HPLC details are described in Table 56 and Table 57. Tandem Mass Spectrometry details are described in Table 58.

TABLE 56

| HPLC Method Details | |
|---|---|
| Column | Luna C18(2) column, 3 μm (150 × 2.1 mm) |
| Mobile Phase A | 100% H2O, 0.1% Formic Acid |
| Mobile Phase B | 100% ACN, 0.1% Formic Acid |
| Injection volume | 10 uL |

TABLE 57

HPLC Method Details

| Total Time (min) | Flow Rate (μL/min) | A % | B % |
|---|---|---|---|
| 0 | 500 | 90 | 10 |
| 0.5 | 500 | 90 | 10 |
| 2 | 500 | 10 | 90 |
| 4 | 500 | 10 | 90 |
| 4.01 | 500 | 90 | 10 |
| 4.25 | 500 | 90 | 10 |

TABLE 58

Tandem Mass Spectrometry Details

| | |
|---|---|
| Ion Source | HESI-II |
| Polarity | Positive |
| SRM transitions | |
| L-Phenylalanine: | 307.1/186.1 |
| L-Phenyld5-alanine | 312.1/186 |
| Trans-cinnamic acid | 290.05/131.1 |
| Trans-cinnamic acid-d7 | 297.05/138.1 |
| Hippuric acid | 321.1/160.1 |
| Hippuric acid-d5 | 326/160 |
| Phenylacetic acid | 278.05/160.1 |
| Phenyllactic acid | 308.05/144.1 |
| Benzoic acid | 264.05/105.1 |
| Phenylpyruvate | 306.05/260.1 |

Example 27. Relative Efficacy of Chromosomal Insertion and Plasmid-Bearing Strains To compare the rate of phenylalanine degradation between engineered bacterial strains with chromosomal insertions and those harboring plasmids, overnight cultures were diluted 1:100 in LB and grown with shaking (250 rpm) at 37° C. After 1.5 hrs of growth, cultures were placed in a Coy anaerobic chamber supplying 90% $N_2$, 5% $CO_2$, 5% $H_2$. After 4 hrs of induction, bacteria were pelleted, washed in PBS, and resuspended in assay buffer (M9 minimal media with 0.5% glucose, 8.4% sodium bicarbonate, and 4 mM Phe). Rates of phenylalanine degradation (i.e., disappearance from the assay solution) or cinnamate accumulation from 30 to 90 min were normalized to 1e9 cells. Table 59 shows the normalized rates for all strains and describes genotypes and the activities of non-limiting examples of engineered plasmid-bearing strains and engineered strains comprising chromosomal insertions.

TABLE 59

Genotype and Activity of engineered plasmid-bearing strains and engineered strains comprising chromosomal insertions.

| Strain Name | Genotype | PAL Activity (umol/hr./10ˆ9 cells) | LAAD activity (umol/hr./10ˆ9 cells) |
|---|---|---|---|
| Plasmid -based strains | | | |
| SYN-PKU101 | Low copy pSC101-Ptet::PAL1, ampicillin resistant | ND | NA |
| SYN-PKU102 | High copy pColE1-Ptet::PAL1, ampicillin resistant, | ND | NA |
| SYN-PKU201 | Low copy pSC101-Ptet::PAL3, ampicillin resistant | ND | NA |
| SYN-PKU202 | High copy pColE1-Ptet::PAL3, ampicillin resistant, | ND | NA |
| SYN-PKU203 | lacZ::Ptet-pheP::cam | 0 | NA |
| SYN-PKU401 | Low copy pSC101-Ptet::PAL1, ampicillin resistant, chromosomal lacZ::Ptet-pheP::cam | 1.1 | NA |
| SYN-PKU402 | High copy pColE1-Ptet::PAL1, ampicillin resistant, chromosomal lacZ::Ptet-pheP::cam | 0.8 | NA |
| SYN-PKU302 | Low Copy pSC101-Ptet::PAL3, ampicillin resistant; chromosomal lacZ::Ptet-pheP::cam | 2.2 | NA |
| SYN-PKU303 | High copy pColE1-Ptet::PAL3, ampicillin resistant, chromosomal lacZ::Ptet-pheP::cam | 7.1 | NA |
| SYN-PKU304 | Low Copy pSC101-PfnrS::PAL3, ampicillin resistant; chromosomal lacZ::PfnrS-pheP::cam | 3 | NA |
| SYN-PKU305 | Low Copy pSC101-PfnrS::PAL3, kanamycin resistant; chromosomal lacZ::PfnrS-pheP::cam | 3 | NA |
| SYN-PKU306 | Low Copy pSC101-PfnrS::PAL3, kanamycin resistant; thyA | 0.3 | NA |
| SYN-PKU307 | Low Copy pSC101-PfnrS::PAL3, ampicillin resistant; | 0.3 | NA |
| SYN-PKU308 | Low Copy pSC101-PfnrS::PAL3, kanamycin resistant; | 0.3 | NA |
| SYN-PKU401 | High Copy pUC57-Ptet::LAAD; kanamycin resistant | NA | 50 ($^{+}O_2$), 0($^{-}O_2$) |

TABLE 59-continued

Genotype and Activity of engineered plasmid-bearing strains and engineered strains comprising chromosomal insertions.

| Strain Name | Genotype | PAL Activity (umol/hr./ 10^9 cells) | LAAD activity (umol/hr./ 10^9 cells) |
|---|---|---|---|
| Integrated strains | | | |
| SYN-PKU501 | malPT:: PfnrS::PAL3::kan | 0.3 | NA |
| SYN-PKU502 | malPT:: PfnrS::PAL3::kan; bicistronic lacZ:: PfnrS::PAL3-pheP::cam | ND | NA |
| SYN-PKU503 | malEK::PfnrS::PAL3:: cam | 0.3 | NA |
| SYN-PKU504 | agaI/rsmI::PfnrS::PAL3 | 0.3 | NA |
| SYN-PKU505 | cea::PfnrS::PAL3 | 0.3 | NA |
| SYN-PKU506 | malEK::PfnrS::PAL3; agaI/rsmI::PfnrS::PAL3; cea::PfnrS::PAL3 | 0.7 | NA |
| SYN-PKU507 | malEK::PfnrS::PAL3; agaI/rsmI::PfnrS::PAL3; cea::PfnrS::PAL3; lacZ::Pfnr-pheP::cam | 5.2 | NA |
| SYN-PKU508 | malEK::PfnrS::PAL3; pheA auxotroph | 0.4 | NA |
| SYN-PKU509 | malEK::PfnrS::PAL3; agaI/rsmI::PfnrS::PAL3; cea::PfnrS::PAL3; lacZ::Pfnr-pheP::cam | 4.9 | NA |
| SYN-PKU601 | malPT::PfhrS-INT5::kan, rrnBUP - [PAL3]; lacZ::Pfnr-pheP::cam (recombinase based strain) | 0.9 | NA |
| SYN-PKU510 | malEK::PfnrS::PAL3; agaI/rsmI::PfnrS::PAL3; cea::PfnrS::PAL3; | 0.6 | NA |
| SYN-PKU511 | malEK:: PfnrS::PAL3; agaI/rsmI::PfnrS::PAL3; cea::PfnrS::PAL3; yicS/nepI::PfnrS-PAL3::kan; malPT::PfnrS::PKL3; lacZ::Pfnr-pheP; ΔthyA | 7.7 | NA |
| SYN-PKU204 | lacZ::Pfnr-pheP::cam | ND | NA |
| SYN-PKU512 | malEK::PfnrS::PAL3; agaI/rsmI::PfnrS::PAL3; cea::PfnrS::PAL3; malPT::pfnrS::PKL3; lacZ::Pfnr-pheP::cam; ΔthyA | 6.7 | NA |
| SYN-PKU513 | malEK:: PfnrS::PAL3; agaI/rsmI::PfnrS::PAL3; cea::PfnrS::PAL3; lacZ::Pfnr-pheP; ΔthyA | 4.9 | NA |
| SYN-PKU514 | malEK:: PfnrS::PAL3; agaI/rsmI::PfnrS::PAL3; cea::PfnrS::PAL3; malPT::PfnrS::PAL3; ΔthyA | 0.8 | NA |
| SYN-PKU515 | malEK:: PfnrS::PAL3; agaI/rsmI::PfnrS::PAL3; cea::PfnrS::PAL3; ΔthyA | 0.7 | NA |
| SYN-PKU516 | agaI/rsmI::PfnrS::PAL3::kan | 0.3 | NA |
| SYN-PKU517 | malEK:: PfnrS::PAL3::cam; malPT::PfnrS::PAL3::kan; lacZ::PfnrS-pheP; ΔthyA | 2.9 | NA |
| SYN-PKU518 | malEK-PfnrS::PAL3::cam; PfnrS::pheP::kan | 1.7 | NA |
| SYN-PKU519 | ParaBC-PAL3::cam; PfnrS-pheP::kan | 1.3 | NA |
| SYN-PKU520 | agaI/rsmI::PfnrS::PAL3::kan; PfnrS-PheP::cam | 2.0 | NA |
| SYN-PKU801 | ΔargR; thyA::cam | ND | NA |
| SYN-PKU701 | ParaBC-LAAD::cam; malEK-PfnrS-PAL3; malPT::PfnrS-PAL3::kan; PfhnrS-pheP | 2.7 | 28 ($^{+}O_2$), 0 ($^{-}O_2$) |
| SYN-PKU521 | yicS/nepI::PfnrS-PAL3::kan; lacZ:: Pfnr-pheP::cam | 2.4 | NA |
| SYN-PKU522 | cea::PfnrS-PAL3::kan; lacZ::Pfnr-pheP::cam | ND | NA |
| SYN-PKU523 | malPT::PfnrS-PAL3::kan; lacZ::Pfnr-pheP::cam | 0.5 | NA |
| SYN-PKU524 | malEK:: PfnrS::PAL3; malPT::PfnrS::PAL3; lacZ::Pfnr-pheP | 2.9 | NA |
| SYN-PKU702 | malEK:: PfnrS::PAL3; lacZ::Pfnr-pheP; Para::LAAD | 1.5 | ND |
| SYN-PKU703 | malEK:: PfnrS::PAL3; malPT::PfnrS::PAL3; lacZ::Pfnr-pheP; agaI/rsmI::PfnrS::pheP; Para::LAAD | 3.1 | ND |
| SYN-PKU704 | malEK:: PfnrS::PAL3; malPT::PfnrS::PAL3; yicS/nepI::PfnrS-PAL3; lacZ::Pfnr-pheP; Para::LAAD | 3.5 | ND |
| SYN-PKU705 | malEK:: PfnrS::PAL3; malPT::PfnrS::PAL3; yicS/nepI:: PfnrS-PAL3::kan; lacZ::Pfnr-pheP; agaI/rsmI::PfnrS::pheP Para::LAAD | 3.7 | ND |
| SYN-PKU602 | malEK:: PT7::PAL3; Para::INT5::cam (recombinase): lacZ::Pfnr-pheP; malPT::Pconstitutive::T7 polymerase (unflipped); | 2.4 | NA |
| SYN-PKU901 | Nissle with streptomycin resistance | NA | NA |

Example 28. Screening for Improved Phe Consumption

Screens using genetic selection are conducted to improve phenylalanine consumption in the genetically engineered bacteria. Toxic phenylalanine analogs exert their mechanism of action (MOA) by being incorporated into cellular protein, causing cell death. These compounds were evaluated for their utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds, and can be screened for and selected on this basis.

Various genetically engineered bacterial strains as well as control Nissle were treated with two analogs, p-fluoro-DL-minimum phenylalanine and o-fluoro-DL-phenylalanine (FIG. 35) at increasing concentrations. Minimum inhibitory concentration (MIC) was determined and the fold change relative to the wild type Nissle was determined. Results are shown in Table 60.

These results indicate that the para-analog appear to be taken up readily by pheP and are potentially a substrate of PAL, and that the ortholog appears to be taken up readily by pheP and is potentially a substrate of PAL. As a result, these compounds have utility for screening for PAL enzymes with greater activity.

TABLE 60

| MIC and Fold Change Relative to WT for various strains | | |
|---|---|---|
| MIC (ug/mL) | fold change (WT) | Strain |
| para-fluoro-Phe | | |
| 1250 | 1 | Wild Type Nissle |
| <2.4 | >↓520X | SYN-PKU203 (Ptet::pheP chr.) |
| 2500 | ↑2X | SYN-PKU202 (Ptet-PAL3 high copy) |
| 19.5 | ↓64X | SYN-PKU302 (Ptet-PAL low copy + Ptet-pheP chr.) |
| 39 | ↓32X | SYN-PKU303 (Ptet-PAL high copy + Ptet-pheP chr.) |
| ortho-fluoro-Phe | | |
| 62.5 | 1 | Wild Type Nissle |
| 1 | ↓64X | SYN-PKU203 (Ptet::pheP chr.) |
| 250 | ↑4X | SYN-PKU202 (Ptet-PAL3 high copy) |
| 31.3 | ↓2X | SYN-PKU302 (Ptet-PAL low copy + Ptet-pheP chr.) |
| 15.6 | ↓4X | SYN-PKU303 (Ptet-PAL high copy + Ptet-pheP chr.) |

Example 29. Repeat-Dose Pharmacokinetic and Pharmacodynamic Study of Genetically Engineered Bacteria Following Daily Nasogastric Gavage Dose Administration for 28-Days in Cynomolgus Monkeys (Non-GLP)

To evaluate any potential toxicities arising from administration of the genetically engineered bacteria or *E coli* Nissle alone, the pharmacokinetics and pharmacodynamics of the genetically engineered bacteria and an *E. coli* Nissle are studied following daily nasogastric gavage (NG) dose administration for 28-days to female cynomolgus monkeys. Cynomolgus monkeys is selected because this species is closely related, both phylogenetically and physiologically, to humans and is a species commonly used for nonclinical toxicity evaluations. The genetically engineered bacteria are administered by nasal gastric gavage, consistent with the proposed route of administration in humans. Animals overall well-being (clinical observations), weight clinical pathology (serum chemistry, hematology, and coagulation) are tracked. Plasma is analyzed for ammonia levels, and fecal samples examined for bacterial load.

The genetically engineered strain comprises one or more copies of PAL3 integrated into the chromosome and one or more copies of PheP integrated into the chromosome, each of which are under the control of an FNRS promoter. In some embodiments, the genetically engineered strain also comprises one or more copies of LAAD, driven by an arabinose inducible promoter, e.g., ParaBAD. In some embodiments, the strain further comprises a auxotrophy mutation, e.g., deltaThyA. In some embodiments, the genetically engineered bacteria further comprise an antibiotic resistance, e.g., kanamycin. In some embodiments, the genetically engineered bacteria do not comprise an auxotrophy mutation. In some embodiments, the genetically engineered bacteria do not comprise an antibiotic resistance.

Materials, Animals and Dosing Regimen

The study is conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C [97]186/Final; effective 1997). The animals are individually housed based on the recommendations set forth in the Guide for the Care and Use of Laboratory Animals (National Research Council 2011).

Animals used in the study are Female Purpose-bred, non-naive cynomolgus monkey (*Macaca fascicularis*) with 3 to 6 kg (at initial physical exam) 3 to 8 years (at initial physical exam) of age (SNBL USA stock, Origin: Cambodia).

For the duration of the study, animals are offered PMI LabDiet® Fiber-Plus® Monkey Diet 5049 biscuits twice daily. Animal are fasted for at least 2 hours prior to dose administration and fed within 1-hour post dose. Animals also are fasted as required by specific procedures (e.g., prior to blood draws for serum chemistry, fecal collection). The diet is routinely analyzed for contaminants and found to be within manufacturer's specifications. No contaminants are expected to be present at levels that would interfere with the outcome of the study. Food analysis records are maintained in the testing facility records.

Fresh drinking water is provided ad libitum to all animals. The water is routinely analyzed for contaminants. No contaminants are present at levels that would interfere with the outcome of the study. Animals are given fruits, vegetables, other dietary supplements, and cage enrichment devices throughout the course of the study.

Previously quarantined animals are acclimated to the study room for 7 days prior to initiation of dosing (day 1). The last dosing occurs on day 28. A stratified randomization scheme incorporating body weights is used to assign animals to study groups. Animals are assigned to groups and treated as indicated in Table 61.

TABLE 61

Group Assignments

| Group | Test/ Control Articles | Dose: Dose Level (cfu/ Animal) | Dose: Conc. (cfu/ mL) | Dose: Volume (mL/ Animal) | Flu: Bicarb. Conc. (M) | Flu: Volume (mL/ Animal) | Number of Females |
|---|---|---|---|---|---|---|---|
| 1 | Control Article | 0 | 0 | 10 | 0.36 | 5 | 3 |
| 2 | *E coli* Nissle | $1 \times 10^9$ | $1 \times 10^9$ | 1 | 0.12 | 14 | 3 |
| 3 | *E coli* Nissle | $1 \times 10^{12}$ | $1 \times 10^{11}$ | 10 | 0.36 | 5 | 3 |
| 4 | Genetically engineered bacteria | $1 \times 10^9$ | $1 \times 10^9$ | 1 | 0.12 | 14 | 3 |
| 5 | Genetically engineered bacteria | $1 \times 10^{12}$ | $1 \times 10^{11}$ | 10 | 0.36 | 5 | 3 |

Nissle control and genetically engineered bacterial stocks are prepared at 1×109 cfu/mL and 1×1011 cfu/mL in 15% glycerol in 1×PBS with 2.2% glucose and 3 mM thymidine and are kept at 86 to −60° C. (see Table 61). PBS made in 20% glycerol with sodium bicarbonate is used as a control vehicle. Carbonate concentration is 0.36M and 0.12M for sodium bicarbonate (see table XXX). On the day of each dosing, bacteria and vehicle control are removed from the freezer and put on ice and thawed and placed on ice until dosing.

Animals are dosed at 0, $1\times10^9$, or $1\times10^{12}$ cfu/animal. All animals are dosed via nasal gastric gavage (NG) followed by control/vehicle flush once daily for 28-days. The concentration of bicarbonate and volume for each group is specified in Table YYY. Vials are inverted at least 3 times prior to drawing the dose in the syringe. The dose site and dose time (end of flush time) is recorded.

Analysis

Overall Condition:

Clinical observations are performed twice daily beginning on the second day of acclimation for each animal. The first observation is in the AM, prior to room cleaning. The second observation is no sooner than 4 hours after the AM observation. During the dosing phase, the second observation is performed 4 hour (+10 minutes) post dose administration. Additional clinical observations are performed, as necessary.

Weight:

Each animal is weighed on Day −6, 1, 8, 15, 22, and 29 prior to the first feeding and also prior to dose administration. Additional body weights are taken as needed if necessary.

Blood Collection:

Blood is collected from a peripheral vein of restrained, conscious animals. Whenever possible, blood is collected via a single draw and then divided appropriately. Specimen collection frequency is summarized in Table 62.

TABLE 62

Specimen collection frequency

| Time Point | Hematology | Coagulation | Serum Chemistry | Plasma Sample (on ice) | Fecal sample (on ice) |
|---|---|---|---|---|---|
| Acclimation Week 1 | 1x | 1x | 1x | 1x | 1x |
| Dosing | Day 2 (Predose) | Day 2 (Predose) | Day 2 (Predose) | Days 2 and 7 | Days 2 and 7 |
| Dosing | Day 14 (Predose) | Day 14 (Predose) | Day 14 (Predose) | Day 14 (Predose) | Day 14-20 |
| Dosing | — | — | — | — | Day 21-27— |
| Dosing | — | — | — | Day28 (Predose) | Day 28-30 |
| Dosing Weeks | Day 30 | Day 30 | Day 30 | Day 30 | Day 35, 40 |

— = Not applicable x = Number of times procedure performed within the week

Hematology:

Approximately 1.3 mL of blood is tested in 2 mL K2EDTA tubes using an Advia automated analyzer. Parameters measured are White Blood Cells, Red Blood Cells, Hemoglobin, Hematocrit, Mean Corpuscular Volume, Mean Corpuscular Hemoglobin, Mean Corpuscular Hemoglobin Concentration, Red Cell Distribution Width, Platelets, Mean Platelet Volume, Differential leukocyte count (absolute): Neutrophils Absolute Lymphocytes Absolute Monocytes Absolute Eosinophils Absolute, Basophils Absolute Reticulocyte Percent, and Reticulocyte Absolute Count.

Coagulation:

Approximately 1.3 mL of blood is tested in 1.8 mL 3.2% sodium citrate tubes. The following Coagulation parameters are determined using a STACompact automated analyzer: Activated Partial Thromboplastin Time, Fibrinogen, and Prothrombin Time. Sodium citrate-treated plasma is stored at −60 to −86° C. prior to analysis and discarded after analysis.

Serum Chemistry:

Animals are fasted for 4 hours prior to removal of sample. The following parameters are tested in approximately 1 mL of blood in 4 mL serum separator tubes using a AU680 analyzer: Albumin, Alkaline Phosphatase, Alanine Aminotransferase Aspartate Aminotransferase, Total Bilirubin, Calcium, Total Cholesterol, Creatine Kinase, Creatinine, Glucose, Inorganic Phosphorus, Total Protein, Triglyceride, Sodium, Potassium, Chloride Globulin, Albumin/Globulin Ratio, Blood Urea Nitrogen, and Gamma Glutamyltransferase.

Residual serum is stored at −60 to −86° C. and disposed of prior to study finalization.

Plasma Samples:

Animals are fasted for 4 hours prior to removal of the sample. Blood samples are collected from the femoral vein at the target time points listed in Table YYY. After aliquotting the target volume of blood in the blood tube, approximately 0.05 mL of mineral oil is added covering the surface of blood. Tubes are not inverted and placed on a rack and wet ice. Blood sample collection dates and times were recorded. The minimum sample volume is 1 ml of blood collected in a 2 ml lithium heparin tube. Within 15 minutes of collection, the samples are centrifuged at 2 to 8° C. to obtain plasma. Plasma is transferred to a vial and stored at −60 to −86° C. Specimens are stored on dry ice prior to analysis. Analysis of specimens is conducted using a blood ammonia analyzer instrument.

Phenylalanine, trans-cinnamic acid, and hippuric acid is measured by liquid chromatography coupled to tandem mass spectrometry (LC-MS/MS) using a Thermo TSQ Quantum Max triple quadrupole mass spectrometer.

Fecal Sample Collection:

Two fecal samples per animal are collected at the target time points listed in Table YYY. Sample collection dates and times are recorded. 50 mL falcon tube with approximately 5 mL PBS are used as the container (If feces is liquid, no PBS is added). To get the fecal sample weight, pre- and post-sampling weight of container was taken. Samples are collected from the bottom of the cage from each animal. To get fresh and un-contaminated samples, remaining food is removed and the cage pan was cleaned and squeegeed to remove debris and/or water before the collection. Sample is put on wet ice immediately after the collection. Samples are stored at −20 to −15° C. until analysis. Analysis of specimens is conducted using a PCR analytical method.

Example 30. 4-Week Toxicity Study in Cynomolgus Monkeys with a 4-Week Recovery (GLP)

To evaluate any potential toxicities arising from administration of the genetically engineered bacteria, the pharmacokinetics and pharmacodynamics of the genetically engineered bacteria is studied following daily nasogastric gavage (NG) dose administration for 28-days to female cynomolgus monkeys under GLP conditions.

The genetically engineered strain comprises one or more copies of PAL3 integrated into the chromosome and one or more copies of PheP integrated into the chromosome, each of which are under the control of an FNRS promoter. In some embodiments, the genetically engineered strain also comprises one or more copies of LAAD, driven by and arabinose inducible promoter, e.g., ParaBAD. In some embodiments, the strains further comprise a auxotrophy mutation, e.g., deltaThyA. In some embodiments, the genetically engineered bacteria further comprise an antibiotic resistance, e.g., kanamycin. In some embodiments, the genetically engineered bacteria do not comprise an auxotrophy mutation. In some embodiments, the genetically engineered bacteria do not comprise an antibiotic resistance.

The study is conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C[97]186/Final; effective 1997). The animals are individually housed based on the recommendations set forth in the Guide for the Care and Use of Laboratory Animals (National Research Council 2011).

Animals are administered the genetically engineered bacteria or control vehicle essentially as described in Example 29, except that all materials are manufactured under GMP standards. Dosing is tabulated in Table 63. Additionally, animals are acclimated for 14 days and the dosing period is daily for 28 days followed by a recovery period of 28 days. Additionally, animals are euthanized at the end of the study to conduct histological analysis.

TABLE 63

Dosing Period and Regimen

| | |
|---|---|
| ACCLIMATION | 14 days |
| TEST ARTICLE PREP | Daily |
| DOSING PERIOD | Daily for 28 days |
| RECOVERY PERIOD | 28 days |
| REGULATIONS | FDA GLP |

| GROUP | TEST ARTICLE | DOSE LEVEL | DOSE ROUTE | NUMBER OF ANIMALS MALES (♂) | NUMBER OF ANIMALS FEMALES (♀) |
|---|---|---|---|---|---|
| 1 | Vehicle | 0 | NG | $3^a + 2^b$ | $3^a + 2^b$ |
| 2 | Genetically engineered bacteria | 1 × 10^9 | NG | $3^a$ | $3^a$ |
| 3 | Genetically engineered bacteria | 1 × 10^10 | NG | $3^a$ | $3^a$ |
| 4 | Genetically engineered bacteria | 1 × 10^11 | NG | $3^a + 2^b$ | $3^a + 2^b$ |

[a]Terminal Necropsy, Day 29
[b]Recovery Necropsy., Day 56

Study Analysis is conducted as described in Table 64. Hematology, Coagulation, Serum Chemistry and Plasma Samples parameters are essentially as described in Example 30, and are analyzed using the methods described in Example 30. Collection and analysis of fecal samples is essentially conducted as described in Example

TABLE 64

Study Analysis

| PROCEDURE | TIME POINTS |
|---|---|
| DOSE CONCENTRATION ANALYSIS | Day 1 and Day 28 |
| CLINICAL OBSERVATIONS | Twice Daily (cageside observations) |
| FOOD CONSUMPTION | Daily (qualitative) |
| BODY WEIGHT | Weekly |
| OPHTHALMOLOGY | Once during acclimation, Week 4, and Week 8 |
| ECGS/HR/BP | Once during acclimation, Week 4, and Week 8 |
| HEMATOLOGY | Twice during acclimation, Day 2 (pre-dose), Day 15 (pre-dose), Day 29, Day 42, and Day 56 |
| COAGULATION | Twice during acclimation, Day 2 (pre-dose), Day 15 (pre-dose), Day 29, Day 42, and Day 56 |
| SERUM CHEMISTRY | Twice during acclimation, Day 2 (pre-dose), Day 15 (pre-dose), Day 29, Day 42, and Day 56 |
| BODY (RECTAL) TEMPERATURE | Twice during acclimation (with at least 7 days between measurements); once weekly during dosing (~6 hrs post-dose), and Weeks 5 and 8 |
| STOOL SAMPLE COLLECTION (BACTERIAL CULTURE) | Once during acclimation, prior to dosing on Days 2, 7, and 14, Day 29, Day 33, and Week 8 Rectal/Fecal swabs are collected via cotton tip applicator; the cotton part of the swab is transferred to a tube with an appropriate broth/media and immediately put on wet ice. Fecal samples are stored at 2 to 8° C. until time of analysis. |
| CYTOKINE BLOOD COLLECTIONS | Once during acclimation, Days 1, 3, 7, 14 and 28 (6 hrs post-dose), and Day 56 |
| ARCHIVE BLOOD SAMPLE COLLECTION (SAMPLES TO BE HELD FOR POSSIBLE ANALYSIS) | Once during acclimation, Days 1, 3, 7, 14 and 28 (6 hrs post-dose), and Day 56; Blood samples are processed to serum; samples are stored frozen. |
| NECROPSY & TISSUE COLLECTION | All animals (e.g., colon, intestine, cecum, liver, spleen) |
| ORGAN WEIGHTS | All animals |
| TISSUE COLLECTION FOR PK/PD ASSESSMENT | All animals |
| HISTOPATHOLOGY | All animals |
| STATISTICAL ANALYSIS | Comparative (Anova/Bartletts) |

Example 31: Genetically Engineered Bacteria with HlyA Tag for Secretion of PMEs Constructs for secretion of PMEs were generated as shown in Table 65. This sequences are subsequently tagged, e.g., with a HIS tag, e.g., inserted before the C terminal secretion sequence. *E. coli* are transformed with the constructs on a low-copy plasmid. Secreted PMEs are isolated from the media using affinity chromatography (His-Tag). PME molecular weight is confirmed by western blot. Activity of the purified enzyme is tested in an in vitro assay in a phenylalanine-containing buffer. Metabolites are measured over time as described in Examples 24-26.

TABLE 65

| Secretion Sequences | | |
|---|---|---|
| SEQ ID NO | Description | Sequence |
| SEQ ID NO: 52 | HylA Secretion tag | LNPLINEISKIISAAGNFDVKEERAAASL<br>LQLSGNASDFSYGRNSITLTASA |
| SEQ ID NO: 53 | PAL (upper case) expressed as fusion protein with the 53 amino acids of the C termini of alpha-hemolysin (hlyA) of *E. coli* CFT073 (lower case). | MKAKDVQPTIIINKNGLISLEDIYDIAIK<br>QKKVEISTEITELLTHGREKLEEKLNSGE<br>VIYGINTGFGGNANLVVPFEKIAEHQQNL<br>LTFLSAGTGDYMSKPCIKASQFTMLLSVC<br>KGWSATRPIVAQAIVDHINHDIVPLVPRY<br>GSVGASGDLIPLSYIARALCGIGKVYYMG<br>AEIDAAEAIKRAGLTPLSLKAKEGLALIN<br>GTRVMSGISAITVIKLEKLFKASISAIAL<br>AVEALLASHEHYDARIQQVKNHPGQNAVA<br>SALRNLLAGSTQVNLLSGVKEQANKACRH<br>QEITQLNDTLQEVYSIRCAPQVLGIVPES<br>LATARKILEREVISANDNPLIDPENGDVL<br>HGGNFMGQYVARTMDALKLDIALIANHLH<br>AIVALMMDNRFSRGLPNSLSPTPGMYQGF<br>KGVQLSQTALVAAIRHDCAASGIHTLATE<br>QYNQDIVSLGLHAAQDVLEMEQKLRNIVS<br>MTILVVCQAIHLRGNISEIAPETAKFYHA<br>VREISSPLITDRALDEDIIRIADAIINDQ<br>LPLPEIMLEE<br>lnplineiskiisaagnfdvkeeraaasl<br>lqlsgnasdfsygrnsitltasa* |
| SEQ ID NO: 54 | LAAD (uppercase)expressed as fusion protein with the 53 amino acids of the C termini of alpha-hemolysin (hlyA) of *E. coli* CFT073 (lower case) | MNISRRKLLLGVGAAGVLAGGAALVPMVR<br>RDGKFVEAKSRASFVEGTQGALPKEADVV<br>IIGAGIQGIMTAINLAERGMSVTILEKGQ<br>IAGEQSGRAYSQIISYQTSPEIFPLHHYG<br>KILWRGMNEKIGADTSYRTQGRVEALADE<br>KALDKAQAWIKTAKEAAGFDTPLNTRIIK<br>GEELSNRLVGAQTPWTVAAFEEDSGSVDP<br>ETGTPALARYAKQIGVKIYTNCAVRGIET<br>AGGKISDVVSEKGAIKTSQVVLAGGIWSR<br>LFMGNMGIDIPTLNVYLSQQRVSGVPGAP<br>RGNVHLPNGIHFREQADGTYAVAPRIFTS<br>SIVKDSFLLGPKFMHLLGGGELPLEFSIG<br>EDLFNSFKMPTSWNLDEKTPFEQFRVATA<br>TQNTQHLDAVFQRMKTEFPVFEKSEVVER<br>WGAVVSPTFDELPIISEVKEYPGLVINTA<br>TVWGMTEGPAAGEVTADIVMGKKPVIDPT<br>PFSLDRFKK<br>lnplineiskiisaagnfdvkeeraaasl<br>lqlsgnasdfsygrnsitltasa |
| SEQ ID NO: 55 | HylA secretion signal | CTTAATCCATTAATTAATGAAATCAGCAA<br>AATCATTTCAGCTGCAGGTAATTTTGATG<br>TTAAAGAGGAAAGAGCTGCAGCTTCTTTA<br>TTGCAGTTGTCCGGTAATGCCAGTGATTT<br>TTCATATGGACGGAACTCAATAACTTTGA<br>CAGCATCAGCATAA |
| SEQ ID NO: 56 | LAAD (bold italics) driven by ParaBAD (underlined) with C terminal HylA Secretion tag (bold) | Acttttcatactcccgccattcagagaag<br>aaaccaattgtccatattgcatcagacat<br>tgccgtcactgcgtcttttactggctctt<br>ctcgctaacccaaccggtaaccccgctta<br>ttaaaagcattctgtaacaaagcgggacc<br>aaagccatgacaaaaacgcgtaacaaaag<br>tgtctataatcacggcagaaaa<br>***atgaacatttcaaggagaaagctacttttt***<br>***aggtgttggtgctgcgggcgttttagcag***<br>***gtggtgcggctttagttccaatggttcgc***<br>***cgtgacggcaaatttgtggaagctaaatc***<br>***aagagcatcatttgttgaaggtacgcaag***<br>***gggctcttcctaaagaagcagatgtagtg***<br>***attattggtgccggtattcaagggatcat***<br>***gaccgctattaaccttgctgaacgtggta***<br>***tgagtgtcactatcttagaaaagggtcag***<br>***attgccggtgagcaatcaggccgtgcata***<br>***cagccaaattattagttaccaaacatcgc***<br>***cagaaatcttcccattacaccattatggg***<br>***aaaatattatggcgtggcatgaatgagaa***<br>***aattggtgcggataccagttatcgtactc***<br>***aaggtcgtgtagaagcgctggcagatgaa***<br>***aaagcattagataaagctcaagcgtggat***<br>***caaaacagctaaagcggcaggttttg*** |

TABLE 65-continued

Secretion Sequences

| SEQ ID NO | Description | Sequence |
|---|---|---|
| | | atacaccattaaatactcgcatcattaaa<br>ggtgaagagctatcaaatcgcttagtcgg<br>tgctcaaacgccatggactgttgctgcat<br>ttgaagaagattcaggctctgttgatcct<br>gaaacaggcacacctgactcgctcgtta<br>tgccaaacaaatcggtgtgaaaatttata<br>ccaactgtgcagtaagaggtattgaaact<br>gcgggtggtaaaatctctgatgtggtgag<br>tgagaaaggggcgattaaaacgtctcaag<br>ttgtactcgctgggggtatctggtcgcgt<br>ttatttatgggcaatatgggtattgatat<br>cccaacgctcaatgtatatctatcacaac<br>aacgtgtctcaggggttcctggtgcacca<br>cgtggtaatgtgcatttacctaatggtat<br>tcatttccgcgaacaagcggatggtactt<br>atgccgttgcaccacgtatctttacgagt<br>tcaatagtcaaagatagcttcctgctagg<br>gcctaaatttatgcacttattaggtggcg<br>gagagttaccgttggaattctctattggt<br>gaagatctatttaattcatttaaaatgcc<br>gacctcttggaatttagatgaaaaaacac<br>cattcgaacaattccgagttgccacggca<br>acacaaaatacgcaacacttagatgctgt<br>tttccaaagaatgaaaacagaattcccag<br>tatttgaaaaatcagaagttgttgaacgt<br>tggggtgccgttgtgagtccaacatttga<br>tgaattacctatcatttctgaggtcaaag<br>aatacccaggcttagtgattaacacggca<br>acagtgtggggtatgacagaaggcccggc<br>agcgggtgaagtgaccgctgatattgtca<br>tgggcaagaaacctgttattgatccaacg<br>ccgtttagtttggatcgttttaagaagta<br>aCTTAATCCATTAATTAATGAAATCAGCA<br>AAATCATTTCAGCTGCAGGTAATTTTGAT<br>GTTAAAGAGGAAAGAGCTGCAGCTTCTTT<br>ATTGCAGTTGTCCGGTAATGCCAGTGATT<br>TTTCATATGGACGGAACTCAATAACTTTG<br>ACAGCATCAGCATAA |
| SEQ ID NO: 57 | PfnrS-PAL3 with C terminal secretion tag. PfnrS (bolded lower case), PAL3 sequence is underlined upper case C terminal secretion tag is bold uppercase | GGTACCagttgttcttattggtggtgttg<br>ctttatggttgcatcgtagtaaatggttg<br>taacaaaagcaatttttccggctgtctgt<br>atacaaaaacgccgtaaagtttgagcgaa<br>gtcaataaactctctacccattcagggca<br>atatctctcttGGATCCctctagaaataa<br>ttttgtttaactttaagaaggagatatac<br>atATGAAAGCTAAAGATGTTCAGCCAACC<br>ATTATTATTAATAAAAATGGCCTTATCTC<br>TTTGGAAGATATCTATGACATTGCGATAA<br>AACAAAAAAAAGTAGAAATATCAACGGAG<br>ATCACTGAACTTTTGACGCATGGTCGTGA<br>AAAATTAGAGGAAAAATTAAATTCAGGAG<br>AGGTTATATATGGAATCAATACAGGATTT<br>GGAGGGAATGCCAATTTAGTTGTGCCATT<br>TGAGAAAATCGCAGAGCATCAGCAAAATC<br>TGTTAACTTTTCTTTCTGCTGGTACTGGG<br>GACTATATGTCCAAACCTTGTATTAAAGC<br>GTCACAATTTACTATGTTACTTTCTGTTT<br>GCAAAGGTTGGTCTGCAACCAGACCAATT<br>GTCGCTCAAGCAATTGTTGATCATATTAA<br>TCATGACATTGTTCCTCTGGTTCCTCGCT<br>ATGGCTCAGTGGGTGCAAGCGGTGATTTA<br>ATTCCTTTATCTTATATTGCACGAGCATT<br>ATGTGGTATCGGCAAAGTTTATTATATGG<br>GCGCAGAAATTGACGCTGCTGAAGCAATT<br>AAACGTGCAGGGTTGACACCATTATCGTT<br>AAAAGCCAAAGAAGGTCTTGCTCTGATTA<br>ACGGCACCCGGGTAATGTCAGGAATCAGT<br>GCAATCACCGTCATTAAACTGGAAAAACT<br>ATTTAAAGCCTCAATTTCTGCGATTGCCC<br>TTGCTGTTGAAGCATTACTTGCATCTCAT<br>GAACATTATGATGCCCGGATTCAACAAGT<br>AAAAAATCATCCTGGTCAAAACGCGGTGG<br>CAAGTGCATTGCGTAATTTATTGGCAGGT<br>TCAACGCAGGTTAATCTATTATCTGGGGT<br>TAAAGAACAAGCCAATAAAGCTTGTCGTC |

TABLE 65-continued

| Secretion Sequences | | |
|---|---|---|
| SEQ ID NO | Description | Sequence |
| | | ATCAAGAAATTACCCAACTAAATGATACC<br>TTACAGGAAGTTTATTCAATTCGCTGTGC<br>ACCACAAGTATTAGGTATAGTGCCAGAAT<br>CTTTAGCTACCGCTCGGAAAATATTGGAA<br>CGGGAAGTTATCTCAGCTAATGATAATCC<br>ATTGATAGATCCAGAAAATGGCGATGTTC<br>TACACGGTGGAAATTTTATGGGGCAATAT<br>GTCGCCCGAACAATGGATGCATTAAAACT<br>GGATATTGCTTTAATTGCCAATCATCTTC<br>ACGCCATTGTGGCTCTTATGATGGATAAC<br>CGTTTCTCTCGTGGATTACCTAATTCACT<br>GAGTCCGACACCCGGCATGTATCAAGGTT<br>TTAAAGGCGTCCAACTTTCTCAAACCGCT<br>TTAGTTGCTGCAATTCGCCATGATTGTGC<br>TGCATCAGGTATTCATACCCTCGCCACAG<br>AACAATACAATCAAGATATTGTCAGTTTA<br>GGTCTGCATGCCGCTCAAGATGTTTTAGA<br>GATGGAGCAGAAATTACGCAATATTGTTT<br>CAATGACAATTCTGGTAGTTTGTCAGGCC<br>ATTCATCTTCGCGGCAATATTAGTGAAAT<br>TGCGCCTGAAACTGCTAAATTTTACCATG<br>CAGTACGCGAAATCAGTTCTCCTTTGATC<br>ACTGATCGTGCGTTGGATGAAGATATAAT<br>CCGCATTGCGGATGCAATTATTAATGATC<br>AACTTCCTCTGCCAGAAATCATGCTGGAA<br>GAATAA**CTTAATCCATTAATTAATGAAAT**<br>**CAGCAAAATCATTTCAGCTGCAGGTAATT**<br>**TTGATGTTAAAGAGGAAAGAGCTGCAGCT**<br>**TCTTTATTGCAGTTGTCCGGTAATGCCAG**<br>**TGATTTTTCATATGGACGGAACTCAATAA**<br>**CTTTGACAGCATCAGCATAA** |

TABLE 66

| HlyB and HlyD protein sequences | | |
|---|---|---|
| SEQ ID NO: 58 | HlyB protein | MDSCHKIDYGLYALEILAQYHNVSVNPEE<br>IKHRFDTDGTGLGLTSWLLAAKSLELKVK<br>QVKKTIDRLNFISLPALVWREDGRHFILT<br>KVSKEANRYLIFDLEQRNPRVLEQSEFEA<br>LYQGHIILIASRSSVTGKLAKFDFTWFIP<br>AIIKYRKIFIETLVVSVFLQLFALITPLF<br>FQVVMDKVLVHRGFSTLNVITVALSVVVV<br>FEIILSGLRTYIFAHSTSRIDVELGAKLF<br>RHLLALPISYFESRRVGDTVARVRELDQI<br>RNFLTGQALTSVLDLLFSFIFFAVMWYYS<br>PKLTLVILFSLPCYAAWSVFISPILRRRL<br>DDKFSRNADNQSFLVESVTAINTIKAMAV<br>SPQMTNIWDKQLAGYVAAGFKVTVLATIG<br>QQGIQLIQKTVMIINLWLGAHLVISGDLS<br>IGQLIAFNMLAGQIVAPVIRLAQIWQDFQ<br>QVGISVTRLGDVLNSPTESYHGKLALPEI<br>NGNITFRNIRFRYKPDSPVILDNINLSIK<br>QGEVIGIVGRSGSGKSTLTKLIQRFYIPE<br>NGQVLIDGHDLALADPNWLRRQVGVVLQD<br>NVLLNRSIIDNISLANPGMSVEKVIYAAK<br>LAGAHDFISELREGYNTIVGEQGAGLSGG<br>QRQRIAIARALVNNPKILIFDEATSALDY<br>ESEHIIMRNMHKICKGRTVIIIAHRLSTV<br>KNADRIIVMEKGKIVEQGKHKELLSEPES<br>LYSYLYQLQSD |
| SEQ ID NO: 59 | HlyD protein | MKTWLMGFSEFLLRYKLVWSETWKIRKQL<br>DTPVREKDENEFLPAHLELIETPVSRRPR<br>LVAYFIMGFLVIAVILSVLGQVEIVATAN<br>GKLTLSGRSKEIKPIENSIVKEIIVKEGE<br>SVRKGDVLLKLTALGAEADTLKTQSSLLQ<br>TRLEQTRYQILSRSIELNKLPELKLPDEP<br>YFQNVSEEEVLRLTSLIKEQFSTWQNQKY<br>QKELNLDKKRAERLTILARINRYENLSRV<br>EKSRLDDFRSLLHKQAIAKHAVLEQENKY<br>VEAANELRVYKSQLEQIESEILSAKEEYQ |

TABLE 66-continued

| HlyB and HlyD protein sequences |
| --- |
| LVTQLFKNEILDKLRQTTDNIELLTLELE<br>KNEERQQASVIRAPVSGKVQQLKVHTEGG<br>VVTTAETLMVIVPEDDTLEVTALVQNKDI<br>GFINVGQNAIIKVEAFPYTRYGYLVGKVK<br>NINLDAIEDQKLGLVFNVIVSVEENDLST<br>GNKHIPLSSGMAVTAEIKTGMRSVISYLL<br>SPLEESVTESLHER |

Example 32: Genetically Engineered Bacteria Comprising Additional Constructs

TABLE 67

| Description | Sequence | SEQ ID NO |
| --- | --- | --- |
| phenylalanine transporter [*Escherichia coli* str. K-12 substr. MG1655] Acc. No. NP_415108 (PheP) | MKNASTVSEDTASNQEPTLHRGLHNRHIQLIA<br>LGGAIGTGLFLGIGPAIQMAGPAVLLGYGVAG<br>IIAFLIMRQLGEMVVEEPVSGSFAHFAYKYWG<br>PFAGFLSGWNYWVMFVLVGMAELTAAGIYMQY<br>WFPDVPTWIWAAAFFIIINAVNLVNVRLYGET<br>EFWFALIKVLAIIGMIGFGLWLLFSGHGGEKA<br>SIDNLWRYGGFFATGWNGLILSLAVIMFSFGG<br>LELIGITAAEARDPEKSIPKAVNQVVYRILLF<br>YIGSLVVLLALYPWVEVKSNSSPFVMIFHNLD<br>SNVVASALNFVILVASLSVYNSGVYSNSRMLF<br>GLSVQGNAPKFLTRVSRRGVPINSLMLSGAIT<br>SLVVLINYLLPQKAFGLLMALVVATLLLNWIM<br>ICLAHLRFRAAMRRQGRETQFKALLYPFGNYL<br>CIAFLGMILLLMCTMDDMRLSAILLPVWIVFL<br>FMAFKTLRRK | 60 |
| aromatic amino acid transport protein AroP [*Escherichia coli* F11] Acc. NO: EDV65095 | MEGQQHGEQLKRGLKNRHIQLIALGGAIGTGL<br>FLGSASVIQSAGPGIILGYAIAGFIAFLIMRQ<br>LGEMVVEEPVAGSFSHFAYKYWGSFAGFASGW<br>NYWVLYVLVAMAELTAVGKYIQFWYPEIPTV<br>SAAVFFVVINAINLTNVKVFGEMEFWFAIIKV<br>IAVVAMIIFGAWLLFSGNGGPQASVSNLWDQG<br>GFLPHGFTGLVMMMAIIMFSFGGLELVGITAA<br>EADNPEQSIPKATNQVIYRILIFYIGSLAVLL<br>SLMPWTRVTADTSPFVLIFHELGDTFVANALN<br>IVVLTAALSVYNSCVYCNSRMLFGLAQQGNAP<br>KALASVDKRGVPVNTILVSALVTALCVLINYL<br>APESAFGLLMALVVSALVINWAMISLAHMKFR<br>RAKQEQGVVTRFPALLYPLGNWVCLLFMAAVL<br>VIMLMTPGMAISVYLIPVWLIVLGIGYLFKEK<br>TAKAVKAH | 61 |
| FNRS promoter (bold, lower case)-PheP (upper case underlined | **GGTACCagttgttcttattggtggtgttgctt**<br>**tatggttgcatcgtagtaaatggttgtaacaa**<br>**aagcaatttttccggctgtctgtatacaaaaa**<br>**cgccgtaaagtttgagcgaagtcaataaactc**<br>**tctacccattcagggcaatatctctcttGGAT**<br>**CCctctagaaataattttgtttaactttaaga**<br>**aggagatatacat**ATGAAAAACGCGTCAACCG<br>TATCGGAAGATACTGCGTCGAATCAAGAGCCG<br>ACGCTTCATCGCGGATTACATAACCGTCATAT<br>TCAACTGATTGCGTTGGGTGGCGCAATTGGTA<br>CTGGTCTGTTTCTTGGCATTGGCCCGGCGATT<br>CAGATGGCGGGTCCGGCTGTATTGCTGGGCTA<br>CGGCGTCGCCGGGATCATCGCTTTCCTGATTA<br>TGCGCCAGCTTGGCGAAATGGTGGTTGAGGAG<br>CCGGTATCCGGTTCATTTGCCCACTTTGCCTA<br>TAAATACTGGGGACCGTTTGCGGGCTTCCTCT<br>CTGGCTGGAACTACTGGGTAATGTTCGTGCTG<br>GTGGGAATGGCAGAGCTGACCGCTGCGGGCAT<br>CTATATGCAGTACTGGTTCCCGGATGTTCCAA<br>CGTGGATTTGGGCTGCCGCCTTCTTTATTATC<br>ATCAACGCCGTTAACCTGGTGAACGTGCGCTT<br>ATATGGCGAAACCGAGTTCTGGTTTGCGTTGA<br>TTAAAGTGCTGGCAATCATCGGTATGATCGGC<br>TTTGGCCTGTGGCTGCTGTTTTCTGGTCACGG<br>CGGCGAGAAAGCCAGTATCGACAACCTCTGGC<br>GCTACGGTGGTTTCTTCGCCACCGGCTGGAAT<br>GGGCTGATTTTGTCGCTGGCGGTAATTATGTT | 62 |

TABLE 67-continued

| Description | Sequence | SEQ ID NO |
|---|---|---|
| | CTCCTTCGGCGGTCTGGAGCTGATTGGGATTA<br>CTGCCGCTGAAGCGCGCGATCCGGAAAAAAGC<br>ATTCCAAAAGCGGTAAATCAGGTGGTGTATCG<br>CATCCTGCTGTTTTACATCGGTTCACTGGTGG<br>TTTTACTGGCGCTCTATCCGTGGGTGGAAGTG<br>AAATCCAACAGTAGCCCGTTTGTGATGATTTT<br>CCATAATCTCGACAGCAACGTGGTAGCTTCTG<br>CGCTGAACTTCGTCATTCTGGTAGCATCGCTG<br>TCAGTGTATAACAGCGGGGTTTACTCTAACAG<br>CCGCATGCTGTTTGGCCTTTCTGTGCAGGGTA<br>ATGCGCCGAAGTTTTTGACTCGCGTCAGCCGT<br>CGCGGTGTGCCGATTAACTCGCTGATGCTTTC<br>CGGAGCGATCACTTCGCTGGTGGTGTTAATCA<br>ACTATCTGCTGCCGCAAAAAGCGTTTGGTCTG<br>CTGATGGCGCTGGTGGTAGCAACGCTGCTGTT<br>GAACTGGATTATGATCTGTCTGGCGCATCTGC<br>GTTTTCGTGCAGCGATGCGACGTCAGGGGCGT<br>GAAACACAGTTTAAGGCGCTGCTCTATCCGTT<br>CGGCAACTATCTCTGCATTGCCTTCCTCGGCA<br>TGATTTTGCTGCTGATGTGCACGATGGATGAT<br>ATGCGCTTGTCAGCGATCCTGCTGCCGGTGTG<br>GATTGTATTCCTGTTTATGGCATTTAAAACGC<br>TGCGTCGGAAATAA | |
| FNRS promoter (bold, lower case)-AroP (upper case underlined, codon optimized) | **GGTACCagttgttcttattggtggtgttgctt**<br>**tatggttgcatcgtagtaaatggttgtaacaa**<br>**aagcaatttttccggctgtctgtatacaaaaa**<br>**cgccgtaaagtttgagcgaagtcaataaactc**<br>**tctacccattcagggcaatatctctcttGGAT**<br>**CCctctagaaataattttgtttaactttaaga**<br>**aggagatatacat**ATGGAGGGGCAGCAGCATG<br>GGGAGCAACTGAAGCGCGGGTTAAAAAATCGT<br>CACATTCAATTAATCGCGCTGGGCGGAGCAAT<br>TGGTACGGGATTGTTCCTGGGTTCAGCGAGCG<br>TCATCCAATCGGCAGGTCCAGGGATCATCTTG<br>GGATATGCGATCGCAGGCTTTATCGCTTTTCT<br>TATTATGCGCCAATTAGGTGAGATGGTGGTCG<br>AGGAGCCTGTAGCTGGCTCCTTCTCACATTTC<br>GCGTACAAGTATTGGGGATCCTTTGCGGGATT<br>TGCTTCTGGTTGGAACTATTGGGTTCTTTATG<br>TCCTGGTGGCCATGGCGGAGCTGACCGCGGTT<br>GGAAAATATATCCAGTTCTGGTACCCCGAGAT<br>CCCGACGTGGGTCTCAGCCGCGGTATTCTTTG<br>TTGTTATCAATGCAATCAATTTAACCAACGTA<br>AAAGTATTTGGTGAAATGGAGTTCTGGTTCGC<br>GATTATCAAAGTAATTGCCGTAGTTGCTATGA<br>TTATTTTTGGGGCATGGTTGCTTTTCTCAGGA<br>AATGGCGGACCACAAGCGTCGGTTTCAAACCT<br>GTGGGATCAAGGGGGATTCCTGCCGCACGGAT<br>TTACGGGCTTGGTGATGATGATGGCTATCATT<br>ATGTTTTCTTTCGGTGGTCTTGAATTAGTGGG<br>TATTACCGCAGCAGAGGCAGATAATCCCGAAC<br>AAAGCATCCCAAAAGCTACTAACCAAGTTATT<br>TACCGTATCCTGATTTTTTATATTGGTTCTCT<br>GGCAGTCCTGCTTTCCTTAATGCCCTGGACAC<br>GTGTAACGGCCGATACATCCCCTTTTGTACTT<br>ATCTTTCACGAACTGGGAGACACGTTCGTCGC<br>CAATGCATTAAACATTGTTGTGCTGACAGCTG<br>CCTTATCTGTGTATAATAGCTGCGTTTATTGC<br>AATTCACGTATGTTATTCGGGCTTGCTCAGCA<br>GGGTAACGCGCCAAAGGCGTTGGCCTCAGTAG<br>ATAAGCGCGGAGTGCCTGTAAATACAATTTTG<br>GTCAGCGCATTAGTCACGGCTCTTTGCGTTCT<br>GATTAACTATCTGGCTCCTGAAAGCGCATTCG<br>GATTACTTATGGCCCTGGTTGTTTCCGCCCTG<br>GTTATCAATTGGGCAATGATTAGTTTGGCACA<br>TATGAAGTTCCGCCGTGCTAAACAAGAACAAG<br>GTGTCGTAACTCGTTTCCCTGCCTTATTGTAT<br>CCGCTGGGGAATTGGGTATGCCTTCTTTTTAT<br>GGCCGCAGTACTGGTAATTATGTTGATGACGC<br>CCGGCATGGCTATTAGTGTATACCTTATTCCG<br>GTATGGTTAATCGTCTTGGGTATCGGCTACTT<br>ATTTAAAGAAAAAACAGCAAAAGCCGTAAAGG<br>CTCAT | 63 |

The invention claimed is:

1. A nucleic acid sequence comprising one or more gene(s) encoding a phenylalanine ammonia lyase (PAL) and one or more gene(s) encoding a phenylalanine transporter, wherein the PAL is from *Anabaena variabilis* (PAL1) or *Photorhabdus luminescens* (PAL3), wherein the one or more genes encoding the PAL is operably linked to an inducible promoter that is not in nature associated with the one or more genes encoding the PAL, wherein the inducible promoter is induced by low oxygen or anaerobic conditions to enable expression of the PAL in an *Escherichia* probiotic bacterium;

wherein the one or more genes encoding the phenylalanine transporter are from *Acinetobacter calcoaceticus, Salmonella enterica*, or *Escherichia coli*; and wherein the one or more genes encoding the phenylalanine transporter is operably linked to an inducible promoter that is not in nature associated with the one or more genes encoding the phenylalanine transporter, wherein the inducible promoter is induced by low oxygen or anaerobic conditions to enable expression of the phenylalanine transporter in the bacterium.

2. The nucleic acid sequence of claim 1, wherein the promoter operably linked to the one or more gene(s) encoding the PAL and the promoter operably linked to the one or more gene(s) encoding the phenylalanine transporter are separate copies of the same promoter sequence.

3. The nucleic acid sequence of claim 1, wherein the promoter operably linked to the one or more gene(s) encoding the PAL and the promoter operably linked to the one or more gene(s) encoding a phenylalanine transporter are different promoters.

4. The nucleic acid sequence of claim 1, wherein the promoter operably linked to the one or more gene(s) encoding the PAL and the promoter operably linked to the one or more gene(s) encoding the phenylalanine transporter are induced by environmental conditions found in a mammalian gut.

5. The nucleic acid sequence of claim 4, wherein the promoter is induced by low-oxygen or anaerobic conditions.

6. The nucleic acid sequence of claim 5, wherein the promoter is selected from the group consisting of an FNR-responsive promoter, an ANR-responsive promoter, and a DNR-responsive promoter.

7. The nucleic acid sequence of claim 1, wherein the phenylalanine transporter is PheP.

8. The nucleic acid sequence of claim 1, wherein the one or more gene(s) encoding the PAL and the one or more gene(s) encoding the phenylalanine transporter are located on a chromosome in the bacterium.

9. The nucleic acid sequence of claim 1, wherein the one or more gene(s) encoding the PAL and the one or more gene(s) encoding the phenylalanine transporter are located on a plasmid in the bacterium.

* * * * *